US012751736B2

(12) United States Patent
Nguyen et al.

(10) Patent No.: US 12,751,736 B2
(45) Date of Patent: Oct. 6, 2026

(54) NEUROVASCULAR CLOT RETRIEVING SYSTEM

(71) Applicant: Cerebrova KP Medical, Inc., Irvine, CA (US)

(72) Inventors: Thanh Van Nguyen, Irvine, CA (US); Rajan Hansji, Irvine, CA (US); Duy Nguyen, Irvine, CA (US)

(73) Assignee: Cerebrova KP Medical, Inc., Irvine, CA (US)

( * ) Notice: Subject to any disclaimer, the term of this patent is extended or adjusted under 35 U.S.C. 154(b) by 0 days.

(21) Appl. No.: 19/535,588

(22) Filed: Feb. 10, 2026

(65) Prior Publication Data

US 2026/0240563 A1 Aug. 20, 2026

Related U.S. Application Data

(60) Provisional application No. 63/903,497, filed on Oct. 22, 2025, provisional application No. 63/807,044, (Continued)

(51) Int. Cl.
*A61B 17/3207* (2006.01)
*A61F 2/01* (2006.01)
(Continued)

(52) U.S. Cl.
CPC .... *A61B 17/32075* (2013.01); *A61B 17/3207* (2013.01); *A61F 2/013* (2013.01); (Continued)

(58) Field of Classification Search
CPC .......... A61B 17/3207; A61B 17/32075; A61B 2017/22038; A61B 2017/22094; A61B 2017/2212; A61F 2/013
See application file for complete search history.

(56) References Cited

U.S. PATENT DOCUMENTS 3,506,011 A 4/1970 Silverman
4,727,873 A 3/1988 Mobin-Uddin
(Continued)

FOREIGN PATENT DOCUMENTS

CN 102036611 4/2011
CN 103841905 6/2014
(Continued)

OTHER PUBLICATIONS

US 8,668,714 B2, 03/2014, Cully et al. (withdrawn)
(Continued)

*Primary Examiner* — Ryan J. Severson
(74) *Attorney, Agent, or Firm* — Knobbe, Martens, Olson & Bear, LLP

(57) ABSTRACT

Various embodiments of devices and methods of use are provided. The device can include a catheter shaft having a proximal end and a distal end. The device can include an extractor. The extractor can include engagement panels located at a first longitudinal location and engagement panels located at a second longitudinal location. The extractor can include a spacer between engagement panels located at the first longitudinal location and engagement panels located at the second longitudinal location. The device can include a sheath, wherein the extractor comprises a collapsed state within the sheath for delivery and an expanded state within a blood vessel. In the expanded state, the engagement panels are configured to engage material between engagement panels located at a first longitudinal location and engagement panels located at a second longitudinal location.

29 Claims, 164 Drawing Sheets

Related U.S. Application Data filed on May 16, 2025, provisional application No. 63/781,754, filed on Apr. 1, 2025, provisional application No. 63/758,844, filed on Feb. 14, 2025.

(51) Int. Cl.
*A61B 17/22* (2006.01)
*A61B 17/221* (2006.01)

(52) U.S. Cl.
CPC ............... *A61B 2017/22038* (2013.01); *A61B 2017/22094* (2013.01); *A61B 2017/2212* (2013.01)

(56) References Cited

U.S. PATENT DOCUMENTS 5,011,488 A 4/1991 Ginsburg
5,102,415 A 4/1992 Guenther et al.
5,135,484 A 8/1992 Wright
5,846,251 A 12/1998 Hart
5,868,708 A 2/1999 Hart
5,895,398 A 4/1999 Wensel et al.
5,935,139 A 8/1999 Bates
5,947,985 A 9/1999 Imran
6,036,720 A 3/2000 Abrams et al.
6,066,149 A 5/2000 Samson et al.
6,126,635 A 10/2000 Simpson et al.
6,165,196 A 12/2000 Stack et al.
6,179,859 B1 1/2001 Bates et al.
6,210,370 B1 4/2001 Chi-Sing et al.
6,221,006 B1 4/2001 Dubrul et al.
6,264,663 B1 7/2001 Cano
6,270,477 B1 8/2001 Bagaoisan et al.
6,319,242 B1 11/2001 Patterson et al.
6,391,044 B1 5/2002 Yadav et al.
6,432,122 B1 8/2002 Gilson et al.
6,458,139 B1 10/2002 Palmer et al.
6,569,181 B1 5/2003 Burns
6,605,102 B1 8/2003 Mazzocchi et al.
6,620,182 B1 9/2003 Khosravi et al.
6,635,070 B2 10/2003 Leeflang et al.
6,645,224 B2 11/2003 Gilson et al.
6,663,650 B2 12/2003 Sepetka et al.
6,824,545 B2 11/2004 Sepetka et al.
6,840,950 B2 1/2005 Stanford et al.
6,945,977 B2 9/2005 Demarais et al.
7,094,249 B1 8/2006 Broome et al.
7,179,273 B1 2/2007 Palmer et al.
7,220,271 B2 5/2007 Clubb et al.
7,232,432 B2 6/2007 Fulton et al.
7,491,210 B2 2/2009 Dubrul et al.
7,621,870 B2 11/2009 Berrada et al.
7,662,165 B2 2/2010 Gilson et al.
7,766,921 B2 8/2010 Sepetka et al.
7,780,696 B2 8/2010 Daniel et al.
7,785,342 B2 8/2010 Gilson et al.
7,901,426 B2 3/2011 Gilson et al.
7,914,549 B2 3/2011 Morsi
8,070,769 B2 12/2011 Broome
8,092,486 B2 1/2012 Berrada et al.
8,236,024 B2 8/2012 Stanford et al.
8,252,017 B2 8/2012 Paul, Jr. et al.
8,255,193 B2 8/2012 Humphrey et al.
8,298,252 B2 10/2012 Krolik et al.
8,313,503 B2 11/2012 Cully et al.
8,337,520 B2 12/2012 Cully et al.
8,361,095 B2 1/2013 Osborne
8,388,644 B2 3/2013 Parker
8,444,661 B2 5/2013 Nair et al.
8,460,335 B2 6/2013 Carpenter
8,475,487 B2 7/2013 Bonnette et al.
8,491,623 B2 7/2013 Vogel et al.
8,545,526 B2 10/2013 Martin et al.
8,613,717 B2 12/2013 Aklog et al.
8,657,849 B2 2/2014 Parker
8,696,622 B2 4/2014 Fiorella
8,734,374 B2 5/2014 Aklog et al.
8,771,289 B2 7/2014 Mohiuddin et al.
8,777,976 B2 7/2014 Brady et al.
8,795,305 B2 8/2014 Martin et al.
8,795,322 B2 8/2014 Cully et al.
8,801,748 B2 8/2014 Martin
8,864,792 B2 10/2014 Eckhouse et al.
8,919,389 B2 12/2014 Gries
8,926,642 B2 1/2015 Nelson
8,932,319 B2 1/2015 Martin et al.
8,948,848 B2 2/2015 Merhi
8,956,384 B2 2/2015 Berrada et al.
8,968,330 B2 3/2015 Rosenbluth et al.
8,998,944 B2 4/2015 Thornton
9,254,371 B2 2/2016 Martin et al.
9,283,066 B2 3/2016 Hopkins et al.
9,301,769 B2 4/2016 Brady et al.
9,308,007 B2 4/2016 Cully et al.
9,358,022 B2 6/2016 Morsi
9,398,946 B2 7/2016 Valaie
9,408,620 B2 8/2016 Rosenbluth et al.
9,427,244 B2 8/2016 Lund-Clausen et al.
9,463,036 B2 10/2016 Brady et al.
9,526,864 B2 12/2016 Quick
9,579,116 B1 2/2017 Nguyen et al.
9,636,206 B2 5/2017 Nguyen et al.
9,744,024 B2 8/2017 Nguyen et al.
9,844,386 B2 12/2017 Nguyen et al.
9,931,495 B2 4/2018 Aboytes
9,999,493 B2 6/2018 Nguyen et al.
10,045,790 B2 8/2018 Cox et al.
10,070,879 B2 9/2018 Nguyen et al.
10,076,347 B2 9/2018 Sepetka et al.
10,143,482 B2 12/2018 Nguyen et al.
10,238,482 B2 3/2019 Nguyen et al.
10,271,863 B2 4/2019 Marks et al.
10,292,723 B2 5/2019 Brady
10,314,600 B2 6/2019 Morsi
10,376,275 B2 8/2019 Nguyen et al.
10,456,236 B2 10/2019 Nguyen et al.
10,512,479 B2 12/2019 Nguyen et al.
10,517,708 B2 12/2019 Gorochow
10,555,745 B1 2/2020 Clark
10,660,645 B2 5/2020 Allen et al.
10,687,834 B2 6/2020 Follmer et al.
10,716,586 B2 7/2020 Krolik et al.
10,939,931 B2 3/2021 Grandfield et al.
11,090,057 B2 8/2021 Allen et al.
11,259,820 B2 3/2022 Walzman
11,471,175 B2 10/2022 Nguyen et al.
11,490,913 B2 11/2022 Nguyen et al.
11,504,150 B2 11/2022 Marks et al.
11,510,691 B2 11/2022 Nguyen et al.
11,793,531 B2 10/2023 Nguyen et al.
12,029,443 B2 7/2024 Nguyen et al.
12,156,671 B2 12/2024 Nguyen et al.
12,161,353 B2 12/2024 Nguyen et al.
12,171,448 B2 12/2024 Nguyen et al.
12,226,112 B1 2/2025 Nguyen et al.
12,390,237 B2 8/2025 Nguyen et al.
12,502,191 B2 12/2025 Nguyen et al.
12,502,192 B2 12/2025 Nguyen et al.
2002/0095171 A1 7/2002 Belef
2002/0123765 A1 9/2002 Sepetka et al.
2002/0147458 A1 10/2002 Hiblar et al.
2002/0169474 A1 11/2002 Kusleika et al.
2003/0176884 A1 9/2003 Berrada et al.
2003/0216770 A1 11/2003 Persidsky et al.
2004/0039411 A1 2/2004 Gilson et al.
2004/0073198 A1 4/2004 Gilson et al.
2004/0087971 A1 5/2004 Arnott
2004/0098025 A1 5/2004 Sepetka et al.
2004/0098033 A1 5/2004 Leeflang et al.
2005/0085826 A1 4/2005 Nair et al.
2005/0085846 A1 4/2005 Carrison et al.
2006/0025804 A1 2/2006 Krolik et al.
2006/0155305 A1 7/2006 Freudenthal et al.
2006/0212062 A1 9/2006 Farascioni

(56) References Cited

U.S. PATENT DOCUMENTS

| | | | |
|---|---|---|---|
| 2006/0224177 | A1 | 10/2006 | Finitsis |
| 2006/0282111 | A1 | 12/2006 | Morsi |
| 2007/0010702 | A1 | 1/2007 | Wang et al. |
| 2007/0088382 | A1 | 4/2007 | Bei et al. |
| 2007/0093744 | A1 | 4/2007 | Elmaleh |
| 2007/0112374 | A1 | 5/2007 | Paul, Jr. et al. |
| 2007/0191866 | A1 | 8/2007 | Palmer et al. |
| 2007/0282303 | A1 | 12/2007 | Nash et al. |
| 2008/0167678 | A1 | 7/2008 | Morsi |
| 2008/0262487 | A1 | 10/2008 | Wensel et al. |
| 2009/0292307 | A1 | 11/2009 | Razack |
| 2010/0211095 | A1 | 8/2010 | Carpenter |
| 2010/0249815 | A1 | 9/2010 | Jantzen et al. |
| 2010/0268264 | A1 | 10/2010 | Bonnette et al. |
| 2010/0268265 | A1 | 10/2010 | Krolik et al. |
| 2011/0125181 | A1 | 5/2011 | Brady et al. |
| 2011/0166586 | A1 | 7/2011 | Sepetka et al. |
| 2011/0196414 | A1 | 8/2011 | Porter et al. |
| 2012/0172915 | A1 | 7/2012 | Fifer et al. |
| 2012/0197285 | A1 | 8/2012 | Martin et al. |
| 2012/0271403 | A1 | 10/2012 | Gries |
| 2012/0310251 | A1 | 12/2012 | Sepetka et al. |
| 2012/0330346 | A1 | 12/2012 | Frimerman |
| 2012/0330350 | A1 | 12/2012 | Jones et al. |
| 2013/0102996 | A1 | 4/2013 | Strauss |
| 2013/0144326 | A1 | 6/2013 | Brady et al. |
| 2013/0178891 | A1 | 7/2013 | Russell et al. |
| 2013/0184738 | A1 | 7/2013 | Laroya et al. |
| 2013/0184741 | A1 | 7/2013 | Laroya et al. |
| 2013/0197567 | A1 | 8/2013 | Brady et al. |
| 2013/0238009 | A9 | 9/2013 | Hopkins et al. |
| 2013/0245670 | A1 | 9/2013 | Fan |
| 2013/0267993 | A1 | 10/2013 | Carpenter |
| 2013/0338703 | A1 | 12/2013 | Hansen et al. |
| 2013/0345739 | A1 | 12/2013 | Brady et al. |
| 2014/0005712 | A1 | 1/2014 | Martin |
| 2014/0005717 | A1 | 1/2014 | Martin et al. |
| 2014/0046358 | A1 | 2/2014 | Cully et al. |
| 2014/0052103 | A1 | 2/2014 | Cully et al. |
| 2014/0128894 | A1 | 5/2014 | Sepetka et al. |
| 2014/0128905 | A1 | 5/2014 | Molaei |
| 2014/0155908 | A1 | 6/2014 | Rosenbluth et al. |
| 2014/0249566 | A1 | 9/2014 | Quinn et al. |
| 2014/0249568 | A1 | 9/2014 | Adams et al. |
| 2014/0276388 | A1 | 9/2014 | Allen et al. |
| 2014/0276403 | A1 | 9/2014 | Follmer et al. |
| 2014/0276922 | A1 | 9/2014 | McLain et al. |
| 2014/0277013 | A1 | 9/2014 | Sepetka et al. |
| 2014/0350593 | A1 | 11/2014 | Laroya et al. |
| 2014/0371781 | A1 | 12/2014 | Morgan |
| 2015/0005781 | A1 | 1/2015 | Lund-Clausen et al. |
| 2015/0018929 | A1 | 1/2015 | Martin et al. |
| 2015/0088190 | A1 | 3/2015 | Jensen |
| 2015/0196380 | A1 | 7/2015 | Berrada et al. |
| 2015/0250497 | A1 | 9/2015 | Marks et al. |
| 2015/0265299 | A1 | 9/2015 | Cooper et al. |
| 2015/0297251 | A1 | 10/2015 | Sos |
| 2015/0306311 | A1 | 10/2015 | Pinchuk et al. |
| 2015/0352325 | A1 | 12/2015 | Quick |
| 2016/0022290 | A1 | 1/2016 | Johnson et al. |
| 2016/0022291 | A1 | 1/2016 | Johnson et al. |
| 2016/0022292 | A1 | 1/2016 | Stigall et al. |
| 2016/0038271 | A1 | 2/2016 | Johnsen et al. |
| 2016/0113666 | A1 | 4/2016 | Quick et al. |
| 2016/0143721 | A1 | 5/2016 | Rosenbluth et al. |
| 2016/0192953 | A1 | 7/2016 | Brady |
| 2016/0256180 | A1 | 9/2016 | Vale et al. |
| 2016/0287276 | A1 | 10/2016 | Cox et al. |
| 2017/0035445 | A1 | 2/2017 | Nguyen et al. |
| 2017/0086960 | A1 | 3/2017 | Nguyen et al. |
| 2017/0143359 | A1 | 5/2017 | Nguyen et al. |
| 2017/0224366 | A1 | 8/2017 | Nguyen et al. |
| 2017/0259042 | A1 | 9/2017 | Nguyen et al. |
| 2018/0055619 | A1 | 3/2018 | Nguyen et al. |
| 2018/0125512 | A1 | 5/2018 | Nguyen et al. |
| 2018/0140315 | A1 | 5/2018 | Bowman et al. |
| 2018/0296315 | A1 | 10/2018 | Nguyen et al. |
| 2019/0015122 | A1 | 1/2019 | Nguyen et al. |
| 2019/0021750 | A1 | 1/2019 | Heilman et al. |
| 2019/0099194 | A1 | 4/2019 | Nguyen et al. |
| 2019/0142445 | A1 | 5/2019 | Morsi |
| 2019/0216589 | A1 | 7/2019 | Nguyen et al. |
| 2019/0307471 | A1 | 10/2019 | Friedman et al. |
| 2019/0380723 | A1 | 12/2019 | Grandfield et al. |
| 2020/0029985 | A1 | 1/2020 | Nguyen et al. |
| 2020/0046390 | A1 | 2/2020 | Brady et al. |
| 2020/0197031 | A1 | 6/2020 | Nguyen et al. |
| 2020/0222171 | A1 | 7/2020 | Nguyen et al. |
| 2020/0297376 | A1 | 9/2020 | Marks et al. |
| 2021/0128185 | A1 | 5/2021 | Nguyen et al. |
| 2021/0307767 | A1 | 10/2021 | Gifford et al. |
| 2022/0071646 | A1 | 3/2022 | Brady et al. |
| 2023/0063701 | A1 | 3/2023 | Horowitz et al. |
| 2023/0066304 | A1 | 3/2023 | Nguyen et al. |
| 2023/0103647 | A1 | 4/2023 | Nguyen et al. |
| 2023/0165599 | A1 | 6/2023 | Nguyen et al. |
| 2023/0285040 | A1 | 9/2023 | Cunniffe et al. |
| 2024/0032954 | A1 | 2/2024 | Nguyen et al. |
| 2024/0173045 | A1 | 5/2024 | Nguyen et al. |
| 2024/0293134 | A1 | 9/2024 | Nguyen et al. |
| 2025/0025193 | A1 | 1/2025 | Nguyen et al. |
| 2025/0025194 | A1 | 1/2025 | Nguyen et al. |
| 2025/0057555 | A1 | 2/2025 | Nguyen et al. |
| 2025/0195095 | A1 | 6/2025 | Nguyen et al. |
| 2025/0281193 | A1 | 9/2025 | Nguyen et al. |
| 2025/0281194 | A1 | 9/2025 | Nguyen et al. |
| 2025/0345082 | A1 | 11/2025 | Nguyen et al. |

FOREIGN PATENT DOCUMENTS

| | | |
|---|---|---|
| CN | 104042304 | 9/2014 |
| CN | 113440214 | 9/2021 |
| EP | 1221307 | 7/2002 |
| EP | 3 539 486 | 9/2019 |
| EP | 3 681 418 | 7/2020 |
| EP | 3 718 492 | 10/2020 |
| FR | 2 694 687 | 2/1994 |
| JP | 2011-508635 | 3/2011 |
| WO | WO 99/39648 | 8/1999 |
| WO | WO 02/36025 | 5/2002 |
| WO | WO 03/077799 | 9/2003 |
| WO | WO 2006/138391 | 12/2006 |
| WO | WO 2007/047818 | 4/2007 |
| WO | WO 2008/070996 | 6/2008 |
| WO | WO 2009/055782 | 4/2009 |
| WO | WO 2009/086482 | 7/2009 |
| WO | WO 2015079401 | 6/2015 |
| WO | WO 2017/024258 | 2/2017 |
| WO | WO 2018/148174 | 8/2018 |
| WO | WO 2021/092235 | 5/2021 |
| WO | WO 2022/236265 | 11/2022 |
| WO | WO 2025/128142 | 6/2025 |

OTHER PUBLICATIONS

Invitation to Pay Additional Fees dated May 20, 2024 in PCT/US2024/016740 in 3 pages.

Tendency Definition and Meaning Britannica Dictionary; 4 pages (2024).

International Search Report and Written Opinion in PCT/US2024/016740 dated Aug. 27, 2024; 29 pages.

Invitation to Pay Additional Fees dated Apr. 20, 2026 in PCT/US2026/014682 in 3 pages.

International Search Report and Written Opinion in PCT/US2026/014682 dated Jun. 17, 2026; in 18 pages.

NEUROVASCULAR CLOT RETRIEVING SYSTEM

CROSS-REFERENCE TO RELATED APPLICATIONS

This application claims priority benefit to U.S. Provisional Patent Application No. 63/758,844, filed Feb. 14, 2025, U.S. Provisional Patent Application No. 63/781,754, filed Apr. 1, 2025, U.S. Provisional Patent Application No. 63/807,044, filed May 16, 2025, and U.S. Provisional Patent Application No. 63/903,497, filed Oct. 22, 2025, the entirety of each is hereby incorporated by reference herein.

BACKGROUND

Field

Some embodiments described herein relate generally to systems and methods for removing a material, such as a blood clot, or foreign materials in the body and, in particular, to methods for treating a neurovascular embolism.

Description of the Related Art

Stroke is the third most common cause of death in the United States and the most disabling neurologic disorder. Approximately 700,000 patients suffer from stroke annually. Stroke is characterized by the acute onset of a neurological deficit that persists for at least 24 hours and is the result of a disturbance of the cerebral circulation. Stroke incidence increases with age. There are hemorrhagic stroke and ischemic stroke. Hemorrhagic stroke accounts for 20% of the stroke population and occurs due to rupture of an aneurysm or arteriovenous malformation bleeding into the brain tissue resulted in cerebral infarction. Ischemic stroke occurs in 80% of the population and is caused by occluded vessels that deprive the brain of oxygen-carrying blood. Ischemic strokes are caused by emboli that have dislodged from different areas of the body or from the cerebral vessels themselves to occlude in the narrow cerebral arteries more distally. Many such occlusions occur in the middle cerebral artery (MCA), although such is not the only site where emboli come to rest.

Traditionally, medical management of acute ischemic stroke consisted mainly of general supportive care. In 1996, the Food and Drug Administration approved the use of thrombolytic drug, tissue plasminogen activator (t-PA) for treating acute stroke. A randomized, double-blind trial, the National Institute of Neurological Disorders and t-PA Stroke Study, revealed a statistically significant improvement in stroke scale scores at 24 hours in the group of patients receiving intravenous t-PA within 3 hours of the onset of an ischemic stroke. Since the approval of t-PA, an emergency room physician could offer stroke patients an effective treatment besides supportive care.

However, treatment with systemic t-PA is associated with increased risk of intracerebral hemorrhage and other hemorrhagic complications. Patients treated with t-PA were more likely to sustain a symptomatic intracerebral hemorrhage during the first 36 hours of treatment. The frequency of symptomatic hemorrhage increases when t-PA is administered beyond 3 hours from the onset of a stroke. Besides the time constraint in using t-PA in acute ischemic stroke, other contraindications include for example if the patient has had a previous stroke or serious head trauma in the preceding 3 months, if the patient has a systolic blood pressure above 185 mmHg or diastolic blood pressure above 110 mmHg, if the patient requires aggressive treatment to reduce the blood pressure to the specified limits, if the patient is taking anticoagulants or has a propensity to hemorrhage, and/or if the patient has had a recent invasive surgical procedure. As a result, there is only a small percentage of stroke patients are qualified to receive t-PA.

Another treatment to remove the emboli is to mechanically remove the clot or emboli from the vessel. However, the need remains to effectively mechanically remove the clot, such as to completely remove the clot from the vessel. As such, the need remains to efficiently mechanically remove the clot, such as by requiring only a single pass with a clot remover. There are additional needs related to the small scale of the neurovascular vessels.

SUMMARY

Devices and methods are disclosed for treating vessels, including blood vessels and other body lumen other than blood vessels. In some embodiments, the devices and methods are tailored to neurovascular vessels. Currently, there are various stent retriever designs attempts to remove clot from the vessel. However, there are several disadvantages with the current stent retriever or mechanical removal devices. When conventional stent retriever deploys, the entire stent retriever has to deploy in order for the stent retriever to be effective. When deploying, the stent retriever is required to expand inside the clot to engage or secure into the clot. First, this requires time to expand which then prohibits immediate blood flow thus prevents immediate recanalization. Second, if the clot is tough or organized, the stent retriever may not have enough radial force to engage into the clot thereby preventing good engagement rendering the stent retriever ineffective. Another disadvantage is that once the stent retriever is deployed and allowed to engage into the clot, the stent retriever is then retracted or pulled proximally to remove the clot. During the retraction or pulling the stent retriever, the stent retriever tends to axially lengthen or elongate under tension thereby pulling away from the clot and therefore the stent retriever does not hold well onto the clot. As a result, it is required to have multiple passes to retrieve and remove the clot with the stent retriever. The multiple passes results in longer time to recanalization and reduces the potential for good clinical outcomes. The current stent retriever designs do not completely secure the clot when retrieving the clot due to the tension causing axially lengthening and the clot potentially releasing downstream emboli. Under tension, these stent retrievers axially lengthen and elongate allowing clot material to escape. Additionally, the current stent retrievers have high vessel surface area contact when the stent retriever is fully expanded. The outer surface of the stent-like structure of the stent retriever contacts the vessel wall and that contact can potentially cause vessel trauma during removing the stent retriever.

Specifically, the current mechanical thrombectomy designs such as stent retrievers used to remove the clot from the neurovascular system have several shortcomings. The stent retrievers when deployed require some time in order for the stent retriever to fully expand. This results in a longer time to restore blood flow. Once deployed, the stent retriever expands and should engage into the clot. However, full engagement with the clot is not always achieved. This engagement of the stent retriever can be achieved with soft acute clot. If there are organized tough clot, then the stent retriever is unable to engage the clot. Furthermore, when the stent retriever retracts proximally to remove the clot, the stent retriever has tendency to stretch or elongate. The stent elongation causes the stent retriever to reduce in diameter thereby pulling away from the clot and potentially disengaging from the clot, thus resulting in downstream emboli. The stent retrievers also have high surface contact to the vessel resulting in high friction force that can potentially cause trauma to the vessel wall.

Advantages of certain embodiments described herein include that the extractor can be effective when partially deployed. For instance, only a distal portion of the extractor can be deployed for smaller clots. The engagement panels at the first longitudinal location can be deployed, but engagement panels at another longitudinal location can remain collapsed. The extractor is effective whether engagement panels at one longitudinal location are deployed or engagement panels at a plurality of longitudinal locations are deployed. When deploying, the extractor can expand distal to the clot and the extractor can be pulled proximally to engage the clot. The extractor does not necessarily need to be expanded inside the clot to engage or secure into the clot. The deployment process of the extractor can save time compared to stent retrievers. Time is of the essence to restore blood flow. The extractor can allow immediate blood flow thus immediate recanalization, and in some cases, within about 120, 90, 60, 45, 40, 30, 20, 10 seconds or less, or ranges including any two of the aforementioned values. Further, the extractor is designed to have enough radial force to engage into tough or organized clot. The engagement panels can be supported in the radial direction. The engagement panels can be stacked. The radial force of the extractor allows good engagement rendering the extractor very effective. The extractor can be engaged with the clot and retracted or pulled proximally to remove the clot. During the retraction or pulling the extractor the extractor resists axially lengthening or elongating under tension. The extractor does not pull away from the clot when retracted and therefore holds onto the clot. The extractor may effectively remove the clot in a single pass. The single pass results in a shorter time to recanalization and increases the potential for good clinical outcomes. The extractor completely secures the clot when retrieving the clot due to the tension and thus reduces the risk that the clot releases downstream emboli. Under tension, the extractor does not axially lengthen and elongate in some cases. Additionally, the extractor has low vessel surface area contact when the engagement panels are fully expanded. The outer surface of the extractor minimally contacts the vessel wall which reduces the risk of vessel trauma during removing the extractor.

The extractor or engager has several advantages, including any number of the following. The extractor or engager when deployed requires little time in order for the extractor to fully expand. This resulted in a shorter time to restore blood flow. Once deployed, the extractor expands and engages into the clot or is pulled into engagement with the clot. The extractor can effectively capture soft acute clot. The extractor can effectively capture organized tough clot. The extractor can capture harder clots that the stent retriever is unable to engage. Furthermore, the extractor does not have a tendency to stretch or elongate. The extractor does not reduce in diameter when retracted. The engagement panels retain their shape when pulled. The engagement panels conform to the vessel wall while maintaining good clot engagement. In some embodiments, the diameter of the engagement panels does not change. In some embodiments, the diameter of the engagement panels conforms to the vessel wall. In some embodiments, the diameter of the engagement panels conforms to the vessel diameter. In some embodiments, the engagement panels are constrained for delivery and open within a vessel to conform to the vessel. The engagement panels can pass along the vessel wall without reducing in diameter. Thereby, the extractor has less tendency to pull away from the clot and potentially disengage from the clot. The extractor has less tendency to create downstream emboli. The extractor also has little surface contact with the vessel resulting in a low friction force that reduces the risk of trauma to the vessel wall. The extractor herein is able to deploy and is fully functional once deployed. Upon retraction of the extractor to remove clot, the engagement panels act independently and do not stretch or elongate under tension thus securing the clot during transit. The engagement panels also have minimal vessel surface contact which reduces the friction between the extractor and vessel, thereby potentially causing less vessel trauma. In some embodiments, the devices and methods completely remove a material from the vessel. In some embodiments, the devices and methods remove a material in a single pass. In some embodiments, the devices and methods can remove a material from other parts of the vascular system such as arterial disease, filtering chronic total occlusion, arteriovenous fistulas, deep vein thrombosis or pulmonary embolism.

In some embodiments, a device for removing material from a patient is provided. The device can include a catheter shaft. The device can include an extractor comprising engagement panels located at a first longitudinal location and engagement panels located at a second longitudinal location. In some embodiments, the extractor comprises a collapsed state for delivery and an expanded state within a blood vessel. In some embodiments, in the expanded state the engagement panels are configured to engage material between engagement panels located at a first longitudinal location and engagement panels located at a second longitudinal location.

In some embodiments, the extractor or engager is unitarily formed from one member. In some embodiments, the extractor can be formed from two or more members. In some embodiments, the member can be a wire. In some embodiments, the member can be solid, tubular and other geometric configurations such as flat ribbon and oval. In some embodiments, the extractor is unitarily formed from one member. In some embodiments, each engagement panel comprises two legs and an arc therebetween. In some embodiments, each engagement panel comprises an eyelet. In some embodiments, legs of the engagement panels at the first longitudinal location do not overlap. In some embodiments, legs of each engagement panels have a constant angle therebetween. In some embodiments, legs of each engagement panels have a different angle therebetween. In some embodiments, legs of each engagement panels extend straight and outwardly. In some embodiments, legs of each engagement panels can have any pattern. In some embodiments, legs of each engagement panels have a curve. In some embodiments, legs of each engagement panels are a zig zag. In some embodiments, each engagement panel comprises an eyelet to receive the catheter shaft. In some embodiments, engagement panels located at the first longitudinal location and engagement panels located at the second longitudinal location are moveable relative to the catheter shaft. In some embodiments, engagement panels located at the first longitudinal location and engagement panels located at the second longitudinal location are fixed relative to the catheter shaft. In some embodiments, engagement panels located at the first longitudinal location comprise three engagement panels. In some embodiments, engagement panels located at the first longitudinal location comprise four engagement panels. In some embodiments, the engagement panels located at the first longitudinal location comprise two engagement panels. In some embodiments, engagement panels located at the first longitudinal location comprise a single helical engagement panel. In some embodiments, engagement panels located at the first longitudinal location comprise a double helical engagement panel. In some embodiments, engagement panels located at the first longitudinal location comprise a plurality helical engagement panels. In some embodiments, the engagement panels initial expanded portion revert proximally when the engagement panels first deploy. In some embodiments, the engagement panels second expanded portion extend outward. In some embodiments, engagement panels located at the first longitudinal location comprise of five, six, seven or more engagement panels. In some embodiments, engagement panels have space between them. In some embodiments, engagement panels can be next to each other in series with no spacer (thereby minimal to no gap). In some embodiments, the engagement panels' initial expanded portion revert proximally when the engagement panels first deploy. In some embodiments, the engagement panels' second expanded portion extend outward. In some embodiments, engagement panels located at the first longitudinal location deploy simultaneously. In some embodiments, the extractor further comprises a spacer between engagement panels located at the first longitudinal location and engagement panels located at the second longitudinal location. In some embodiments, the spacer comprises a tube. In some embodiments, the spacer comprises a coil. In some embodiments, the spacer comprises a single ring or a plurality of rings. In some embodiments, the spacer is integrally formed with the engagement panels located at the first longitudinal location and engagement panels located at the second longitudinal location. In some embodiments, the spacer provides an open space between the engagement panels located at the first longitudinal location and engagement panels located at the second longitudinal location. In some embodiments, the spacer is movable relative to the catheter shaft. In some embodiments, the spacer is fixed relative to the catheter shaft. In some embodiments, engagement panels located at the first longitudinal location are configured to engage a clot while the engagement panels located at the second longitudinal location are collapsed. In some embodiments, engagement panels located at the first longitudinal location and engagement panels located at the second longitudinal location are configured to engage a clot while additional engagement panels are collapsed. In some embodiments, the device can include a connecting member between engagement panels located at the first longitudinal location and engagement panels located at the second longitudinal location. In some embodiments, the connecting member is radially offset from a central axis of the catheter shaft. In some embodiments, the catheter shaft is a core wire. In some embodiments, the core wire has a taper at the distal end. The corewire can be produced in the form of laser cut hypotube or any geometric configurations. In some embodiments, the engagement panels do not comprise sharp edges and are configured to be atraumatic with respect to the blood vessel. In some embodiments, a device for removing material from a patient, comprising any number of features as disclosed herein.

In some embodiments, the extractor or engager is unitarily 3D printed from one super elastic, shape memory material member. In some embodiments, the extractor can be 3D printed from two or more materials members such as super elastic material and high density materials, such as but not limited to platinum, gold, or tungsten. In some embodiments, the extractor can be 3D printed. In some embodiments, the extractor can be formed from subtractive methods including CNC machining, casting, forging, laser cutting, plasma cutting, photoetching, or waterjet cutting. In some embodiments, the extractor can be formed from additive manufacturing. In some embodiments, the extractor can be formed from bending and heat setting. In some embodiments, the extractor can be formed from shape memory methods. In some embodiments, the extractor can comprise shape memory materials. In some embodiments, the extractor can comprise shape memory alloys or polymers. In some embodiments, the extractor can comprise a material having the ability to recover original shapes. In some embodiments, the extractor can comprise a super-elastic material. In some embodiments, the extractor can comprise a material with high fatigue resistance. In some embodiments, the extractor can comprise a biocompatible material. In some embodiments, the extractor can comprise a material that has shape recovery. In some embodiments, the extractor can comprise a durable material with high density. In some embodiments, the extractor can comprise a heavy metal. In some embodiments, the extractor can comprise one material. In some embodiments, the extractor can comprise two or more materials. In some embodiments, the extractor can comprise any material described herein, or any combination of materials described herein.

In some embodiments, a device for removing material from a patient is provided. The device can include a catheter shaft or corewire. The device can include an extractor comprising engagement panels located at a first longitudinal location and engagement panels located at a second longitudinal location. The device can include a sheath. In some embodiments, the extractor comprises a collapsed state within the sheath for delivery and an expanded state within a blood vessel. In some embodiments, in the expanded state the engagement panels are configured to engage material between engagement panels located at a first longitudinal location and engagement panels located at a second longitudinal location.

In some embodiments, engagement panels located at the first longitudinal location are configured to engage a clot while the engagement panels located at the second longitudinal location are collapsed within the sheath. In some embodiments, engagement panels located at the first longitudinal location and engagement panels located at the second longitudinal location are configured to engage a clot while additional engagement panels are collapsed within the sheath. In some embodiments, the engagement panels do not comprise sharp edges and are configured to be atraumatic with respect to the blood vessel. In some embodiments, the extractor further comprises a spacer between engagement panels located at the first longitudinal location and engagement panels located at the second longitudinal location.

In some embodiments, a device for removing material from a patient is provided. The device can include a catheter shaft or corewire. The device can include a distal member. The device can include an extractor comprising engagement panels located at a first longitudinal location and engagement panels located at a second longitudinal location. In some embodiments, the extractor further comprises an open space or spacer between engagement panels located at the first longitudinal location and engagement panels located at the second longitudinal location. In some embodiments, the distal member and the extractor comprise a collapsed state for delivery and an expanded state within a blood vessel. In some embodiments, in the expanded state the engagement panels are configured to engage material between engagement panels located at a first longitudinal location and engagement panels located at a second longitudinal location. The device can include a sheath. In some embodiments, the extractor comprises a collapsed state within the sheath for delivery and an expanded state within a blood vessel.

In some embodiments, engagement panels located at the first longitudinal location are configured to engage a clot while the engagement panels located at the second longitudinal location are collapsed within the sheath. In some embodiments, engagement panels located at the first longitudinal location and engagement panels located at the second longitudinal location are configured to engage a clot while additional engagement panels are collapsed within the sheath. In some embodiments, the extractor further comprises a spacer between engagement panels located at the first longitudinal location and engagement panels located at the second longitudinal location.

In some embodiments, a device for removing material from a patient is provided. The device can include a distal member. The device can include an extractor comprising engagement panels located at a first longitudinal location and engagement panels located at a second longitudinal location. In some embodiments, the distal member and the extractor comprise a collapsed state for delivery and an expanded state within a blood vessel. In some embodiments, in the expanded state the engagement panels are configured to engage material between engagement panels located at a first longitudinal location and engagement panels located at a second longitudinal location.

In some embodiments, the distal member is positioned distal, within, or proximal to the extractor. In some embodiments, the distal member is configured to straighten in the collapsed state. In some embodiments, the distal member is comprised of plurality of members. In some embodiments, the engagement panels located at the first longitudinal location form a relatively complete circle configured to be in contact with a vessel. In some embodiments, the engagement panels located at the first longitudinal location and the engagement panels are configured to have minimal surface contact with a vessel wall. In some embodiments, the engagement panels located at the first longitudinal location and the engagement panels are separated longitudinally by a connecting member. In some embodiments, the engagement panels located at the first longitudinal location are configured to expand without stretching or shortening.

In some embodiments, a device for removing material from a patient is provided. The device can include a distal member. The device can include an extractor comprising engagement panels located at a first longitudinal location and engagement panels located at a second longitudinal location. In some embodiments, the distal member and the extractor comprise a collapsed state for delivery and an expanded state within a blood vessel. In some embodiments, in the expanded state the engagement panels are configured to engage material between engagement panels located at a first longitudinal location and engagement panels located at a second longitudinal location.

In some embodiments, the distal member is positioned distal to the extractor. In some embodiments, the distal member is configured to collect loose clot, soft clot and/or in transit clot. In some embodiments, the distal member is configured to straighten in the collapsed state. In some embodiments, the distal member comprises a tubular portion and an expanded portion in the expanded state. In some embodiments, there are three or four engagement panels located at the first location. In some embodiments, there are three or four engagement panels located at the second location. In some embodiments, the engagement panels located at the first longitudinal location comprise a first eyelet and the engagement panels located at the second longitudinal location comprise a second eyelet. In some embodiments, the engagement panels located at the first longitudinal location are formed from a single wire. In some embodiments, the engagement panels located at the first longitudinal location and the engagement panels at the second longitudinal location are formed from a single wire. In some embodiments, the engagement panels located at the first longitudinal location form a relatively complete circle configured to be in contact with a vessel. In some embodiments, the engagement panels located at the first longitudinal location are configured to have minimal surface contact with a vessel wall. In some embodiments, the engagement panels located at the first longitudinal location and the engagement panels located at the second longitudinal location are configured to have minimal surface contact with a vessel wall. In some embodiments, the engagement panels located at the first longitudinal location and the engagement panels located at the second longitudinal location are configured to move relative to each other. In some embodiments, the engagement panels located at the first longitudinal location comprise pores radially inward from the perimeter of the engagement panels. In some embodiments, the engagement panels located at the first longitudinal location and the engagement panels located at the second longitudinal location are separated longitudinally by a connecting member. In some embodiments, the engagement panels located at the first longitudinal location are configured to expand without stretching or shortening. In some embodiments, the engagement panels located at the first longitudinal location are configured to radially expand to open. In some embodiments, the engagement panels located at the first longitudinal location comprise a double wire.

In some embodiments, a device for removing material from a patient is provided. The device can include a catheter shaft. The device can include an extractor comprising a first array of engagement panels located at a first longitudinal location and a second array of engagement panels located at a second longitudinal location. In some embodiments, the extractor further comprises a spacer between the first array of engagement panels located at the first longitudinal location and the second array of engagement panels located at the second longitudinal location. In some embodiments, the extractor comprises a collapsed state for delivery and an expanded state within a blood vessel. In some embodiments, in the expanded state the engagement panels are configured to engage material between the first array of engagement panels located at the first longitudinal location and the second array of engagement panels located at the second longitudinal location.

In some embodiments, the first array of engagement panels comprises a first engagement panel and a second engagement panel operably coupled to the catheter shaft, wherein the first engagement panel and the second engagement panel are configured to at least partially contact each other when the extractor is in the expanded state. In some embodiments, the second array of engagement panels comprises a first engagement panel and a second engagement panel operably coupled to the catheter shaft, wherein the first engagement panel and the second engagement panel are configured to at least partially contact each other when the extractor is in the expanded state. In some embodiments, the first array of engagement panels comprises at least four engagement panels. In some embodiments, the second array of engagement panels comprises at least four engagement panels.

In some embodiments, the device can include a distal member. In some embodiments, the catheter shaft comprises a plurality of segments. In some embodiments, the plurality of segments of the catheter shaft are operably connected via a sleeve connector. In some embodiments, each of the arrays of engagement panels comprises at least one radiopaque marker. In some embodiments, the at least one radiopaque marker is operably connected to a leg of an engagement panel. In some embodiments, the at least one radiopaque marker is operably connected to an arc of an engagement panel. In some embodiments, the engagement panels do not comprise sharp edges and are configured to be atraumatic with respect to the blood vessel.

In some embodiments, a method of removing a thrombus from a target cerebral blood vessel is provided. The method can include deploying a guidewire into an access vessel. The method can include advancing the guidewire into the target cerebral blood vessel and across the thrombus. The method can include advancing a catheter across the thrombus. In some embodiments, the catheter houses an extractor comprising a first array of engagement panels located at a first longitudinal location and a second array of engagement panels located at a second longitudinal location. The method can include deploying at least a portion of the extractor such that the first array of engagement panels is positioned distal to the thrombus and the second array of engagement panels is positioned within the thrombus or proximal to the thrombus. The method can include withdrawing the extractor from the target cerebral vessel, thereby capturing at least a portion of the thrombus.

In some embodiments, the extractor further comprises a spacer or free space between the first array of engagement panels location at the first longitudinal location and the second array of engagement panels located at the second longitudinal location. In some embodiments, the second array of engagement panels located at the second longitudinal location are configured to engage the thrombus while additional engagement panels are collapsed. In some embodiments, the thrombus is located within the middle cerebral artery. In some embodiments, as the catheter is retracted proximally, the first array of engagement panels revert proximally. In some embodiments, as the catheter is retracted proximally, the first array of engagement panels move outward until the engagement panels are relatively aligned with a respective eyelet. In some embodiments, as the catheter is retracted proximally, the first array of engagement panels expand to the diameter of the target cerebral blood vessel.

In some embodiments, the extractor or engager is unitarily formed from one member. In some embodiments, the extractor can be formed from two or more members. In some embodiments, the extractor can be formed of two or more elongated members. In some embodiments, the member can be a wire. In some embodiments, the member can be a single wire. In some embodiments, the member can be a double wire. In some embodiments, the member can be a triple wire. In some embodiments, the elongate members are side-by-side. In some embodiments, the elongated members are twisted or woven. In some embodiments, the wire can be made of solid super elastic nitinol wire. In some embodiments, the wire can be made of DFT wire (drawing filled tubing) Nitinol with platinum core. In some embodiments, the member can be solid, tubular, and other geometric configurations such as flat ribbon and oval. In some embodiments, each engagement panel comprises two legs and an arc therebetween. In some embodiments, each engagement panel comprises an eyelet. In some embodiments, legs of the engagement panels at the first longitudinal location do not overlap. In some embodiments, legs of each engagement panels have a constant angle therebetween. In some embodiments, legs of each engagement panels have a different angle therebetween. In some embodiments, legs of each engagement panels extend straight and outwardly. In some embodiments, legs of each engagement panels can have any pattern. In some embodiments, legs of each engagement panels have a curve. In some embodiments, the panel has radiopaque marker bands. In some embodiments, the radiopaque marker band is a coil. The marker bands can be made of platinum/iridium tube or coils. In some embodiments, the radiopaque marker band is cylindrical or circular. In some embodiments, there is one marker band. In some embodiments, there are a plurality of marker bands. In some embodiment, there is one or more marker bands along the length of the distal end of the catheter. In some embodiment, there is one or more marker bands along the length of the proximal end of the catheter. In some embodiments, legs of each engagement panels are a zig zag. In some embodiments, the engagement panels at each longitudinal location comprises an eyelet to receive the catheter shaft. In some embodiments, the engagement panels located at the first longitudinal location and the engagement panels located at the second longitudinal location are moveable relative to the catheter shaft. In some embodiments, the engagement panels located at the first longitudinal location and the engagement panels located at the second longitudinal location are fixed relative to the catheter shaft. In some embodiments, the engagement panels located at the first longitudinal location comprise three engagement panels. In some embodiments, the engagement panels located at the first longitudinal location comprise four engagement panels. In some embodiments, the engagement panels located at the first longitudinal location comprise a single helical engagement panel. In some embodiments, the engagement panels located at the first longitudinal location comprise a double helical engagement panel. In some embodiments, the engagement panels located at the first longitudinal location comprise a plurality helical engagement panels.

In some embodiments, an initial expanded portion of engagement panels revert proximally when the engagement panels first deploy. In some embodiments, a second expanded portion of engagement panels extend outward. In some embodiments, the arcs of the engagement panels at the first longitudinal location are in a first, constrained position where the arcs of the engagement panels are distal to the eyelet at the first longitudinal location. The arcs of the engagement panels can be folded downward toward the catheter shaft or core wire. The arcs of the engagement panels can lie down. The arcs of the engagement panels can be coaxial with the catheter shaft or core wire. The arcs of the engagement panels can extend distally. The arcs of the engagement panels can extend toward the distal member. The arcs of the engagement panels can be within a loading tube assembly or microcatheter in in the first, constrained position. In some embodiments, the arcs of the engagement panels at the second longitudinal location are in the first, constrained position where the arcs of the engagement panels are distal to the eyelet at the second longitudinal location. In some embodiments, the arcs of the engagement panels at the third longitudinal location are in the first, constrained position where the arcs of the engagement panels are distal to the eyelet at the third longitudinal location. The engagement panels at the first longitudinal location and the second longitudinal location can fold in the same direction, such as distally. The engagement panels at the second longitudinal location and the third longitudinal location can fold in the same direction, such as distally. The engagement panels at the first longitudinal location and the third longitudinal location can fold in the same direction, such as distally. The engagement panels at the first longitudinal location and the second longitudinal location can fold in opposite directions, such as distally for the engagement panels at the first longitudinal location and proximally for the engagement panels at the second longitudinal location. The engagement panels at the second longitudinal location and the third longitudinal location can fold in opposite directions, such as distally for the engagement panels at the second longitudinal location and proximally for the engagement panels at the third longitudinal location. The engagement panels at the first longitudinal location and the third longitudinal location can fold in opposite directions, such as distally for the engagement panels at the first longitudinal location and proximally for the engagement panels at the third longitudinal location.

In some embodiments, the arcs of the engagement panels at the first longitudinal location are in the second, expanded position where the arcs revert proximally and outwardly. The arcs of the engagement panels at the first longitudinal location can be relatively inline with the eyelet at the first longitudinal location. The arcs of the engagement panels can be substantially perpendicular to the catheter shaft or core wire. The arcs of the engagement panels can be radially outward from the eyelet. The arcs of the engagement panels can be substantially perpendicular to the eyelet. The arcs of the engagement panels can extend to the vessel wall. The arcs of the engagement panels can extend can expand to the diameter of the vessel. The arcs of the engagement panels can be distal to a loading tube assembly or microcatheter in the second, expanded position. In some methods, reverting from the first, constrained position to the second, expanded position will scrap along the vessel wall and/or grab the material as the engagement panels move from the first, constrained position to the second, expanded position. In some embodiments, the legs of the engagement panels at the first longitudinal location are next to each other along the length of the catheter or core wire in the first, constrained position. The legs of the engagement panels are folded inward along the catheter or core wire. The legs of the engagement panels can lie down. In some embodiments, the legs of the engagement panels at the first longitudinal location are farther apart in the second, expanded position. The legs of the engagement panels extend outward from the respective eyelet in the second, expanded position.

For example, the arc of the engagement panels initially expands proximally, where the arc portions of the engagement panels move proximally or revert proximally as the loading tube assembly or microcatheter or delivery catheter is retracted. Reverting the arcs of the engagement panels proximally will allow the engagement panels to capture and secure the clot better. As the delivery catheter is further retracted, the legs of the engagement panels extends outward in the second, expanded position. In some embodiments, the engagement panels located at the first longitudinal location comprise of two, three, four, five, six, seven, eight, nine, ten, or more engagement panels.

In some embodiments, the engagement panels have space between them. In some embodiments, the engagement panels can be next to each other in series with no spacer (thereby minimal to no gap). In some embodiments, the engagement panels located at the first longitudinal location deploy simultaneously. In some embodiments, the engagement panels located at the first longitudinal location deploy independently. In some embodiments, the engagement panels located at the first longitudinal location deploy sequentially. In some embodiments, the eyelet of the engagement panels is stacked together with no gap. The elongate member or wire forms a portion of the eyelet, the leg of the first engagement panel at the first longitudinal location, the arc of the first engagement panel, and the leg of the first engagement panel. Then, with little to no gap, the elongate member forms a portion of the eyelet, the leg of the second engagement panel at the first longitudinal location, the arc of the second engagement panel, and the leg of the second engagement panel. Then, with little to no gap, the elongate member can form additional engagement panels at the first longitudinal location. The eyelet can be formed such that the engagement panels at the first longitudinal location deploy together or substantially together from the first, constrained position to the second, expanded position. In some embodiments, the eyelet of the engagement panels has a gap so that the engagement panels at the first longitudinal location deploy independently. The elongate member or wire forms a portion of the eyelet, the leg of the first engagement panel at the first longitudinal location, the arc of the first engagement panel, and the leg of the first engagement panel. Then, in some embodiments, the elongate member can form multiple coils to form a gap. Then, after the gap, the elongate member forms a portion of the eyelet, the leg of the second engagement panel at the first longitudinal location, the arc of the second engagement panel, and the leg of the second engagement panel. Then, with additional gaps therebetween, the elongate member can form additional engagement panels at the first longitudinal location. The eyelet can be formed such that the engagement panels at the first longitudinal location deploy independently from the first, constrained position to the second, expanded position. The eyelet can be formed such that the engagement panels at the first longitudinal location deploy sequentially from the first, constrained position to the second, expanded position. In some embodiments, the engagement panels located at the first longitudinal location and the engagement panels at the second longitudinal location deploy independently. In some embodiments, the engagement panels located at the first longitudinal location and the engagement panels at the second longitudinal location deploy sequentially.

In some embodiments, the extractor includes a spacer between the engagement panels at the first longitudinal location and the engagement panels at the second longitudinal location. In some embodiments, the spacer comprises a tube. In some embodiments, the spacer comprises a coil. In some embodiments, the spacer is located between the engagement panels at the first longitudinal location and the engagement panels at the second longitudinal location. In some embodiments, the spacer is continuous with the eyelets. In some embodiments, the spacer is integrally formed with the engagement panels located at the first longitudinal location and the engagement panels located at the second longitudinal location. In some embodiments, the spacer provides an open space between the engagement panels located at the first longitudinal location and the engagement panels located at the second longitudinal location. In some embodiments, the engagement panels located at the first longitudinal location are configured to engage a clot while the engagement panels located at the second longitudinal location are collapsed. In some embodiments, the engagement panels located at the first longitudinal location and the engagement panels located at the second longitudinal location are configured to engage a clot while additional engagement panels are collapsed. In some embodiments, the device can include a connecting member between the engagement panels located at the first longitudinal location and the engagement panels located at the second longitudinal location. In some embodiments, the spacer is movable relative to the catheter shaft. In some embodiments, the spacer is fixed relative to the catheter shaft. In some embodiments, the catheter shaft is a core wire. In some embodiments, the core wire has a taper at the distal end. In some embodiments, the core wire can be produced in the form of laser cut hypotube or any geometric configurations. In some embodiment, the extractor includes a distal member or distal plug. The distal member is positioned distal to the extractor to collect loose clot, soft clot and/or in transit clot.

In some embodiments, a device for removing material from a patient is provided. The device can include a catheter shaft or corewire. The device can include an extractor comprising engagement panels located at a first longitudinal location and engagement panels located at a second longitudinal location. In some embodiments, the extractor further comprises a spacer between engagement panels located at the first longitudinal location and engagement panels located at the second longitudinal location. The device can include a distal member. The device can include a loading tube or sheath or a tubular member. In some embodiments, the extractor comprises a collapsed state within the sheath or tubular member for delivery and an expanded state within a blood vessel. In some embodiments, in the expanded state the engagement panels are configured to engage material between engagement panels located at a first longitudinal location and engagement panels located at a second longitudinal location.

In some embodiments, engagement panels located at the first longitudinal location are configured to engage a clot while the engagement panels located at the second longitudinal location are collapsed within the sheath or tubular member. In some embodiments, engagement panels located at the first longitudinal location and engagement panels located at the second longitudinal location are configured to engage a clot while additional engagement panels are collapsed within the sheath or tubular member. In some embodiments, the extractor further comprises a spacer between engagement panels located at the first longitudinal location and engagement panels located at the second longitudinal location. In some embodiments, systems and methods as disclosed herein can include any number of the following advantages. In some embodiments, clots or other unwanted material within a body lumen can be removed without requiring deployment, expansion, and/or unsheathing of the entire length of the extractor as sets of engagement panels can act independently relative to other sets of engagement panels. In some embodiments, the atraumatic sets of engagement panels can control clot removal by pinching or otherwise exerting forces, such as axial forces, between adjacent sets of longitudinally spaced-apart engagement panels. In some embodiments, the spacer between engagement panels can control the distance and force exerted between adjacent sets of longitudinally spaced-apart engagement panels. In some embodiments, the engagement panels can be integrally formed from a single wire, a single material and/or a tubular member for improved durability and manufacturing. In some embodiments, each engagement panel forms a perimeter surrounding a free space or pore devoid of material. The pore advantageously reduces size and weight of the extractor and improves maneuverability of the extractor without adversely affecting control of clot removal. In some embodiments, each set of engagement panels are operably connected to each other with one or more connecting elements. The connecting elements can be discrete from and radially offset from the catheter or core wire. The arrangement of the connecting elements can further modulate actuation between adjacent sets of engagement panels while still allowing each set of engagement panels to act independently of one another. In some embodiments, one or more of the engagement panels have radiopaque markers or material to improve visualization. In some embodiments, the engagement panel has a distal member to prevent clot distal migration. In some embodiments, the engagement panels can be adjusted at the proximal ends to increase the space or opening between the engagement panels at the first and second longitudinal locations or decrease the space or opening between the engagement panels at the first and second longitudinal locations. In some embodiments, a system, device, or method can include any number of features as disclosed herein. In some embodiments, a system, device, or method does not comprise one or more features disclosed herein.

In some embodiments, a device for removing material from a patient is provided. The device can include a core wire. The device can include an extractor comprising engagement panels located at a first longitudinal location and engagement panels located at a second longitudinal location. In some embodiments, the engagement panels located at the first longitudinal location comprises an eyelet to receive the core wire. In some embodiments, the engagement panels are configured to aid in removal of a clot from a vessel.

In some embodiments, the engagement panels located at the first longitudinal location comprise a plurality of petals with a center loop. In some embodiments, the engagement panels located at the first longitudinal location comprise a loop at an apex to increase clot engagement. In some embodiments, the engagement panels located at the first longitudinal location are angled proximally when deployed. In some embodiments, the engagement panels located at the first longitudinal location are angled distally when deployed. In some embodiments, the engagement panels located at the first longitudinal location comprises a circular loop that goes over the clot. In some embodiments, the eyelet to receive the core wire is centrally located. In some embodiments, the engagement panels located at the first longitudinal location are slideable relative to the core wire. In some embodiments, the device can include a distal member. In some embodiments, the engagement panels located at the first longitudinal location comprises fingers configured to increase grasping of the clot. In some embodiments, at least one engagement panel located at the first longitudinal location comprises an open panel. In some embodiments, the engagement panels located at the first longitudinal location comprise eight panels. In some embodiments, the engagement panels located at the first longitudinal location comprise an eyelet at a tip to increase clot engagement. In some embodiments, the engagement panels located at the first longitudinal location are inverted. In some embodiments, the device can include one or more suture coupled to the engagement panels located at the first longitudinal location. In some embodiments, the device can include a funnel. In some embodiments, the engagement panels located at the first longitudinal location are configured to be retracted toward a funnel. In some embodiments, the engagement panels located at the first longitudinal location comprise v-shaped petals. In some embodiments, the engagement panels located at the first longitudinal location are fixed and the engagement panels located at the second longitudinal location are slidable. In some embodiments, the eyelet and the core wire are biased from center. In some embodiments, the engagement panels located at the first longitudinal location comprise open loops. In some embodiments, the engagement panels located at the first longitudinal location are configured for clot encapsulation. In some embodiments, the engagement panels located at the first longitudinal location comprise full loops. In some embodiments, the device can include an element distal to the engagement panels located at the first longitudinal location. In some embodiments, the device can include an element positioned within the engagement panels located at the first longitudinal location. In some embodiments, the device can include an element positioned near the engagement panels located at the first longitudinal location. In some embodiments, the device can include an element comprising a figure eight shape. In some embodiments, the device can include an element configured to fill or cover an opening of the engagement panels located at the first longitudinal location. In some embodiments, the engagement panels are laser cut. In some embodiments, the engagement panels are laser cut as a continuous loop. In some embodiments, the engagement panels are laser cut as a non-continuous loop.

In some embodiments, a device for removing material from a patient is provided. The device can include an extractor comprising engagement panels located at a first longitudinal location, a spacing, and engagement panels located at a second longitudinal location. In some embodiments, the engagement panels located at the first longitudinal location comprises an eyelet. In some embodiments, the engagement panels are configured to aid in removal of a clot from a vessel.

In some embodiments, the engagement panels located at the first longitudinal location comprise a plurality of helical segments. In some embodiments, the eyelet is fixed relative to a core wire. In some embodiments, the device can include a distal member. In some embodiments, the engagement panels located at the first longitudinal location have a loading direction that is distal. In some embodiments, the engagement panels located at the second longitudinal location have a loading direction that is proximal. In some embodiments, the engagement panels located at the second longitudinal location have a loading direction that is distal.

In some embodiments, a device for removing material from a patient is provided. The device can include a first array of engagement panels at a first longitudinal location. The device can include a second array of engagement panels at a second longitudinal location. The device can include a space between the first array of engagement panels at the first longitudinal location and the second array of engagement panels at the second longitudinal location.

In some embodiments, when expanded within a blood vessel, the first array of engagement panels is configured to be positioned distal to the material and the second array of engagement panels is configured to be positioned within the material. In some embodiments, the first array of engagement panels comprises an open end and a closed end. In some embodiments, the closed end is an element that is porous or non-porous. In some embodiments, the first array of engagement panels is configured to engulf the material during retraction. In some embodiments, the first array of engagement panels is configured to retain the material during retraction. In some embodiments, the second array of engagement panels is configured to collapse in a delivery configuration and deploy in a second configuration. In some embodiments, the material is configured to reside within the space during retraction. In some embodiments, when expanded within a blood vessel, the first array of engagement panels and the second array of engagement panels are configured to engage the material between the first array of engagement panels and the second array of engagement panels. In some embodiments, upon retraction of the device to remove the material, the second array of engagement panels is configured to act independently and does not stretch or elongate under tension. In some embodiments, upon retraction of the device to remove the material, the first array of engagement panels is configured to act independently and does not stretch or elongate under tension. In some embodiments, the second array of engagement panels is configured to pinch the clot radially. In some embodiments, the second array of engagement panels faces distally when deployed. In some embodiments, the second array of engagement panels faces proximally when deployed. In some embodiments, a distal portion of the second array of engagement panels faces distally when deployed and a proximal portion of the second array of engagement panels faces proximally when deployed. In some embodiments, the device can include two core wires connected to the first array of engagement panels and the second array of engagement panels.

In some embodiments, a device for removing material from a patient is provided. The device can include a core wire. The device can include a first array of engagement panels comprising a first series of helical segments or loops connected by a series of first eyelets configured to receive the core wire. In some embodiments, the first series of helical segments or loops are configured to sweep along a wall of a vessel. The device can include a second array of engagement panels comprising a second series of helical segments or loops connected by a series of second eyelets configured to receive the core wire. In some embodiments, the second series of helical segments are configured to sweep along the wall of the vessel. In some embodiments, the core wire is eccentrically located relative to the first array of engagement panels and the second array of engagement panels.

In some embodiments, the first array of engagement panels is formed from a first continuous wire. In some embodiments, the second array of engagement panels is formed from a second continuous wire. In some embodiments, the device can include a spacing between the first array of engagement panels and the second array of engagement panels. In some embodiments, the device can include a third array of engagement panels comprising a third series of helical segments of loops connected by a series of third eyelets configured to receive the core wire, wherein the core wire is eccentrically located relative to the third array of engagement panels. In some embodiments, the first array of engagement panels comprises a first lumen, wherein the first lumen is configured to approximate a lumen of the vessel. In some embodiments, the first array of engagement panels and the second array of engagement panels comprise a different number of engagement panels. In some embodiments, the first array of engagement panels and the second array of engagement panels comprise a different length. In some embodiments, the first array of engagement panels and the second array of engagement panels comprise the same diameter. In some embodiments, the first array of engagement panels and the second array of engagement panels comprise a different number of eyelets. In some embodiments, the first array of engagement panels and the second array of engagement panels are tubular. In some embodiments, the first array of engagement panels comprises a pair of eyelets of the first series of eyelets for each helical segment or loop of the first series of helical segments or loops. In some embodiments, the series of first eyelets comprise coiled eyelets. In some embodiments, the series of first eyelets is fixed relative to the core wire. In some embodiments, the device can include a distal member, wherein the distal member is distal to the first array of engagement panels. In some embodiments, the first array of engagement panels further comprises a single coil spaced apart from the eyelet. In some embodiments, the first array of engagement panels further comprises an infinity loop configured to function as a back stop for material in transit. In some embodiments, the core wire is eccentrically located relative to the first array of engagement panels to maximize a lumen of the first array of engagement panels. In some embodiments, the first array of engagement panels is configured to form a low-friction barrier. In some embodiments, the first array of engagement panels is configured to scrape the material from the wall of the vessel. In some embodiments, the first array of engagement panels is configured to fold relative to the series of first eyelets. In some embodiments, the device can include an infinity loop located distal to the first array of engagement panels.

In some embodiments, a method for removing material from a patient is provided. The method can include expanding a first array of engagement panels within a vessel. In some embodiments, the first array of engagement panels comprises a first series of helical segments or loops connected by a series of first eyelets receiving a core wire. The method can include expanding a second array of engagement panels within the vessel. In some embodiments, the second array of engagement panels comprises a second series of helical segments or loops connected by a series of second eyelets receiving the core wire. In some embodiments, the core wire is eccentrically located relative to the first array of engagement panels and the second array of engagement panels. The method can include sweeping along a wall of the vessel with the first array of engagement panels and the second array of engagement panels.

In some embodiments, the first array of engagement panels has low friction with minimal surface area in contact with the wall of the vessel. In some embodiments, the first array of engagement minimizes pushing the material against the wall of the vessel. In some embodiments, the second array of engagement panels forms a barrier around the material for transit. In some embodiments, the method can include retracting the first array of engagement panels and the second array of engagement panels which causes the material to roll distally. In some embodiments, a spacing between the first array of engagement panels and the second array of engagement panels receives the material for transit. In some embodiments, the first array of engagement panels forms a barrier around the material for transit.

BRIEF DESCRIPTION OF THE DRAWINGS

The structure and method of use will be better understood with the following detailed description of embodiments, along with the accompanying illustrations, in which.

DETAILED DESCRIPTION

Figure 1:
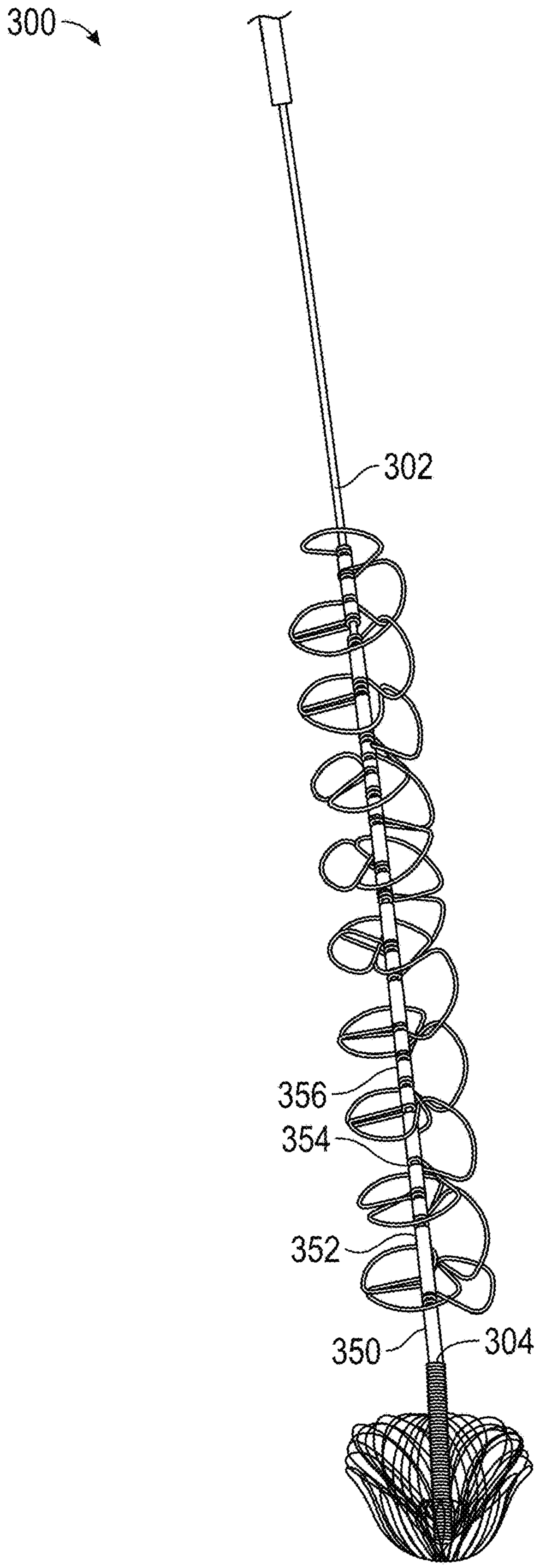
FIG. 1 is a side view of an embodiment of a helical engagement panel extractor.

Mechanical therapies can be provided such as capturing and removing a clot or emboli, dissolving the clot, disrupting and suctioning the clot, and/or creating a flow channel through the clot. The MERCI Retriever System was one of the first mechanical devices developed for stroke treatment. The retriever consists of a wire with a helical coil formed at the distal end. For the procedure, a guide catheter with a balloon at the tip is placed in the internal carotid artery (ICA). A microcatheter is threaded through the balloon guide catheter and used to introduce the MERCI retriever across the clot. The microcatheter is then pulled back to deploy the retriever around the clot or emboli. The microcatheter and retriever are then pulled back together, along with the clot or emboli, into the balloon guide catheter. The balloon of the guide catheter is inflated, and a syringe is connected to the balloon guide catheter to aspirate the guide catheter while the clot or emboli are inside the guide catheter. There remains a need for mechanical systems to retrieve clots. Some systems and methods do not include any balloon members.

Physicians currently perform thrombectomies with new generation stent retrievers to resolve ischemic stroke. Stent retrievers can be stent-like devices to capture material. Generally, the physician deploys the stent retriever into the clot to engage within the clot. The physician then withdraws the stent retriever while it is expanded against and engaging within the clot. The physician must be able to withdraw the clot through the vasculature into a guide catheter positioned within vessels. Even in successful procedures, a physician's objective is to prevent the vessel wall or lumen from experiencing trauma. The physician also desirably prevents dislodging the clot or emboli as the stent retriever passes through the vasculature when removing the stent retriever. Another risk in such a procedure is that the clot or emboli can break free from the stent retriever and lodge in smaller downstream vessels causing more concern than the original blockage. If the clot or emboli breaks free from the device and flows downstream, the loose clot or emboli may become trapped in smaller and more tortuous vessels. This will be difficult for the physician to use the same stent retriever device to again remove the clot because the device may be too large in the new obstruction location. There remain some disadvantages using this approach. There remains a need for better mechanical systems to retrieve clots.

One challenge with designing clot or emboli removal devices is the nature of the neurovascular vasculature around the clot or emboli. The neurovascular vasculature system is fragile and delicate. Neurovascular vessels are more fragile than similarly sized vessels in other parts of the body. Applying excessive force to these vessels could result in perforations and hemorrhage. Another challenge is the wide range of clot composition and morphologies. More mature and organized subacute clot material is less compressible than softer, fresher acute clot. In some instances, the organized clot is tightly wedged in the blood vessel due to the flow of blood and pressure exerted onto the clot or emboli. This further causes additional difficulties and challenges for retriever devices, such as for extraction and aspiration devices, to pull the clot or emboli away. Aspiration may require additional suction pressure which tends to be not effective with small bore catheters. Extraction devices, like the stent retriever, may have shortcomings since the radial force may not be high enough to engage or grab the clot securely especially if the clot is robust and organized. In situations where the clot is more organized, the stent retriever device may tend to slide against the vessel wall and not engage the clot or emboli. With the higher radial force produced by the stent retriever device, there is a risk of extending the vessel causing further difficulty retrieving the clot and potentially creating vessel trauma. Additionally, during retraction of the stent retriever device, the radial force exerted on the vessel wall causes the vessel perforators to extend and potentially cause vessel damage and hemorrhage. Thus, the current devices are typically not suited for material removal in the neurovascular vasculature.

Current devices include stent retrievers, stent-like devices, that are being used to remove clots. Stent retrievers are self-expanding devices attached to the end of a long catheter shaft, which are advanced through a microcatheter and deployed across clot obstructions to engage and remove the clot.

One disadvantage of some stent retrievers is that they can mainly rely on an outward radial force to retain and grip on the clot. If the radial force is too low, then the stent retrievers is unable to encapsulate or engage the clot radially, particularly when the clot is tough and/or organized. The stent retrievers may lose their grip on the clot. If the radial force is too high, then the stent retrievers can damage the vessel wall and also the stent retrievers may require excessive force to withdraw or pull the stent retrievers from the vessel. The stent retrievers that apply sufficient radial force to deal with all clot types may cause vessel trauma and the stent retrievers that have low radial force to remain atraumatic may not effectively retrieve all clot types. Furthermore, during retraction of the stent retriever through tortuous anatomy, the stent retriever will axially lengthen or elongate, and this stretching causes the stent retriever diameter to reduce in size thereby pulling away from the clot and causing potential emboli.

Another potential disadvantage with some stent retrievers is with the pinning mechanism itself. The stent retrievers that rely exclusively on pinning clots against a vessel wall may not restrain the clot effectively when retrieving the clot, passing a branch vessel or when passing into a vessel that is larger than the fully expanded diameter of the stent retrievers.

Another disadvantage with the stent retrievers is the lack of distal protection. During retrieval, the stent retrievers may have potential clot fragments that are released downstream into smaller vessel causing further damage.

Another potential disadvantage is that the stent retriever may not sufficiently retain the clot as it pulls the clot to the catheter. In such a case, some or all of the clot or emboli might remain in the vasculature. As the stent retriever moves the clot, the clot might not adhere to the stent retriever as the stent retriever is withdrawn. Even if the clot is successfully withdrawn to the tip of the guide catheter, the clot may be sheared from the stent retriever as the stent retriever is retrieved along with the clot into the guide catheter. Withdrawing the expanded stent retriever, either fully or partially expanded, by itself can result in undesired trauma to the vessel. In most cases, since the stent retriever is oversized compared to the vessel, dragging a fixed metallic structure can pull the arteries and/or strip the inner lining of the vessel causing further trauma such as a hemorrhagic stroke or leakage of blood from a cerebral vessel. The stent retriever can get stuck on plaque on the vessel walls resulting in further vascular damage.

Another potential disadvantage is that the stent retriever axially lengthen or elongates and stretches under tension. Specifically, when the stent retriever is retracted to capture the clot, the stent retriever tends to axially lengthen or elongate and stretch due to the tension exerted onto the stent retriever. The tension will cause the stent retriever to axially lengthen and reduce its diameter and cause the stent retriever to release or pull away from the clot. This will potentially loosen the grip of the stent retriever on the clot and allow the clot to dislodge.

Another potential disadvantage are concerns about dislodged or fragmented clot. The migration of dislodged fragments can increase the time of the procedure. During a procedure, restoration of blood flow is critical. Furthermore, a physician might be unaware of one or more fragments that dislodge from the initial obstruction and cause blockage of smaller more distal vessels.

While utilizing mechanical thrombectomy may lead to clot removal, there are several potential risks and disadvantages. There is a high occurrence of patients that do not achieved adequate reperfusion after the first pass through the vessel due to the clot not being retrieved completely. This is due to the structural and functional disadvantages of many existing and previous stent retrievers. There is a need for, among other things, an improved retriever device that can improve the grip on, or otherwise effectively control the removal of an occlusive clot without necessarily increasing the outward radial force on the clot, thereby protecting the surrounding vasculature. Some embodiments described herein address one, two, or more of the shortcomings and disadvantages of the stent retrievers.

Although certain embodiments and examples are disclosed below, it will be understood by those in the art that the disclosure extends beyond the specifically disclosed embodiments and/or uses of the invention and obvious modifications and equivalents thereof. Thus, it is intended that the scope should not be limited by the particular disclosed embodiments described herein.

The systems and methods described herein relate, for example, to embodiments of extractors. The methods can include treating a body lumen, such as a vessel, such as a neurovascular vessel. The methods can include expanding the extractor within a vessel to capture material, such as clot or emboli. The extractors can have several advantages over stent retrievers.

Figure 2:
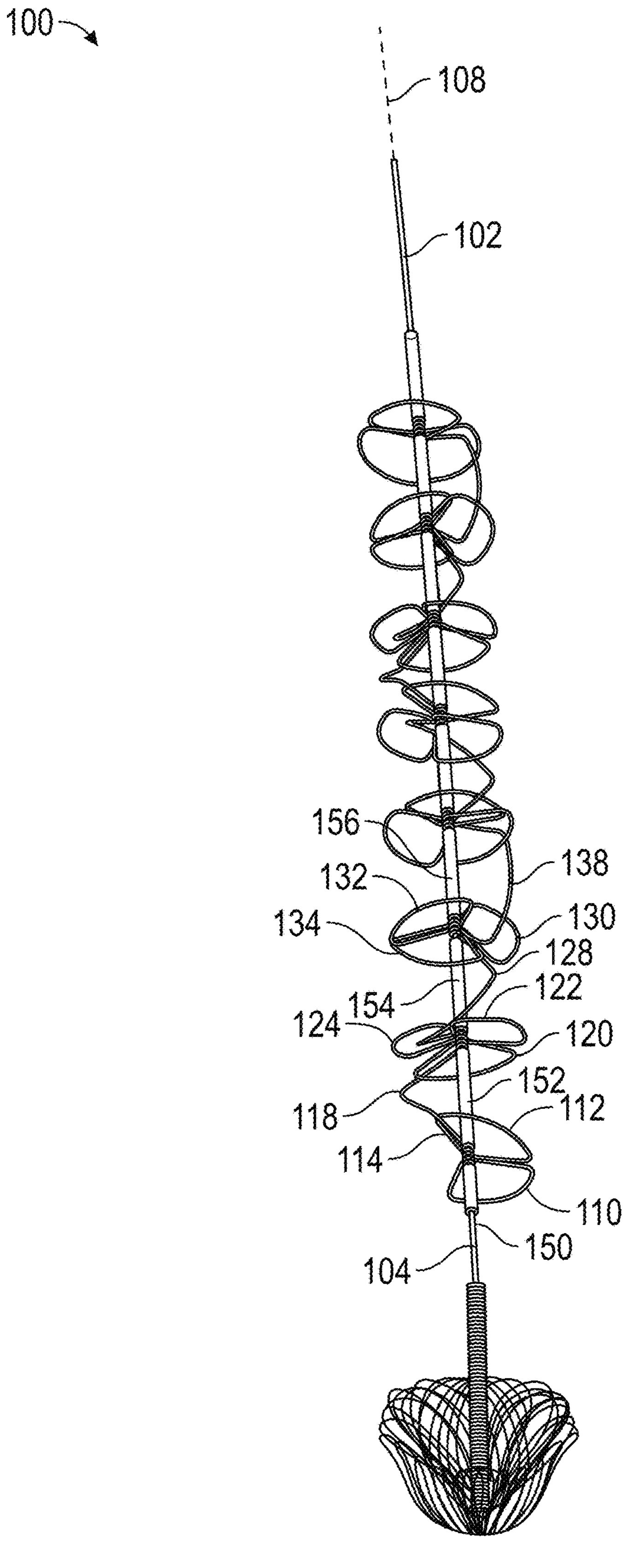
FIG. 2 is a side view of an embodiment of a three engagement panel extractor.
Figure 3:
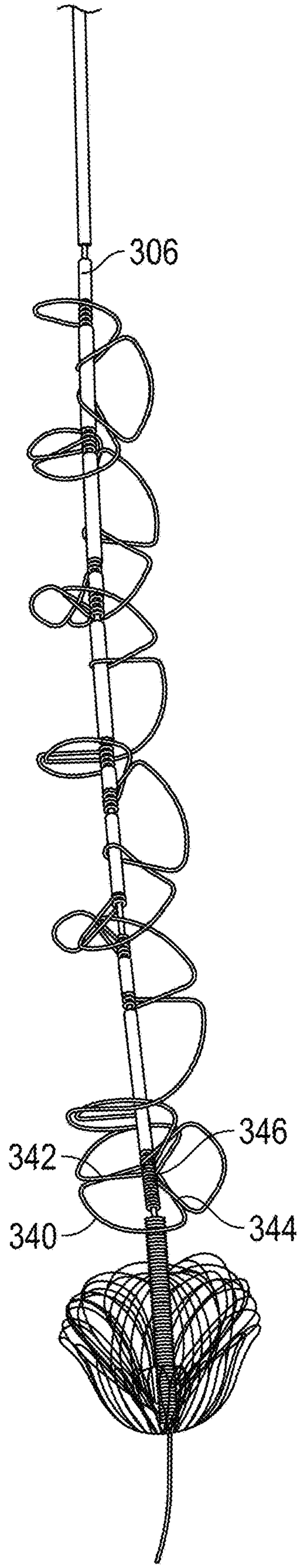
FIG. 3 is a side view of an embodiment of a helical engagement panel extractor.
Figure 4A:
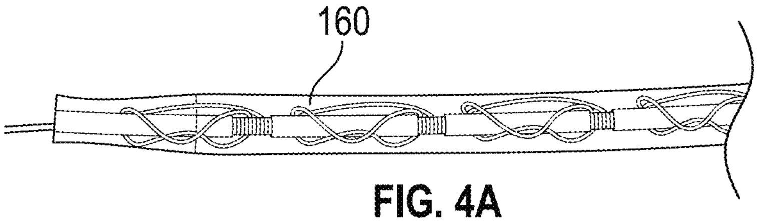
FIGS. 4A-4G are views of deployment of the first panel of the first embodiment of the three engagement panels extractor.
Figure 4B:
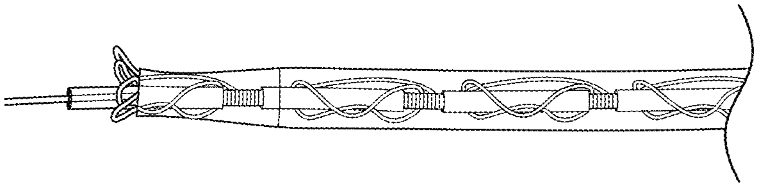
Figure 4C:
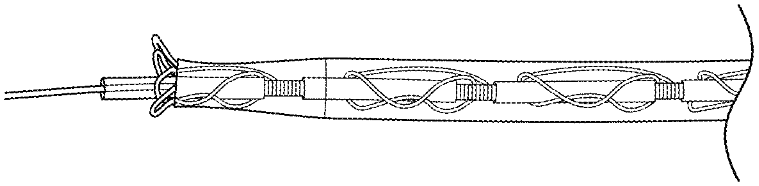
Figure 4D:
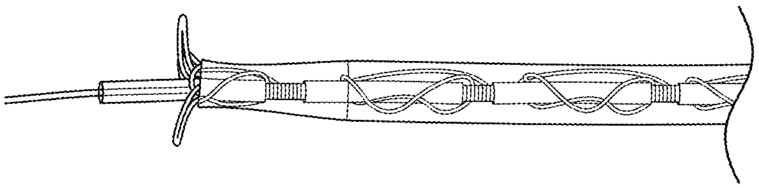
Figure 4E:
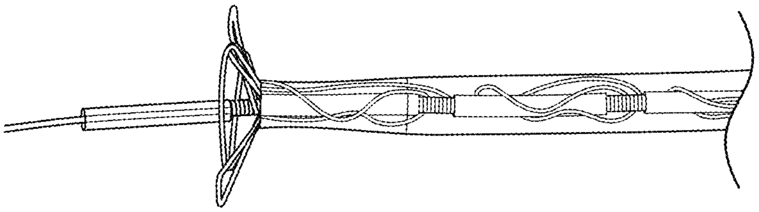
Figure 4F:
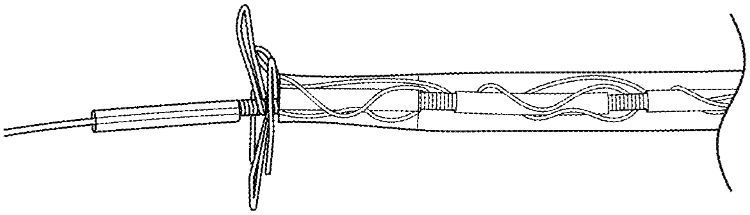
Figure 4G:
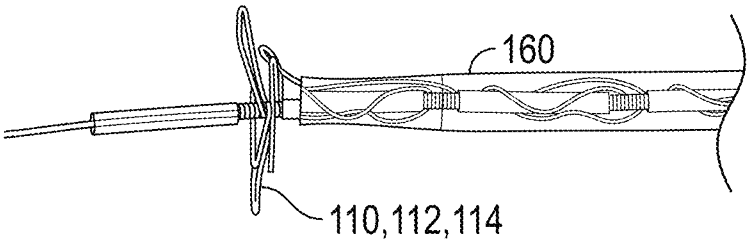

FIGS. 1-3 illustrate embodiments of an extractor 100. Other embodiments include extractor 200, the extractor 300, the extractor 400, and the extractor 500. The embodiments can include any feature described herein. The extractor 100 is configured for removal of clot material from a treatment site within a vessel. The extractor 100 can be particularly suited for neurovascular retrieval, wherein the vessels are fragile and delicate. The extractor 100 can be designed for the removal and retrieval of material by way of mechanical extraction within a lumen of a vessel.

The extractor 100 can include a proximal end 102 and a distal end 104. The extractor 100 can be a generally elongate member. The extractor 100 can include a length between the proximal end 102 and the distal end 104. In some embodiments, the proximal end 102 extends through the vasculature and is disposed outside of the body of the patient. The distal end 104 is configured to be advanced to a treatment site within a lumen of the patient. The extractor 100 can include one or more sections along the length of the extractor 100. The extractor 100 can include a distal member 180. The distal member 180 can include any feature described herein.

In some embodiments, a catheter shaft 106 is provided. The catheter shaft 106 can be advanced through the vasculature of the patient. The catheter shaft 106 can be a tubular shape with a lumen. The catheter shaft 106 can be a solid shaft. The catheter shaft 106 can be considered part of the extractor 100. The catheter shaft 106 can be considered separate from the extractor 100. The catheter shaft 106 can be made of, for example, metal such as stainless steel or nitinol, or another appropriate material. The distal end of the catheter shaft 106 can have a taper, such as a reduced outer diameter taper from proximal to distal, for example, to provide flexibility. The proximal end of the catheter shaft 106 can have a lubricious coating, or a PTFE jacket, or bare metal, as some examples. In some embodiments, the catheter shaft 106 is a core wire.

The extractor 100 can have a plurality of engagement panels 110, 112, 114, 120, 122, 124, 130, 132, 134. There can be a number of engagement panels at a single longitudinal location. There can be a number of engagement panels at a single location along the shaft 106. The engagement panels 110, 112, 114 are located at a first longitudinal location. The engagement panels 120, 122, 124 are located at a second longitudinal location spaced axially apart from the first longitudinal location. The engagement panels 130, 132, 134 are located at a third longitudinal location spaced axially apart from the first and second longitudinal locations. The first longitudinal location can be distal to the second longitudinal location. The second longitudinal location can be distal to the third longitudinal location. In other embodiments, the first longitudinal location can be proximal to the second longitudinal location. In other embodiments, the second longitudinal location can be proximal to the third longitudinal location. There can be any number of panels at a longitudinal location (e.g., one engagement panel, two engagement panels, three engagement panels, four engagement panels, five engagement panels, six engagement panels, seven engagement panels, eight engagement panels, nine engagement panels, ten engagement panels, or more or less or any range of two of the foregoing values). The longitudinal locations can be spaced apart at fixed regular intervals. The longitudinal locations can be spaced apart irregular intervals. In some embodiments, engagement panels located at the first longitudinal location comprise one engagement panel, two engagement panels, three engagement panels, four engagement panels, five engagement panels, six engagement panels, seven engagement panels, eight engagement panels, nine engagement panels, ten engagement panels, or more, or less or any range of two of the foregoing values. In some embodiments, engagement panels located at the second longitudinal location comprise one engagement panel, two engagement panels, three engagement panels, four engagement panels, five engagement panels, six engagement panels, seven engagement panels, eight engagement panels, nine engagement panels, ten engagement panels, or more or less, or any range of two of the foregoing values. In some embodiments, engagement panels located at the third longitudinal location comprise one engagement panel, two engagement panels, three engagement panels, four engagement panels, five engagement panels, six engagement panels, seven engagement panels, eight engagement panels, nine engagement panels, ten engagement panels, or more or less or any range of two of the foregoing values. In the illustrated embodiment, there are three engagement panels at each longitudinal location. It is contemplated that the extractor diameter can have any diameter combination thereof from the engagement panel at the first longitudinal location to the last engagement panel at the last longitudinal location. In some embodiments, the extractor 100 can be of the same diameter from the first longitudinal location to the last longitudinal location where engagement panels extend therefrom. In some embodiments, the engagement panels at the first longitudinal location have the same expanded diameter as engagement panels at the second longitudinal location. In some embodiments, the engagement panels at the second longitudinal location have the same expanded diameter as engagement panels at the third longitudinal location. In some embodiments, the extractor 100 can be various tapered geometries where the extractor diameter of the first longitudinal location is larger than the last longitudinal location. In some embodiments, the extractor 100 can be various tapered geometries where the extractor diameter can be tapered where the first longitudinal location is smaller than the last longitudinal location. In some embodiments, the extractor 100 can be various tapered geometries where the extractor diameter can be tapered the extractor middle members are larger than the first longitudinal location and the last longitudinal location. For example, the extractor diameter can be of the same diameter from the first longitudinal location to last longitudinal location end. For example, the extractor diameter can be 0.5 mm, 1 mm, 2 mm, 3 mm, 4 mm, 5 mm, 6 mm, 7 mm, 8 mm or higher or lower, or any range of two of the foregoing values. The extractor diameter can also differ from each longitudinal location. For example, the extractor diameter of the engagement panels 110, 112, 114 in the first longitudinal location can be 4 mm. The extractor diameter of the engagement panels 120, 122, 124 in the second longitudinal location can be 5 mm. The extractor diameter of the engagement panels 130, 132, 134 in the third longitudinal location can be 4 mm. The extractor diameter in the fourth longitudinal location can be 5 mm. In another embodiment, the extractor diameter of the engagement panels 110, 112, 114 in the first longitudinal location is larger than the extractor diameter of the engagement panels in the last longitudinal location at the distal end. For example, the engagement panels 110, 112, 114 in the first longitudinal location can be at 8 mm diameter and gradually transition to 7.5 mm, 7.0 mm, 6.5 mm, 6.0 mm, 5.5 mm, 5.0 mm, 4.5 mm, 4.0 mm, 3.5 mm, 3.0 mm, 2.5 mm, 2.0 mm and any diameter combination thereof at other longitudinal locations. In addition, the extractor diameter at the first longitudinal location can be smaller than the extractor diameter at the last longitudinal location. In some embodiments, the extractor 100 can have single layer of engagement panels at a longitudinal location (e.g., first longitudinal location, second longitudinal location, and/or third longitudinal location). In some embodiments, the extractor 100 can have double layers of engagement panels at a longitudinal location (e.g., first longitudinal location, second longitudinal location, and/or third longitudinal location). In some embodiments, the extractor can have three layers of engagement panels at a longitudinal location (e.g., first longitudinal location, second longitudinal location, and/or third longitudinal location). In some embodiments, the extractor 100 can have a plurality of layers of engagement panels. The engagement panels can extend along the circumference once. The engagement panels can extend along the circumference twice. The engagement panels can extend along the circumference three times. In some embodiments, the extractor 100 can have a combination of series of plurality of engagement panels such as single layer engagement panels at the first longitudinal location, double layers engagement panels at the second longitudinal location, single layer engagement panels at the third longitudinal location, and double layers of engagement panels at a fourth longitudinal location, for example. In some embodiments, the extractor 100 can have a series of double layers of engagement panels at the first longitudinal location, three layers of engagement panels at the second longitudinal location, and double layers of engagement panels at the third longitudinal location. In some embodiments, there can be any combinations thereof of layers of engagement panels.

In some embodiments, the extractor 100 can be adjusted or articulated at the proximal end using a control wire to either increase the diameter, distance, space, or opening between the engagement panels at the first longitudinal location and the engagement panels at the second longitudinal location or decrease the diameter, distance, space or opening between the engagement panels at the first longitudinal location and the engagement panels at the second longitudinal location. For example, the proximal end of the extractor 100 includes a control wire attached to the engagement panels. The control wire extends proximally and is attached to a control mechanism wherein the control wire can articulate to slidably move the eyelets of the engagement panels at the first longitudinal location and the second longitudinal location over the catheter shaft 106 or core wire to increase the diameter, distance, space, or opening between the engagement panels at the first longitudinal location and the second longitudinal location thereby creating a larger space or void for clot to reside into between the engagement panels at the first and second longitudinal locations. The control mechanism can also release to slidably allow the eyelets of the engagement panels at the first longitudinal location and the engagement panels at the second longitudinal location to shorten or move closer together reducing the distance, space, or opening between the engagement panels at the first and second longitudinal locations. The engagement panels at the first longitudinal location and the engagement panels at the second longitudinal location can be controlled to move relative to the catheter shaft 106 or core wire. The distance, space, or opening between the engagement panels at the first longitudinal location and the engagement panels at the second longitudinal location can be adjusted by a control mechanism.

The extractor 100 can have a plurality of connecting members 118, 128, 138. The connecting member 118 can connect the engagement panels 110, 112, 114 at the first longitudinal location and the engagement panels 120, 122, 124 at the second longitudinal location. The connecting member can be directed connected to one panel 110 at the first longitudinal location and one panel 120 at the second longitudinal location. The connecting member 128 can connect the engagement panels 120, 122, 124 at the second longitudinal location and the engagement panels 130, 132, 134 at a third longitudinal location. The connecting member 138 can connect the engagement panels 130, 132, 134 at a third longitudinal location and another set of engagement panels. The connecting members 118, 128, 138 can be helical. The connecting members 118, 128, 138 can be linear. The connecting members 118, 128, 138 can be curved. The connecting members can be coiled. The connecting members 118, 128, 138 can be radially offset or otherwise spaced apart from the longitudinal axis of the extractor 100 as shown. The connecting members 118, 128, 138 can be radially offset from the catheter shaft 106. The connecting members 118, 128, 138 can be inward from the outer circumference of the engagement panels. The connecting members 118, 128, 138 can be made of the same material as the engagement panels 110, 112, 114, 120, 122, 124, 130, 132, 134. The connecting members 118, 128, 138 can be made of a different material than the engagement panels 110, 112, 114, 120, 122, 124, 130, 132, 134. The connecting members 118, 128, 138 can be integrally formed with the engagement panels 110, 112, 114, 120, 122, 124, 130, 132, 134. The connecting members 118, 128, 138 can otherwise attached with the engagement panels 110, 112, 114, 120, 122, 124, 130, 132, 134, such as bonded together. The connecting members 118, 128, 138 can have the same flexibility than the engagement panels 110, 112, 114, 120, 122, 124, 130, 132, 134. The connecting members 118, 128, 138 can have more flexibility than the engagement panels 110, 112, 114, 120, 122, 124, 130, 132, 134. The connecting members 118, 128, 138 can have less flexibility than the engagement panels 110, 112, 114, 120, 122, 124, 130, 132, 134.

Figure 21:
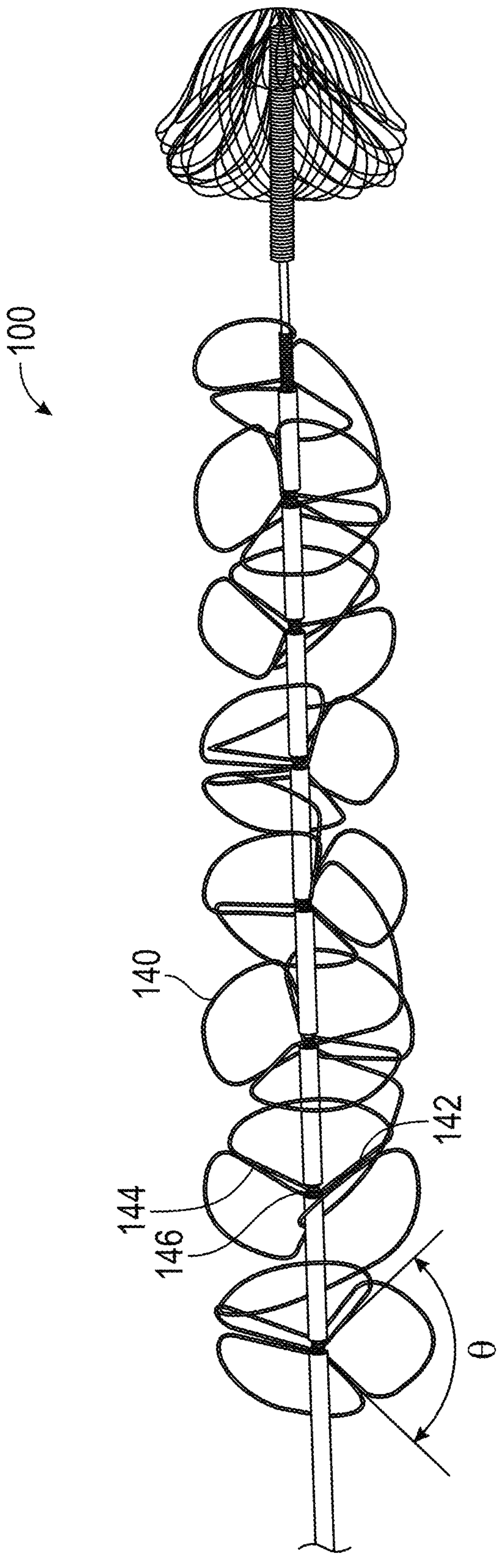
Figure 22:
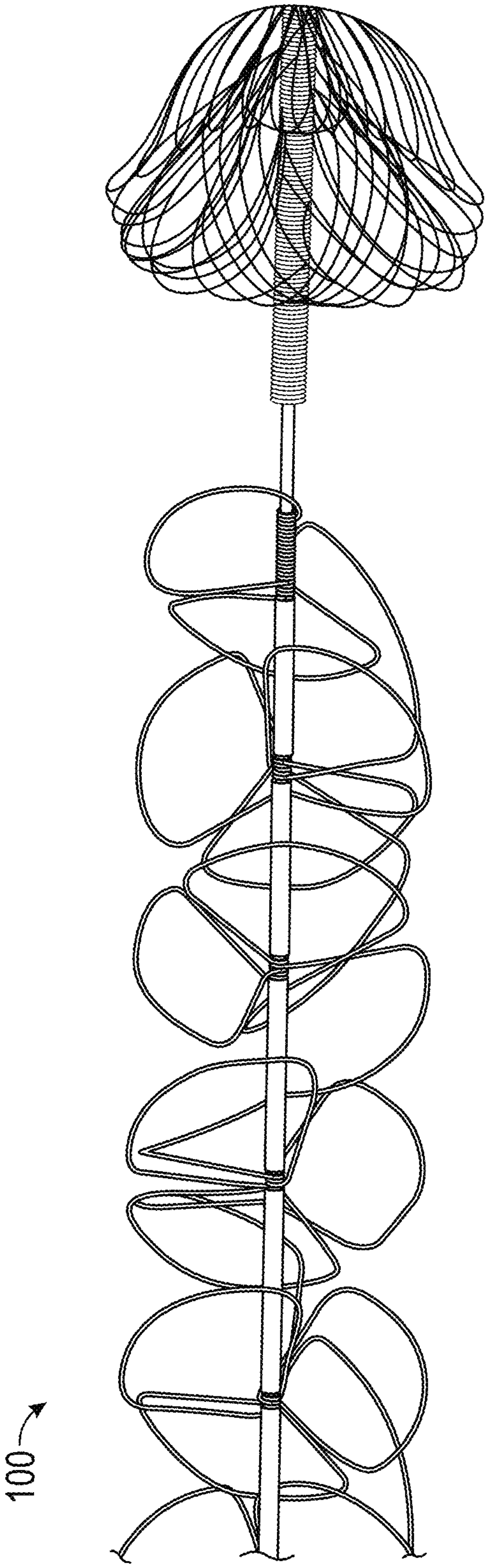
Figure 23:
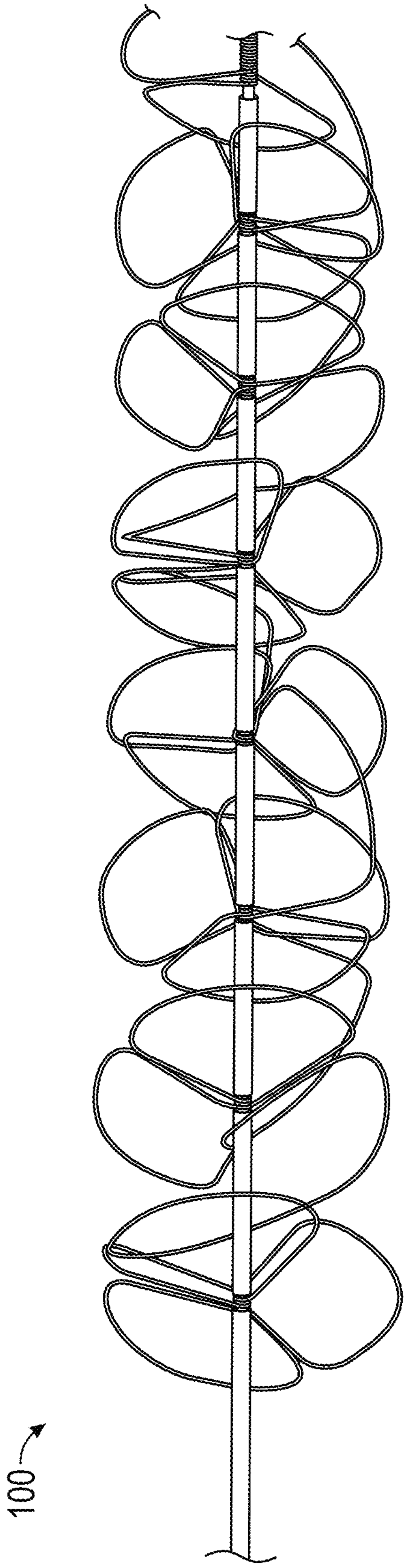
Figure 24:
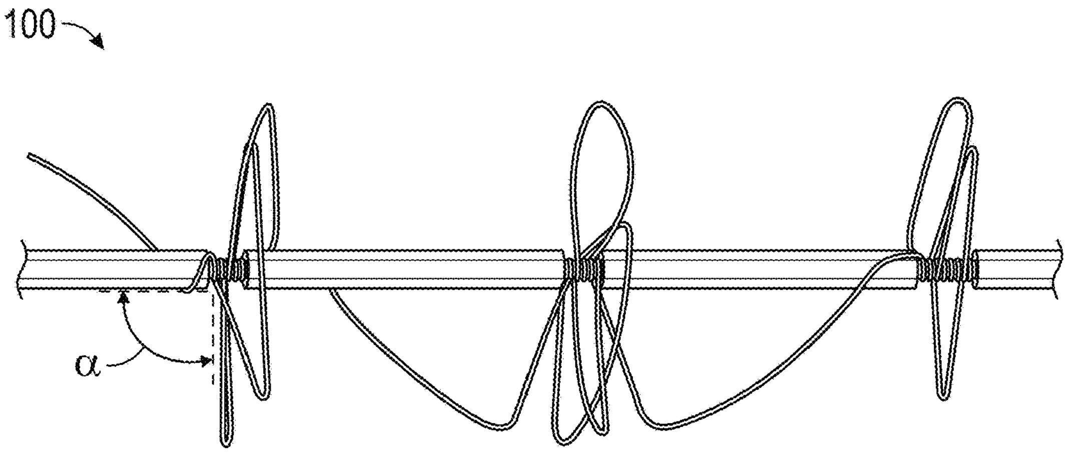
Figure 25:
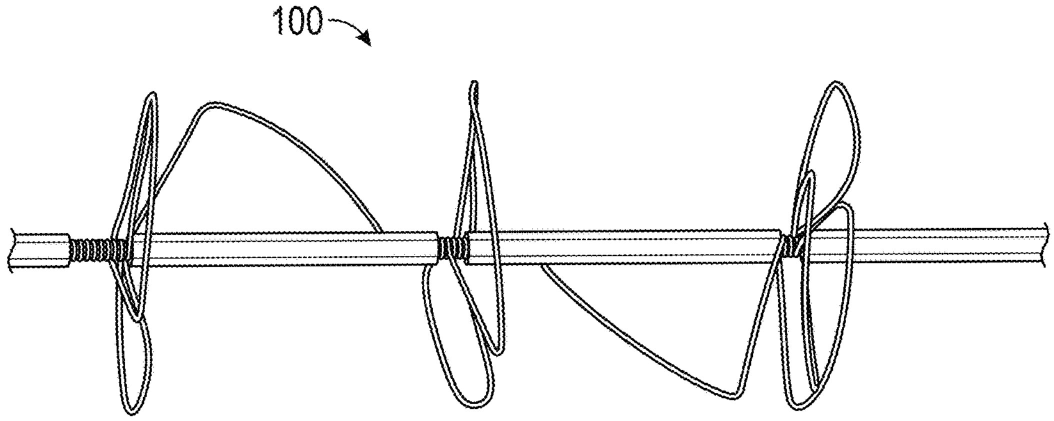
Figure 26:
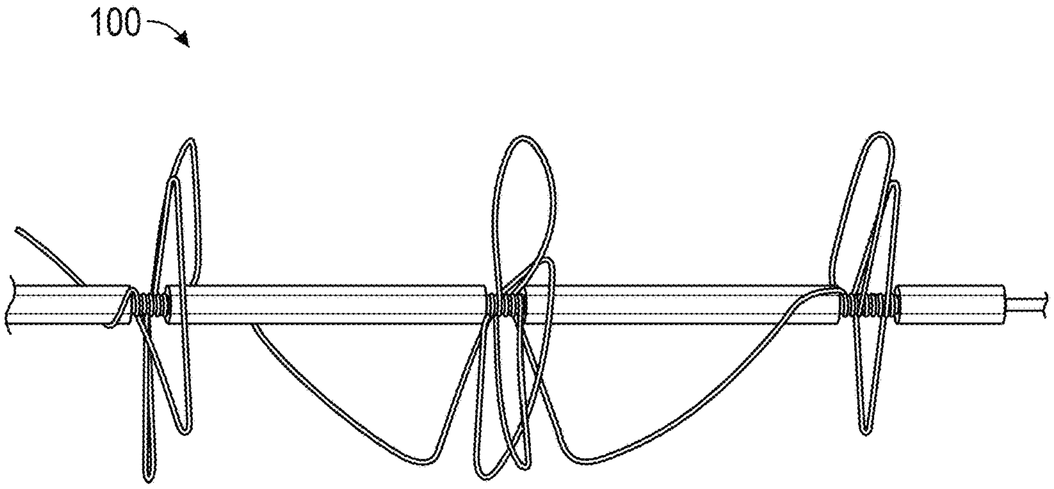
Figure 27:
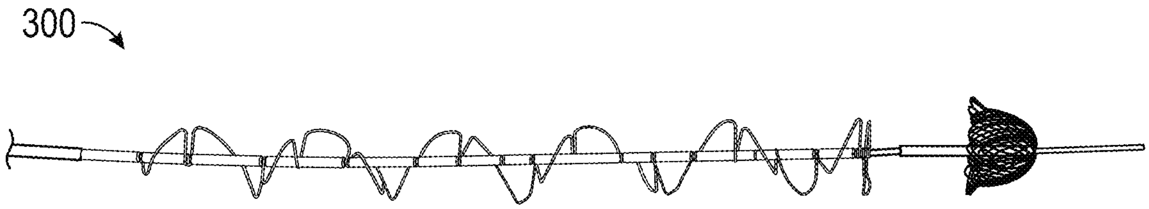
FIGS. 27-30 are views of the third embodiment of the helical engagement panel extractor.
Figure 28:
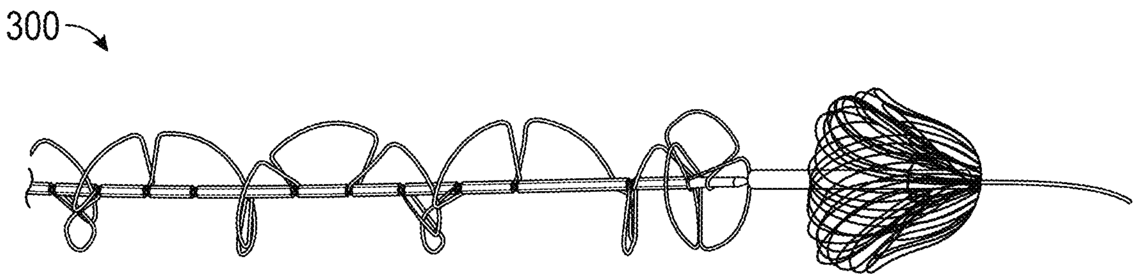
Figure 29:
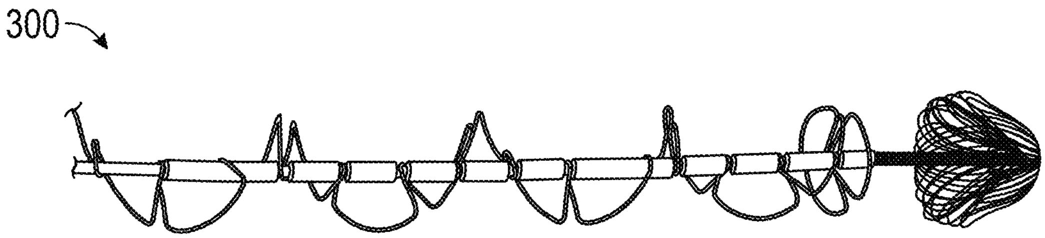
Figure 30:
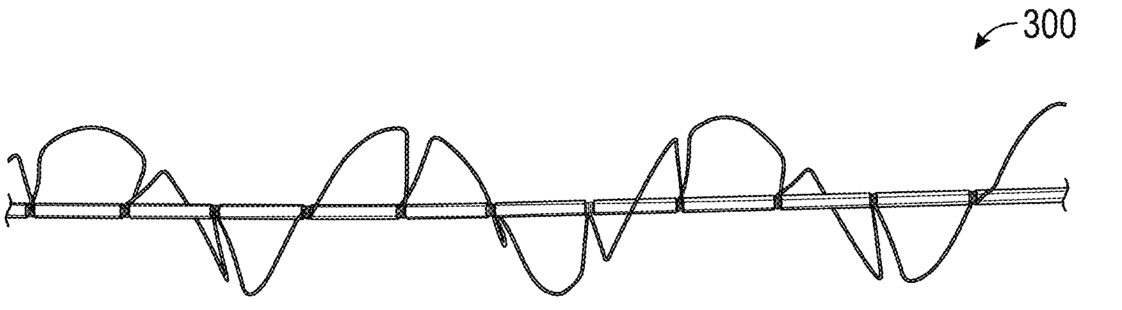

The engagement panels 110, 112, 114 can each form an arc 140 as shown in FIG. 21. The arc 140 can form a generally arcuate profile. The arc 140 can have round, circular, ellipse, or oval profile. The arc 140 can be configured to be atraumatic to the vessel wall. In some embodiments, the engagement panels 110, 112, 114 do not comprise barbs, or other sharp elements or vertices that are likely to pierce a luminal wall. In some embodiments, the engagement panels 110, 112, 114 form rounded corners. While the extractor 100 illustrated has three panels at a longitudinal location, other embodiments are contemplated. In some embodiments, the engagement panels located at a longitudinal location comprise one engagement panel, two engagement panels, three engagement panels, four engagement panels, five engagement panels, six engagement panels, seven engagement panels, eight engagement panels, nine engagement panels, ten engagement panels, or any range of two of the foregoing values. The engagement panels 110, 112, 114 at a single longitudinal location can form a circular profile. The engagement panels 110, 112, 114 at a single longitudinal location can extend around the circumference. Each engagement panel 110, 112, 114 can form a portion of a circle. Each arc 140 of the engagement panel 110, 112, 114 can form an segment of the circumference. Each arc 140 of the engagement panel 110, 112, 114 can include an approximately 120 degree arc. Each arc 140 of the engagement panel 110, 112, 114 can form an arc of, e.g. about 85 degrees, 90 degrees, 95 degrees, 105 degrees, 110 degrees, 111 degrees, 112 degrees, 113 degrees, 114 degrees, 115 degrees, 116 degrees, 117 degrees, 118 degrees, 119 degrees, 120 degrees, 125 degrees, 130 degrees, approximately 120 degrees, less than 120 degrees, greater than 110 degrees, more or less or any range of two of the foregoing values. Each arc 140 of the engagement panel 110, 112, 114 can form an arc that forms part of a circular, oval, or other arcuate profile. Each arc 140 of the engagement panels 110, 112, 114 can form the same arc. Each arc 140 of the engagement panels 110, 112, 114 can form the same degree of arc. Each arc 140 of the engagement panels 110, 112, 114 can form the same length of arc. Each arc 140 of the engagement panels 110, 112, 114 can form the arc with the same radius. Each arc 140 of the engagement panels 110, 112, 114 can form the arc with the same radius of curvature. Each arc 140 of the engagement panels 110, 112, 114 can be identical. Each arc 140 of the engagement panels 110, 112, 114 can be similar. Two or more arc 140 of the engagement panels 110, 112, 114 can be the same. Each arc 140 of the engagement panels 110, 112, 114 can form a different arc. Each arc 140 of the engagement panels 110, 112, 114 can form a different degree of arc. Each arc 140 of the engagement panels 110, 112, 114 can form a different length of arc. Each arc 140 of the engagement panels 110, 112, 114 can form the arc with a different radius. Each arc 140 of the engagement panels 110, 112, 114 can form the arc with a different radius of curvature. Each arc 140 of the engagement panels 110, 112, 114 can be different. Two or more engagement panels 110, 112, 114 can be different. Two or more arc 140 of the engagement panels 110, 112, 114 can have different diameters. Two or more arc 140 of the engagement panels 110, 112, 114 can have different arc angles.

Each engagement panels 110, 112, 114 can be formed by, or otherwise include one, or a plurality of legs, such as two legs 142, 144 shown in FIG. 21. The two legs 142, 144 connect to the arc 140 of engagement panel 110, 112, 114. The legs 142, 144 and the arc 140 can form rounded corners. The arc can form an atraumatic surface. The two legs 142, 144 can be radially outward from the longitudinal axis of the extractor 100. The two legs 142, 144 can be angled relative to each other. The two legs 142, 144 can be straight. The two legs 142, 144 can be linear. The two legs 142, 144 can have a constant angle therebetween. The two legs 142, 144 can connect to the ends of the arc 140. In some embodiments, the legs 142, 144 are integrally formed with the arc 140. In some embodiments, the legs 142, 144 are operably attached together with the arc 140. The legs 142, 144 and the arc 140 can be, made of the same material. The legs 142, 144 can be made of different material than the arc 140. The two legs 142, 144 can form a radius toward the arc 140. In some embodiments, legs 142, 144 of each engagement panel 110, 112, 114 can have any pattern. In some embodiments, legs 142, 144 of each engagement panel 110, 112, 114 can have a zig zag pattern. In some embodiments, legs 142, 144 of each engagement panel 110, 112, 114 can have a slight curve. In some embodiments, the legs 142, 144 and the arc

142 define the perimeter of a void or free space area that is devoid or substantially devoid of any material, thus advantageously minimizing the size/weight of the device. The legs 142, 144 and the arc 142 define a pore. Each engagement panel 110, 112, 114 comprises a pore.

In some embodiments, the engagement panels 110, 112, 114 of the first longitudinal location do not overlap. In some embodiments, the legs 142, 144 of the engagement panel 110 do not overlap with the legs 142, 144 of the engagement panels 112, 114. In some embodiments, the legs 142, 144 of the engagement panel 112 do not overlap with the legs 142, 144 of the engagement panels 110, 114. In some embodiments, the legs 142, 144 of the engagement panel 114 do not overlap with the legs 142, 144 of the engagement panels 110, 112. In some embodiments, the legs 142, 144 of the engagement panels 110, 112, 114 of the first longitudinal location do not touch. In some embodiments, the legs 142, 144 of the engagement panels 110, 112, 114 of the first longitudinal location are adjacent. In some embodiments, the legs 142, 144 of the engagement panels 110, 112, 114 of the first longitudinal location are spaced apart. In some embodiments, the legs 142, 144 of the engagement panels 110, 112, 114 of the first longitudinal location about each other. In some embodiments, the legs 142, 144 of the engagement panels 110, 112, 114 of the first longitudinal location are in contact along their length. In some embodiments, the legs 142, 144 of the engagement panels 110, 112, 114 of the first longitudinal location are in contact along a portion of the radius of the arc 140.

The engagement panels 110, 112, 114 can form an eyelet 146 as shown in FIG. 21. The engagement panels 110, 112, 114 are located at the first longitudinal location. The eyelet 146 can be located at the first longitudinal location. The engagement panels 110, 112, 114 can form a generally round eyelet 146. The engagement panels 110, 112, 114 can form a circular eyelet 146 at the single longitudinal location. Each engagement panel 110, 112, 114 can form a portion of the eyelet 146. In some embodiments, the legs 142, 144 of the engagement panels 110, 112, 114 form the eyelet 146. The legs 142, 144 of the engagement panels 110, 112, 114 can lie along the same plane. The legs 142, 144 of the engagement panels 110, 112, 114 can form a perimeter of the eyelet 146. The legs 142, 144 of the engagement panels 110, 112, 114 can be circumferentially spaced. The legs 142, 144 of the engagement panels 110, 112, 114 can have ends along the perimeter of the eyelet 146. In some embodiments, another portion of the engagement panels 110, 112, 114 forms the eyelet 146.

The eyelet 146 can accommodate the catheter shaft 106. The eyelet 146 can be wrapped around the outer diameter of the elongate member of the extractor. In some embodiments, the eyelet 146 is fixed to the catheter shaft 106. In some embodiments, the eyelet is moveable relative to the catheter shaft 106. The eyelet 146 of the engagement panels 110, 112, 114 is located at the first longitudinal location. The eyelet 146 of the engagement panels 120, 122, 124 is located at the second longitudinal location. The eyelet 146 of the engagement panels 130, 132, 134 is located at a third longitudinal location.

Figure 34:
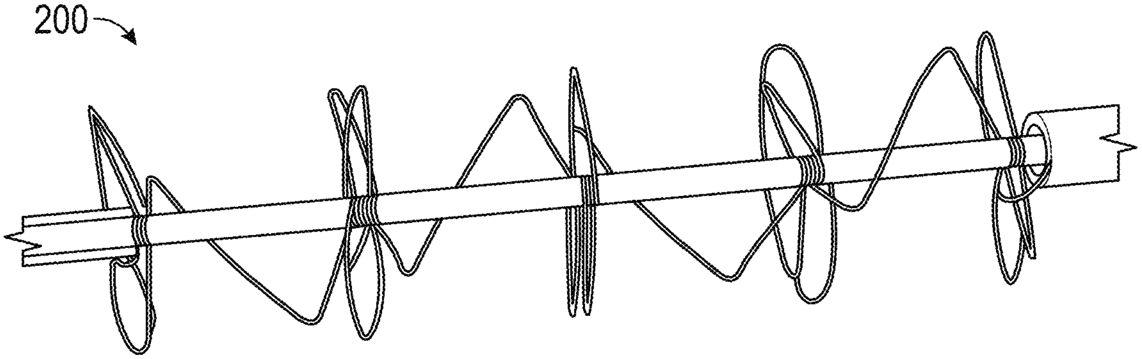
Figure 35:
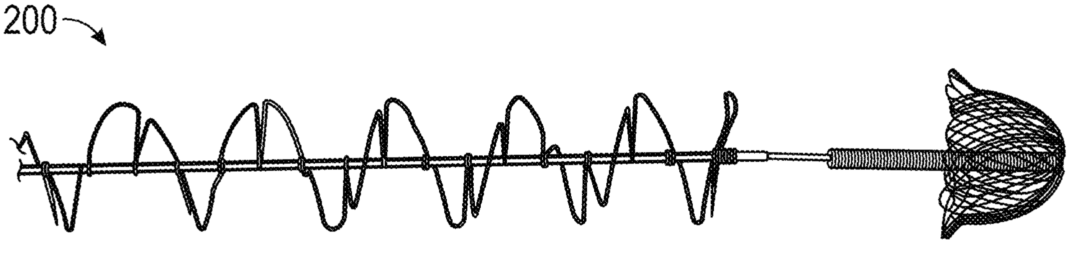
FIGS. 35-39 are views of the first embodiment of the helical engagement panel extractor with spacer in between the engagement panels and eyelets.
Figure 36:
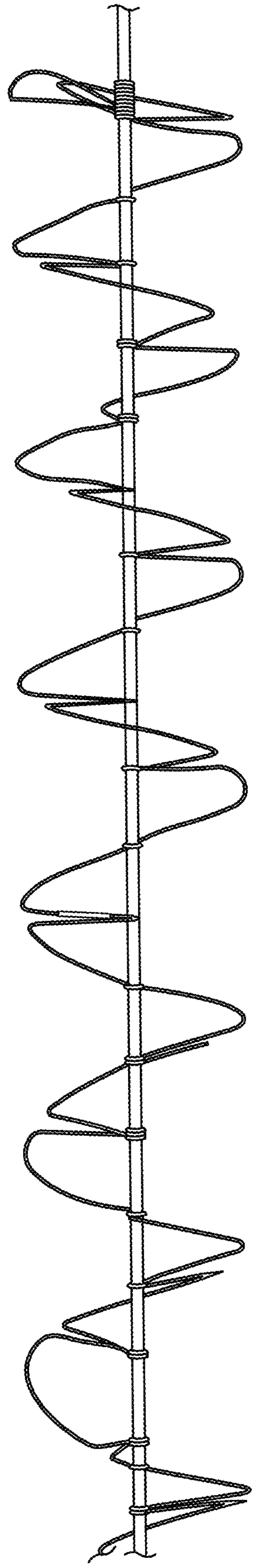
Figure 37:
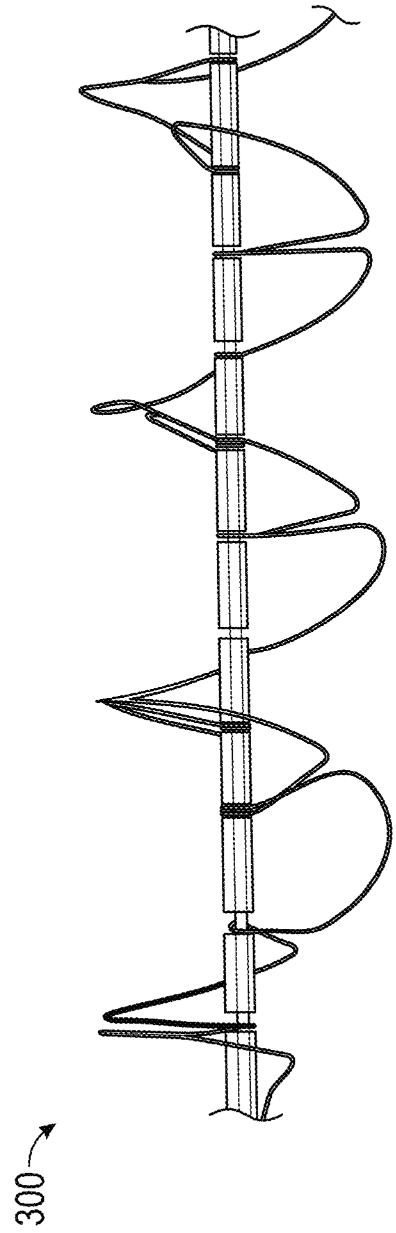
Figure 38:
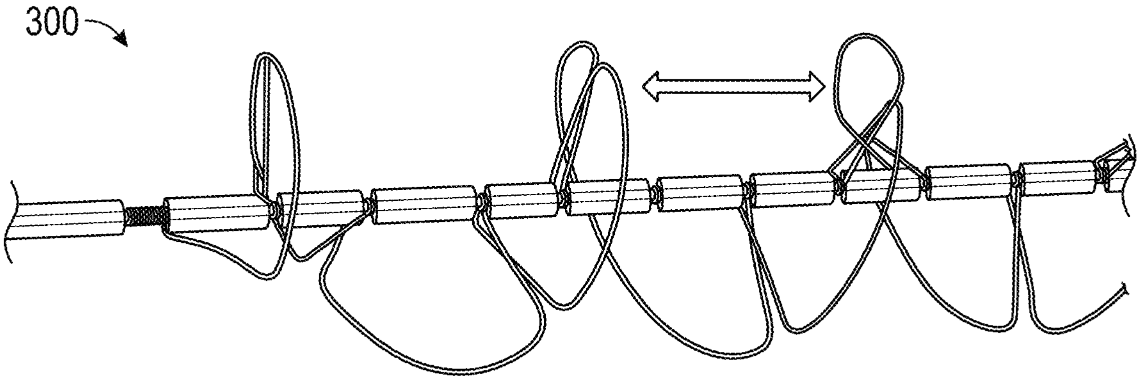
Figure 39:
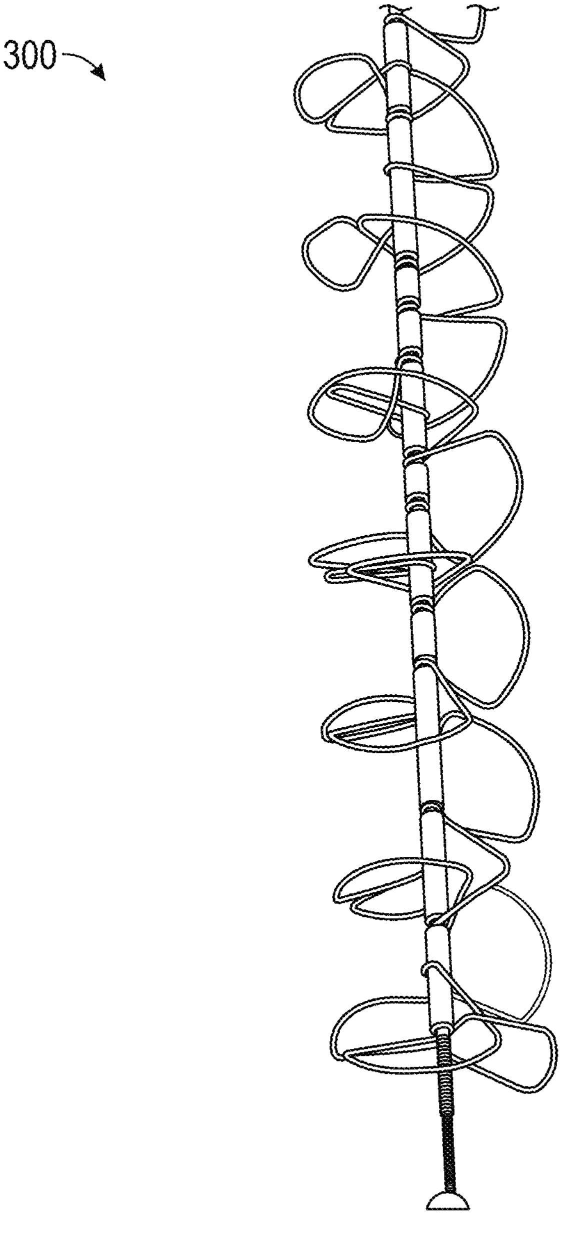

The extractor 100 can include a plurality of spacers 150, 152, 154, 156. The spacer 150 can be located between the distal end 104 and the engagement panels 110, 112, 114. The spacer 152 can be located between the engagement panels 110, 112, 114 and the engagement panels 120, 122, 124. The spacer 152 can be between the first longitudinal location and the second longitudinal location. The spacer 154 can be located between the engagement panels 120, 122, 124 and the engagement panels 130, 132, 134. The spacer 154 can be between the second longitudinal location and the third longitudinal location. In some embodiments, the spacer 156 can be located between the engagement panels 130, 132, 134 and another set of engagement panels. In some embodiments, the spacer 156 can be located between the engagement panels 130, 132, 134 and the proximal end 102. In some embodiments, engagement panels have space between them without spacers (FIG. 34). In some embodiments, engagement panels have space between them without a discrete structural feature. For example, the extractor or engager's engagement panels can couple directly to the catheter shaft or corewire. The Engagement panels at the first location is coupled to the catheter shaft or corewire. The engagement panels at the second panels is coupled at a distance away from the engagement panels at the first location. The engagement panels can be coupled to the catheter shaft or corewire either by laser, chemical or mechanical bond for example. In some embodiments, a spacer is interspersed in between some, or every adjacent set of engagement panels. The space can be located between the engagement panels 110, 112, 114 and the engagement panels 120, 122, 124. The space can be between the first longitudinal location and the second longitudinal location. The space can be located between the engagement panels 120, 122, 124 and the engagement panels 130, 132, 134. The spacer 154 can be between the second longitudinal location and the third longitudinal location. In some embodiments, engagement panels can be next to each other in series with no spacer, thereby minimal to no gap. The engagement panels 110, 112, 114 and the engagement panels 120, 122, 124 can be next to each other in in series with minimal to no gap. The first longitudinal location and the second longitudinal location can be next to each other. The engagement panels 120, 122, 124 and the engagement panels 130, 132, 134 can be next to each other in in series with minimal to no gap. The second longitudinal location and the third longitudinal location can be next to each other.

The spacers 150, 152, 154, 156 can include a lumen. The spacers 150, 152, 154, 156 can receive the catheter shaft 106 there through. The catheter shaft 106 can be a corewire or laser cut hypotube and any combination thereof. The connecting members 118, 128, 138 can be located within the lumen of the spacers 152, 154, 156. The connecting members 118, 128, 138 can be located outside of the spacers 152, 154, 156.

The extractor 100 can be used with a sheath 160. The sheath 160 can be an outer sheath. The sheath 160 can cover the extractor 100. The sheath 160 can cover the plurality of engagement panels 110, 112, 114, 120, 122, 124, 130, 132, 134, such that engagement panels are configured to move between radially expanded and radially compressed configurations. The sheath 160 can cover the shaft 106, or a portion thereof. The sheath 160 can cover additional components of the system, such as a filter.

The extractor 100 can be used with other components of a system. The extractor 100 can be used with a filter. The filter can be any filter. The filter can be any distal extraction member. The extractor 100 can be used with a collection chamber or collection bag. The extractor 100 can be used with a macerator tool. The extractor 100 can be used with an expanding filter. The extractor 100 can be used with an expanding guide catheter. The extractor 100 can be used with a suction catheter. The extractor 100 can be used with the catheter shaft 106.

In some embodiments, the extractor includes a distal member or distal plug 180. The distal member 180 functions to trap or capture loose emboli in transit or remove and capture soft emboli distal to the extractor. The distal member 180 is designed to have a low profile to be delivered through a small lumen. The distal member 180 is made of braided filaments, wires or woven. The braided wire or filaments can be a single or double layer. The braided wires or filaments can be metallic such as Nitinol, stainless steel, platinum iridium for example. The braided wires or filaments can also be polymeric materials such as polyethylene, PTFE, FEP for example. The braided wires can also include radiopaque metal such as tungsten or gold to aid with better visualization. The distal member 180 can form using laser stent cut hypotube. The distal member 180 can be formed in any geometrical configuration, including, but not limited to, circular, umbrella, ball, elliptical, and/or disc. The distal member 180 can be expandable. The distal member 180 can be compressible. The distal member 180 can conform to the vessel wall.

The extractor 100 can include the catheter shaft 106. The extractor 100 can have the plurality of engagement panels 110, 112, 114, 120, 122, 124, 130, 132, 134. The plurality of engagement panels 110, 112, 114, 120, 122, 124, 130, 132, 134 can be deployed. In some embodiments, the engagement panels are deployed by retracting a sheath 160. The sheath 160 will uncover engagement panels 110, 112, 114 at the first longitudinal location. The extractor 100 is fully functional to remove clot material with just the engagement panels 110, 112, 114 at the first longitudinal location. The sheath 160 will then uncover engagement panels 120, 122, 124 at the second longitudinal location, if needed. The extractor 100 is fully functional to remove clot material with just the engagement panels 110, 112, 114 at the first longitudinal location and engagement panels 120, 122, 124 at the second longitudinal location. The sheath 160 will then uncover engagement panels 130, 132, 134 at the third longitudinal location, if needed.

The extractor 100 consists of a series of engagement panels 110, 112, 114, 120, 122, 124, 130, 132, 134. The engagement panels 110, 112, 114, 120, 122, 124, 130, 132, 134 function to remove the clot away from the vessel wall. The engagement panels 110, 112, 114 at the first longitudinal location can form a generally circular profile similar to the circumference of the vessel wall. The engagement panels 110, 112, 114 at the first longitudinal location can sweep against the vessel wall with the arc 140. The engagement panels 110, 112, 114 at the first longitudinal location can include legs 142, 144 which support the arc 140 as the arc 140 removes the clot away from the vessel wall. The engagement panels 110, 112, 114 can be segmented to effectively oppose the vessel wall.

The engagement panels 110, 112, 114, 120, 122, 124, 130, 132, 134 can function to control, such as pinch the clot securely, in either or both axially and/or radially compressed directions. The engagement panels 110, 112, 114, 120, 122, 124, 130, 132, 134 can be used to pinch the clot during retrieving into a collection funnel or other device. The clot can be pinched between the engagement panels 110, 112, 114 at the first longitudinal location and the engagement panels 120, 122, 124 at the second longitudinal location. The clot can be pinched between the engagement panels 120, 122, 124 at the second longitudinal location and the engagement panels 130, 132, 134 at the third longitudinal location. For example, in some embodiments, the first longitudinal location engagement panels expand radially and outward to capture or pinch a portion of the clot either against the vessel wall and/or in between the open cavity. As the second longitudinal location engagement panels expand radially and outward, the engagement panels continue to capture or pinch a portion of the clot either against the vessel wall and/or in between the open cavity. The connect member, bridge extension 138 between the first longitudinal location and the second longitudinal location has tendency to pull the engagement panels of the first longitudinal location and the second longitudinal location together thereby creating a pinching effect and hold the clot better.

The engagement panels 110, 112, 114, 120, 122, 124, 130, 132, 134 are placed apart from each other creating a space or cavity for the clot or emboli to reside in. There is a space or cavity between the engagement panels 110, 112, 114 at the first longitudinal location and the engagement panels 120, 122, 124 at the second longitudinal location. There is a space between the first longitudinal location and the second longitudinal location for the clot or emboli. There is a space or cavity between the engagement panels 120, 122, 124 at the second longitudinal location and the engagement panels 130, 132, 134 at the third longitudinal location. There is a space between the second longitudinal location and the third longitudinal location for the clot or emboli.

The engagement panels 110, 112, 114, 120, 122, 124, 130, 132, 134 collapse, e.g., radially during delivery. The engagement panels 110, 112, 114, 120, 122, 124, 130, 132, 134 can be collapsed within the sheath 160. The engagement panels 110, 112, 114, 120, 122, 124, 130, 132, 134 can be folded inward. The engagement panels 110, 112, 114, 120, 122, 124, 130, 132, 134 can be folded against the catheter shaft 106.

The engagement panels 110, 112, 114, 120, 122, 124, 130, 132, 134 then expand or open at the treatment site in a manner that engage and pinch the clot securely for removal. The engagement panels 110, 112, 114, 120, 122, 124, 130, 132, 134 expand from the sheath 160. The legs 142, 144 bias each arc 140 radially outward toward the vessel wall. The legs 142, 144 provide support for the expanded engagement panel. The engagement panels 110, 112, 114, 120, 122, 124, 130, 132, 134 open at the treatment site. The engagement panels 110, 112, 114, 120, 122, 124, 130, 132, 134 capture the clot in the spaces between the first longitudinal location and the second longitudinal location. The engagement panels 110, 112, 114, 120, 122, 124, 130, 132, 134 capture the clot in the spaces between the second longitudinal location and the third longitudinal location. The engagement panels 110, 112, 114, 120, 122, 124, 130, 132, 134 can pull together along with the clot disposed in the spaces between the longitudinal locations. The engagement panels 110, 112, 114, 120, 122, 124, 130, 132, 134 can pull together along with the filter. The engagement panels 110, 112, 114, 120, 122, 124, 130, 132, 134 can pull together into a collection funnel, a guide catheter, or other device.

There are several potential advantages of the extractor 100. The engagement panels 110, 112, 114, 120, 122, 124, 130, 132, 134 open to deploy rather than radially expand like the stent retriever device. The engagement panels 110, 112, 114, 120, 122, 124, 130, 132, 134 open in some cases like petals of a flower. The engagement panels 110, 112, 114, 120, 122, 124, 130, 132, 134 pop outward once beyond the tip of the sheath 160. The engagement panels 110, 112, 114, 120, 122, 124, 130, 132, 134 radially expand without an axial movement, and unlike conventional expandable balloon or other retrieval members for example. The engagement panels 110, 112, 114, 120, 122, 124, 130, 132, 134 radially expand without axially shortening. The engagement panels 110, 112, 114, 120, 122, 124, 130, 132, 134 radially contract without axially lengthening. In contrast, conventional stent retriever devices can radially expand through a mesh-like structure. The stent retriever device can axially shorten as the device radially expands. When pulled, the stent retriever device can axially lengthen and pull away from the vessel wall.

The extractor 100 is functional when the engagement panels 110, 112, 114, 120, 122, 124, 130, 132, 134 open. The extractor 100 is functional when the engagement panels 110, 112, 114 at the first longitudinal location open. The extractor 100 is functional when the engagement panels 110, 112, 114 at the first longitudinal location and the engagement panels 120, 122, 124 at the second longitudinal location open. The extractor 100 is functional when the engagement panels 110, 112, 114 at the first longitudinal location, the engagement panels 120, 122, 124 at the second longitudinal location, and the engagement panels 130, 132, 134 at the third longitudinal location open. The extractor 100 is functional when one or more engagement panels 110, 112, 114 open. The extractor 100 is functional when partially deployed. The extractor 100 is functional to engage a clot once the engagement panels 110, 112, 114 are opened. The functional length of the extractor 100 is adjustable. The complete length of the extractor 100 is not required to be open to be functional, depending on the size of the clot and the desired clinical result. A partial, and less than full length of the extractor 100 can be opened, such as unsheathed in some cases, for the extractor 100 to be able to engage and remove the clot. The length of the extractor can range from, for example, 0.1 cm to 30 cm. In some embodiments, preferably, the extractor length is about 5 cm. In some embodiments, the extractor length is about 6 cm. In some embodiments, the extractor length is about 4 cm, or ranges including any two values as disclosed herein. The number of extractor engagement panels can range from, for example, one engagement panel to 150 engagement panels.

In contrast, conventional stent retriever devices generally must be fully deployed to be functional. The entire length of the stent retriever device must be opened from the catheter. The functional length of the stent retriever device is typically not adjustable.

The sheath 160 can unsheath the extractor 100 partially, such as half-way or even less in some cases, to expose some engagement panels while retaining some engagement panels inside the sheath 160. The engagement panels 110, 112, 114 at the first longitudinal location and the engagement panels 120, 122, 124 at the second longitudinal location can be opened (e.g., radially expanded), while the engagement panels 130, 132, 134 at the third longitudinal location can remain within the sheath 160. The engagement panels 110, 112, 114 at the first longitudinal location and the engagement panels 120, 122, 124 at the second longitudinal location can function to engage the clot. The engagement panels 110, 112, 114 at the first longitudinal location and the engagement panels 120, 122, 124 at the second longitudinal location can function to control, e.g., pinch the clot between the first longitudinal location and the second longitudinal location. The sheath 160 can unsheath the remaining engagement panels if needed for example. The sheath 160 can unsheath the engagement panels 130, 132, 134 at the third longitudinal location.

As the engagement panels 110, 112, 114, 120, 122, 124, 130, 132, 134 pull back, e.g., proximally within the body lumen to remove the clot obstruction, the engagement panels can be more resistant to compression or bending upon interacting with a clot obstruction. The engagement panels 110, 112, 114, 120, 122, 124, 130, 132, 134 can include legs 142, 144 which support the arc 140. The legs 142, 144 resist compression of the arc 140 of the engagement panels 110, 112, 114, 120, 122, 124, 130, 132, 134. The arc 140 of the engagement panels 110, 112, 114, 120, 122, 124, 130, 132, 134 can advantageously remain open even when the arc encounters a tough resistance such as an organized clot obstruction. The legs 142, 144 provide structural support to prevent the arc 140 from sliding past the clot without engaging the clot. The legs 142, 144 provide structural support to remove tough clots. The legs 142, 144 provide structural support to remove clots wedged against the vessel wall due to blow flow or pressure. In some embodiment, the legs of the engagement panels are longitudinally aligned. In some embodiments, the legs of the engagement panels can be offset from each other from, for example, about 1 to 179 degrees. For example, in some embodiments, the legs of the engagement panels are offset by 45 degrees. In some embodiment, the legs are offset by 90 degrees. In some embodiment, the legs of each engagement panel are offset from relative to the next engagement panel. As compared to conventional stent retriever devices, the stent retriever device will compress, and slide pass the clot against the vessel wall when encounter a tough resistance such as an organized clot obstruction particularly when the clot obstruction is further wedged due to blood flow or pressure.

The engagement panels 110, 112, 114, 120, 122, 124, 130, 132, 134 also can be configured to function independently. Each engagement panels 110, 112, 114, 120, 122, 124, 130, 132, 134 comprises the arc 140 and legs 142, 144 which are independent from the other engagement panels. There are multiple positions where the clot can engage and be captured with respect to the engagement panels during the retrieval. As the clot is trapped in the spaces between the engagement panels, the engagement panels 110, 112, 114 at the first longitudinal location and the engagement panels 120, 122, 124 at the second longitudinal location have a pinching effect to ensure the clot does not move relative to the extractor while in transit. The longitudinal separation between the engagement panels 110, 112, 114 at the first longitudinal location and the engagement panels 120, 122, 124 at the second longitudinal location creates a cavity or space for the clot to reside. As the clot is trapped in the spaces between the engagement panels, the engagement panels 120, 122, 124 at the second longitudinal location and the engagement panels 130, 132, 134 at the third longitudinal location have a pinching effect to ensure the clot does not move while in transit. The longitudinal separation between the engagement panels 120, 122, 124 at the second longitudinal location and the engagement panels 130, 132, 134 at the third longitudinal location creates a cavity or space for the clot to reside. There are multiple longitudinal separations between the engagement panels for the clot to reside.

The extractor 100 can include the plurality of spacers 150, 152, 154, 156. The spacer 150 can be located between the distal end 104 and the engagement panels 110, 112, 114. The spacer 150 can keep the engagement panels 110, 112, 114 apart from the filter. The spacer 152 can be located between the engagement panels 110, 112, 114 and the engagement panels 120, 122, 124. The spacer 152 can keep the engagement panels 110, 112, 114 apart from the engagement panels 120, 122, 124. The spacer 154 can be located between the engagement panels 120, 122, 124 and the engagement panels 130, 132, 134. The spacer 154 can keep the engagement panels 120, 122, 124 apart from the engagement panels 130, 132, 134. In some embodiments, the spacer 156 can be located between the engagement panels 130, 132, 134 and another set of engagement panels or the proximal end 102. The spacers 150, 152, 154, 156 keep the engagement panels apart. The spacers 150, 152, 154, 156 distance the sets of engagement panels from each other in a longitudinal direction. The spacer can be made of, for example, polymeric materials such as Pebax, Polyester, polyethylene, polypropylene, Polyurethane, silicone, or any combination of these materials. In some embodiments, the spacer can be made of metallic materials such as stainless steel, platinum, gold, silver, nitinol, or any combination of these materials. The spacer can be integrated into the extractor and the material can be, e.g., nitinol. The spacer 150, 152, 154, 156 can provide a pinching force. The spacer 150, 152, 154, 156 can provide a spring force. The spacer 150, 152, 154, 156 can provide a resistive force. The spacer 150, 152, 154, 156 can provide a compressive force. The spacer 150, 152, 154, 156 can bias the engagement panels toward each other. The spacer 150, 152, 154, 156 can function as a spring. The spacer 150, 152, 154, 156 can be passive. The engagement panels 110, 112, 114 can be biased toward the engagement panels 120, 122, 124 by the spacer 152. The engagement panel 120, 122, 124 can be biased toward the engagement panels 130, 132, 134 by the spacer 154. The spacers 150, 152, 154, 156 are not actuated in some cases. The spacers 150, 152, 154, 156 are not actively pulled toward each other in some cases. Rather, the spacers 150, 152, 154, 156 are passively actuated in some cases. The engagement panels 110, 112, 114 and the engagement panels 120, 122, 124 can be inherently biased toward each other. The engagement panels 120, 122, 124 and the engagement panels 130, 132, 134 can be inherently biased toward each other. The spacer 150, 152, 154, 156 can help to keep the engagement panels 110, 112, 114, 120, 122, 124, 130, 132, 134 open. The spacer 150, 152, 154, 156 can allow movement of the engagement panels 110, 112, 114, 120, 122, 124, 130, 132, 134. The spacer 150, 152, 154, 156 create a certain amount of biasing force. The spacers 150, 152, 154, 156 can be connected to eyelets of the engagement panels 110, 112, 114, 120, 122, 124, 130, 132, 134. The spacer 150, 152, 154, 156 can abut the eyelets.

The spacers 150, 152, 154, 156 can provide a force to separate the engagement panels from each other. The spacers 150, 152, 154, 156 can provide a separation force. The spacers 150, 152, 154, 156 provide a resistive force to keep the engagement panels separated. The force can range from, for example, 0.01 grams to 50 grams. The spacers 150, 152, 154, 156 can bias the engagement panels away from each other. The spacers 150, 152, 154, 156 can bias the engagement panels toward each other. The spacers 150, 152, 154, 156 can comprise a coiled wire. The spacers 150, 152, 154, 156 can comprise a tubular member. The spacers 150, 152, 154, 156 can comprise a polymer material such as Pebax, Polyester, polyethylene, polypropylene, Polyurethane, silicone or any combination of these materials. The spacers 150, 152, 154, 156 can comprise a shape memory material. The spacers 150, 152, 154, 156 can comprise a spring. The spacers 150, 152, 154, 156 can comprise a metal such as stainless steel, platinum, gold, silver, nitinol or any combination of these materials. The spacers 150, 152, 154, 156 can exert a force on adjacent engagement panels. The spacers 150, 152, 154, 156 can exert a force on engagement panels and an adjacent structure.

In some embodiments, the first longitudinal location has one engagement panel 110. The engagement panel 110 can form a generally circular profile, or a portion thereof. The engagement panel 110 can form the arc 140. The engagement panel 110 can include an approximately 360 degree arc. The engagement panel 110 can form a complete circle. In some embodiment, the eyelet 146 is located at the center of the one engagement panel configuration.

In some embodiments, the first longitudinal location has two engagement panels 110, 112. Each engagement panels 110, 112 can be considered a section or loop. Each engagement panel 110, 112 can include an arc 140 which forms a portion of a circle or other arcuate geometry. Each engagement panel 110, 112 can include the arc 140 of approximately 180 degrees or more or less. Each engagement panel 110, 112 can include the arc 140 that is semi-circular. In some embodiment, the engagement panel 110, 112 does not form a complete circular shape such as a semi-circular shape, three-quarter of a circular shape, a partial of a circular shape, or any partial circular shape less than 360 degrees. In some embodiments, the partial circular shape is offset from one engagement panel to the next. In some embodiments, the engagement panel 110, 112 form a complete circular shape. In some embodiments, the eyelet 146 is located at the center of the multi, e.g., two engagement panel configuration.

In some embodiment, the first longitudinal location has three engagement panels 110, 112, 114. Each engagement panels 110, 112, 114 can be considered a section or loop. Each engagement panel 110, 112, 114 can include an arc 140 which forms a portion of a circle. Each engagement panel 110, 112, 114 can include the arc 140 of approximately 120 degree. In some embodiments, the three engagement panels arc does not form a complete circular shape. In some embodiments, the three engagement panels arc form a partial circular shape such as three-quarter shape, semi-circular shape, or any partial circular shape less than 360 degrees. The engagement panels 110, 112, 114 have three sections or loops at a single longitudinal location. In some embodiment, the eyelet 146 is located at the center of the three engagement panel configuration.

In some embodiments, the first longitudinal location has four engagement panels. Each engagement panel can include an arc which forms a portion of a circle. Each engagement panel can include the arc of approximately 90 degree. In some embodiments, the four engagement panels arc does not form a complete circular shape. In some embodiments, the three engagement panels arc form a partial circular shape such as three-quarter shape, semi-circular shape, or any partial circular shape less than 360 degrees. In some embodiments, the eyelet 146 is located at the center of the four engagement panel configuration. In some embodiments, the first longitudinal location has five engagement panels. Each engagement panel can include the arc of approximately 72 degrees. In some embodiments, the eyelet 146 is located at the center of the five engagement panel configuration. In some embodiments, the first longitudinal location has six engagement panels. Each engagement panel can include the arc of approximately 60 degrees. In some embodiments, the eyelet 146 is located at the center of the six engagement panel configuration.

The eyelet 146 can be formed at the center of the engagement panels. The eyelet 146 can be formed at the center of the engagement panels 110, 112, 114. In some embodiment, the multiple engagement panel configuration generally surrounds the eyelet 146. In some embodiment, the engagement panels 110, 112, 114 is continuously connecting over the catheter shaft 106 in a spiral configuration. Each engagement panels 110, 112, 114 can include an additional arc that forms the eyelet 146. Each engagement panels 110, 112, 114 can form a portion of the eyelet 146. At the center of the engagement panels 110, 112, 114 is the eyelet 146. The eyelet 146 can be a shaped set circular eyelet. The eyelet 146 can be multiple coils members.

The engagement panels 110, 112, 114 can be made from one continuous wire. The engagement panels 110, 112, 114 can be made from individual wire members for each engagement panel. The individual wire members can be coupled to form the engagement panels 110, 112, 114 at the first longitudinal location. The engagement panels 110, 112, 114 can include additional segments that form the eyelet. The engagement panels 110, 112, 114 can include coils that reinforce the eyelet.

The spacers 150, 152, 154, 156 can help to maintain the separation between the engagement panels 110, 112, 114, 120, 122, 124, 130, 132, 134. When the clot is ready to be retrieved, the extractor 100 can be pulled. This pulling tension creates a pinching effect upon contacting the clot. In some embodiment, the spacers 150, 152, 154, 156 can be integrated onto the extractor 100. Each spacer 150, 152, 154, 156 can be formed with a member that is coiled along the length of extractor and connecting the eyelets 146. Each spacer 150, 152, 154, 156 can be integrally formed with the engagement panels 110, 112, 114, 120, 122, 124, 130, 132, 134. Each spacer 150, 152, 154, 156 can be integrally formed with the eyelets 146.

In some embodiment, the spacers 150, 152, 154, 156 can be separately formed from the engagement panels 110, 112, 114, 120, 122, 124, 130, 132, 134. Each spacer 150, 152, 154, 156 can be a tubular member disposed along the length of the extractor 100. Each spacer 150, 152, 154, 156 can be formed with a member that is coiled. Each spacer 150, 152, 154, 156 can be separately formed from the engagement panels 110, 112, 114, 120, 122, 124, 130, 132, 134. Each spacer 150, 152, 154, 156 can be separately formed from the eyelets 146. In some embodiment, the engagement panels couple to the catheter shaft without the spacer. In some embodiment, the engagement panels couple to the catheter shaft without a space therebetween. In some embodiment, the engagement panels couple to the catheter shaft in series, adjacent to one another.

The engagement panels 110, 112, 114, 120, 122, 124, 130, 132, 134 can be at various angles relative to a center axis 108. The center axis 108 can extend along the length of the catheter shaft 106. The engagement panels 110, 112, 114 can be at a first angle relative to the center axis 108. The first angle can range from 45 degrees to 135 degrees relative to the center axis 108. The engagement panels 120, 122, 124 can be at a second angle relative to the center axis 108. The second angle can range from 45 degrees to 135 degrees relative to the center axis 108. The engagement panels 130, 132, 134 can be at a third angle relative to the center axis 108. The third angle can range from 45 degrees to 135 degrees relative to the center axis 108. The first angle and the second angle can be the same angle. The first angle and the second angle can be different angles. The first angle, the second angle, and the third angle can be the same angle. The first angle, the second angle, and the third angle can be different angles. The extractor 100 can include a plurality of engagement panels 110, 112, 114, 120, 122, 124, 130, 132, 134.

The engagement panels 110, 112, 114, 120, 122, 124, 130, 132, 134 can angle in the same direction distally. The engagement panels 110, 112, 114, 120, 122, 124, 130, 132, 134 can angle in the same direction proximally. The engagement panels 110, 112, 114 and the engagement panels 120, 122, 124 can angle in the same direction. The engagement panels 110, 112, 114 and the engagement panels 120, 122, 124 can angle in different direction. The engagement panels 110, 112, 114 and the engagement panels 120, 122, 124 can angle in alternate manner. The engagement panels 120, 122, 124 and the engagement panels 130, 132, 134 can angle in alternate manner. The engagement panels 110, 112, 114, 120, 122, 124, 130, 132, 134 can angle in alternate manner for each engagement panels at a longitudinal location such that one engagement panels at the first longitudinal location can angle toward distally and the adjacent engagement panels at the second longitudinal location angle toward proximally.

The engagement panels 110, 112, 114 can have a diameter. The diameter of the engagement panels 110, 112, 114 can be, e.g., about 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, or more or less, between 2 and 8 mm, or any range of the foregoing values. The engagement panels 120, 122, 124 can have a diameter. The diameter of the engagement panels 120, 122, 124 can be, e.g. about 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, or more or less, between 2 and 8 mm, or any range of the foregoing values. The diameter of the engagement panels 110, 112, 114, and the diameter of the engagement panels 120, 122, 124 can be the same. The diameter of the engagement panels 110, 112, 114, and the diameter of the engagement panels 120, 122, 124 can be different. The diameter of the engagement panels can be different or alternating diameter between the engagement panels.

In some embodiments, the diameter of the engagement panels 110, 112, 114 and the diameter of the engagement panels 120, 122, 124 are about 4 mm. In some embodiments, the diameter of the engagement panels 110, 112, 114, the diameter of the engagement panels 120, 122, 124, the diameter of the engagement panels 130, 132, 134 are about 4 mm. In some embodiments, the diameter of the engagement panels 110, 112, 114 and the diameter of the engagement panels 120, 122, 124 are about 5 mm. In some embodiments, the diameter of the engagement panels 110, 112, 114, the diameter of the engagement panels 120, 122, 124, the diameter of the engagement panels 130, 132, 134 are about 5 mm. In some embodiments, the diameter of the engagement panels 110, 112, 114 and the diameter of the engagement panels 120, 122, 124 are about 6 mm. In some embodiments, the diameter of the engagement panels 110, 112, 114, the diameter of the engagement panels 120, 122, 124, the diameter of the engagement panels 130, 132, 134 are about 6 mm. In some embodiments, the diameter of the engagement panels 110, 112, 114, the diameter of the engagement panels 120, 122, 124, the diameter of the engagement panels 130, 132, 134 have an alternating diameter of about 4 mm and about 6 mm along the length of the extractor 100. In some embodiments, the diameter of the engagement panels 110, 112, 114, the diameter of the engagement panels 120, 122, 124, the diameter of the engagement panels 130, 132, 134 have an alternating diameter of about 4 mm and about 5 mm along the length of the extractor 100. In some embodiments, the diameter of the engagement panels 110, 112, 114, the diameter of the engagement panels 120, 122, 124, the diameter of the engagement panels 130, 132, 134 have an alternating diameter of about 3 mm and about 4 mm along the length of the extractor 100.

In some embodiments, the spacers 150, 152, 154, 156 can be loosely fit. The spacers 150, 152, 154, 156 can be movable along the catheter shaft 106. The spacers 150, 152, 154, 156 can be moveable relative to the eyelets 146. The spacers 150, 152, 154, 156 can be movable relative to the engagement panels 110, 112, 114, 120, 122, 124, 130, 132, 134. The spacers 150, 152, 154, 156 can create tension between the engagement panels 110, 112, 114, 120, 122, 124, 130, 132, 134. In some embodiments, the spacers 150, 152, 154, 156 can be fixed to remove the tension between the engagement panels 110, 112, 114, 120, 122, 124, 130, 132, 134.

FIGS. 1-3 illustrate the extractor 100, the spacers 150, 152, 154, 156, and the collection funnel. The extractor 100 can be made of a wire member. The extractor 100 can be formed in a helix-like shape. The extractor 100 can be formed with a series of round eyelets 146. The extractor 100 can be formed with a series of legs 142, 144. The extractor 100 can be formed with a series of arcs 140. The extractor 100 can be formed with connecting members 118, 128, 138. The extractor 100 can be formed with one continuous wire member defining all, or a subset of the engagement members, including legs, arcs, and/or spacers. The extractor 100 can be formed with one or more wires.

The eyelet 146 connects to the legs 142, 144. The leg 142 extend outward where the leg 142 is connected to the arc 140. The arc 140 is connected to the next leg 144 where the leg 144 is connected to the next eyelet 146. The continuation of the series of eyelets 146, legs 142, 144, and arcs 140 form the extractor 100. Each eyelet 146 can be independent of other eyelets. Each eyelet 146 can be connected together. The legs 142, 144 and the arc 140 aid in applying tension when the eyelets 146 are spaced apart. In the unconstrained position, the eyelets 146 are positioned adjacent to each other. The eyelets 146 are separated by the spacer 150, 152, 154, 156 to keep the eyelets 146 apart. In some embodiment, the spacer 150, 152, 154, 156 can be integrated as part of the extractor 100.

The wire member of the extractor 100 can be made of metallic material. The wire member of the extractor 100 can be made, for example, of a shape memory material such as Nitinol. The wire member of the extractor 100 can have a diameter of, e.g. about 0.0005", 0.001", 0.0015", 0.002", 0.0025", 0.003", 0.0035", 0.004", 0.0045", 0.005", or more or less, from 0.0005" to 0.005", or any range of two of the foregoing values.

The filter can be positioned at the distal end of the catheter shaft 106. The filter can be made, in some cases, of dual nitinol braid layer. The filter can attach to the distal end of the catheter shaft 106. The extractor 100 can be proximal to the filter. The spacers 150, 152, 154, 156 can be positioned between the eyelets 146 to keep the eyelets 146 apart and to create a space to capture the clot.

The extractor 100 can be made of a wire member that is formed with a series of round eyelets 146, spacers 150, 152, 154, 156 formed as coils, the legs 142, 144 and the arcs 140. The eyelet 146 connects to the leg 142 that extends outward where the leg 142 is connected to the arc 140. The arc 140 is connected to the next leg 144 where it is connected to the next eyelet 146. The continuation of the series of the eyelets 146, the legs 142, 144 and the arc 140 form the extractor 100. The legs 142, 144 and the arc 140 aid in applying tension when the eyelets 146 are spaced apart. In the unconstrained position, the eyelets 146 are positioned adjacent to each other. The eyelets 146 are separated by the spacer 150, 152, 154, 156 to keep the eyelets 146 apart. The spacer 150, 152, 154, 156 is positioned between the eyelets 146 to keep the eyelets 146 apart and to create a space opening to capture the clot. In some embodiment, the spacer 150, 152, 154, 156 is made of coil. The spacer 150, 152, 154, 156 formed from the coil can be part of the extractor 100. The spacer 150, 152, 154, 156 formed from the coil can be separate from the extractor 100. The spacer 150, 152, 154, 156 formed from the coil can be close pitch or loose pitch which can be spring-like.

The extractor 100 can be made of a wire member that is formed in a helix-like shaped with series of round eyelets 146, the legs 142, 144, and the arcs 140. The helix-like shaped can be a single helix. In some embodiments, the helix can be a double helix. In some embodiments, the helix can be a triple helix or more. The eyelet 146 connects to the leg 142 that extends outward where the leg 142 is connected to the arc 140. The other end of the arc 140 is connected to the next leg 144 that is connected to the next eyelet 146. Continuation of the series of eyelets 146, the legs 142, 144 and the arcs form the extractor 100. Each eyelet 146 can be independent of the other eyelet 146 or connected to the adjacent eyelet 146. In some embodiments, the eyelets 146, the legs 142, 144 and the arcs 140 are connected by a single wire. The legs 142, 144 and the arcs 140 can apply tension when the eyelets 146 are spaced apart. In the unconstrained position, the eyelets 146 are position adjacent to each other. The eyelets 146 are separated by the spacer 150, 152, 154, 156 to keep the eyelets 146 apart. In some embodiment, the spacer 150, 152, 154, 156 can be integrated with the extractor. The wire member can be made of, e.g., one or more metallic materials such as nitinol. The wire member diameter can range from, e.g., 0.0005" to 0.005". The extractor 100 can be compressed in the delivery configuration to the intended treatment site through a sheath or a catheter. The extractor 100 is expanded as it is unsheathed. The extractor length can be unsheathed as needed for use as the entire length of the extractor 100 does not need to be open for the extractor 100 to be functional. In some embodiment, a filter can be used and is positioned distal to the extractor and aids in capturing fragmented clot or emboli during the removal of the extractors. The filter can be compressed during delivery and expand when unsheathed. The filter aids in capturing potential fragmented clot or emboli when retrieving the clot or emboli. In some embodiment, there is a collection funnel used to capture the extractor 100 and the filter with clot. The collection funnel can be positioned proximal to the extractor 100.

To use the extractor 100, a guidewire can be used to access the treatment area. A guide catheter with balloon tip can be placed in the carotid artery. The sheath 160 can be introduced through the guide catheter to the treatment site. The extractor 100, the filter and the collection funnel can introduced over the guidewire to the treatment site via the sheath 160. The sheath 160 is then unsheathed to deploy the filter and the extractor 100 and the collection funnel. The sheath 160, the extractor 100 and the filter then withdraw into the collection funnel. Once inside the collection funnel, the entire system is withdrawn into the guide catheter. In some embodiment, a collection funnel is introduced and position near the treatment site via the balloon catheter. The sheath 160 is introduced via the collection funnel to the treatment site. The extractor 100 and the filter are introduced through the sheath 106 to the treatment site. The sheath 160 is then retracted to deploy the extractor 100 and the filter. The sheath 160, the extractor 100 and the filter withdraw into the collection funnel. The entire assembly is then withdrawn into the guide catheter from the vascular system.

FIG. 4A through 4G represents the extractor deployment. The extractor 100 is first inside the sheath 160 in FIG. 4A. Then, the sheath 160 is unsheathed (e.g., moved in a direction longitudinally along the extractor) to fully deploy the engagement panels 110, 112, 114 of the extractor 100 in FIG. 4G. The extractor 100 has three engagement panels 110, 112, 114. The engagement panels 110, 112, 114 are at the first longitudinal location. The engagement panels 110, 112, 114 can deploy together. The engagement panels 110, 112, 114 can deploy simultaneously. The engagement panels 110, 112, 114 can deploy as the sheath 160 moves past the first longitudinal location. The engagement panels 110, 112, 114 open like a flower. The arcs 140 of the engagement panels 110, 112, 114 deploy first as the sheath 160 moves. The legs 142, 144 gradually deploy as the sheath 160 moves. The legs 142, 144 fully deploy thereby expanding the arcs 140. The engagement panels 110, 112, 114 open to the expanded diameter when the legs 142, 144 are unsheathed. The engagement panels 110, 112, 114 are fully deployed. The engagement panels 110, 112, 114 can function to engage a clot.

Figure 5A:
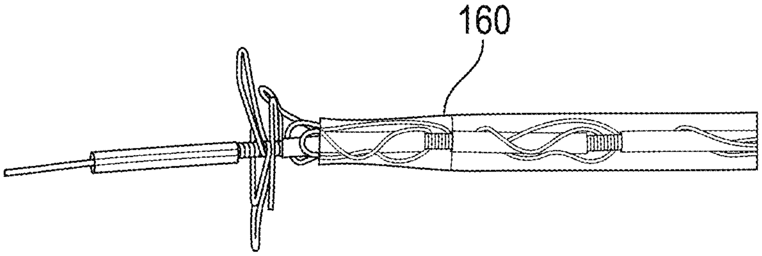
FIGS. 5A-5G are views of deployment of the second panel of the first embodiment of the three engagement panels extractor.
Figure 5B:
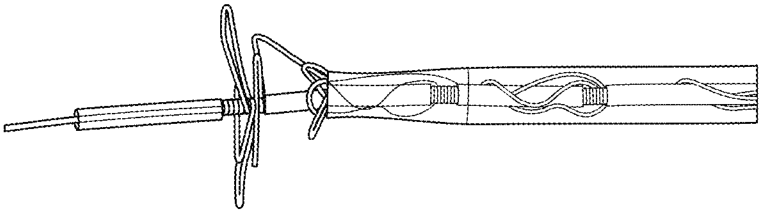
Figure 5C:
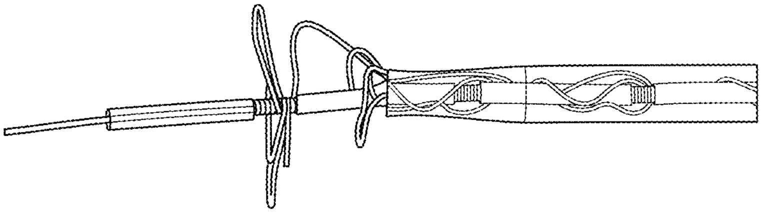
Figure 5D:
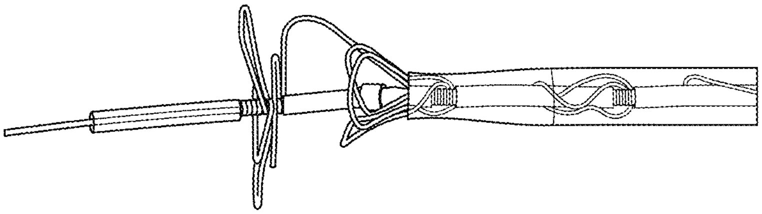
Figure 5E:
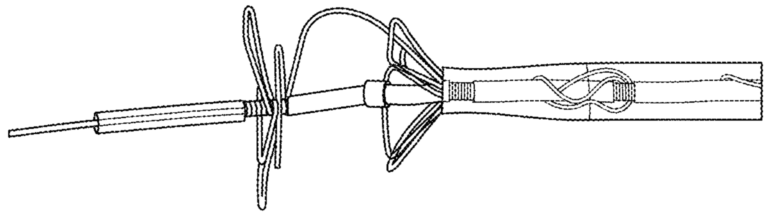
Figure 5F:
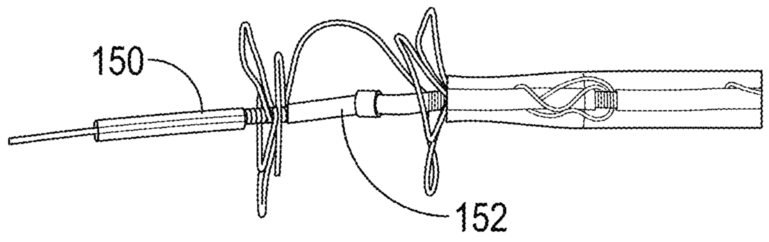
Figure 5G:
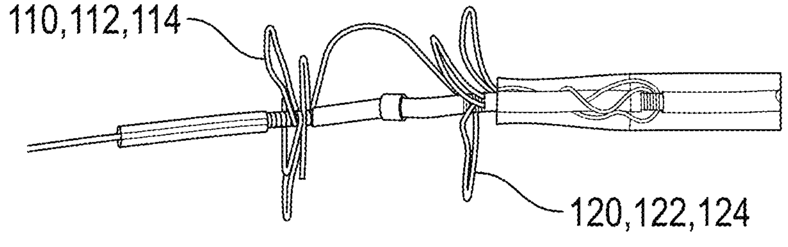

FIG. 5A though 5G represents the deployment of the engagement panels 120, 122, 124 of the extractor 100. The engagement panels 110, 112, 114 are fully deployed. The engagement panels 120, 122, 124 of the extractor 100 are first inside the sheath 160 in FIG. 5A. Then, the sheath 160 is unsheathed to fully deploy the engagement panels 120, 122, 124 of the extractor 100 in FIG. 5G. The extractor 100 has three engagement panels 120, 122, 124. The engagement panels 120, 122, 124 are at the second longitudinal location. The engagement panels 120, 122, 124 can deploy together. The engagement panels 120, 122, 124 can deploy simultaneously. The engagement panels 120, 122, 124 can deploy as the sheath 160 moves past the second longitudinal location. The engagement panels 120, 122, 124 open like a flower. The arcs 140 of the engagement panels 120, 122, 124 deploy first as the sheath 160 moves. The legs 142, 144 gradually deploy as the sheath 160 moves. The legs 142, 144 fully deploy thereby expanding the arcs 140. The engagement panels 120, 122, 124 open to the expanded diameter when the legs 142, 144 are unsheathed. The engagement panels 120, 122, 124 are fully deployed. The engagement panels 120, 122, 124 can function to engage a clot. The engagement panels 110, 112, 114 and the engagement panels 120, 122, 124 can function to pinch a clot therebetween.

FIG. 6A through 6G represents the extractor deployment of an extractor 200. The extractor 200 can have any of the features described herein. The extractor 200 can have a plurality of engagement panels 210, 212, 214, 216, 220, 222, 224, 226, 230, 232, 234, 236. The engagement panels 210, 212, 214, 216 are located at a first longitudinal location. The engagement panels 220, 222, 224, 226 are located at a second longitudinal location. The engagement panels 230, 232, 234, 236 are located at a third longitudinal location. The first longitudinal location can be distal to the second longitudinal location. The second longitudinal location can be distal to the third longitudinal location. In the illustrated embodiment, there are four engagement panels at each longitudinal location. The engagement panels 210, 212, 214, 216 can form a generally round profile. The engagement panels 210, 212, 214, 216 at a single longitudinal location can form a circular profile. Each engagement panel 210, 212, 214, 216 can form a portion of a circle. Each engagement panel 210, 212, 214, 216 can form an arc 240. Each engagement panel 210, 212, 214, 216 can include an approximately 90 degree arc. Each engagement panel 210, 212, 214, 216 can form an arc of, e.g. about 75 degrees, 80 degrees, 81 degrees, 82 degrees, 83 degrees, 84 degrees, 85 degrees, 86 degrees, 87 degrees, 88 degrees, 90 degrees, less than 90 degrees, greater than 80 degrees, or any range of two of the foregoing values. Each engagement panel 210, 212, 214, 216 can form an arc that forms part of a circular profile. Each engagement panel 210, 212, 214, 216 can form the same arc. Each engagement panel 210, 212, 214, 216 can form a different arc. The two legs 242, 244 connect to an arc 240 of engagement panel 210, 212, 214, 216. The two legs 242, 244 can be linear. The two legs 242, 244 can have a constant angle therebetween. The two legs 242, 244 can connect to the ends of the arc 240.

Figure 6A:
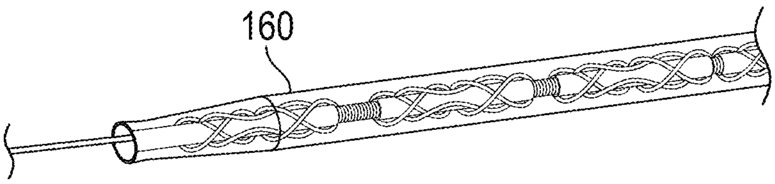
FIGS. 6A-6G are views of deployment of the first panel of a second embodiment of the four engagement panels extractor.
Figure 6B:
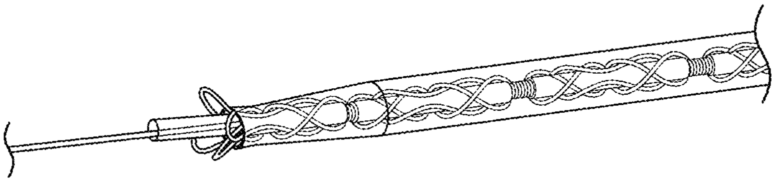
Figure 6C:
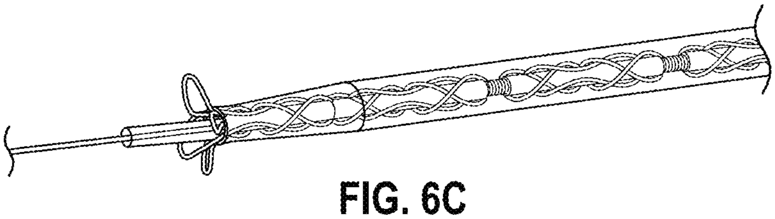
Figure 6D:
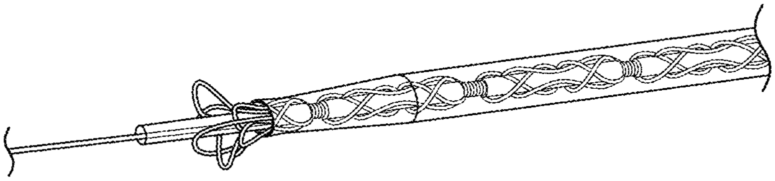
Figure 6E:
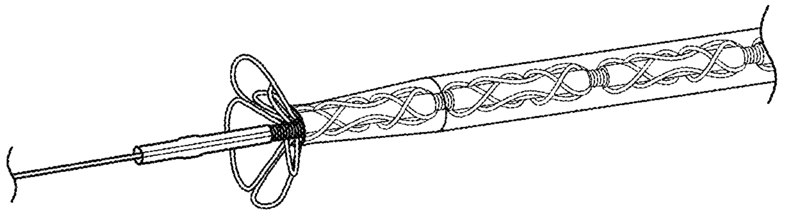
Figure 6F:
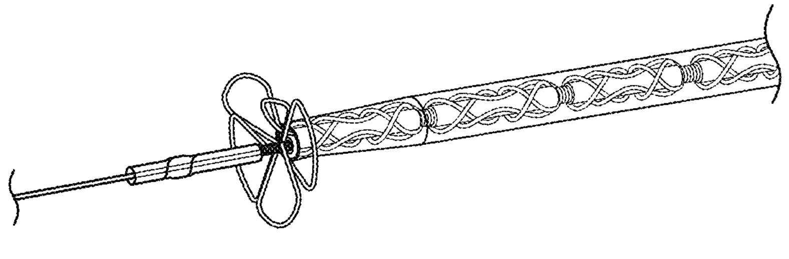
Figure 6G:
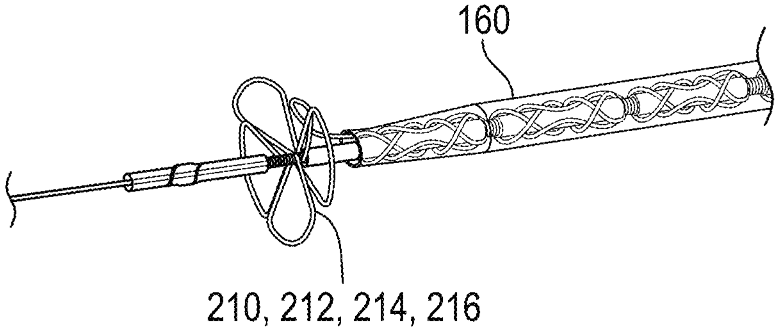

The extractor 200 is first inside the sheath 160 in FIG. 6A. Then, the sheath 160 is unsheathed to fully deploy the engagement panels 210, 212, 214, 216 of the extractor 200 in FIG. 6G. The extractor 200 has three engagement panels 210, 212, 214, 216. The engagement panels 210, 212, 214, 216 are at the first longitudinal location. The engagement panels 210, 212, 214, 216 can deploy together. The engagement panels 210, 212, 214, 216 can deploy simultaneously. The engagement panels 210, 212, 214, 216 can deploy as the sheath 160 moves past the first longitudinal location. The engagement panels 210, 212, 214, 216 open like a flower. The arcs 240 of the engagement panels 210, 212, 214, 216 deploy first as the sheath 160 moves. The legs 242, 244 gradually deploy as the sheath 160 moves. The legs 242, 244 fully deploy thereby expanding the arcs 240. The engagement panels 210, 212, 214, 216 open to the expanded diameter when the legs 242, 244 are unsheathed. The engagement panels 210, 212, 214, 216 are fully deployed. The engagement panels 210, 212, 214, 216 can function to engage a clot. In some embodiments, the extractor 200 can include a distal member 280. The distal member 280 can include any feature described herein. In some embodiments, the distal member 280 can deploy before the engagement panels 210, 212, 214, 216.

Figure 7A:
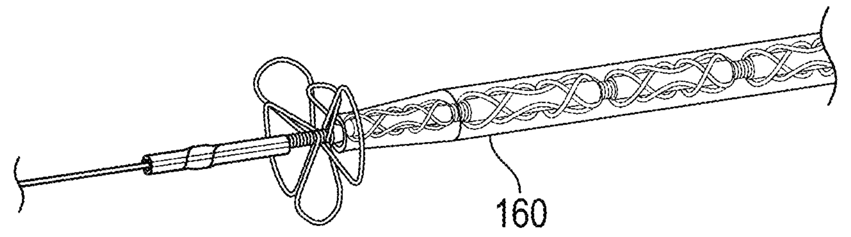
FIGS. 7A-7G are views of deployment of the second panel of an extractor the second embodiment of the four engagement panels extractor.
Figure 7B:
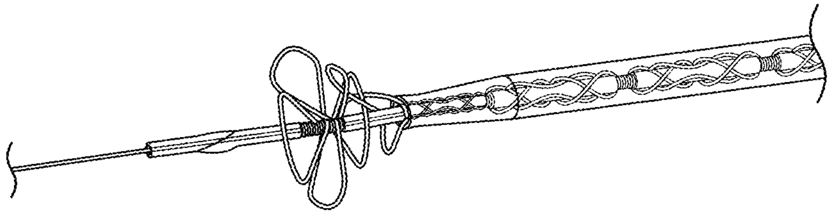
Figure 7C:
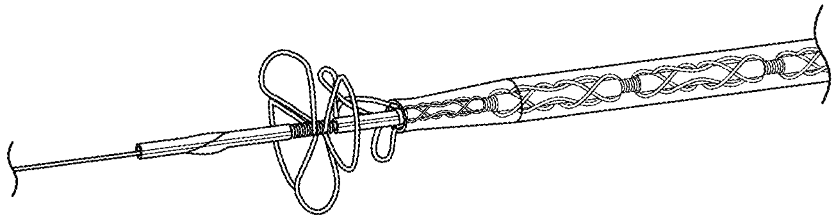
Figure 7D:
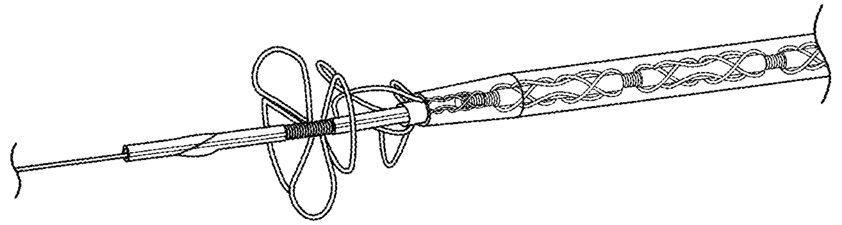
Figure 7E:
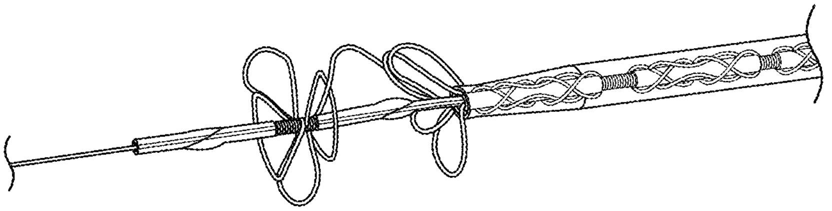
Figure 7F:
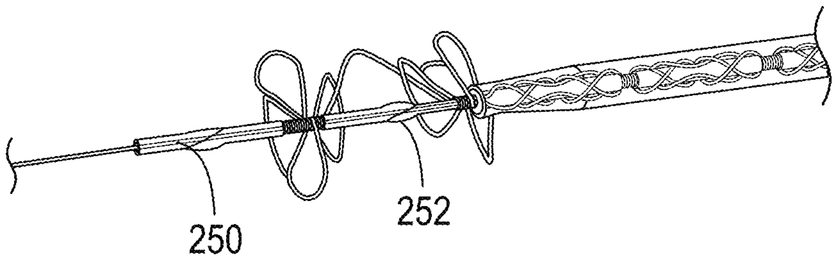
Figure 7G:
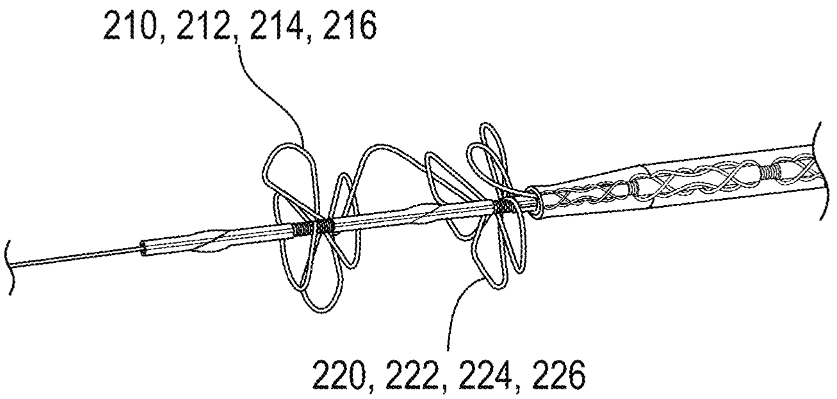

FIG. 7A though 7G represents the deployment of the engagement panels 220, 222, 224, 226 of the extractor 200. The engagement panels 210, 212, 214, 216 are fully deployed. The engagement panels 220, 222, 224, 226 of the extractor 200 are first inside the sheath 160 in FIG. 7A. Then, the sheath 160 is unsheathed to fully deploy the engagement panels 220, 222, 224, 226 of the extractor 200 in FIG. 7G. The extractor 200 has three engagement panels 220, 222, 224, 226. The engagement panels 220, 222, 224, 226 are at the second longitudinal location. The engagement panels 220, 222, 224, 226 can deploy together. The engagement panels 220, 222, 224, 226 can deploy simultaneously. The engagement panels 220, 222, 224, 226 can deploy as the sheath 160 moves past the second longitudinal location. The engagement panels 220, 222, 224, 226 open like a flower. The arcs 240 of the engagement panels 220, 222, 224, 226 deploy first as the sheath 160 moves. The legs 242, 244 gradually deploy as the sheath 160 moves. The legs 242, 244 fully deploy thereby expanding the arcs 240. The engagement panels 220, 222, 224, 226 open to the expanded diameter when the legs 242, 244 are unsheathed. The engagement panels 220, 222, 224, 226 are fully deployed. The engagement panels 220, 222, 224, 226 can function to engage a clot. The engagement panels 210, 212, 214, 216 and the engagement panels 220, 222, 224, 226 can function to pinch a clot therebetween.

Figure 8A:
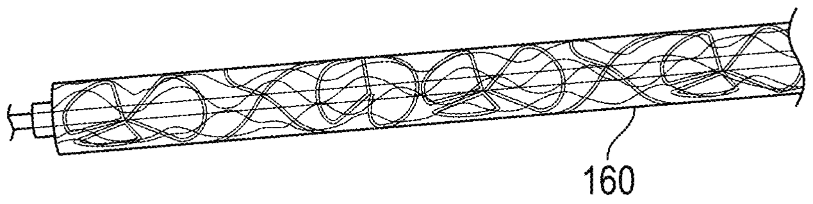
FIGS. 8A-8G are views of further detailed deployment of the first panel of the first embodiment of the extractor.
Figure 8B:
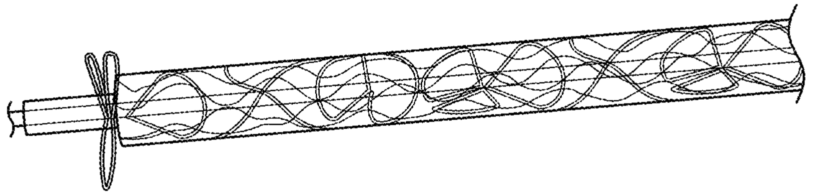
Figure 8C:
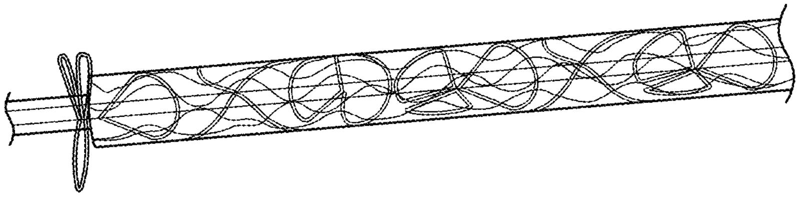
Figure 8D:
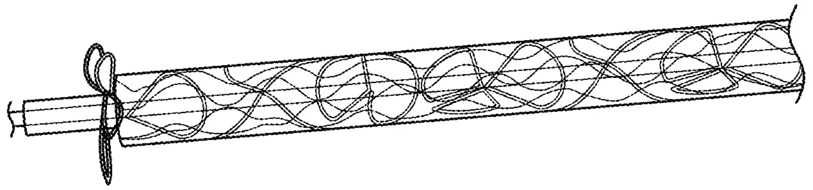
Figure 8E:
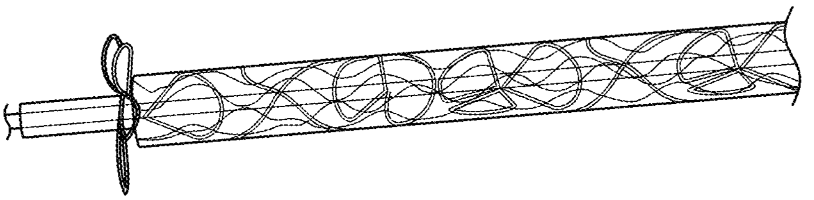
Figure 8F:
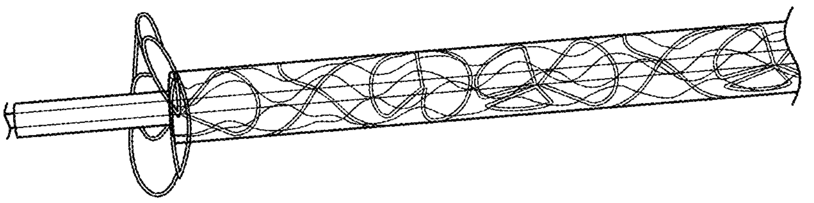
Figure 8G:
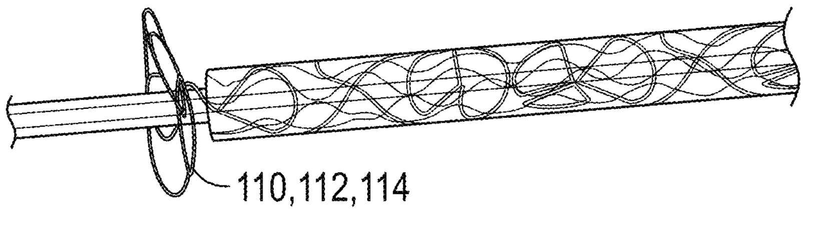
Figure 9A:
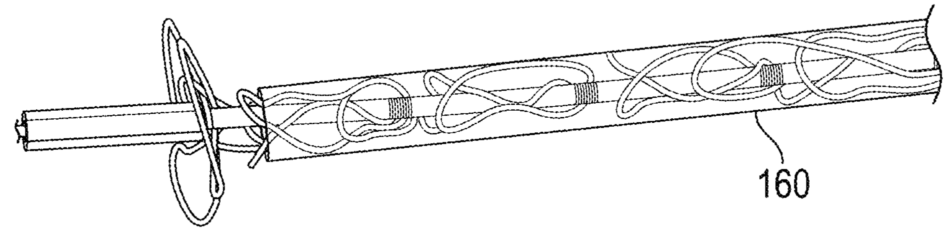
FIGS. 9A-9H are views of further detailed deployment of the second panel of the first embodiment of the extractor.
Figure 9B:
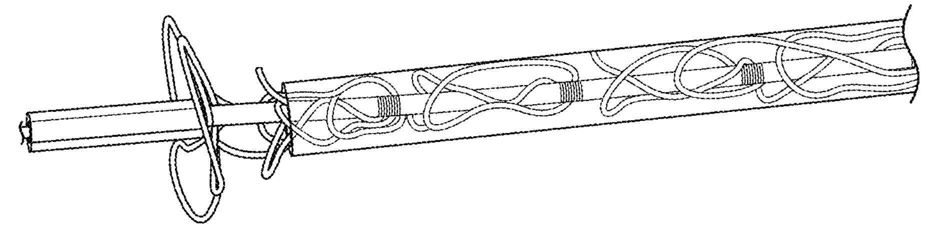
Figure 9C:
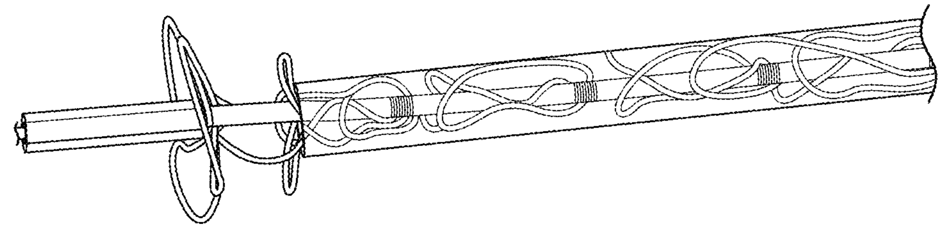
Figure 9D:
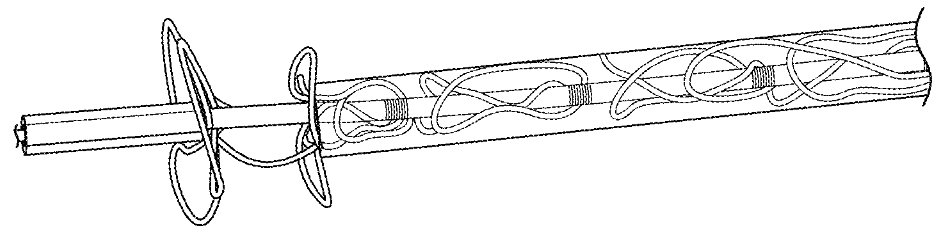
Figure 9E:
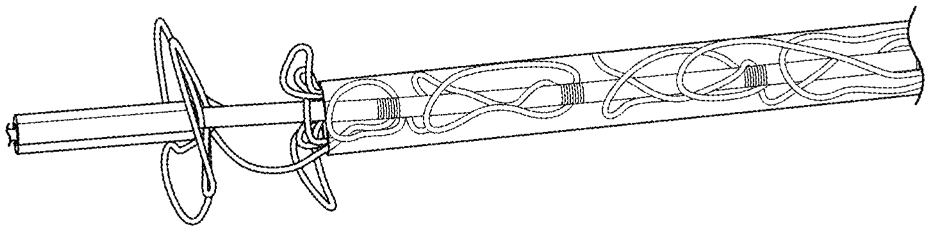
Figure 9F:
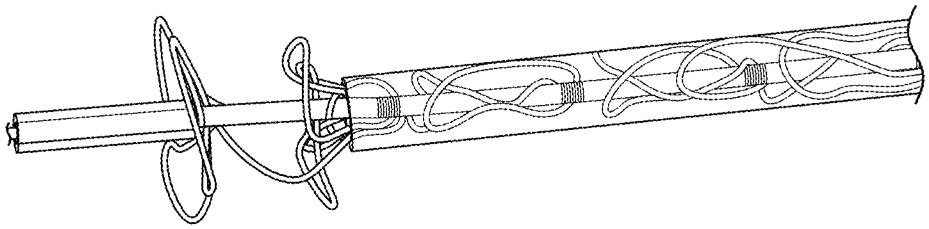
Figure 9G:
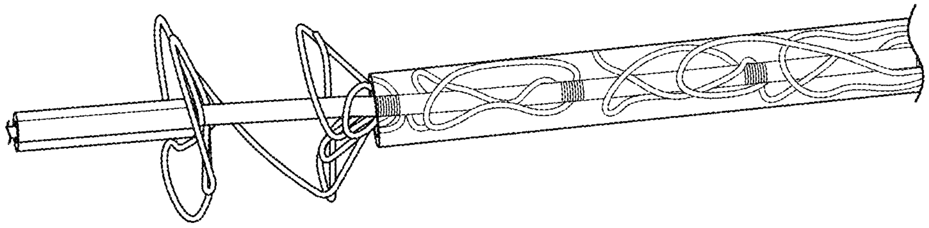
Figure 9H:
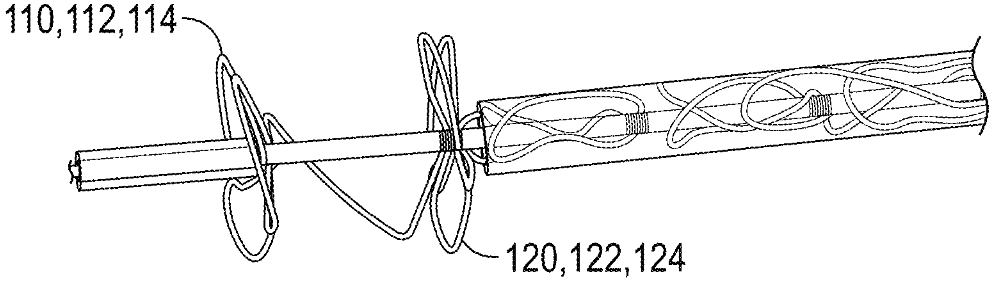

FIG. 8A through 8G represents the extractor deployment where the extractor 100 is first inside the sheath in FIG. 8A, then the sheath 106 is unsheathed to fully deploy the engagement panels 110, 112, 114 in FIG. 8G. FIG. 9A though 9H represents the deployment of the engagement panels 120, 132, 134 of the extractor 100. The engagement panels 110, 112, 114 are fully deployed. The engagement panels 120, 122, 124 of the extractor 100 are first inside the sheath 160 in FIG. 9A. Then, the sheath 160 is unsheathed to fully deploy the engagement panels 120, 122, 124 of the extractor 100 in FIG. 9H. The extractor 100 has three engagement panels 120, 122, 124. The engagement panels 120, 122, 124 are at the second longitudinal location. The engagement panels 120, 122, 124 can deploy together. The engagement panels 120, 122, 124 can deploy such that a portion of the engagement panels 120, 122, 124 is proximal to the distal end of the sheath 160 in FIG. 9E. The engagement panels 120, 122, 124 can wrap around the distal end during deployment. The engagement panels 120, 122, 124 can extend proximally during deployment. The engagement panels 120, 122, 124 can be distal to the distal end of the sheath 160 when fully deployed. The initial expanded portion of the engagement panels revert proximally when the engagement panels first deploy.

Figure 10:
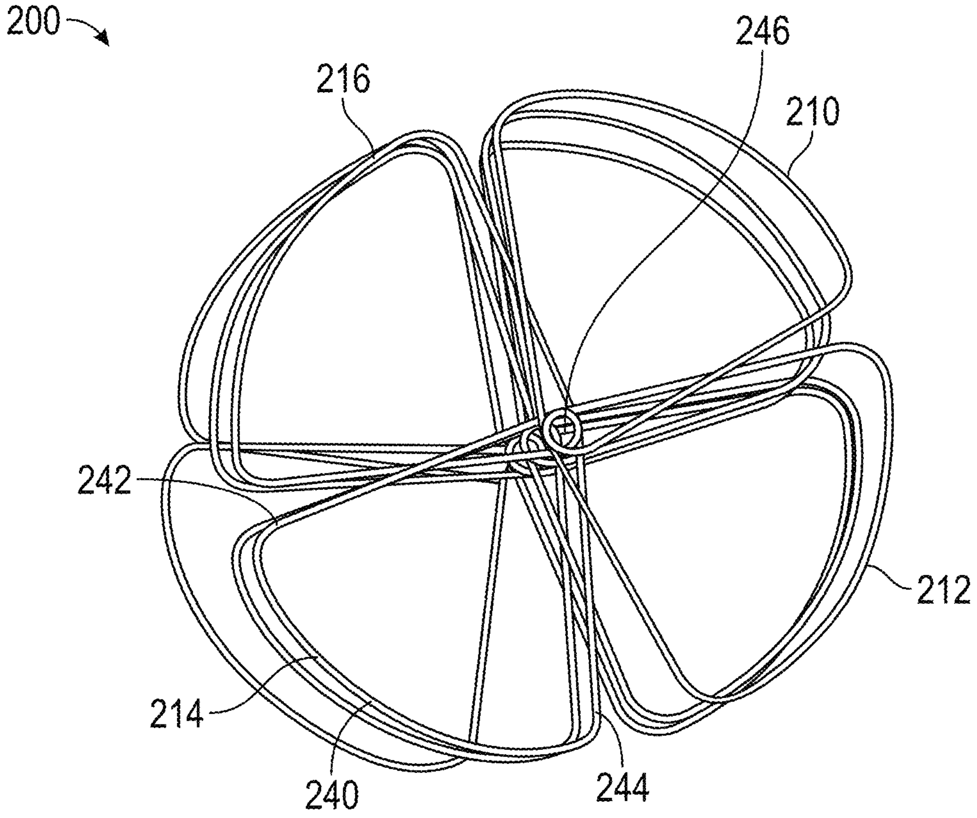
FIG. 10 is a top view of the second embodiment of the four engagement panels extractor.
Figure 11:
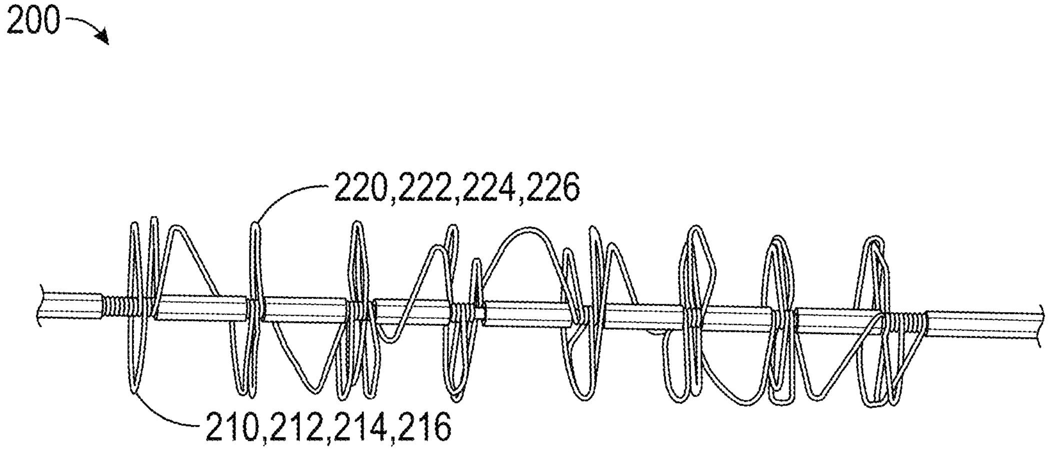
FIGS. 11-14 are side views of the second embodiment of the four engagement panels extractor.
Figure 12:
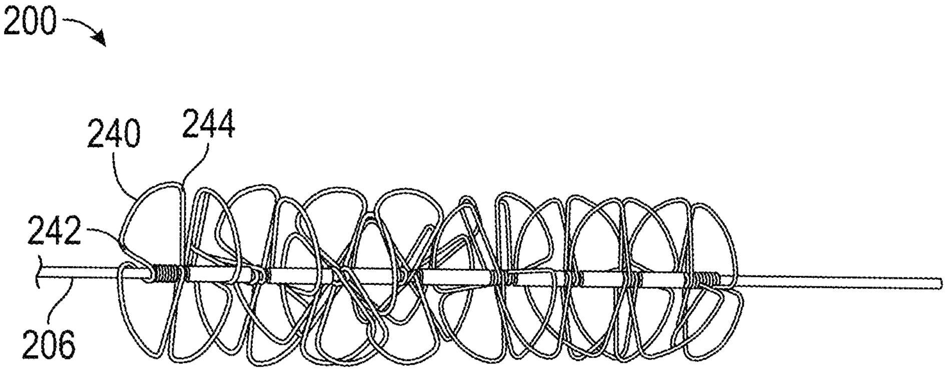
Figure 13:
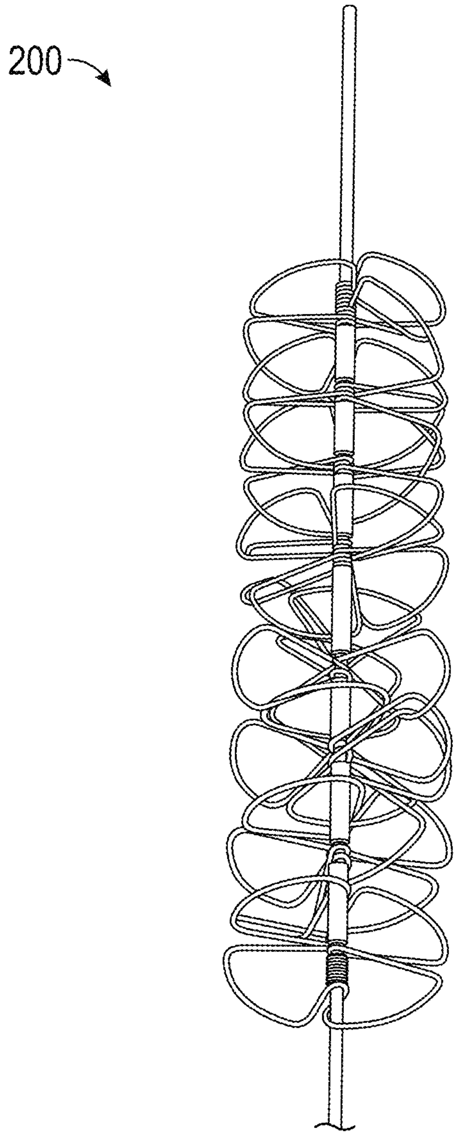
Figure 14:
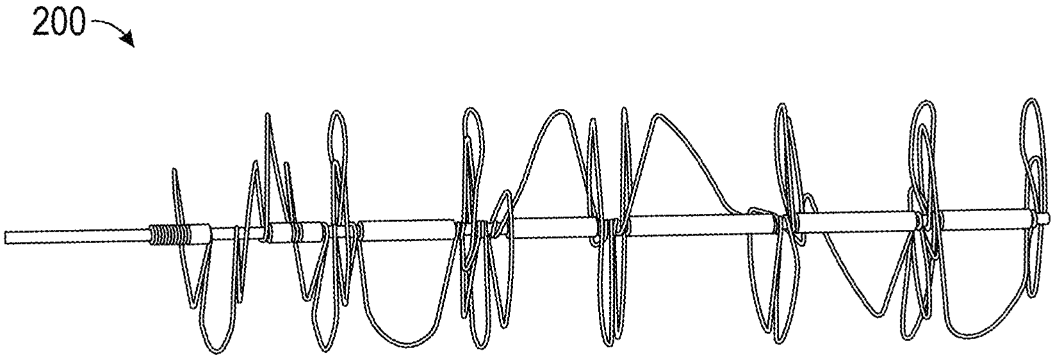

FIG. 10 represents a top view of the extractor 200. FIGS. 11-14 represent side views of the extractor 200. The engagement panels 210, 212, 214, 216 can be configured to be approximately 90 degrees to the catheter shaft 206.

The engagement panels 210, 212, 214, 216, 220, 222, 224, 226, 230, 232, 234, 236 can be at various angles relative to a center axis 208. The center axis 208 can extend along the length of the catheter shaft 206. The engagement panels 210, 212, 214, 216 can be at a first angle relative to the center axis 208. The first angle can range from, e.g., 30 degrees to 150 degrees relative to the center axis 208. The engagement panels 220, 222, 224, 226 can be at a second angle relative to the center axis 208. The second angle can range from, e.g., 30 degrees to 150 degrees relative to the center axis 208. The engagement panels 230, 232, 234, 236 can be at a third angle relative to the center axis 208. The third angle can range from 30 degrees to 150 degrees relative to the center axis 208. The first angle and the second angle can be the same angle. The first angle and the second angle can be different angles. The first angle, the second angle, and the third angle can be the same angle. The first angle, the second angle, and the third angle can be different angles.

The engagement panels 210, 212, 214, 216, 220, 222, 224, 226, 230, 232, 234, 236 can angle in the same direction distally. The engagement panels 1 210, 212, 214, 216, 220, 222, 224, 226, 230, 232, 234, 236 can angle in the same direction proximally. The engagement panels 210, 212, 214, 216 and the engagement panels 220, 222, 224, 226 can angle in the same direction. The engagement panels 210, 212, 214, 216 and the engagement panels 220, 222, 224, 226 can angle in different direction. The engagement panels 210, 212, 214, 216 and the engagement panels 220, 222, 224, 226 can angle in a different, e.g., alternate manner. The engagement panels 220, 222, 224, 226 and the engagement panels 230, 232, 234, 236 can angle in alternate manner. The engagement panels 210, 212, 214, 216, 220, 222, 224, 226, 230, 232, 234, 236 can angle in an alternate manner for each engagement panels at a longitudinal location such that one engagement panels at the first longitudinal location can angle toward distally and the adjacent engagement panels at the second longitudinal location angle toward proximally. In some embodiments, the engagement panels 210, 212, 214, 216 and the engagement panels 220, 222, 224, 226 can angle in the same direction. In some embodiments, the engagement panels 210, 212, 214, 216 and the engagement panels 220, 222, 224, 226 can alternate pointing distally or proximally and vice versa. Each engagement panels 210, 212, 214, 216 can angle in the same direction or alternate direction, e.g., facing distally or proximally or any combination thereof. When the engagement panel first exposes or exit the microcatheter, the first portion of the panel revert back proximally behind the tip of the sheath. Then the latter portion of the engagement panel expand or flare outward. The reverting back of the panel tip will grab and pull the clot away from the vessel wall.

In some embodiments, the diameter of the engagement panels 110, 112, 114, 120, 122, 124, 130, 132, 134 can be adjusted to a larger or smaller diameter depending on the vessel diameter as needed. The arcs 140 can expand to be against the vessel wall. The engagement panels 110, 112, 114, 120, 122, 124, 130, 132, 134 can partially flare outward to contact the vessel wall. The engagement panels 110, 112, 114, 120, 122, 124, 130, 132, 134 can fully flare outward to contact the vessel wall. The engagement panels 110, 112, 114, 120, 122, 124, 130, 132, 134 can function when the legs 142, 144 are partially expanded. The engagement panels 110, 112, 114, 120, 122, 124, 130, 132, 134 can function when the legs 142, 144 when the legs are straight. The engagement panels 110, 112, 114, 120, 122, 124, 130, 132, 134 can function when the legs 142, 144 are perpendicular to the catheter shaft 106. The engagement panels 110, 112, 114, 120, 122, 124, 130, 132, 134 can function when the legs 142, 144 are angled to the catheter shaft 106.

Figure 15:
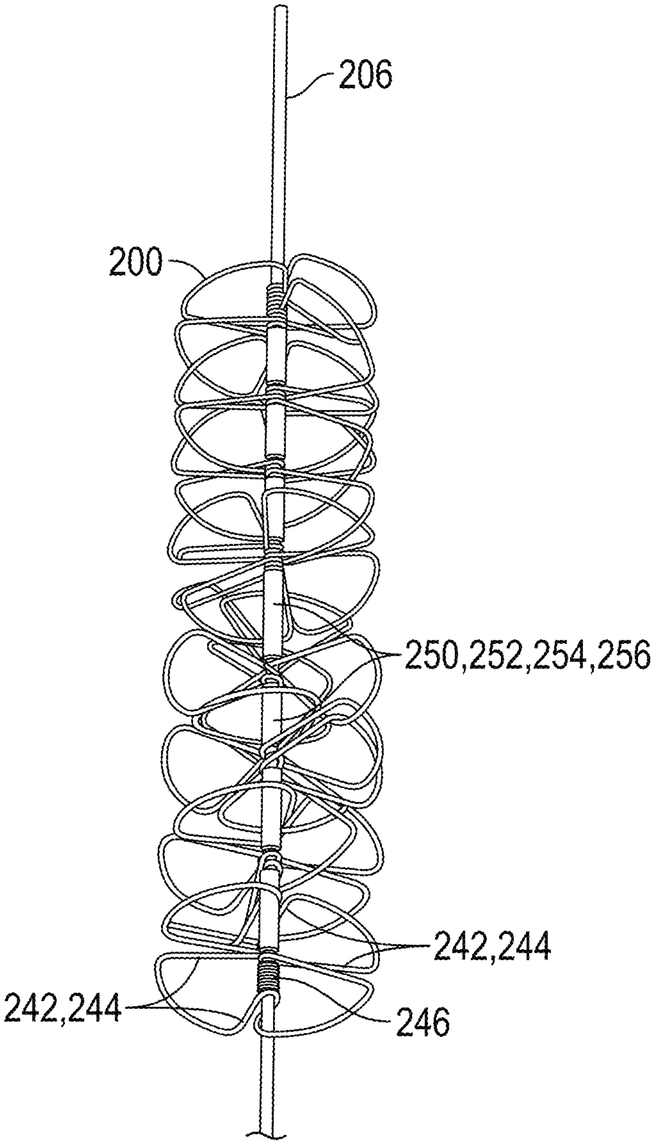
FIG. 15 is another view of the second embodiment of the extractor.

FIG. 15 is another view of the extractor 200. The extractor 200 can include the legs 242, 244. The extractor 200 can include the eyelets 246. The extractor 200 can include the spacers 250, 252, 254, 256. The extractor 200 can include the catheter shaft 206. The extractor 200 can include any of the features described herein.

Figure 16:
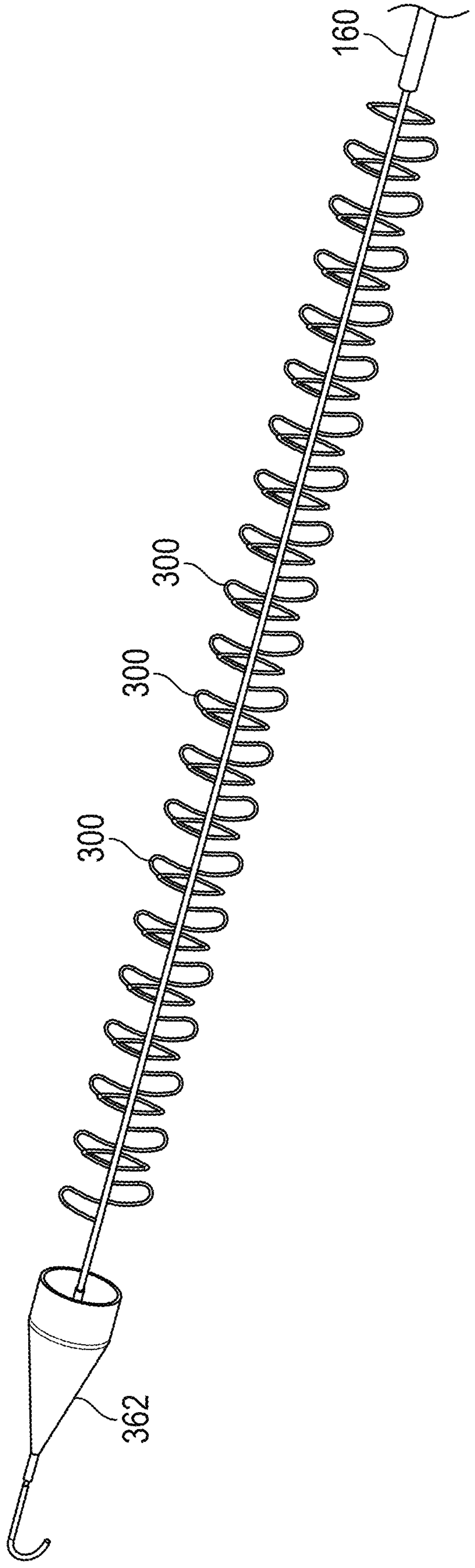
FIGS. 16-18 are views of the third embodiment of the helical engagement panel extractor.
Figure 17:
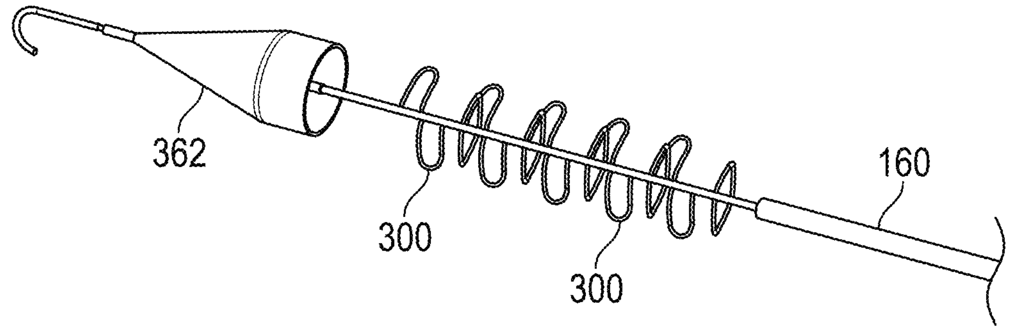
Figure 18:
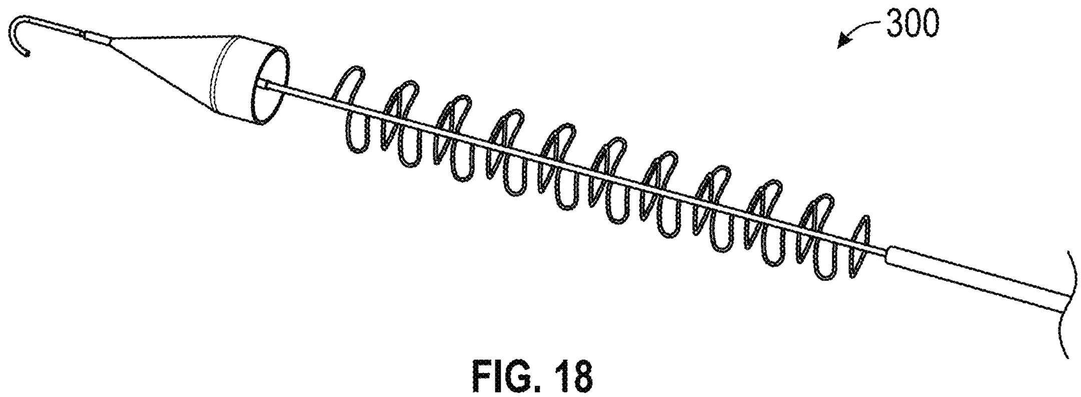

FIG. 16 is a view of an extractor 300. The extractor 300 can have any of the features described herein. The engagement panels 310, 320, 330 can be arranged in a helical configuration. FIG. 17 is a view of the extractor 300. The engagement panels 310, 320, 330 can be partially deploy distal to the sheath 160. FIG. 18 is a view of the extractor 300 and sheath 160. The extractor 300 can include a distal member 380. The distal member 380 can include any feature described herein.

Figure 19:
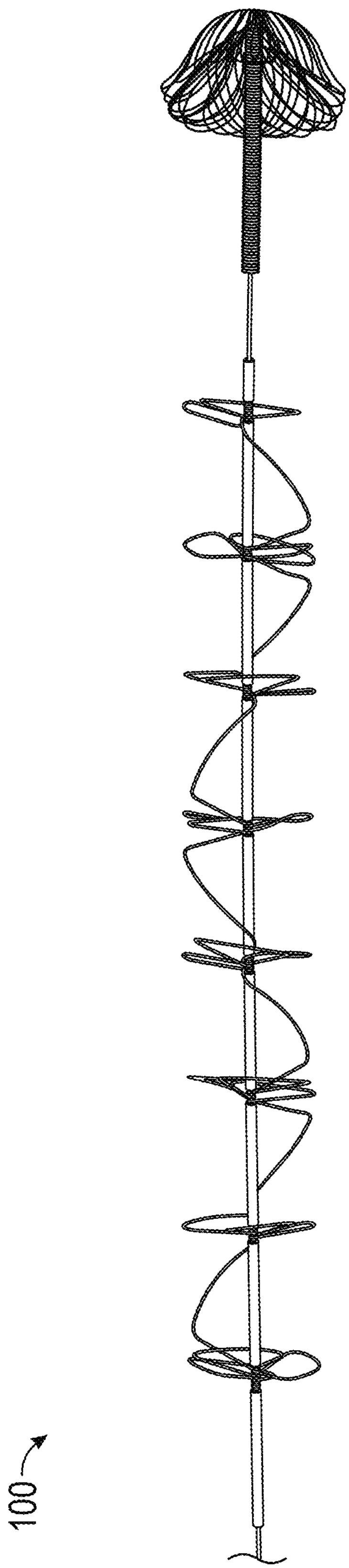
FIGS. 19-26 are views of the first embodiment of the three engagement panels extractor.

FIG. 19 is a view of the extractor 100. The engagement panels 110, 112, 114, 120, 122, 124, 130, 132, 134 can expand or open from the right to left. The engagement panels 110, 112, 114, 120, 122, 124, 130, 132, 134 can open upward. The engagement panels 110, 112, 114, 120, 122, 124, 130, 132, 134 can create a scraping effect. The engagement panels 110, 112, 114, 120, 122, 124, 130, 132, 134 can create a pinching effect.

Figure 20:
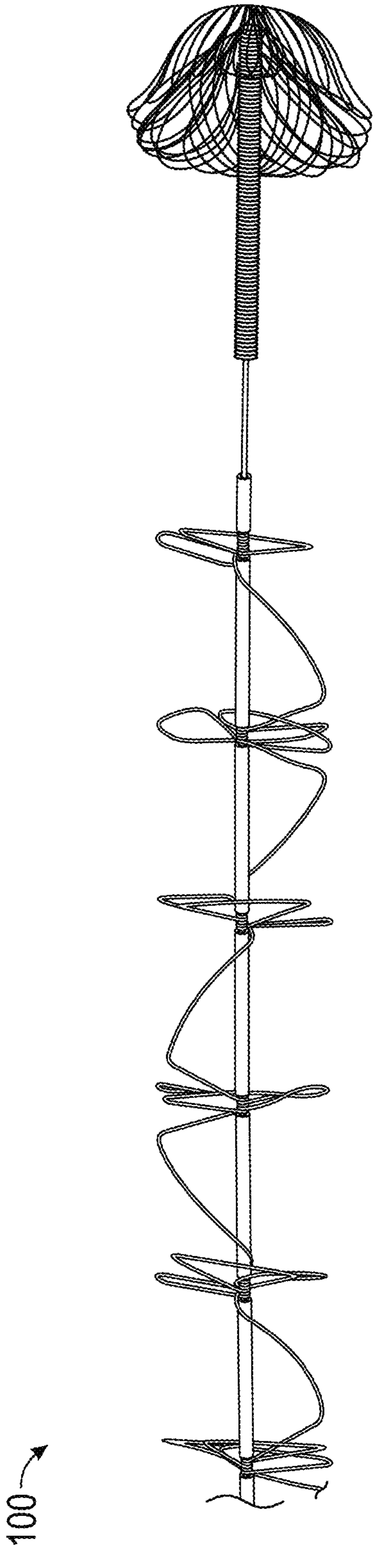

FIG. 20 is another view of the extractor 100.

FIG. 21 is a view of the extractor 100. The engagement panels 110, 112, 114 can each form an angle theta relative to the central axis 108. The engagement panels 110, 112, 114 can each form an angle theta of approximately 120 degrees.

FIGS. 22-26 are views of the extractor 100. The engagement panels 110, 112, 114 can each form an angle alpha relative to the central axis 108. The engagement panels 110, 112, 114 can each form an angle alpha approximately 90 degrees.

FIGS. 27-30 are views of the extractor 300.

Figure 31:
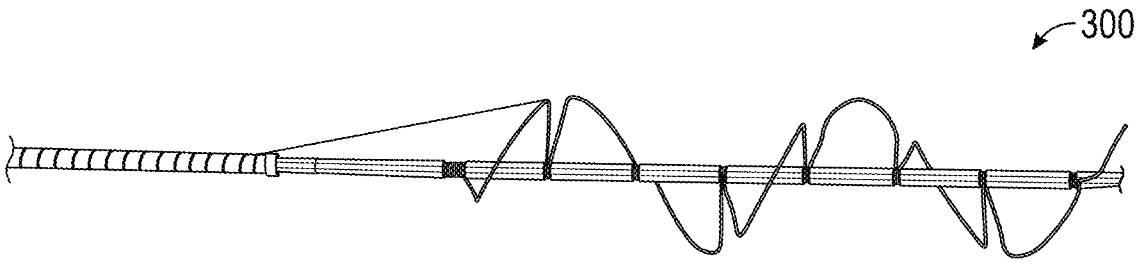
FIG. 31 is a view of the third embodiment of the helical engagement panels extractor.
Figure 32:
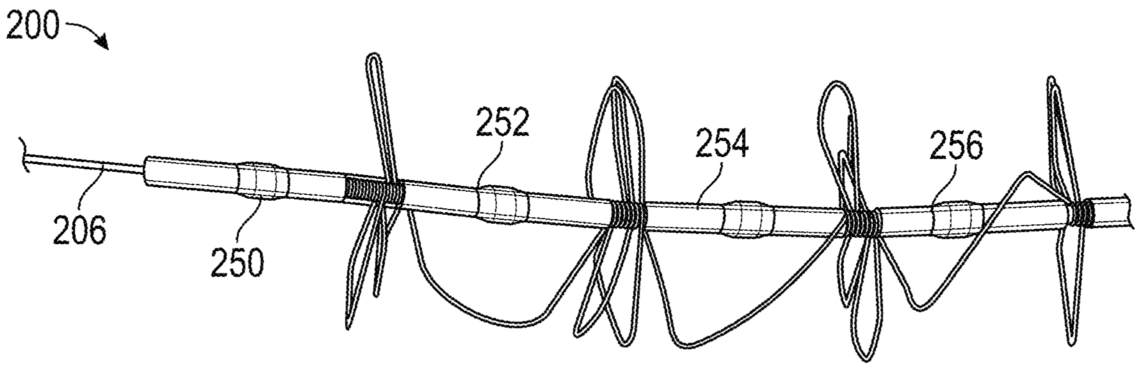
FIGS. 32-34 are views of the second embodiment of the three engagement panels extractor deployed.
Figure 33:
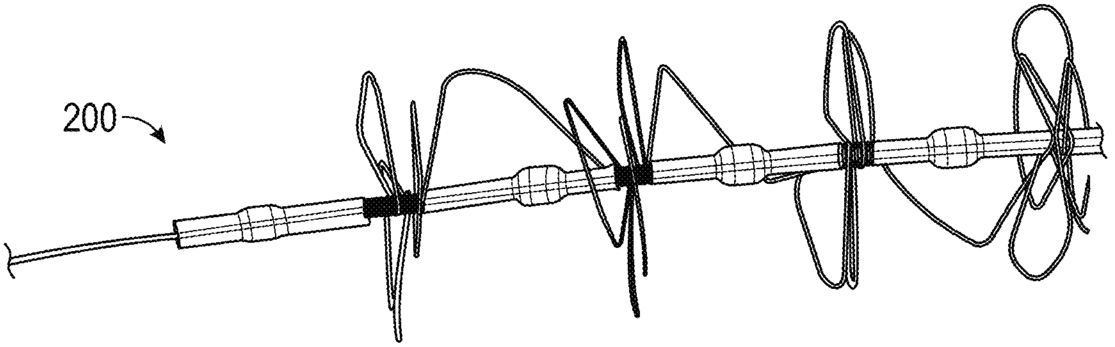

FIG. 31 is a view of the extractor 300.

FIG. 32-35 are views showing the extractor 200. FIGS. 36-39 show the extractor with the engagement panels in a helical shape.

Figure 40:
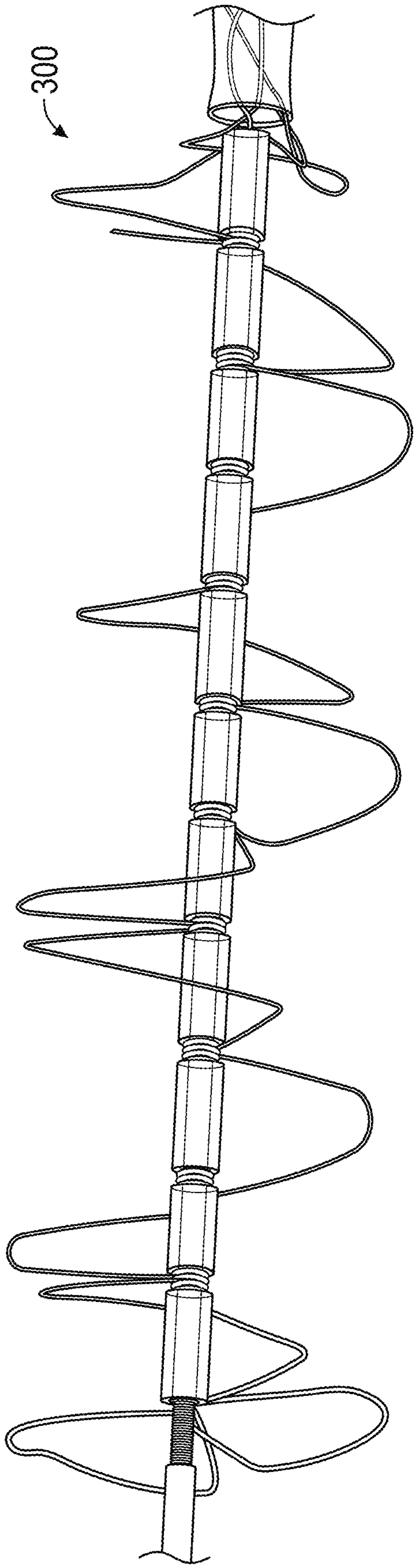
FIGS. 40-42 are views of the third embodiment of the helical engagement panel extractor with spacer in between the engagement panel.
Figure 41:
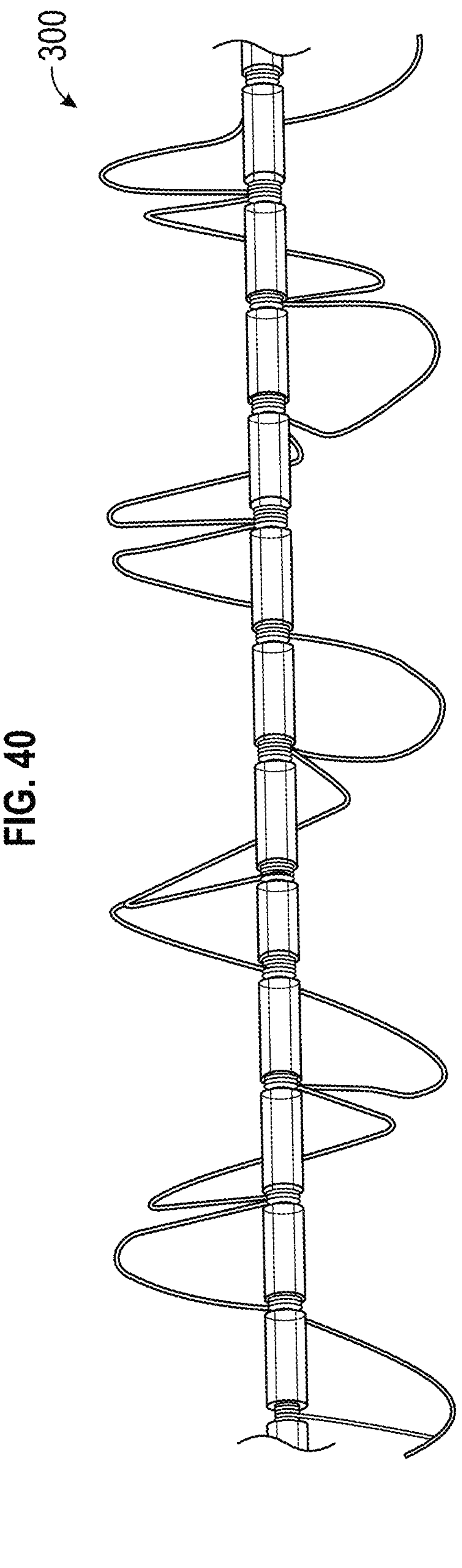
Figure 42:
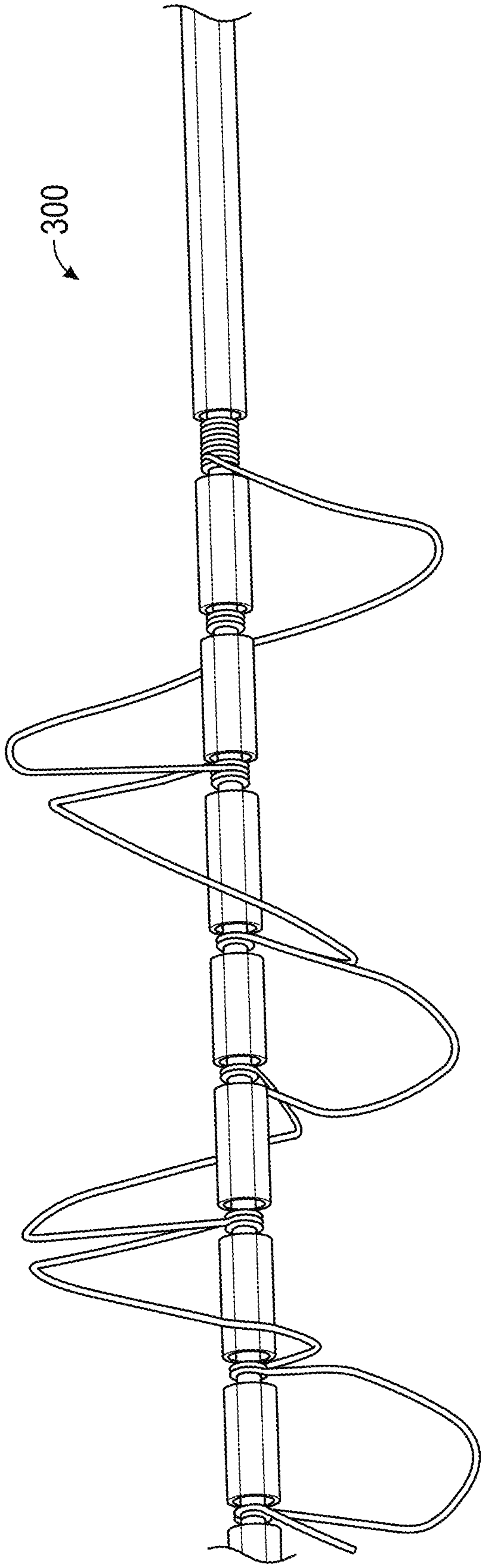

FIGS. 40-42 are views of the third embodiment of the extractor 300. The engagement panels can be arranged in a helical configuration.

Figure 43:
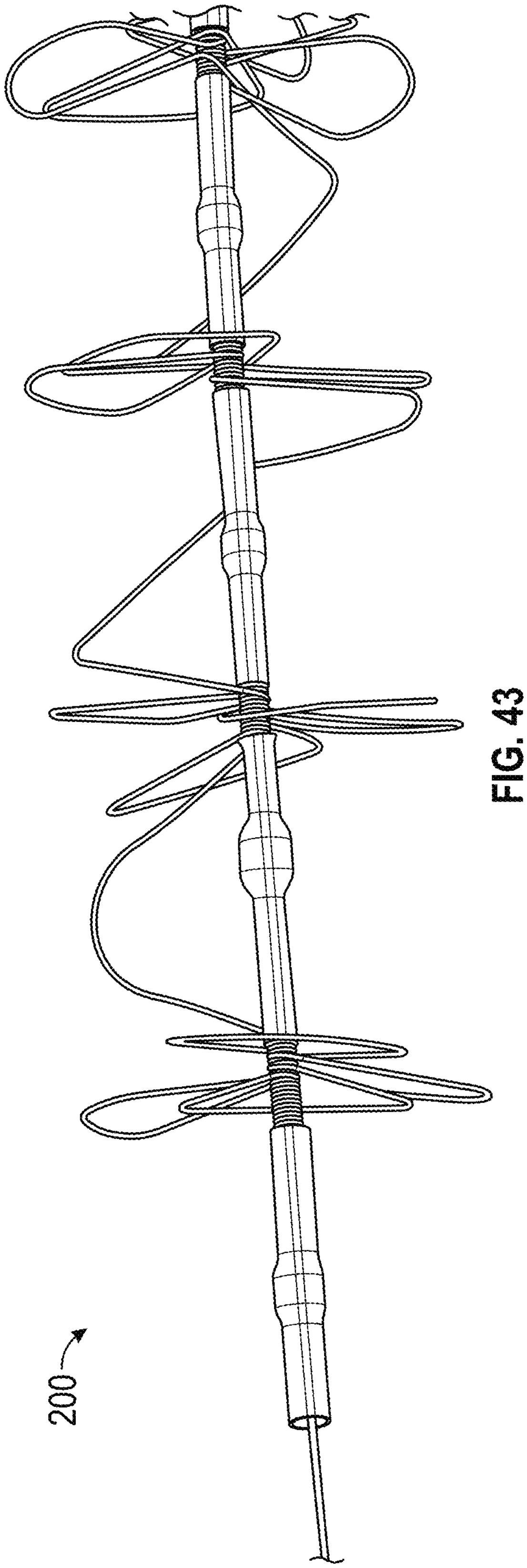
FIGS. 43-44 are view of the second embodiment of the four engagement panel extractor with spacer in between the engagement panels and eyelets.
Figure 44:
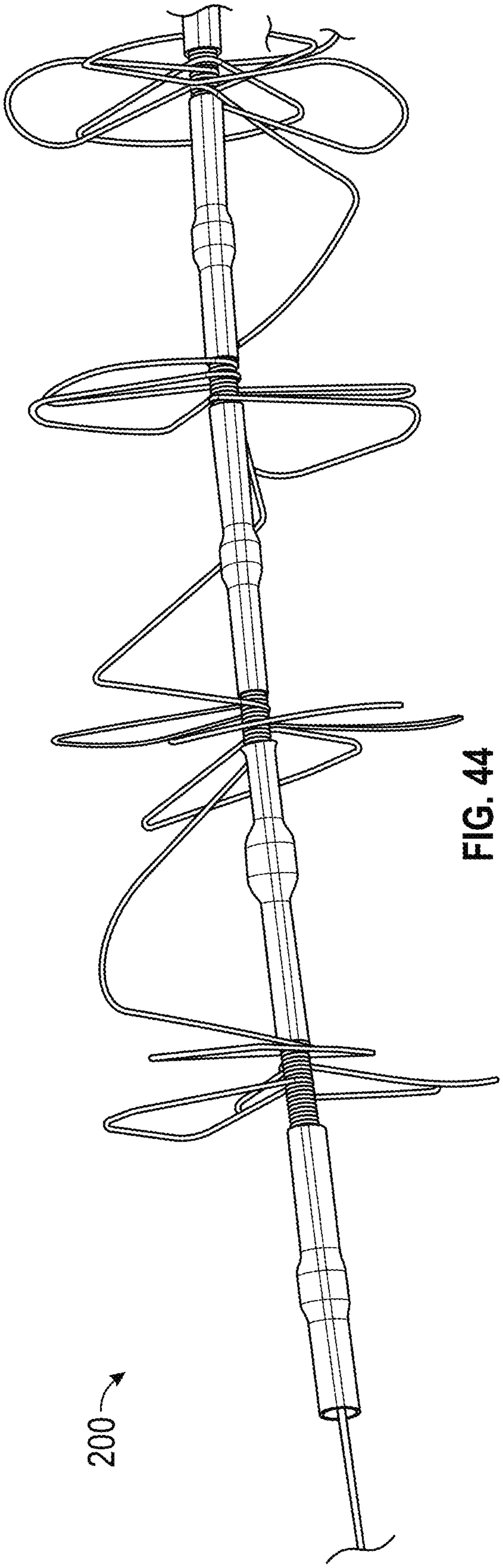

FIGS. 43-44 are views of the second embodiment of the extractor 200. The extractor 200 can have four engagement panels per longitudinal location.

Figure 45:
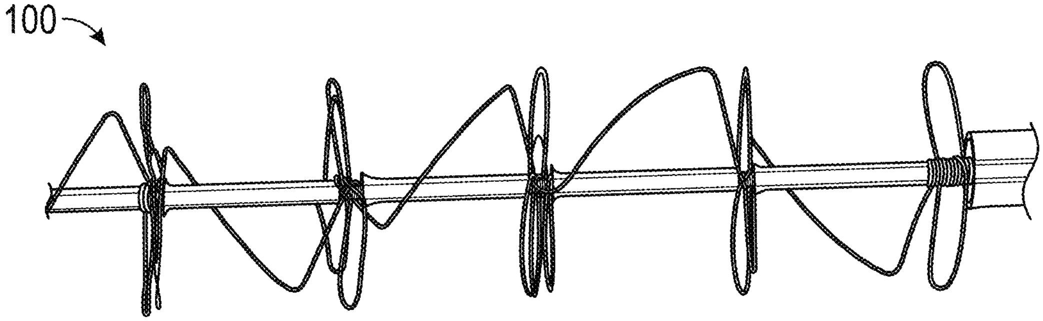
FIGS. 45-47 are view of the first embodiment of the three engagement panel extractor fixed on the catheter shaft.
Figure 46:
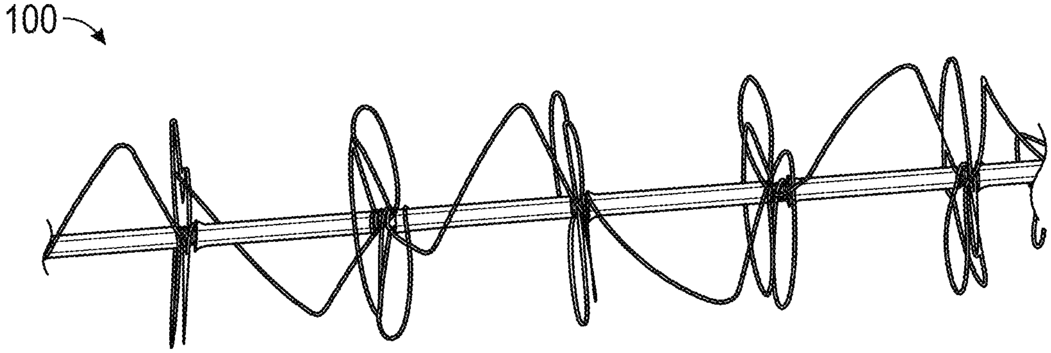
Figure 47:
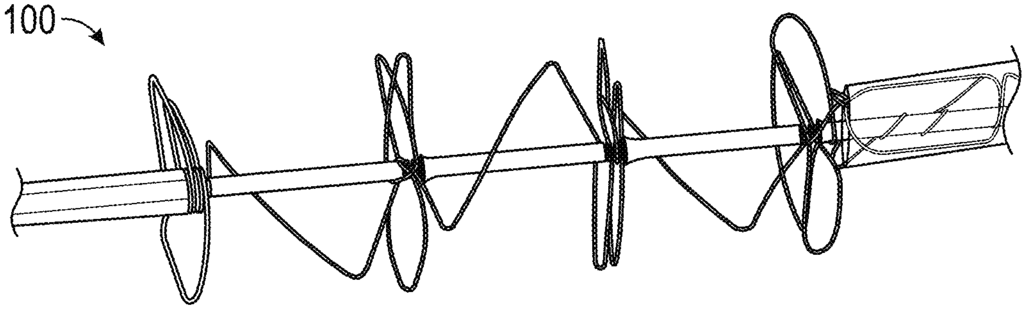
Figure 48:
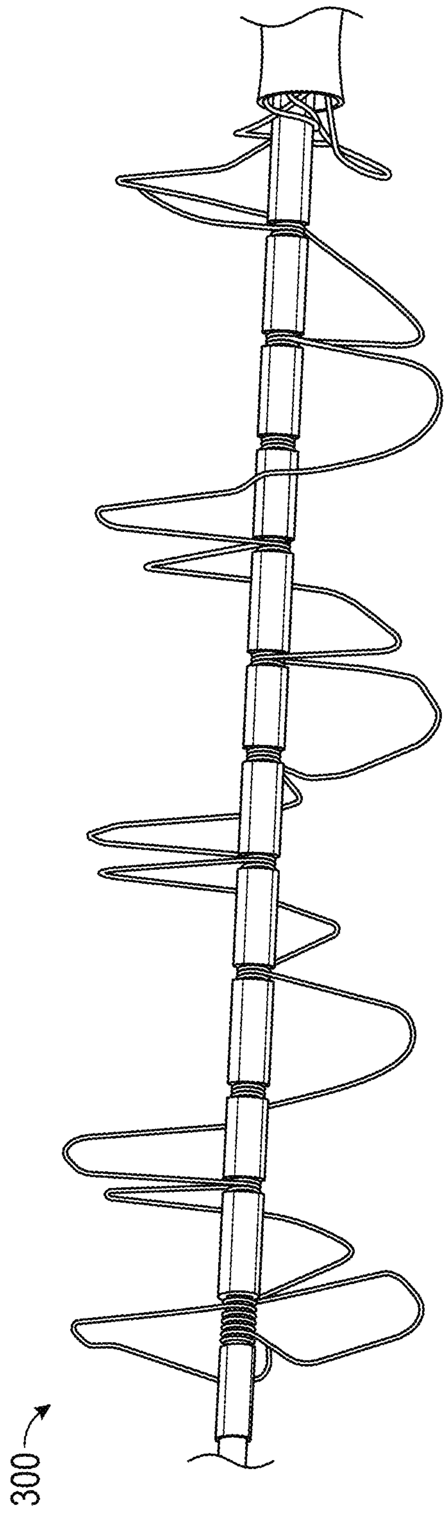
FIGS. 48-52 are views of the third embodiment of the helical engagement panel extractor with spacers between the engagement panels and eyelets.
Figure 49:
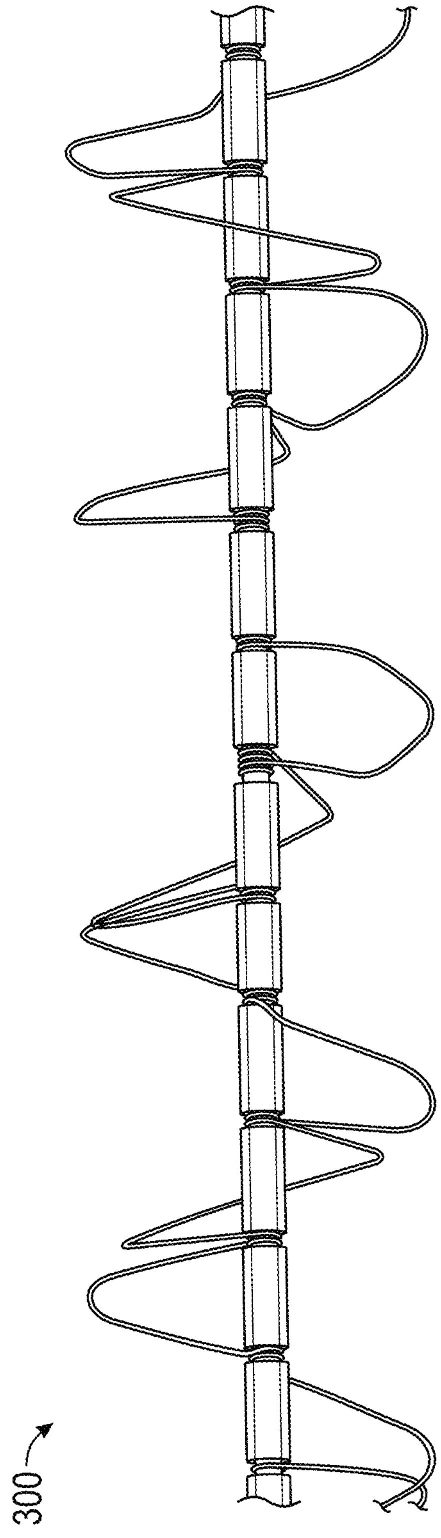
Figure 50:
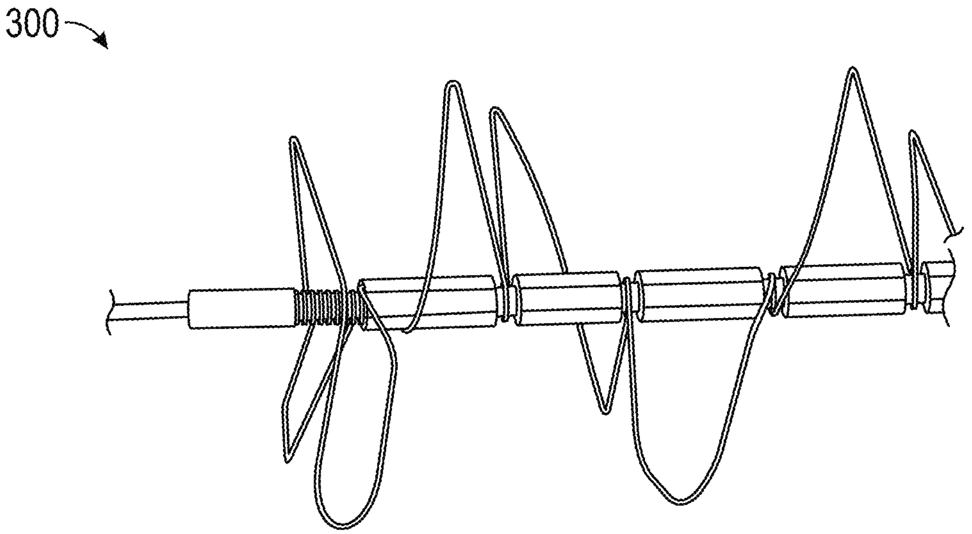
Figure 51:
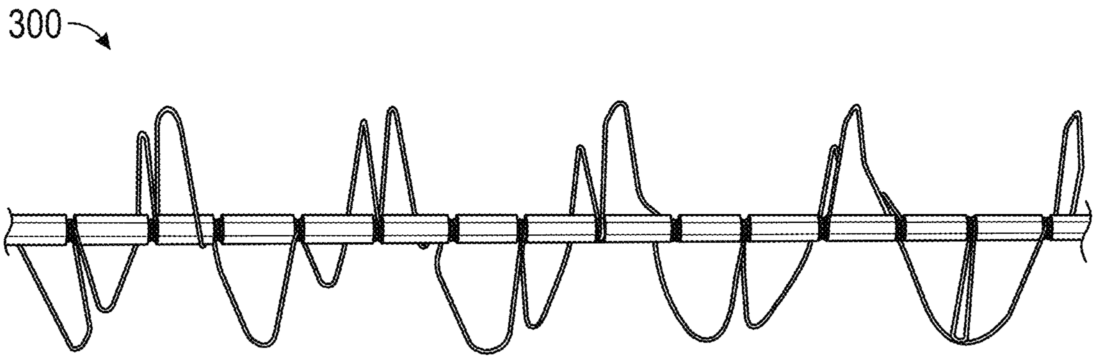
Figure 52:
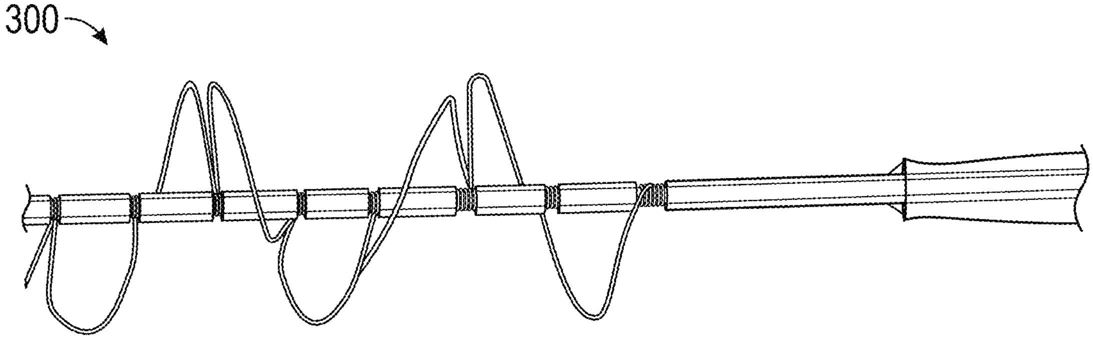
Figure 53:
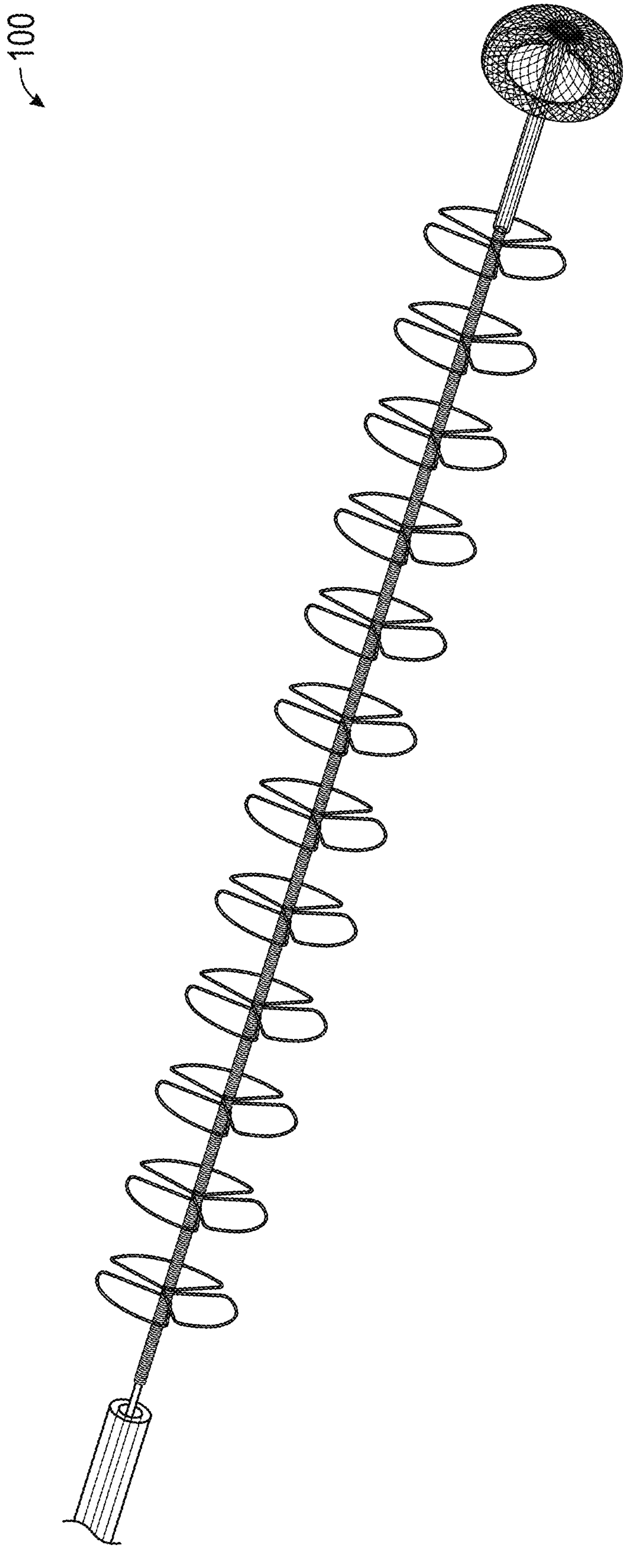
FIG. 53 is view of a three engagement panels extractor system.

FIGS. 45-47 are views of the first embodiment of the extractor 100. The extractor 100 can have three engagement panels per longitudinal location. The engagement panels can be3 coupled to the catheter shaft.

FIGS. 48-52 are views of the third embodiment of the extractor 300. The engagement panels can be a helix engagement panel.

Figure 54:
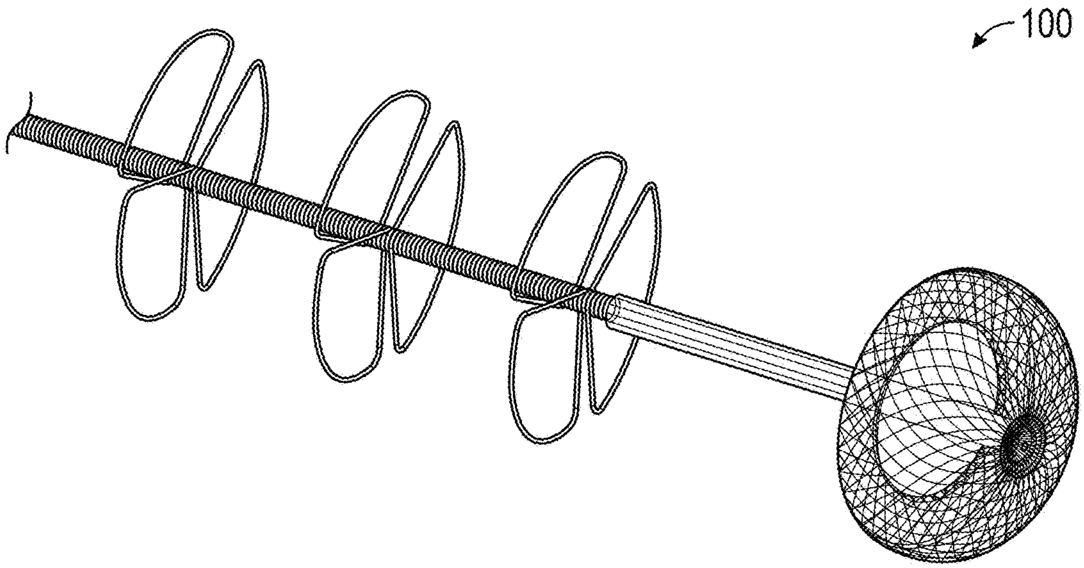
FIG. 54 is view of a three engagement panels extractor system with integral coil spacer.
Figure 55:
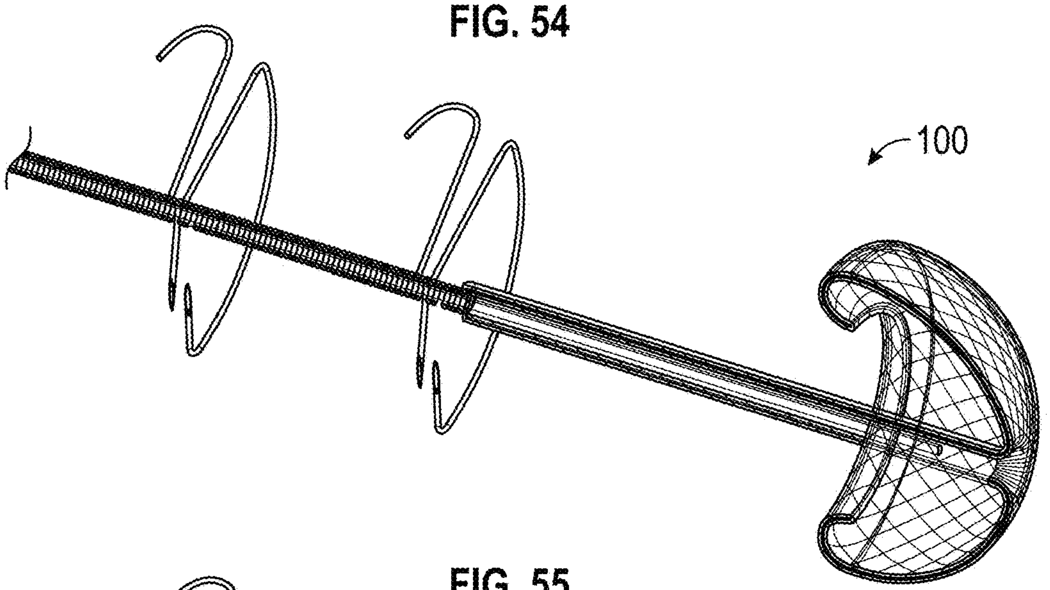
FIG. 55 is view showing a panel and coil spacer.
Figure 56:
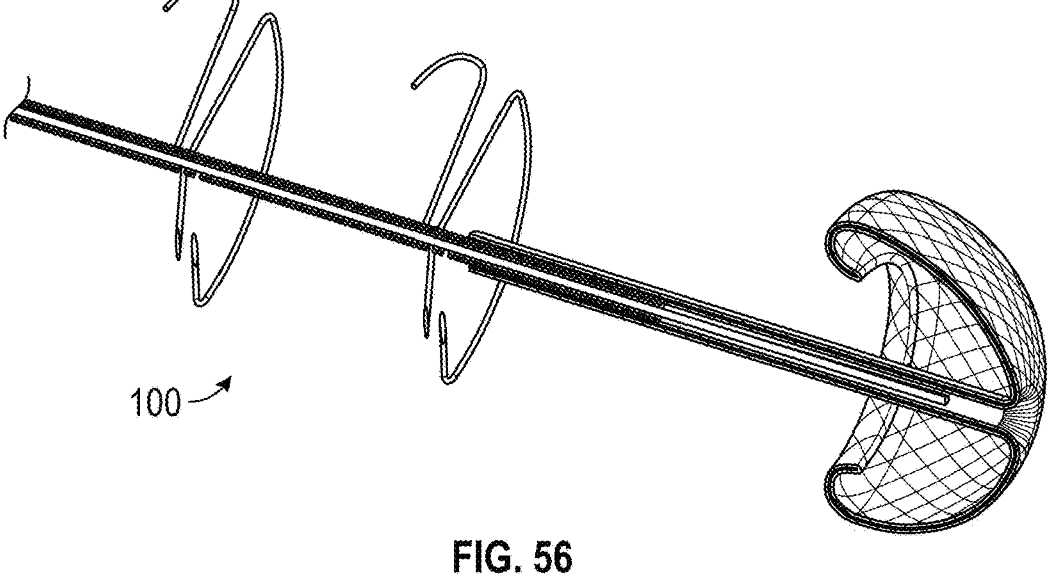
FIG. 56 is another view showing the engagement panel.
Figure 57:
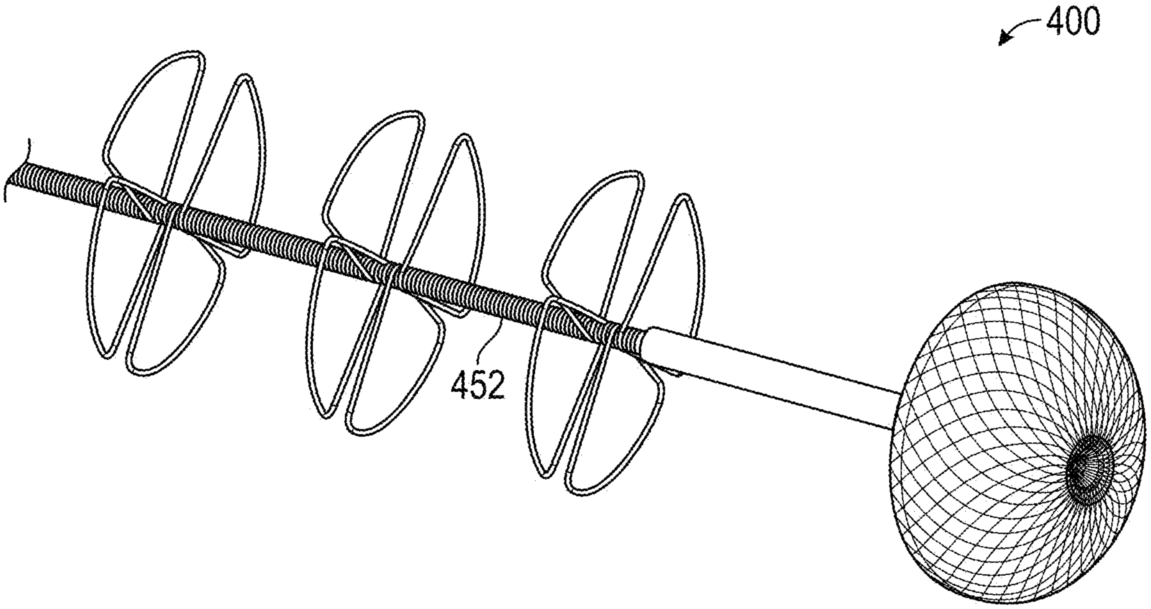
FIG. 57 is view of a four engagement panels extractor system with coil spacer of a fourth embodiment.
Figure 58:
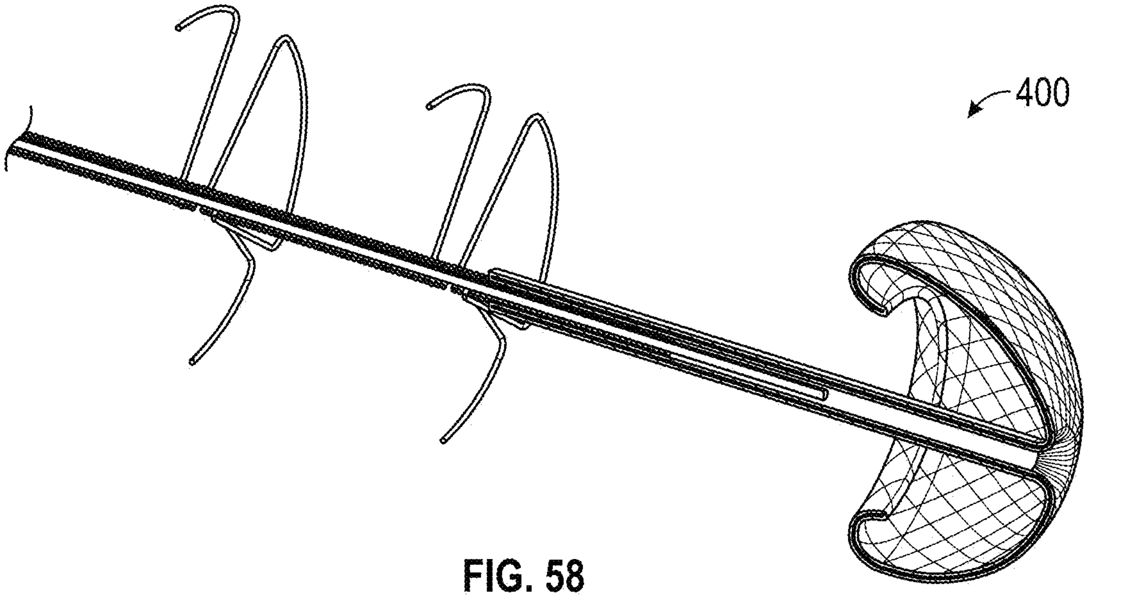
FIG. 58 is view showing a panel of a four engagement panels extractor system of the fourth embodiment.
Figure 59:
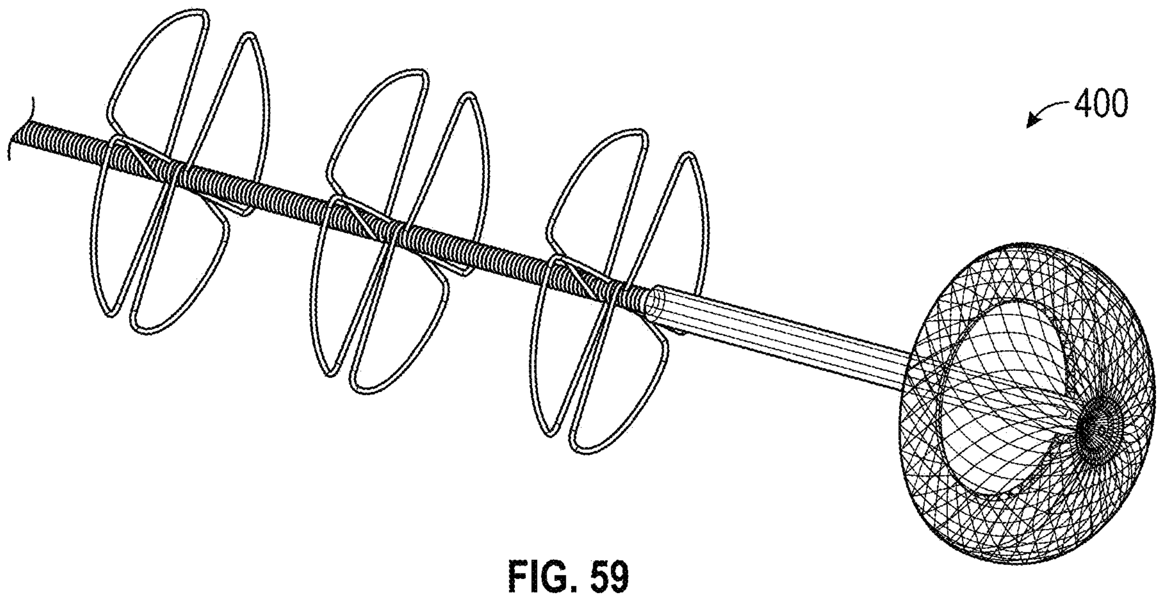
FIG. 59 is view of a four engagement panels extractor system with integral coil spacer of the fourth embodiment.
Figure 60:
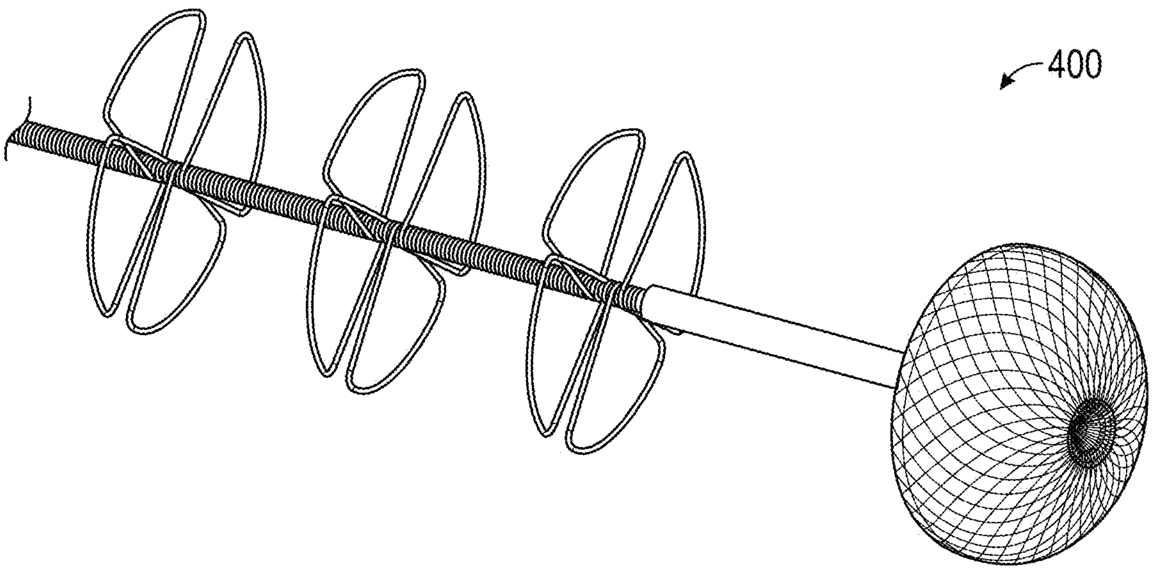
FIG. 60 is view of another four engagement panels extractor system with integral coil spacer of the fourth embodiment

FIGS. 53-56 are views of a system. The system can include a cover sheath to load the extractor. The system can include a distal filter. The system can include any of the extractors described herein, with the extractor 100 illustrated. The system can include any of the engagement panels described herein. The system can include any of the spacers described herein. The system can include a core wire. FIG. 54 is an enlarged view of the extractor. FIG. 55 is a cross-sectional view. FIG. 56 is a cross-sectional view.

FIGS. 57-64 are views of a fourth embodiment of the extractor 400. The extractor 400 can have any of the features described herein. The extractor 400 can have a plurality of engagement panels 410, 412, 414, 416, 420, 422, 424, 426, 430, 432, 434, 436. The engagement panels 410, 412, 414, 416 are located at a first longitudinal location. The engagement panels 420, 422, 424, 426 are located at a second longitudinal location. The engagement panels 430, 432, 434, 436 are located at a third longitudinal location. In the illustrated embodiment, there are four engagement panels at each longitudinal location. The engagement panels 410, 412, 414, 416 at a single longitudinal location can form a circular profile. The extractor 400 can include a plurality of spacers 450, 452, 454, 456. The spacer 450 can be located between a distal end and the engagement panels 410, 412, 414, 416. The spacer 452 can be located between the engagement panels 410, 412, 414, 416, and the engagement panels 420, 422, 424, 426. The spacer 452 can be between the first longitudinal location and the second longitudinal location. The spacer 454 can be located between the engagement panels 420, 422, 424, 426, and the engagement panels 430, 432, 434, 436. The spacer 454 can be between the second longitudinal location and the third longitudinal location. In some embodiments, the spacer 456 can be located between the engagement panels 430, 432, 434, 436 and another set of engagement panels. In some embodiments, the spacer 456 can be located between the engagement panels 430, 432, 434, 436 and a proximal end.

Figure 61:
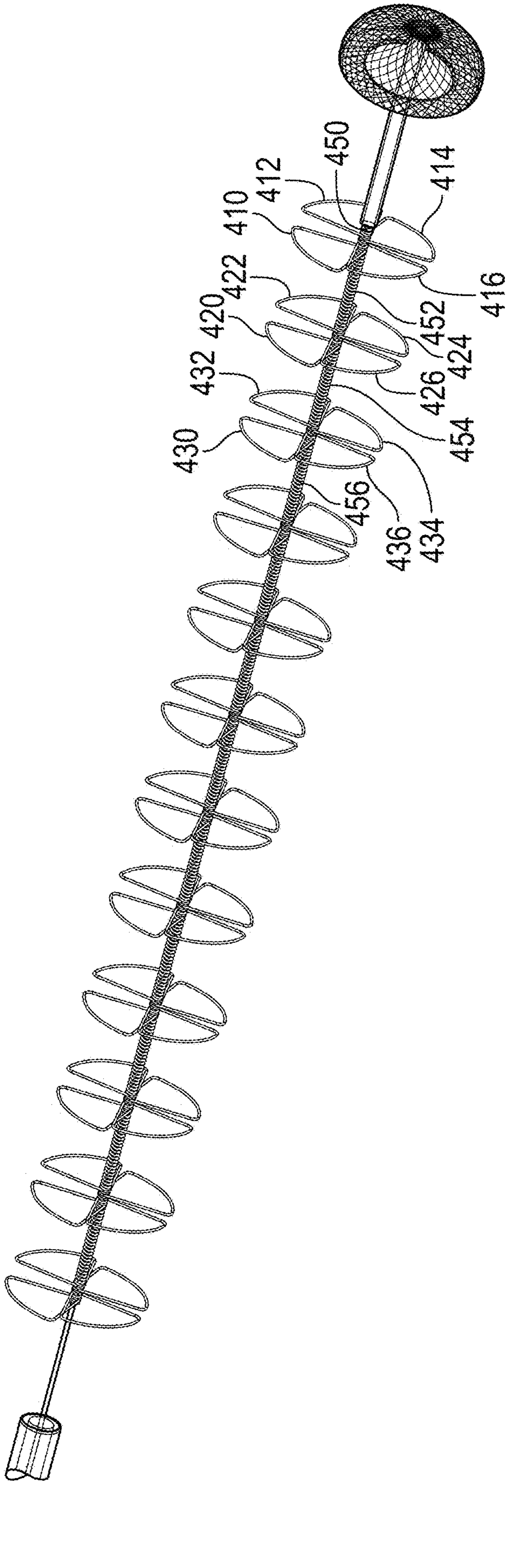
FIG. 61 is view of the four engagement panels extractor system of the fourth embodiment.
Figure 62:
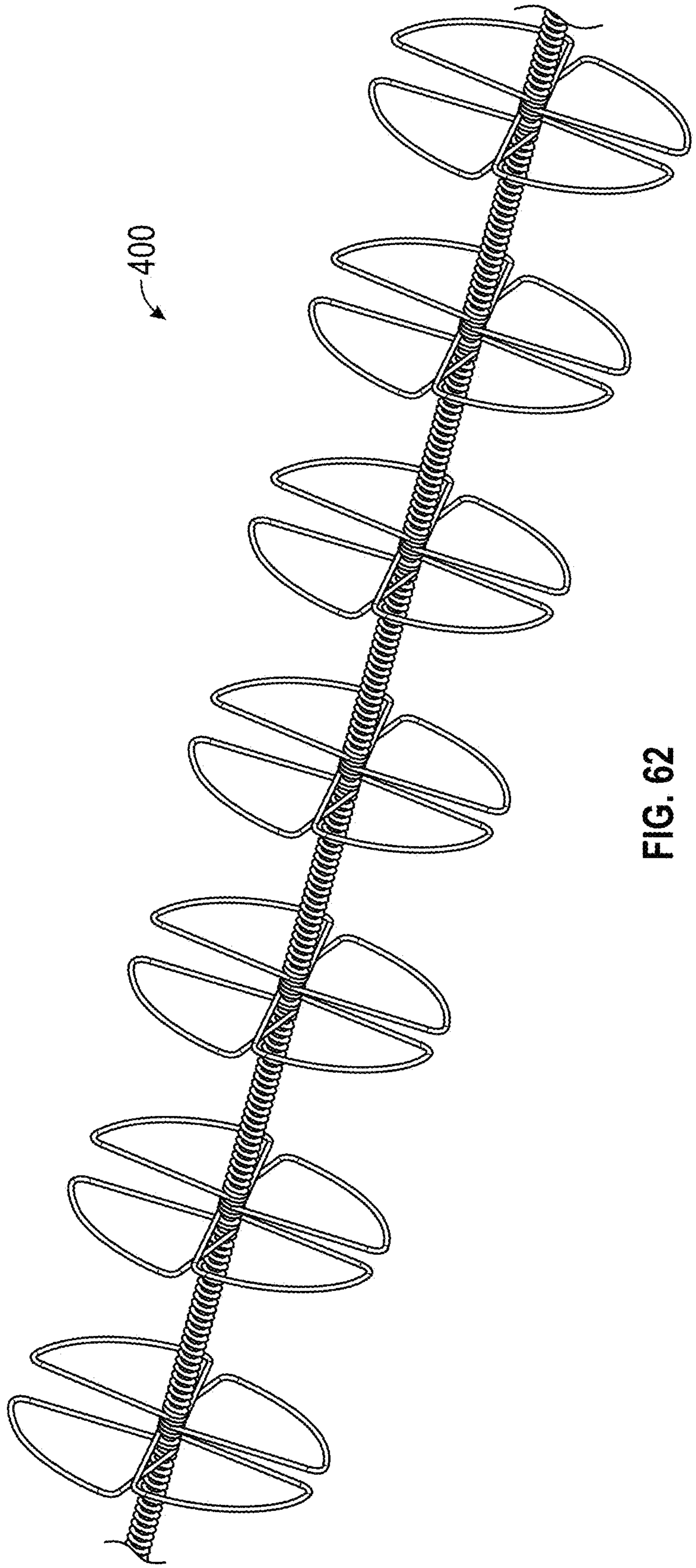
FIG. 62 is view of the four engagement panels extractor system with coil spacer of the fourth embodiment.
Figure 63:
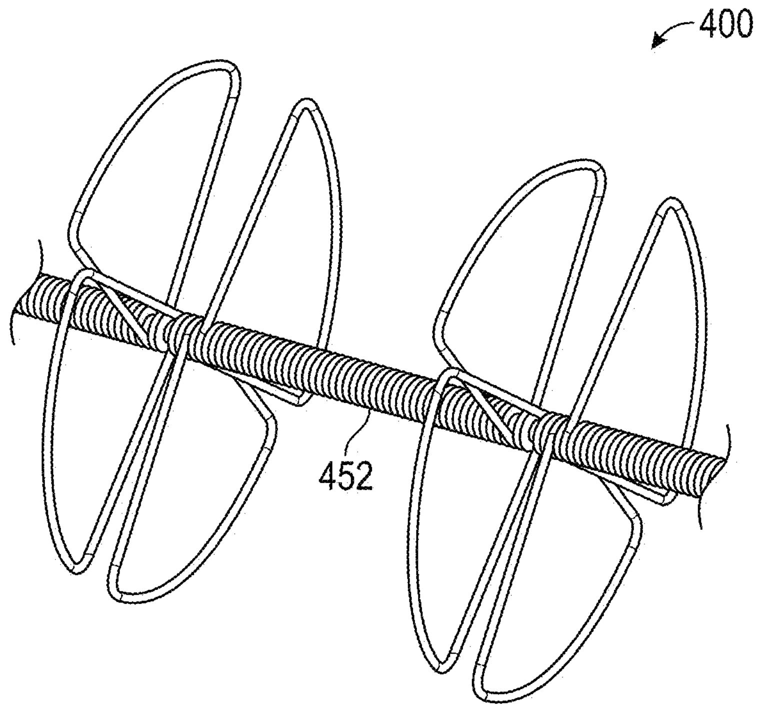
FIG. 63 is another view of the four engagement panels with closed gap coil spacer of the fourth embodiment.
Figure 64:
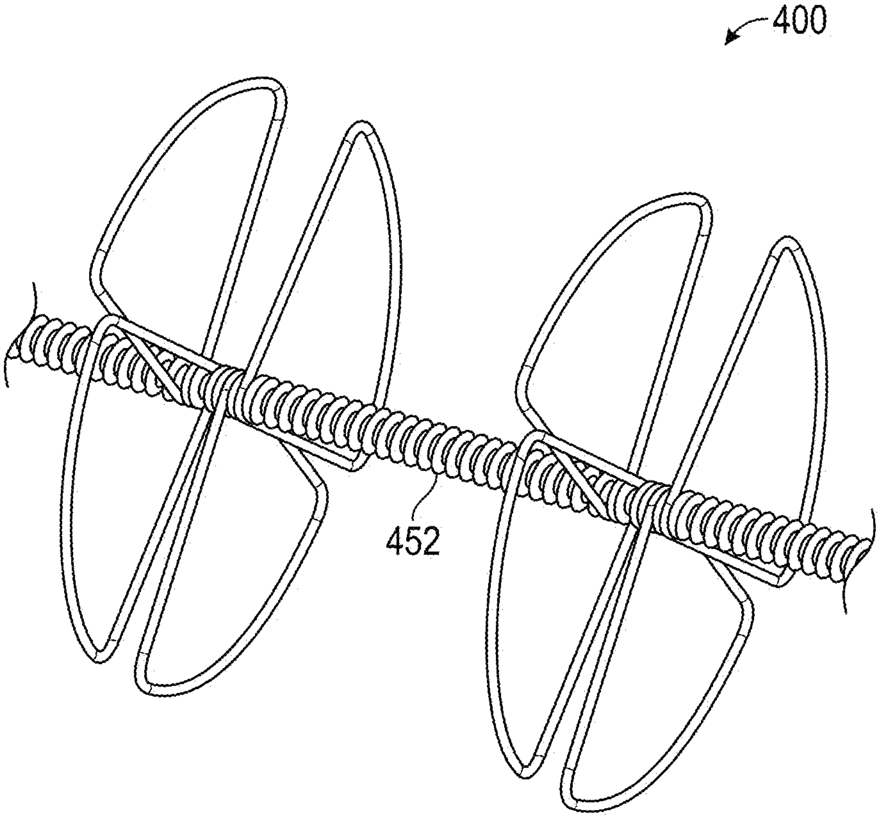
FIG. 64 is another view of the four engagement panels with open gap coil spacer of the fourth embodiment.

The spacers 450, 452, 454, 456 can be formed from a coil. The coil of the spacer can be integral with the engagement panels. The coil of the spacer can be unitarily formed with the engagement panels. The coil of the spacer can be separate from the with the engagement panels. In some embodiments, the spacer can be formed from a hypo tube. FIG. 61 is a cross-sectional view. FIGS. 62-67 are additional views. The spacer 450, 452, 454, 456 can have a close gap. The spacer 450, 452, 454, 456 can be a tight coil. The spacer 450, 452, 454, 456 can have a loose gap. The spacer 450, 452, 454, 456 can be a looser coil or spring.

Figure 65:
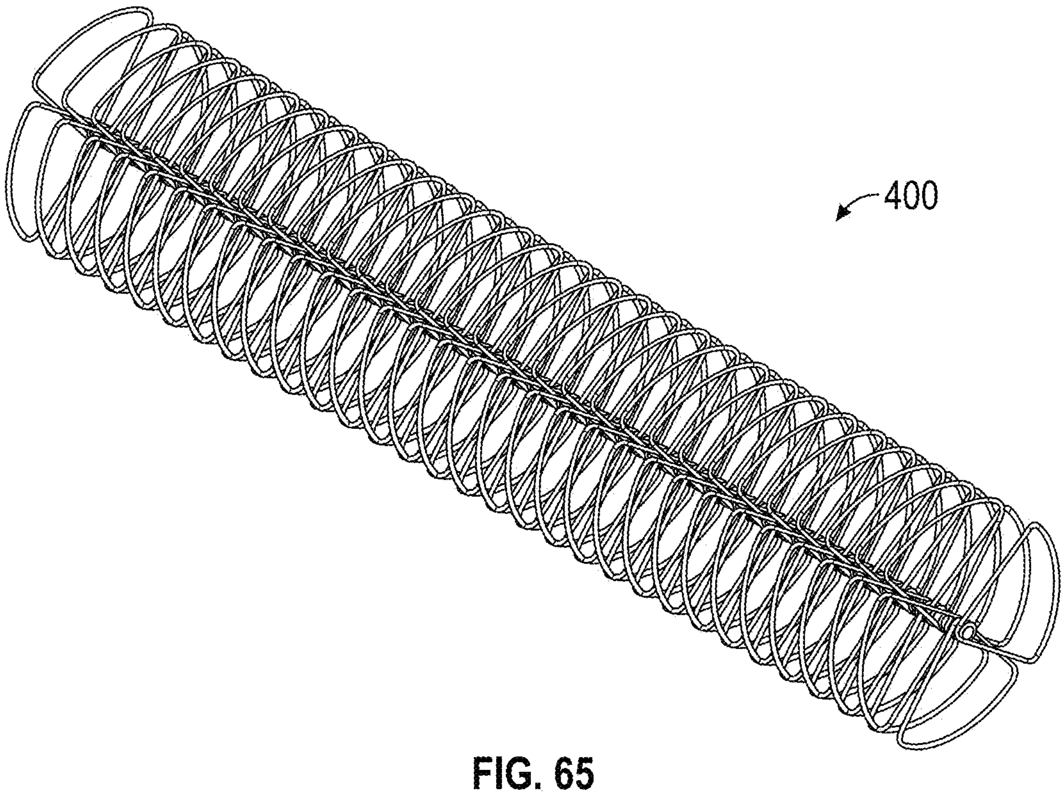
FIG. 65 is view of the four engagement panels extractor without spacer. The extractor engagement panels are in an unconstrained or unstretched position of the fourth embodiment.
Figure 66:
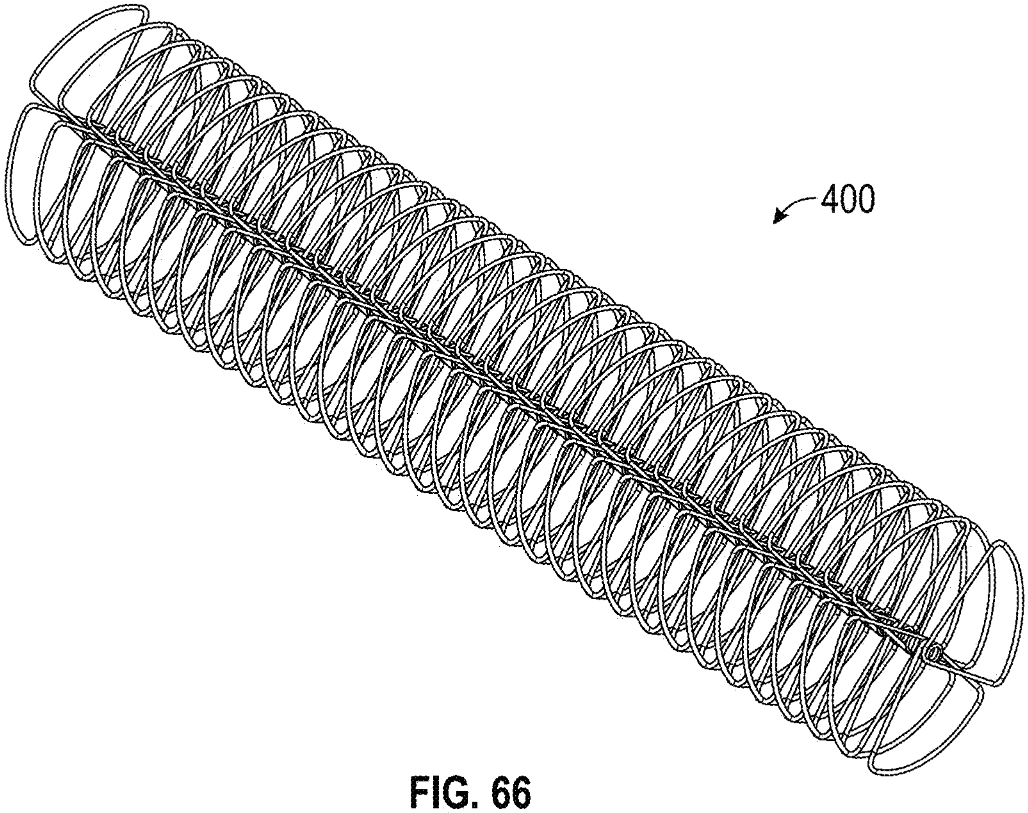
FIG. 66 is another view of the four engagement panels extractor with spacer and is in an unconstrained unstretched position of the fourth embodiment.

FIGS. 65-66 are views of the extractor 400. The extractor can be biased to for the engagement panels to move toward each other. The biased for the engagement panels to move towards each other have a compressive force thereby a pinch force where it can pinch a clot during clot capture.

The extractors 100, 200, 300 describe herein can include engagement panels. The engagement panels can form a diameter. The diameter can be formed from engagement panels at a single longitudinal location. The engagement panels can have a single diameter. The single diameter can be 3 mm, 4 mm, 5 mm, or more. The engagement panels can have multiple diameters. The diameters can be, e.g., 4 mm at a longitudinal location, 5 mm at the next longitudinal location, 4 mm at the next longitudinal location, and 5 mm at the next longitudinal location. The diameter formed from engagement panels can alternate in different sizes along the extractor 100.

The engagement panels can form a round perimeter. The engagement panels can form a elliptical perimeter. The engagement panels can form an oblong perimeter. The engagement panels can form an angle relative to catheter shaft. The angle can be, e.g. about 1 degree, 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, range from 1 degrees to 360 degrees, or any range of two of the foregoing values.

The engagement panels can have equal longitudinal spacing. The engagement panels can have unequal longitudinal spacing. The spacing between adjacent engagement panels can be, e.g. about 1 mm, 2 mm, 3 mm, 4 mm, 5 mm, 6 mm, 7 mm, 8 mm, 9 mm, 10 mm, 15 mm, range from 2 mm to 15 mm, or any range of two of the foregoing values. The engagement panels can have a custom distance between adjacent engagement panels. The spacing between adjacent engagement panels can be 3 mm, then the spacing between adjacent engagement panels can be 4 mm, and then spacing between adjacent engagement panels can be 5 mm.

In some embodiments, the engagement panels can have one leg. In some embodiments, the engagement panels can have two legs. In some embodiments, the engagement panels can have three legs. In some embodiments, the engagement panels can be connected. The extractor can include connecting members. There can be connection between engagement panels. There can be no connection between engagement panels. In some embodiments, the engagement panels can be formed of a single wire. In some embodiments, the engagement panels can be formed of multiple wires.

Figure 67:
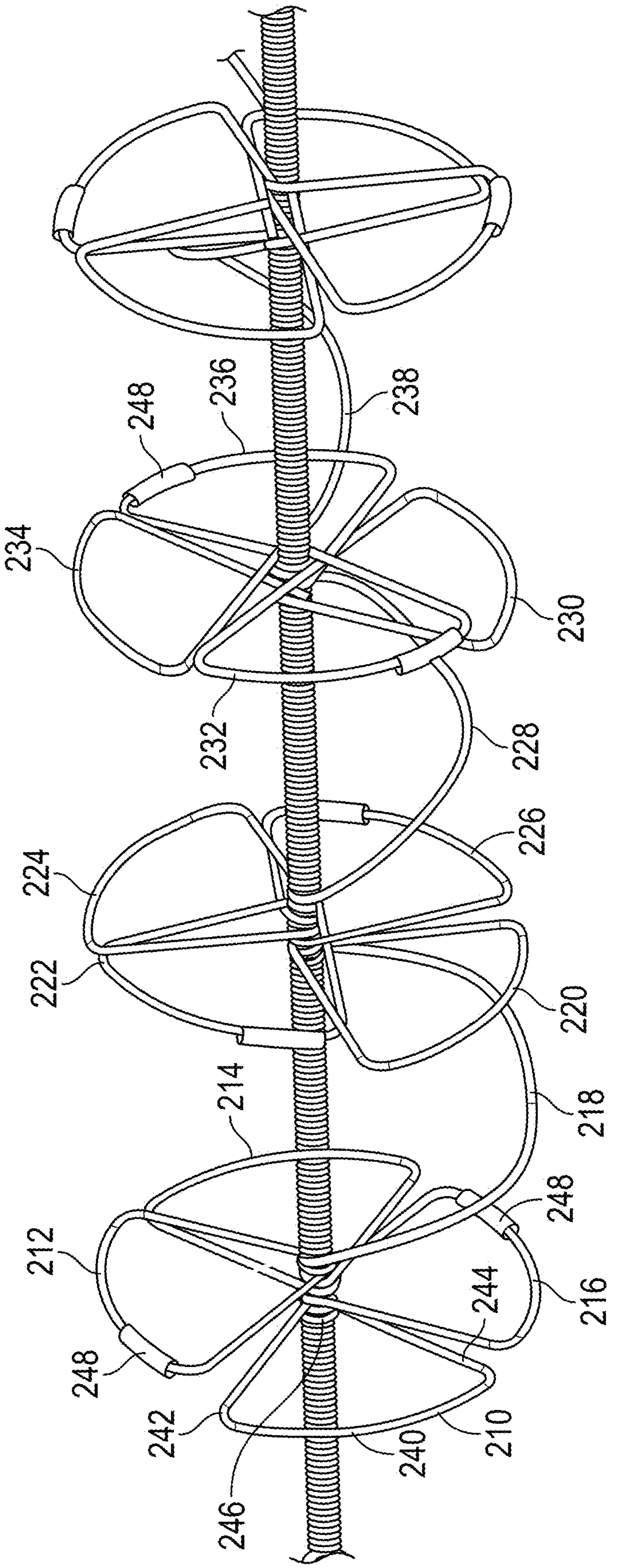
FIG. 67 is another view of the extractor of the second embodiment.
Figure 68:
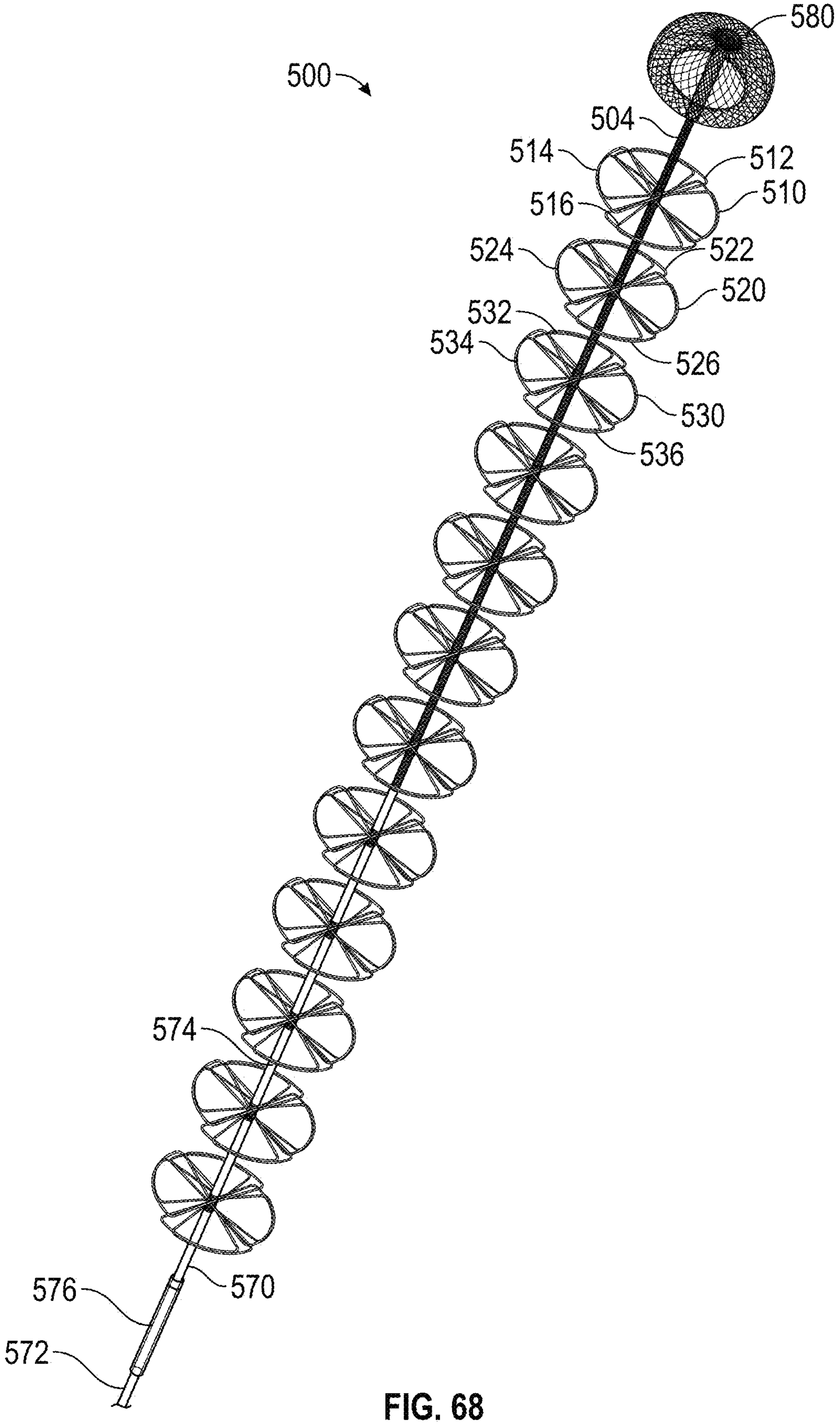
FIG. 68 is a view of an extractor with double four engagement panels with a proximal core wire, sleeve connector and distal core wire of a fifth embodiment.

FIG. 67 is another view of the extractor 200. The extractor 200 can include any feature of the extractor 100 described herein. Each engagement panels 210, 212, 214, 216 can be formed by two legs 242, 244 shown in FIG. 67. The two legs 242, 244 connect to the arc 240 of engagement panel 210, 212, 214, 216. The two legs 242, 244 can be radially outward from the longitudinal axis of the extractor 200. The two legs 242, 244 can be angled relative to each other. The two legs 242, 244 can be straight. The two legs 242, 244 can have a constant angle therebetween. The two legs 242, 244 can connect to the ends of an arc 240. The extractor 200 can include the eyelet 246. The eyelet can form a lumen. The extractor can include the connecting member, extension or bridge 218. The engagement panels 210, 212, 214, 216 can be at the first longitudinal location. The engagement panels 220, 222, 224, 226 can be at the second longitudinal location. The engagement panels 230, 232, 234, 236 can be at the third longitudinal location. The engagement panels 210, 212, 214, 216 can be continuous with no loop ends. The engagement panels 220, 222, 224, 226 can be continuous with no loop ends. The engagement panels 230, 232, 234, 236 can be continuous with no loop ends. In some embodiments, the engagement panels 220, 222, 224, 226, 230, 232, 234, 236 can be continuous with no loop ends. In some embodiments, all the engagement panels of the extractor is one single unit with no loop ends. The arc 240 of each engagement panel 210, 212, 214, 216, 220, 222, 224, 226, 230, 232, 234, 236 can be configured to be in contact with the vessel wall preferably. The arc 240 of each engagement panel 210, 212, 214, 216, 220, 222, 224, 226, 230, 232, 234, 236 can also be configured to be near the vessel wall without contact with the vessel wall. The arc 240 of each engagement panel 210, 212, 214, 216, 220, 222, 224, 226, 230, 232, 234, 236 can form a smooth, atraumatic edge.

In some embodiments, the eyelet 246 can allow the engagement panels 210, 212, 214, 216 at the first longitudinal location to move longitudinally. In some embodiments, the eyelet 246 can allow the engagement panels 220, 222, 224, 226 at the second longitudinal location to move longitudinally. In some embodiments, the eyelet 246 can allow the engagement panels 230, 232, 234, 236 at the third longitudinal location to move longitudinally.

The extractor 200 can have a plurality of connecting members 218, 228, 238. The connecting member 218 can connect the engagement panels 210, 212, 214, 216 at the first longitudinal location and the engagement panels 220, 222, 224, 226 at the second longitudinal location. The connecting member 228 can connect the engagement panels 220, 222, 224, 226 at the second longitudinal location and the engagement panels 230, 232, 234, 236 at the third longitudinal location. The connecting member 338 can connect the engagement panels 230, 232, 234, 236 at the third longitudinal location and another set of engagement panels. The connecting members 218, 228, 238 and the engagement panels 210, 212, 214, 216, 220, 222, 224, 226, 230, 232, 234, 236 can be continuous and integrally formed. The connecting members 218, 228, 238 can be formed of the same material as the engagement panels 210, 212, 214, 216, 220, 222, 224, 226, 230, 232, 234, 236. The connecting members 218, 228, 238 can be separately formed from the engagement panel 210, 212, 214, 216, 220, 222, 224, 226, 230, 232, 234, 236. The connecting members 218, 228, 238 can be formed of a different material as the engagement panels 210, 212, 214, 216, 220, 222, 224, 226, 230, 232, 234, 236.

The extractor 200 can include one or more radiopaque markers 248. The radiopaque marker 248 can be located on the arc 240. The first longitudinal location can include one or more radiopaque markers 248. Two arcs 240 at the first longitudinal location can include radiopaque markers 248. Two diametrically opposed arcs 240 at the first longitudinal location can include radiopaque markers 248. The second longitudinal location can include one or more radiopaque markers 248. The third longitudinal location can include one or more radiopaque markers 248. Other configuration and location are contemplated.

FIG. 68-73 are views of an extractor 500. The extractor 500 can include any feature described herein. The extractor 500 can include double layers engagement panels. The extractor 500 can include radiopaque markers. The extractor 500 can include a distal end 504. The extractor 500 can include a catheter shaft 506. The extractor 500 can have a plurality of engagement panels 510, 512, 514, 516, 520, 522, 524, 526, 530, 532, 534, 536. The engagement panels 510, 512, 514, 516 are located at a first longitudinal location. The engagement panels 520, 522, 524, 526 are located at a second longitudinal location. The engagement panels 530, 532, 534, 536 are located at a third longitudinal location. In some embodiments, the extractor 500 can include four engagement panels at each longitudinal location. The extractor 500 can include a distal member 580. The distal member 580 can include any feature described herein.

The extractor 500 can include a core wire 570. The core wire 570 can be made of one, two, three or more components. The core wire 570 can include a proximal core wire 572. The proximal core wire 572 can comprise stainless steel, nitinol, laser cut tube, polymers, and/or combinations thereof. The core wire 570 can include a distal core wire 574. The distal core wire 574 can comprise stainless steel, nitinol, laser cut tube, polymers, and/or combinations thereof. The extractor 500 can include a sleeve connector 576. The sleeve connector 576 can comprise stainless steel, nitinol, laser cut tube, polymers, and/or combinations thereof. The sleeve can be of radiopaque material for better visualization.

Figure 69:
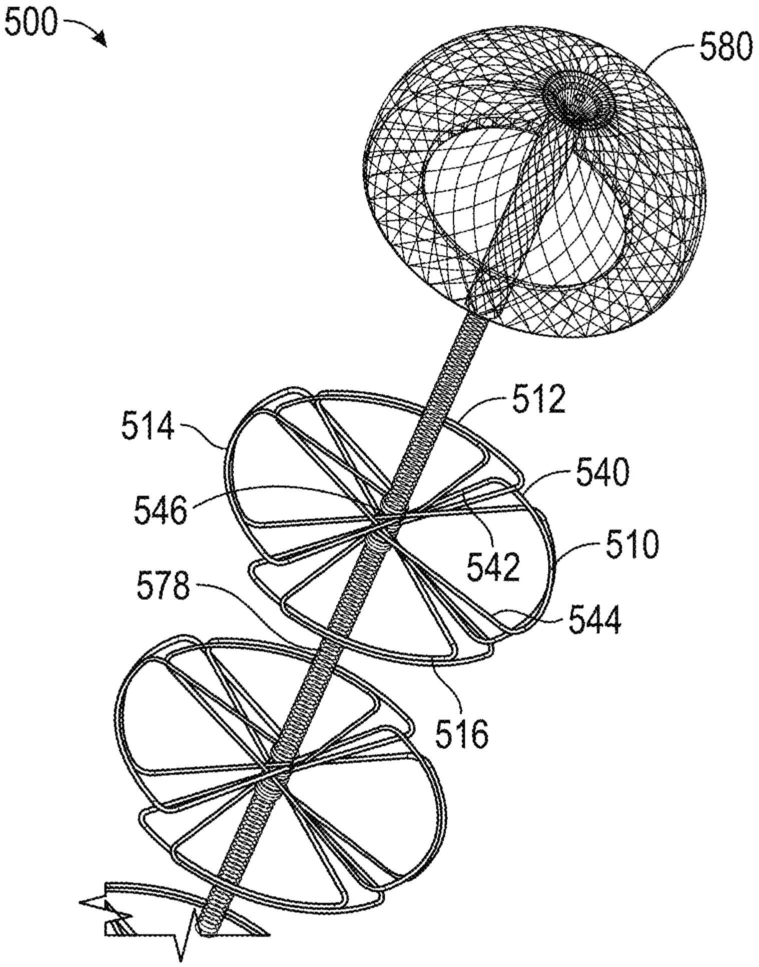
FIG. 69 is a view of the double four engagement panels of the fifth embodiment.
Figure 70:
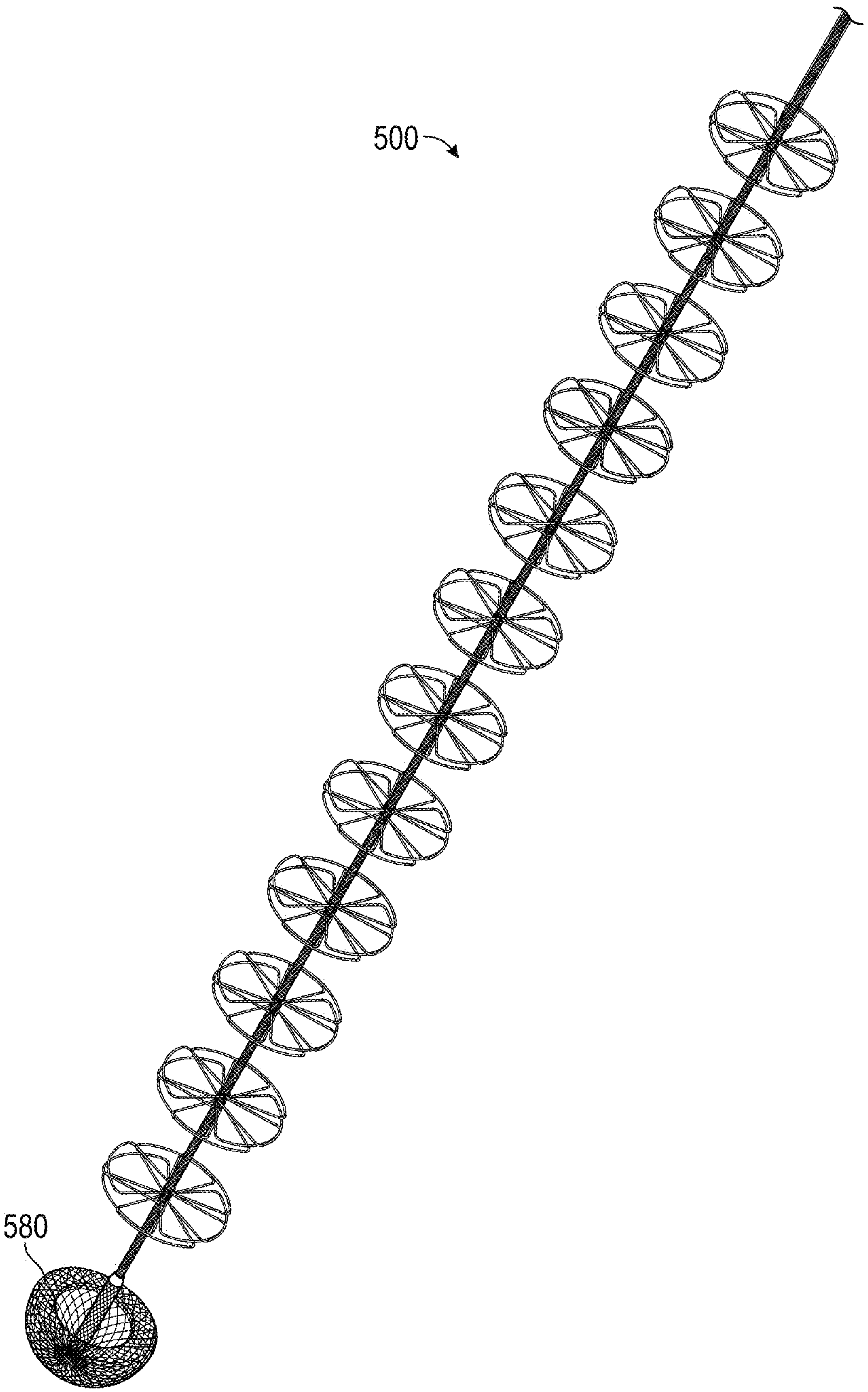
FIG. 70 is another view of the double four engagement panels of the fifth embodiment.
Figure 71:
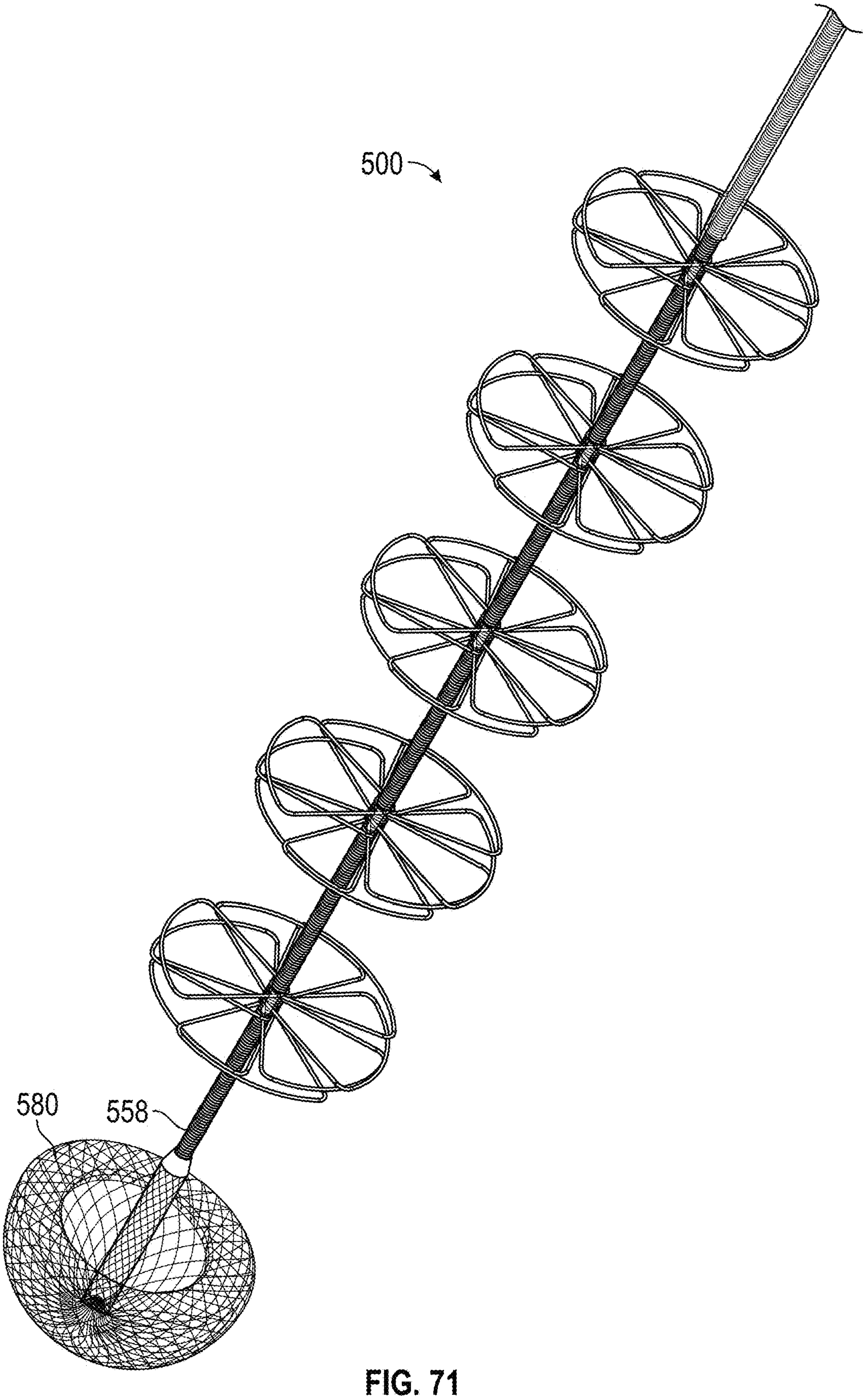
FIG. 71 is another view of the double four engagement panels where the panels can be 1, 2, 3 or more layers of nitinol, Stainless steel or shape memory polymers of the fifth embodiment.

FIG. 69 illustrates the engagement panels. The extractor 500 can include double layer engagement panels. Each engagement panel 510, 512, 514, 516 can be formed from two layers. The two layers can be aligned. The two layers can be offset. The first layer can form one substantially complete circumference. The second layer can form one substantially complete circumference.

Each engagement panels 510, 512, 514, 516 can be formed by two legs 542, 544. The two legs 542, 544 connect to the arc 540 of engagement panel 510, 512, 514, 516. The two legs 542, 544 can be radially outward. The two legs 542, 544 can be angled relative to each other. The two legs 542, 544 can connect to the ends of the arc 540. The two legs 542, 544 of the first layer can be offset from the two legs 542, 544 of the second layer. The arc 540 of the first layer can be offset from the arc 540 of the second layer. The layers can be circumferentially offset. The layers can be twisted relative to a eyelet 546. The layers can be offset by a small degree. The layers can partially overlap. The two legs 542, 544 of the first layer can be aligned with the two legs 542, 544 of the second layer. The arc 540 of the first layer can be aligned with the arc 540 of the second layer. The layers can be longitudinally aligned. The layers can abut. The layers can overlap. The layers can be stacked. The layers can completely align. The first layer can be distal to the second layer.

The extractor 500 can include a coil 578. The coil 578 can form a lumen for the core wire 570. The coil 578 can function as a connecting member. The coil 578 can function as a spacer. The coil 578 can connect the engagement panels 510, 512, 514, 516 at the first longitudinal location and the engagement panels 520, 522, 524, 526 at the second longitudinal location. The coil 578 can connect the engagement panels 520, 522, 524, 526 at the second longitudinal location and the engagement panels 530, 532, 534, 536 at a third longitudinal location. The coil 578 can connect the engagement panels 530, 532, 534, 536 at a third longitudinal location and another set of engagement panels. The coil 578 and the engagement panels 510, 512, 514, 516, 520, 522, 524, 526, 530, 532, 534, 536 can be continuous. The coil 578 and the engagement panels 510, 512, 514, 516, 520, 522, 524, 526, 530, 532, 534, 536 can be integrally formed. The coil 578 and the engagement panels 510, 512, 514, 516, 520, 522, 524, 526, 530, 532, 534, 536 can be separately formed and connected together. The coil 578 can include a radiopaque marker. The coil 578 can include a radiopaque material. The coil 578 is substantially inside an outer member 568. The outer member 568 can be made of polymeric materials such as polyethylene, PTFE, FEP, polyurethane, nylon, PEBAX for example. The outer member 568 can be made of metallic materials. The coil 578 can include a distal marker 558 shown in FIG. 71.

The engagement panels 510, 512, 514, 516, 520, 522, 524, 526, 530, 532, 534, 536 can be made of 1, 2, 3 or more layers. The engagement panels 510, 512, 514, 516, 520, 522, 524, 526, 530, 532, 534, 536 can be made of nitinol, stainless steel, shape memory polymers and/or combinations thereof.

Figure 72:
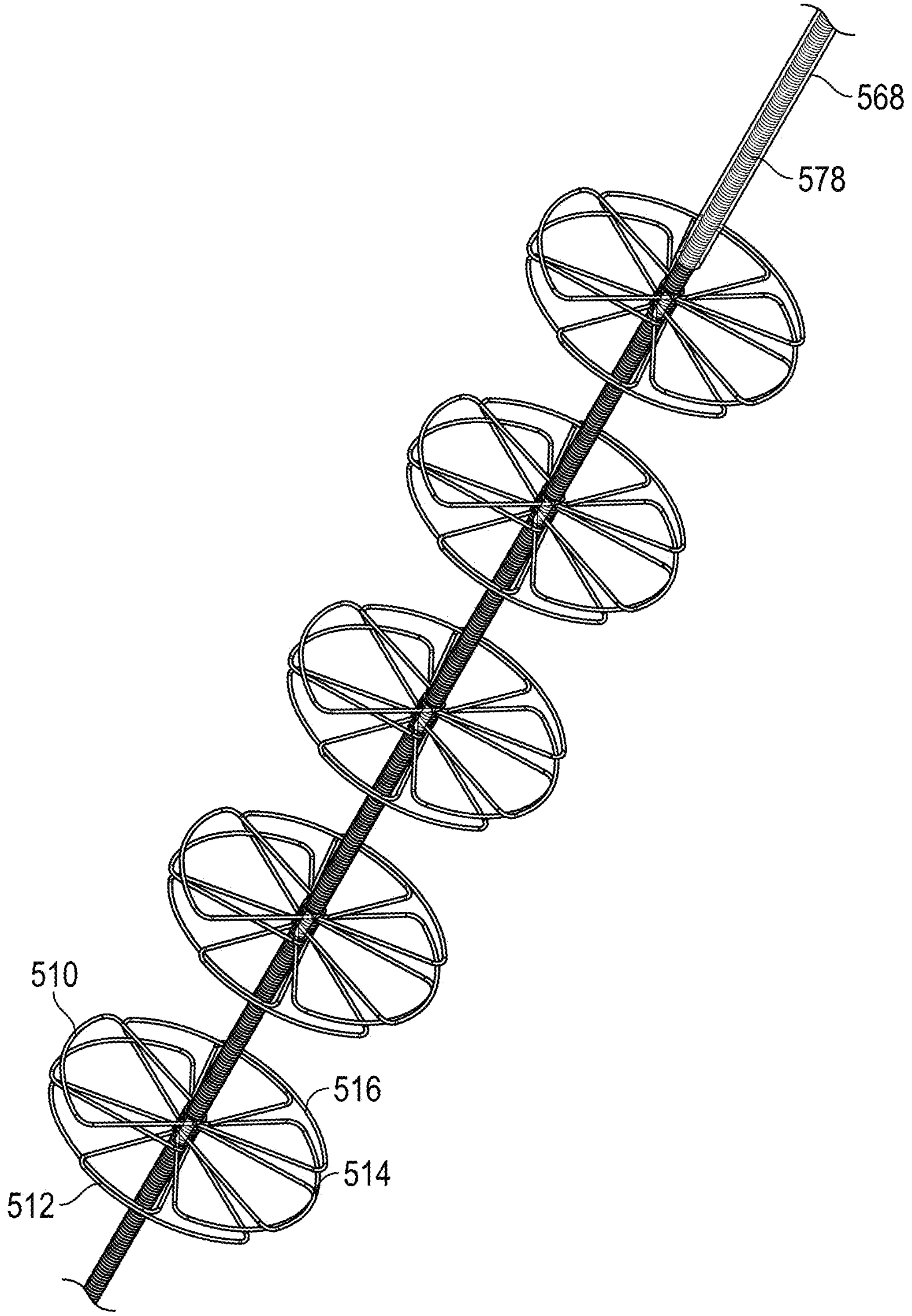
FIG. 72 is another view of the double four engagement panels with support coils and PTFE jacket of the fifth embodiment.

FIG. 72 illustrates the extractor 500 with a triple layer engagement panel. The two legs 542, 544 of the first layer can be offset from the two legs 542, 544 of the second layer. The two legs 542, 544 of the second layer can be offset from the two legs 542, 544 of the third layer. The arc 540 of the first layer can be offset from the arc 540 of the second layer. The arc 540 of the second layer can be offset from the arc 540 of the third layer. The layers can be circumferentially offset. The layers can be offset by a small degree. The layers can be offset by a large degree. The layers can at least partially overlap. The two legs 542, 544 of the first layer can be aligned with the two legs 542, 544 of the second layer and the two legs 542, 544 of the third layer. The arc 540 of the first layer can be aligned with the arc 540 of the second layer and the arc 540 of the third layers. The plurality of layers can be longitudinally aligned. The plurality of layers can abut. The plurality of layers can overlap. The plurality of layers can be stacked. The plurality of layers can completely align. The first layer can be distal to the second layer. The second layer can be distal to the third layer. The coil 578 can function as a support coil. The coil 578 can include a jacket 568. The jacket 568 can comprise PTFE.

Figure 73:
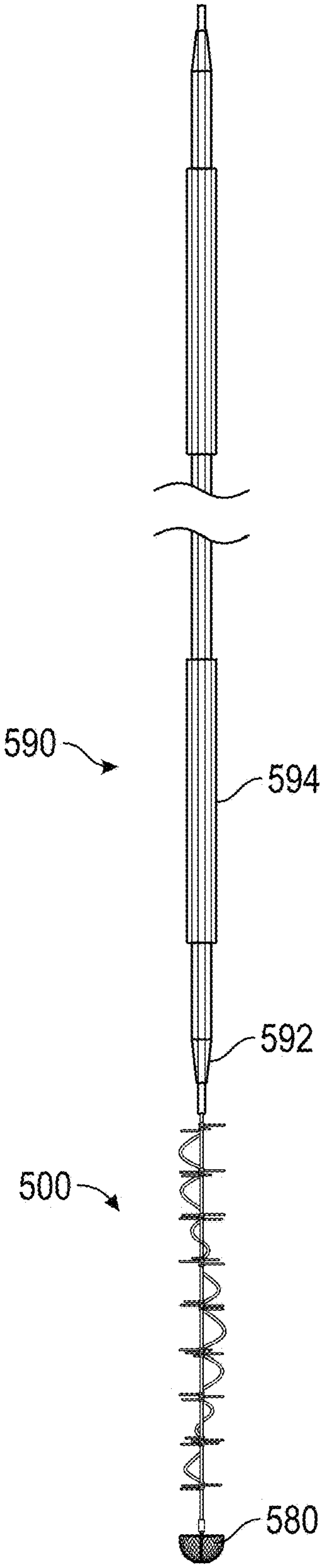
FIG. 73 is a view of the loading tube assembly used to load the extractor into the delivery catheter. The loading tube assembly can also be a sheath or a tubular member.
Figure 74:
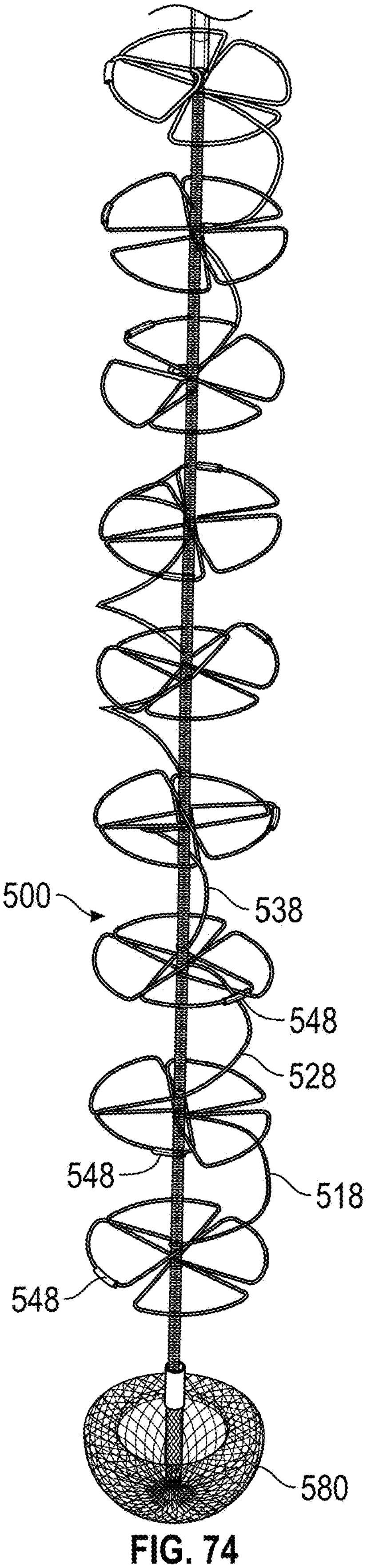
FIG. 74 is a view of the single four engagement panels of the fifth embodiment.
Figure 75:
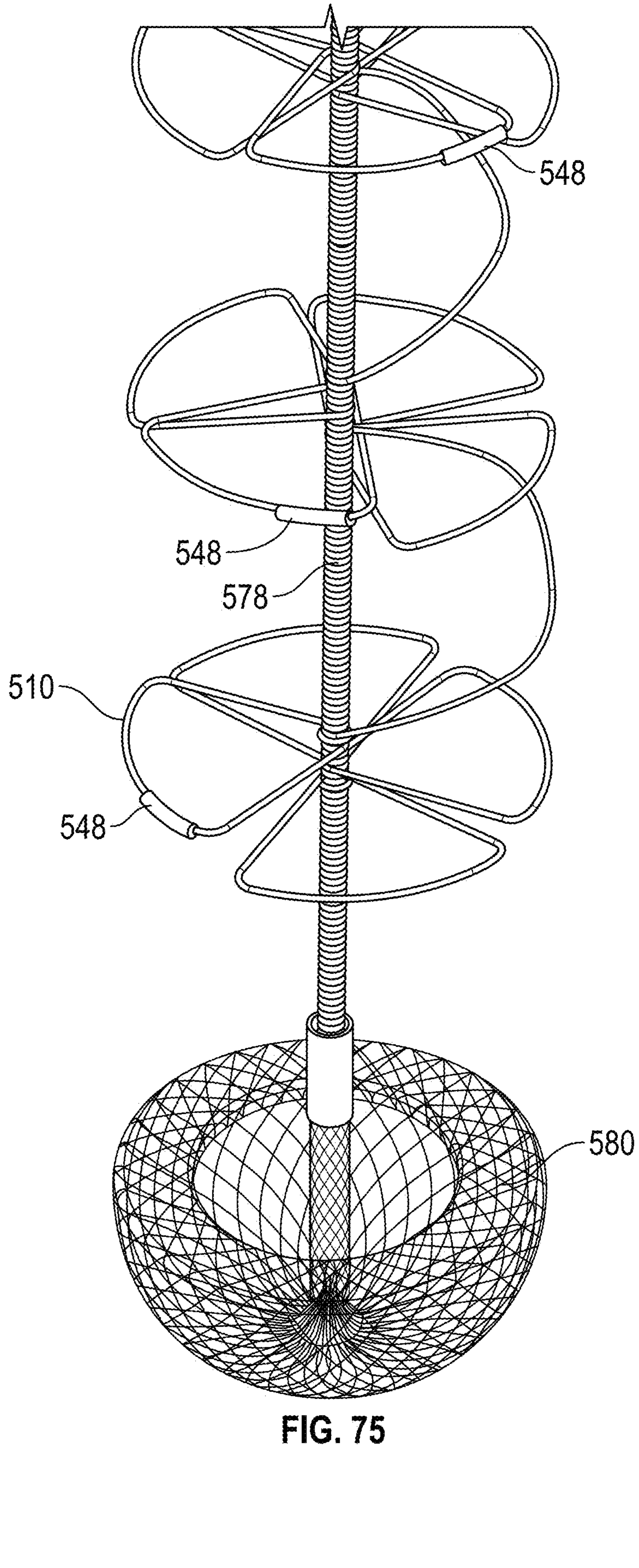
FIG. 75 is a view of the single four engagement panels with marker bands that can be made of platinum/iridium tube or coils. The engagement panels can be made of solid elastic nitinol wire or DFT wire (drawn filled tubing) Nitinol with platinum core of the fifth embodiment.
Figure 76A:
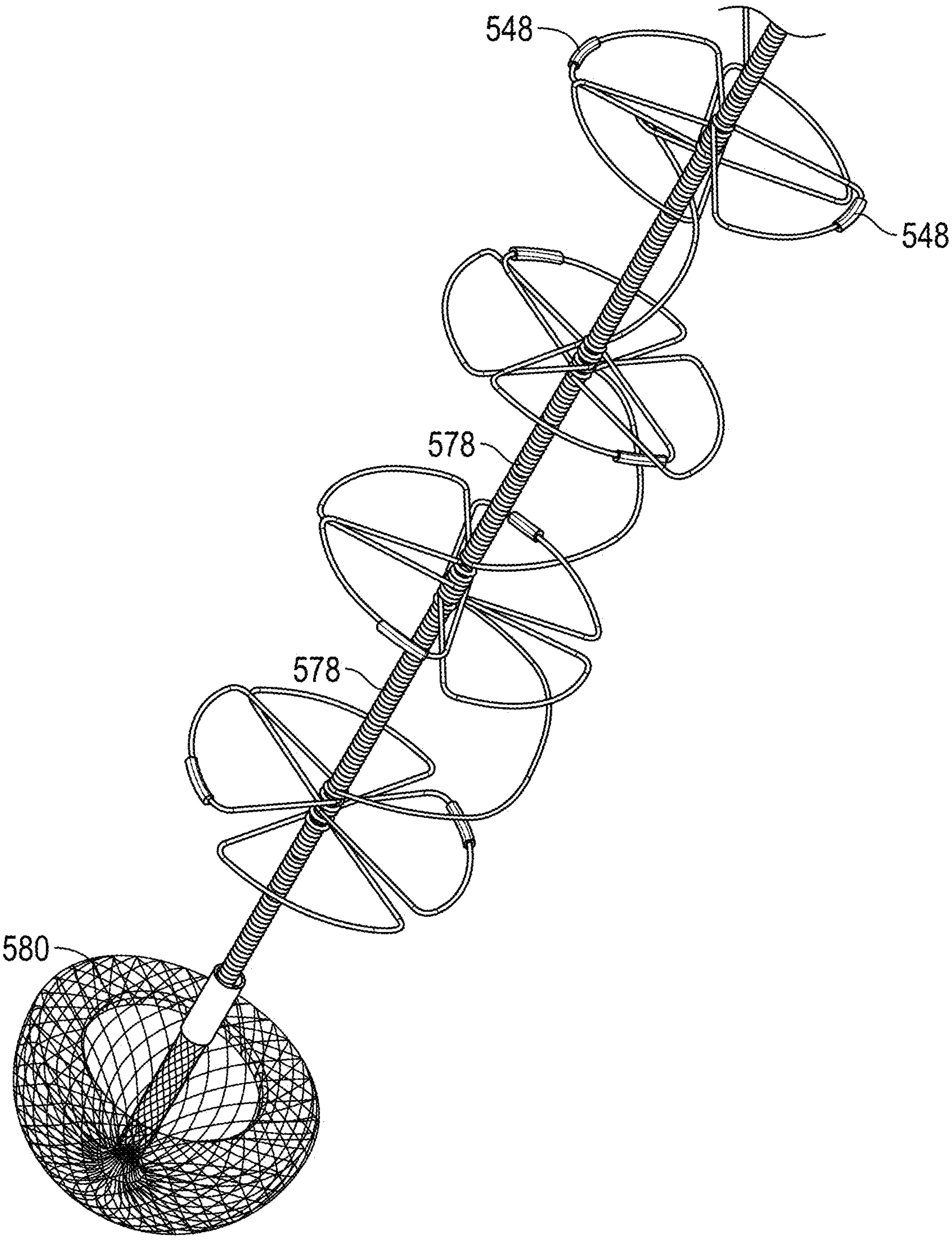
FIGS. 76A-76B are views of the single four engagement panels with platinum coils and radiopaque markers of the fifth embodiment.
Figure 76B:
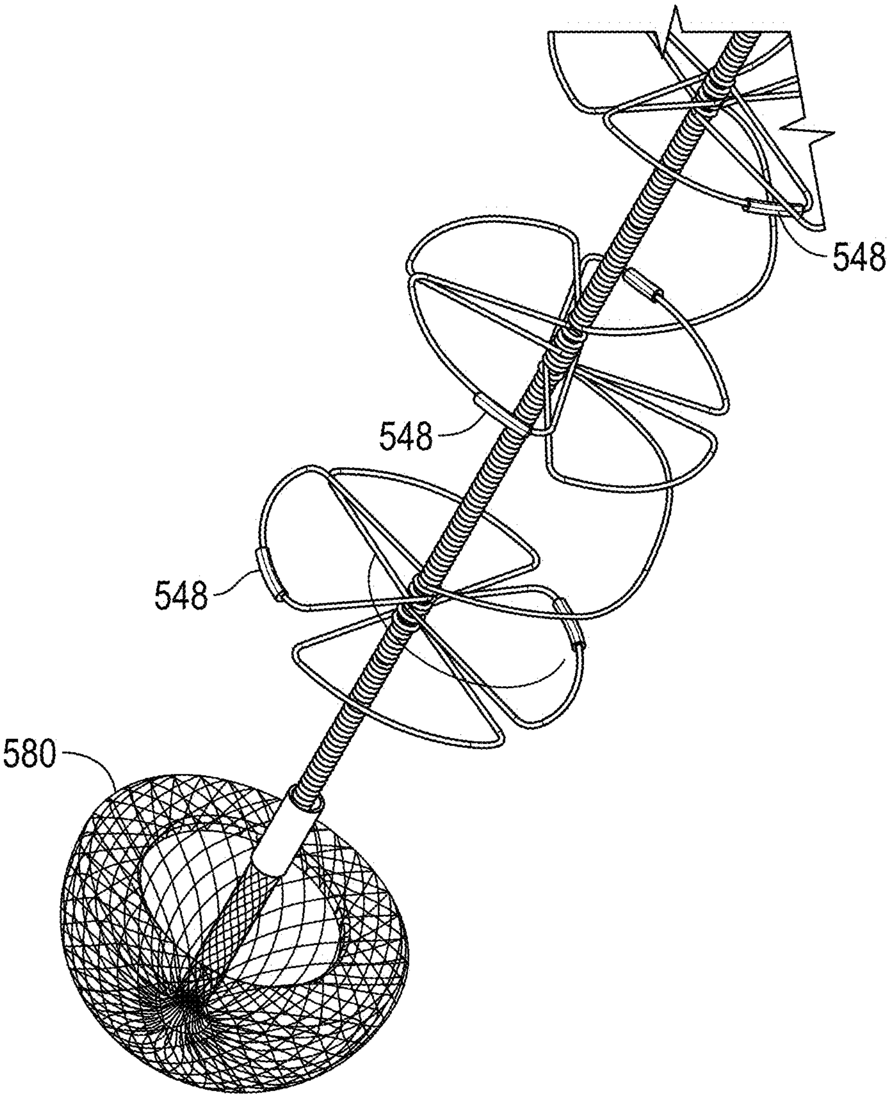
Figure 77:
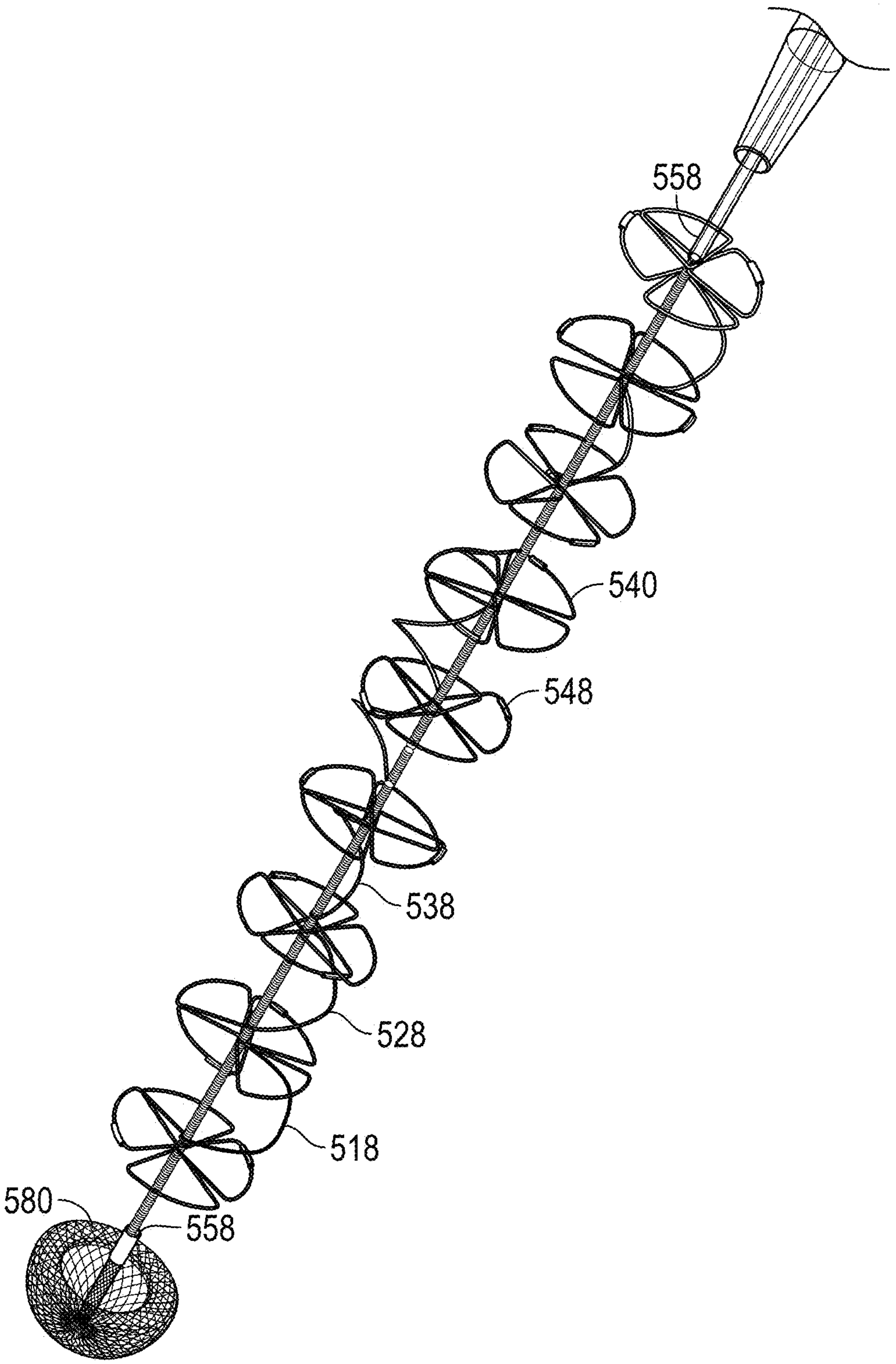
FIG. 77 is another view of the single four engagement panels with marker bands showing at both ends of the fifth embodiment.
Figure 78A:
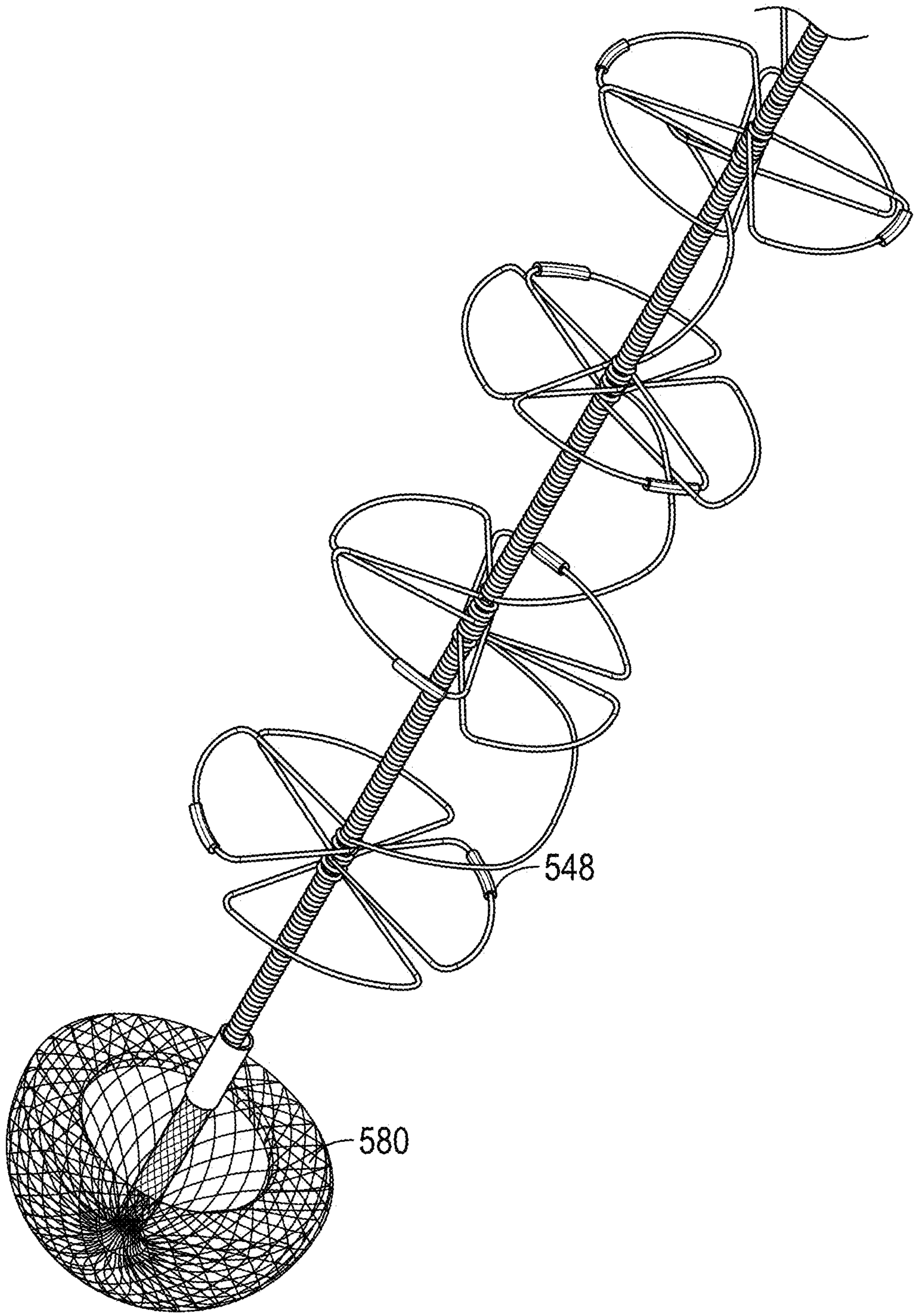
FIG. 78A is a view of the single four engagement panels of the fifth embodiment.
Figure 78B:
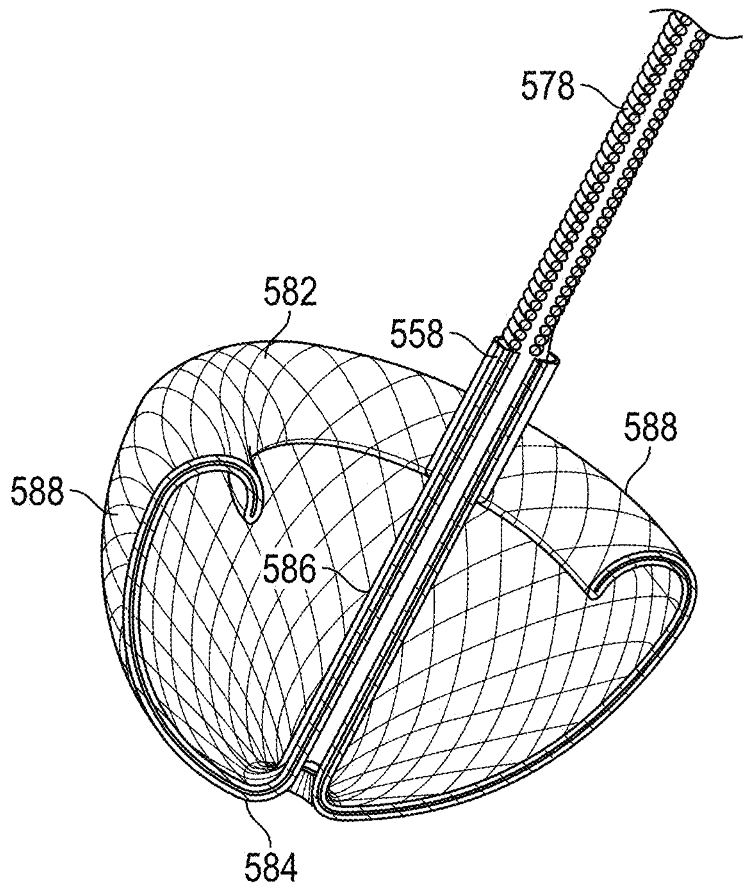
FIG. 78B is a view of a distal member.
Figure 79:
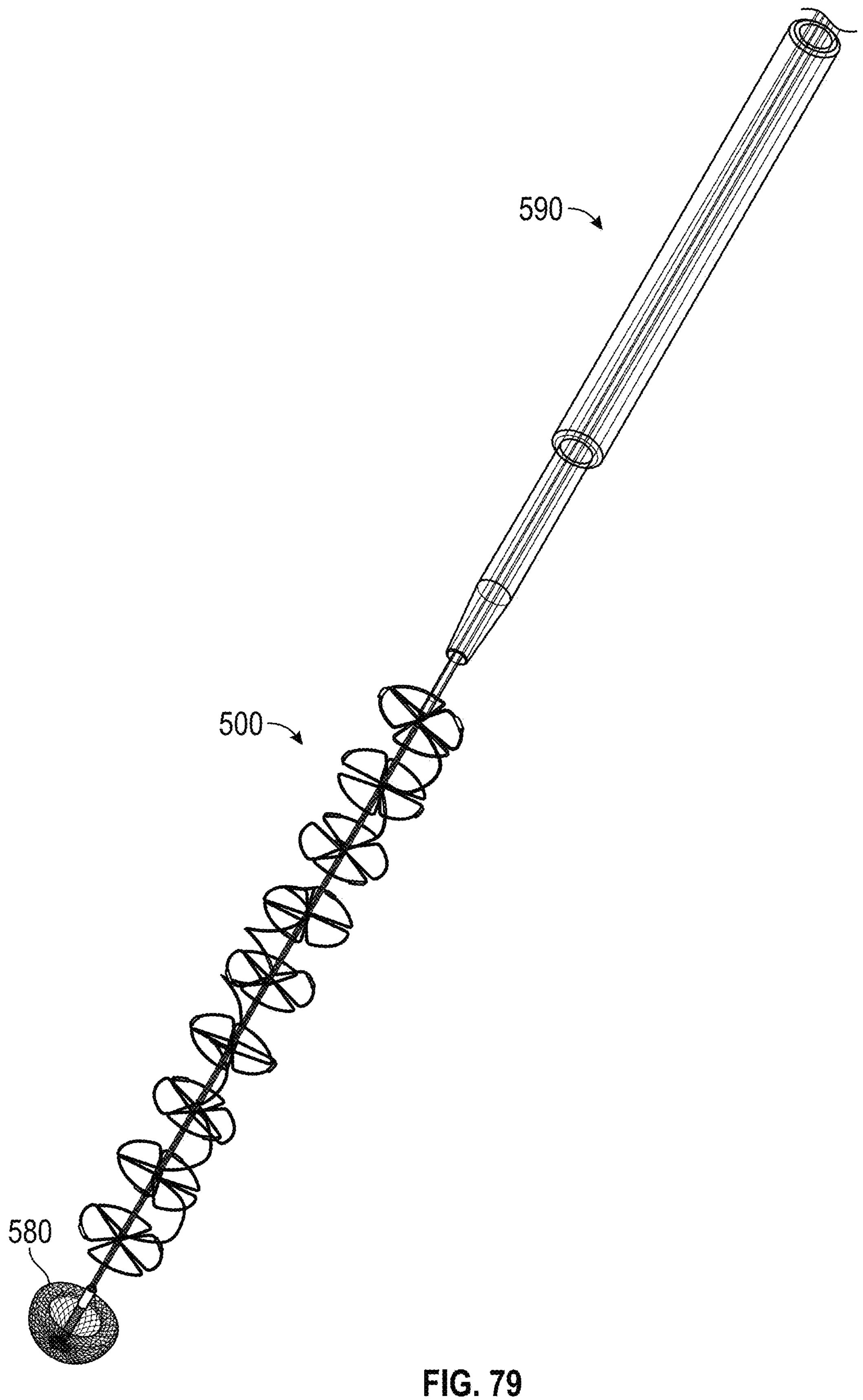
FIG. 79 is a view of the extractor in the expanded configuration and loading tube assembly. The loading tube assembly can also be a tubular member or a sheath.

FIG. 73 illustrates the loading tube assembly 590. The loading tube assembly 590 can include a taper end 592 for engagement with the microcatheter. The loading assembly 590 can include a larger section 594 to minimize slippage during device insertion. The loading tube aids to introduce the device into the microcatheter or delivery catheter and advance within the microcatheter or delivery catheter to the treatment site. The loading tube can be made of polymeric materials such as Polyethylene, PTFE, FEP, Nylon, Polyurethane, PEBAX or PET for example. The loading tube assembly can also be a tubular member or a sheath.

FIG. 74-79 are view of the extractor 500 with single layer engagement panels. The extractor 500 can include radiopaque markers on the engagement panels. The extractor 500 can include one or more radiopaque markers 548. The radiopaque marker 548 can be located on the arc 540. The first longitudinal location can include one or more radiopaque markers 548. One arc 540 can include radiopaque markers 548 at the first longitudinal location. The second longitudinal location can include one or more radiopaque markers 548. The third longitudinal location can include one or more radiopaque markers 548. Other configuration are contemplated. The coil segment in between the engagement panels can be radiopaque. For example, the coil segment between the first longitudinal location and the second longitudinal location is made of platinum/iridium or tungsten. The radiopaque markers 548 can be marker bands. The radiopaque markers 548 can be made of platinum and/or iridium. The radiopaque markers 548 can be made of tubes or coils. The extractor 500 can also connecting members, extension or bridge 518, 528, 538. The engagement panels 510, 512, 514, 516, 520, 522, 524, 526, 530, 532, 534, 536 can be made of solid super elastic nitinol wire. The engagement panels 510, 512, 514, 516, 520, 522, 524, 526, 530, 532, 534, 536 can be made of DFT (drawing filled tubing) nitinol with a platinum core.

The engagement panels 510, 512, 514, 516, 520, 522, 524, 526, 530, 532, 534, 536 can be formed from a single layer. The two legs 542, 544 of the engagement panel 510 can be angled from the two legs 542, 544 of the engagement panel 512. The two legs 542, 544 of the engagement panel 510 can be separated from the two legs 542, 544 of the engagement panel 512. The arcs 540 of the engagement panels 510, 512, 514, 516, 520 can form an incomplete circle. The arcs 540 of the engagement panels 510, 512, 514, 516, 520 can form segments of a circle. There can be one radiopaque marker 548 on the engagement panels 510, 520, 530. The extractor 500 can include platinum coils along the core wire 570. The extractor 500 can include one or more additional bands 558. There can be a band 558 at the distal end. There can be a band 548 at or near the proximal end. There can be a band 558 at any location along the length. There can be a band 558 at both ends. The coil 578 can include platinum coils. There can be one, two, or more radiopaque marker 558 at a longitudinal location.

The extractor 500 can have a plurality of connecting members 518, 528, 538. The connecting member 518 can connect the engagement panels 510, 512, 514, 516 at the first longitudinal location and the engagement panels 520, 522, 524, 526 at the second longitudinal location. The connecting member 528 can connect the engagement panels 520, 522, 524, 526 at the second longitudinal location and the engagement panels 530, 532, 534, 536 at the third longitudinal location. The connecting member 538 can connect the engagement panels 530, 532, 534, 536 at the third longitudinal location and another set of engagement panels. The connecting members 518, 528, 538 can be curved.

The distal member 580 can be made from a single layer nitinol braid. The distal member 580 can be made from a double layer nitinol braid. The distal member 580 can be made from closed end single layer nitinol braid. The distal member 580 can be made from closed end double layer nitinol braid. The distal member 580 can be straightened in a loaded configuration. In some embodiments, the distal member 580 can be straightened distally. In some embodiments, the distal member 580 can invert during deployment. In some embodiments, the distal member 580 can invert to sweep the vessel wall. The distal member 580 can fold proximally when unsheathed.

In some embodiments, the distal member 580 can include a proximal end 582. The proximal end 582 can be cupped. The proximal end 582 can be folded distally. The proximal end 582 can be folded inward. The proximal end 582 can function as a funnel into the distal member 580. The distal member 580 can collect material within the distal member. In some embodiments, the distal member 580 can include a distal end 584. The distal end 584 can be a floating end. The distal end 584 of the distal member 580 can form the distal end of the device. The distal member 580 can include a tubular portion 586. The tubular portion 586 can extend along a longitudinal or central axis. The tubular portion 586 can extend to the distal end 584. The distal member 580 can include an expanded portion 588. The expanded portion 588 flares outward from the tubular portion 586. The expanded portion 588 encircles the tubular portion 586. The space between the tubular portion 586 and the expanded portion 588 allows for the collection of material. The space between the tubular portion 586 and the expanded portion 588 is enclosed.

In some embodiments, the distal member 580 can be coupled to the core wire 570. In some embodiments, the distal member 580 can be coupled to the coil 578. In some embodiments, the distal member 580 can be coupled to distal marker 558. The distal marker 558 can be coupled to the tubular portion 586 of the distal member 580. The distal marker 558 can be laser welded to the distal member 580. The distal marker 558 can be bonded with an adhesive to the distal member 580. The distal marker 558 can be crimped or swaged or press fit to the distal member 580.

The loading tube assembly 590 can compress the extractor 500. The loading tube assembly 590 can compress the engagement panels. The loading tube assembly 590 can compress the distal member 580. The distal member can straighten in the loading tube assembly 580.

Figure 80A:
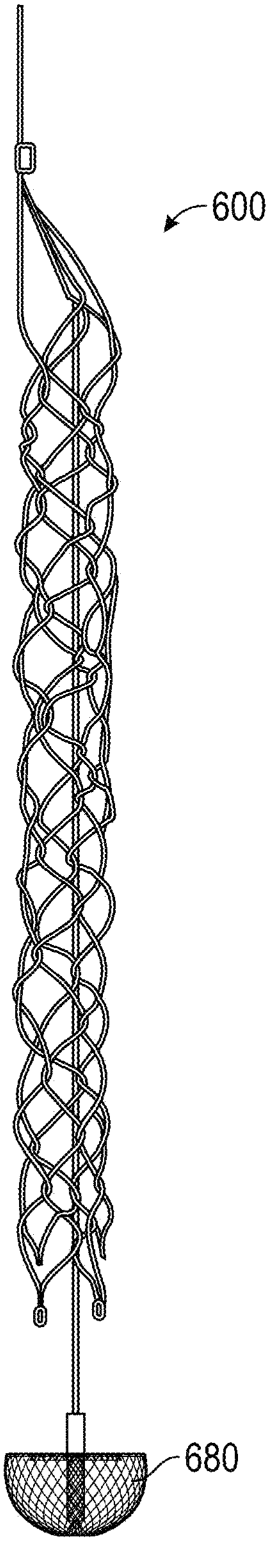
FIGS. 80A-80B are views of a stent retriever assembly.
Figure 80B:
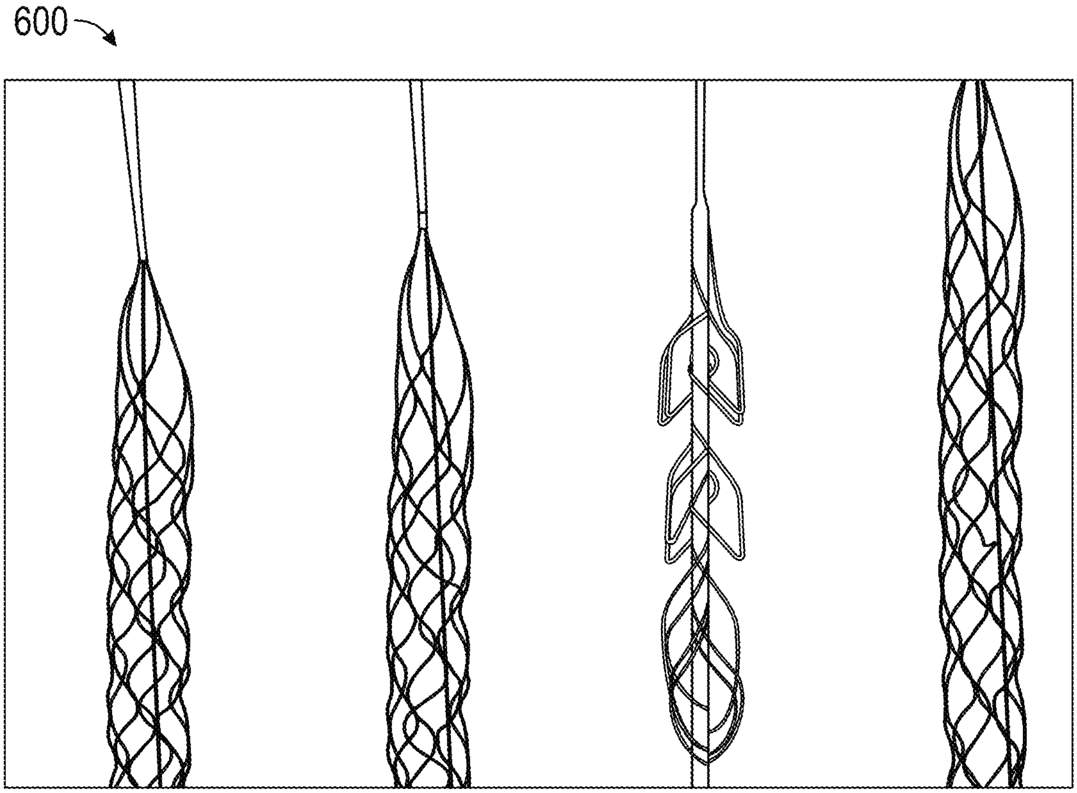

FIGS. 80A-80B are views of examples of a stent retriever 600. The stent retriever 600 can be laser cut. The stent retriever 600 can be self-expandable. The stent retriever 600 can be any shape including the shapes shown. The extractors 100, 200, 300, 400, 500 can be used in combination with the stent retriever 600. The stent retriever 600 can include a distal member 680. The distal member 680 can include any feature described herein. The distal member 680 can capture debris.

Figure 81A:
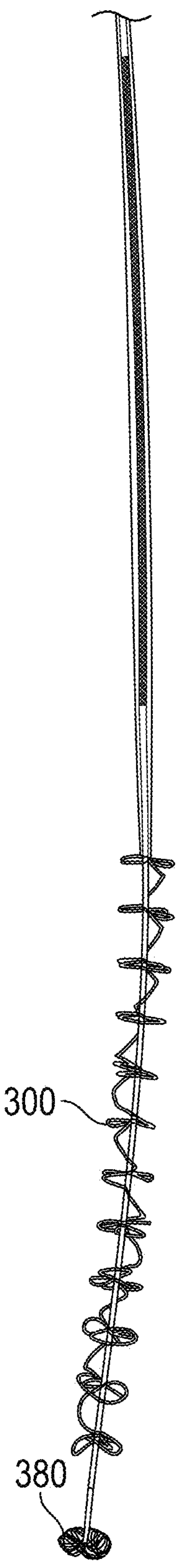
FIGS. 81A-C are views of the extractor and a proximal funnel assembly.
Figure 81B:
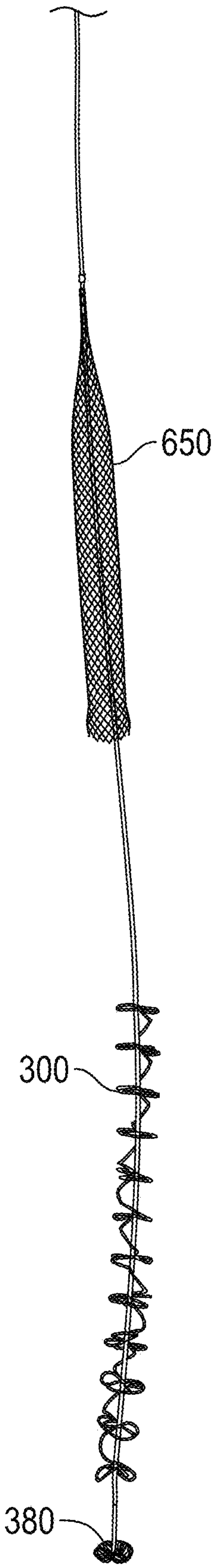
Figure 81C:
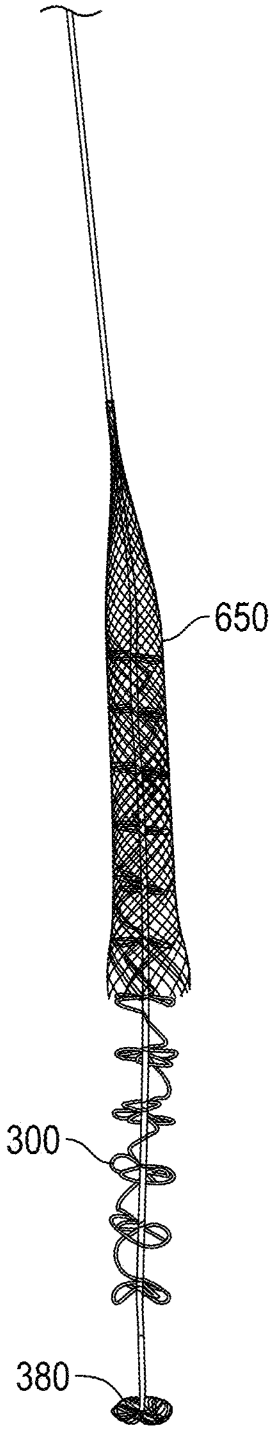

FIGS. 81A-81C are views of the extractor 300 and proximal funnel or collection bag 650. The extractor 300 can include the distal member 380. The extractor 100, 200, 300, 400, 500 can be used in combination with the proximal funnel or collection bag 650. The proximal funnel or collection bag 650 can be built-in. The proximal funnel or collection bag 650 can be proximal to the extractor 100, 200, 300, 400, 500. FIG. 81A illustrates the funnel loaded configuration. FIG. 81B illustrates the funnel deployed configuration. There can be a proximal stopper and a distal stopper. FIG. 81C illustrates the extractor 300 retracted into the proximal funnel or collection bag 650.

Figure 82A:
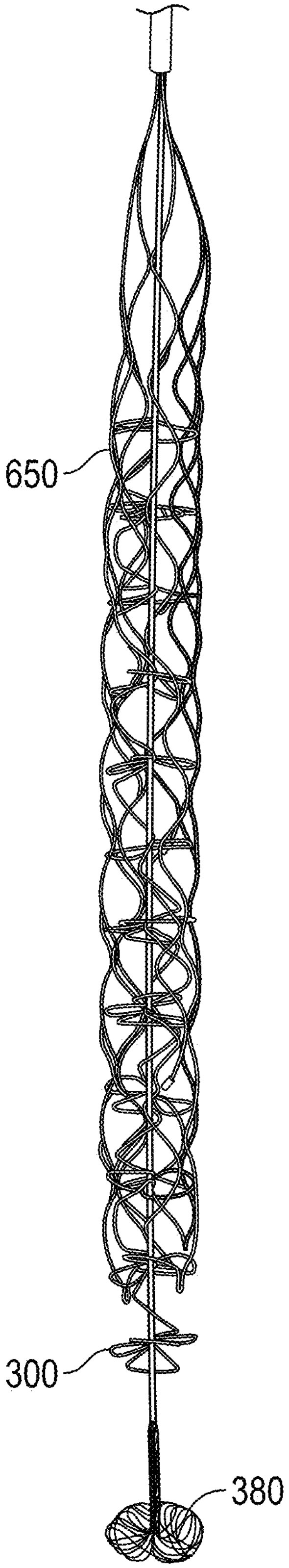
FIGS. 82A-82B are views of the extractor that is within the stent retriever assembly.
Figure 82B:
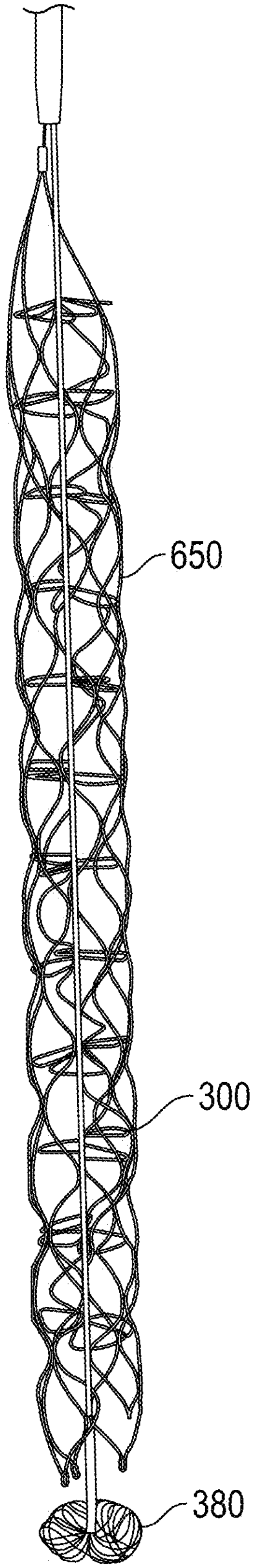

FIGS. 82A-82B are views of the extractor 300 and a stent retriever 600. The extractor 300 can be positioned distal to the stent retriever 600 to enable better clot removal. The extractor 300 can be positioned outside the stent retriever 650. The extractor 300 can be positioned within the stent retriever 650. The extractor 300 can include the distal member 380.

Figure 83A:
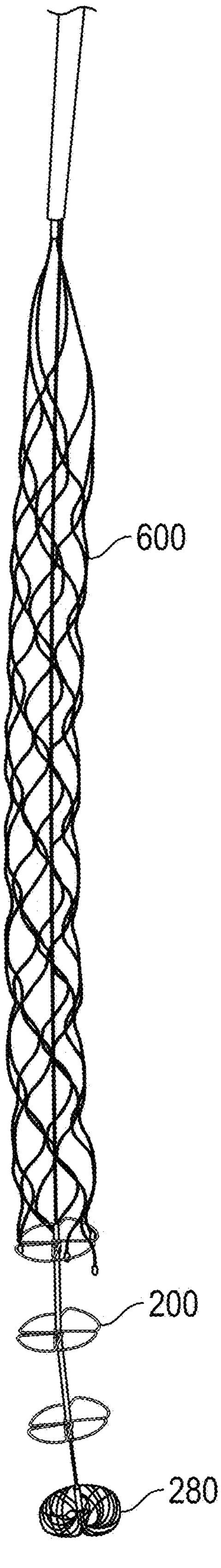
FIGS. 83A-83C are views of the extractor that can be distal to and/or within the stent retriever.
Figure 83B:
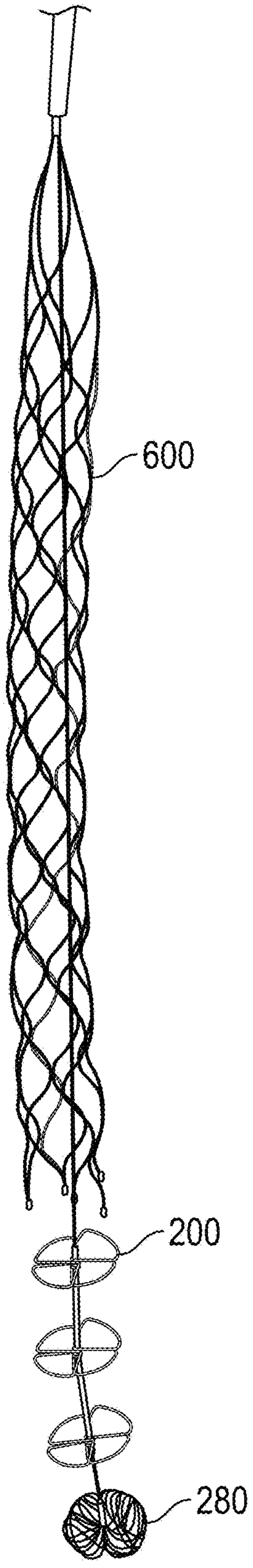
Figure 83C:
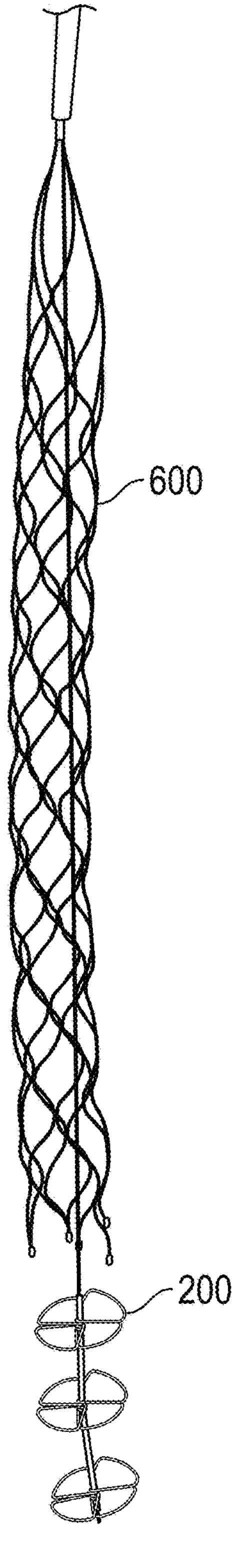
Figure 84A:
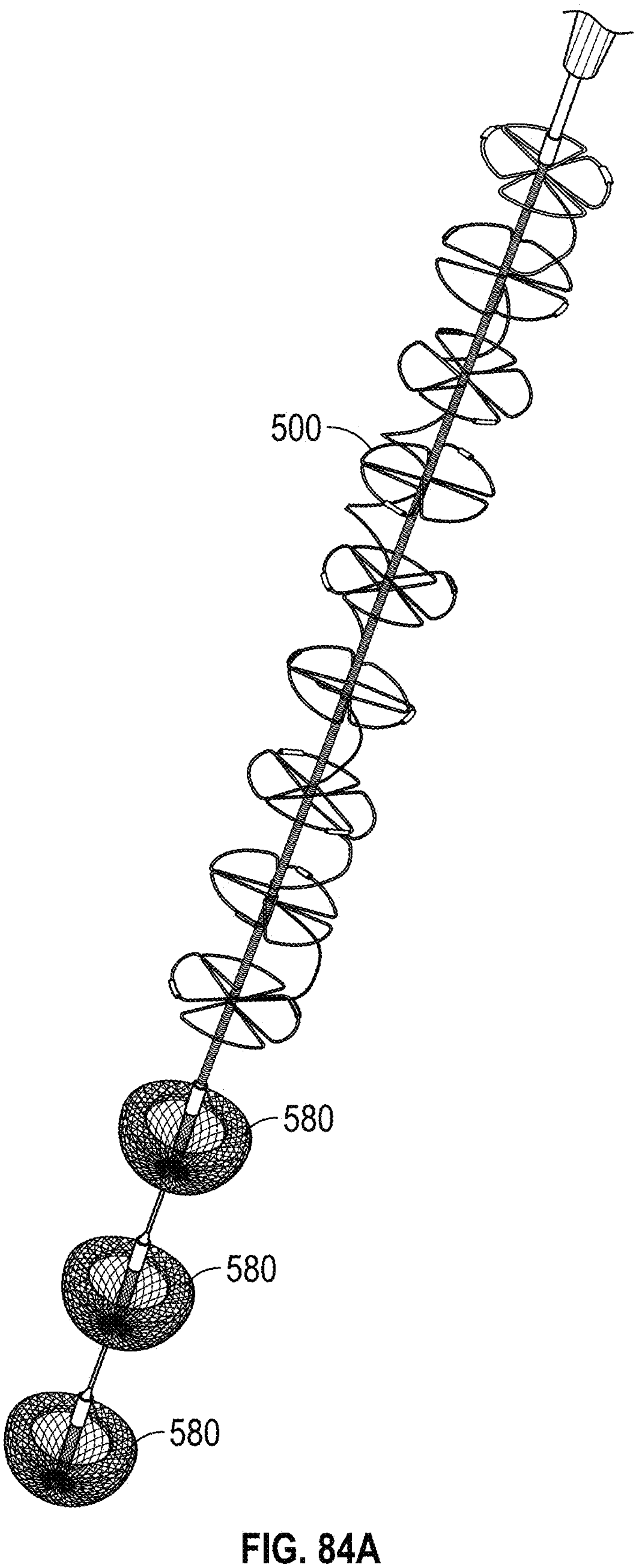
FIGS. 84A-84D are views of the single four engagement panels with multiple distal members. The distal member can be positioned at any location along the extractor to collect loose clot, soft clot, or in transit clot.
Figure 84B:
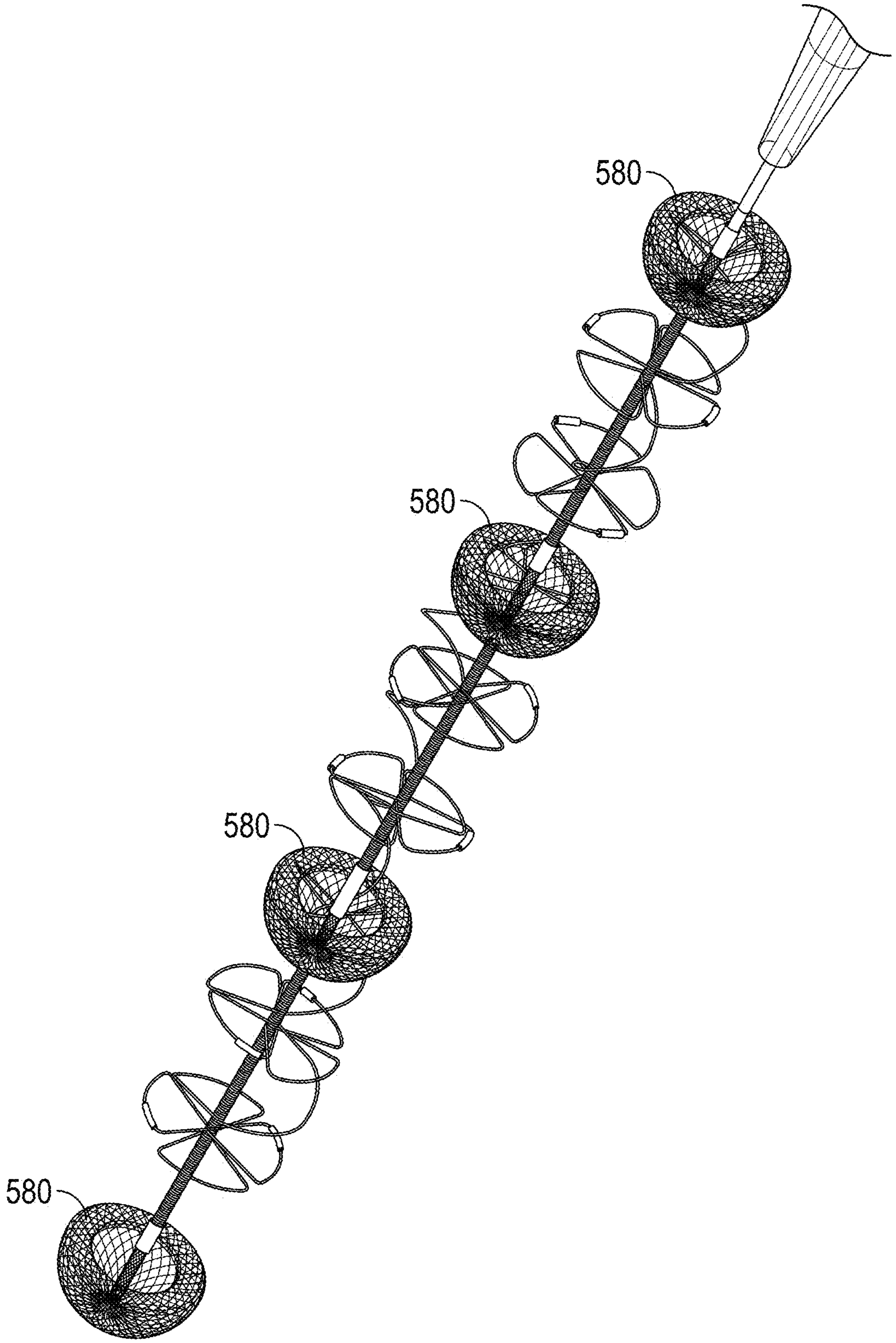
Figure 84C:
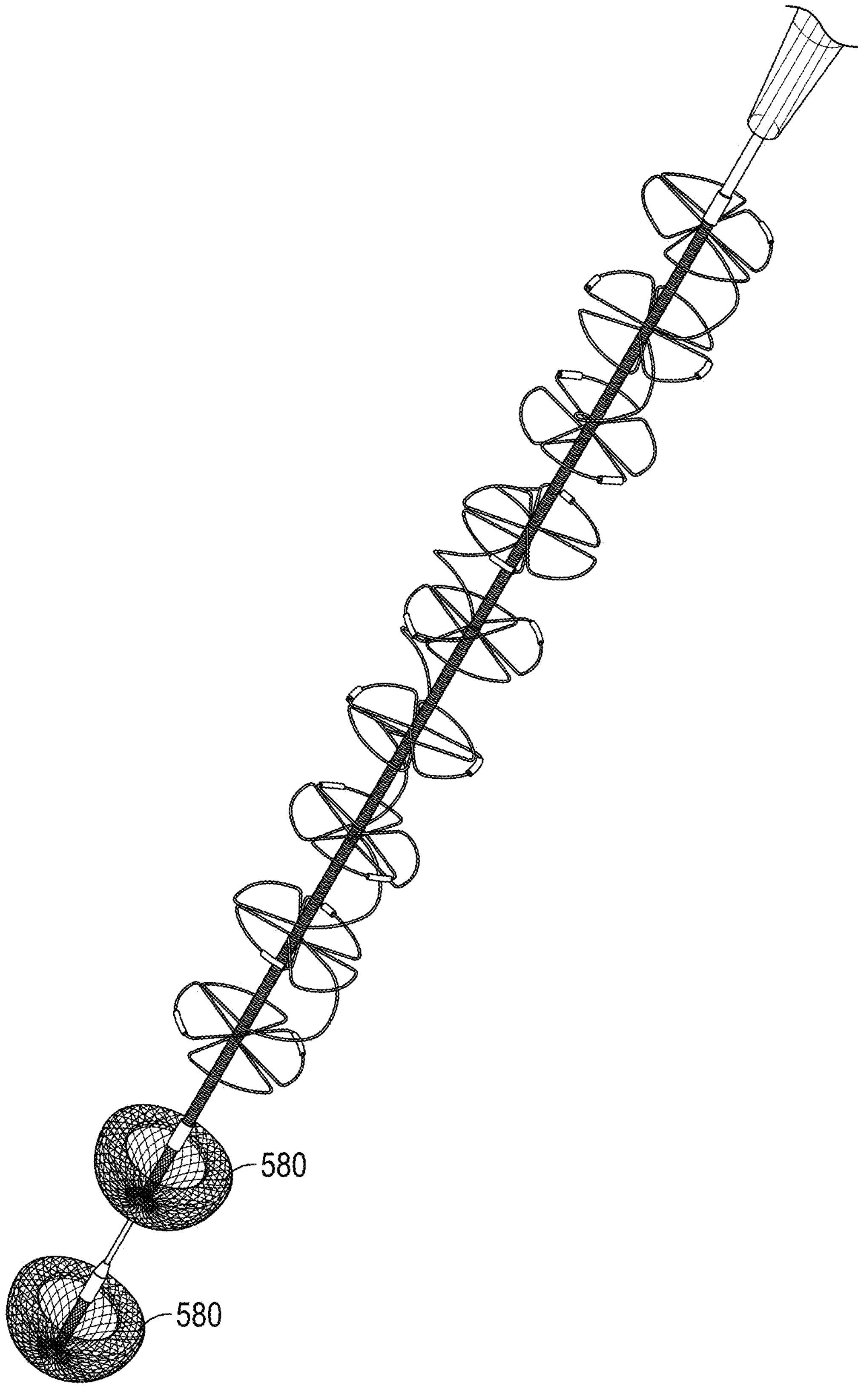
Figure 84D:
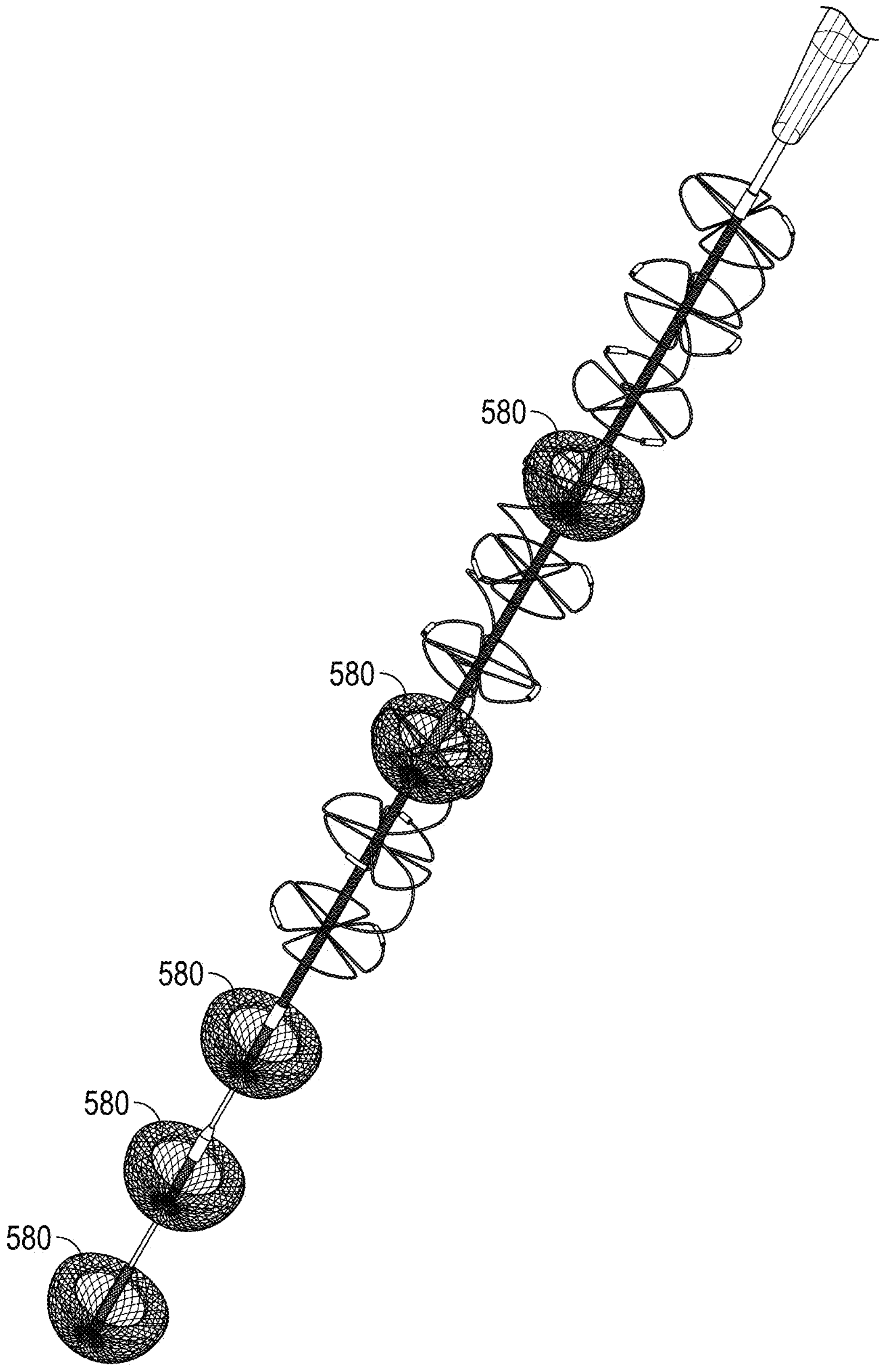

FIGS. 83A-83C views of the extractor 200 stent retriever 600. The extractor 200 can include the distal member 280.

FIGS. 84A-84D are views of the extractor 500. The extractor 500, or any embodiment disclosed herein, can include one or more distal members. FIGS. 84A-84D are views of multiple distal members 580. The distal member 580 can be positioned at any location along the extractor 500. The distal member can collect loose clot, soft clot, or in transit clot. The figures illustrates that the distal end of the device can include one, two, three, four, five, six, or more distal members 580. The distal members 580 can function as end caps. The distal members 580 can be located at various positions of the extractor 500. In some embodiments, the distal member 580 can be located distal to the first longitudinal location. Two or more distal members 580 can be located distal to the first longitudinal location. The engagement panel 510, 512, 514, 516 can be located at the first longitudinal location. The engagement panel 520, 522, 524, 526 can be located at the second longitudinal location. The engagement panel 530, 532, 534, 536 can be located at the second longitudinal location. In some embodiments, one or more distal members 580 can be located between the first longitudinal location and the second longitudinal location. In some embodiments, no distal members 580 are located between the first longitudinal location and the second longitudinal location. In some embodiments, one or more distal members 580 can be located between the second longitudinal location and the third longitudinal location. In some embodiments, no distal members 580 are located between the second longitudinal location and the third longitudinal location. In some embodiments, one or more distal members 580 can be located proximal to the third longitudinal location. In some embodiments, no distal members 580 are located proximal to the third longitudinal location. In some embodiments, one or more distal members 580 are regularly spaced. In some embodiments, one or more distal members 580 are irregularly spaced. In some embodiments, the engagement panel 510, 512, 514, 516 and the engagement panel 520, 522, 524, 526 are between adjacent distal members 580.

Figure 85A:
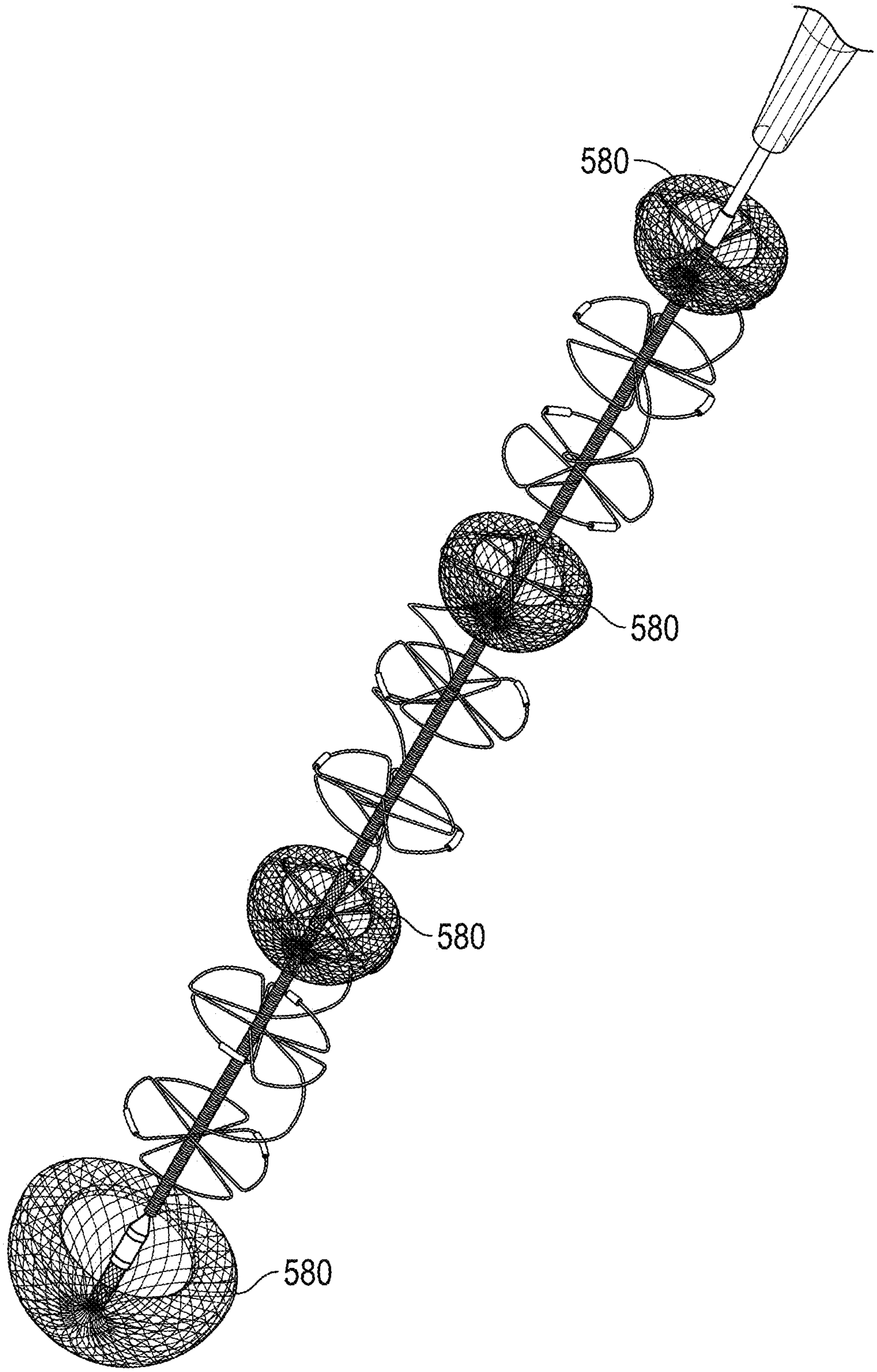
FIGS. 85A-85B are views of the single four engagement panels showing a single distal member configuration and a multiple distal members configuration.
Figure 85B:
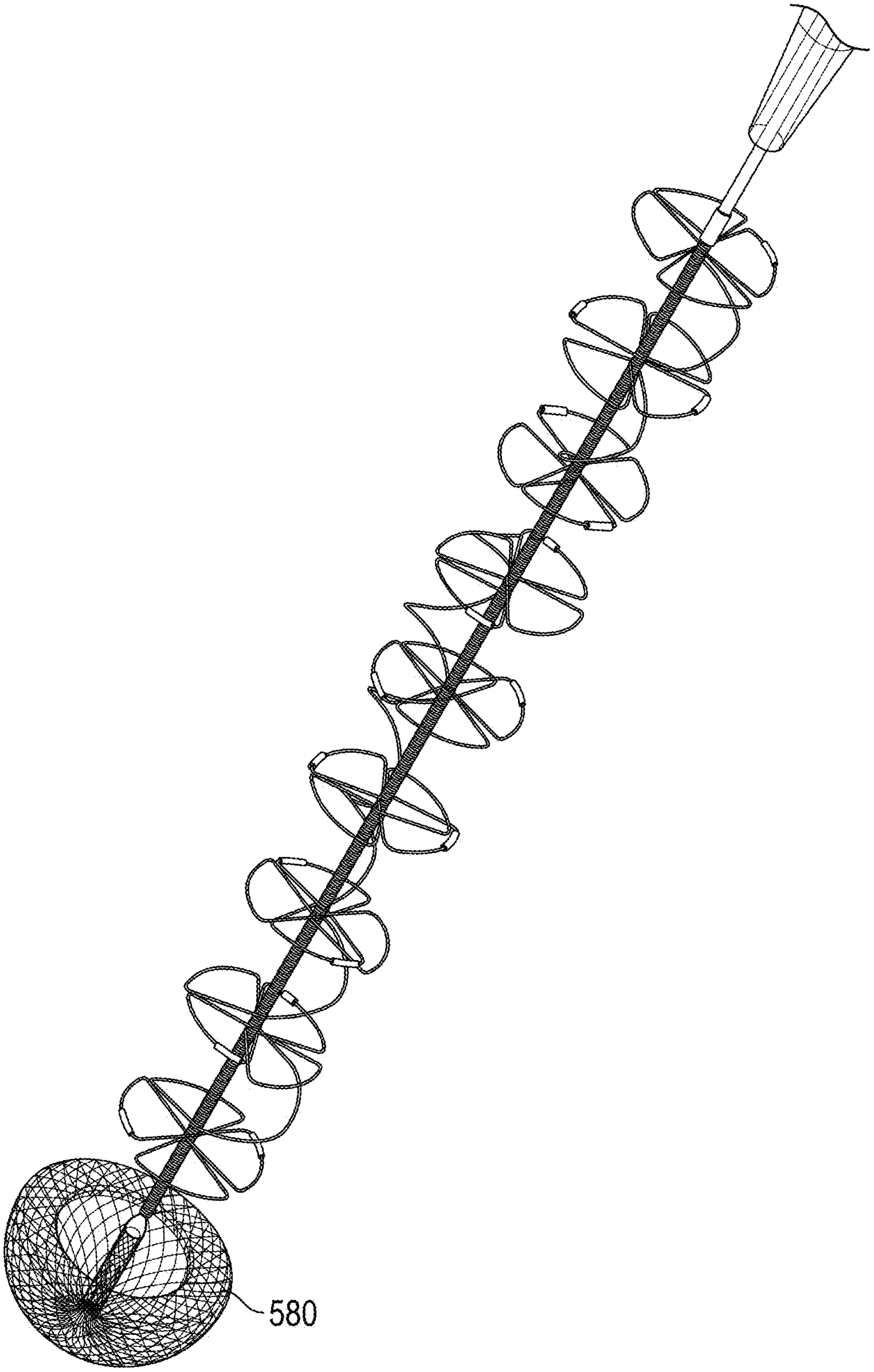

FIGS. 85A-85B are views of the extractor 500. The extractor 500 can include a single distal member configuration. The extractor 500 can include a multiple distal members configuration. In some embodiments, the distal member 580 can have the same diameter as the engagement panel 510, 512, 514, 516. In some embodiments, the distal member 580 can have the same diameter as the engagement panel 520, 522, 524, 526. In some embodiments, the distal member 580 can have the same diameter as the engagement panel 530, 532, 534, 536. In some embodiments, the distal member 580 can have the same diameter as the engagement panels with the largest diameter. In some embodiments, the distal member 580 can have the same diameter as the engagement panels with the smallest diameter. In some embodiments, the distal member 580 can have a different diameter than the engagement panels. In some embodiments, the distal member 580 can have a smaller diameter as the engagement panel 510, 512, 514, 516. In some embodiments, the distal member 580 can have a smaller diameter as the engagement panel 520, 522, 524, 526. In some embodiments, the distal member 580 can have a smaller diameter as the engagement panel 530, 532, 534, 536. In some embodiments, the distal member 580 can have a smaller diameter than the smallest diameter engagement panels. In some embodiments, the distal member 580 can have a larger diameter as the engagement panel 510, 512, 514, 516. In some embodiments, the distal member 580 can have a larger diameter as the engagement panel 520, 522, 524, 526. In some embodiments, the distal member 580 can have a larger diameter as the engagement panel 530, 532, 534, 536. In some embodiments, the distal member 580 can have a larger diameter than the largest diameter engagement panels. In some embodiments, two or more distal members 580 have the same diameter. In some embodiments, two or more distal members 580 have different diameters. In some embodiments, the distal member 580 with the larger diameter is distal to the distal member with the smaller diameter.

Figure 86A:
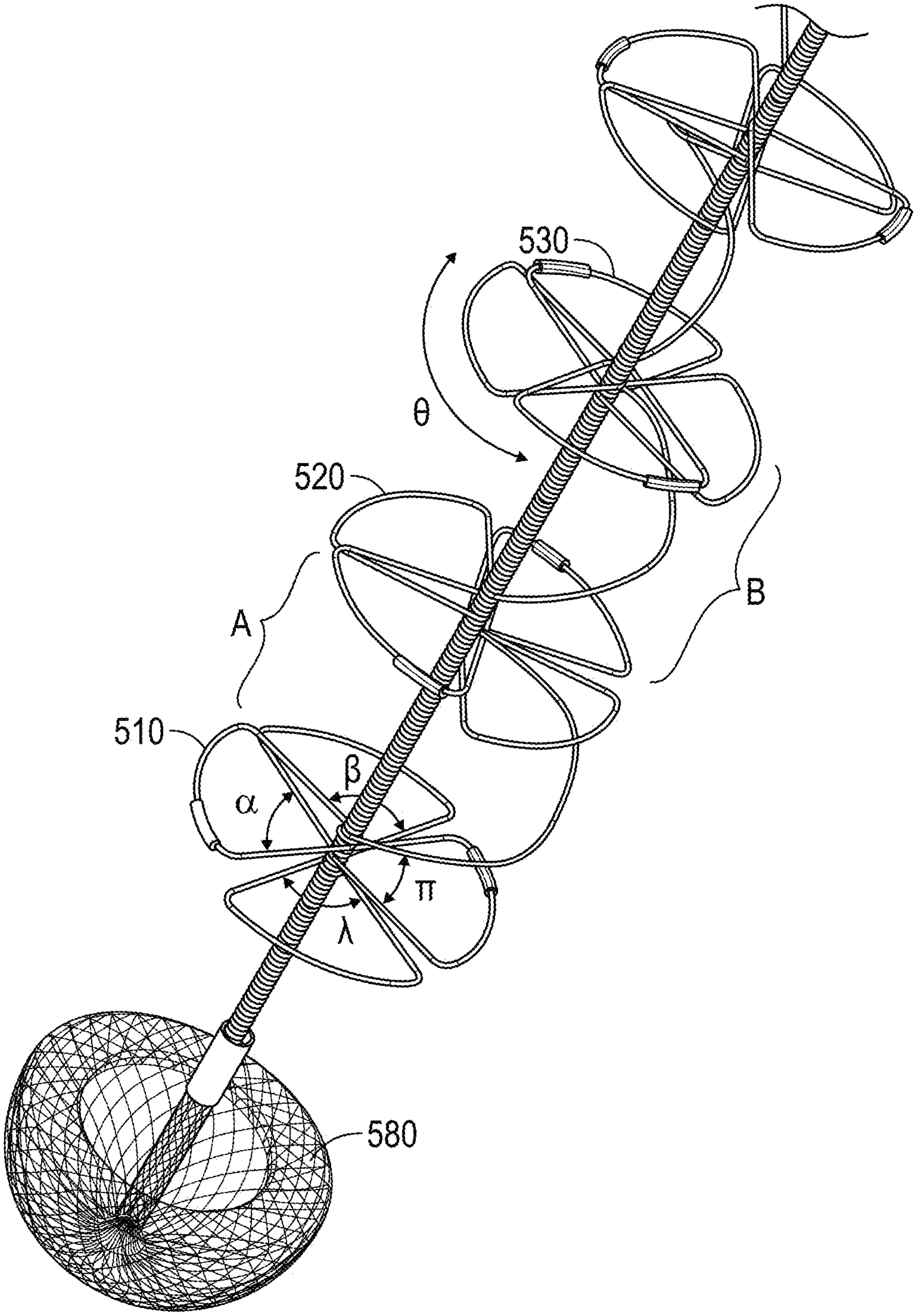
FIGS. 86A-86B are views of the single four engagement panels of the fifth embodiment. The panels can have angles alpha, beta, pi, lamda. The panels can have arcs theta.
Figure 86B:
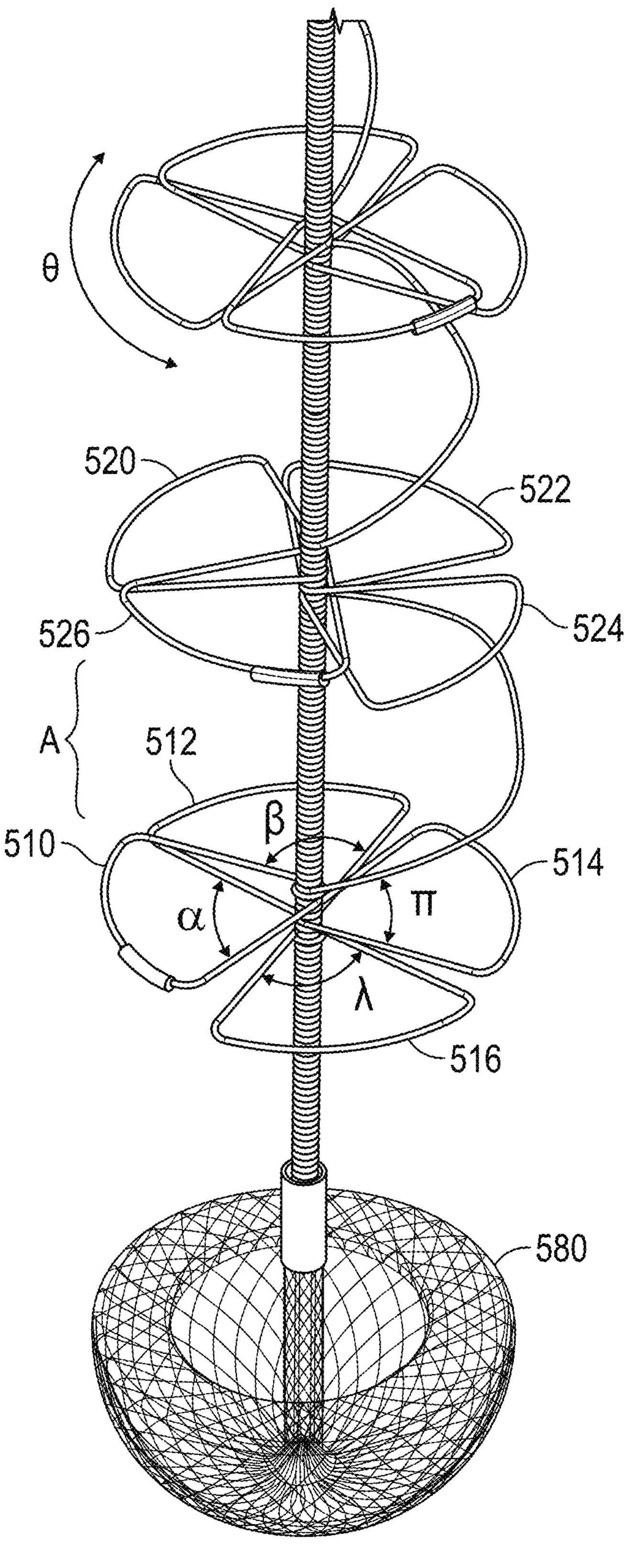

FIGS. 86A-86B are views of the extractor 500. The engagement panels 510, 512, 514, 516 can have two or more different angles alpha, beta, pi, lambda. The engagement panels 510, 512, 514, 516 can have one or more same angles alpha, beta, pi, lambda. The engagement panels 510, 512, 514, 516 can have two more different arcs 540 theta. The engagement panels 510, 512, 514, 516 can have one or more of the same arcs 540 theta. Two, three, or four of the engagement panels 510, 512, 514, 516 at the first longitudinal location have the same angle. Two, three, or four of the engagement panels 510, 512, 514, 516 at the first longitudinal location have the same arc. Two, three, or four of the engagement panels 510, 512, 514, 516 at the first longitudinal location have different angles. Two, three, or four of the engagement panels 510, 512, 514, 516 at the first longitudinal location have different arcs 540.

The engagement panels 510, 512, 514, 516 at the first longitudinal location A and the engagement panels 520, 522, 524, 526 at the second longitudinal location B can be different. The engagement panels 510, 512, 514, 516 at the first longitudinal location A and the engagement panels 520, 522, 524, 526 at the second longitudinal location B can be the same. The engagement panels 520, 522, 524, 526 at the second longitudinal location B and the engagement panels 530, 532, 534, 536 at the third longitudinal location C can be different. The engagement panels 520, 522, 524, 526 at the second longitudinal location B and the engagement panels 530, 532, 534, 536 at the third longitudinal location C can be the same. The engagement panels 510, 512, 514, 516 at the first longitudinal location A and the engagement panels 530, 532, 534, 536 at the third longitudinal location C can be different. The engagement panels 510, 512, 514, 516 at the first longitudinal location A and the engagement panels 530, 532, 534, 536 at the third longitudinal location C can be the same.

Figure 87A:
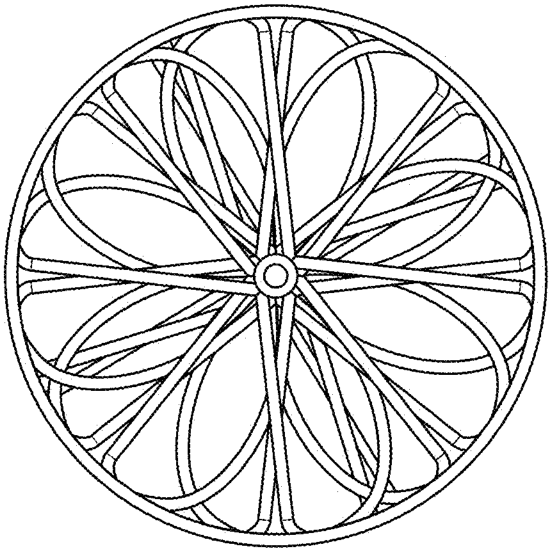
FIGS. 87A-87C are view of the extractor showing the engagement panels and connecting members.
Figure 87B:
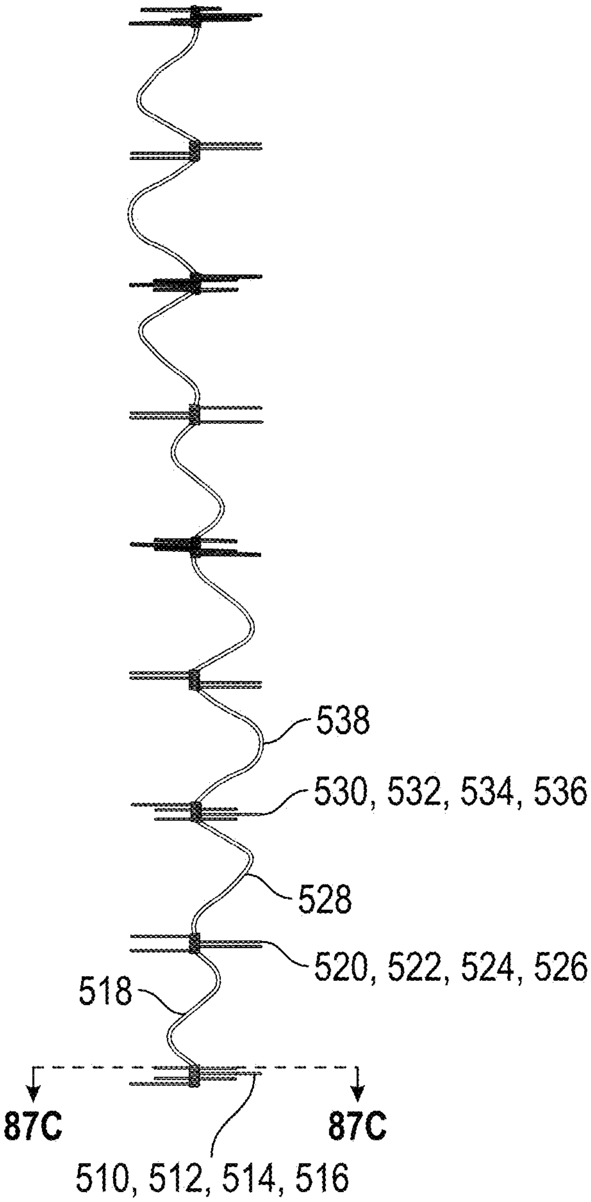
Figure 87C:
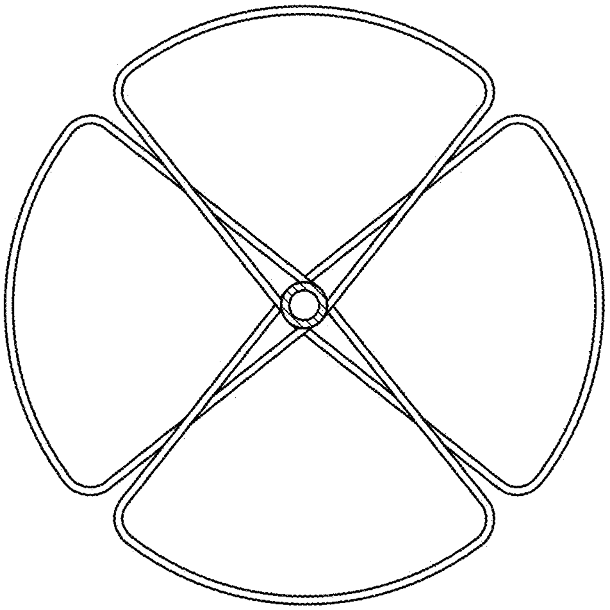

FIGS. 87A-87C are view of the extractor 500. FIG. 87B is a side view of the extractor showing the engagement panels 510, 512, 514, 516, 520, 522, 524, 526, 530, 532, 534, 536 and the connecting members 518, 528, 538. The engagement panels are stacked and next to each other.

Figure 88A:
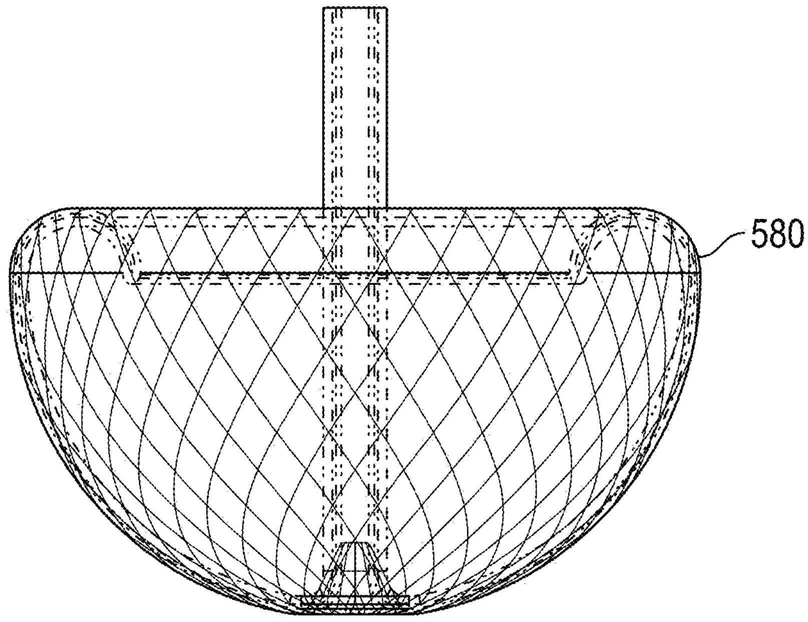
FIGS. 88A-88B are view of the distal member.
Figure 88B:
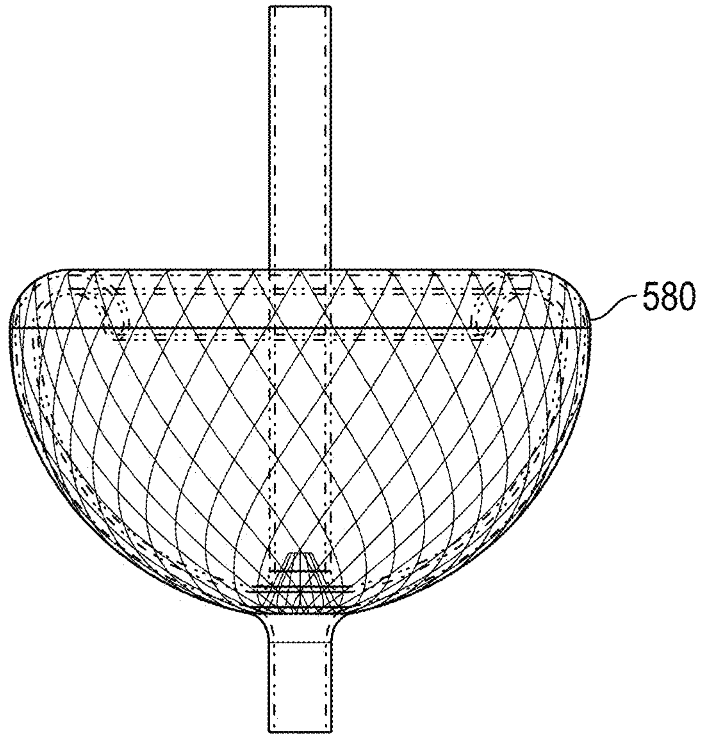

FIGS. 88A-88B are view of the distal member. FIG. 88A illustrates a distal member 580 with a double layer construction. FIG. 88B illustrates a distal member with a single layer construction.

Figure 89A:
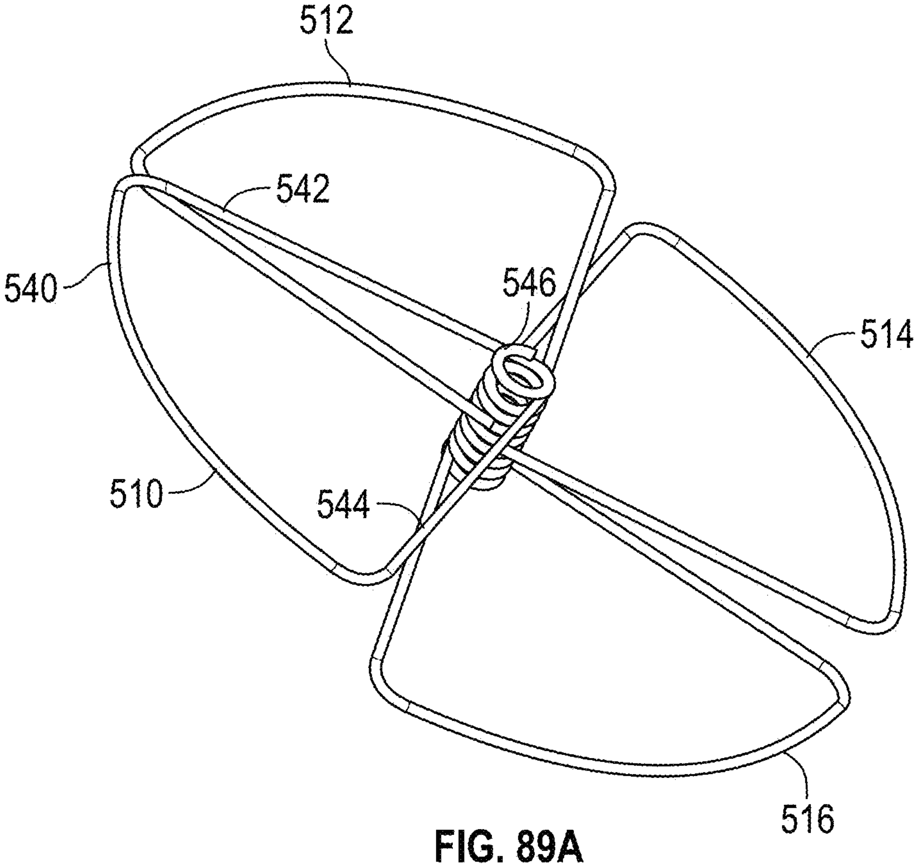
FIGS. 89A-89C are views of the single four engagement panels of the fifth embodiment.
Figure 89B:
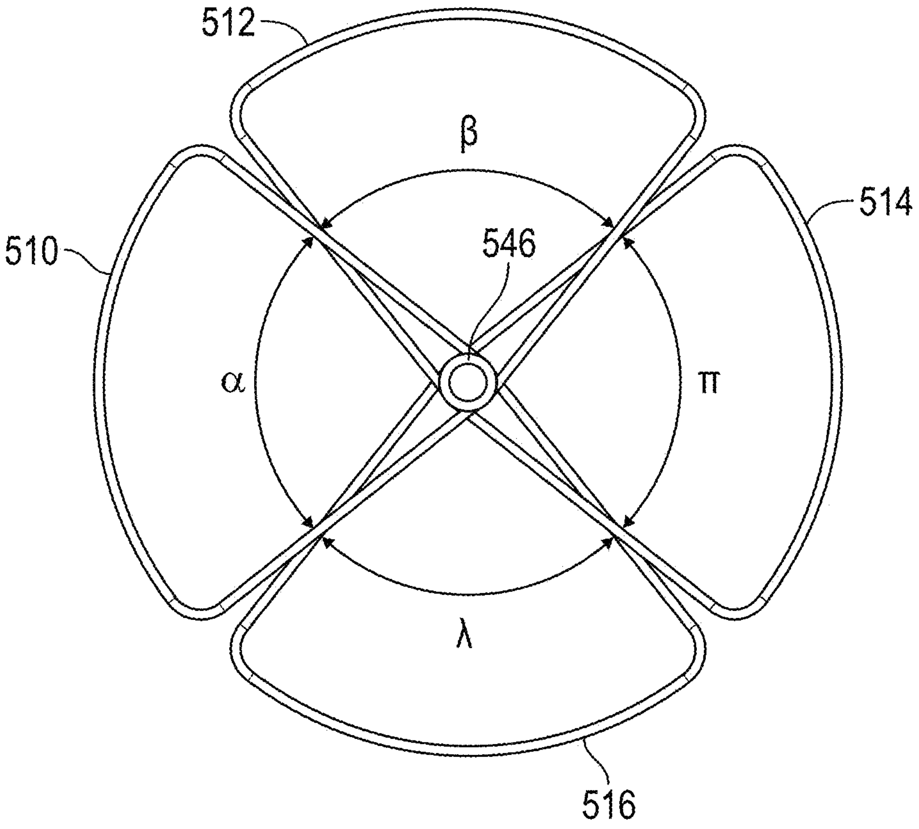
Figure 89C:
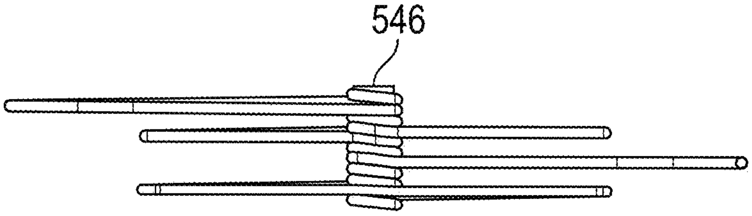

FIGS. 89A-89C illustrate a single layer engagement panel of the extractor 500. FIG. 89A is a perspective view. FIG. 89B is a front view. FIG. 89C is a side view. Each engagement panel 510, 512, 514, 516 forms a portion of the eyelet 546. The elongate member forms a portion of the eyelet 546, the leg 542 of the engagement panel 510, the arc 540 of the engagement panel 510, and the leg 544 of the engagement panel 510. Then the elongate member forms a portion of the eyelet 546, the leg 542 of the engagement panel 512, the arc 540 of the engagement panel 512, and the leg 544 of the engagement panel 512. Then the elongate member forms a portion of the eyelet 546, the leg 542 of the engagement panel 514, the arc 540 of the engagement panel 514, and the leg 544 of the engagement panel 514. Then the elongate member forms a portion of the eyelet 546, the leg 542 of the engagement panel 516, the arc 540 of the engagement panel 516, and the leg 544 of the engagement panel 516. The elongate member can be continuous. Each engagement panel 510, 512, 514, 516 can form an angle with the legs 542, 544. The angles alpha, beta, pi, lambda can be the same. The angles alpha, beta, pi, lambda can be different. In some embodiments, the legs 542, 544 can cross. In some embodiments, the legs 542, 544 can stack. In some embodiments, the legs 542, 544 can be longitudinally offset. There can be one or more portions of the eyelet 546 between adjacent engagement panel 510, 512, 514, 516. The engagement panel 510, 512, 514, 516 can be spaced apart along the length of the eyelet. The elongate wire member of the extractor can have a diameter of, e.g. about 0.0005", 0.001", 0.0015", 0.002", 0.0025", 0.003", 0.0035", 0.004", 0.0045", 0.005", or more or less, from 0.0005" to 0.005", or any range of two of the foregoing values. The arc length of each panel can be of any size such that the total arc length of all panels will substantially form a 360 degrees circle. For example, a four engagement panels will have 90 degrees arc length for each panel. For example, a three engagement panels will have a 120 degree arc length for each panel. The total arc length for all engagement panels at each longitudinal location will form a 360 degrees circle. In some embodiments, the total arc length is less than 360 degrees. The eyelet diameter can have different luminal diameters. The luminal diameter can be 0.005", 0.010", 0.014", 0.017", 0.024", 0.027", 0.035", 0.040", 0.050" for example. The luminal diameter can range from 0.005" to 0.050". The angles alpha, beta, pi, lambda can have the same or different angles such that in total all angles alpha, beta, pi, lambda will be 360 degrees. For example, angles alpha, beta, pi, lambda can be 90 degrees each in some embodiment. The angles can be different for example, alpha and pi angles are 80 degrees and beta and lambda are 100 degrees. The angles can vary in some embodiments. Similarly, a three engagement panels will have similar angles configuration where the total angle of all three panels will be 360 degrees. The length of the eyelet can range from 0.1 cm to 100 cm. The distance between the engagement panels can range from 1 mm to 30 mm. The diameter of the engagement panels can range from 1 mm to 40 mm. In some embodiments with multiple engagement panels layer, the offset layers can range from 1 degree to 180 degrees. The engagement panels at each longitudinal location can be tightly packed where each panel is next to each other. In some embodiment, the engagement panels at each longitudinal location can be loosely packed where there is gap between the panels. In some embodiment, the entire length of the extractor engagement panels and eyelets are loosely packed where there is gap in between. In some embodiment, the entire length of the extractor engagement panels and eyelets are tightly packed where there are no gap in between. In some embodiment, the entire length of the extractor engagement panels and eyelets has certain portion that is tightly packed where there are no gaps and has certain portion that is loosely packed where there are gaps in between the engagement panels and eyelets.

The extractor, or a portion thereof, can be manufactured from a single elongate member, such as a wire. The engagement panels 510, 512, 514, 516 and the eyelet 546 at the longitudinal location can be manufactured from a single elongate member. The single elongate member can form a portion of the eyelet 546. The portion of the eyelet can be a complete circle, or a portion of a circle such as, e.g. about 45 degrees, 60 degrees, 75 degrees, 90 degrees, 105 degrees, 120 degrees, 135 degrees, 150 degrees, 165 degrees, 180 degrees, 195 degrees, 210 degrees, 225 degrees, 240 degrees, 255 degrees, 270 degrees, 285 degrees, 300 degrees, 360 degrees, more or less, or any range of two of the foregoing values. The single elongate member can extend to form the leg, the arc, and the leg of the first engagement panel 510. There is a gap in the eyelet 546 between the legs 542, 544 of the engagement panel 510, 512, 514, 516. Each leg 542, 544 begins and ends at the eyelet 546. However, the single wire forms the arc 540 between the legs 542, 544 and not a portion of the eyelet. The single elongate member can extend from the leg 544 to form another portion of the eyelet. The single elongate member can extend to form the leg 542, the arc 540, and the leg 544 of the second engagement panel 512. The engagement panel are offset longitudinally by the diameter of the single elongate member. The engagement panel are offset longitudinally by a portion of the eyelet 546. The single elongate member continues to form a plurality of panels and a plurality of sections of the eyelet 546. The engagement panels 510, 512, 514, 516 at the longitudinal location are offset around the circumference of the eyelet 546. The engagement panels 510, 512, 514, 516 and the eyelet 546 at the longitudinal location are spaced to form a circumferential engagement surface with the arcs 540. The arcs 540 form nearly an entire circumference. The engagement panels 510, 512, 514, 516 are stacked. The first engagement panel 510 is distal to the second engagement panel 512. The second engagement panel 512 is distal to the third engagement panel 514. The third engagement panel 514 is distal to the fourth engagement panel 516. The eyelet 546 is formed by a plurality of partial coils. While four engagement panels are shown, the same method can be used to form any number of panels at the first longitudinal location (e.g., one, two, three, four, five, six, seven, eight, nine, ten, or any range of two of the foregoing values. While the panels at the first longitudinal location are shown, the process can be repeated to form additional arrays at the second longitudinal location and third longitudinal location. The elongate member can form the coil 578 between the eyelets 546.

Figure 90A:
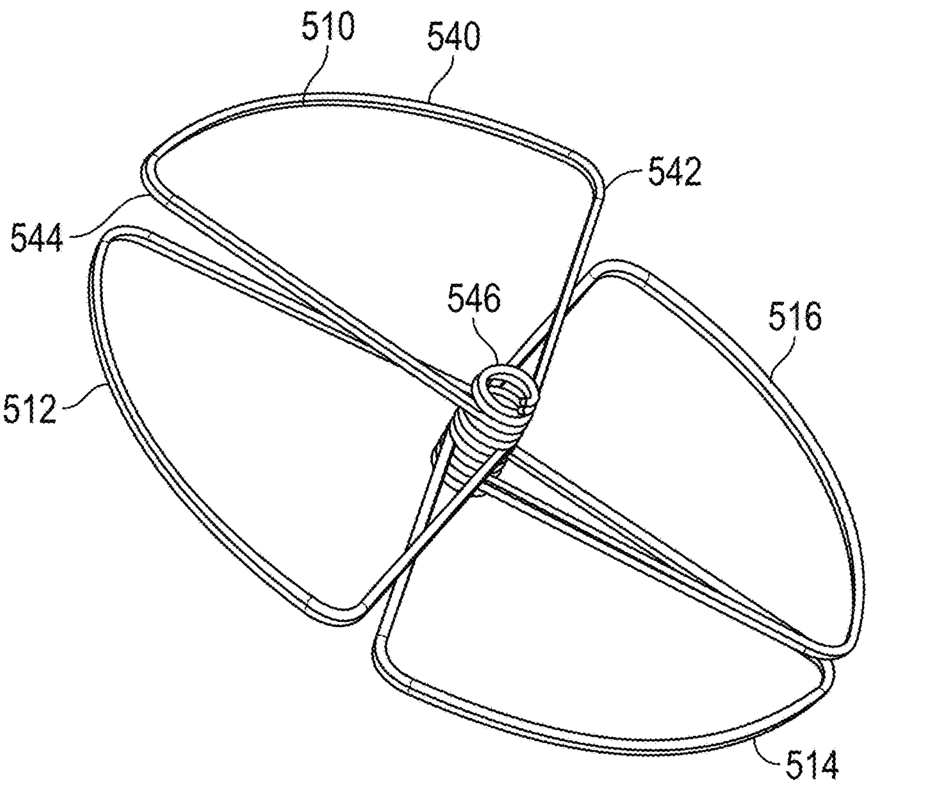
FIGS. 90A-90C are views of the double four engagement panels of the fifth embodiment.
Figure 90B:
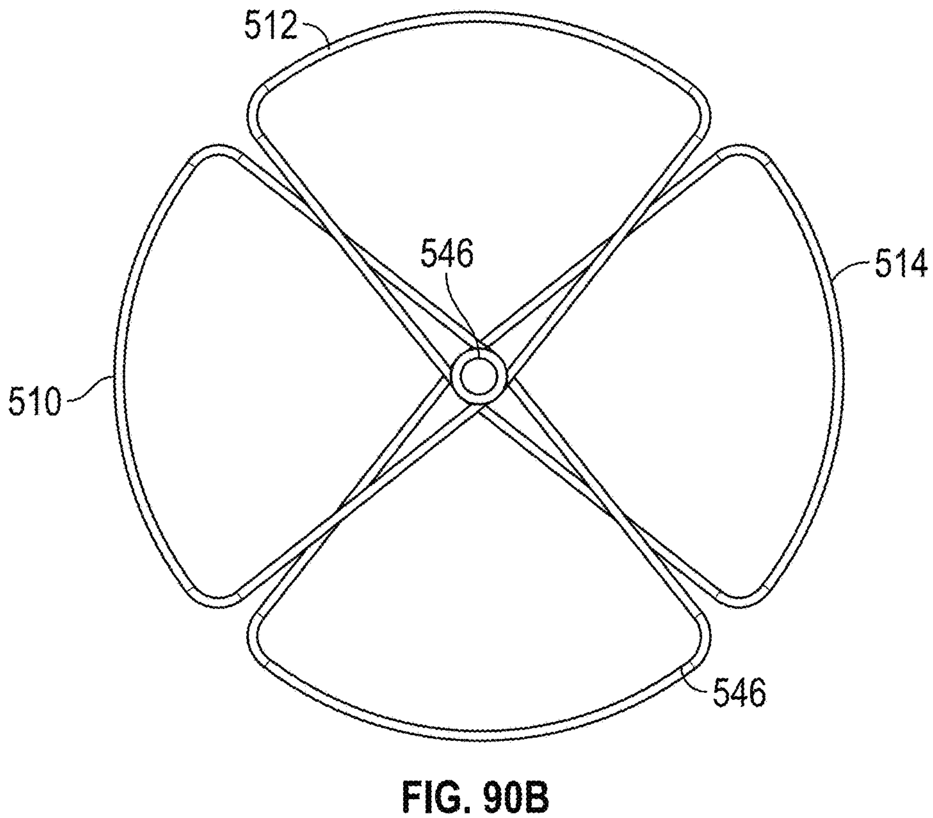
Figure 90C:
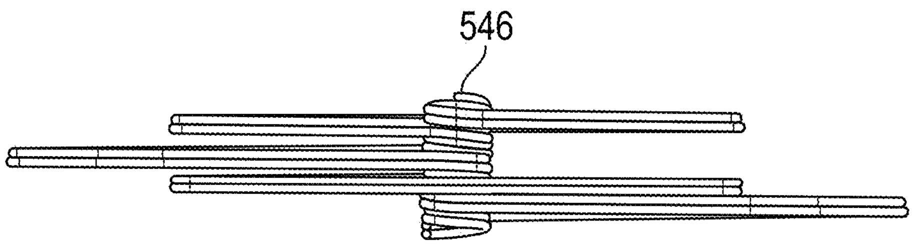

FIGS. 90A-90C illustrate a double layer engagement panel of the extractor 500. FIG. 90A is a perspective view.

FIG. 90B is a front view. FIG. 90C is a side view. The first layer and the second layer can be stacked. The first layer and the second layer can follow the same path. The first layer and the second layer are aligned when viewed from the front in FIG. 90B. In some embodiments, the first layer and the second layer are offset. The two layers can be separated and/or offset from each other. The offset angle can be 5 degrees, 10 degrees, 15 degrees, 20 degrees, 25 degrees, 35 degrees. The offset angle can range from 5 degrees up to 175 degrees.

The extractor, or a portion thereof, can be manufactured from a two or more elongate members, such as a double wire as shown in FIG. 90A or a triple wire. The double wire can be side-by-side as shown. The double wire can be offset. Each elongate member can form a layer. The double layers can extend or wrap together as illustrated in FIGS. 90A-90C. The double layers can be offset as illustrated in FIG. 69. The engagement panels and the eyelet at the longitudinal location can be manufactured from double elongate members. The double elongate members can form a portion of the eyelet 546. The portion of the eyelet 546 can be a complete circle, or a portion of a circle such as, e.g. about 45 degrees, 60 degrees, 75 degrees, 90 degrees, 105 degrees, 120 degrees, 135 degrees, 150 degrees, 165 degrees, 180 degrees, 195 degrees, 210 degrees, 225 degrees, 240 degrees, 255 degrees, 270 degrees, 285 degrees, 300 degrees, 360 degrees, more or less, or any range of two of the foregoing values. The double elongate members can extend to form the leg 542, the arc 540, and the leg 544 of the first engagement panel 510. The double elongate members can be a mirror image. The double elongate members can be stacked directly on top of each other. The double elongate members can be axially aligned. The double elongate members can be offset. The double elongate members can be twisted about the eyelet 546. There is a gap in the eyelet 546 between the legs 542, 544 of the engagement panel 510. This gap can be the diameter of the double elongate members. Each leg 542, 544 begins and ends at the eyelet 546. Each leg 542, 544 of the double elongate members can begin at the same location. Each leg of the double elongate members can begin at a different location. However, the double elongate members forms the arc 540 between the legs 542, 544 and not a portion of the eyelet 546. The double elongate members can extend to form another portion of the eyelet 546. The double elongate members can extend to form the leg 542, the arc 540, and the leg 544 of the second engagement panel 512. The engagement panel are offset longitudinally by the diameter of the double elongate members. The engagement panel are offset longitudinally by a portion of the eyelet 546. The double elongate members continues to form a plurality of panels 510, 512, 514, 516 and a plurality of sections of the eyelet 546. The eyelet 546 can be thicker for the double elongate members than the single elongate member. The engagement panel can be thicker for the double elongate members than the single elongate member. In some embodiments, the double elongate members can form panels of different panel size. The smaller panel can be halved the size of the larger panel. The smaller panel can be a third the size of the larger panel.

Figure 91A:
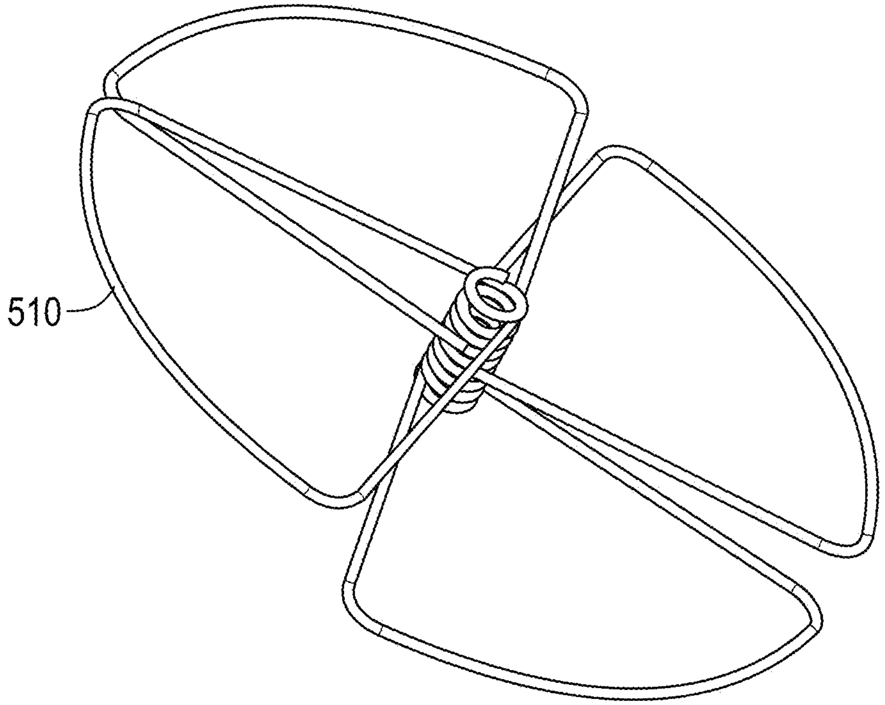
FIGS. 91A-91C are additional views of the single four engagement panels of the fifth embodiment.
Figure 91B:
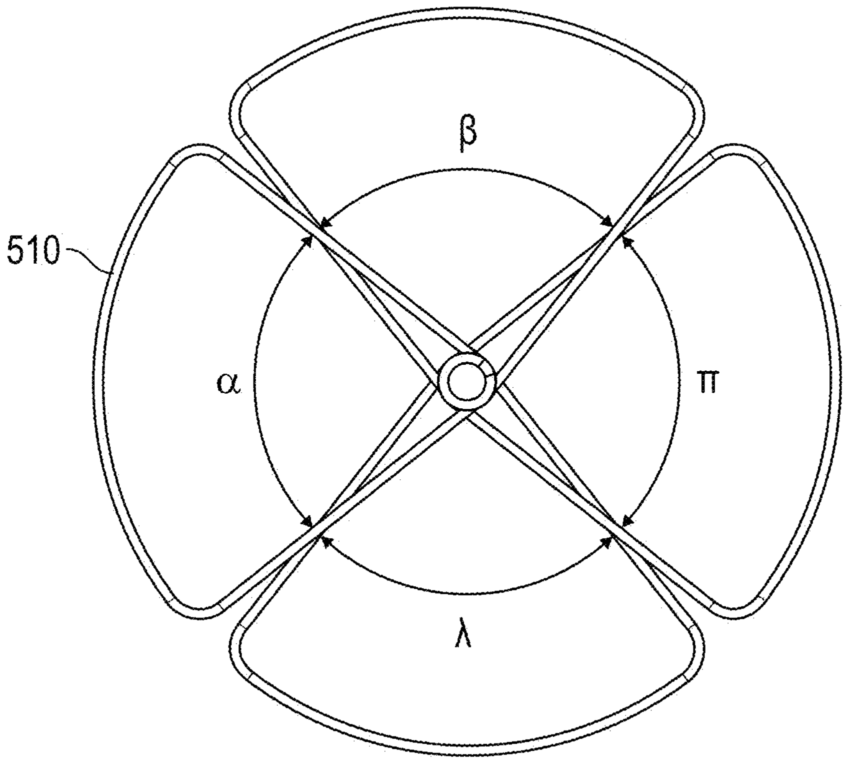
Figure 91C:
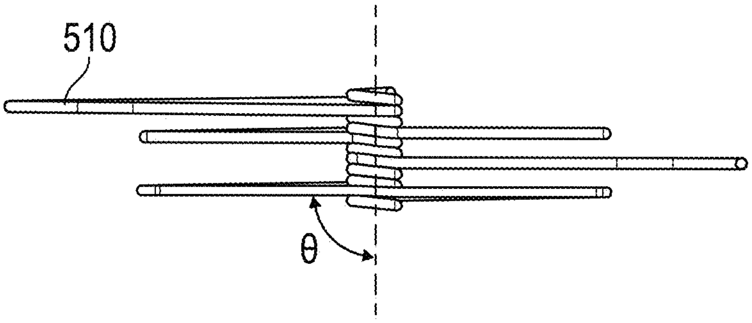

FIGS. 91A-91C are additional view of the extractor 500. Relatively to the corewire, the angle theta (FIG. 91C) can range from 1 degree to 89 degrees.

Figure 92A:
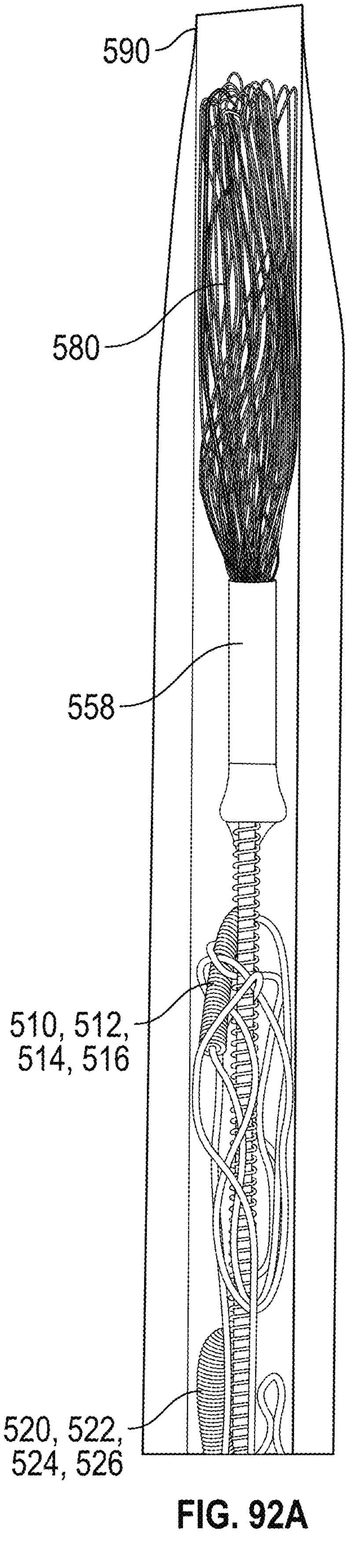
FIGS. 92A-92H are views of the distal member and the loading tube assembly.
Figure 92B:
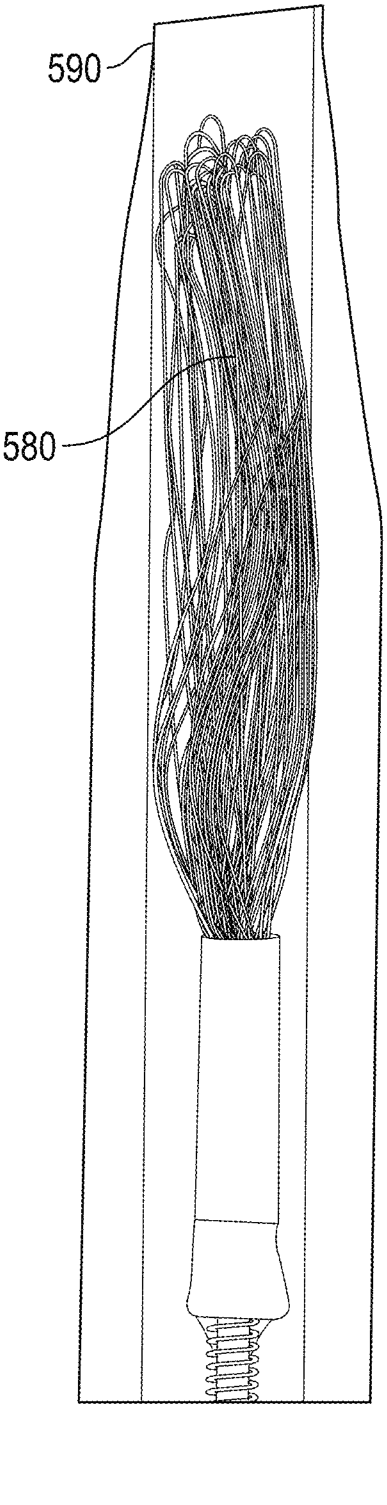

FIGS. 92A-92H are views of the distal member 580 and the loading tube assembly 590. FIGS. 92A and 92B indicates the distal member 580 is constrained in the loading tube assembly 590. The distal member 580 is designed to have a low profile for delivery. The distal member 580 can be made of braided or woven material. The distal member 580 can be made of wires or filaments. The distal member 580 can have a single or double layer. The distal member 580 can comprise a metal such as Nitinol, stainless steel, platinum, iridium, or combinations thereof. The distal member 580 can comprise polymeric materials such as polyethylene, PTFE, FEP, or combinations thereof. The distal member 580 can comprise a shape memory material such as a shape memory metal or polymer. In the constrained position, the distal member 580 is elongated to maintain a low profile.

The distal member 580 can include a radiopaque material such as tungsten or gold to aid with visualization. The distal member 580 can include a radiopaque marker. The distal marker 558 can be coupled to the distal member 580. The distal marker 558 can comprise platinum and/or iridium. The distal marker 558 can provide visualization of the distal member. The distal marker 558 can facilitate securing the distal member 580 to the distal end of the catheter shaft 506 or core wire 570. As described herein, proximal to the distal member 580 are the engagement panels 510, 512, 514, 516 at the first longitudinal location, the engagement panels 520, 522, 524, 526 at the second longitudinal location, and the engagement panels 530, 532, 534, 536 at the third longitudinal location. The engagement panels 510, 512, 514, 516, 520, 522, 524, 526, 530, 532, 534, 536 are constrained within the loading tube assembly 590. FIG. 92A shows the proximal engagement panels and the distal member 580 in a loaded configuration. FIG. 92B is a close up view.

Figure 92C:
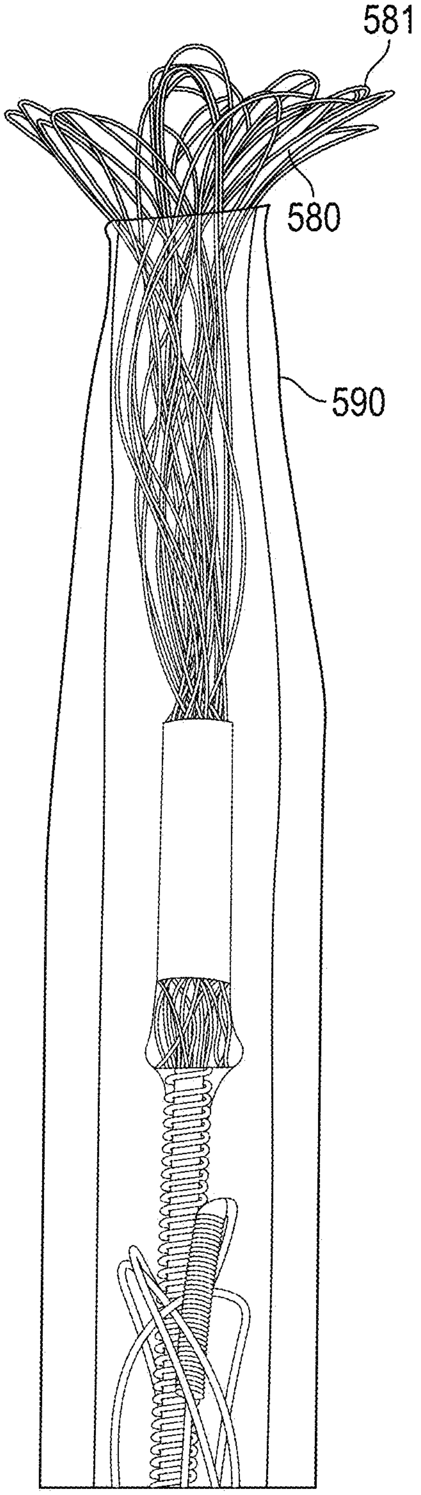

FIG. 92C indicates the distal portion of the distal member 598 is in the initial deployed position as the loading tube assembly 590 is retracted. The loading tube assembly 590 can be retracted by being pulled proximally. As the loading tube assembly 590 is retracted proximally, the leading edge 581 of distal member 580 begins to open upward. The distal portion of the distal member 580 extends beyond the end of the loading tube assembly 590. The distal portion of the distal member 580 extends distally. The distal portion of the distal member 580 flares outward from the loading tube assembly 590. The majority of the distal member 580 remains constrained in the loading tube assembly 590. FIG. 92C shows retracting the loading tube assembly 590 to deploy the distal member 580.

Figure 92E:
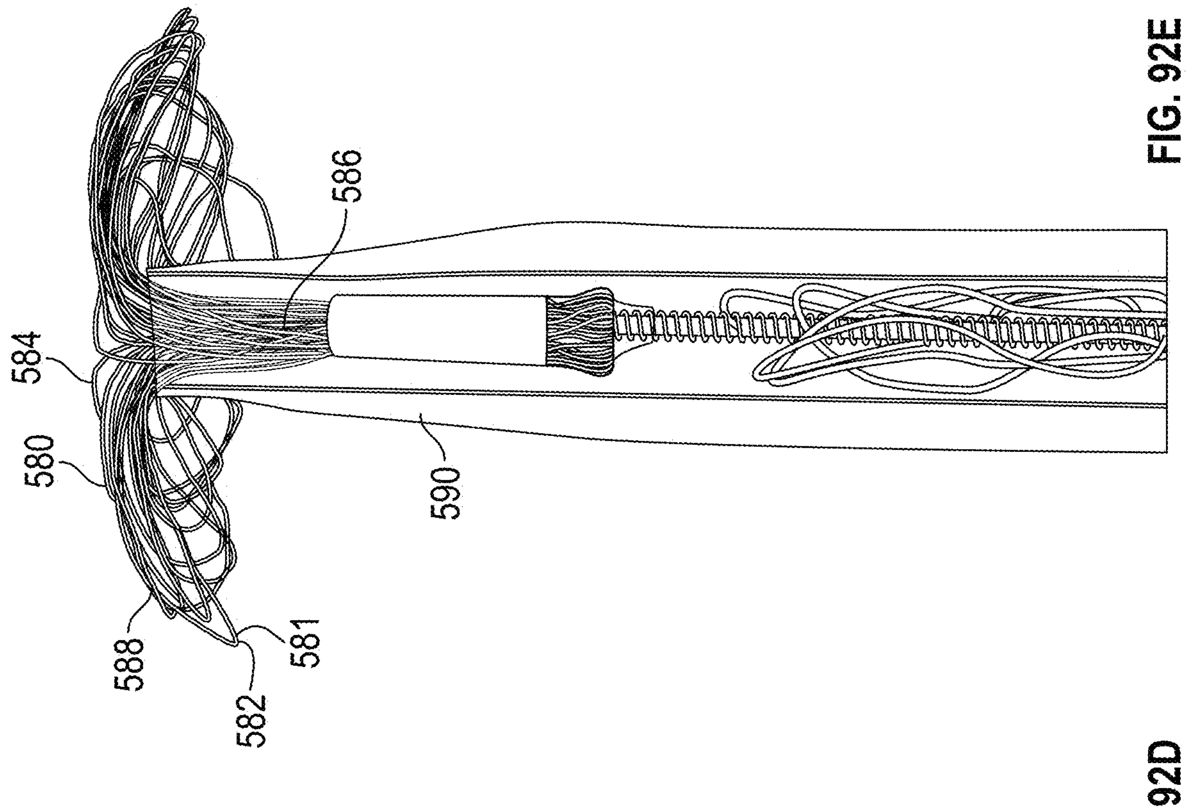
Figure 92D:
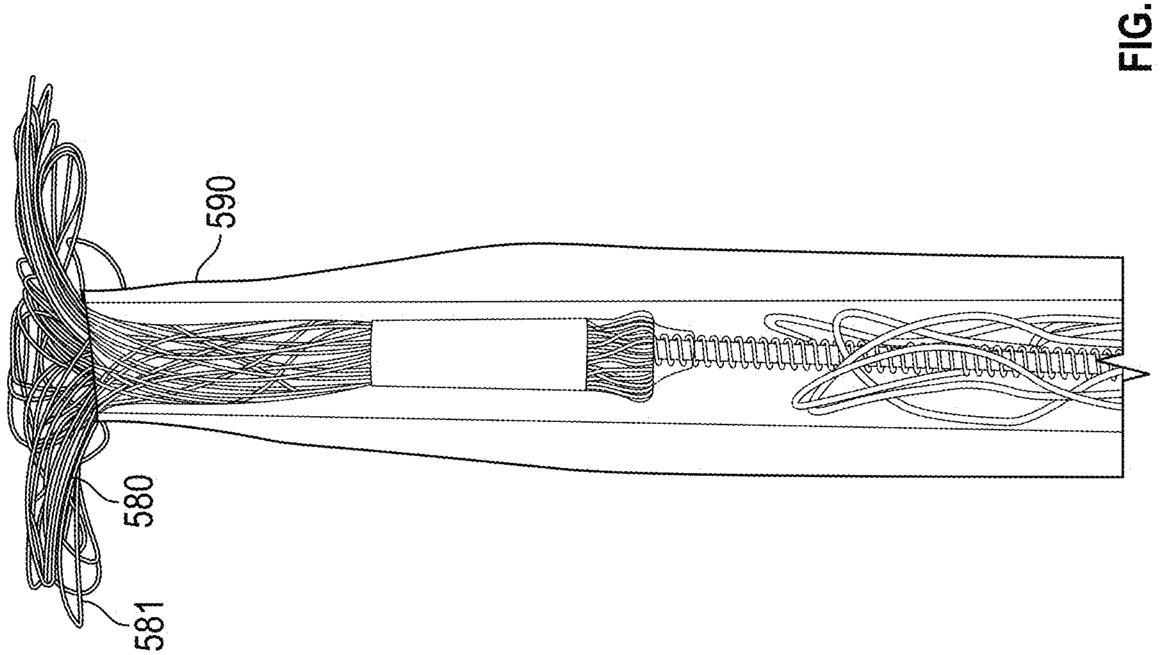

FIG. 92D is a view of the distal member 580. The distal member 580 can have a partially deployed position at approximately half-way. The distal member 580 can open upward. As the loading tube assembly 590 retracts, the distal member 580 curls. As the loading tube assembly 590 retracts, the distal member 580 moves in the proximal direction as shown in FIG. 92D. The leading edge 581 of the distal member 580 forms a cup or lip. The curling or moving proximally enable the distal member 580 to collect and capture more efficiently. In some embodiments, the leading edge 581 can form a pronounced curl wherein the edge turns back. In some embodiments, the leading edge 581 does not form a pronounced curl. The leading edge 581 can form any straight or curved edge in the fully deployed configuration. FIG. 92D shows a view when continuing to deploy the distal member 580.

FIG. 92E is a view of a position of the distal member 580 when being deployed. In some embodiments, the front edge 581 is proximal or behind the distal end of the loading tube assembly 590. The leading edge 581 can form the proximal end 582 of the distal member 580 when the distal member 580 is being deployed. The proximal end 582 can function as a funnel into the distal member 580. The distal member 580 can include a distal end 584 when the distal member 580 is being deployed. The distal end 584 can be a floating end. The distal member 580 can include a tubular portion 586. The tubular portion 586 can extend along a longitudinal or central axis of the loading tube assembly 580. The distal member 580 can include an expanded portion 588. The expanded portion 588 flares outward from the tubular portion 586 toward the proximal end 582.

Figure 92F:
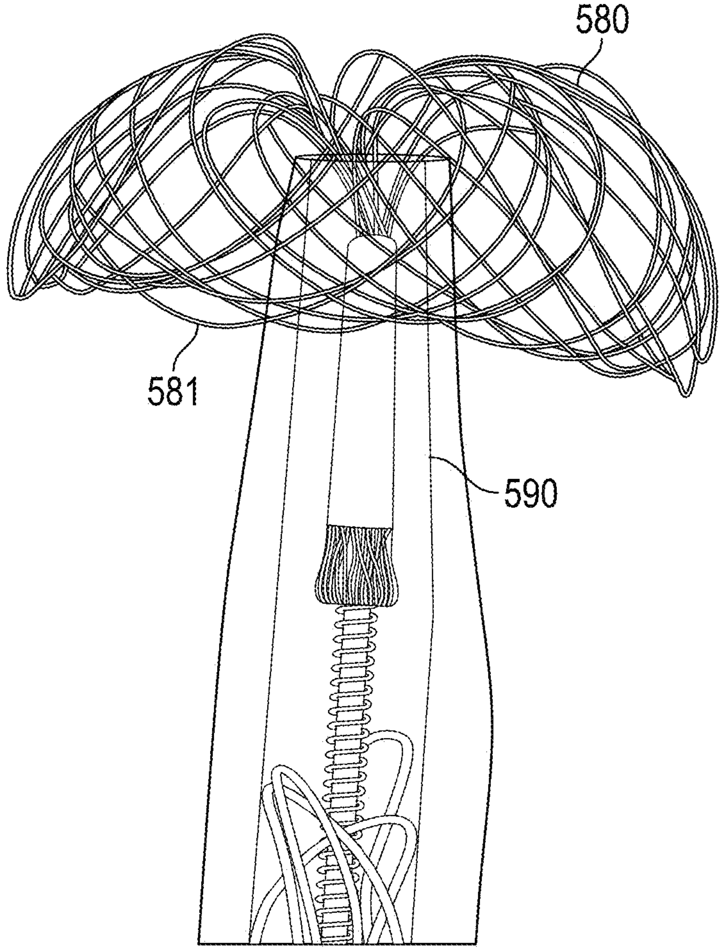
Figure 92G:
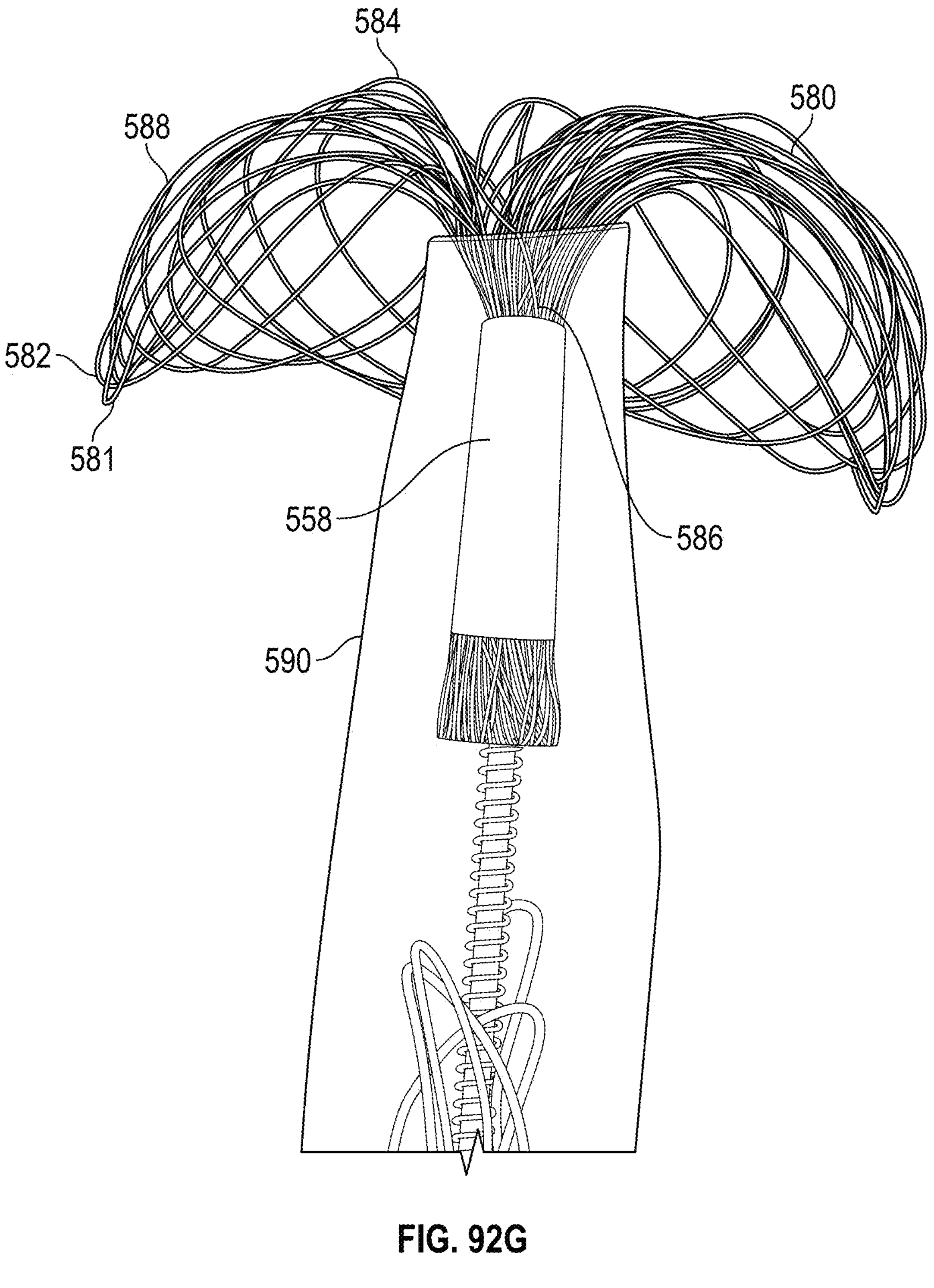

FIGS. 92F and 92G show the distal member 580 is completely expanded. In some embodiments, when the loading tube assembly 590 is retracted to the distal marker 558, the distal member 580 is fully deployed. The front edge 581 of the distal member 580 is proximal to the loading tube assembly 590. The expanded portion 588 surrounds the tubular portion 586 along a portion of the length of the tubular portion 586. The expanded portion 588 surrounds the distal marker 558 along a portion of the length of the distal marker 558. The space between the tubular portion 586 and the expanded portion 588 allows for the collection of material. In some embodiments, the distal member 580 is porous. The distal member 580 can allow blood to flow through the distal member 580. The distal member 580 can be configured to trap or capture loose emboli in transit or remove and capture soft emboli. The distal member 580 can capture material distal to the engagement panels 510, 512, 514, 516, 520, 522, 524, 526, 530, 532, 534, 536.

The distal member 580 can be made of braided material. The distal member 580 can also be made metals such as nitinol, stainless steel, platinum, tungsten, gold, and combinations thereof. The distal member 580 can be made of polymeric filaments such as Polyethylene, PET, nylon, FEP, PTFE, polyurethane, or combinations thereof. The distal member 580 can comprise wire or filaments having a diameter or cross-section between 0.0005" and 0.010", such as, e.g. about 0.0005", 0.001", 0.0015", 0.002", 0.0025", 0.003", 0.0035", 0.004", 0.0045", 0.005", 0.0055", 0.006", 0.0065", 0.007", 0.0075" 0.008", 0.0085", 0.009", 0.0095", 0.01", or any range of two of the foregoing values.

The distal member 580 can include a number of filaments or wire that range from, e.g. about 1 to 144 wires, such as 5 to 20, 10 to 50, 20 to 70, 30 to 100, 50 to 100, 60 to 120, or any range of two of the foregoing values. The distal member 580 can have an expanded diameter that can range from 1 mm to 40 mm, such as 1 mm, 5 mm, 10 mm, 15 mm, 20 mm, 25 mm, 30 mm, 35 mm, 40 mm, or any range of two of the foregoing values. The distal member 580 can have a pore size that can range from, e.g. about 25 microns to 2000 microns, such as 25 microns, 50 microns, 75 microns, 100 microns, 150 microns, 200 microns, 250 microns, 375 microns, 500 microns, 750 microns, 1000 microns, 1250 microns, 1500 microns, 2000 microns, or any range of two of the foregoing values.

Figure 92H:
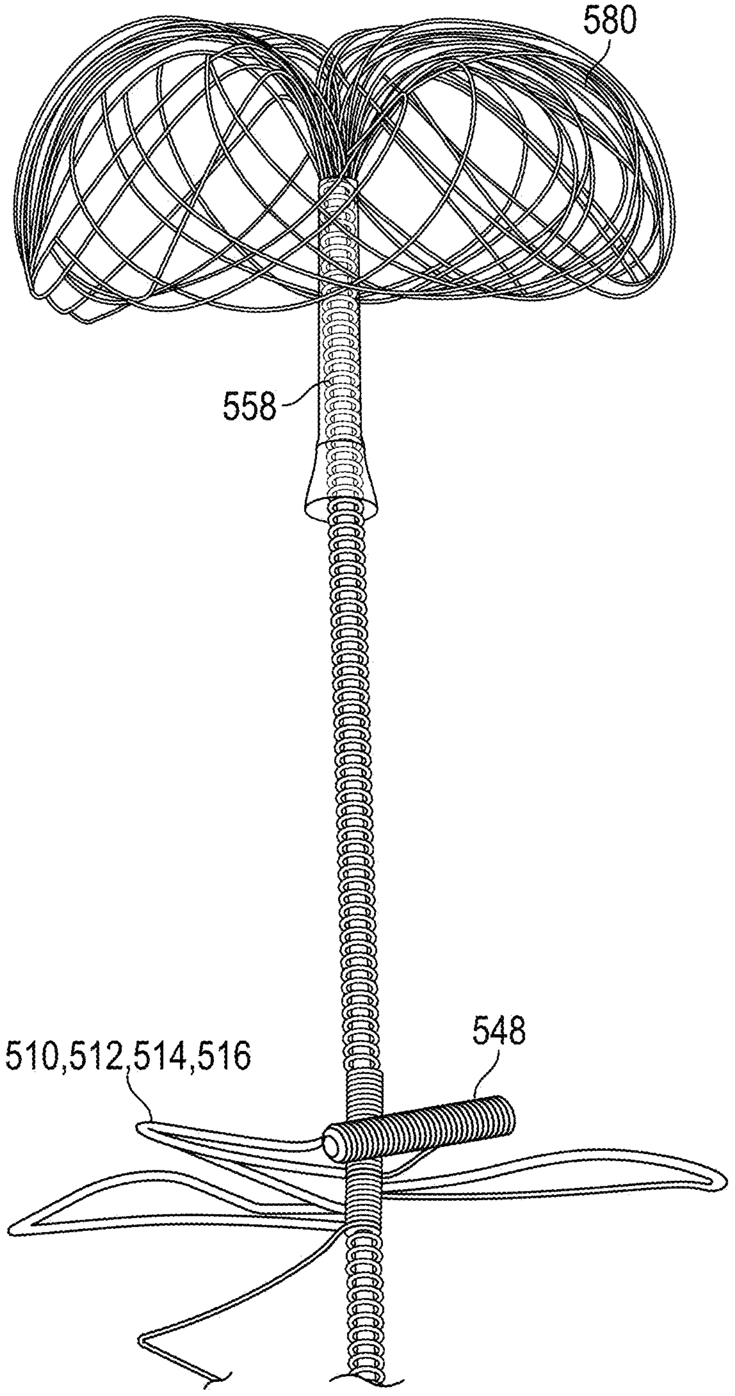

FIG. 92H shows the distal marker 558. The distal marker 558 can include a platinum/iridium tube. The distal marker 558 can function as a radiopaque marker. FIG. 92H shows the fully deployed position with the distal member 580 and the deployed engagement panels 510, 512, 514, 516. The extractor 500 can include one or more radiopaque markers 548. The radiopaque marker 548 can be located on the arc 540 of one of the engagement panels 510, 512, 514, 516. The first longitudinal location can include one or more radiopaque markers 548. The radiopaque marker 548 can include a platinum/iridium coil.

There are several advantages of the extractors described herein. The extractor can include the eyelet with a lumen to receive a catheter shaft or core wire. Each engagement panel can include the eyelet, or a portion thereof. The engagement panels at the first longitudinal location can form the first eyelet. The engagement panels at the second longitudinal location can form the second eyelet. The engagement panels at the third longitudinal location can form the third eyelet. In some embodiments, the eyelet can allow movement along the catheter shaft or core wire. In some embodiments, the eyelet can allow the engagement panel to move relative to the catheter shaft or core wire. In some embodiments, the eyelet can allow the engagement panels to move together to pinch material between two engagement panels. In some embodiments, the eyelet can allow the engagement panels to move apart to accept material between two engagement panels. In some embodiments, the eyelet can allow the space between two engagement panels to lengthen and/or shorten. In some embodiments, the eyelet can allow the engagement panels to move longitudinally along the catheter shaft or core wire. In some embodiments, the engagement panel are not fixed to a longitudinal location along the catheter shaft or core wire. In some embodiments, the extractor can include an eyelet with a lumen to receive a catheter shaft or core wire. In some embodiments, the extractor is distinguished from devices without an eyelet.

Figure 93A:
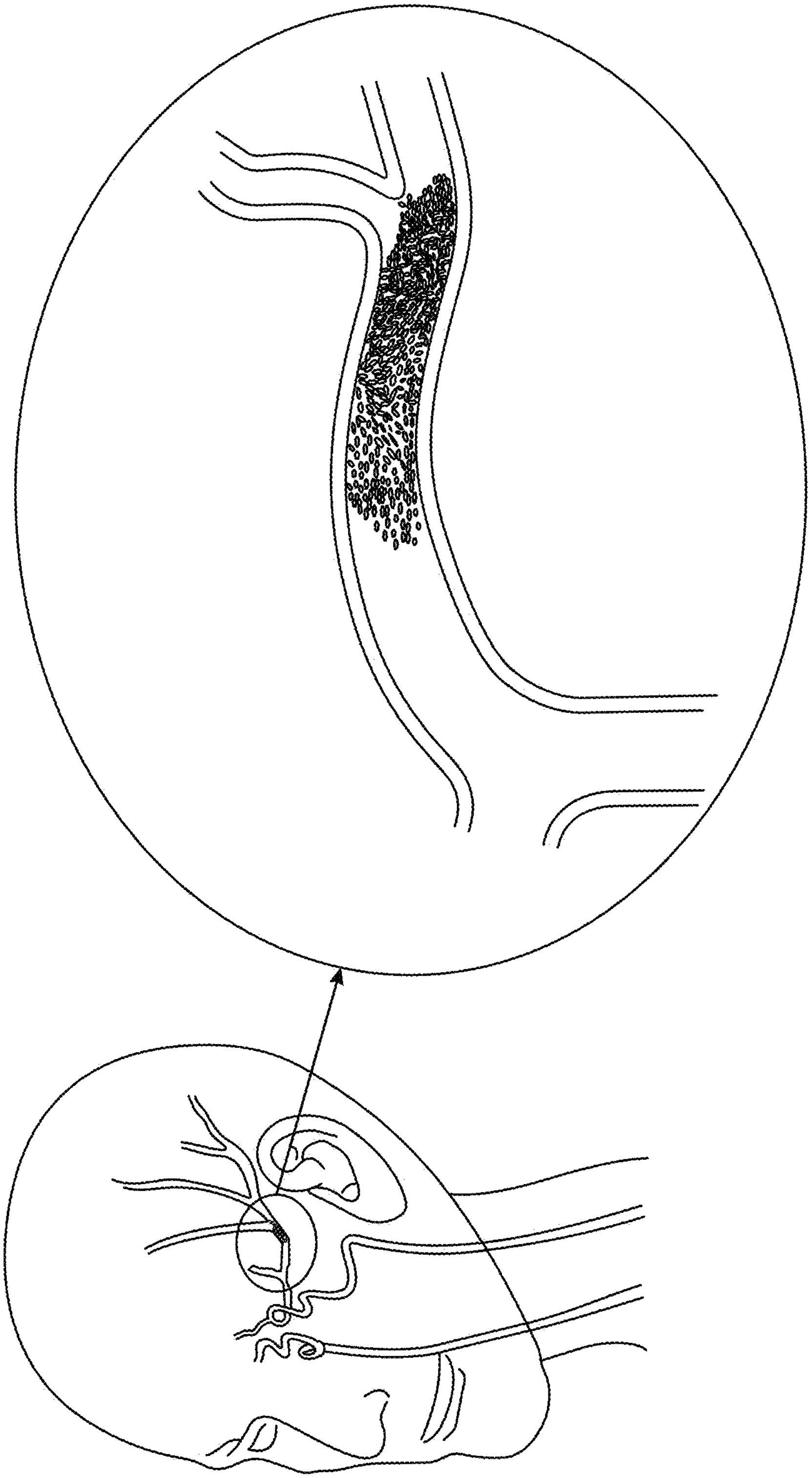
FIGS. 93A-93F are views of methods of use.
Figure 93B:
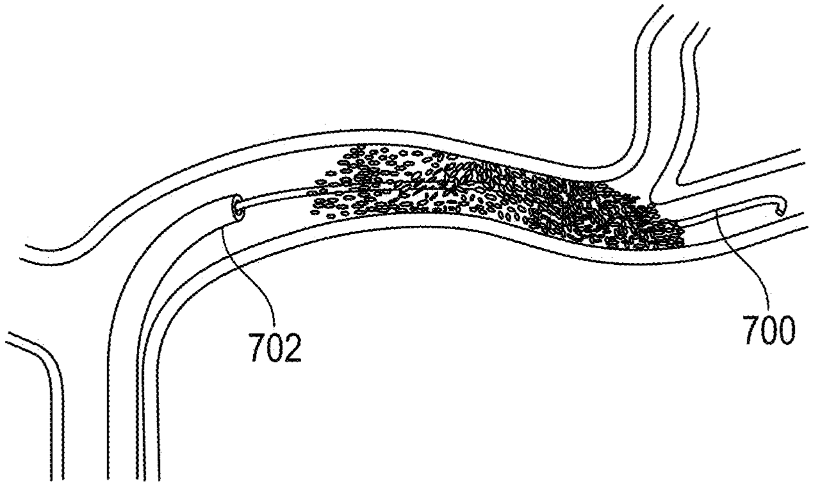
Figure 93C:
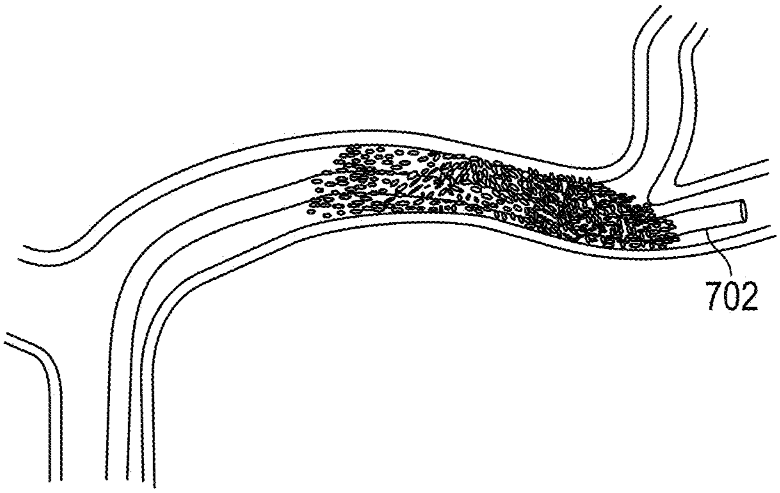

FIGS. 93A-93F are views of methods of use of some embodiments of extraction systems as described elsewhere herein, such as, for example, the extraction system of FIG. 92A-92H. FIG. 93A illustrates a blood clot within a blood vessel. In the illustrated embodiment, the clot blockage is located within the middle cerebral artery. FIG. 93B illustrates a guidewire 700 with its distal end passed entirely through the clot. The guidewire 700 can be used with any system described herein. The method can include a microcatheter 702 to be passed along the guidewire 700. The microcatheter 702 can be positioned proximal to the clot as shown in FIG. 93B. The microcatheter 702 can be any microcatheter system used to deliver the extractors described herein. In some embodiments, the standard Seldinger technique is used to access an access vessel, e.g., the femoral artery and to introduce a preliminary guidewire. The preliminary guidewire can be, e.g., a 0.035" guidewire. In some embodiments, a balloon guide catheter is advanced over the preliminary guidewire to the carotid artery. In some embodiments, the guidewire 700 is exchange for the preliminary guidewire. In some embodiments, the guidewire 700 is an 0.018" guidewire. In some embodiments, an 0.018" guidewire (e.g., a first, smaller diameter guidewire) is exchanged for an 0.035" guidewire (e.g., a second, larger diameter guidewire). The microcatheter 702 is introduced over the guidewire 700 through the balloon guide catheter to the occlusion treatment area. The guidewire 700 then advances through the clot and is positioned distal to the clot. The microcatheter 702 is then advanced through the clot and positioned distal to the clot. FIG. 93C illustrates the microcatheter 702 passed through the clot. The guidewire 700 can be removed.

Figure 93D:
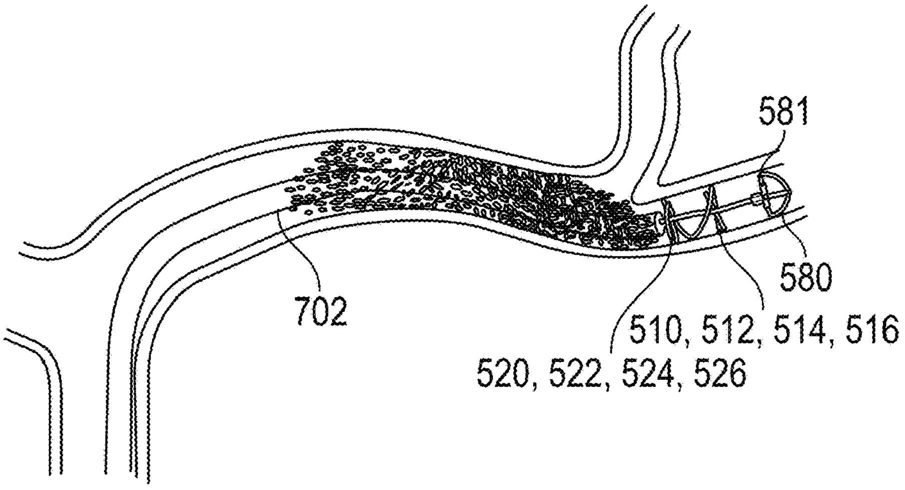

FIG. 93D illustrates the extractor 500 at least partially deployed. The distal member 580 including leading edge 581 can be deployed distal to the clot blockage. The extractor 500 is at least partially deployed. The engagement panels 510, 512, 514, 516 at the first longitudinal location can be deployed. The engagement panels 520, 522, 524, 526 at the second longitudinal location can be deployed. The engagement panels at the third longitudinal location can be constrained within the microcatheter 700. In some embodiments, the extractor 500 can be pre-loaded in the loading tube assembly 590. The loading tube assembly 590 can be introduced into the microcatheter 702. The extractor 500 can continue to be inserted into the microcatheter 702. The loading tube assembly 590 can be removed. The extractor

Figure 93E:
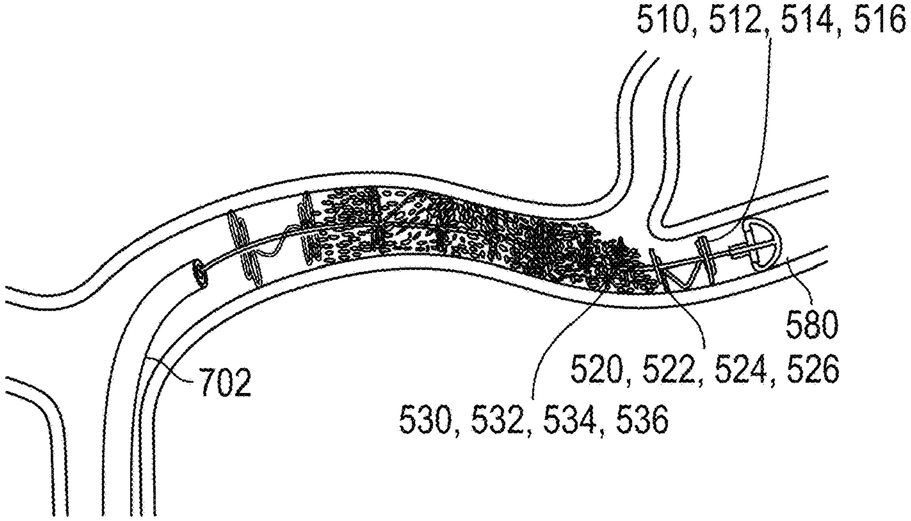

500 can be advanced under fluoroscopy to the distal tip of the microcatheter 702. The microcatheter 702 can be retracted to deploy at least a portion of the extractor 500 distal to the clot as shown in FIG. 93D. The microcatheter 702 can be retracted to deploy at least a portion of the extractor 500 within to the clot as shown in FIG. 93E. The microcatheter 702 can be retracted to deploy at least a portion of the extractor 500 proximal to the clot as shown in FIG. 93E. In some methods, one or more arrays of engagement panels are distal to the clot. In some methods, one or more arrays of engagement panels are within the clot. In some methods, one or more arrays of engagement panels are proximal to the clot.

The engagement panels can be folded within the loading tube assembly 590. The engagement panels can be folded distally such that the arcs of the engagement panels at the first longitudinal location are distal to the respective eyelet. The engagement panels can be laid down such that the arcs of the engagement panels are toward the distal member 580. The extractor 500 can be constrained within the loading tube assembly 590 with the engagement panels at the first, second, and third longitudinal location folded distally. The extractor 500 can be inserted into the microcatheter 702 with the engagement panels at the first, second, and third longitudinal location folded distally. The extractor 500 can be advanced until the distal member 580 is near the distal tip of the microcatheter 702.

The microcatheter can be retracted and the distal member 580 can expand. As the microcatheter 702 is retracted proximally, the leading edge 581 of distal member 580 begins to open. The distal portion of the distal member 580 extends beyond the distal end of the microcatheter 702. The distal portion of the distal member 580 flares outward from the microcatheter 702. As the microcatheter 702 retracts, the distal member 580 curls. As the microcatheter 702 retracts, the distal member 580 moves in the proximal direction. The curling or moving proximally enable the distal member 580 to collect and capture more efficiently. FIG. 93D is a view of a position of the distal member 580 when being deployed from the microcatheter 702.

As the microcatheter 702 is retracted proximally, the engagement panels at the first longitudinal location deploy. The engagement panels at the first longitudinal location can deploy at approximately the same time from the distal end of the microcatheter 702, for instance if there is little or no gap in the eyelet. The engagement panels at the first longitudinal location can deploy sequentially or independently from the distal end of the microcatheter 702, for instance if there is a gap in the eyelet.

In some embodiments, the engagement panels at the first longitudinal location are in a first, constrained position within the microcatheter 702. The arcs of the engagement panels are distal to the eyelet at the first longitudinal location. The legs of the engagement panels are distal to the eyelet at the first longitudinal location. The engagement panels at the first longitudinal location can be folded downward toward the catheter shaft or core wire. The engagement panels at the first, second, and third longitudinal location can be similarly folded.

As the microcatheter 702 is retracted proximally, the engagement panels revert proximally. The engagement panels move outward until the engagement panels are relatively aligned with the respective eyelet. In some embodiments, the arcs of the engagement panels can be substantially perpendicular to the catheter shaft or core wire. The engagement panels moved in an arc from the constrained state toward the inner wall of the vessel. The engagement panels can expand to the diameter of the vessel. The engagement panels can expand to any size vessel up to the maximum diameter wherein the engagement panels are perpendicular to the eyelet.

Figure 93F:
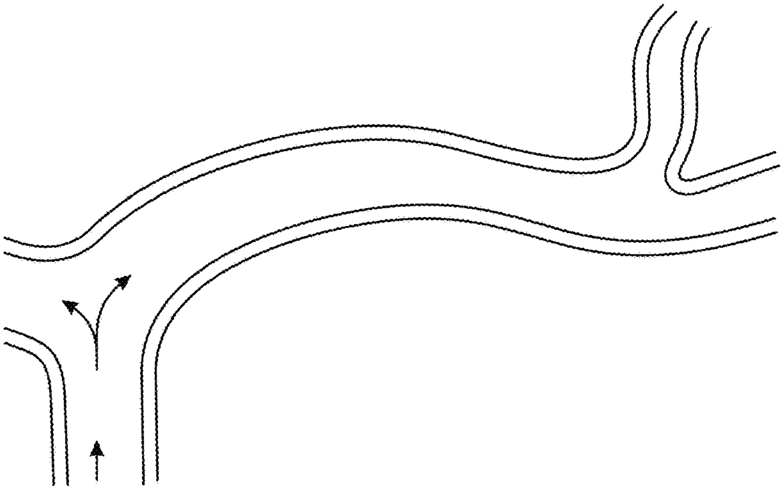

Once the extractor 500 is deployed, the extractor 500 and the microcatheter 702 are withdrawn into the balloon guide catheter to remove the system from the vascular system. Aspiration can be used to assist when retracting the extractor 500 and the microcatheter 702. FIG. 93E illustrates the distal member 580 and the extractor 500 when completely deployed. FIG. 93F illustrates the microcatheter 702 and the extractor 500 when completely removed with the clot.

Figure 94A:
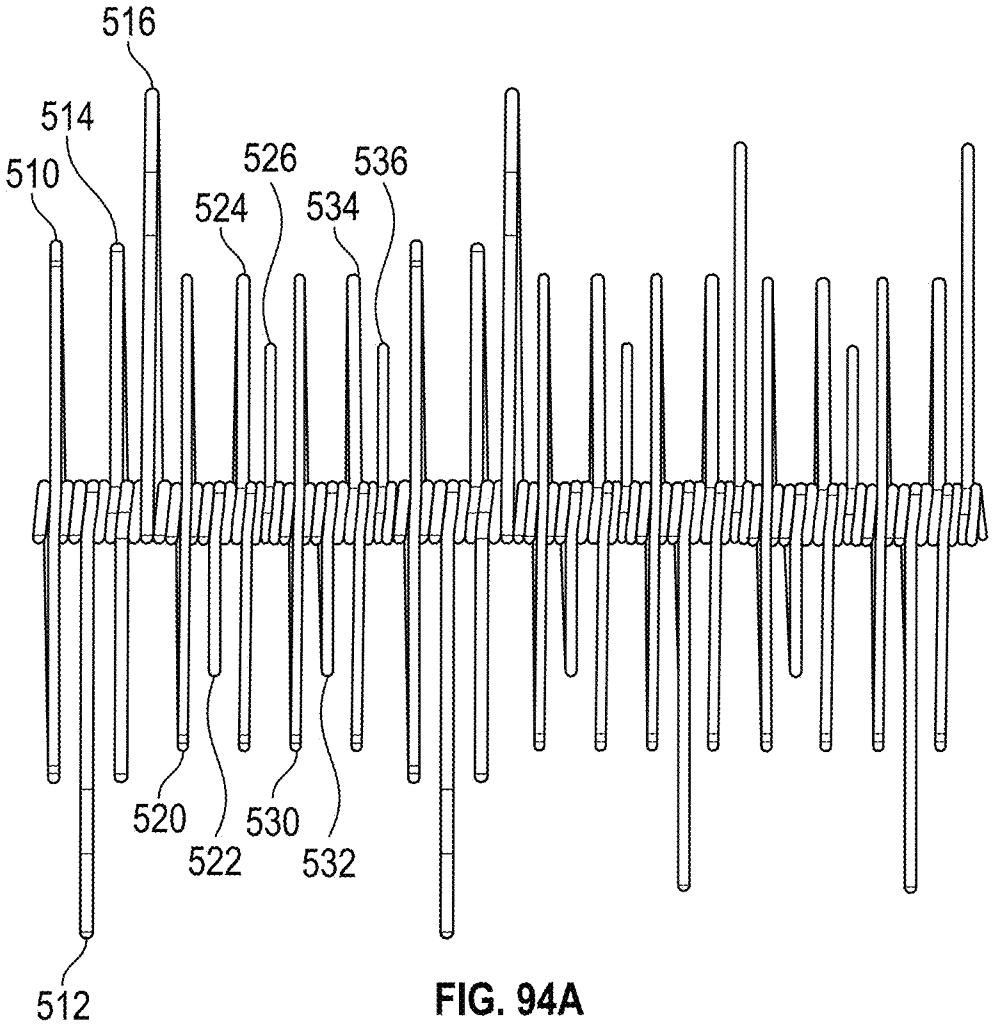
FIGS. 94A-94B are views of engagement panels.
Figure 94B:
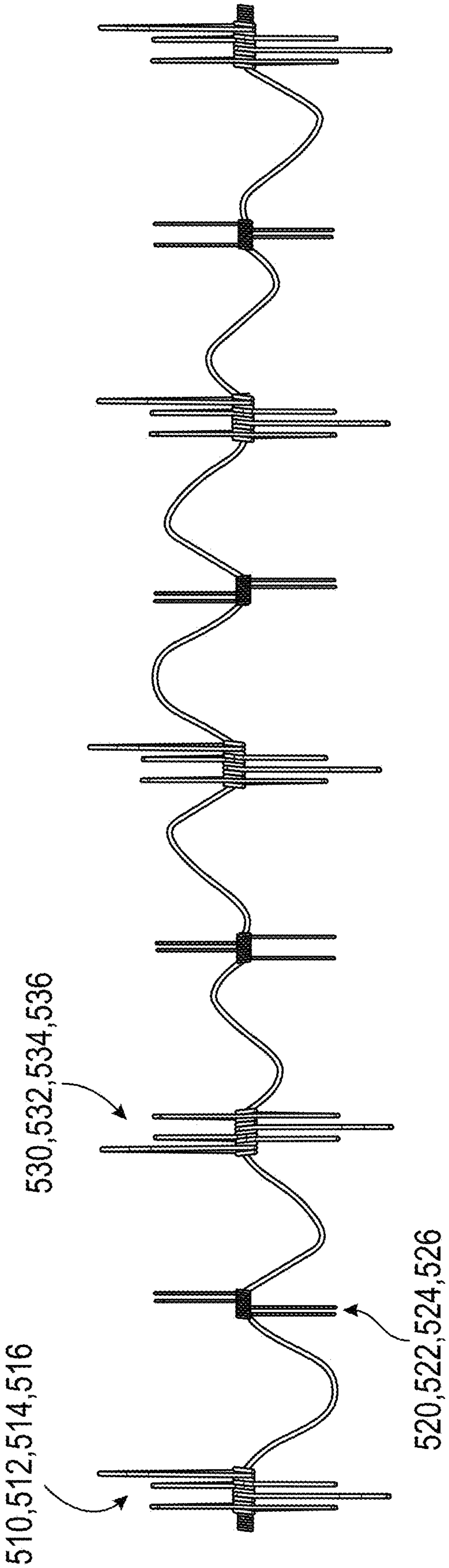

FIGS. 94A-94B illustrate a side views of a single layer engagement panels of the extractor 500. The engagement panels can have a different diameter at each location. Each engagement panel 510, 512, 514, 516 at the first longitudinal location forms a portion of a first diameter. The engagement panels at the first longitudinal location form the first diameter. The total arc length of the engagement panel 510, 512, 514, 516 at the first longitudinal location can substantially form a 360 degrees circle. The total arc length of the engagement panel 510, 512, 514, 516 at the first longitudinal location can be less than a 360 degrees circle. Each engagement panel 520, 522, 524, 526 at the second longitudinal location forms a portion of a second diameter. The engagement panels at the second longitudinal location form the second diameter. The total arc length of the engagement panel 520, 522, 524, 526 at the second longitudinal location can substantially form a 360 degrees circle. The total arc length of the engagement panel 520, 522, 524, 526 at the second longitudinal location can be less than a 360 degrees circle. Each engagement panel 530, 532, 534, 536 at the third longitudinal location forms a portion of a third diameter. The engagement panels at the third longitudinal location form the third diameter. The total arc length of the engagement panel 530, 532, 534, 536 at the third longitudinal location can substantially form a 360 degrees circle. The total arc length of the engagement panel 530, 532, 534, 536 at the third longitudinal location can be less than a 360 degrees circle. The extractor 500 can have engagement panels at a fourth longitudinal location. The extractor 500 can have engagement panels at a fifth longitudinal location. The extractor 500 can have engagement panels at a sixth longitudinal location. The extractor 500 can have engagement panels at a seventh longitudinal location. The extractor 500 can have engagement panels at a eighth longitudinal location. The extractor 500 can have engagement panels at any number of longitudinal locations such as one, two, three, four, five, six, seven, eight, nine, ten, eleven, twelve, thirteen, fourteen, fifteen, sixteen, seventeen, eighteen, nineteen, twenty, or any range of two of the foregoing values.

The first diameter can be greater than the second diameter. The first diameter can be less than the second diameter. The first diameter can be the same as the second diameter. The first diameter can be different from the second diameter. The first diameter can be greater than the third diameter. The first diameter can be less than the third diameter. The first diameter can be the same as the third diameter. The first diameter can be different from the third diameter. The second diameter can be greater than the third diameter. The second diameter can be less than the third diameter. The second diameter can be the same as the third diameter. The second diameter can be different from the third diameter.

The extractor 500 can have engagement panels that have diameters which form a repeating pattern. The extractor 500 can have engagement panels that have diameters which form a random pattern. The extractor 500 can have engagement panels that are symmetric. The extractor 500 can have engagement panels that are asymmetric. The extractor 500 can have engagement panels that have one diameter, two diameters, three diameter, four diameter, five diameter, six diameters, or any range of two of the foregoing values.

The elongate member can form the engagement panels. Each engagement panel 510, 512, 514, 516 at the first longitudinal location forms a portion of the eyelet 546. Each engagement panel 520, 522, 524, 526 at the second longitudinal location forms a portion of the eyelet 546. Each engagement panel 5530, 532, 534, 536 at the third longitudinal location forms a portion of the eyelet 546. The coil 578 can extend between the eyelets 546. The elongate member can form the eyelets 546. The elongate member can form the coil 578. The engagement panels can be spaced apart by the coil 578. The length of coil 578 between the eyelets 546 can be the same length. The length of coil 578 between the eyelets 546 can be different lengths. The distance between the engagement panels can be 1 mm, 5 mm, 10 mm, 15 mm, 20 mm, 25 mm, 30 mm, 35 mm, 40 mm, 45 mm, 50 mm, 55 mm, or any range of two of the foregoing values. The engagement panels at each longitudinal location can be spaced close to each other, such as a gap of 1 mm, 2 mm, 3 mm, 4 mm, 5 mm, 6 mm, 7 mm, 8 mm, 9 mm, 10 mm, or any range of two of the foregoing values. The engagement panels at each longitudinal location can be spaced farther apart from each other, such as a gap of 20 mm, 30 mm, 40 mm, 50 mm, or any range of two of the foregoing values. The length of the eyelet can be 1 mm, 5 mm, 10 mm, 15 mm, 20 mm, 25 mm, 30 mm, 35 mm, 40 mm, 45 mm, 50 mm, 55 mm, or any range of two of the foregoing values. The extractor 500 can be manufactured from a single elongate member. The eyelet 546 can be located in the center of the first diameter. The eyelet 546 can be located offset from the center of the first diameter. The eyelet 546 can be located in the center of the second diameter. The eyelet 546 can be located offset from the center of the second diameter. The eyelet 546 can be located in the center of the third diameter. The eyelet 546 can be located offset from the center of the third diameter.

The luminal diameter of the vessel can be 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, or any range of two of the foregoing values. The first diameter of the engagement panel 510, 512, 514, 516 at the first longitudinal location can be 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, or any range of two of the foregoing values. The second diameter of the engagement panel 520, 522, 524, 526 at the second longitudinal location can be 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, or any range of two of the foregoing values. The third diameter of the engagement panel 530, 532, 534, 536 at the third longitudinal location can be 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, or any range of two of the foregoing values.

The extractor can include the coil. The coil can be in the space between two engagement panels. The coil and the engagement panels can be continuously formed. The coil and the engagement panels can be unitary or integrally formed. The coil and the engagement panels can be formed of the same material. The coil and the engagement panels can be connected. The coil and the engagement panels can be formed of different materials. The coil can be more flexible than the engagement panels. The engagement panels can be more flexible than the coil. In some embodiments, the coil allows flexible spacing of the engagement panels. In some embodiments, the coil allows the space between two engagement panels to lengthen and/or shorten. In some embodiments, the coil allows the extractor to bend within the vasculature. In some embodiments, the coil allows the extractor to follow the tortuous path of a vessel. In some embodiments, the coil is freely bendable. In some embodiments, the coil has column strength to allow pushability of the extractor.

The extractor can include the connecting member. The connecting member can be in the space between two engagement panels. The connecting member and the engagement panels can be continuously formed. The connecting member and the engagement panels can be unitary or integrally formed. The connecting member and the engagement panels can be formed of the same material. The connecting member and the engagement panels at two longitudinal locations can be connected. The connecting member and the engagement panels can be formed of different materials. The connecting member can be more flexible than the engagement panels. The engagement panels can be more flexible than the connecting member. The connecting member can be helical. The connecting member can be spaced inward from the circumference of the engagement panels. The connecting member can be sized not to make contact with the vessel wall. In some embodiments, the connecting member allows flexible spacing of the engagement panels. In some embodiments, the connecting member allows the space between two engagement panels to lengthen and/or shorten. In some embodiments, the connecting member acts as a biasing member to maintain a space between two engagement panels. In some embodiments, the connecting member acts as a biasing member to maintain a space between the first longitudinal location and the second longitudinal location. In some embodiments, the connecting member acts as a biasing member to maintain a space between the second longitudinal location and the third longitudinal location.

In some embodiments, the extractor can be formed from a single wire. In some embodiments, the extractor is not formed with multi-loop ends. The engagement panels can have no discrete ends. In some embodiments, the single wire can form the connecting members. In some embodiments, the single wire can form the coil. In some embodiments, the single wire can form the engagement panels. The single wire can form the coil near the distal end. The single wire can form the engagement panels at the first longitudinal location. The single wire can form the coil between the engagement panels at the first longitudinal location and the engagement panels at the second longitudinal location. The single wire can form the engagement panels at the second longitudinal location. The single wire can form the coil between the engagement panels at the second longitudinal location and the engagement panels at the third longitudinal location. The single wire can form the engagement panels at the third longitudinal location. The single wire can form the coil near the proximal end. In some embodiments, the extractor is distinguished from devices with multi-loop ends. In some embodiments, the extractor has one single wire where each engagement panel has no discrete ends.

The engagement panel include the arc. The arc can be supported by legs. The legs can extend radially outward from the eyelet. The arc of the engagement panel is in relatively complete contact with vessel wall. In some embodiments, the arcs of the engagement panel at the first longitudinal location form a nearly complete circle. In some embodiments, the arcs of the engagement panel at the first longitudinal location contact more than 80% of the circumference of the vessel wall, more than 85% of the circumference of the vessel wall, more than 90% of the circumference of the vessel wall, more than 95% of the circumference of the vessel wall, nearly all of the circumference of the vessel wall, more or less, or any range of two of the forgoing values. In some embodiments, the arcs of the engagement panel at the second longitudinal location form a nearly complete circle. In some embodiments, the arcs of the engagement panel at the third longitudinal location form a nearly complete circle. The engagement panels each have a partial circumferential arc that together have more vessel wall contact. In some embodiments, the engagement panels arc is relatively complete contact with vessels. In some embodiments, the engagement panel circumferential arc has more vessel wall contact.

The engagement panel has minimal surface contact with the vessel wall along the length of the extractor. This is based on the total surface contact of the extractor compared with other devices, such as the stent retriever. The arcs of the engagement panels form a nearly complete ring at the longitudinal locations. The space between longitudinal locations does not have a structure that contacts the vessel wall. The engagement panels are relatively thin. The engagement panels can be formed by a single wire. The engagement panels can be formed by a double or triple wire. The engagement panels thereby reduce the friction forces against the vessel wall. The engagement panels result in low pull force. In some embodiments, the low pull force is critical when retracting the extractor inside a neurovascular vessel. The low pull force can prevent sub-arachnoid hemorrhage. For example, the current stent retriever has high surface area contact against the vessel wall. This creates high friction and tension force. As a result, when the stent retriever is retracted, the stent retriever will pull the vessel more aggressively that will potentially damage the surrounding tissue and smaller blood vessels. Whereas the extractor or engager engagement panels have lower material to vessel wall surface contact thereby minimize the friction force and prevent the pulling of the blood vessels or lesser tension applies to the vessels. This will help keeping the vessels stable during the retraction of the device resulting in minimal damage to the blood vessels. In some embodiments, the engagement panels have minimal surface contact to vessel wall, based on device total surface area as compared to a conventional stent retriever. Thereby reducing the friction force against vessel wall result in low pull force. In some embodiments, this is an advantage when retracting the device inside the neurovascular vessel to prevent sub-arachnoid hemorrhage.

The extractor can include an arrays of movable engagement panels. The engagement panels can include an open-space radially inward from the perimeter of the engagement panels. The engagement panels can include an outlined perimeter and a pore therethrough. The engagement panels can be operably connected together. In some embodiments, the engagement panels can be separated longitudinally by the spacer. In some embodiments, the engagement panels can be separated longitudinally by the coil. In some embodiments, the engagement panels can be separated longitudinally by the connecting member. In some embodiments, the extractor or engager has arrays of movable engagement panels and open-space radially inward to the perimeter of the panels, all operably connected together, but separated longitudinally by a spacer.

The extractor can include a method of expansion of the engagement panels as compared to a conventional stent retriever. For example, when stent retriever deploys and expands, the length of the stent retriever is shortened or contracted when fully deploy. The engagement panels when deploy and expands, the length of the device is not shortened. The engagement panels can expand by radial expansion without axial movement. The engagement panels can expand radially outward. The engagement panels can expand or contract without stretching or shortening as compared to stent retrievers. The engagement panels can expand can radially expand or open. In some embodiments, the engagement panels are in a first, constrained position and the arcs of the engagement panels at the first longitudinal location are positioned distal to the eyelet at the first longitudinal location. In some embodiments, the engagement panels are in a first, constrained position and the legs of the engagement panels at the first longitudinal location are compressed and positioned next to each other. The legs of the engagement panels at the first longitudinal location can be coaxial with the catheter shaft or core wire. The legs of the engagement panels at the first longitudinal location can be positional longitudinally inline with the legs of the engagement panels at the second longitudinal location. As the loading tube assembly or sheath is retracted, the engagement panels at the first longitudinal location open, the arcs of the engagement panels at the first longitudinal location expand and the legs of the engagement panels at the first longitudinal location move farther apart. As the loading tube assembly or sheath continues to retract, the arcs of the engagement panels at the first longitudinal location continue to expand and the legs of the engagement panels at the first longitudinal location continue to move apart. In some embodiments, the engagement panels also revert or move proximally and radially outward. The arcs and legs of the engagement panels at the first longitudinal location are fully expanded at the second, expanded position and positioned relatively inline with the eyelet at the first longitudinal location. As the loading tube assembly or sheath is retracted, the engagement panels at the second longitudinal location expand and then the engagement panels at the third longitudinal location expand. In some embodiments, when the extractor is positioned at the distal end of the delivery catheter, the engagement panels are contained inside the delivery catheter and constrained. As the delivery catheter is retracted to deploy the engagement panels at the first longitudinal location, the engagement panels will expand outward radially while maintaining the same length and the eyelet relatively stay fixed and does move. As the engagement panels at the second longitudinal location are expanded, the previous deployed or expanded engagement panels at the first longitudinal location do not contract. The engagement panels at the second longitudinal location deploy and expand radially without shortening. Once the engagement panels at the second longitudinal location is expanded, the panels will stay relatively fixed to the first longitudinal location. As the delivery catheter is retracted to deploy or expand additional engagement panels, the extractor length does not shorten or contract. In some embodiments, the method of expansion includes radial expansion without axial movement. In some embodiments, the extractor expands or contracts without stretching or shortening as compare to stent retrievers. In some embodiments, engagement panel can radially expand or open.

The extractor can include engagement panels formed of a single layer. Each engagement panel can be formed of a single wire. The extractor can include engagement panels formed of a double layer. Each engagement panel can be formed of a double wire. The layers can be longitudinally aligned. The layers can be stacked. The layers can form the same profile or perimeter. The layers can be offset. The layers can be circumferentially twisted. Each engagement panel can be formed of a triple wire. There can be multiple sets of engagement panels at a longitudinal location. The engagement panels can be offset to each other by certain degrees including, e.g. about 0 degrees, 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, between 0 and 20 degrees, between 0 and 45 degrees, between 0 and 179 degrees, more or less, or any range of two of the foregoing values. The engagement panels that are offset can reduce pore sizes. The engagement panels can bifurcate the opening through the engagement panel. In some embodiments, the extractor includes multiple sets of engagement panels between arrays (e.g. double layer design). In some embodiments, engagement panels can be offset to each other by certain degrees from 0 to 179 degrees. In some embodiments, offset engagement panels can be designed to reduce pore sizes.

In some embodiments, the extractor can include a distal plug or distal member. In some embodiments, the distal member can be located at the distal end. The distal member can be distal to all engagement panels. In some embodiments, the distal member can be near the distal end. The distal member can be distal to some, but not all, engagement panels. There can be one or more engagement panels distal to the distal member. There can be one or more engagement panels proximal to the distal member. In some embodiments, the distal member is located at the first longitudinal location. In some embodiments, the distal member is located at the second longitudinal location. In some embodiments, the distal member is located at the third longitudinal location. In some embodiments, the distal member is located at the fourth longitudinal location.

In some embodiments, the engagement panels can compress upon removal of the spacer. In some embodiments, the engagement panels may not have compressive strength. In some embodiments, the engagement panels comprise double wires. In some embodiments, the engagement panel is designed to reduce deflection force. In some embodiments, the engagement panel can be formed from a large diameter wire. In some embodiments, the engagement panel can be formed from two or more smaller diameter wires. In some embodiments, the engagement panel forms a pore. The pore can be along the longitudinal direction in the direction of blood flow. The pore can allow blood to flow through the extractor. The pore size can be smaller if the engagement panels comprise offset layers. The pore size or opening between the offset layers will enable the engagement panels to capture smaller clot size or prevent smaller clot size to pass through. In some embodiments, the engagement panels are formed from one or more wires. In some embodiments, the engagement panels and the eyelet are formed from loops bonded to a hypotube. In some embodiments, the engagement panels and the eyelet can be formed using polymer via extrusion. In some embodiments, the engagement panels and the eyelet can be formed from other method like molding. In some embodiments, the engagement panels can compress upon removal of the spacer. In some embodiments, the engagement panels may not have compressive strength.

In some embodiments, the extractor can be formed from a single wire. In some embodiments, the extractor can be formed from a double wire. In some embodiments, the double wire has a smaller diameter wire. In some embodiments, creating the diameter smaller reduces the deflection force.

In some embodiments, the device can include a stent retriever. The device can include a stent like structure. The stent retriever can include a distal member. In some embodiments, the extractor is deployed within the stent retriever. In some embodiments, the extractor is deployed distal to the stent retriever. In some embodiments, the extractor is deployed proximal to the stent retriever.

In some embodiments, the extractor can include an eyelet. In some embodiments, the eyelet can be formed from one or more partial arcs. In some embodiments, the eyelet can be formed from one or more complete arcs. In some embodiments, the eyelet can be formed from a helical wire. In some embodiments, the eyelet can be formed from a coil. In some embodiments, the eyelet can form a central hole.

In some embodiments, the extractor is formed from a wire. In some embodiments, the extractor can be formed from loops. In some embodiments, the extractor can be formed from loops bonded to a hypotube. In some embodiments, the extractor can be formed from extrusion. In some embodiments, the engagement panels and the eyelet can be produced using polymer via extrusion. In some embodiments, the engagement panels and the eyelet can be produced by other methods such as molding.

The extractor can be used to remove material, such as clot material. The extractor can be deployed at or near a treatment site. The treatment site can be in a blood vessel, including but not limited to a neurovascular blood vessel. The extractor can include engagement panels at a first longitudinal location and a second longitudinal location. The extractor can be easy to use compared to complex systems. The extractor can reduce trauma to the blood vessel. The extractor can be easy to navigate to the treatment site. The extractor can be cost effective to manufacture. The extractor can remove material on a first pass, reducing hospitalization and leading to quicker recovery. The extractor can target remove of specific material such as hardened or chronic material from the vasculature. The functional portion of the extractor can include spaced apart arrays of engagement panels. The engagement panels are not covered by material thereby allowing blood flow through the pores of the engagement panels. The engagement panels at a longitudinal location can be in substantially continuous contact with the vessel wall along a circumference of the vessel wall. The engagement panels can be pre-formed with legs and the arc. The engagement panels expand from a collapsed state to an expanded state. The engagement panels expand into engagement with the vessel wall.

The extractor can have column strength to move longitudinally within a vessel. The expanded engagement panels at the longitudinal location are approximately equal to the diameter of the vessel. The engagement panels are segments of the complete circumference. The expanded engagement panels at the longitudinal location have a diameter of, e.g.

about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, more or less, or any range of two of the foregoing values.

The extractor can be pulled proximally without axially lengthening. The extractor can be pulled proximally without radially compressing. The extractor can be pulled proximally and the engagement panels can scrape along the surface of the vessel. The extractor can be pulled proximally to compress the material between engagement panels at the first longitudinal location and the second longitudinal location. The extractor can retain the material between engagement panels at the first longitudinal location and the second longitudinal location.

In some embodiments, a filter is provided. The filter can prevent downstream emboli and fragmented clot. In some embodiments, the filter can be formed of nitinol. In some embodiments, the filter can be formed of polymeric materials and/or metallic materials.

In some embodiments, the spacer is fixed. The spacer can be unable to move or slide along the length of catheter shaft. In some embodiments, the spacer is movable. The spacer is able to move or slide along the length of the catheter shaft creating a tension variation and/or release.

In some embodiments, a collection bag is provided. The collection bag can encapsulate captured clot for removal. In some embodiments, the collection bag can be formed from nitinol. In some embodiments, the collection bag can be formed from polymeric materials.

In some embodiments, the extractor has a one piece construction. In some embodiments, the extractor comprises distinct members. The extractor can comprise the engagement panels, the spacers, and/or the catheter shaft. The spacers can keep the engagement panels apart. The engagement panels can have distinct legs. The legs can be straight. In some embodiments, the legs do not overlap. The legs provide sufficient support without overlapping. The engagement panels can form a segment of a larger circular profile. In some embodiments, the engagement panels are not loops. The engagement panels can have straight or linear legs connected to the arc. The engagement panels can define an eyelet. The engagement panels can define a lumen. The eyelet can be centrally located among the engagement panels.

In some embodiments, the engagement panels can be dynamic. The engagement panels can move. The engagement panels can have tension. The engagement panels can be spring-like. The engagement panels can be biased to compress toward each other. The engagement panels can be biased to create a pinching force. The engagement panels can include the arc. The arc can be greater than an apex. The arc can provide more surface contact with the vessel wall. In some embodiments, the engagement panels do not stretch. In some embodiments, the engagement panels collapse for delivery. In some embodiments, the engagement panels open for clot engagement. In some embodiments, the engagement panels fold toward the catheter shaft.

Figure 95:
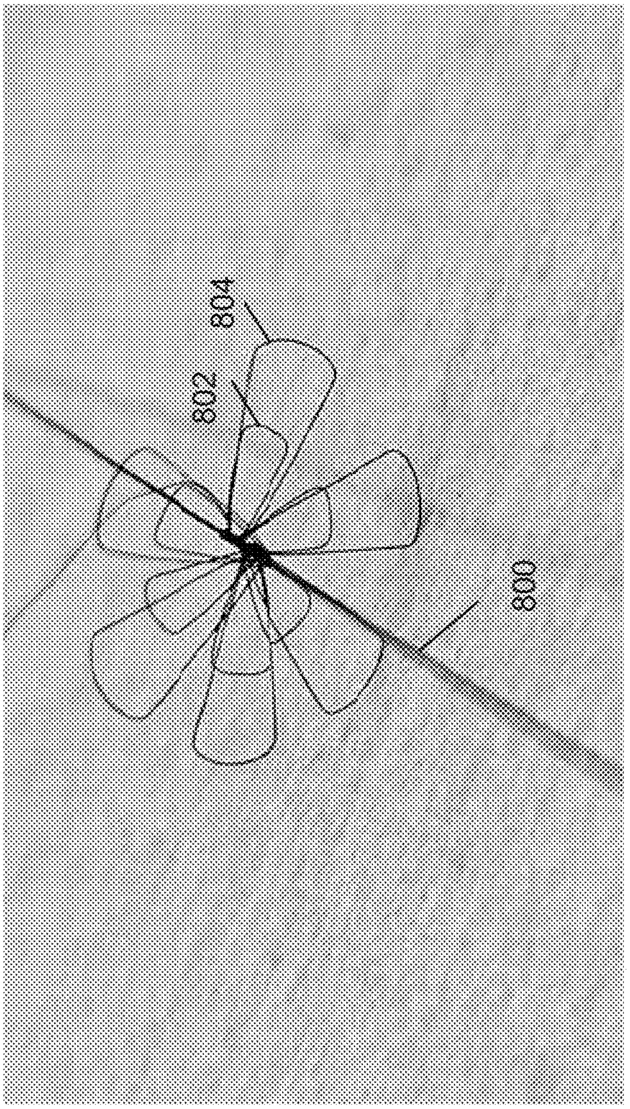
FIG. 95 is a view of engagement panel with an outer engagement panels and an inner smaller engagement panels.
Figure 146:
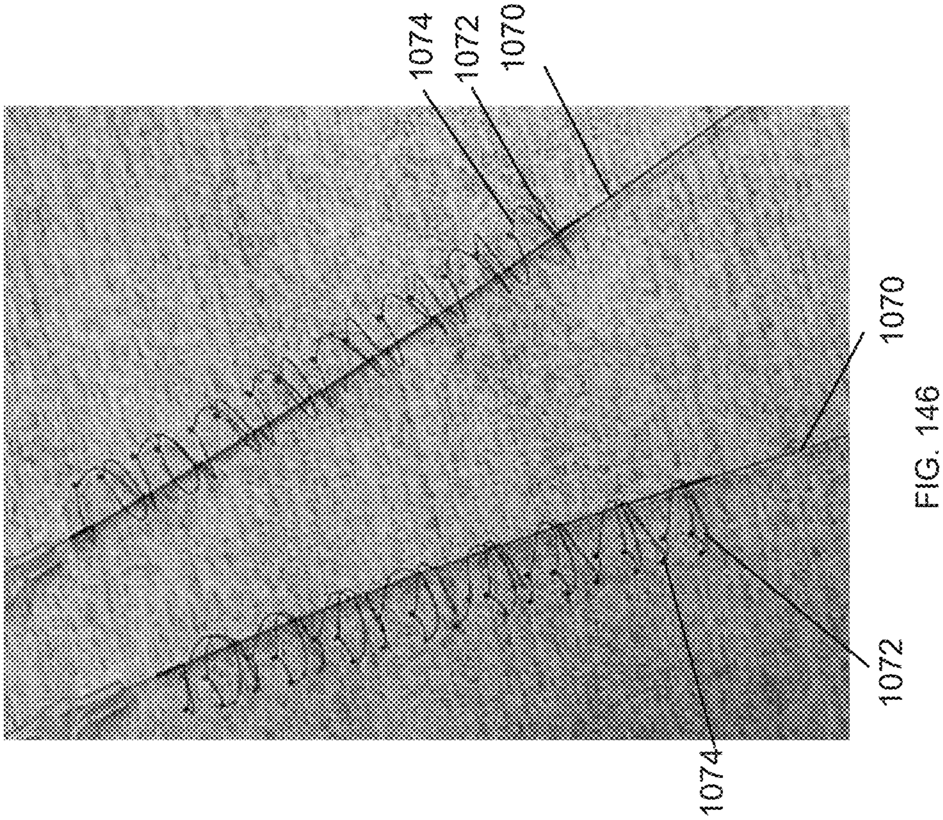
FIG. 146 are views of extractors. The extractor can be a series of helical loop and circular loop alternating.

FIGS. 95-146 illustrate various improvements on the extractors described herein. The extractor can include any feature of any extractor described herein. The distal member extractor can include any feature of any distal member described herein. The device can include any feature of any device described herein. The engagement panel can include any feature of any engagement panel described herein. The engagement panels located at the first longitudinal location panel can include any feature of any engagement panels described herein. The engagement panels located at the second longitudinal location panel can include any feature of any engagement panels described herein. The engagement panels located at the third longitudinal location panel can include any feature of any engagement panels described herein.

The engagement panels can be formed from one continuous wire. The engagement panels can include a first array of engagement panels located at the first longitudinal location formed from the one continuous wire. The engagement panels can include the second array of engagement panels located at the second longitudinal location formed from the one continuous wire. The engagement panels can include the third array of engagement panels located at a third longitudinal location formed from the one continuous wire. The engagement panels can have a three-dimensional shape. The engagement panels can have a shape to scrape the vessel wall. The engagement panels can have a shape that engages at least a portion of the circumference of the vessel wall. The engagement panels can extend radially outward from a coiled eyelet. The engagement panels can extend circumferentially outward from a coiled eyelet. The engagement panels can have a shape that engages clot.

FIG. 95 is a view of engagement panels 800. The engagement panels 800 can include a double panel. The engagement panels 800 can include a small panel 802 inside a large panel 804. The small panel 802 can be an inner engagement panel. The large panel 804 can be an outer engagement panel. The small panel 802 and the large panel 804 can be stacked. The small panel 802 and the large panel 804 can be spaced apart. The small panel 802 and the large panel 804 can be aligned. The small panel 802 and the large panel 804 can be offset. The engagement panels 800 can include a continuous wire. In some embodiments, the continuous wire forms the small panels 802 and the large panels 804. In some embodiments, the continuous wire forms the small panels and the large panels can be different wire. In some embodiment, the continuous wire can be a plurality of wires. In some embodiments, the continuous wire forms the outer engagement panels and the inner engagement panels. The engagement panels 800 can be reinforced. The small panel 802 can reinforce the large panel 804. The small panel 802 can stiffen the large panel 804. The double panel can be less prone to collapse when encountering material. The double panel can be less prone to collapse when scraping the vessel wall. In some embodiments, the engagement panels 802 can be almost flat. The engagement panels can include one, two, three, four, five, six, seven, eight, nine, ten, eleven, twelve, thirteen, fourteen, fifteen, sixteen, seventeen, eighteen, nineteen, or twenty, or any range of the foregoing number of panels at each longitudinal location. The engagement panels can be in two rows with a row of small panels and a row of large panels.

Figure 96:
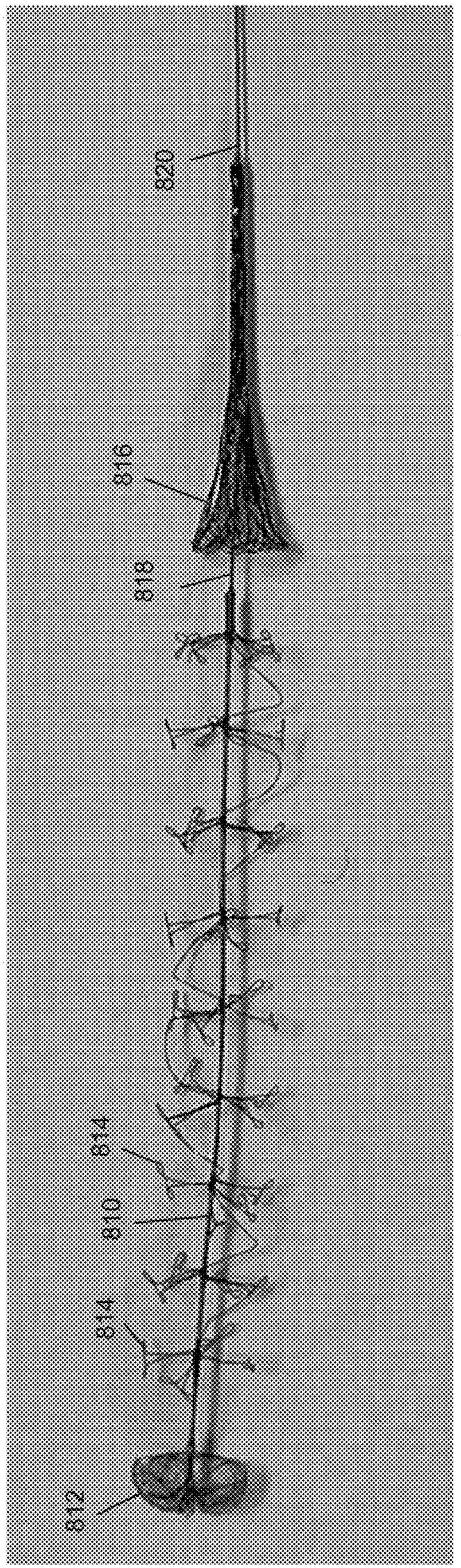
FIGS. 96-97 are views of a distal member, funnel and an extractor.
Figure 97:
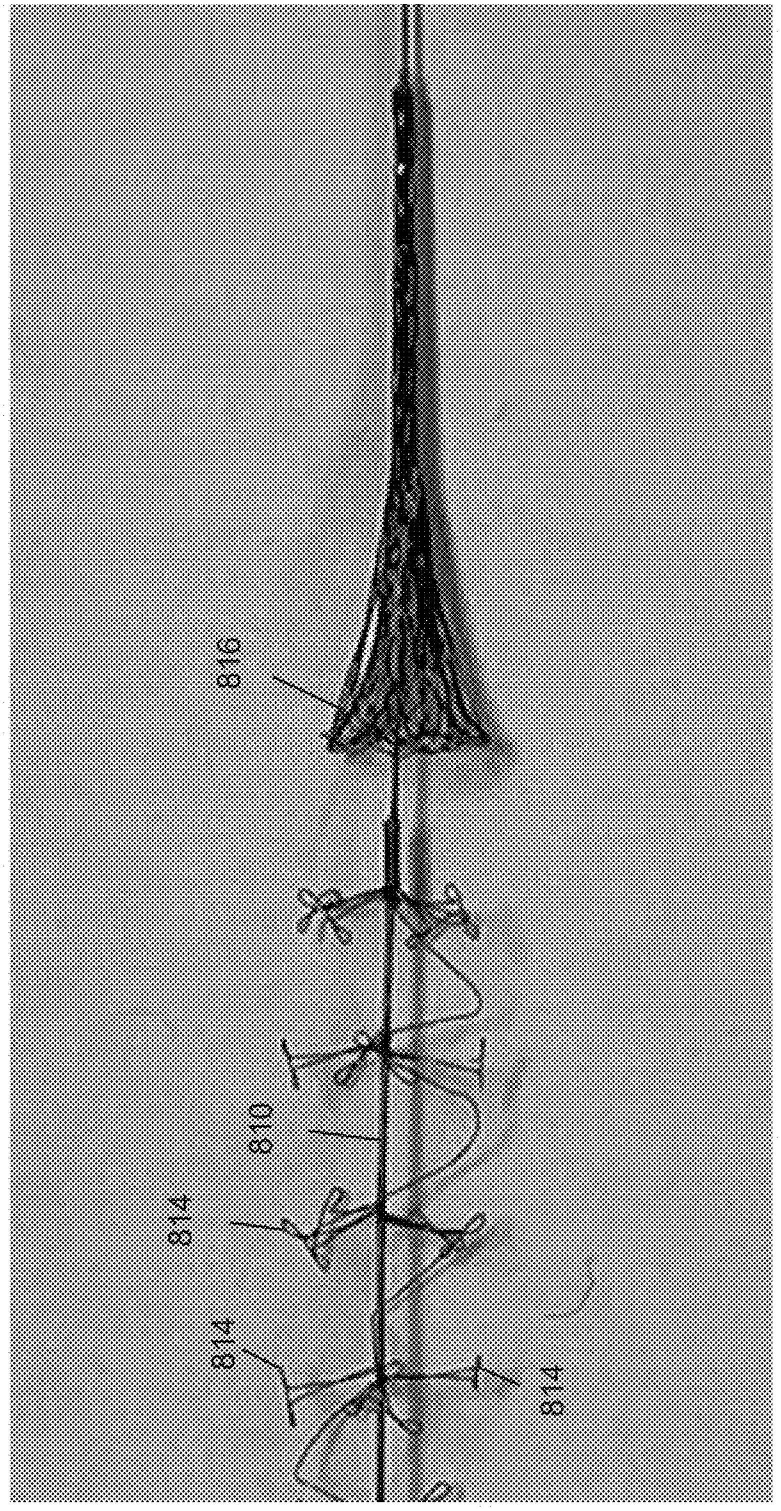

FIGS. 96-97 are views of an extractor 810. The device can include a distal member 812. The extractor 810 can include engagement panels 814. The engagement panels 814 can include a T-shape feature. The engagement panels 814 can be formed from a continuous wire. The continuous wire can be one, two, three or plurality of wires. The continuous wire can form the T-shape feature. The T-shape feature can extend radially. The T-shape feature can be formed from one continuous wire from the eyelet. The T-shape feature can be a plurality of elements. The T-shape feature can engage the vessel wall. The engagement panel 814 can include a leg that radially extends from the coiled eyelet, a transverse element, and another leg that extends to the coiled eyelet. The legs can form a V-shape. The legs can twist. The transverse element can include one or more loops. The transverse element can include a figure eight. The transverse element can form an arc. The transverse element can be straight. The transverse element can be curved. The transverse element can scrape the surface of the vessel wall. The legs can support the transverse element as the engagement panels 814 encounter material. The engagement panels 814 can each include a T-shape feature. The engagement panels 814 can be a plurality of panels. The engagement panels 814 can include four panels at the first longitudinal location. The engagement panels 814 at the first longitudinal location can be circumferential offset. The engagement panels 814 at the first longitudinal location can be spaced apart by approximately 90 degrees. The engagement panels 814 at the first longitudinal location can engage less than the full circumference of the vessel wall, such as 10% of the circumference of the vessel wall, 20% of the circumference of the vessel wall, 30% of the circumference of the vessel wall, 40% of the circumference of the vessel wall, 50% of the circumference of the vessel wall, 60% of the circumference of the vessel wall, or any range of two of the foregoing values. The engagement panels 814 can include four panels at the second longitudinal location. The engagement panels 814 at the second longitudinal location can be circumferential offset. The engagement panels 814 at the second longitudinal location can be spaced apart by approximately 90 degrees. The engagement panels 814 can include four panels at the third longitudinal location. The engagement panels 814 at the third longitudinal location can be circumferential offset. The engagement panels 814 at the third longitudinal location can be spaced apart by approximately 90 degrees. The engagement panels 814 at the first longitudinal location can be circumferential offset from the engagement panels 814 at the second longitudinal location. The engagement panels 814 at the second longitudinal location can be circumferential offset from the engagement panels 814 at the third longitudinal location. The T-shape feature can function to grasp the clot. The T-shape feature can increase engagement with the clot.

The device can include a funnel 816. The funnel 816 can be positioned proximal to the engagement panels 814. The device can include a distal stopper 818 and proximal stopper 820. The distal stopper 818 and the proximal stopper 820 can limit the movement of the funnel 816. The distal stopper 818 can be positioned between the last engagement panel 814 and the funnel 816. The proximal stopper 820 can be positioned behind the proximal end of the funnel 816. The extractor 810 can include floris with proximal funnel. The mechanism of action is to push the clot into the proximal funnel 816. The engagement panels 814 can be positioned distal to the clot. The proximal funnel 816 can be positioned proximal to the clot. The engagement panels 814 can be retracted proximally to push the clot into funnel 816 to secure the clot for removal. The distal stop 818 attaches to the core wire. The distal stop 818 can aid in limiting the engagement panels 814 from entering into the funnel 816. The proximal stop 820 attaches to the core wire. The proximal stop 820 can aid in advancing the funnel 816.

Figure 98:
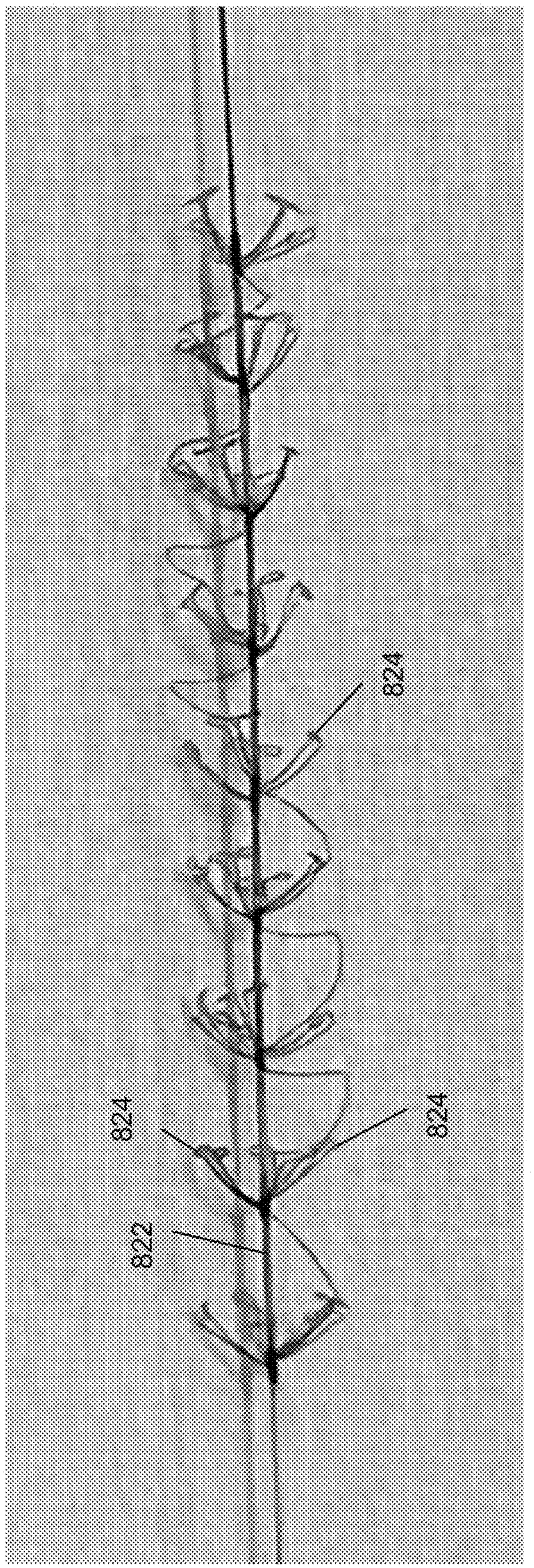
FIG. 98 is a view of an extractor. The extractor has a T-shape like engagement panels or elements where the elements are biased or directed toward the proximal end.

FIG. 98 is a view of an extractor 822. The extractor 822 can include engagement panels 824. The engagement panels 824 can include a T-shape feature. In some embodiments, the T-shape feature can be biased or directed toward the proximal end. In some embodiments, the T-shape feature can be biased or directed toward the distal end. The engagement panels 824 can form a cup shape. The engagement panels 824 can form a three dimensional shape. The engagement panels 824 can form a concave shape. The engagement panel 814 can include a leg that radially extends from the coiled eyelet, a transverse element, and another leg that extends to the coiled eyelet. The legs can form an arc. The legs can bend toward the vessel wall. The transverse element can scrape the surface of the vessel wall. The legs can support the transverse element as the engagement panels 814 encounter material.

Figure 99:
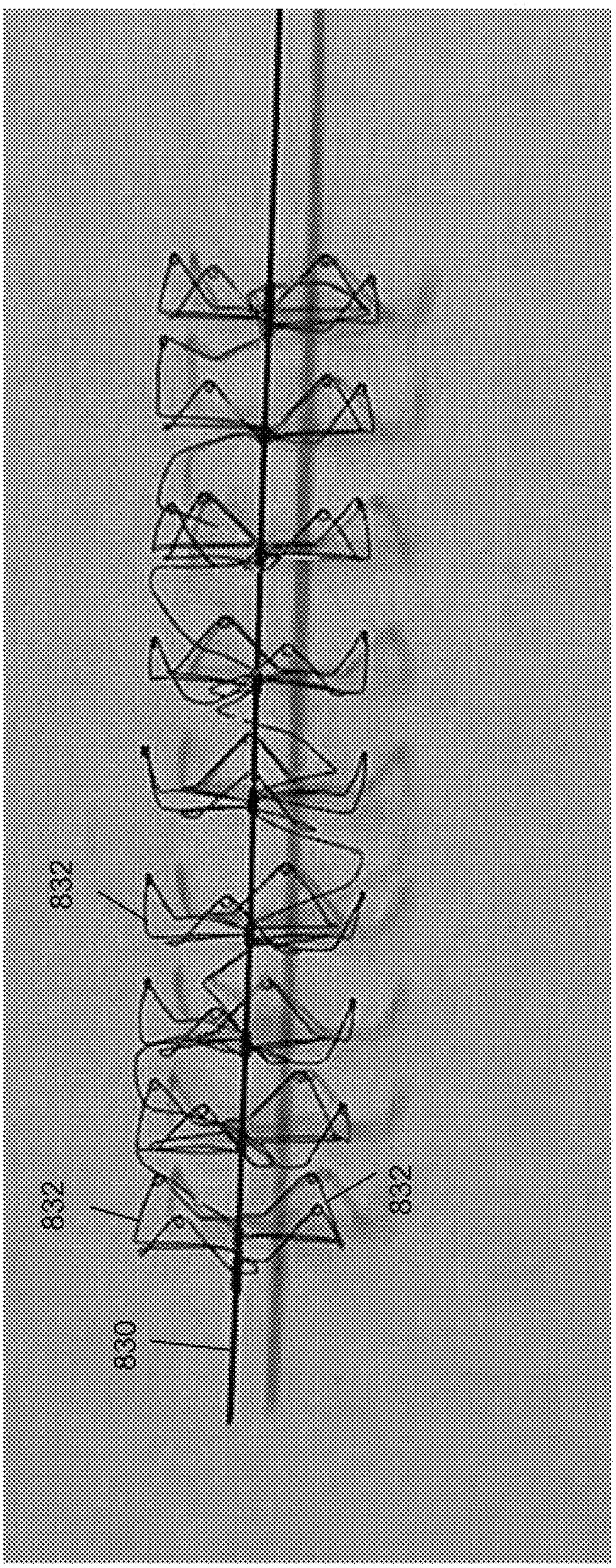
FIG. 99 is a view of an extractor, the extractor with engagement panels where the apex of the panel has an eyelet.

FIG. 99 is a view of an extractor 830. The extractor 830 can include engagement panels 832 and eyelet. The engagement panels 832 and eyelets can be formed from a continuous wire. The eyelets can attach to the corewire centrally located (at the center). The eyelets can attach to the corewire off-center. The engagement panels 832 can include an apex. The apex of the panel can include a rounded element. The apex of the panel can include a circular element. The apex of the panel can include an elliptical like element. The apex of the panel can include a coil. The apex of the panel can include a loop. The apex can be reinforced. The apex can include a rounded element to reinforce the shape of the apex. The apex of the panel can include additional support. The apex of the panel can include a doubling of the wire. The apexes of the panels can be biased or directed toward the proximal end. The apexes of the panels can be biased or directed toward the distal end. The apex of the panel can be configured to engage clot material. The apex of the panel can include a loop of wire that entangles the clot. The apex of the panel can include an eyelet spaced apart from the eyelet that receives the core wire. The apex of the panel can include an eyelet that functions to engage clot material. The apex of the panel can be the point of engagement with the clot. The apex of the panel can be the point of engagement with the vessel wall.

The engagement panels 832 can include four panels at the first longitudinal location. The engagement panels 832 at the first longitudinal location can be circumferential offset. The engagement panels 832 at the first longitudinal location can be spaced apart by approximately 90 degrees. In some embodiments, the apexes of the panels can engage the vessel wall. The engagement panels 832 at the first longitudinal location can engage less than the full circumference of the vessel wall, such as 10% of the circumference of the vessel wall, 20% of the circumference of the vessel wall, 30% of the circumference of the vessel wall, 40% of the circumference of the vessel wall, 50% of the circumference of the vessel wall, 60% of the circumference of the vessel wall, or any range of two of the foregoing values. The engagement panels 832 at the second longitudinal location and the third longitudinal location can include similar features as the first longitudinal location. The engagement panels 832 at the second longitudinal location and the third longitudinal location can include different features as the first longitudinal location. The engagement panels 832 at the first longitudinal location, the second longitudinal location and the third longitudinal location can be offset to scrap different areas of the vessel wall. The engagement panels 832 at the first longitudinal location, the second longitudinal location and the third longitudinal location can be offset to engage different radial segments of the clot.

Figure 100:
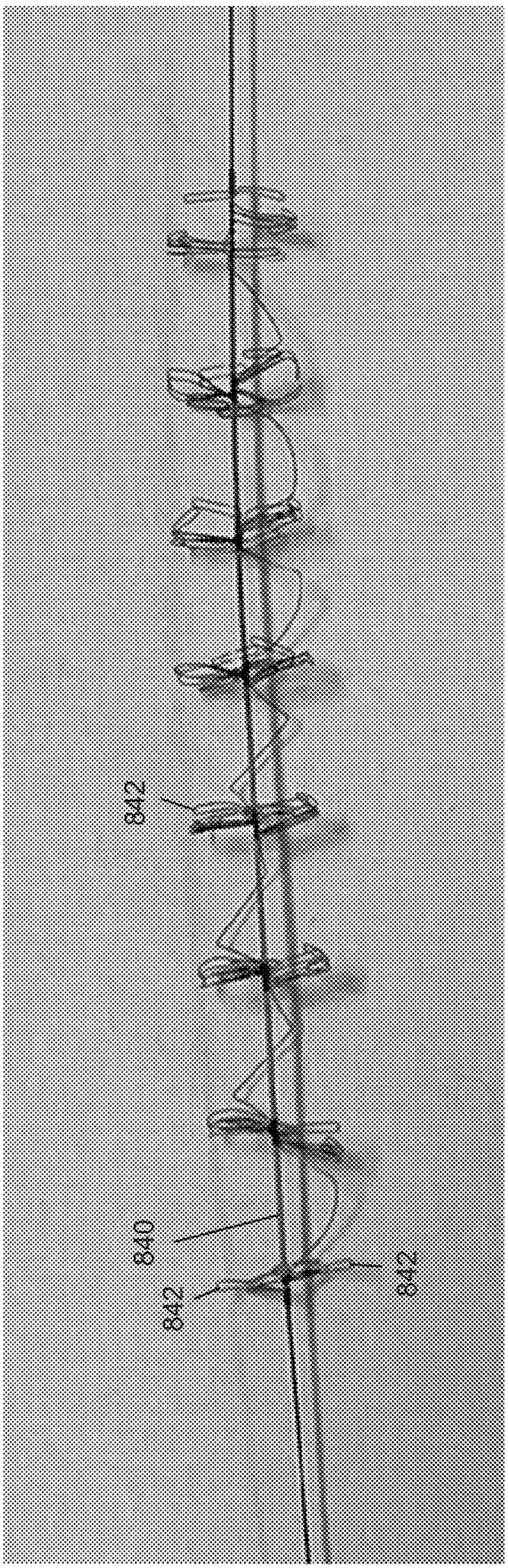
FIGS. 100-101 are views of an extractor.
Figure 101:
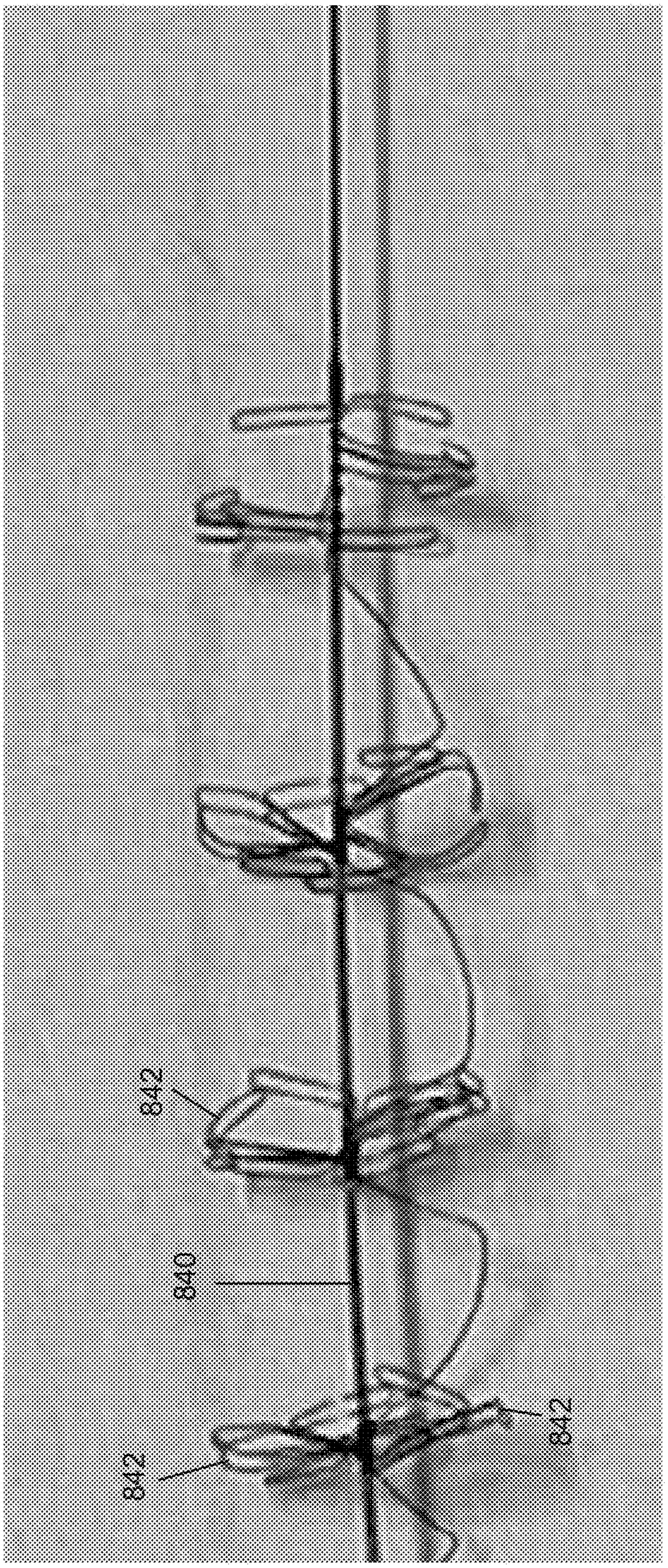
Figure 102:
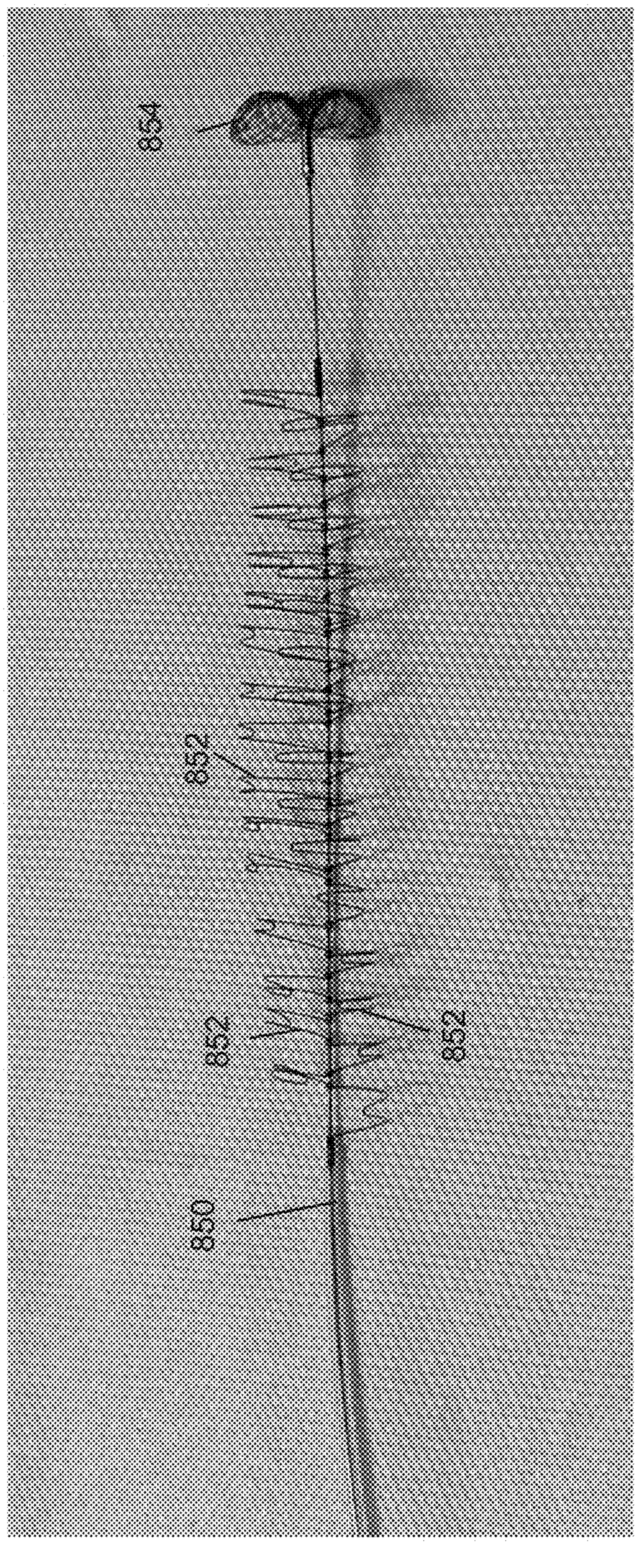
FIGS. 102-105 are views of an extractor with a crescent shape engagement panel and the eyelet receives the corewire off-center.
Figure 103:
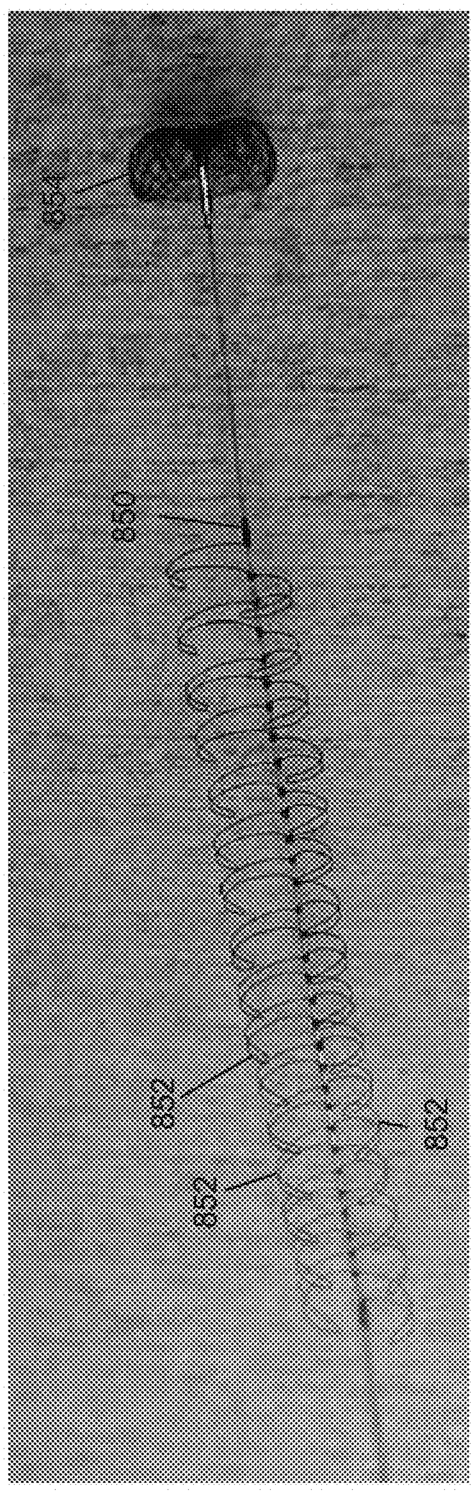
Figure 104:
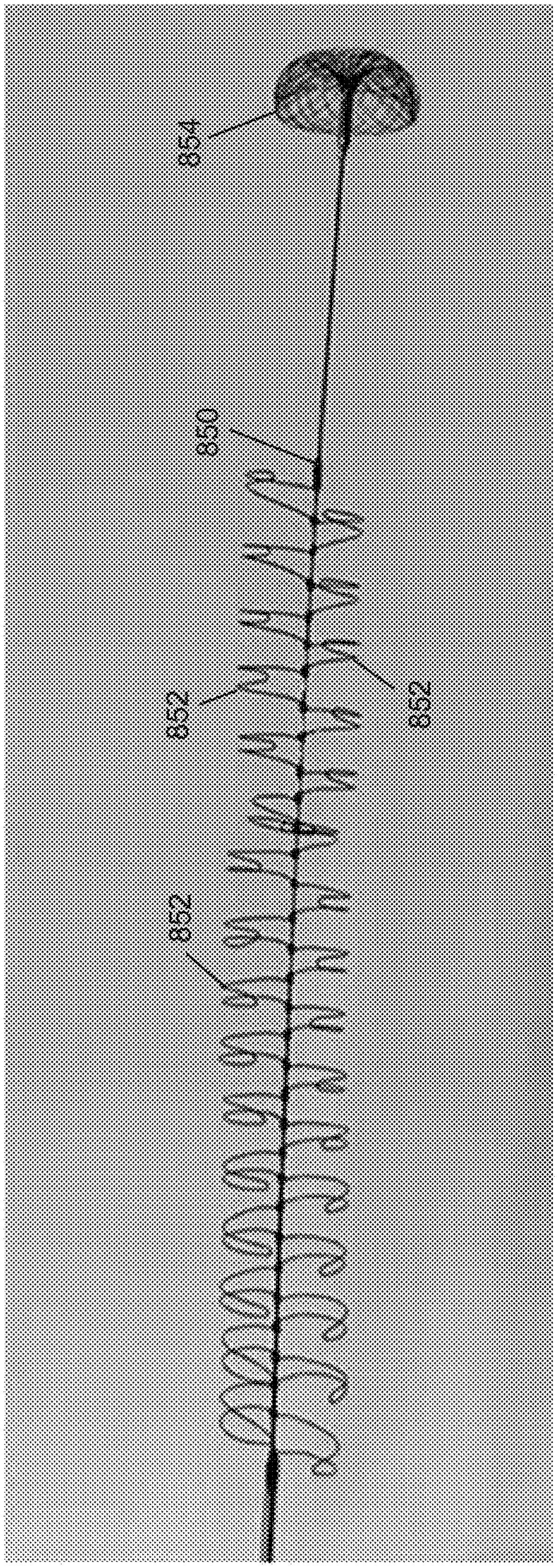
Figure 105:
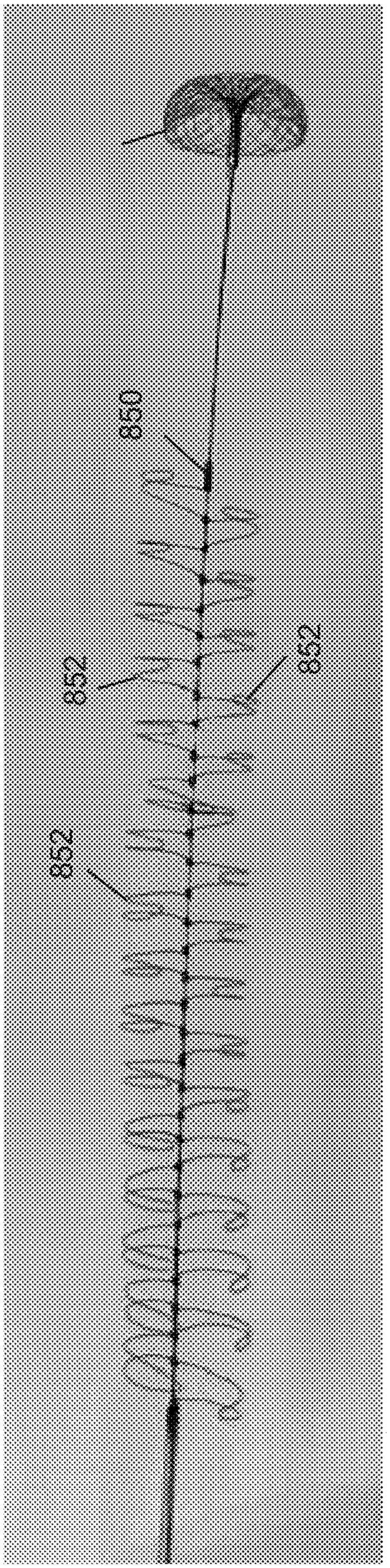
Figure 106:
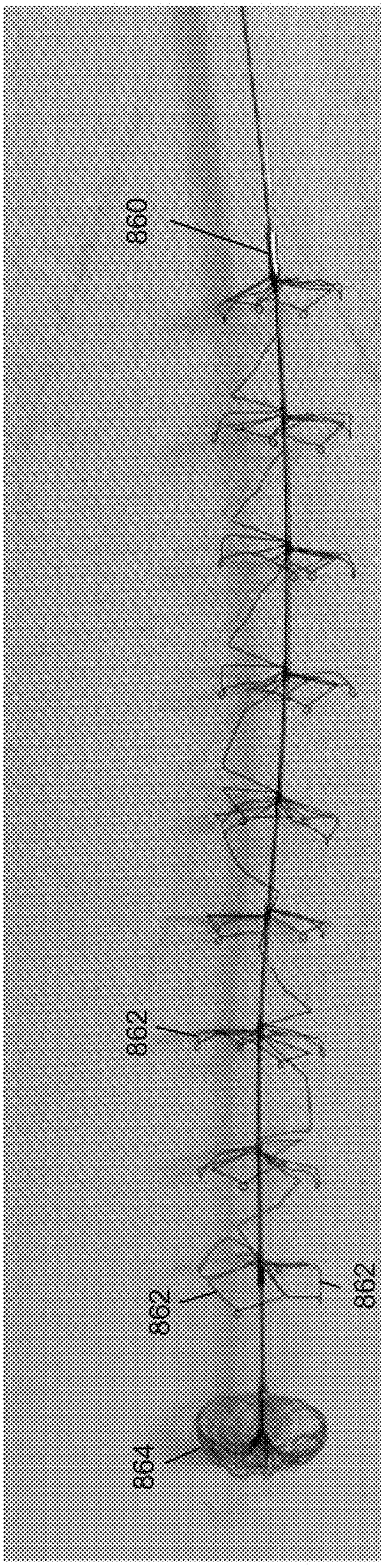
FIGS. 106-109 are views of a distal member and an extractor. The extractor has engagement panels where the panels have an eyelet at the tip and directed either in the proximal direction.
Figure 107:
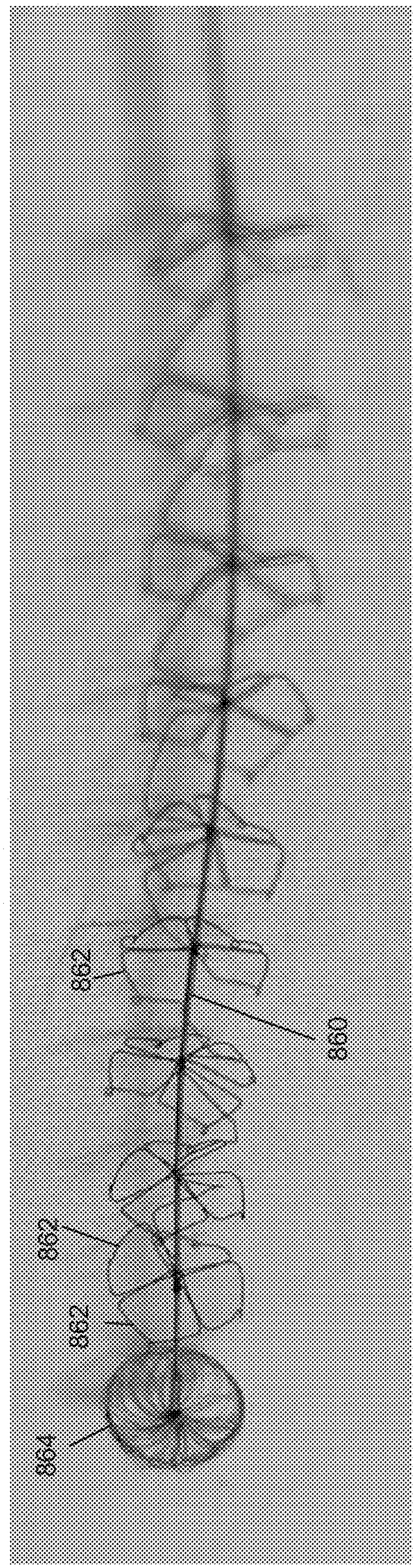
Figure 108:
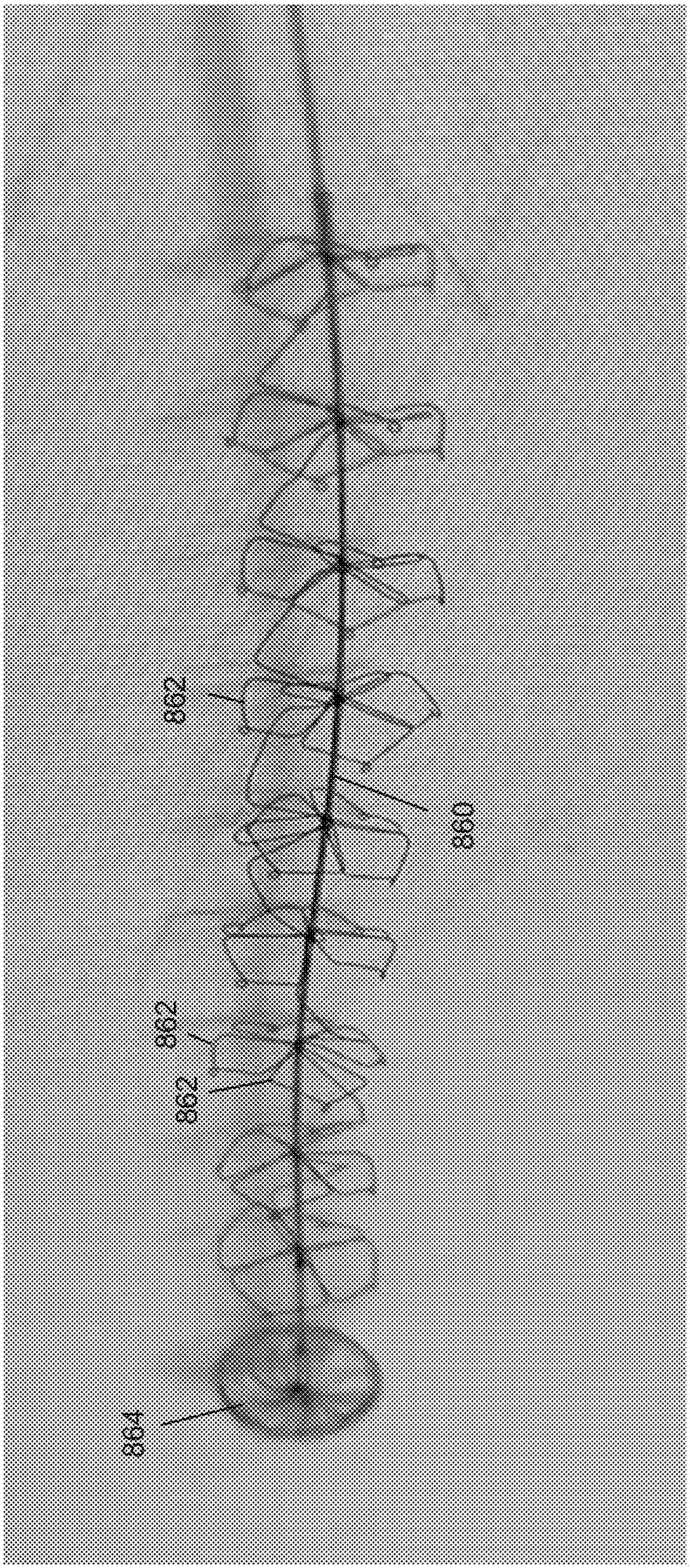
Figure 109:
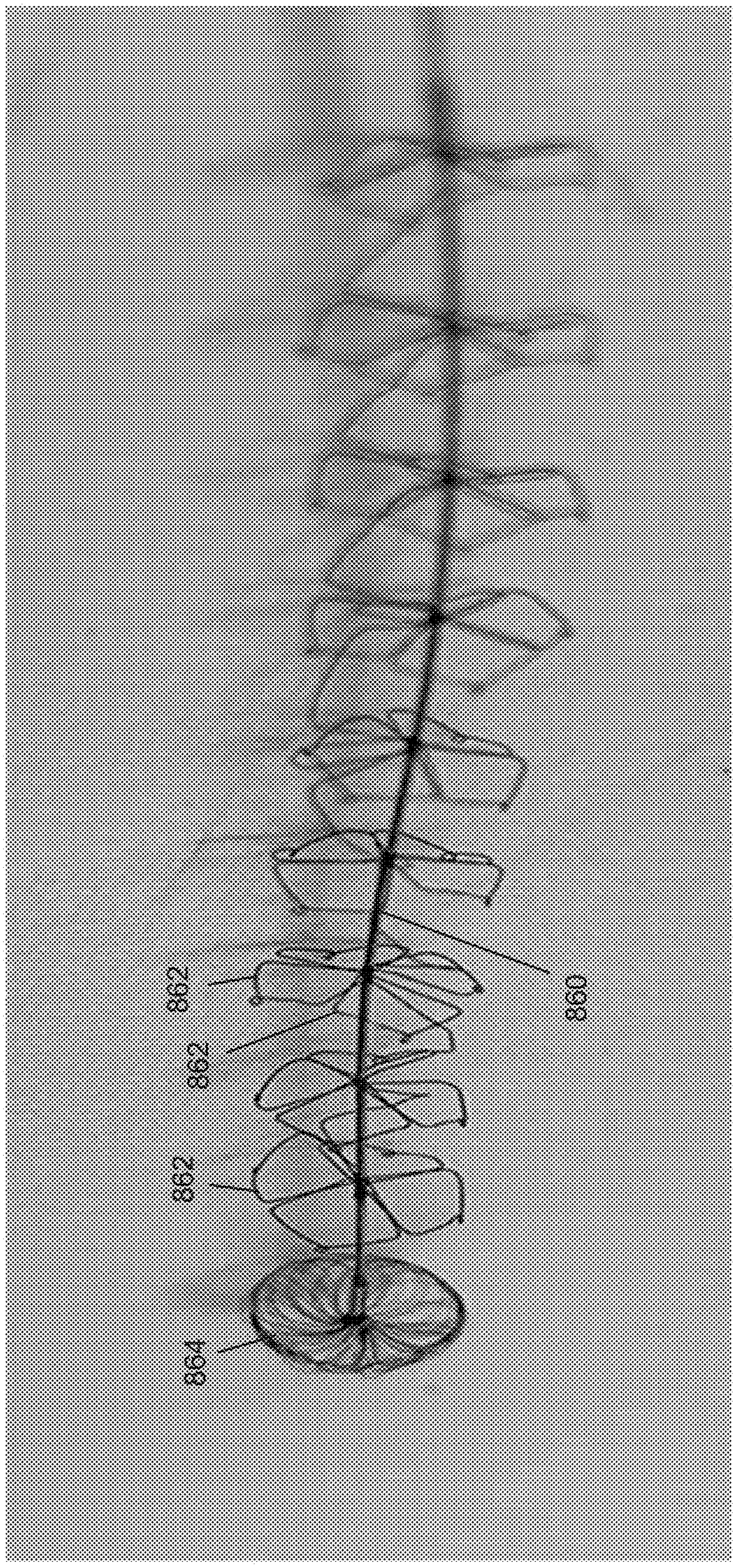

FIGS. 100-101 are views of an extractor 840. The extractor 840 can include engagement panels 842. The engagement panels 842 can be formed from one continuous wire. The engagement panels 842 forms an eyelet and legs. The one continuous wire extends radially to form legs that extend circumferentially and connect together. The leg of one engagement panel can be connected to the adjacent engagement panel leg. The engagement panel 842 can include a leg that forms an arc extending from the eyelet, a connecting transverse arc, and a leg that forms an arc extending to the eyelet. The engagement panel 842 can form a crescent shape. The engagement panel 842 can form a shape that forms a portion of a circumference of the vessel. The engagement panels 842 can be circumferentially offset. The engagement panels 842 can be randomly oriented. The engagement panels can be non-periodic. The engagement panels 842 can include fingers that grasp the clot. The engagement panels 842 can include fingers that entangle the clot. The engagement panels 842 can include fingers that touch. The engagement panels 842 can include fingers that do not touch.

FIGS. 102-105 are views of an extractor 850. The extractor 850 can include engagement panels 852 and eyelets. The engagement panels 852 and eyelets can include a plurality of elements formed from a continuous wire. The engagement panels 852 can have an eyelet and legs that extend circumferentially and meet together. The eyelet can attach to the corewire off-center relative to the engagement panels. The leg from one element is connected to the adjacent element by the eyelet. The extractor 850 can have one element or multiple elements. The device can include a distal member 854. The engagement panel 852 can include a leg that forms an arc extending from the eyelet, a connecting transverse arc, and a leg that forms an arc extending to the eyelet. The engagement panel 852 can form a crescent shape. The engagement panel 852 can form a wave shape. The engagement panel 852 can form a shape that forms a portion of a circumference of the vessel. The engagement panels 852 can be aligned. The engagement panels 852 can be periodic. The engagement panels can be non-periodic. The engagement panels arc can be the same. The engagement panels arc can be different. The engagement panels arc can varies or alternate of different arc. The first longitudinal location can have one engagement panel, two engagement panels, three engagement panels, four engagement panels, or any number of panels described herein. The one or more engagement panels 852 at the first longitudinal location can engage less than the full circumference of the vessel wall, such as 10% of the circumference of the vessel wall, 20% of the circumference of the vessel wall, 30% of the circumference of the vessel wall, 40% of the circumference of the vessel wall, 50% of the circumference of the vessel wall, 60% of the circumference of the vessel wall, or any range of two of the foregoing values. The extractor 850 can include a biased core wire. The core wire can be offset relative to center. The extractor 850 can include opened loops that form the engagement panels 852. The engagement panels 852 form less than a full circle. The engagement panels 852 have an open shape. The engagement panels can have a loop at the end. The extractor 850 can include opened loops that allow clot encapsulation. The extractor can include opened loop with a small loop (or eyelet) at the end (or tip) that allow clot encapsulation. The extractor 850 can have an open engagement panels or loops in order for the engagement panels have a better engagement with the clot. The engagement panels 852 can include an eyelet to receive the core wire. The core wire and eyelet can be positioned to side. The core wire and eyelet are not centrally located. The core wire can be biased. The core wire can be offset from center. The extractor 850 can include opened loops. The extractor 850 can allow for clot encapsulation.

FIGS. 106-109 are views of an extractor 860. The extractor 860 can include engagement panels 862. The engagement panels 862 can be formed from a continuous wire. The engagement panels 862 can include an apex. The apex of the panel can include a loop. The apex of the panel can include an eyelet. The apex of the panel can include a feature to help with folding of the engagement panel 862. The apex of the panel can a feature at the tip. The apex can be reinforced. The apexes of the panels can be biased or directed toward the proximal end. The apexes of the panels can be biased or directed toward the distal end. The device can include a distal element 864. The engagement panel 862 can be a 5 mm diameter petal. The engagement panel 862 can include a center loop or eyelet. The eyelet can receive the corewire centrally. In some embodiment, the eyelet can receive the corewire off-center. The mechanism of action can be a preset folding loop to increase clot engagement. The extractor 870 can aid in more secure removal of the clot from the blood vessels. When clot is removed from the vasculature and particularly in the neurovascular system, the clot must travel through extreme tight tortuous vessels and therefore poses a high risk of the clot dislodging in transit. In comparison, the stent retriever when deployed will tend to push the clot against the vessel wall and as the stent retriever is retracted proximally to remove the clot, the stent retriever slides pass the clot and does not grab clot securely. The extractor 870 when deployed can fully engage the clot without pushing the clot against the vessel wall. The extractor 870 when deployed entangles with the clot. The extractor 870 when deployed does not compress the clot. The extractor 870 when deployed effectively grasps the clot between engagement panels at the first longitudinal location and the engagement panels at the second longitudinal location. The extractor 870 when deployed effectively grasps the clot between engagement panels at the second longitudinal location and the engagement panels at the third longitudinal location. The engagement panel 862 can include a preset folding loop and eyelet element on the panel that can help increase the clot engagement. The engagement panels attach to the corewire at the center position. The engagement panel can attach to the corewire at the off-center position.

Figure 110:
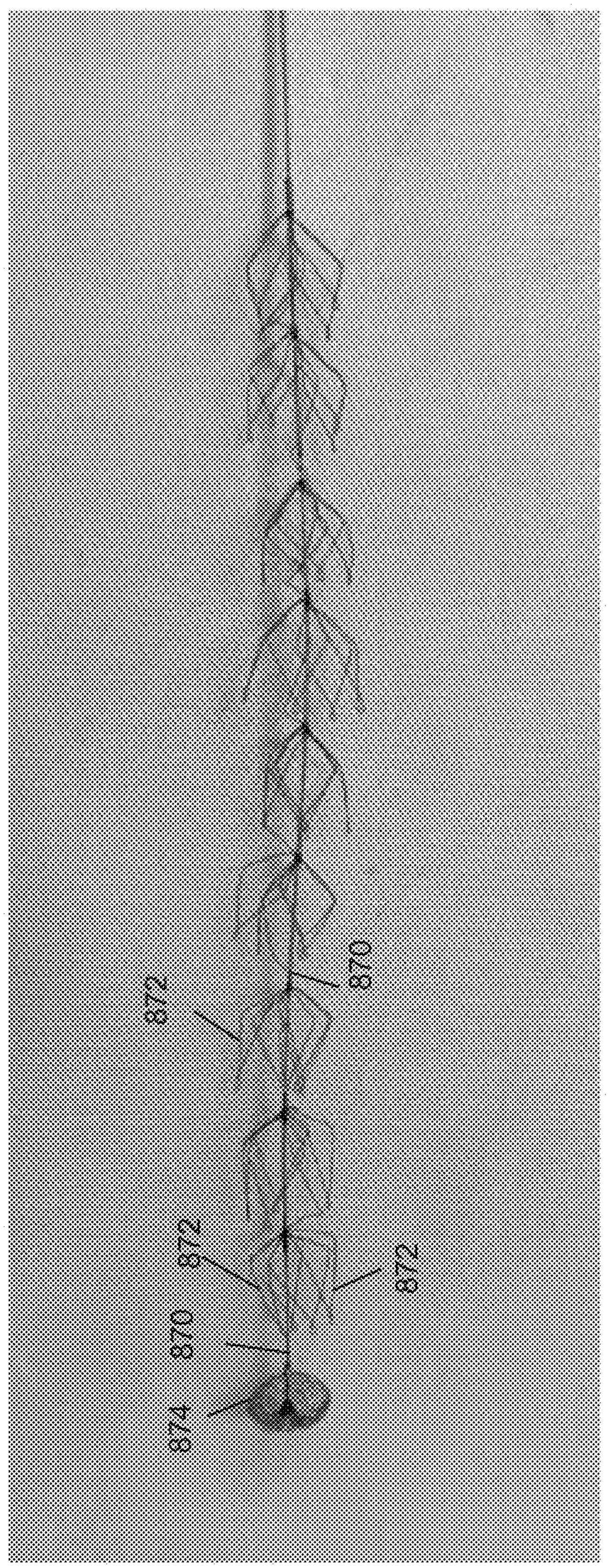
FIGS. 110-111 are views of the distal member and an extractor where the engagement panel apex has an eyelet and the engagement panel is directed distally.
Figure 111:
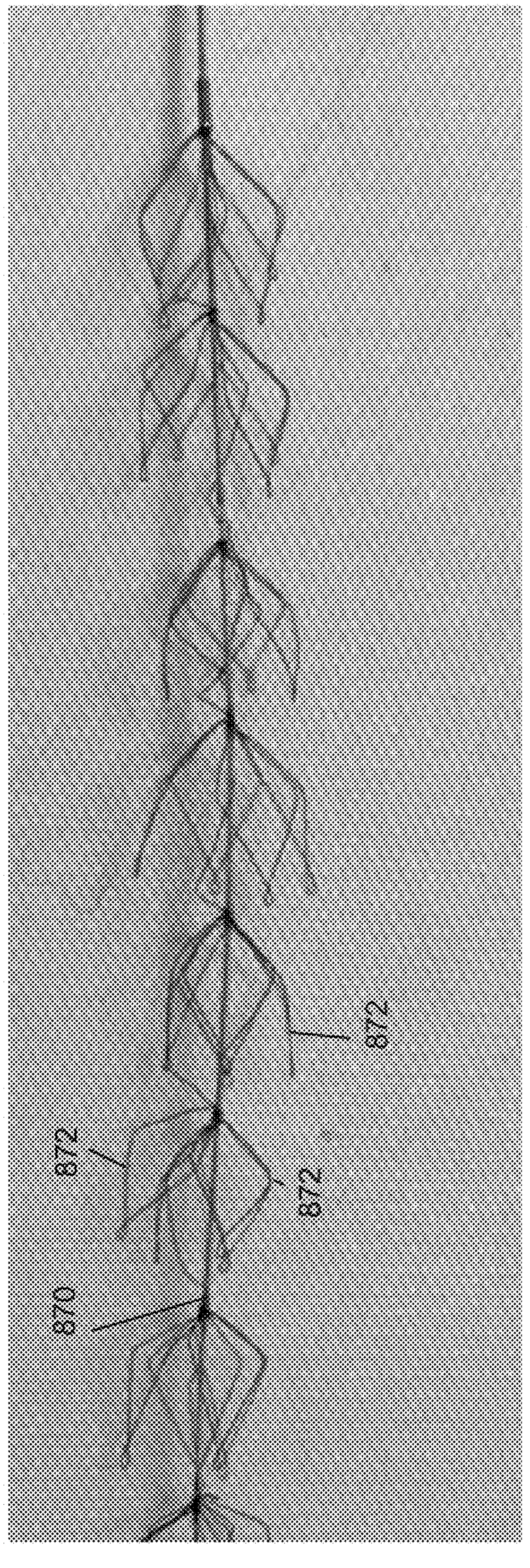

FIGS. 110-111 are views of an extractor 870. The extractor 870 can include engagement panels 872. The engagement panels 872 can be formed from a continuous wire. The engagement panel 872 can include an eyelet and legs extending radially towards the distal direction. The legs can extend radially outward toward a vessel wall. The legs can extend longitudinally along a vessel wall toward the distal end. The engagement panel 872 can include an eyelet and legs extending towards the proximal direction. The legs can extend radially outward toward a vessel wall. The legs can extend longitudinally along a vessel wall toward the proximal end. The engagement panels 872 can include an apex. The apex of the panel can include a loop. The apex of the panel can include an eyelet. The apex of the panel can include a feature to help with folding of the engagement panel 872. The panels can be connected together by a series of eyelets. The engagement panels 872 can be diamond shaped. The engagement panels 872 can be petal shaped. The engagement panels 872 can be v-shaped petals. The engagement panels 872 can grasp the clot. The extractor 870 can have a v-shaped engagement panels 872 with a loop or eyelet at the distal tip to grasp onto the clot for better clot engagement. The v-shaped engagement panels 872 can have different sizes. The v-shaped engagement panels 872 can have different shapes. The v-shaped engagement panels 872 can be angled in the proximal direction. The v-shaped engagement panels 872 can be angled in the distal direction.

Figure 112:
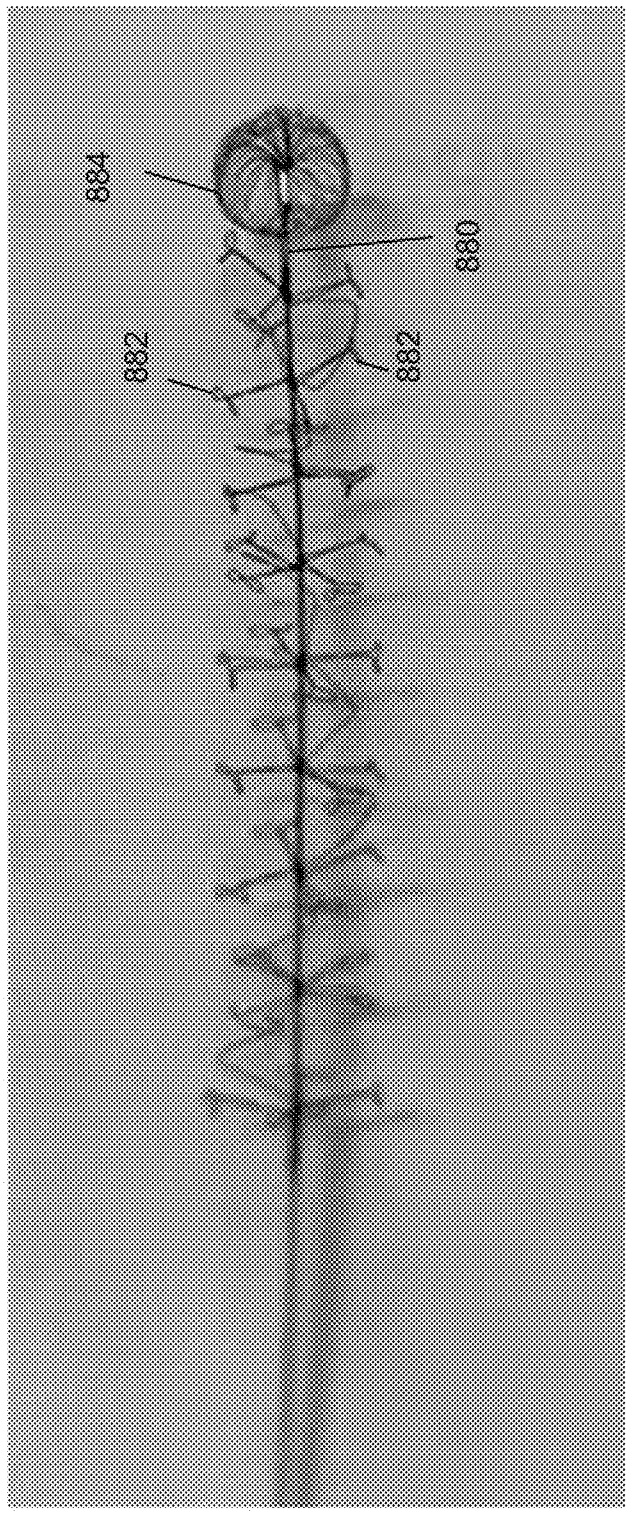
FIGS. 112-113 are views of the distal member and an extractor where the extractor engagement panels have traverse elements extends radially
Figure 113:
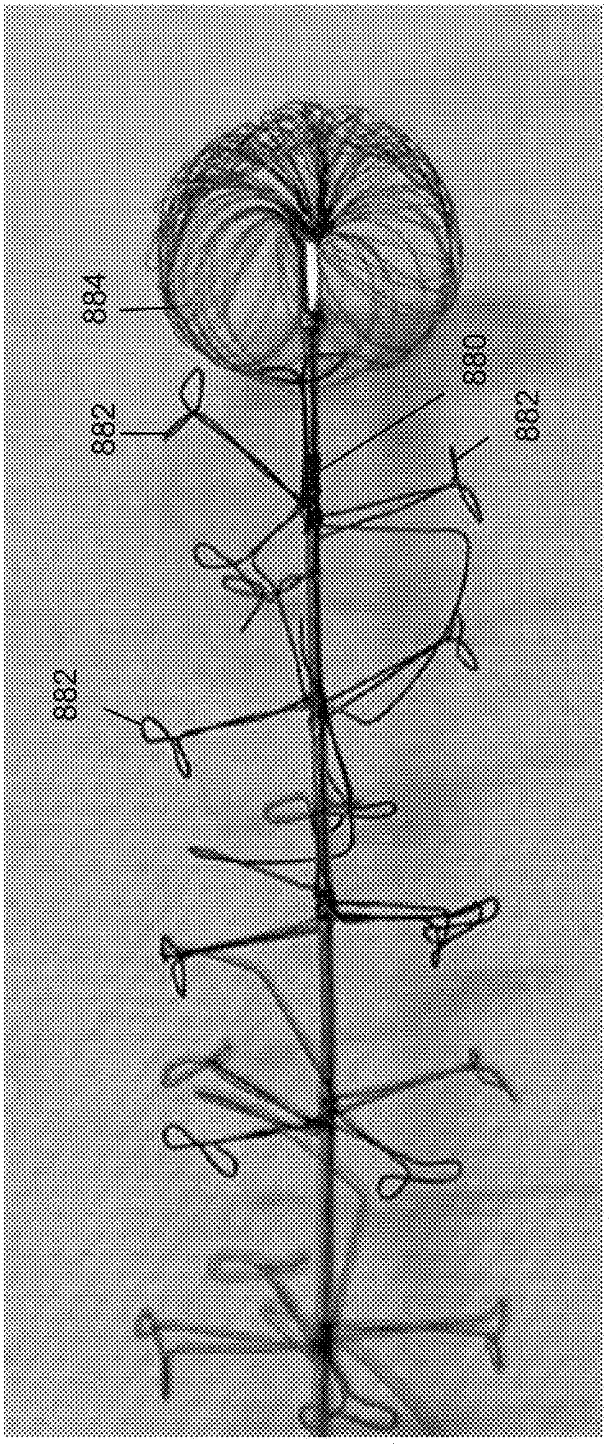

FIGS. 112-113 are views of an extractor 880. The extractor 880 can include engagement panels 882. The engagement panels 882 can be formed from a continuous wire. The engagement panels 882 can include an eyelet and legs extending radially. The engagement panels 882 can include a transverse element extending circumferentially. The engagement panels 882 can include a transverse element extending at an angle relative to the legs. The legs can extend radially. The transverse element can extend transverse to the legs. The engagement panels 882 can include a transverse element that connects together the legs. The legs extending radially may cross each other. The legs can twist. The transverse element can form a FIG. 8. The transverse element can form one or more loops. The transverse element can form a clover shape. The device can include a distal member 884.

Figure 114:
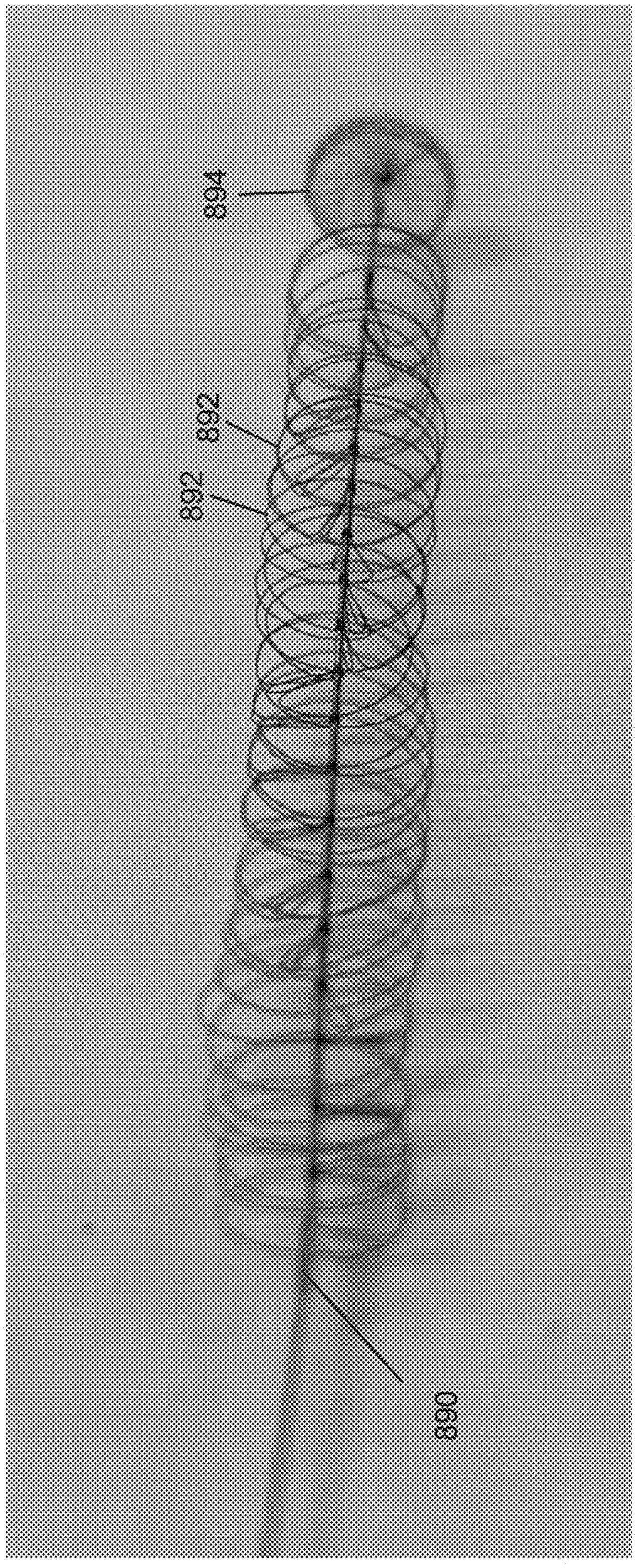
FIGS. 114-115 are views of an extractor. The extractor with the engagement panels form from a continuous wire. The engagement panel consists of eyelet and legs extending circumferentially.
Figure 115:
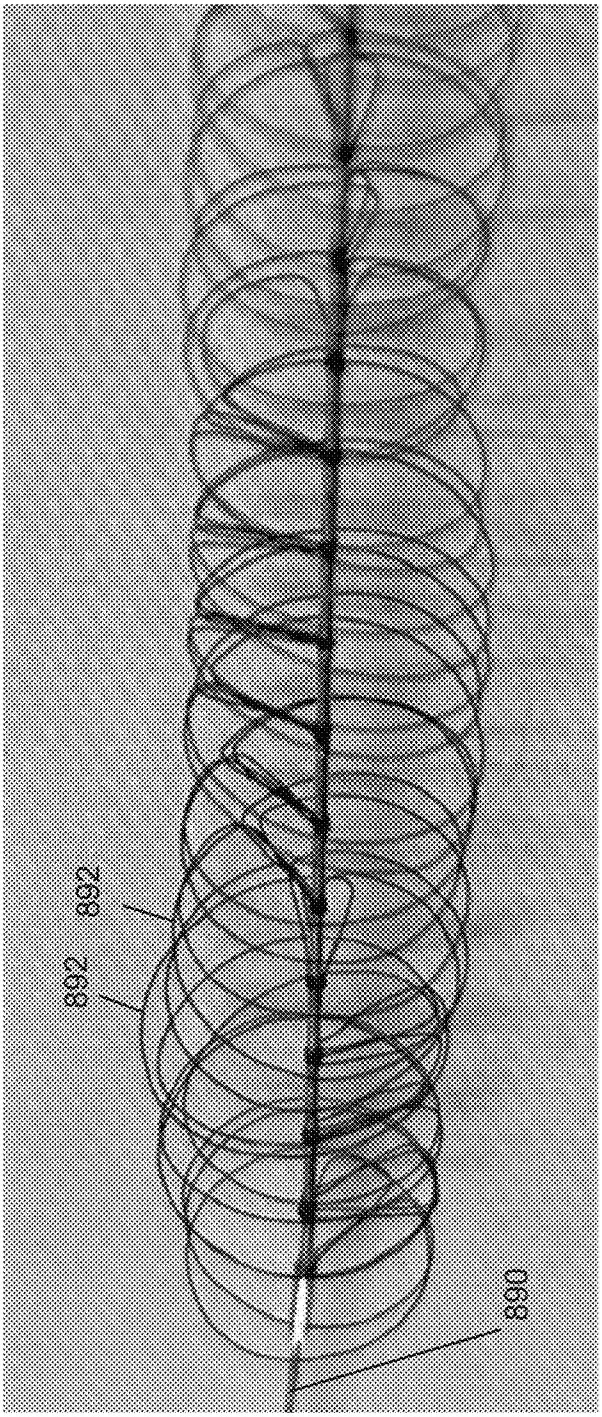

FIGS. 114-115 are views of an extractor 890. The extractor 890 can include engagement panels 892. The engagement panels 892 can be formed from a continuous wire. The engagement panels 892 can include an eyelet and legs extending circumferentially. The legs can extend up to 360 degrees. The legs can extend in a circular shape. The eyelet can receive the corewire centrally. In some embodiment, the eyelet can receive the corewire off-center. The device can include a distal member 894. The engagement panels 892 can include multi-loops. The engagement panels 892 can include an eyelet to receive a center core wire. The engagement panels can include an eyelet locate off-center relative to the panels to receive the corewire. The engagement panels 892 can include loops to go over the clot. The engagement panels 892 can be circular or looped shape. The engagement panels can be a polygon shape such as pentagon, hexagon, heptagon, octagon, etc. The engagement panels 892 can have a loop which has an opening or lumen to go over the clot and further increase the clot engagement. The core wire is centrally located in the engagement panels 892. The engagement panels 892 can have a central eyelet through which the core wire passes.

Figure 116:
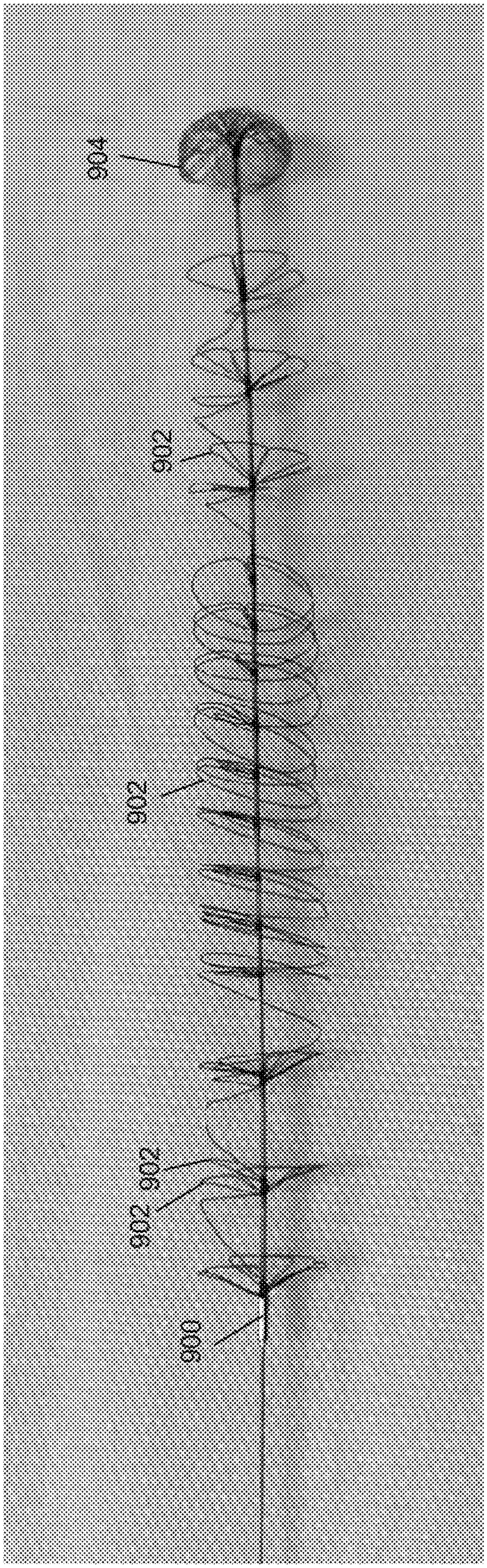
FIGS. 116-117 are views of the distal member and an extractor where the extractor has different arrays of engagement panels.
Figure 117:
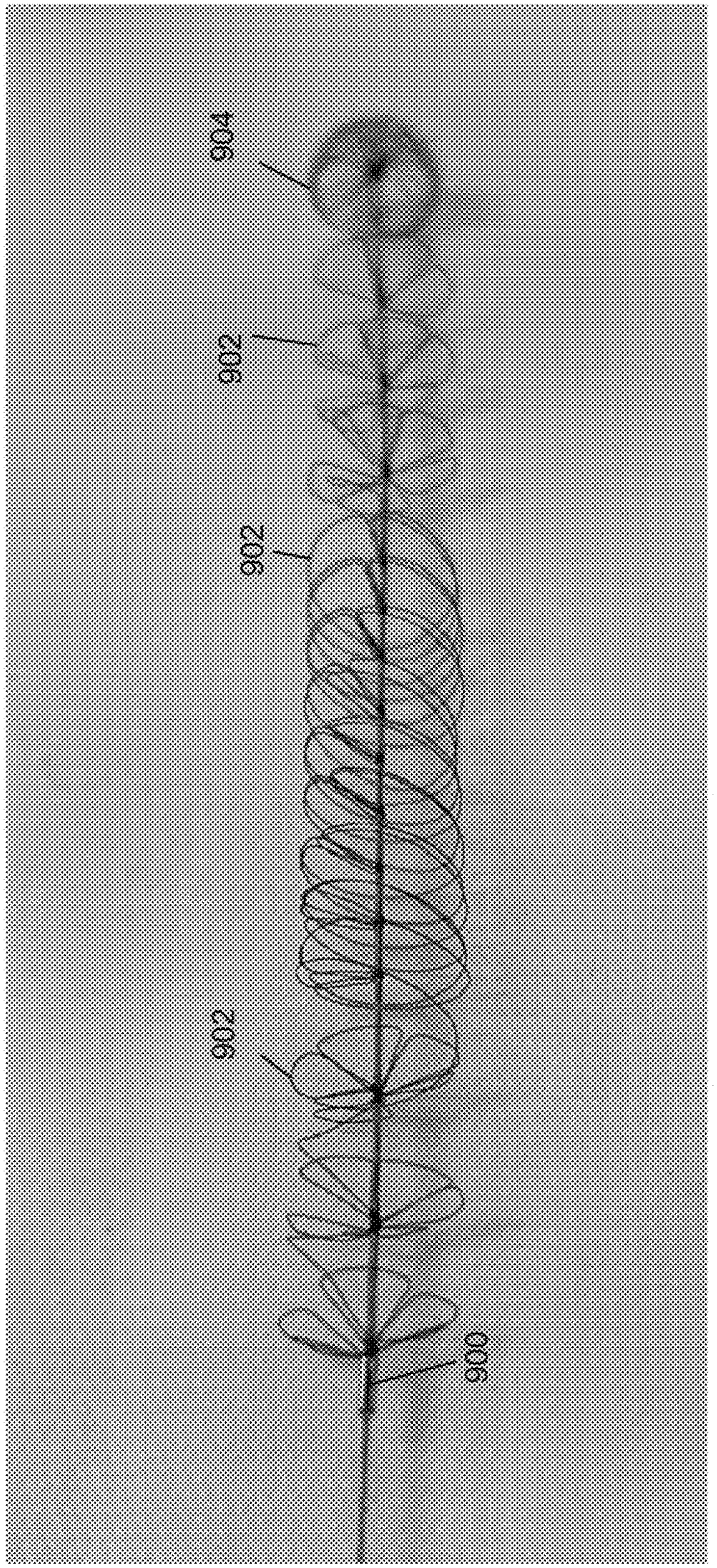

FIGS. 116-117 are views of an extractor 900. The extractor 900 can include engagement panels 902. The engagement panels 902 can be formed from a continuous wire. The extractor 900 can have different arrays at different longitudinal locations. The engagement panels 902 at the first longitudinal location can be at or near a distal segment. The engagement panels 902 at the first longitudinal location can have a plurality of panels such as four panels configuration. The engagement panels 902 at the second longitudinal location can be near a middle segment. The engagement panels 902 at the second longitudinal location can have a different panel configuration such as circular in shape. The engagement panels 902 at the third longitudinal location can be near a proximal segment. The engagement panels 902 at the third longitudinal location can have engagement panels with plurality of panels such as four panel configurations. The engagement panels 902 at the first longitudinal location can have any configuration described herein. The engagement panels 902 at the second longitudinal location can have any configuration described herein. The engagement panels 902 at the third longitudinal location can have any configuration described herein. The device can include a distal member 904. In some embodiments, the engagement panels 902 can be almost flat. The engagement panels can include one, two, three, four, five, six, seven, eight, nine, ten, or any range of the foregoing number of panels at each longitudinal location. The extractor 900 can include an engagement panels and loop design. The mechanism of action can be that the loops go over the clot. The extractor has four engagement panels 902 at each longitudinal location. The engagement panels 902 positioned at the distal section and proximal section of the extractor 900 can have the same configuration. The engagement panels 902 positioned at the distal section and proximal section of the extractor 900 can have a petal design. The middle section of the extractor 900 can have engagement panels 902 of a different configuration. The middle section of the extractor 900 can have engagement panels 902 with circular configuration or loops that can go over the clot. The core wire is centrally located in the engagement panels 902. The engagement panels 902 can have a central eyelet through which the core wire passes. In some embodiment, the engagement panels can have an off-center eyelet through which the core wire passes.

Figure 118:
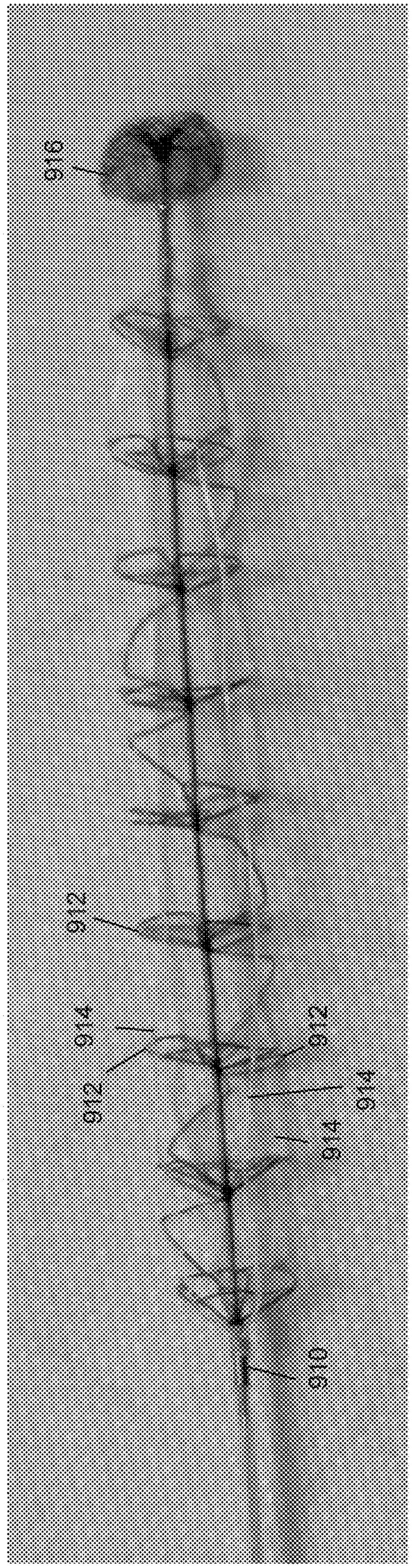
FIGS. 118-119 are views of the distal member and an extractor where the engagement panels are connected by an element to support the panels.
Figure 119:
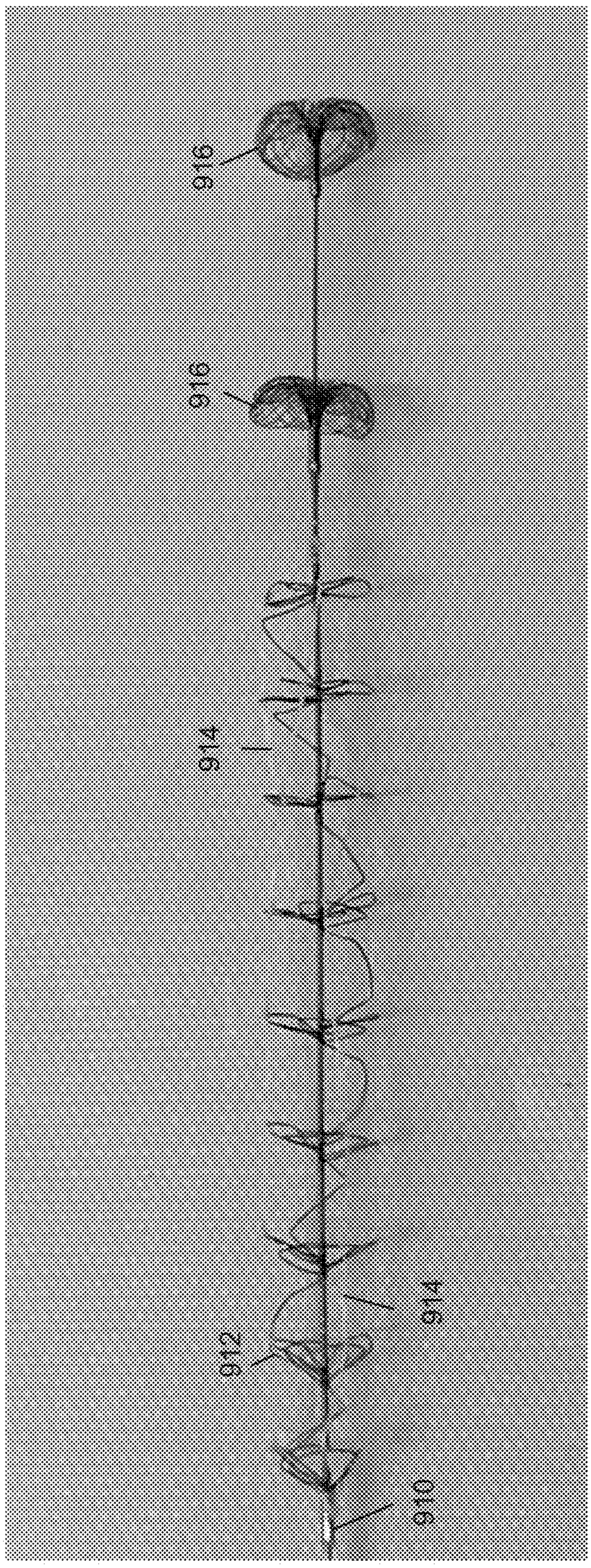

FIGS. 118-119 are views of an extractor 910. The extractor 900 can include engagement panels 912. The engagement panels 912 can be formed from a continuous wire. The device can include a connecting element 914 connecting all the engagement panels 912. The engagement panels are connected by the element 914 to maintain rigidity. In some embodiments, the connecting element 914 is a thread. In some embodiments, the connecting element 914 is formed from the continuous wire. In some embodiments, the connecting element 914 is formed separately from the continuous wire. In some embodiments, the connecting element 914 is formed from the same material as the continuous wire. In some embodiments, the connecting element 914 is formed from a different material than the continuous wire. The device can have a distal member 916. The device can have one distal member 916. The device can have a plurality of distal members 916.

Figure 120:
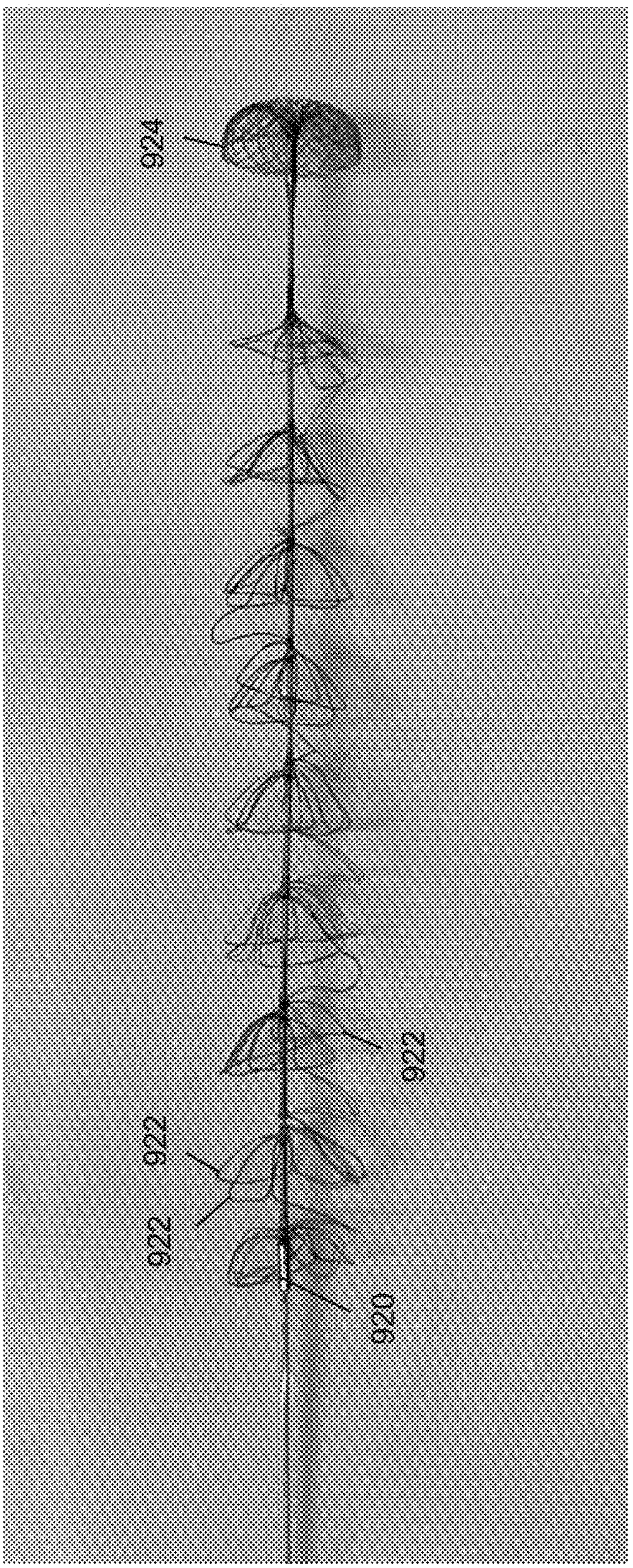
FIGS. 120-121 are views of an extractor where the engagement panels are directed proximally.
Figure 121:
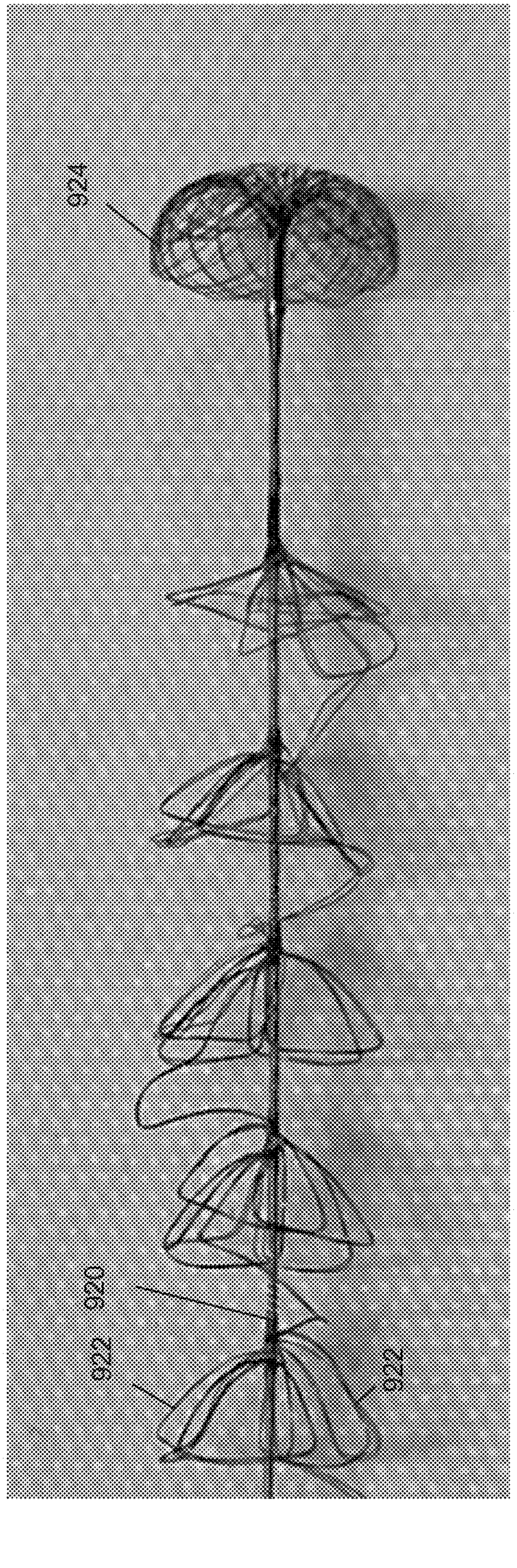

FIGS. 120-121 are views of an extractor 920. The extractor 920 can include engagement panels 922. The engagement panels 922 can be formed from a continuous wire. The engagement panels 922 can be angled or directed proximally. The engagement panels 922 can be angled or directed distally. The engagement panels 922 can form a cup shape. The engagement panels 922 can flare outward. The device can include a distal element 924.

Figure 122:
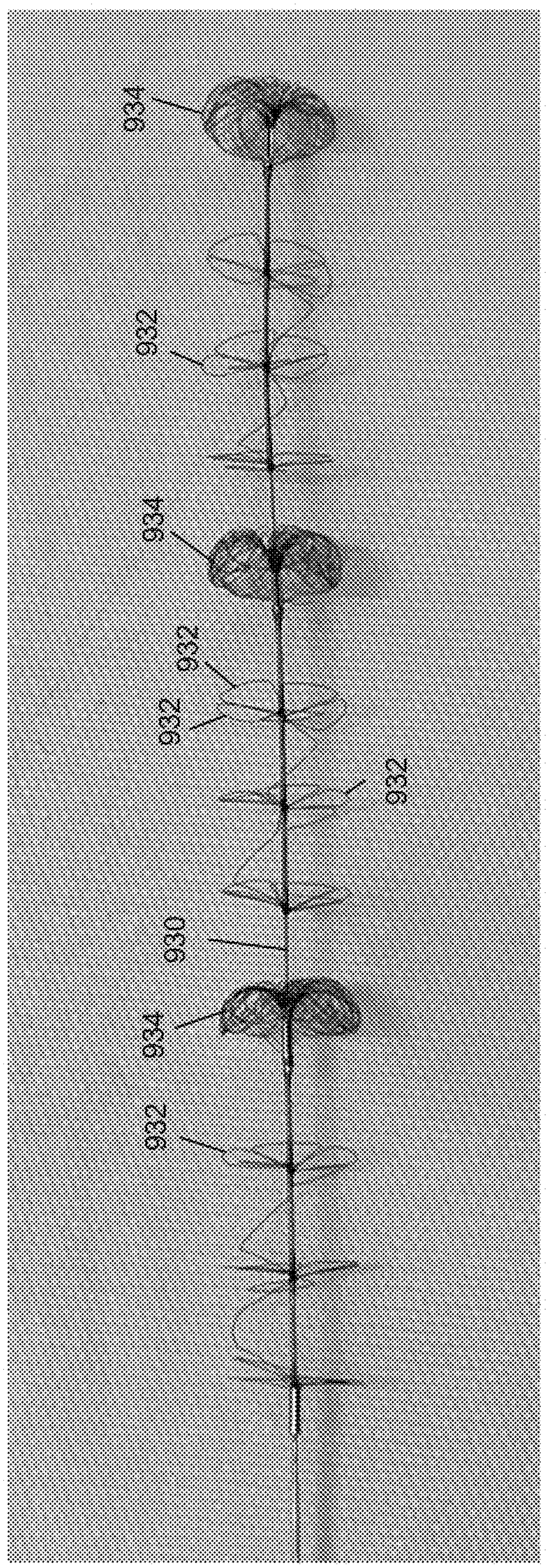
FIGS. 122-123 are views of distal member and extractor. The distal members positioned within and between the engagement panels.
Figure 123:
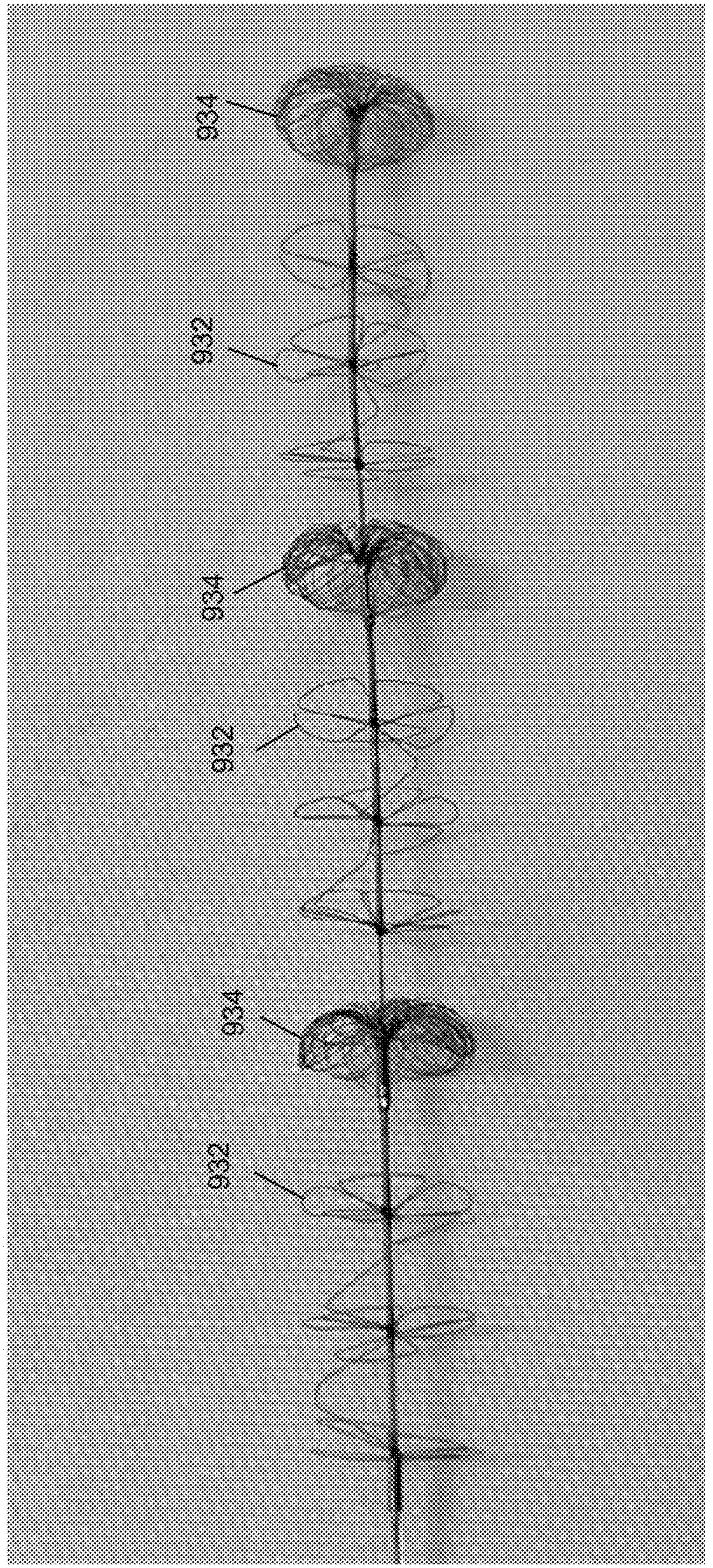

FIGS. 122-123 are views of an extractor 930. The extractor 930 can include engagement panels 932. The engagement panels 932 can be formed from a continuous wire. The device can include one or more distal members 934. The device can include a plurality of distal members and a plurality of arrays of engagement panels 932. The distal members 934 can be positioned within and between the engagement panels 932. The extractor 930 can include multiple distal members 934. The extractor 930 can have distal members 934 positioned between the engagement panels 932.

Figure 124:
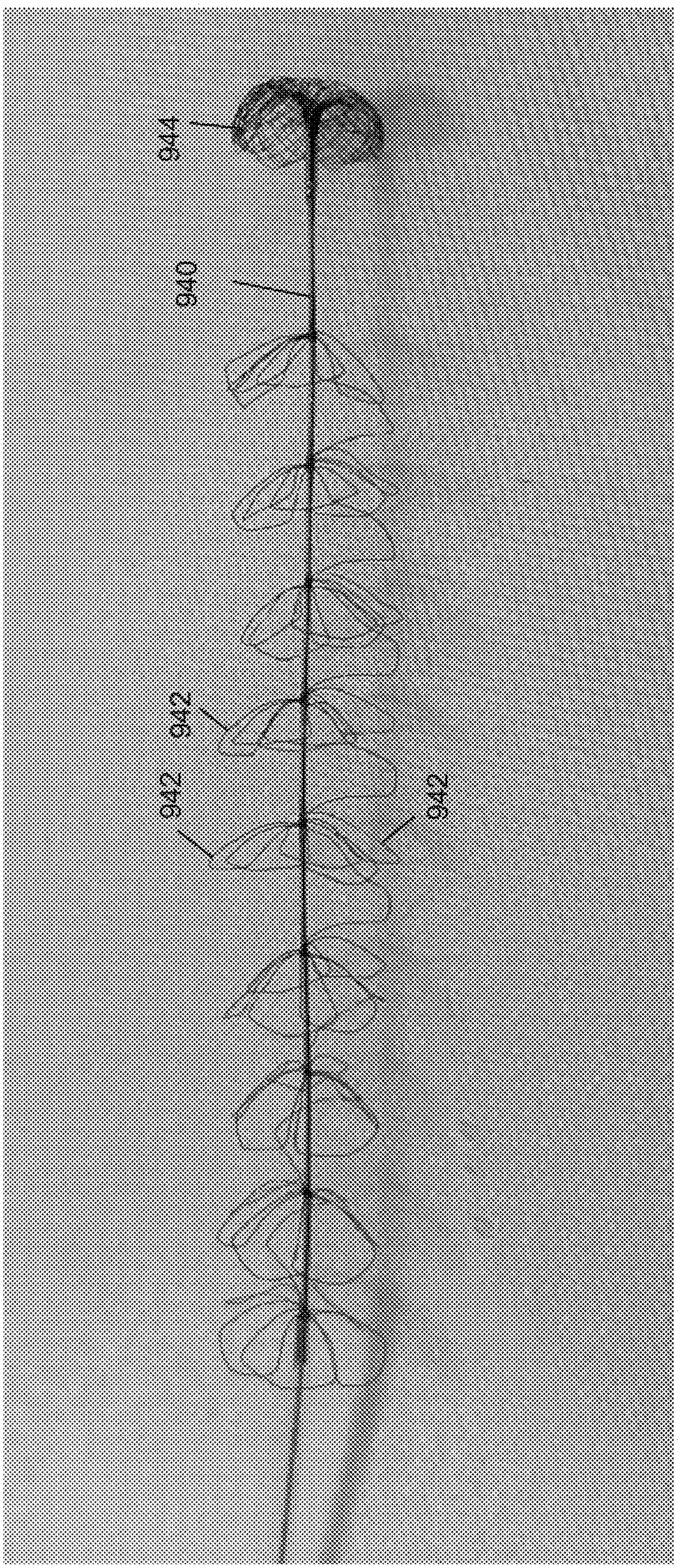
FIGS. 124-125 are views of an extractor.
Figure 125:
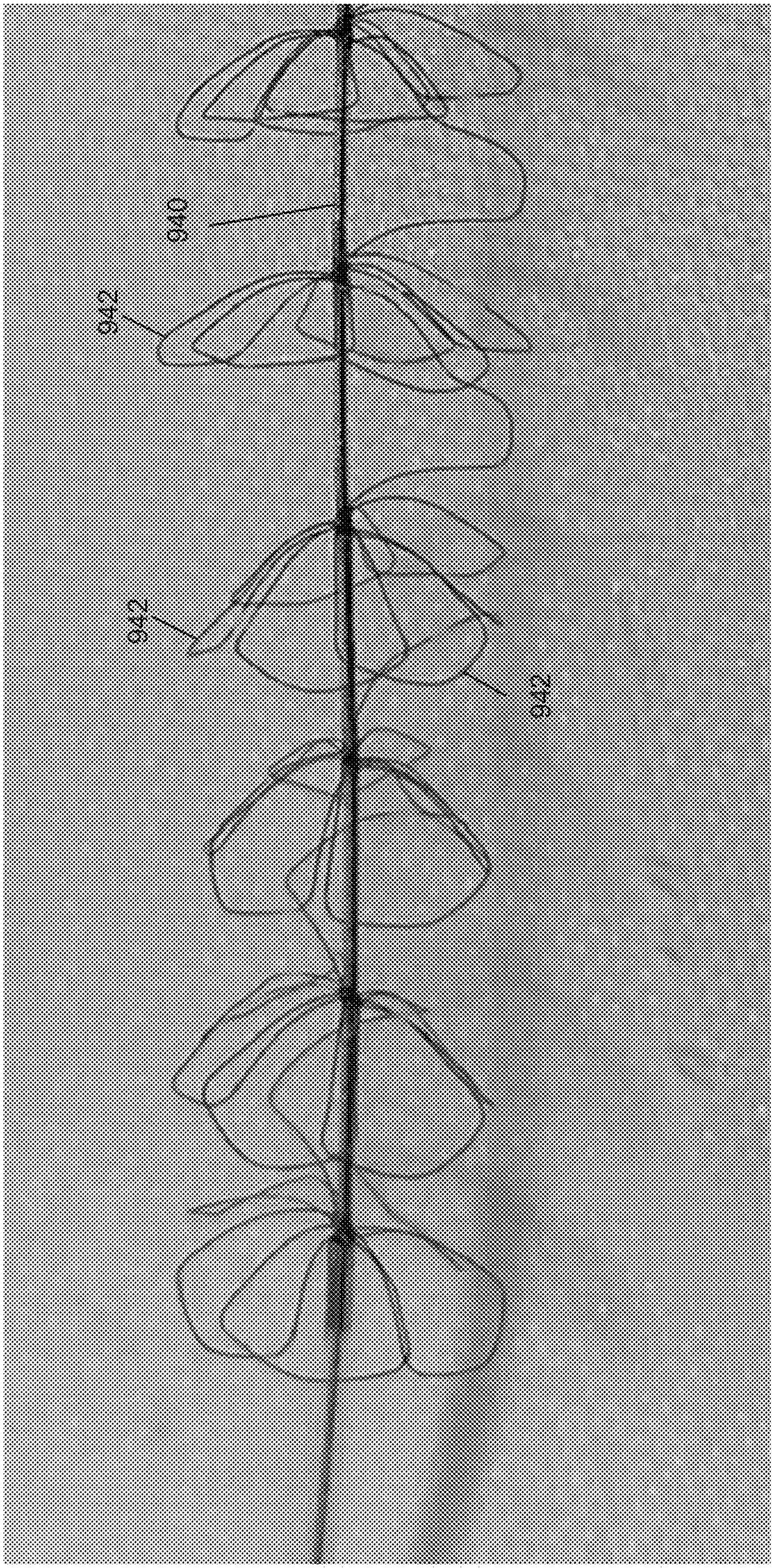

FIGS. 124-125 are views of an extractor 940. The extractor 940 can include engagement panels 942. The engagement panels 942 can be formed from a continuous wire. The engagement panels 942 can form multiple overlapping petals. The engagement panels 942 can be angled or directed proximally. The engagement panels 942 can be angled or directed distally. The device can include a distal element 944. The engagement panels 942 can be oval. The engagement panels 942 can be ovate. The engagement panels 942 can be obovate. The engagement panels 942 can be cup shaped. The engagement panels 942 can be in a circular pattern. The engagement panels 942 can enclose the center. The engagement panels 942 can be tucked together. The engagement panels 942 can divide the circumference in equal parts. The engagement panels 942 can be overlapping. The engagement panels 942 can be the same size. The engagement panels 942 can be different sizes. The engagement panels 942 can be in several rows. The engagement panels 942 can include six floris. The mechanism of action is to increase clot engagement. The engagement panels 942 can have six panels at each longitudinal location. The engagement panels 942 can be angled proximally to increase the rigidity of the panels and further increase the clot engagement.

Figure 126:
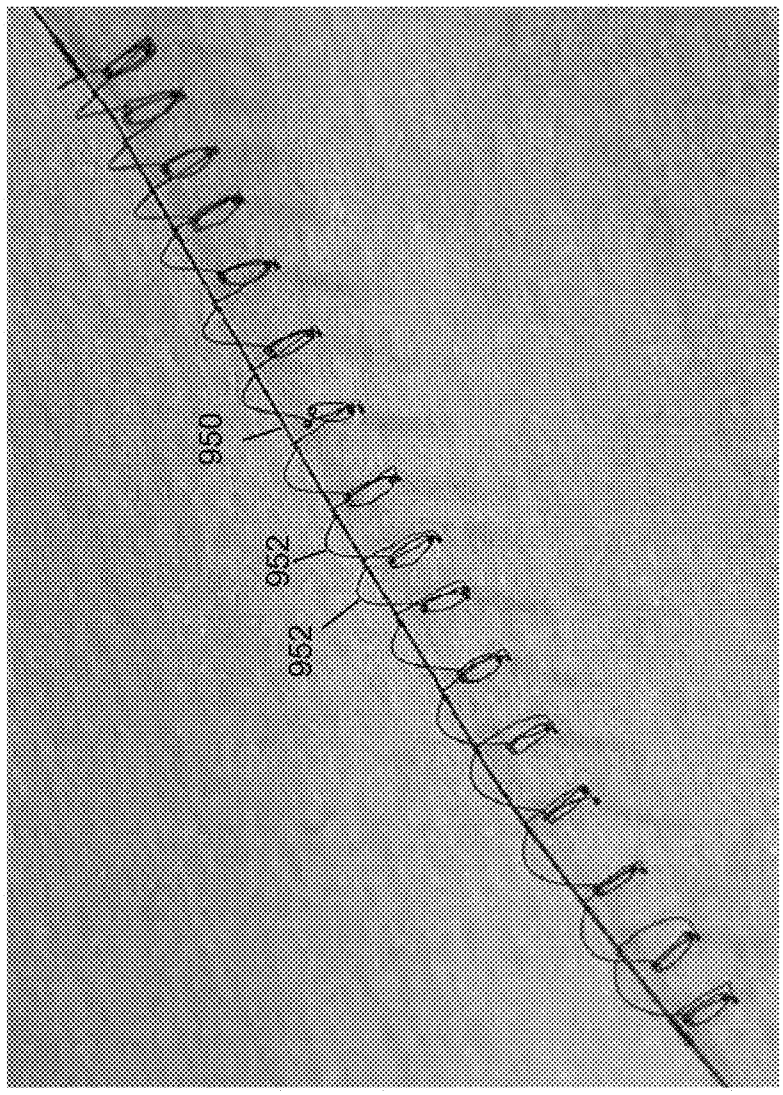
FIGS. 126-127 are views of an extractor where the engagement panel is a helical shape and an element to aid removing clot.
Figure 127:
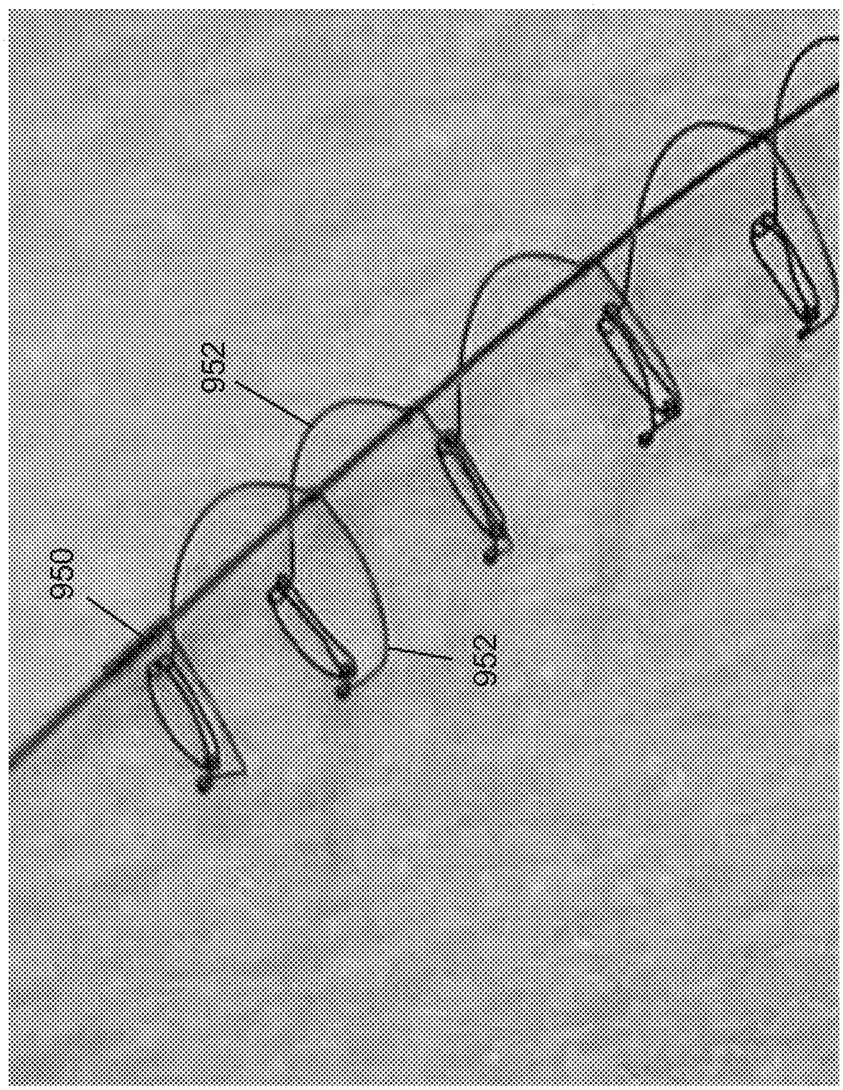

FIGS. 126-127 are views of an extractor 950. The extractor 950 can include engagement panels 952. The engagement panels 952 can be formed from a continuous wire. The engagement panel 952 can be a helical shape. The engagement panel 952 can include an eyelet and legs extending circumferentially. The legs can form an element. The element can include one or more eyelets. The element can include one or more loops. The element can include one or more overlapping sections. The element can scrape the vessel wall. The element can reinforce the helix. The element can entangle the clot. The engagement panels 952 can include aligned elements on each panel.

Figure 128:
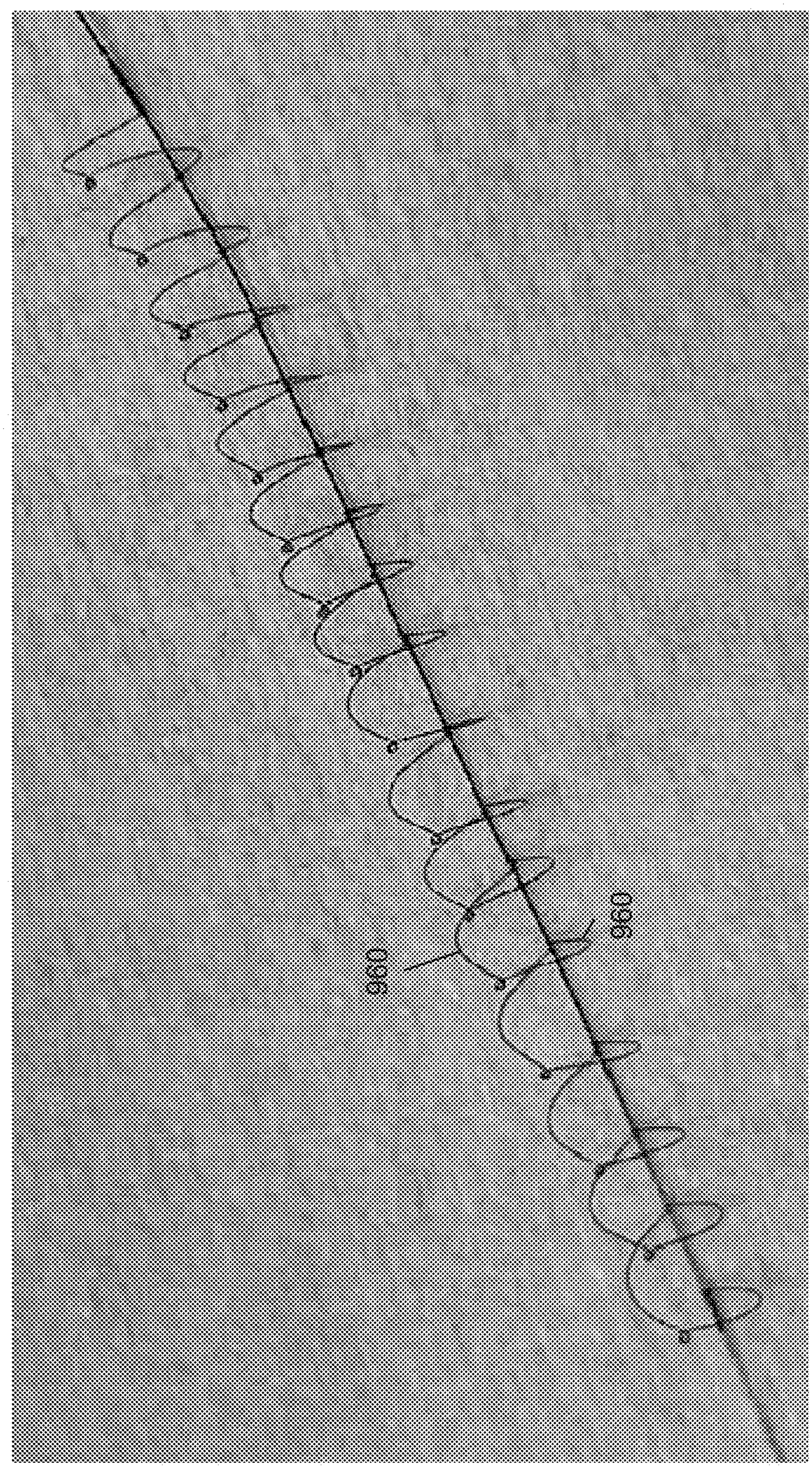
FIGS. 128-129 are views of an extractor. The extractor engagement panels are helical loops connected by the eyelets.
Figure 129:
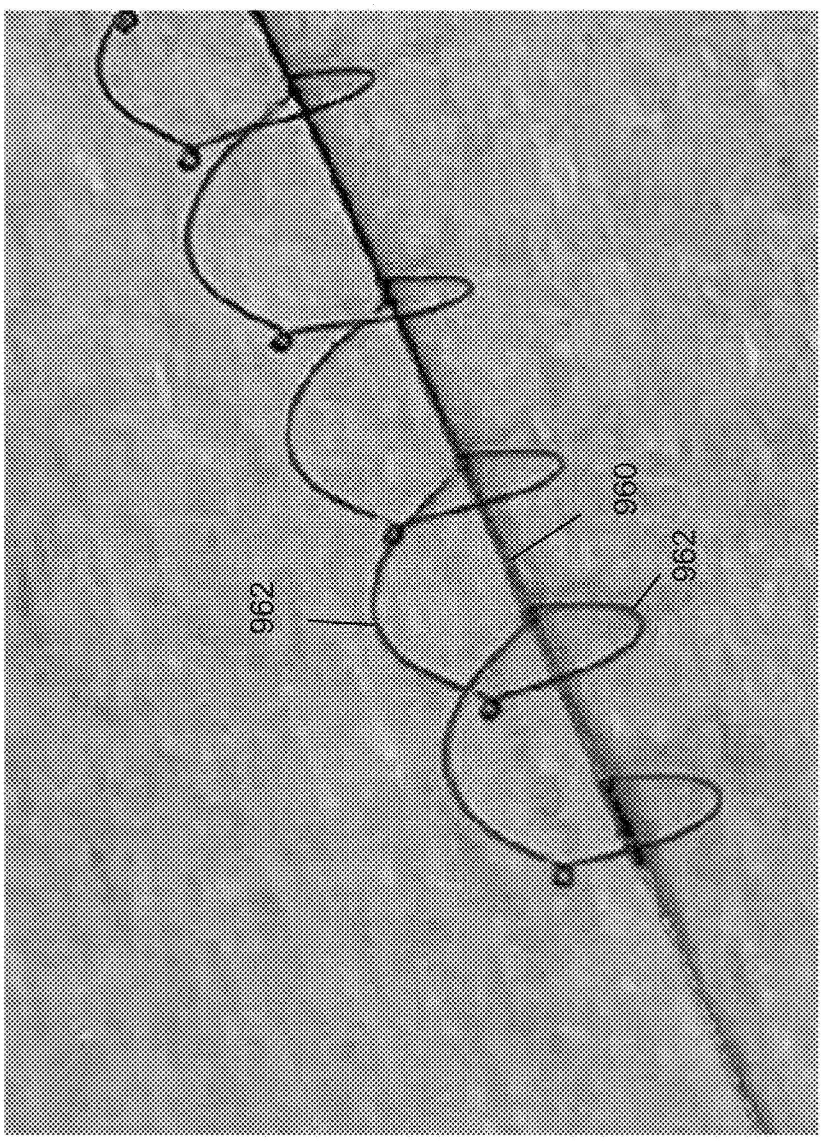
Figure 130:
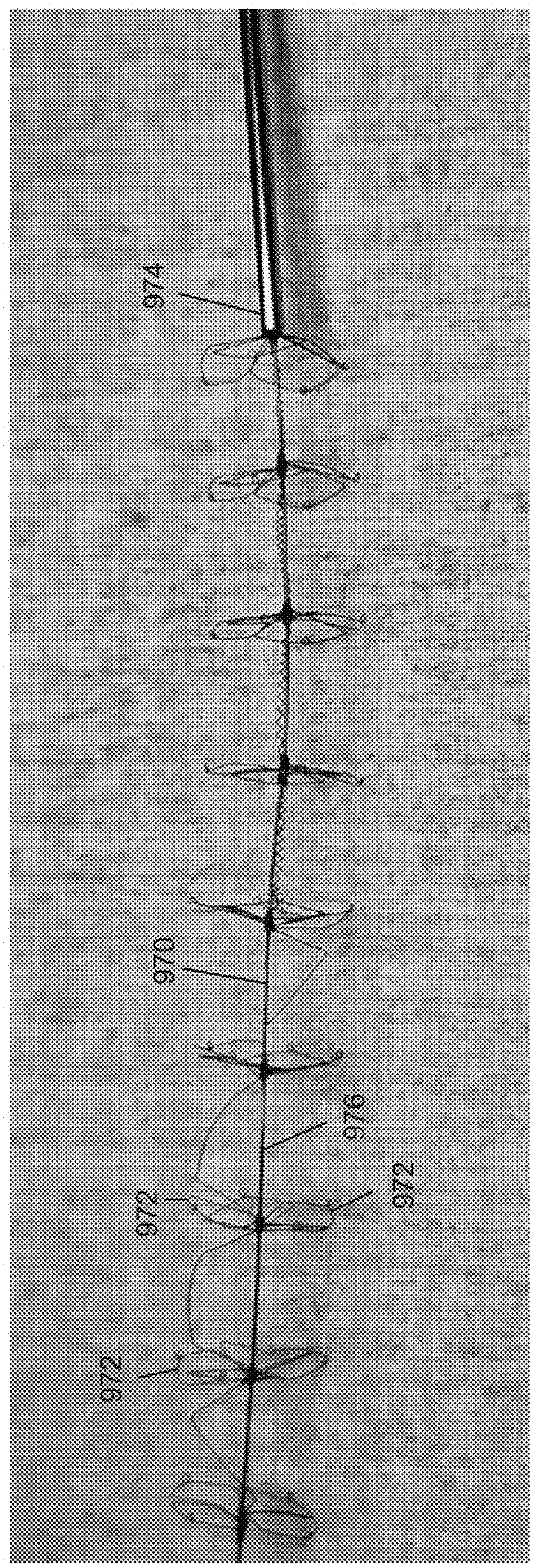
FIGS. 130-133 are views of an extractor where a portion of the engagement panels is slidable and a portion of the engagement panels is fixed to the corewire.
Figure 131:
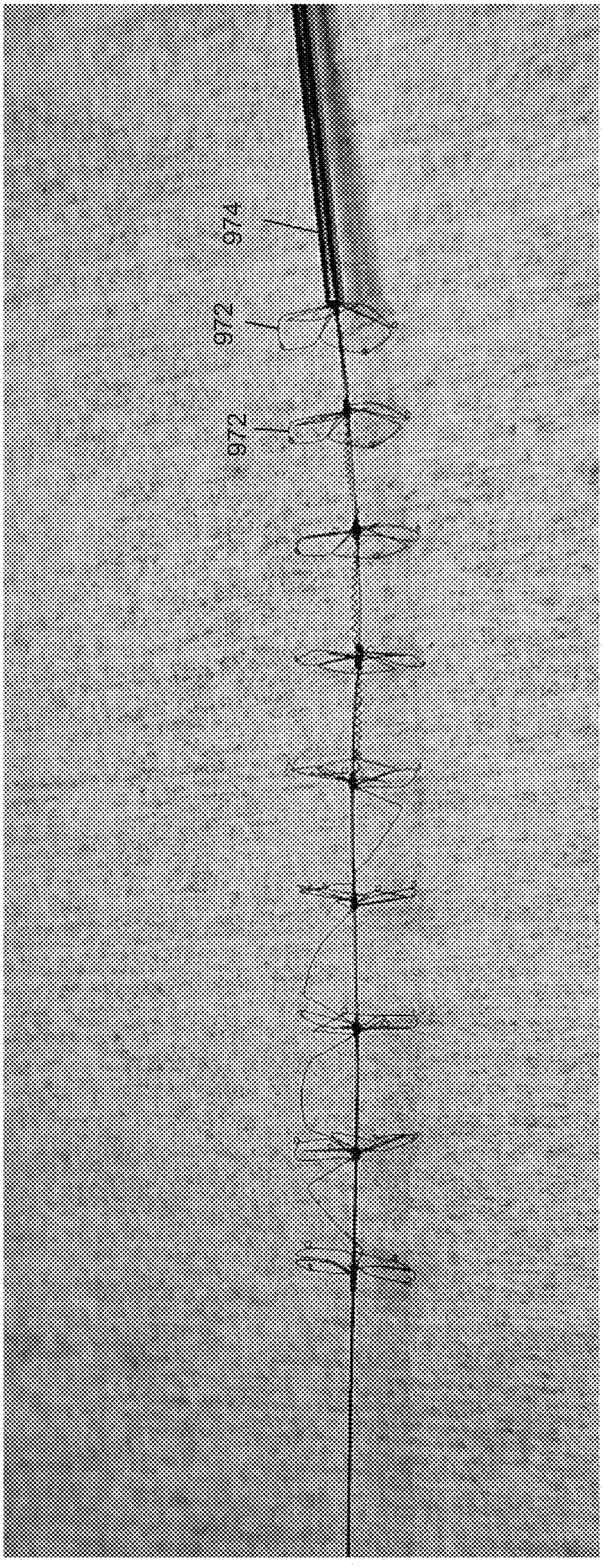

FIGS. 128-129 are views of an extractor 960. The extractor 960 can include engagement panels 962. The engagement panels 962 can be formed from a continuous wire. The engagement panel 962 can include a series of loops connected by the eyelets. The engagement panel 962 can include an eyelet and loop extending circumferentially from the eyelet. The loops can form an element. The element can be located at an apex or top of the engagement panel 962. The element can include an eyelet. The element can include a single eyelet or a plurality of eyelets. The element can scrape the vessel wall. The element can reinforce the series of loops. The element can entangle the clot. The engagement panels 962 can include a full loop. The engagement panels 962 can extend 360 degrees. The engagement panels 962 can form a complete circle. The engagement panels 962 can scrape the vessel wall. The engagement panels 962 can go over the clot. The engagement panels 962 can grasp the clot with one or more loops or eyelets at the apex. The engagement panels 962 can include a lumen. The engagement panels 962 can a coiled eyelet. The extractor 960 can include a biased core wire which is offset from center. The coiled eyelet can be offset from center. The coiled eyelet can receive the core wire. The coiled eyelet that receives the core wire can be spaced apart from the eyelet that entangles the clot. The coiled eyelet that receives the core wire can be diametrically opposed to the eyelet that entangles the clot. The engagement panels 962 can go over and grasp the clot.

The extractor 960 can have open engagement panels 962. The engagement panels 962 can be a full loop with an opening or lumen. The engagement panels 962 can be designed to go over the clot and grasp onto the clot. The engagement panels 962 can have small loop or eyelet element. The small loop or eyelet element is different than the eyelet that attaches or receives the core wire. The engagement panels 962 can have small loop or eyelet element at an apex. The engagement panels 962 can have small loop or eyelet element to function to pinch the clot. The engagement panels 962 can have a coiled eyelet to receive the corewire. The corewire and eyelet can be positioned to the side. The core wire and eyelet can be eccentrically located. Once the engagement panels 962 advance over the clot, the loop will secure the clot during retrieval. Under compression or tension, the engagement panels 962 will compress to secure the clot circumferentially in some embodiments. The loop or eyelet element of the engagement panels 962 will also pinch the clot under compression to secure the clot in some embodiments. The loop or eyelet element of the engagement panels 962 can grasp onto the clot.

FIGS. 130-133 are views of an extractor 970. The extractor 970 can include engagement panels 972. The engagement panels can have eyelet at the tip of the panel. The engagement panels at the first longitudinal location are attached to an outer elongate member 974 and slidable over an inner member 976. The engagement panels at the second longitudinal location, the engagement panels at the third longitudinal location, the engagement panels at the fourth longitudinal location, and the engagement panels at the fifth longitudinal location are separated. The engagement panels at the second longitudinal location, the engagement panels at the third longitudinal location, and the engagement panels at the fourth longitudinal location are slidable over the inner member 976.

Figure 132:
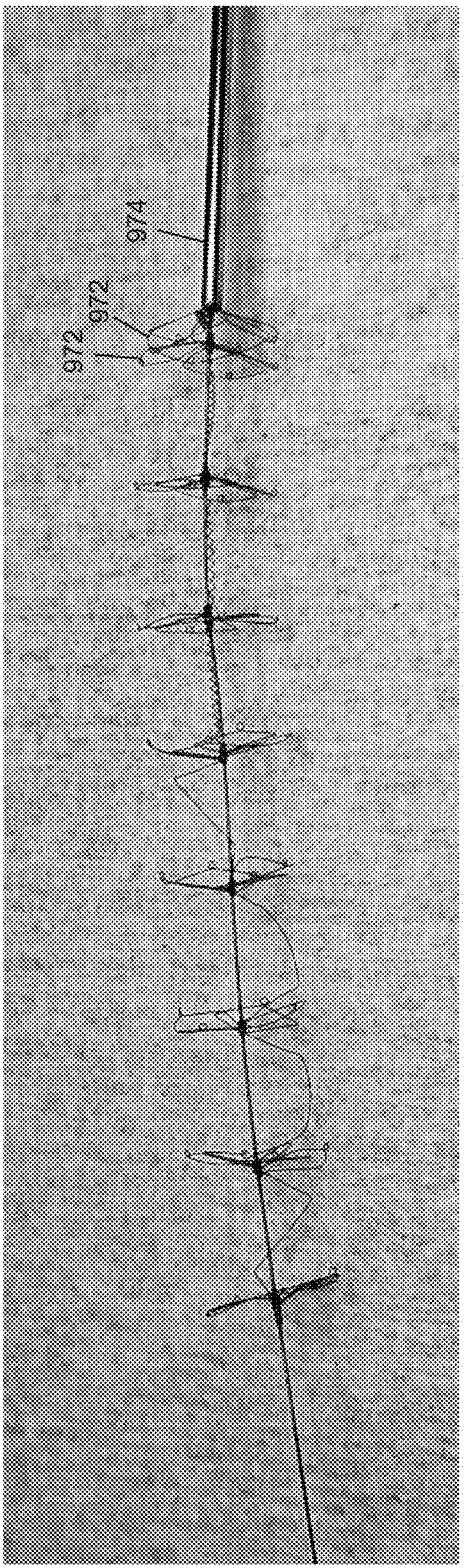

FIG. 132 is a view of the extractor where the engagement panels at the second longitudinal location are slidable over the inner member 976. The engagement panels at the second longitudinal location are positioned next to the first engagement panels at the first longitudinal location after they slide.

Figure 133:
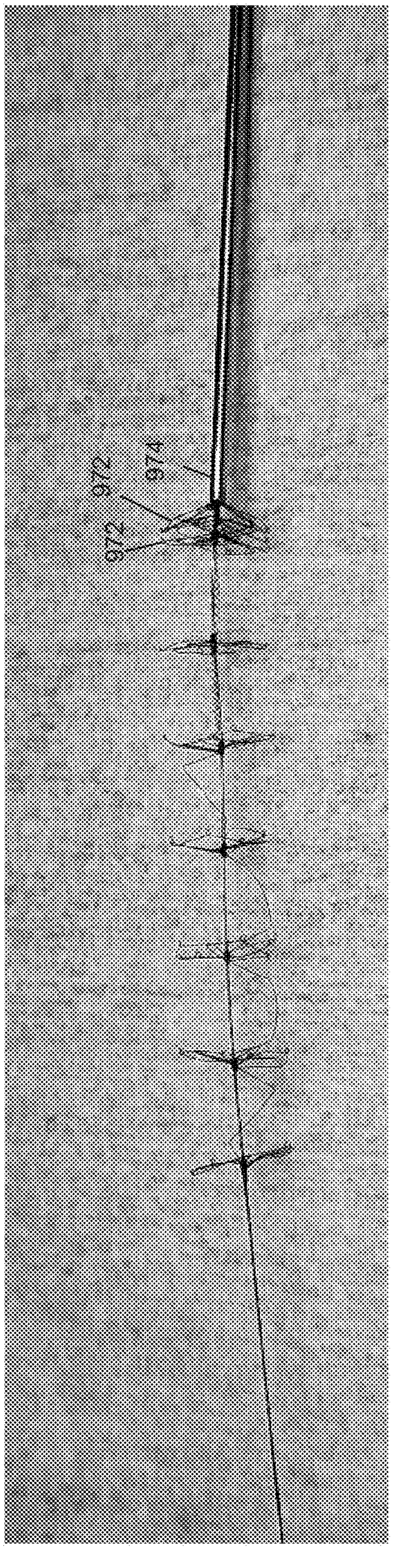

FIG. 133 is a view of the extractor where engagement panels at the third longitudinal location slidable over the inner member 976. The engagement panels at the third longitudinal location are positioned next to the first and second engagement panels at the first longitudinal location after they slide.

In some embodiments, the engagement panels at the first longitudinal location are slidable over the inner member 976. In some embodiments, the engagement panels at the second longitudinal location are slidable over the inner member 976. In some embodiments, the engagement panels at the third longitudinal location are slidable over the inner member 976. The engagement panels at the first longitudinal location are adjustable panels. The engagement panels at the second longitudinal location are adjustable panels. The engagement panels at the third longitudinal location are adjustable panels. The engagement panels at the first longitudinal location, the engagement panels at the second longitudinal location, and the engagement panels at the third longitudinal location can collapse toward each other.

In some embodiments, the engagement panels at the fourth longitudinal location are not slidable over the inner member 976. In some embodiments, the engagement panels at the fifth longitudinal location are not slidable over the inner member 976. The engagement panels at the fourth longitudinal location are fixed panels. The engagement panels at the fifth longitudinal location are fixed panels.

In some embodiments, the engagement panels can include panels with proximal ends loose and distal fixed to the inner member 976. The inner member 976 can be a core wire. The proximal end panels can come together. The proximal end panels can be spaced apart. The distal end engagement panels can be fixed in position.

The extractor 970 can include fixed and slidable engagement panels 972. The slidable engagement panels 972 slide together to increase clot removal. The extractor 970 can include fixed engagement panels 972 attached to the outer elongate member 974. The extractor 970 can include one or more arrays of slidable engagement panels 972. The extractor 970 can include one or more arrays of fixed engagement panels 972. The extractor 970 can include one or more arrays of sliceable engagement panels 972 in between fixed engagement panels 972. The extractor 970 can include one or more arrays of slidable engagement panels 972 that slide toward the outer elongate member 974. The slideable engagement panels 972 slide relative to the core wire. The fixed engagement panels 972 can be fixed relative to the core wire. The extractor 970 can have fixed engagement panels 972 that are fixed to the core wire. The extractor 970 can have slidable engagement panels 972 that slide over the core wire. The extractor 970 can have slidable engagement panels 972 that have a eyelet that slides relative to the core wire. The fixed engagement panels 972 and the slidable engagement panels 972 can have the same or similar petal shape. The fixed engagement panels 972 and the slidable engagement panels 972 can have different shapes.

The proximal engagement panels 972 can be attached to the outer member 974. The proximal engagement panels 972 can be positioned relative to the clot obstruction. In some embodiments, the proximal engagement panels 972 attached to the outer member 974 are positioned distal to the clot obstruction. The first slidable array of engagement panels 972 is retracted proximally to the array of the engagement panels 972 attached to the outer member 974. Further retracting of the core wire will move the slidable array of engagement panels 972 to the first slidable array of engagement panels 972. Continued retraction of the core wire will move the third slidable array of engagement panels 972 to the second slidable array of engagement panels 972. The core wire and outer member 974 can be locked in place and retracted together to remove the clot.

Figure 134:
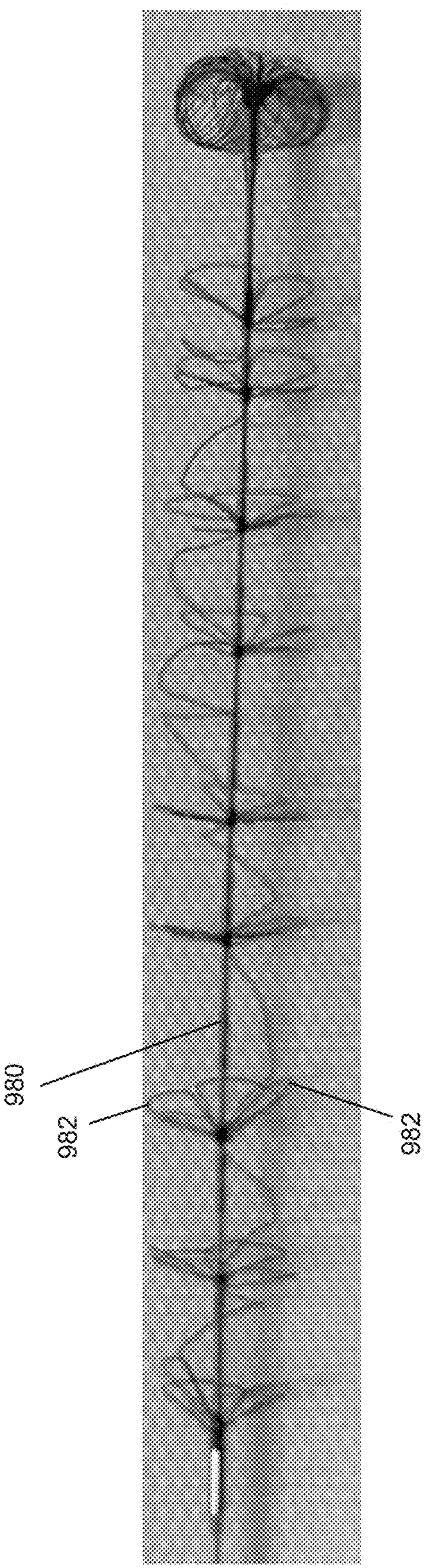
FIG. 134 is a view of an extractor. The extractor engagement panels are slidable panels to pinch the clot. The corewire is centrally located in the engagement panels.

FIG. 134 is a view of an extractor 980. The extractor 980 can include engagement panels 982. The engagement panels 982 can be slidable. The engagement panels 982 can slide relative to the core wire. The engagement panels 982 can include the eyelet. The eyelet of the engagement panels 982 can slide relative to the core wire. The engagement panels 982 can pinch the clot. The engagement panels 982 are slidable panels to pinch the clot to increase clot engagement. The core wire is centrally located in the engagement panels 982.

Figure 135:
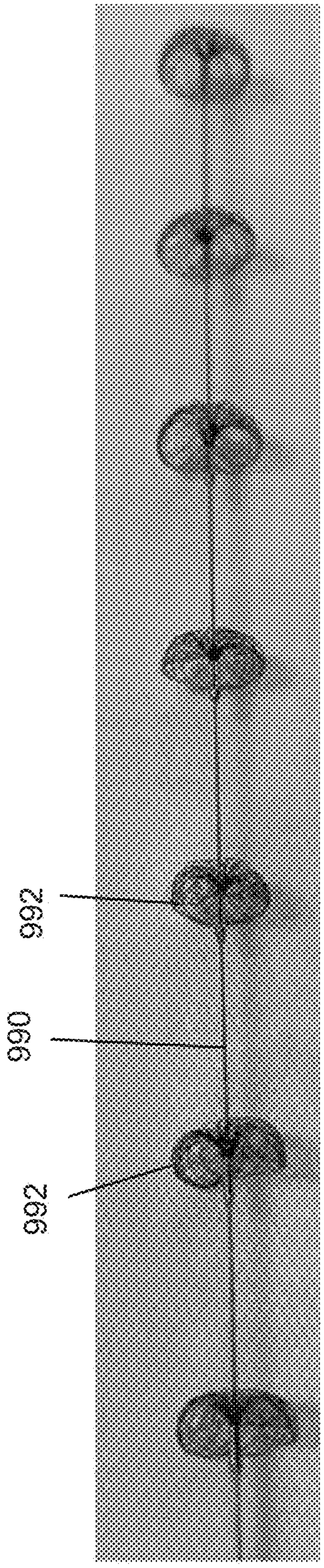
FIG. 135 is a view of an extractor with a plurality of distal member.

FIG. 135 is a view of an extractor 990. The extractor 990 can include distal members 992. The distal members 992 can be used in place of the engagement panels. The distal members 992 can engage the clot.

Figure 136:
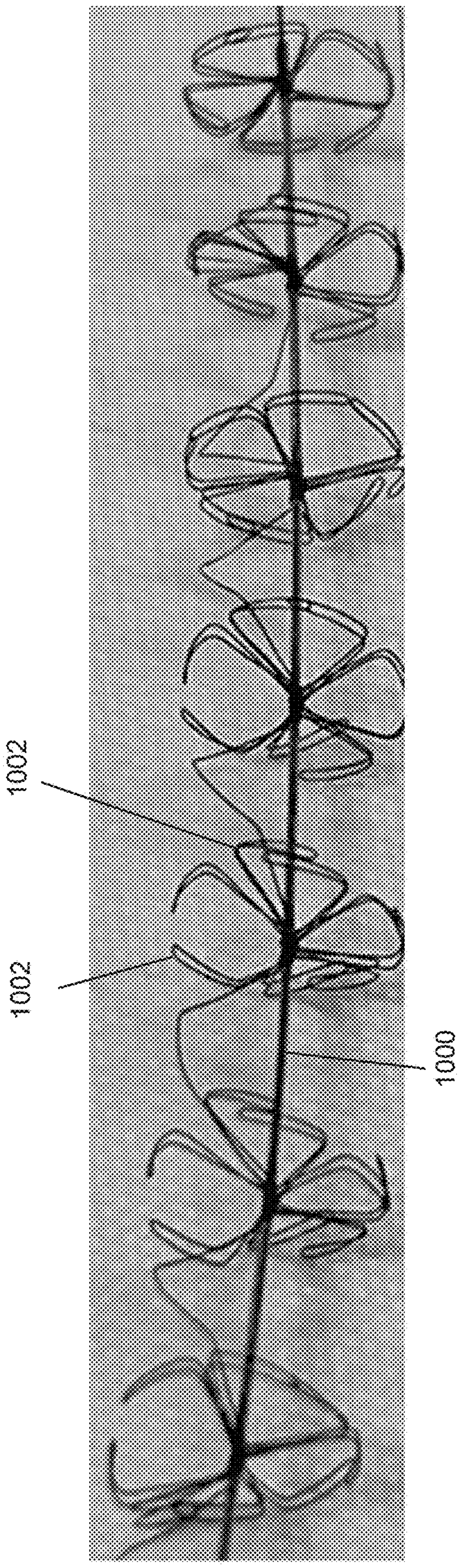
FIGS. 136-137 are views of an extractor. The extractor has engagement panels that are open or have finger-like end.
Figure 137:
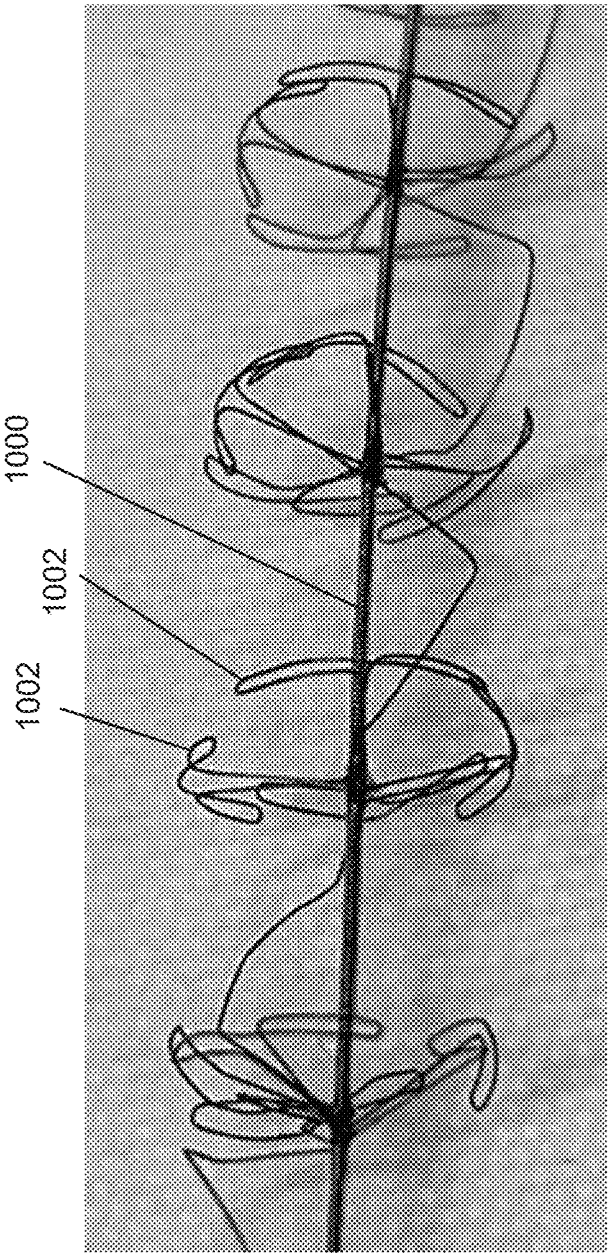

FIGS. 136-137 are views of an extractor 1000. The extractor 1000 can include engagement panels 1002. The engagement panels 1002 can include at least one open panel. The engagement panels 1002 can include fingers that grasp the clot. The open engagement panel 1002 can include a first leg, a first rounded end forming a portion of the arc, and a second leg. The open engagement panel 1002 can include a third leg, a second rounded end forming a portion of the arc, and a fourth leg. The open engagement panel 1002 can include two fingers that form an open panel. The extractor 1000 can have engagement panels that are open or have fingers-like end to increase the grasping of the clot.

Figure 138:
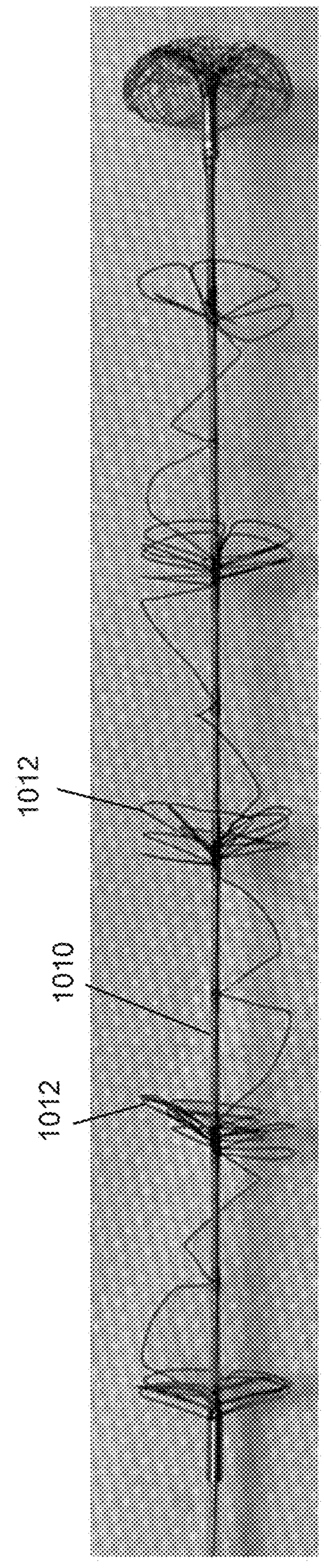
FIGS. 138-139 are views of an extractor. The extractor has eight engagement panels.
Figure 139:
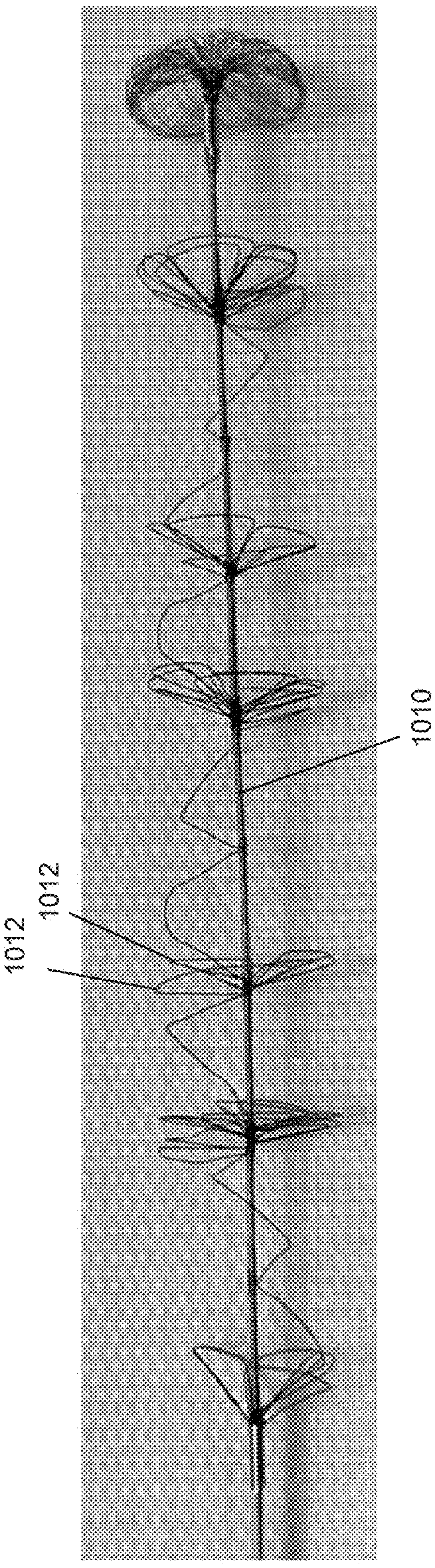

FIGS. 138-139 are views of an extractor 1010. The extractor 1010 can include engagement panels 1012. The engagement panels 1012 can include a eight engagement panels configuration. The engagement panels 1012 can include eight panels at each longitudinal location. The engagement panels 1012 can include a plurality of panels at each longitudinal location. The engagement panels 1012 can include a plurality of panels to increase petal strength. The engagement panels 1012 can include a plurality of panels to engage with the clot. The engagement panels 1012 can include eight engagement panels to increase the strength in order to engage with the clot.

Figure 140:
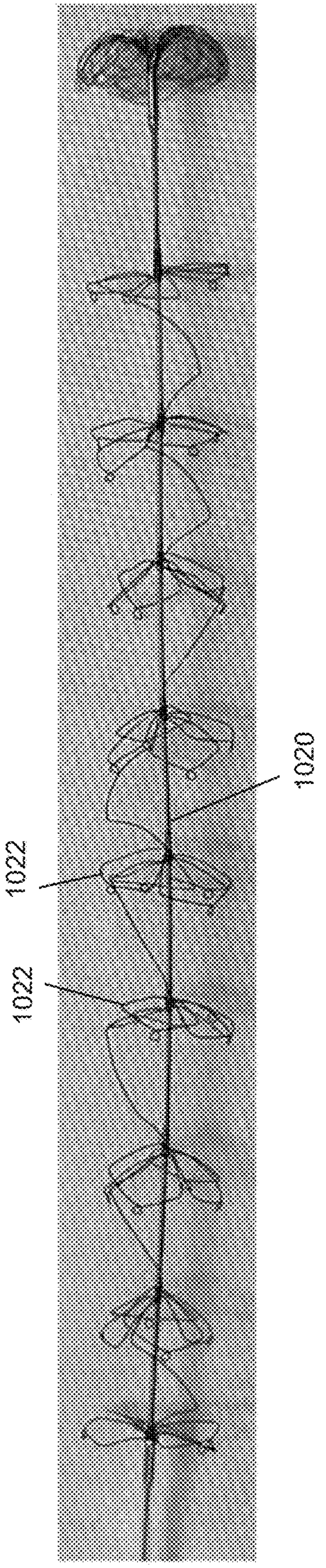
FIGS. 140-141 are views of a distal member and an extractor. The extractor has four engagement panels with eyelet element at the tip.
Figure 141:
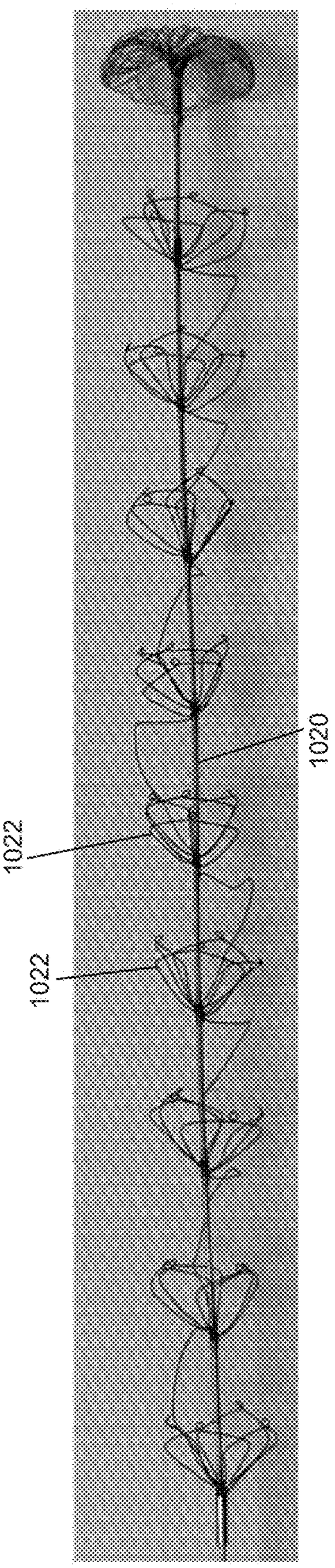

FIGS. 140-141 are views of an extractor 1020. The extractor 1020 can include engagement panels 1022. The engagement panels 1022 can be tapered. The engagement panels 1022 can be inverted. The engagement panels 1022 can be designed to increase petal engagement into the clot. The extractor 1020 can have engagement panels 1022 that have a loop or eyelet element at the tip. The engagement panels 1022 can be tapered or inverted to increase clot engagement. The engagement panels 1022 can be tapered toward the proximal end. The engagement panels 1022 can be tapered toward the distal end.

Figure 142:
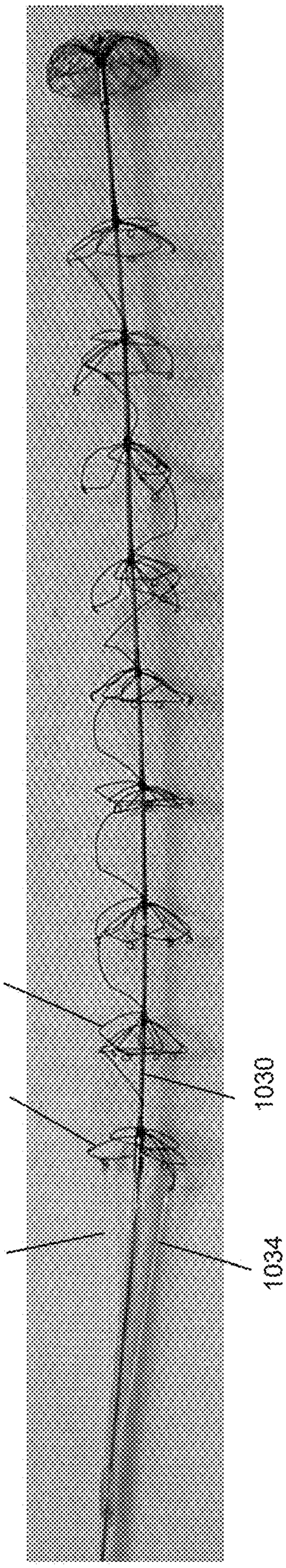
FIG. 142 is a view of an extractor. The extractor has engagement panels with eyelet at the tip and where the proximal engagement panels have suture.

FIG. 142 is a view of an extractor 1030. The extractor 1030 can include engagement panels 1032. The extractor 1030 can include one or more proximal sutures 1034. The proximal sutures 1034 can keep the engagement panels 1032 rigid to engage the clot. The extractor 1030 has engagement panels 1032 where the proximal engagement panels have a suture 1034 to maintain sufficient rigidity and tension to engage the clot as the extractor is retracted proximally.

Figure 143:
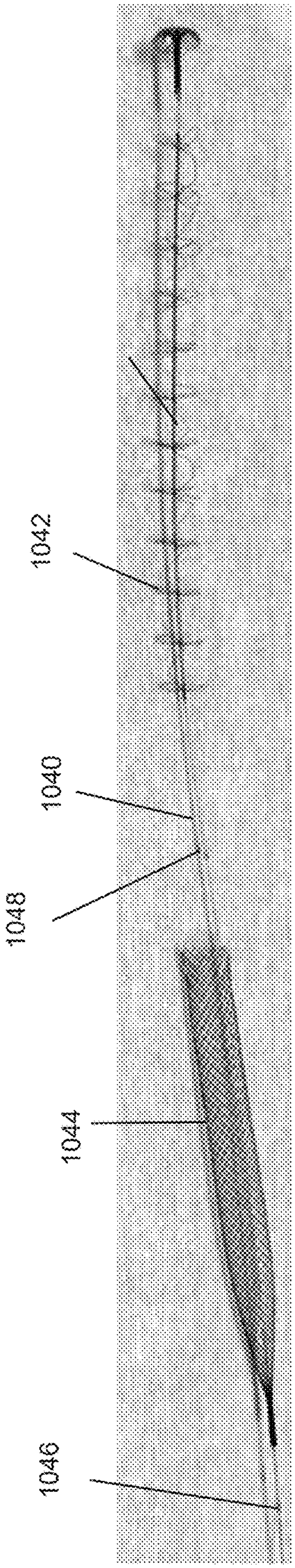
FIGS. 143 and 144 are views of an extractor with a funnel. The extractor engagement panels is positioned distal to the funnel and can be retracted into the funnel.

FIG. 143 is a view of an extractor 1040. The extractor 1040 can include engagement panels 1042. The extractor 1040 can include a proximal funnel 1044. The engagement panels 1042 be used to push the clot toward or into the proximal funnel 1044. The extractor 1040 can include a proximal stop 1046 and a distal stop 1048. The engagement panels 1042 can be positioned distal to the clot and the proximal funnel 1044 can positioned proximal to the clot. The engagement panels 1042 can be retracted proximally to push the clot into funnel to secure the clot for removal. The distal stop 1048 attaches to the core wire to aid in limiting the engagement panels from entering into the funnel 1044. The proximal stop 1046 attaches to the core wire to aid in advancing the funnel 1044.

Figure 144:
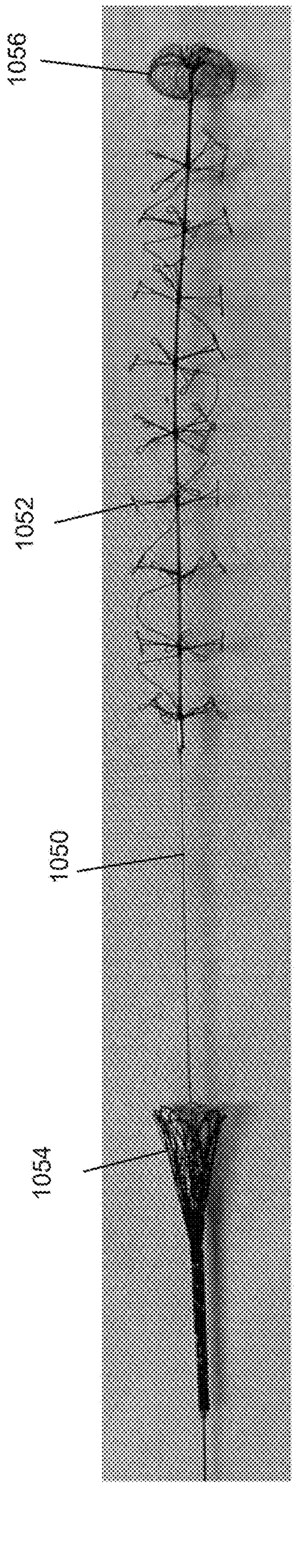

FIG. 144 is a view of an extractor 1050. The extractor 1050 can include engagement panels 1052. The engagement panels 1052 can include T-shape features. The extractor 1050 can include a proximal funnel 1054. The engagement panels 1052 be used to push the clot toward or into the proximal funnel 1054. The extractor 1050 can include a distal member 1056. The engagement panels 1052 can be positioned distal to the funnel 1054. The engagement panels 1052 can be retracted into the funnel 1054.

Figure 145A:
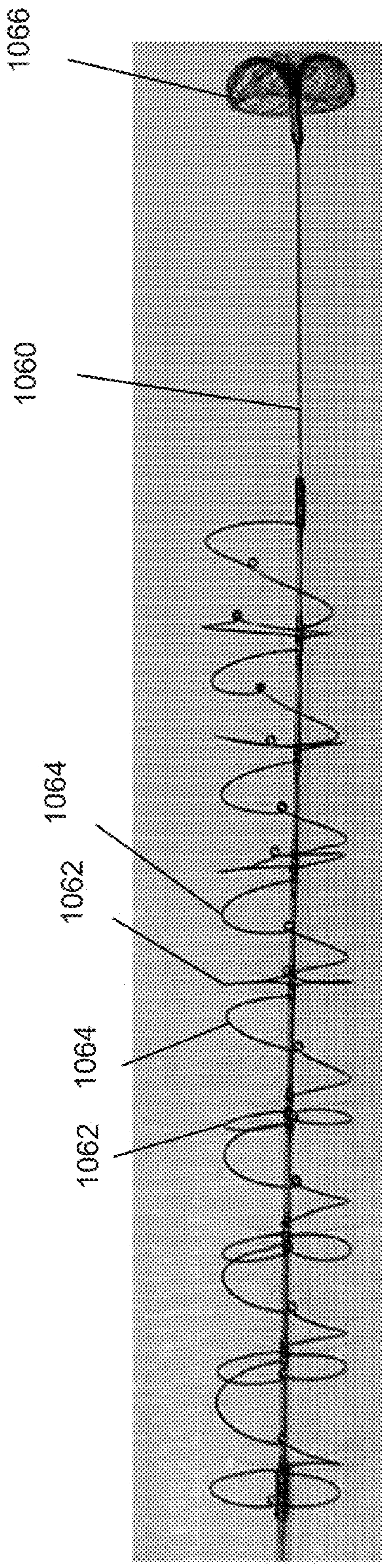
FIGS. 145A, 145B and 145C are views of an extractor. The extractor can be a series of engagement panels or loops.
Figure 145B:
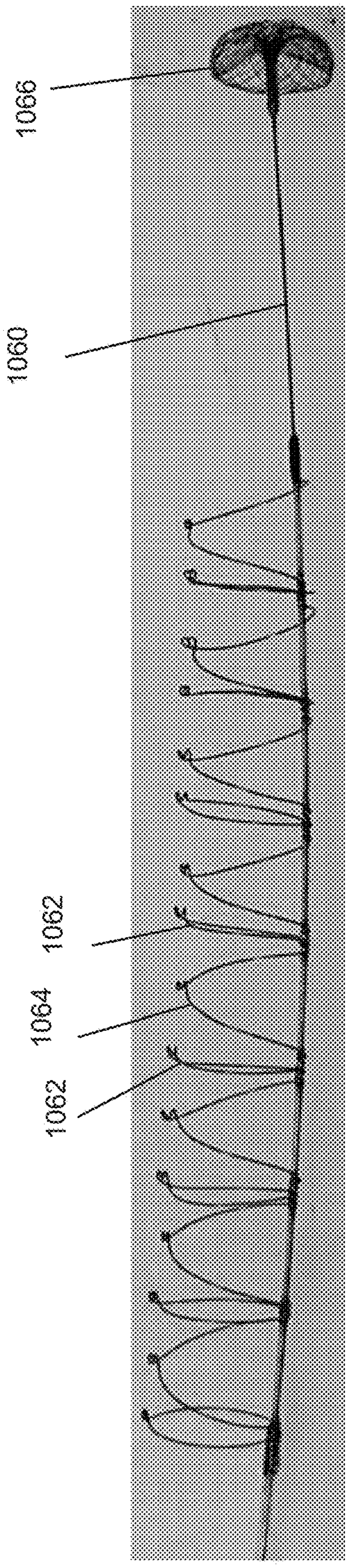
Figure 145C:
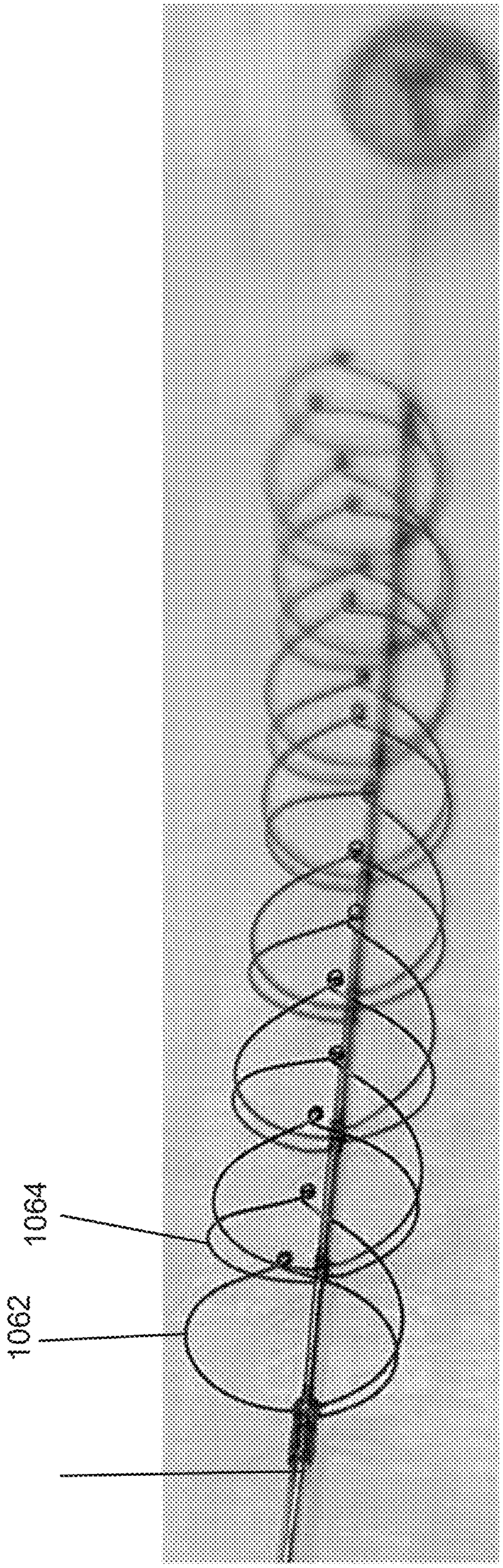

FIGS. 145A, 145B and 145C are views of an extractor 1060. The extractor 1060 can include engagement panels 1062. The engagement panels 1062 can form loops. The engagement panels 1062 can form a fully complete circle. The extractor 1060 can include helical loops 1064. The extractor can be a series of engagement panels 1062 and helical loops 1064 formed from one continuous wire. The extractor 1060 can include the helical loops 1064 forming within. The extractor 1060 can include eyelets connecting the loops of the engagement panels 1062 and helical loops 1064. The eyelets can be coiled to receive the core wire. The helical loops 1064 can span between adjacent engagement panels 1062. The helical loops 1064 can span between two or more engagement panels. The helical loops 1064 can skip an engagement panel. The helical loops 1064 can span indiscriminately between the engagement panels. The loops of the engagement panels 1062, the helical loops 1064, and eyelets can be formed from a continuous wire. The loops of the engagement panels 1062 and/or the helical loops 1064 can have an opening (or lumen) to go over the clot and grasp onto the clot. The engagement panel 1062 can have an eyelet element at the tip and function to pinch the clot when the loop of the engagement panel 1062 is under compression. The helical loop 1064 can have an eyelet element at the tip and function to pinch the clot when the helical loop 1064 is under compression. The extractor 1060 can include eyelets to receive the core wire. The eyelets to receive the core wire can be off-center relative to the engagement panels 1062. The eyelets to receive the core wire can be off-center relative to the helical loops 1064. Once the loops of the engagement panels 1062 advances over the clot, the loops of the engagement panels 1062 will secure the clot during retrieval. Once the helical loops 1064 advances over the clot, the helical loops 1064 will secure the clot during retrieval. Under compression or tension, the loops of the engagement panels 1062 will compress to secure the clot circumferentially. Under compression or tension, the loops of the helical loops 1064 will compress to secure the clot circumferentially. Additionally, the eyelet at the tip of the engagement panel 1062 can pinch the clot to secure the clot. Additionally, the eyelet at the tip of the helical loops 1064 can pinch the clot to secure the clot. The extractor 1060 can include a distal member 1066. In some embodiments, the extractor can include a distal member in between the helical loop and circular loop. In some embodiments, the extractor can include a two or more engagement panels in between the helical loop and the circular loop.

FIG. 146 are views of the extractor 1070. The extractor 1070 can include engagement panels 1072 that can form circular loops. The extractor 1070 can include helical loops 1074. The extractor 1070 can include a series of helical loops and circular loops alternating. The extractor 1070 can include a helical loop 1074 with a circular loop 1072 in between. In some embodiments, there is an eyelet element at the tip of the helical loop 1074 and the circular loop 1072 to aid in grasping the clot. In some embodiments, there are two eyelet elements at the tip of the helical loop 1074 and the circular loop 1072. In some embodiments, the helical loop 1074 and the circular loop 1072 have the same diameter throughout the length of the extractor 1070. In some embodiment, the helical loop 1074 and the circular loop each have a diameter that progressively or gradually reduces from proximal end to distal end. In some embodiment, the helical loop 1074 and the circular loop each have a diameter that progressively or gradually reduces in diameter from the distal end to the proximal end. In some embodiments, the helical loop 1074 and the circular loop 1072 varies in diameter indiscriminately. In some embodiments, the diameter of the helical loop 1074 varies while the circular loop 1072 maintains the same diameter. In some embodiment, the diameter of the helical loop 1074 has the same diameter throughout while the circular loop 1072 varies in diameter. The extractor 1060 can include a distal member 1066. In some embodiments, the extractor can include a distal member in between the helical loop and circular loop. In some embodiments, the extractor can include a four engagement panels in between the helical loop and the circular loop.

Figure 147:
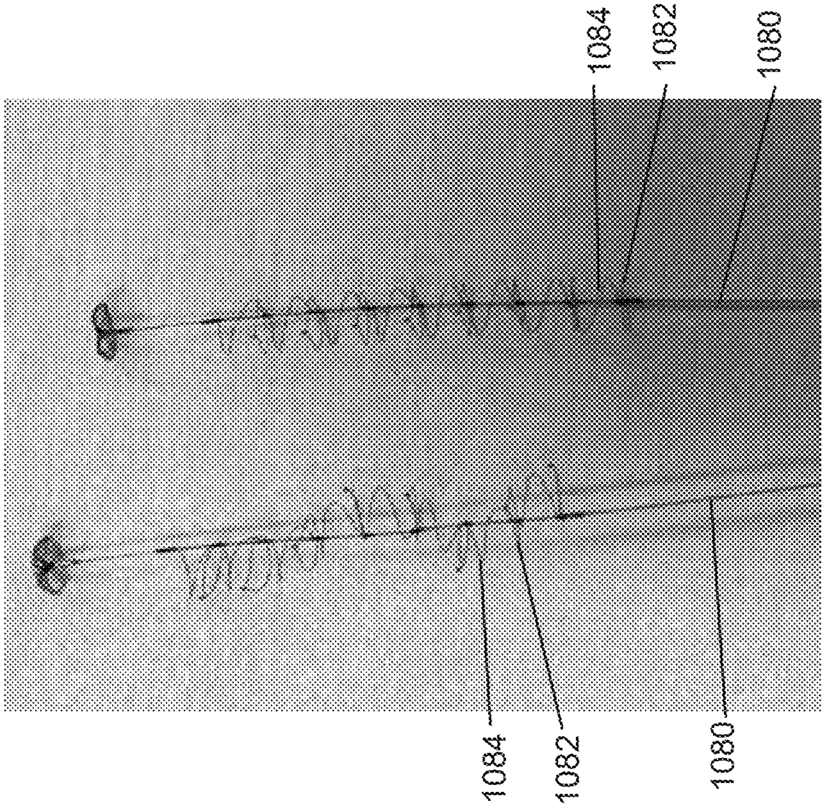
FIG. 147 are views of extractors. The extractor can be a series of helical loop and circular loop alternating.

FIG. 147 are views of the extractor 1080. The extractor 1080 can include engagement panels 1082 that can form circular loops. The extractor 1080 can include helical loops 1084. The extractor 1080 can include a series of helical loops and circular loops alternating. The extractor 1080 can include helical loops 1084 extending the length of the extractor 1080 with as series of circular loops 1082 in between the helical loops 1084. In some embodiments, there is an eyelet element at the tip of the helical loop 1084 and the circular loop 1082 to aid in grasping the clot. In some embodiments, there are two eyelets element at the tip of the helical loop 1084 and the circular loop 1082. In some embodiment, the are plurality of eyelets element at the tip of the helical loop and the circular loop. In some embodiment, the helical loops 1084 and the circular loops 1082 are in the center-line relative to the eyelet receive the core wire. In some embodiment, the helical loops 1084 and the circular loops 1082 are off-center relative to the eyelet receiving the core wire. In some embodiments, the helical loops 1084 and the circular loops 1082 have the same diameter throughout the length of the extractor 1080. In some embodiment, the helical loops 1084 and the circular loop 1082 have a diameter that progressively or gradually reduces from proximal end to distal end. In some embodiment, the helical loops 1084 and the circular loop 1082 have a diameter that progressively or gradually reduces in diameter from the distal end to the proximal end. In some embodiments, the helical loop 1084 and the circular loop 1082 varies in diameter in discriminately. In some embodiments, the helical loop 1084 has a diameter that varies while the circular loop 1082 maintains the same diameter. In some embodiment, the helical loop 1084 has the same diameter throughout while the circular loop 1082 varies in diameter. The extractor 1060 can include a distal member 1066. In some embodiments, the extractor can include a distal member in between the helical loop and circular loop. In some embodiments, the extractor can include a four engagement panels in between the helical loop and the circular loop.

Figure 148:
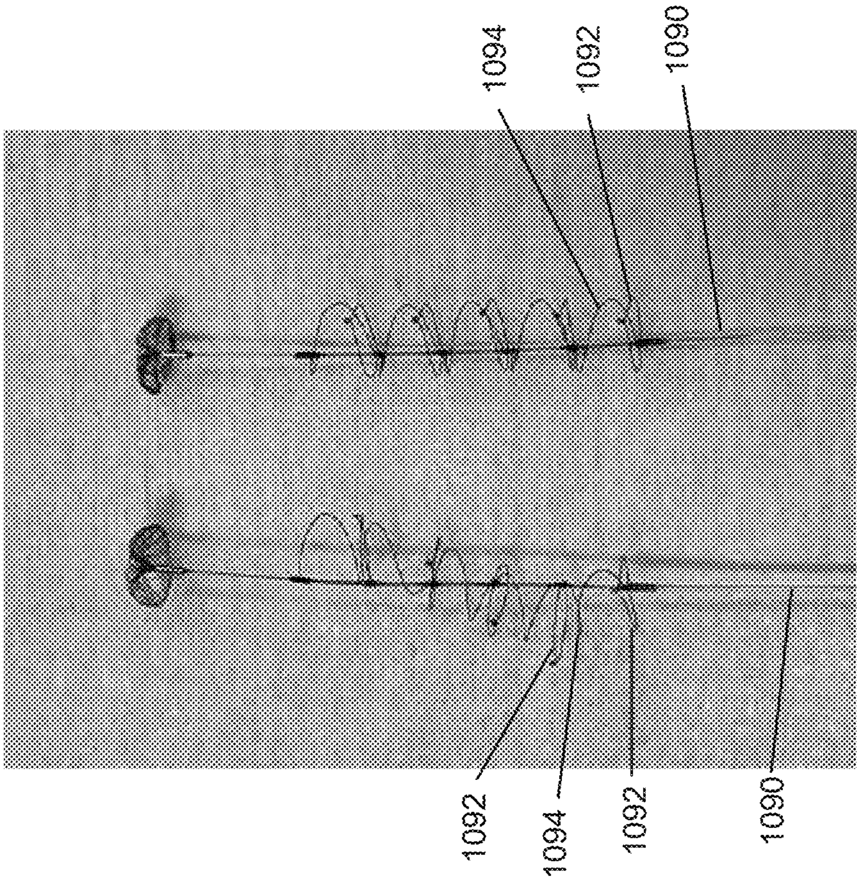
FIG. 148 are views of extractors. The extractor can be a series of helical loop and circular loop alternating.

FIG. 148 is a view of an extractor 1090. The extractor 1090 can include engagement panels 1092 that can form circular loops. The extractor 1090 can include helical loops 1094. The extractor 1090 can include a series of helical loops 1094 and circular loops 1092 alternating. The extractor 1080 can include a helical loop 1094 extending the length of the engager with a series of circular loops 1092 in between the helical loop. The helical loop 1094 and the circular loop 1092 can be in center-line or off-center relative to the eyelet receiving the core wire. The helical loop 1094 and the circular loop 1092 diameter can be the same diameter throughout the length of the extractor 1090. In some embodiment, the helical loop 1094 and the circular loop 1092 can have a diameter that is progressively tapered in diameter. In some embodiments, the helical loop 1094 and the circular loop 1092 diameter changes indiscriminately. In some embodiment, there are one, two, three, four or plurality of eyelets element at the tip of the helical loop and circular loop. The extractor 1060 can include a distal member 1066. In some embodiments, the extractor can include a distal member in between the helical loop and circular loop. In some embodiments, the extractor can include a four engagement panels in between the helical loop and the circular loop.

Figure 149:
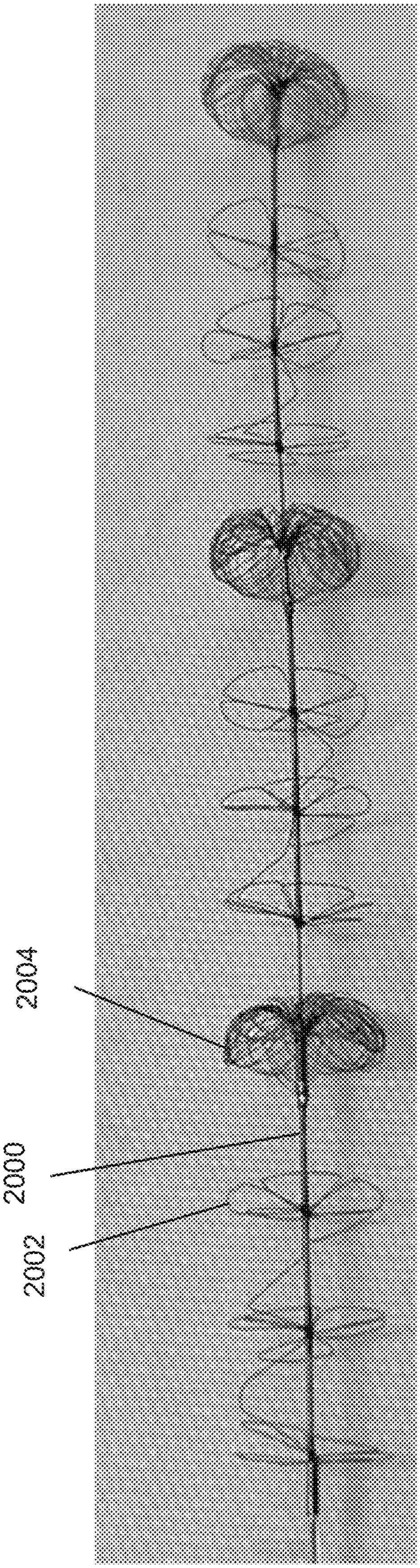
FIG. 149 is a view of an extractor.

FIG. 149 is a view of an extractor 2000. The extractor 2000 can have engagement panels 2002. The extractor 2000 can have distal members 2004. The extractor 2000 can have the distal member 2004 in between the engagement panels 2002.

Figure 150:
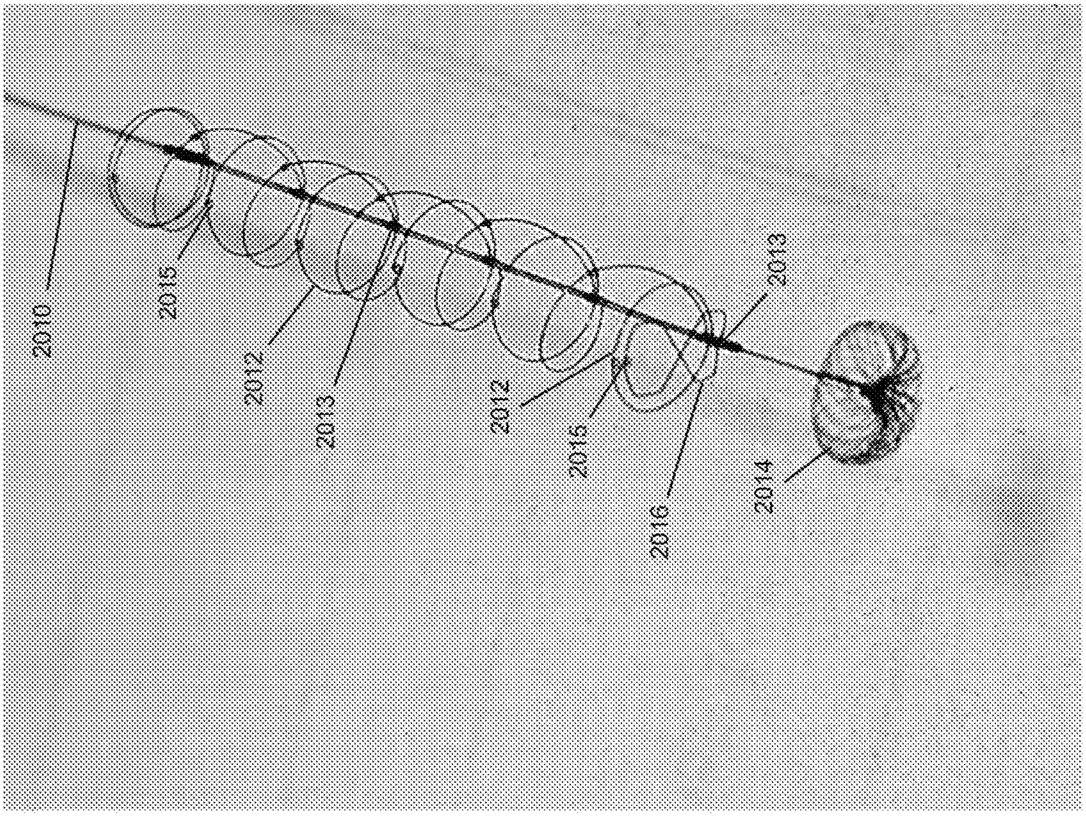
FIG. 150 is a view of an extractor.
Figure 151:
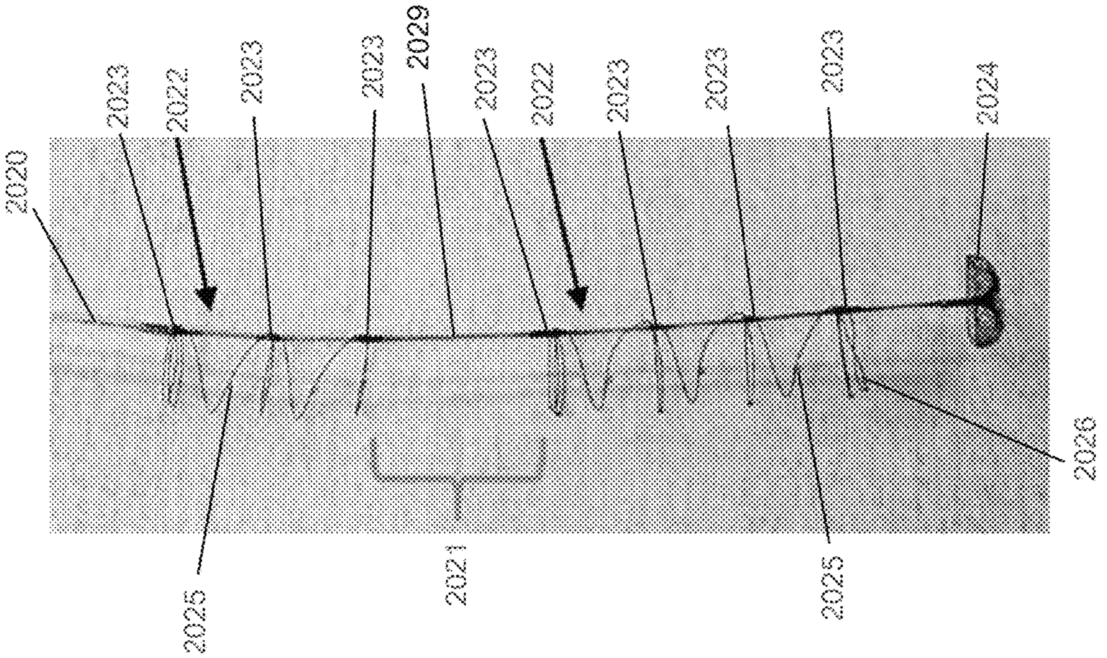
FIGS. 151-154 are views of an extractor.
Figure 152:
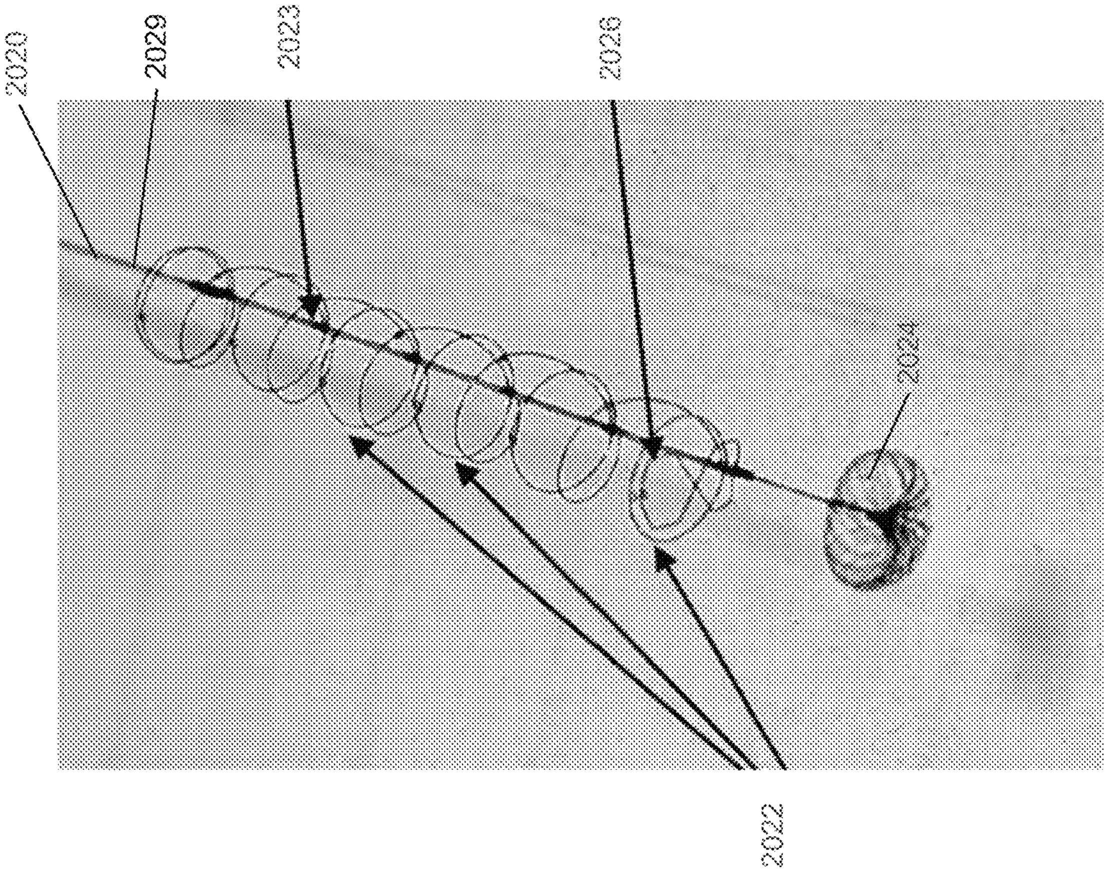

FIG. 150 is a view of an extractor 2010. The extractor 2010 can include engagement panels 2012. The engagement panels 2012 can be formed from a continuous wire. The engagement panels 2012 can include legs extending circumferentially. The engagement panels 2012 can include a full loop. The engagement panels from the first location is connected to the engagement panels at the second engagement panels by a helical element. The engagement panels 2012 can extend 360 degrees. The engagement panels 2012 can extend in a circular shape. The engagement panels 2012 can include multi-loops. The engagement panel 2012 can be a helical shape. The engagement panel 2012 can be a polygon shape such as a pentagon, hexagon, heptagon, octagon, etc. The loops can scrape the vessel wall. The loops can entangle the clot. The engagement panels 2012 can form a complete circle. The engagement panels 2012 can scrape the vessel wall. The engagement panels 2012 can go over the clot. The engagement panels 2012 can grasp the clot with one or more loops. The engagement panels 2012 can include loops to go over the clot. The engagement panels 2012 can be circular or looped shape. The engagement panels 2012 can form a lumen. In some embodiments, the lumen of the engagement panels 2012 can approximate the lumen of the vessel. The lumen of the engagement panels 2012 can be circular.

The engagement panels 2012 can include an eyelet 2013. The engagement panel 2012 can include a loop extending circumferentially from the eyelet 2013. The engagement panel 2012 can include a series of loops connected by the eyelets 2013. The engagement panels 2012 can include a coiled eyelet 2013. The coiled eyelet 2013 can be offset from center. In some embodiments, the eyelet 2013 is located in the center of the engagement panels 2012. In some embodiments, the eyelet 2013 is located off center. In some embodiments, the eyelet 2013 is along the circumference of the loop. The eyelet 2013 can be positioned to maximize the lumen of the engagement panels 2012. The eyelet 2013 can be positioned along the curve of the loop.

The engagement panels 2012 can include the eyelet 2013 to receive a core wire. The engagement panels can include the eyelet 2013 that is centrally located relative to the panels to receive the core wire. The engagement panels can include the eyelet 2013 located off-center relative to the panels to receive the core wire. The core wire can be positioned to maximize the lumen of the engagement panels 2012. The core wire can be positioned along the curve of the loop. The core wire can be off-center in the engagement panels 2012. The engagement panels 2012 can have an off-center eyelet 2013 through which the core wire passes. The extractor 2010 can include a biased core wire which is offset from center. The core wire is off-centrally positioned relative to the loop of the engagement panels 2012.

The engagement panels 2012 can include a lumen. The engagement panels 2012 can have a loop which has the lumen. The lumen can be configured to go over the clot. The lumen can be configured to further increase the clot engagement. The engagement panels 2012 can go over and grasp the clot.

The device can include a distal member 2014. The distal member 2014 can be distal to the first array of engagement panels 2012 located at the first location. The distal member 2014 can be distal to all engagement panels 2012. The distal member 2014 can be proximal to all engagement panels. The distal member 2014 can be within or in between each engagement panels array.

The engagement panel 2012 can form an element 2015. The element 2015 can be located at an apex or top of the engagement panel 2012. The element 2015 can include an eyelet. The element 2015 can include a single eyelet or a plurality of eyelets. The element 2015 can scrape the vessel wall. The element 2015 can reinforce the series of loops. The element 2015 can entangle the clot. The engagement panels 2012 can include a full loop. The engagement panels 2012 can grasp the clot with one or more elements 2015 at the apex. The engagement panels 2012 can include the coiled eyelet 2013. The coiled eyelet 2013 can be offset from center. The coiled eyelet 2013 that receives the core wire can be spaced apart from the element 2015 that entangles the clot. The coiled eyelet 2013 that receives the core wire can be diametrically opposed to the element 2015 that entangles the clot. The coiled eyelet 2013 that receives the core wire can spaced about 180 degrees relative to the element 2015.

The extractor 2010 can have open engagement panels 2012. The engagement panels 2012 can be a full loop with an opening or lumen. In some embodiments, the engagement panels 2012 can be a helix with a defined opening or lumen. The engagement panels 2012 can be designed to go over the clot and grasp onto the clot. The engagement panels 2012 can have small loop or eyelet element 2015. The small loop or eyelet element 2015 is different than the eyelet 2013 that attaches or receives the core wire. The engagement panels 2012 can have small loop or eyelet element 2015 at an apex. The engagement panels 2012 can have small loop or eyelet element 2015 to function to pinch the clot. The engagement panels 2012 can have the eyelet 2013 to receive the core wire. The core wire and eyelet 2013 can be positioned to the side. The core wire and eyelet 2013 can be eccentrically located. Once the engagement panels 2012 advance over the clot, the engagement panels 2012 will secure the clot during retrieval. Under compression or tension, the engagement panels 2012 will compress longitudinally against the clot to secure the clot circumferentially in some embodiments. Under compression or tension, the engagement panels 2012 will not compress longitudinally in some embodiments. The loop or eyelet element 2015 of the engagement panels 2012 will pinch the clot under compression to secure the clot in some embodiments. The loop or eyelet element 2015 of the engagement panels 2012 can grasp onto the clot. The engagement panels 2012 can function to pinch the clot. The clot against the vessel wall can create resistance. The clot against the vessel wall can create friction. The resistance and friction can cause the clot to roll. The engagement panels 2012 function to encapsulate the clot. The engagement panels 2012 minimize pushing clot against the vessel wall. The engagement panels 2012 result in low friction. The engagement panels 2012 allow the clot to move easier.

The device can include an element 2016. The element 2016 can be an infinity loop. The element 2016 can be shaped as a figure eight. The element 2016 can be curved. The element 2016 can be shaped like the infinity symbol. The element 2016 can be shaped like the number 8. The element 2016 can be a single loop. The element 2016 can be a double loop. The element 2016 can be a plurality of loops. The element 2016 can have any geometric shape. The element 2016 can be a polygon shape such as pentagon, hexagon, heptagon, octagon, etc. The element 2016 can be formed from a continuous wire. The element 2016 and the engagement panels 2012 can be formed from a continuous wire. The element 2016 can be formed separately from the engagement panels 2012.

The element 2016 can be a loop configuration. The element 2016 can allow better entrapment of material in some embodiments. The element 2016 can allow better entrapment of the clot in some embodiments. The element 2016 can allow securing of the material in some embodiments. The element 2016 can allow securing of the material during transit in some embodiments. The element 2016 can allow securing of the clot during transit in some embodiments. The element 2016 can consist of one element in some embodiments. The extractor can have only one element 2016. The extractor can have a plurality of elements 2016 in some embodiments.

The engagement panels 2012 and the element 2016 can form a double panel. The element 2016 can be a small panel inside a larger engagement panels 2012 in some embodiments. The element 2016 can be an inner panel in some embodiments. The engagement panels 2012 can be an outer panel in some embodiments. The engagement panels 2012 and the element 2016 can be stacked. The engagement panels 2012 and the element 2016 can be spaced apart. The engagement panels 2012 and the element 2016 can be aligned. The engagement panels 2012 and the element 2016 can be offset. The engagement panels 2012 and the element 2016 can include a continuous wire. In some embodiments, the continuous wire forms the engagement panels 2012 and the element 2016. In some embodiments, the continuous wire forms all of the engagement panels 2012 and the element 2016 can be different wire. In some embodiment, the continuous wire can be a plurality of wires. The engagement panels 2012 can be reinforced. The element 2016 can reinforce the engagement panels 2012. The element 2016 can reinforce only the engagement panels 2012 at the first longitudinal location. The element 2016 can stiffen the engagement panels 2012. The element 2016 can stiffen only the engagement panels 2012 at the first longitudinal location. The engagement panels 2012 at the first longitudinal location can be less prone to collapse when encountering material. The engagement panels 2012 at the first longitudinal location can be less prone to collapse when scraping the vessel wall. In some embodiments, the engagement panels 2012 at the first longitudinal location can be flat. In some embodiments, the element 2016 can be flat. The engagement panels 2012 can include one panel at each longitudinal location. The engagement panels 2012 can include one loop at each longitudinal location. The engagement panels 2012 can include a plurality of panels at each longitudinal location. The engagement panels 2012 can include a plurality of loops at each longitudinal location.

The element 2016 can be positioned within the engagement panels 2012 located at the first location. The element 2016 can be positioned near the engagement panels 2012 located at the first location. The element 2016 can be distal to the engagement panels 2012 located at the first location. The distal member 2014 can be distal to all engagement panels 2012. The element 2016 can be positioned within the lumen of the engagement panels 2012. The element 2016 can be positioned to fill the lumen of the engagement panels 2012. The element 2016 can be positioned to cover the lumen of the engagement panels 2012. The element 2016 can be positioned to obstruct at least a portion of the lumen of the engagement panels 2012. The element 2016 can be positioned at the distalmost engagement panel 2012. The element 2016 can be positioned at the engagement panels 2012 located at the first location. The element 2016 can be positioned at any engagement panel 2012 along the length of the extractor 2010. The element 2016 can be positioned at the engagement panels 2012 located at the second location. The element 2016 can be positioned at the engagement panels 2012 located at the third location. The element 2016 can be positioned proximal to the engagement panels 2012, The element 2016 can be positioned distal to the engagement panels 2012, The element 2016 can be positioned within the engagement panels 2012. The element 2016 can be a back stop for the clot in transit. The element 2016 can limit or prevent distal movement of the clot. The element 2016 can contain the clot between the engagement panels 2012.

The element 2016 can include the element 2015. The element 2015 can be located at an apex or top of the element 2016. The element 2015 can include an eyelet. The element 2015 can include a single eyelet or a plurality of eyelets. The element 2015 can scrape the vessel wall. The element 2015 can reinforce the element 2016. The element 2015 can entangle the clot. The element 2016 can include a full loop or a plurality of loops. The element 2016 can grasp the clot with one or more elements 2015 at the apex. The element 2016 can include the coiled eyelet 2013. The coiled eyelet 2013 can be offset from center. The eyelet 2013 that receives the core wire can be spaced apart from the element 2015 that entangles the clot of the element 2016. The eyelet 2013 that receives the core wire can be diametrically opposed to the element 2015 that entangles the clot of the element 2016.

The extractor 2010 can be formed from a series of individual loop and helical segment element with eyelet to receive the corewire. The extractor can include a series of individual separate loops. The extractor can include a series of helical segments or continuous segment. The extractor can include a combination of a series of individual loops and helical segments. The extractor includes element 2016 locating at the engagement panels at the first position. The extractor includes a distal element 2014. The extractor 2010 can be a series of individual loops with the helical portion. The extractor 2010 can be a series of individual loops without the helical portion. The extractor 2010 can have eyelet to receive the core wire. The embodiment can include a series of individual loop with or without the helical portion and have eyelet to receive the core wire.

In some embodiments, the extractor 2010 can include engagement panels 2012. The engagement panels 2012 can be formed from a continuous wire. The engagement panels 2012 can include legs extending circumferentially. The engagement panels 2012 can include a full loop. The engagement panels from the first location is connected to the engagement panels at the second engagement panels by a helical element. The engagement panels 2012 can extend 360 degrees. The engagement panels 2012 can extend in a circular shape. The engagement panels 2012 can include multi-loops. The engagement panels 2012 can include the eyelet 2013 to receive a core wire. The engagement panels can include the eyelet 2013 located off-center relative to the panels to receive the core wire. The core wire can be positioned to maximize the lumen of the engagement panels 2012. The core wire can be positioned along the curve of the loop. The core wire can be off-center in the engagement panels 2012. The engagement panels 2012 can have an off-center eyelet 2013 through which the core wire passes. The extractor 2010 can include a biased core wire which is offset from center. The core wire is off-centrally positioned relative to the loop of the engagement panels 2012. The engagement panels 2012 can include a lumen. The engagement panels 2012 can have a loop which has the lumen. The lumen can be configured to go over the clot. The lumen can be configured to further increase the clot engagement. The engagement panels 2012 can go over and grasp the clot. The device can include a distal member 2014. The distal member 2014 can be distal to the first array of engagement panels 2012 located at the first location. The distal member 2014 can be distal to all engagement panels 2012. The distal member 2014 can be proximal to all engagement panels. The distal member 2014 can be within or in between each engagement panels array. The engagement panel 2012 can form an element 2015. The element 2015 can be located at an apex or top of the engagement panel 2012. The element 2015 can include an eyelet. The element 2015 can include a single eyelet or a plurality of eyelets. The engagement panels 2012 can include a full loop. The engagement panels 2012 can include the coiled eyelet 2013. The coiled eyelet 2013 can be offset from center. The coiled eyelet 2013 that receives the core wire can be spaced apart from the element 2015 that entangles the clot. The coiled eyelet 2013 that receives the core wire can be diametrically opposed to the element 2015 that entangles the clot. The coiled eyelet 2013 that receives the core wire can spaced about 180 degrees relative to the element 2015. The device can include an element 2016. The element 2016 can be an infinity loop. The element 2016 can be shaped as a figure eight. The element 2016 can be curved. The element 2016 can be shaped like the infinity symbol. The element 2016 can be shaped like the number 8. The element 2016 can be a single loop. The element 2016 can be a double loop. The element 2016 can be a plurality of loops. The element 2016 can have any geometric shape. The element 2016 can be a polygon shape such as pentagon, hexagon, heptagon, octagon, etc. The element 2016 can be formed from a continuous wire. The element 2016 and the engagement panels 2012 can be formed from a continuous wire. The element 2016 can be formed separately from the engagement panels 2012. The element 2016 can include the element 2015. The element 2015 can be located at an apex or top of the element 2016. The element 2015 can include an eyelet. The element 2015 can include a single eyelet or a plurality of eyelets. The element 2016 can include a full loop or a plurality of loops. The element 2016 can grasp the clot with one or more elements 2015 at the apex. The element 2016 can include the coiled eyelet 2013. The coiled eyelet 2013 can be offset from center. The eyelet 2013 that receives the core wire can be spaced apart from the element 2015 that entangles the clot of the element 2016. The eyelet 2013 that receives the core wire can be diametrically opposed to the element 2015 that entangles the clot of the element 2016. In some embodiments, the extractor 2010 can include an element position distalmost to the distal member 2014 and all the engagement panels. The distal element can cross the clot obstruction. The element positioned distalmost to the distal member 2014 can function like a guidewire tip. The element positioned distalmost to the distal member 2014 can be in front the front of the distal member 2014. The element positioned distalmost to the distal member 2014 can be used in place of the guidewire to cross the clot obstruction as one unit with the device.

In some embodiments, there is an element located proximally to the extractor. The element has an opening or lumen to receive the clot. The element can be made of a wire form or laser cut metallic materials such as nitinol or stainless steel. The element can form a geometric shape such as circular, elliptical, round. The element can also form any geometric shape and define a lumen to receive the clot. The element has an eyelet to receive the corewire. The element can be continuous with the extractor or separate from the extractor. The element can form a single a plurality proximal to the extractor. In some embodiments, the element has legs extending from the eyelet and axially relative to the corewire and then radially to form a lumen.

The extractor 2010 can be laser cut to the final loop configuration. The extractor 2010 can be expanded to the final loop configuration. The extractor 2010 can be produced to the final loop configuration. The laser cut manufacturing can form a continuous loop. The laser cut manufacturing can form a non-continuous loop. The extractor 2010 can have components formed from one continuous wire. The extractor 2010 can have components formed from laser cutting. The extractor 2010 can have components comprising metal such as steel, carbon steel, stainless steel, steel alloys, aluminum, titanium, brass, copper, or combinations thereof. The extractor 2010 can have components comprising polymers such as acrylic, styrene, polyimide, thermoplastic polyamides, high density polyethylene, polypropylene, polyethylene, or combinations thereof. In some embodiments, the engagement panels 2012 are laser cut. In some embodiments, the eyelets 2013 are laser cut. In some embodiments, the distal member 2014 is laser cut. In some embodiments, the elements 2015 are laser cut. In some embodiments, the elements 2016 are laser cut. In some embodiments, the engagement panels 2012 and the eyelets 2013 are formed from a continuous material. In some embodiments, the engagement panels 2012 and the elements 2015 are formed from a continuous material. In some embodiments, the engagement panels 2012, the eyelets 2013, and the elements 2015 are formed from a continuous material. In some embodiments, the engagement panels 2012 and the element 2016 are formed from a continuous material. In some embodiments, the element 2016 and the eyelet 2013 of the element 2016 are formed from a continuous material. In some embodiments, the element 2016 and the element 2015 of the element 2016 are formed from a continuous material.

FIGS. 151-154 are views of an extractor 2020. The extractor 2020 can include engagement panels 2022. The engagement panels 2022 can have a loop design. The engagement panels 2022 can extend in a circular shape. The engagement panels 2022 can function to pinch material such as a clot. The engagement panels 2022 can function to anchor the clot. The engagement panels 2022 can function to encapsulate the clot. The engagement panels 2022 can include a first array at a first longitudinal location. The engagement panels 2022 at the first longitudinal location can be formed from a continuous wire. In some embodiment, the engagement panels 2022 at the first longitudinal location can be formed from a plurality of wires. In some embodiments, the engagement panels 2022 at the first longitudinal location can be formed from two or more wires. In some embodiments, the engagement panels 2022 at the first longitudinal location can be formed from multiple wire segments. In some embodiments, the engagement panels 2022 at the first longitudinal location can be made from multiple wires into segments and placed next to each other to form the engagement panels. The engagement panels 2022 can include a second array at a second longitudinal location. The engagement panels 2022 at the second longitudinal location can be formed from a continuous wire. In some embodiment, the engagement panels 2022 at the second longitudinal location can be formed from a plurality of wires. In some embodiments, the engagement panels 2022 at the second longitudinal location can be formed from two or more wires. In some embodiments, the engagement panels 2022 at the second longitudinal location can be formed from multiple wire segments. In some embodiments, the engagement panels 2022 at the second longitudinal location can be made from multiple wires into segments and placed next to each other to form the engagement panels. The engagement panels 2022 can include a third array at a third longitudinal location. The engagement panels 2022 at the third longitudinal location can be formed from a continuous wire. In some embodiments, the engagement panels 2022 at third longitudinal location can be formed from a plurality of wires. The engagement panels 2022 can include a fourth array at a fourth longitudinal location. The engagement panels 2022 can include a plurality of arrays.

The extractor 2020 can include a spacing 2021 between the engagement panels 2022 at the first longitudinal location and the engagement panels 2022 at the second longitudinal location. The extractor 2020 can include a spacing 2021 between the engagement panels 2022 at the second longitudinal location and the engagement panels 2022 at the third longitudinal location. The extractor 2020 can include the spacing 2021 between adjacent arrays of engagement panels 2022. The extractor 2020 can include a cavity between adjacent arrays of engagement panels 2022. The extractor 2020 can include an opening between adjacent arrays of engagement panels 2022. The engagement panels 2022 at the first longitudinal location and the engagement panels 2022 at the second longitudinal location can be spaced apart. The engagement panels 2022 at the first longitudinal location and the engagement panels 2022 at the second longitudinal location can be separated. In some embodiments, the continuous wire that forms the engagement panels 2022 at the first longitudinal location is separated from the continuous wire that forms the engagement panels 2022 at the second longitudinal location. In some embodiments, the continuous wire that forms the engagement panels 2022 at the first longitudinal location is continuous from the wire that forms the engagement panels 2022 at the second longitudinal location. In some embodiments, the continuous wire that forms the engagement panels 2022 at the first longitudinal location is continuously form all the arrays of engagement panels.

The extractor 2020 can be made from two separate elements such as proximal element and a distal element. The proximal element can be a tubular element. The distal element can be a tubular element. The proximal element can be laser cut. The distal element can be laser cut. The proximal element can be stent-like. The distal element can be stent-like. The proximal element can be made of formed wires. The distal element can be made of formed wires. The engagement panels 2022 at the first longitudinal location can be replaced with a tubular stent. The engagement panels 2022 at the second longitudinal location can be replaced with a tubular stent. The extractor 2020 can include a tubular stent in addition to the engagement panels 2022 at the first longitudinal location and the engagement panels 2022 at the second longitudinal location. In some embodiments the proximal element comprises a tubular, laser cut stent and the distal element comprises wire formed engagement panels 2022. In some embodiments the distal element comprises a tubular, laser cut stent and the proximal element comprises wire formed engagement panels 2022. The extractor 2020 can be made from two separate elements such as the proximal element that is made from a tubular, laser cut stent like structure, and the distal element is made as formed wire. The extractor 2020 can be made from two separate elements such as the proximal element that is made as wire formed, and the distal element that is made from a tubular, laser cut stent like structure.

The engagement panels 2022 can be made of a wire member. The engagement panels 2022 can be formed in a helix-like shape. The helix-like shaped can be a single helix. In some embodiments, the helix can be a double helix. In some embodiments, the helix can be a triple helix or more. The engagement panels 2022 can form a complete helix. The engagement panels 2022 can include one or more loops extending circumferentially. The engagement panels 2022 can include a full loop. The engagement panels 2022 can include one or more helical segments. The engagement panels 2022 at the first longitudinal location can extend 360 degrees. The engagement panels 2022 at the first longitudinal location can include at least one full revolution. The engagement panels 2022 at the first longitudinal location can extend 720 degrees. The engagement panels 2022 at the first longitudinal location can include at least two full revolutions. The engagement panels 2022 at the first longitudinal location can extend 1080 degrees. The engagement panels 2022 at the first longitudinal location can include at least three full revolutions. The engagement panels 2022 can include multiple spirals at the first longitudinal location. The engagement panels 2022 can include multiple spirals at the second longitudinal location. The engagement panels 2022 can include multiple spirals at the third longitudinal location. In some embodiments, the engagement panels 2022 can include alternating spiral and loop at the first longitudinal location. In some embodiments, the engagement panels 2022 at the first longitudinal location are not continuous with the engagement panels 2022 at the second longitudinal location. In some embodiments, the engagement panels 2022 at the first longitudinal location are isolated from the engagement panels 2022 at the second longitudinal location.

In some embodiments, the engagement panels 2022 can have a diameter similar to the diameter of the vessel containing the material. In some embodiments, the engagement panels 2022 can have a diameter greater than the diameter of the vessel containing the material. In some embodiments, the engagement panels 2022 can have a diameter less than the diameter of the vessel containing the material. The engagement panels 2022 can have a circumference that is approximately equal to the circumference of the vessel. The engagement panels 2022 can be perpendicularly oriented within the vessel. The engagement panels 2022 can scrape the vessel wall. The engagement panels 2022 can entangle the clot. The engagement panels 2022 can go over the clot. The engagement panels 2022 can grasp the clot. The engagement panels 2022 can encircle the clot. The engagement panels 2022 can form a lumen. In some embodiments, the lumen of the engagement panels 2022 can approximate the lumen of the vessel. The lumen of the engagement panels 2022 can be circular. The lumen of the engagement panels 2022 can receive the material therewithin. In some embodiments, the engagement panels 2022 at the first longitudinal location can surround the material. In some embodiments, the engagement panels 2022 at the first longitudinal location can pass along the vessel wall. In some embodiments, the engagement panels 2022 at the first longitudinal location can pass around the material. In some embodiments, the clot can go into the engagement panels 2022 at the first longitudinal location. In some embodiments, the engagement panels 2022 at the first longitudinal location can have any geometric configuration described herein. In some embodiments, the engagement panels 2022 at the first longitudinal location can have one continuous helical loop.

In some embodiments, the engagement panels 2022 at the first longitudinal location and the engagement panels 2022 at the second longitudinal location can include the same number of engagement panels. In some embodiments, the engagement panels 2022 at the first longitudinal location and the engagement panels 2022 at the second longitudinal location can include a different number of engagement panels. In some embodiments, the engagement panels 2022 at the first longitudinal location and the engagement panels 2022 at the second longitudinal location can have the same length. In some embodiments, the engagement panels 2022 at the first longitudinal location and the engagement panels 2022 at the second longitudinal location can have different lengths. In some embodiments, the engagement panels 2022 at the first longitudinal location and the engagement panels 2022 at the second longitudinal location can have the same diameter. In some embodiments, the engagement panels 2022 at the first longitudinal location and the engagement panels 2022 at the second longitudinal location can have different diameters. In some embodiments, the engagement panels 2022 at the first longitudinal location and the engagement panels 2022 at the second longitudinal location have different geometric shapes. In some embodiments, the engagement panels 2022 at the first longitudinal location and the engagement panels 2022 at the second longitudinal location are tubular. In some embodiments, the engagement panels 2022 at the first longitudinal location and the engagement panels 2022 at the second longitudinal location are wire formed. In some embodiments, the engagement panels 2022 at the first longitudinal location and the engagement panels 2022 at the second longitudinal location are stent-like.

The engagement panels 2022 can include one or more eyelets 2023. The engagement panel 2022 can include a helical segment extending circumferentially from the eyelet 2023. The engagement panel 2022 at the first longitudinal location can include one eyelet 2023. The engagement panel 2022 at the first longitudinal location can include two eyelets 2023. The engagement panel 2022 at the first longitudinal location can include a proximal eyelet 2023 and a distal eyelet 2023. The engagement panel 2022 at the first longitudinal location can include multiple eyelets 2023. The engagement panel 2022 at the first longitudinal location can include an eyelet 2023 for each circumferential loop or helix. In some embodiments, each helical segment of the engagement panel 2022 at the first longitudinal location is connected to an eyelet 2023. In some embodiments, a proximal end of the engagement panel 2022 at the first longitudinal location is connected to an eyelet 2023. In some embodiments, a distal end of the engagement panel 2022 at the first longitudinal location is connected to an eyelet 2023. In some embodiments, a proximal end of the engagement panel 2022 at the second longitudinal location is connected to an eyelet 2023. In some embodiments, a distal end of the engagement panel 2022 at the second longitudinal location is connected to an eyelet 2023. In some embodiments, the engagement panels 2022 at the first longitudinal location and the engagement panels 2022 at the second longitudinal location can include the same number of eyelets 2023. In some embodiments, the engagement panels 2022 at the first longitudinal location and the engagement panels 2022 at the second longitudinal location can include a different number of eyelets 2023.

In some embodiments, the eyelets 2023 are fixed. In some embodiments, a proximal eyelet 2023 of the engagement panel 2022 at the first longitudinal location is fixed. In some embodiments, a proximal end of the engagement panel 2022 at the first longitudinal location is fixed. In some embodiments, a distal eyelet 2023 of the engagement panel 2022 at the first longitudinal location is fixed. In some embodiments, a distal end of the engagement panel 2022 at the first longitudinal location is fixed. In some embodiments, each eyelet 2023 of the engagement panel 2022 at the first longitudinal location is fixed. In some embodiments, each engagement panel 2022 at the first longitudinal location is fixed. In some embodiments, at least one engagement panel 2022 at the first longitudinal location is not fixed.

In some embodiments, a proximal eyelet 2023 of the engagement panel 2022 at the second longitudinal location is fixed. In some embodiments, a proximal end of the engagement panel 2022 at the second longitudinal location is fixed. In some embodiments, a distal eyelet 2023 of the engagement panel 2022 at the second longitudinal location is fixed. In some embodiments, a distal end of the engagement panel 2022 at the second longitudinal location is fixed. In some embodiments, each eyelet 2023 of the engagement panel 2022 at the second longitudinal location is fixed. In some embodiments, each engagement panel 2022 at the second longitudinal location is fixed. In some embodiments, at least one engagement panel 2022 at the second longitudinal location is not fixed.

In some embodiments, a proximal end of the engagement panel 2022 at the first longitudinal location is spaced apart from a distal end of the engagement panel 2022 at the second longitudinal location. In some embodiments, the spacing 2021 is located between the ends of the engagement panel 2022 at the first longitudinal location and the engagement panel 2022 at the second longitudinal location. In some embodiments, the spacing 2021 is free from engagement panels. In some embodiments, the spacing 2021 is free from eyelets.

The engagement panel 2022 at the first longitudinal location can include a series of helical segments connected by the eyelets 2023. The engagement panel 2022 at the second longitudinal location can include a series of helical segments connected by the eyelets 2023. The first longitudinal location and the second longitudinal location can be separated by a cavity or spacing 2021. In some embodiments, the engagement panel 2022 at the first longitudinal location can have at least one fixed point each engagement panel. In some embodiments, the engagement panel 2022 at the first longitudinal location can fold relative to the fixed point. In some embodiments, the engagement panel 2022 at the first longitudinal location can fold relative to the eyelet 2023. In some embodiments, the engagement panel 2022 at the first longitudinal location can fold proximally. In some embodiments, the engagement panel 2022 at the first longitudinal location can fold distally.

The eyelet 2023 can include a coiled eyelet. The eyelet 2023 can include multiple coils. The eyelet 2023 can include multiple segments of coils. The one or more eyelets 2023 can be formed from the continuous wire that forms the engagement panel 2022 at the first longitudinal location. The one or more eyelets 2023 can be formed from the continuous wire that forms the engagement panel 2022 at the second longitudinal location. The eyelet 2023 can be offset from center. In some embodiments, the eyelet 2023 is located off center relative to the engagement panels 2022. In some embodiments, the eyelet 2023 is along the circumference of the helix. In some embodiments, the eyelet 2023 is along the circumference of the loop. The eyelet 2023 can be positioned to maximize the lumen of the engagement panels 2022. The eyelet 2023 can be positioned along the curve of the helix.

In some embodiments, the eyelet 2023 can be fixed relative to a core wire 2029. The engagement panel 2022 at the first longitudinal location can be fixed relative to the core wire 2029. The spacing 2021 can be fixed relative to the core wire 2029. The engagement panel 2022 at the second longitudinal location can be fixed relative to the core wire 2029. In some embodiments, the eyelet 2023 can receive a core wire 2029. The engagement panels can include the eyelet 2023 that is eccentrically located relative to the engagement panels 2022. The extractor 2020 can include the core wire 2029 that is eccentrically located relative to the engagement panels 2022.

The engagement panels 2022 can include a lumen. The engagement panels 2022 can have a lumen through the helixes of the engagement panels 2022. The engagement panels 2022 can have a lumen through the loops of the engagement panels 2022. The lumen can be configured to receive the clot. The lumen can be configured to go over the clot. The lumen can be configured to further increase the clot engagement. The engagement panels 2022 can go over and grasp the clot.

The extractor 2020 can include a distal member 2024. The distal member 2024 can be distal to the first array of engagement panels 2022 located at the first longitudinal location. The distal member 2024 can be distal to the spacing 2021 between engagement panels 2022. The distal member 2024 can be distal to the second array of engagement panels 2022 located at the second longitudinal location. The distal member 2024 can be distal to all engagement panels 2022.

The engagement panel 2022 can form an element 2025. The element 2025 can be located opposite the eyelet 2023. The element 2025 can include a micro feature. The element 2025 can include a single loop. The element 2025 can include a single coil. The element 2025 can create roughness along the helix. The element 2025 can scrape the vessel wall. The element 2025 can reinforce the apex of the helix. The element 2025 can strengthen the helix. The element 2025 can entangle the clot. The eyelet 2023 can be spaced apart from the element 2025. The eyelet 2023 can be diametrically opposed to the element 2025. The eyelet 2023 can spaced about 180 degrees relative to the element 2025. The element 2025 and the first array of engagement panels 2022 located at the first longitudinal location can be made from a continuous wire. The element 2025, the eyelet 2023, and the first array of engagement panels 2022 located at the first longitudinal location can be made from a continuous wire.

The extractor 2020 can have open engagement panels 2022. The engagement panels 2022 can be a full helix with an opening or lumen. The engagement panels 2022 can be a full loop with an opening or lumen. The engagement panels 2022 can be designed to go over the clot and grasp onto the clot. The engagement panels 2022 can slide around the clot. The engagement panels 2022 can minimize pushing the clot against the vessel wall. The engagement panels 2022 can scrape the clot from the vessel wall. The engagement panels 2022 can have minimal surface area in contact with the vessel wall. The engagement panels 2022 can result in low friction. The engagement panels 2022 can allow the clot to move easier.

The extractor 2020 can include an element 2026. The element 2026 can be an infinity loop. The element 2026 can be shaped as a figure eight. The element 2026 can be a double loop. The element 2026 can be shaped like the number 8. The element 2026 can have different geometries that are smaller or the same diameter as the engagement panel 2022 or substantially the diameter of the vessel. The geometries can be a double infinity loop, three or four panels configuration. The element 2026 can have a smaller diameter or cross-section compared with the engagement panel 2022. The element 2026 can have the same diameter or cross-section compared with the engagement panel 2022. The element 2026 can have the same diameter or cross-section compared with the diameter of the vessel. The element 2026 can comprise a single infinity loop. The element 2026 can comprise a double infinity loop. The element 2026 can comprise a single loop or helical segment. The element 2026 can comprise a single panel. The element 2026 can comprise a double panel. The element 2026 can comprise three panels. The element 2026 can comprise four panels. The element 2026 can have a different geometry than the engagement panel 2022. The element 2026 can function as a back stop for the clot in transit. The element 2026 can have a smaller lumen than the engagement panels 2022. The core wire 2029 can be off-centrally positioned relative to the engagement panels 2022. The core wire 2029 can be off-centrally positioned to maximize the lumen of the engagement panels 2022. The element 2026 can obstruct the lumen of the engagement panels 2022. The element 2026 can be formed from the continuous wire at the first longitudinal location. The element 2026 and the first array of engagement panels 2022 located at the first longitudinal location can be made from a continuous wire. The eyelet 2023 and the first array of engagement panels 2022 located at the first longitudinal location can be made from a continuous wire. The eyelet 2023 and the element 2026 can be made from a continuous wire. The element 2026, the eyelet 2023, and the first array of engagement panels 2022 located at the first longitudinal location can be made from a continuous wire. The element 2026 can be formed separately from the engagement panels 2022 at the first longitudinal location. The element 2026 can be formed separately from the eyelet 2023. The extractor can include a second continuous wire. The eyelet 2023 and the second array of engagement panels 2022 located at the second longitudinal location can be made from a second continuous wire.

The element 2026 can be distal to the engagement panels 2022 at the first longitudinal location. The element 2026 can obstruct the lumen of the engagement panels. The element 2026 can obstruct the distal end of the engagement panels. The element 2026 can prevent distal movement of material in some embodiments. The element 2026 can be a distal stop. The element 2026 can be a back stop for the material during transit in some embodiments. The element 2026 can allow pulling of the clot proximally in some embodiments. The element 2026 can consist of one element in some embodiments. The extractor 2020 can have only one element 2026. The element 2026 can be positioned between the engagement panels 2022 at the first longitudinal location and the distal member 2024.

The first array of engagement panels 2022 located at the first longitudinal location and the second array of engagement panels 2022 located at the second longitudinal location can collapse for loading into a sheath for delivery to the vascular. The first array of engagement panels 2022 located at the first longitudinal location can have a loading direction. The first array of engagement panels 2022 can collapse distally. The first array of engagement panels 2022 can have a loading direction that is distal. The first array of engagement panels 2022 can collapse toward the distal member 2024.

Figure 153:
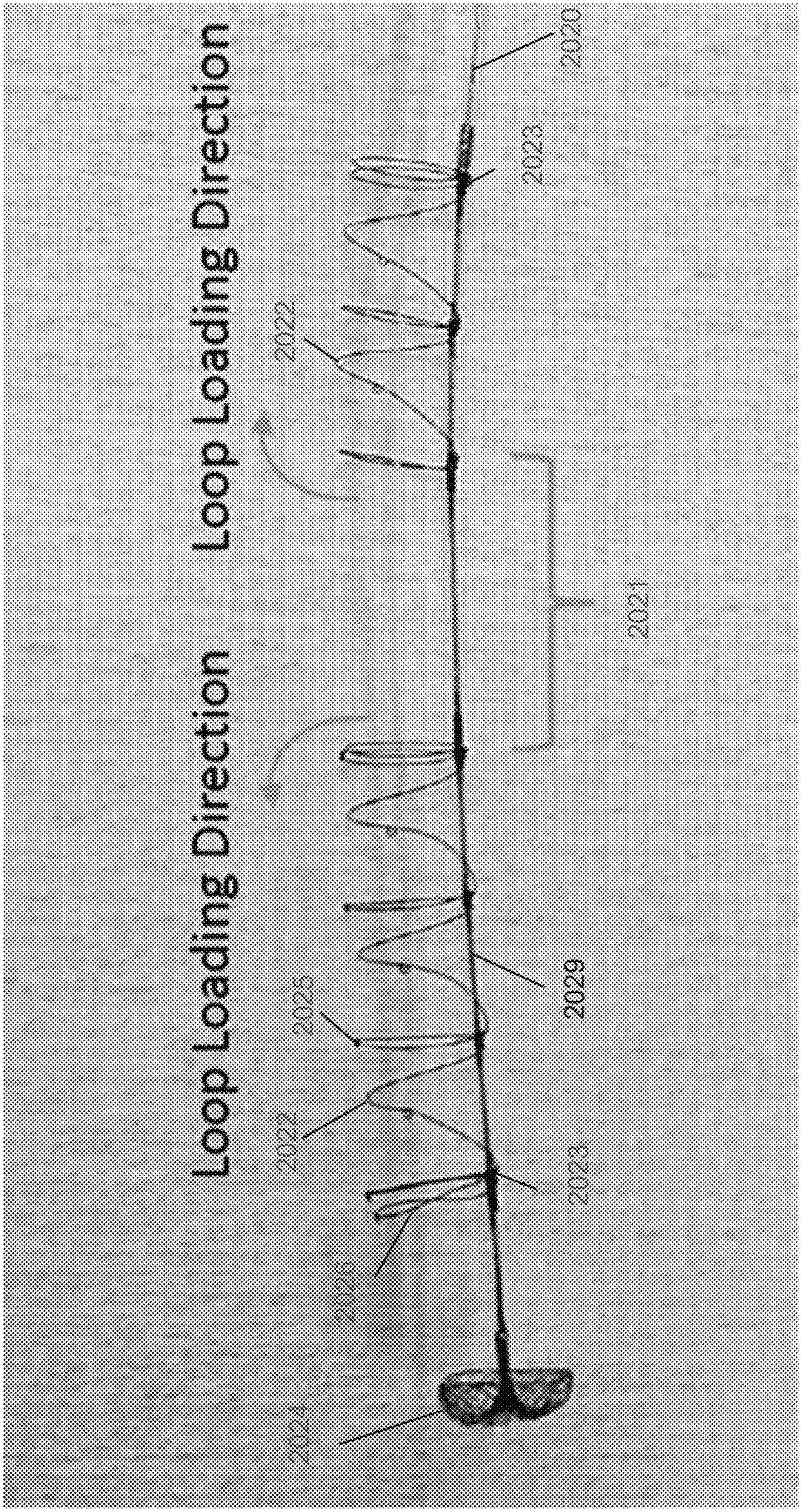

The second array of engagement panels 2022 located at the second longitudinal location can have a loading direction. In some embodiments, the second array of engagement panels 2022 located at the second longitudinal location can collapse proximally, as shown in FIG. 153. The second array of engagement panels 2022 can have a loading direction that is proximal. The second array of engagement panels 2022 can collapse way from the distal member 2024. The first array of engagement panels 2022 located at the first longitudinal location can have a loading direction that is opposite to the second array of engagement panels 2022 located at the second longitudinal location.

Figure 154:
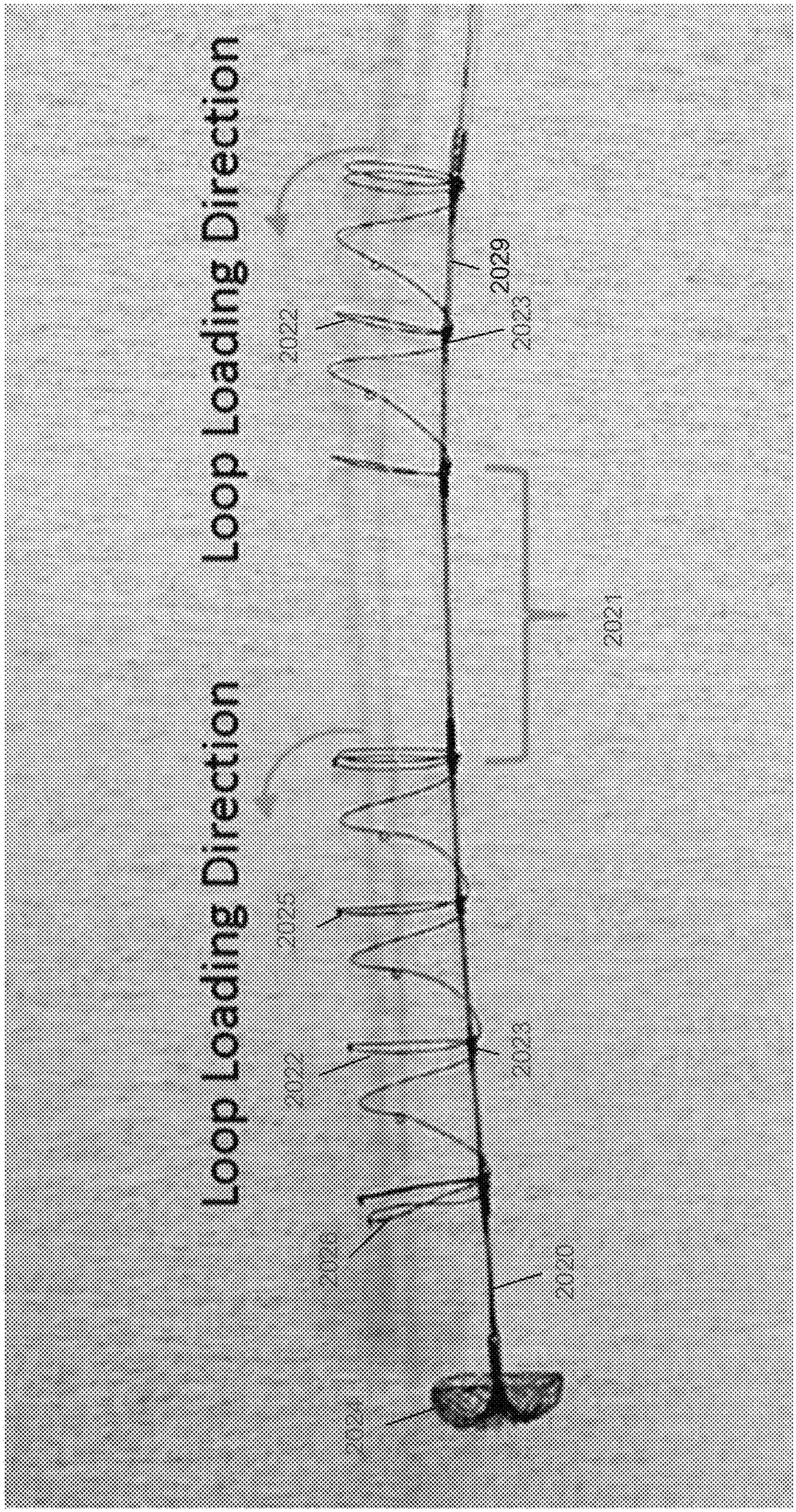

In some embodiments, the second array of engagement panels 2022 located at the second longitudinal location can collapse distally, as shown in FIG. 154. The first array of engagement panels 2022 can have a loading direction that is proximal. The first array of engagement panels 2022 located at the first longitudinal location can have a loading direction that is the same as the second array of engagement panels 2022 located at the second longitudinal location. The first array of engagement panels 2022 located at the first longitudinal location and the second array of engagement panels 2022 located at the second longitudinal location can collapse toward the distal member 2024.

In some embodiments, the engagement panels 2022 at the first longitudinal location can be positioned distal to the material. In some embodiments, the engagement panels 2022 at the second longitudinal location can be positioned proximal to the material. In some embodiments, the material can be positioned in the spacing 2021 between the engagement panels 2022 at the first longitudinal location and the engagement panels 2022 at the second longitudinal location. In some embodiments, the extractor can be retracted proximally. In some embodiments, the material can go into the lumen of the engagement panels 2022 at the first longitudinal location as the extractor is retracted. In some embodiments, the material can entangle with the engagement panels 2022 at the first longitudinal location during transit. In some embodiments, the material is stopped from distal movement by the element 2026. In some embodiments, the material is stopped from distal movement by the distal member 2024.

In some embodiments, the engagement panels 2022 at the first longitudinal location can invert. The engagement panels 2022 at the first longitudinal location can be collapsed distally for delivery. The engagement panels 2022 at the first longitudinal location can be collapsed distally with the vessel. The engagement panels 2022 at the first longitudinal location can be collapsed if the vessel is smaller in diameter than the engagement panels 2022. The engagement panels 2022 at the first longitudinal location can be collapsed longitudinally. The engagement panels 2022 at the first longitudinal location can be collapsed to point toward the distal member 2024. During retraction, the engagement panels 2022 at the first longitudinal location can invert to be collapsed proximally. The engagement panels 2022 at the first longitudinal location can change directions. The engagement panels 2022 at the first longitudinal location can sweep in an arc along the vessel wall. The engagement panels 2022 at the first longitudinal location can sweep the vessel wall. The engagement panels 2022 at the first longitudinal location can swing in an arc. The engagement panels 2022 at the first longitudinal location can initially be pointed distally and then be pointed proximally. The engagement panels 2022 at the first longitudinal location can be retracted while pointed proximally.

In some embodiments, the loading direction can impact material capture. The loading direction with the engagement panels 2022 at the first longitudinal location collapsed distally and the engagement panels 2022 at the second longitudinal location collapsed proximally can have certain advantages. The loading direction can facilitate sweeping of the vessel wall. The loading direction can facilitate disengagement of the material with the wall. The loading direction can facilitate moving the material toward the lumen of the engagement panels 2022. The loading direction can facilitate moving the material toward the spacing 2021 between the engagement panels 2022 at the first longitudinal location and the engagement panels 2022 at the second longitudinal location.

The element 2026 can stiffen the engagement panels 2022 at the first longitudinal location. The element 2026 can facilitate the inversion of the engagement panels 2022 at the first longitudinal location. The element 2026 can facilitate the scraping of the vessel wall as the extractor 2020 is retracted. The engagement panels 2022 at the first longitudinal location can be less prone to collapse when encountering material with the reinforcing element 2026. The engagement panels 2022 at the first longitudinal location can be less prone to collapse when scraping the vessel wall with the reinforcing element 2026. The engagement panels 2022 can include a plurality of panels at each longitudinal location. The engagement panels 2022 can include a plurality of helical segments at each longitudinal location. The element 2026 can be distal to the engagement panels 2022 located at the first location. The element 2026 can be positioned at the distalmost engagement panel 2022.

The extractor 2020 can be formed from a series of loop and/or helical segment element. In some embodiments, the length of the engagement panels 2022 located at the first location is fixed. In some embodiments, the length of spacing 2021 is fixed. In some embodiments, the length of the engagement panels 2022 located at the second location is fixed. In some embodiments, the location of the eyelets 2023 are fixed. In some embodiments, the location of the element 2026 is fixed. In some embodiments, the location of the distal member 2024 is fixed. The engagement panels 2022 located at the first longitudinal location is separated from the engagement panels 2022 at the second longitudinal location. The engagement panels 2022 located at the first longitudinal location is spaced longitudinally from the engagement panels 2022 at the second longitudinal location.

The extractor 2020 can include any feature described herein. The extractor 2020 can be used in any method described herein. The extractor 2020 can have advantages for dislodging material within a vessel. The extractor 2020 can have advantages for moving material toward a catheter for removal. The extractor 2020 can have advantages for preventing material from flowing downstream of the distal member 2024 and the loop element 2026. The extractor 2020 can have advantages for pinching the material. The extractor 2020 can have advantages for sweeping the material. The extractor 2020 can have advantages for securing the material radially. The extractor 2020 can have advantages for securing the material axially. The extractor 2020 can have advantages for moving the material from the second array of engagement panels 2022 to the space 2021 between the first array of engagement panels 2022 and the second array of engagement panels 2022. The extractor 2020 can have advantages for moving the material from the space 2021 between the first array of engagement panels 2022 and the second array of engagement panels 2022 to the lumen of the first array of engagement panels. The extractor 2020 can have advantages for moving the material into a lumen of the first array of engagement panels 2022. The extractor 2020 can have advantages wherein during retraction, the material can roll, migrate or move and reside in the space 2021. The extractor 2020 can have advantages wherein during retraction, the material can roll, migrate or move and reside in the lumen of the first array of engagement panels 2022. The extractor 2020 can have advantages wherein the first array of engagement panels 2022 encapsulates the material within its lumen and transports the material. Additional advantages are described herein.

Figure 155:
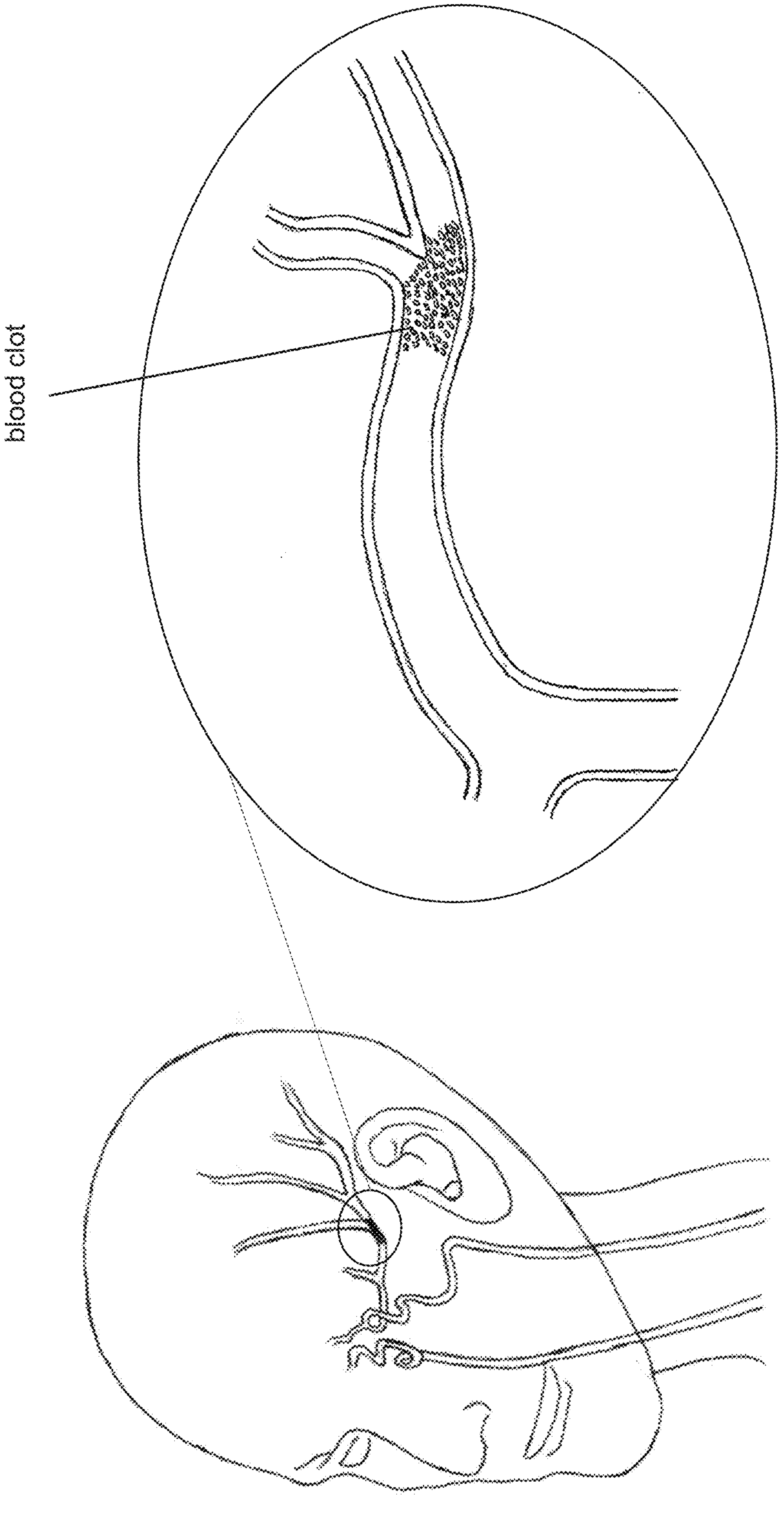
FIG. 155 is a view of the blood clot.

FIG. 155 is a view of the material. In some embodiments, the material can be a neurovascular blood clot. The material can be in a vessel of the brain. The material can be within a vessel of the nervous system. The material can be solid. The material can be hardened. The material can be semi-solid. The material can be an aggregated mass from one or more components of the blood. The material can include one or more of the following: platelets, fibrin, red blood cells, and/or white blood cells. The material can include a fatty deposit. The material can have different morphologies. The material can include coagulated blood. In some embodiments, the material can be located within any portion of the circulatory system. The material can be a microclot. The material can be a thrombus that forms in a vessel of the brain. The material can be an embolus that forms elsewhere and travels to a vessel of the brain. The material can be any clot. In some embodiments, the patient can be a candidate for mechanical thrombectomy. The devices described herein can be used to physically remove the material from the vessel. In some embodiments, the devices described herein can be designed for removal of material within a neurovascular vessel. In some embodiments, the devices described herein can be designed for removal of material within any vessel. In some embodiments, the devices described herein can be designed for removal of material from any bodily lumen.

Figure 157:
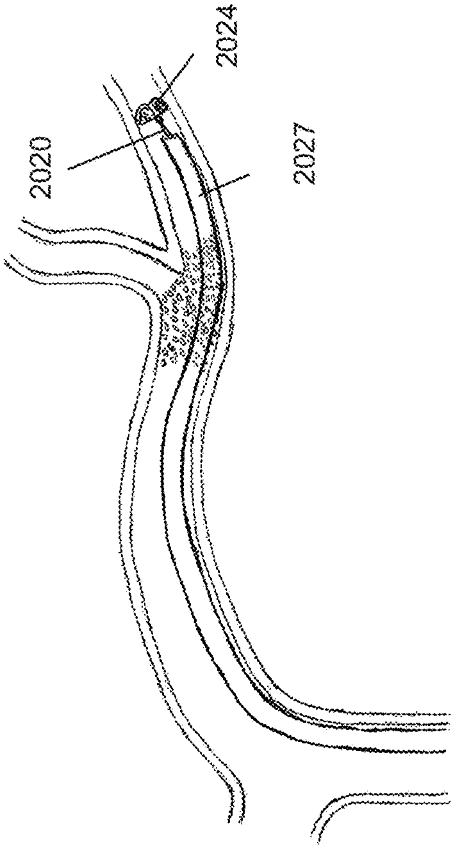
FIGS. 156-157 are views of a method of deploying the extractor.
Figure 156:
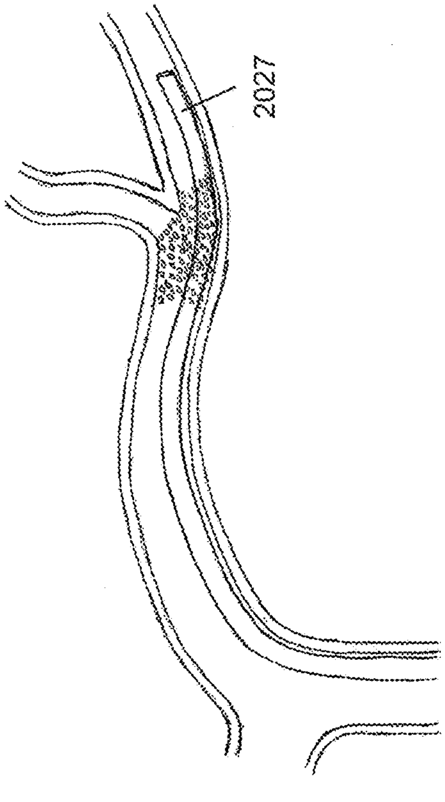
Figure 159:
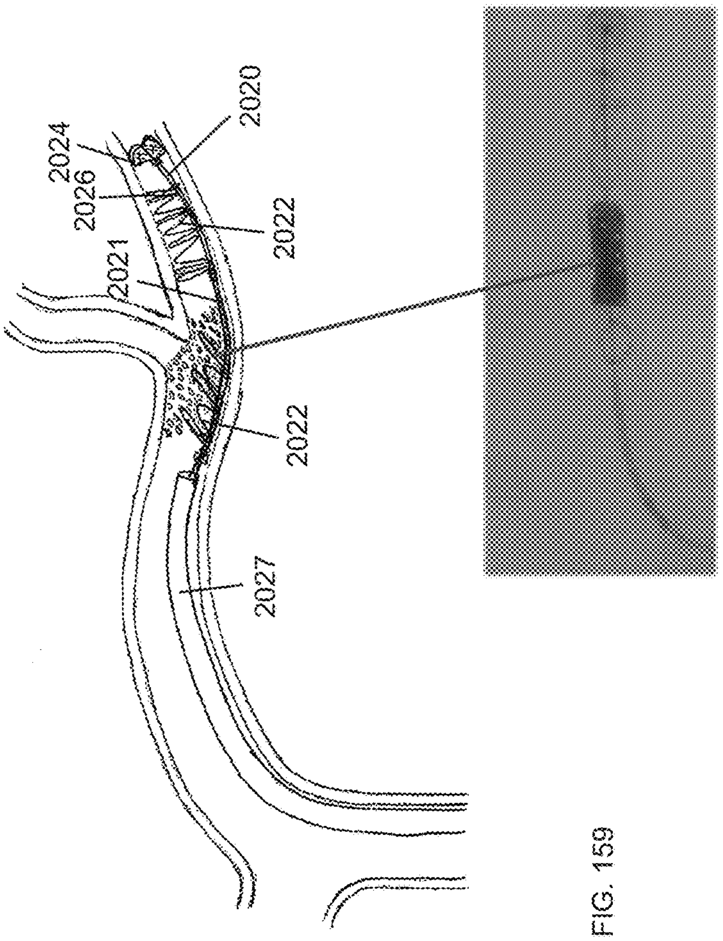
FIGS. 158-161 are views of a method of deploying the extractor.
Figure 158:
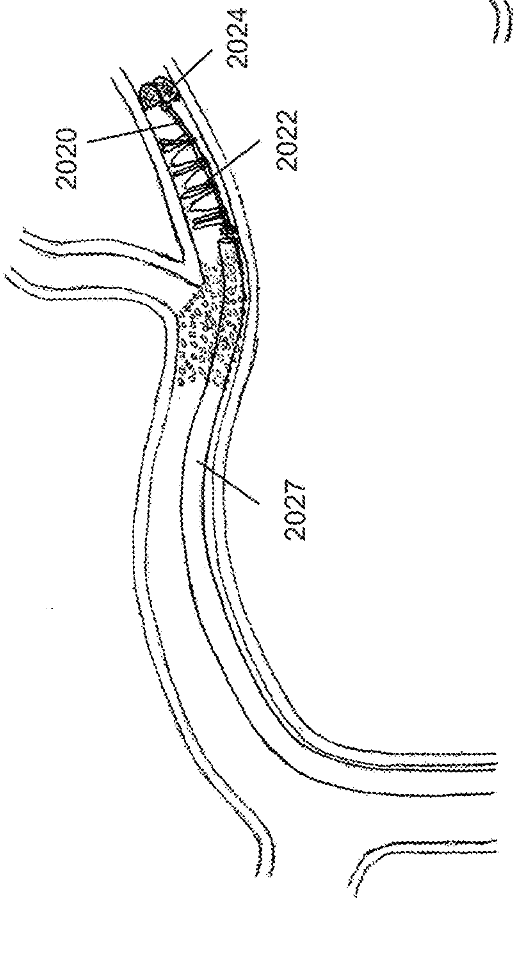
Figure 161:
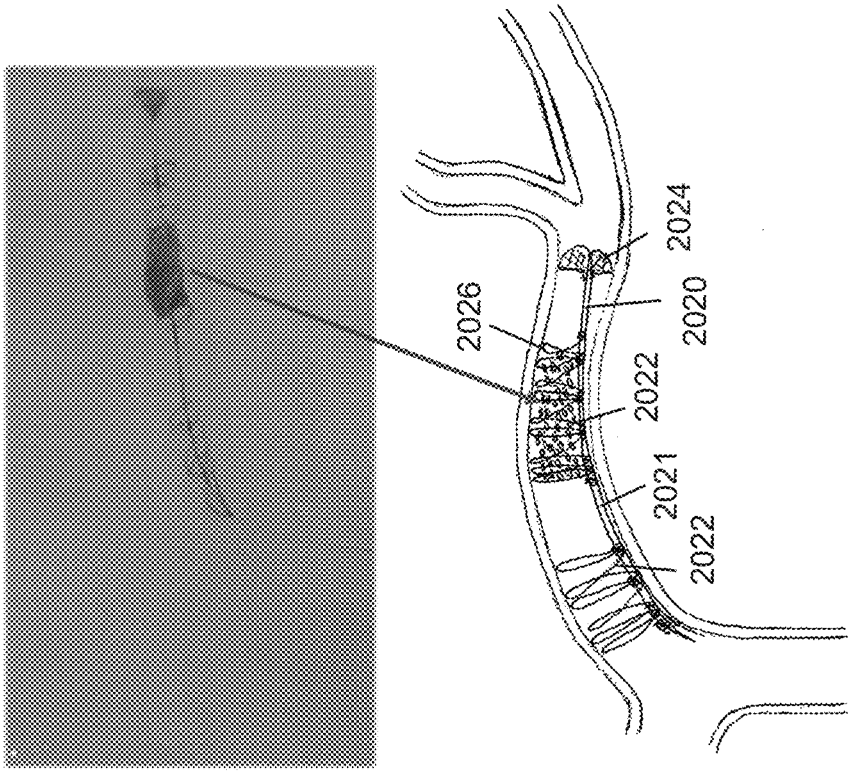
Figure 160:
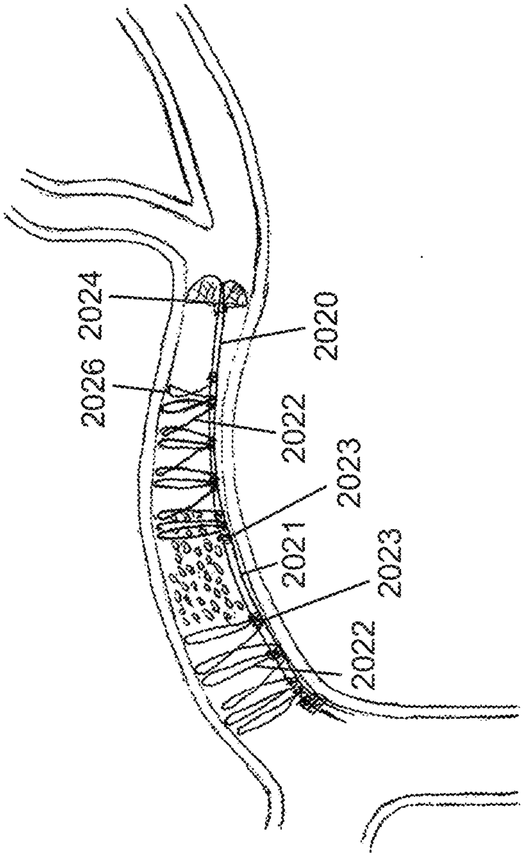
Figure 163:
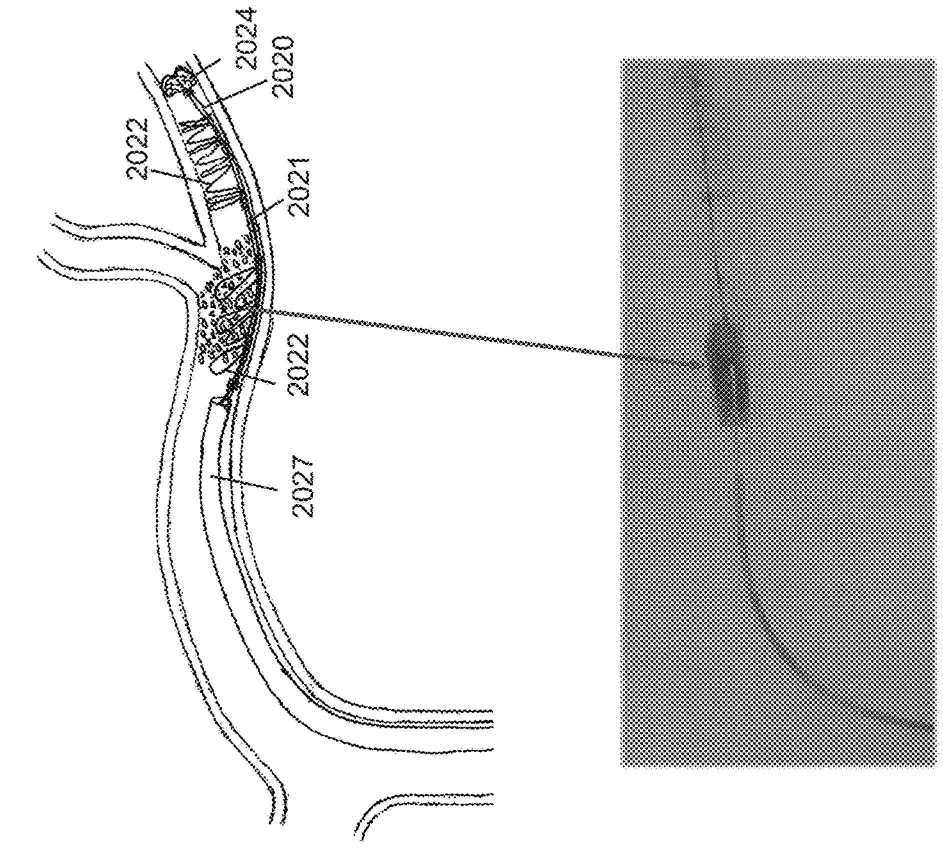
FIGS. 162-165 are views of a method of deploying the extractor.
Figure 162:
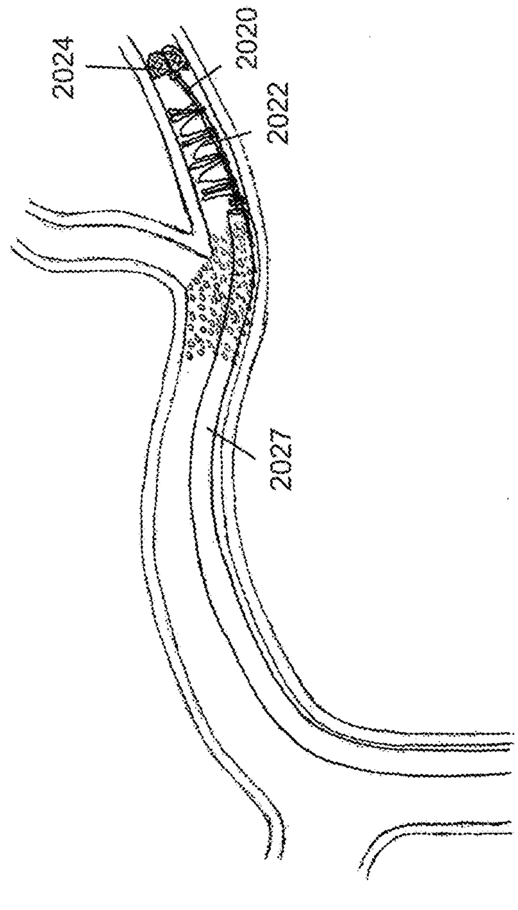
Figure 165:
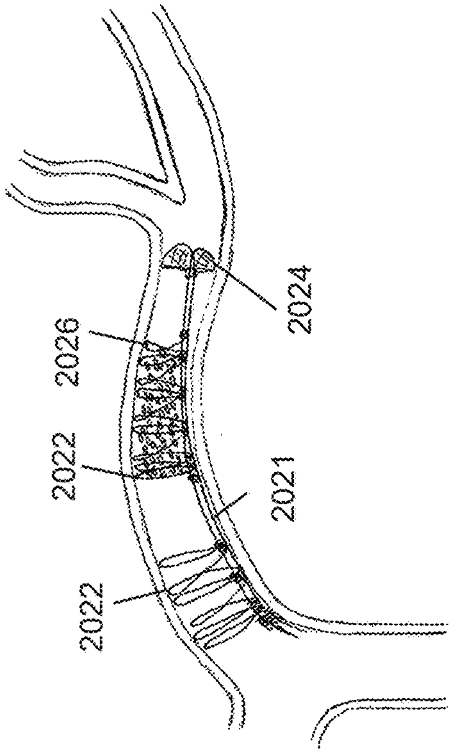
Figure 164:
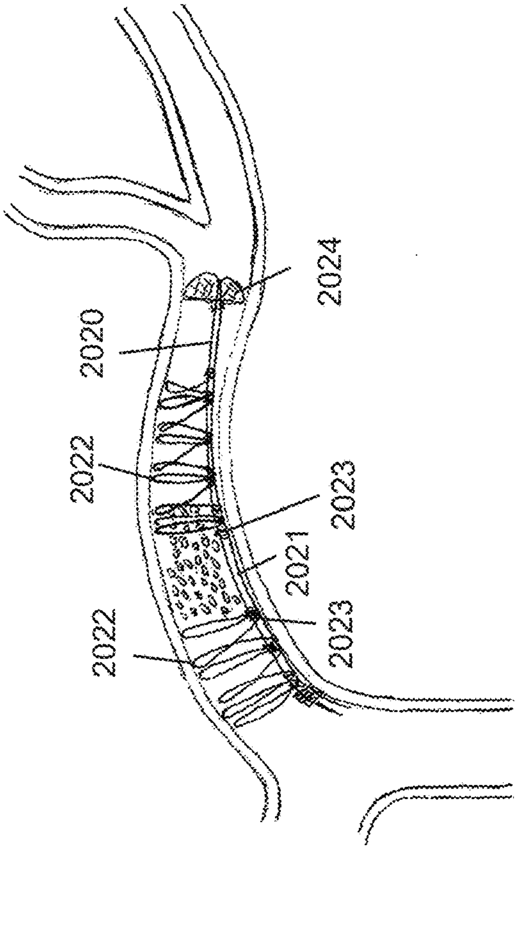
Figure 167:
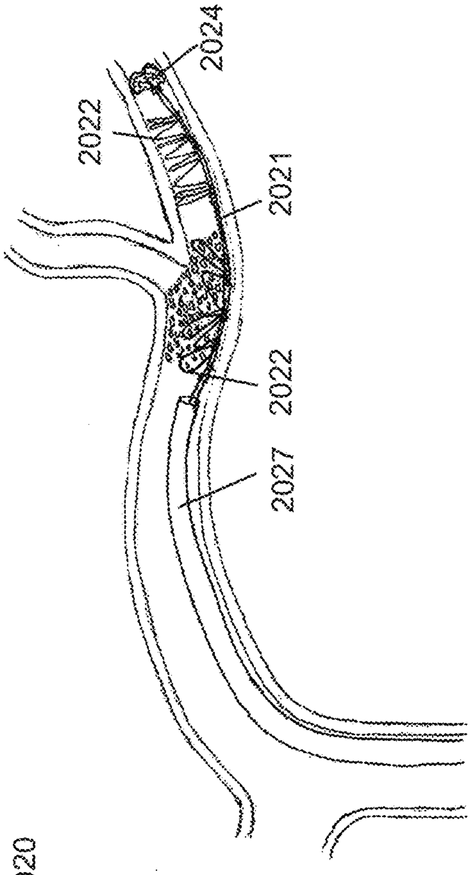
FIGS. 166-169 are views of a method of deploying the extractor.
Figure 166:
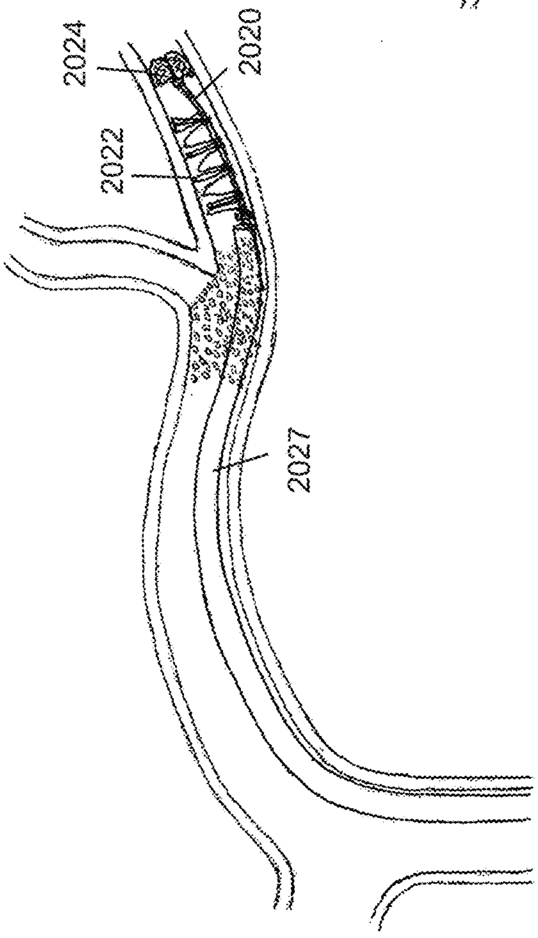
Figure 168:
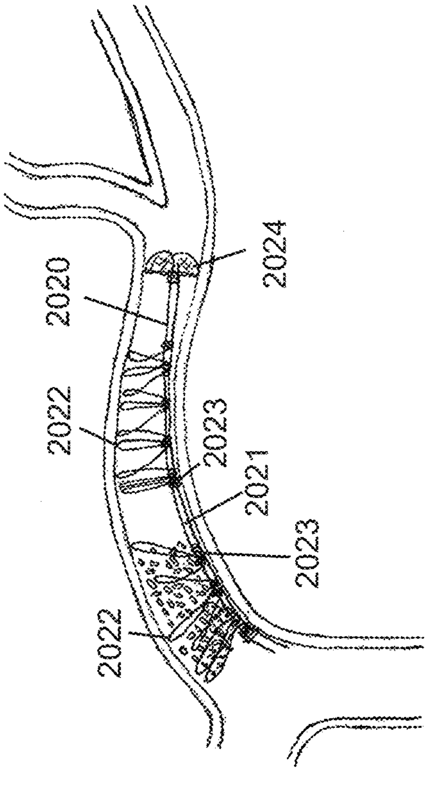
Figure 169:
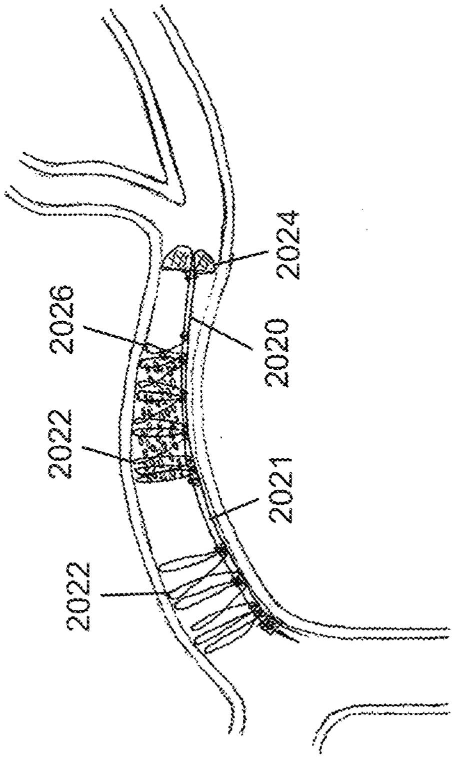

FIGS. 156-157 are views of a method of deploying the extractor. The microcatheter 2027 can be positioned within the vessel. In some embodiments, the microcatheter 2027 is positioned within a neurovascular vessel. The neurovascular vessels can be small capillaries ranging from 2 μm to 5 μm. The neurovascular vessels can be larger arteries with a diameter approximately 4.75 mm, or in some cases about, at least about, or no more than 0.5 mm, 1 mm, 1.5 mm, 2 mm, 2.5 mm, 3 mm, 3.5 mm, 4 mm, 4.5 mm, 5 mm, 5.5 mm, 6 mm, or ranges including any two of the foregoing values. In some embodiments, the blood continues to flow relative to the microcatheter 2027. The microcatheter 2027 can be smaller in diameter than the vessel. In some embodiments, the microcatheter 2027 extends through the material. In some embodiments, the microcatheter 2027 extends past the material. In some embodiments, the microcatheter 2027 is positioned such that the opening of the catheter is distal to the material.

In some embodiments, the extractor 2020 is deployed from the microcatheter 2027. While extractor 2020 is illustrated, the microcatheter 2027 can deploy any extractor described herein. In some embodiments, the microcatheter 2027 is retracted to deploy the extractor 2020. In some embodiments, the extractor 2020 is pushed distally relative to the microcatheter 2027 to deploy. The extractor 2020 can extend from the microcatheter 2027. The distal member 2024 can be deployed. In some embodiments, the distal member 2024 can invert during deployment. In some embodiments, the distal member 2024 can invert to sweep against the vessel wall. The distal member 2024 can extend backwards toward the microcatheter 2027 once deployed. The distal member 2024 can open to a diameter greater than the microcatheter 2027. The distal member 2024 can open to a diameter equal to the diameter of the vessel. The distal member 2024 can rest against the vessel wall. The distal member 2024 can open to a diameter greater than the diameter of the vessel. The distal member 2024 can slightly expand the diameter of the vessel. The distal member 2024 can open to a vessel diameter smaller than its expanded diameter. The distal member 2024 can push outward against the vessel wall. The distal member 2024 can be porous. The blood can continue to flow through the vessel when the distal member 2024 is deployed. The blood can flow through the distal member 2024.

Referring back to FIGS. 151-154, the extractor 2020 can have any feature described herein. The extractor 2020 can include engagement panels 2022. The engagement panels 2022 can form one or more loops. The engagement panels 2022 can form one or more helixes. Each engagement panel 2022 can extend in a 360-degree shape. Each engagement panel 2022 can form a closed loop. Each engagement panel 2022 can begin and end at the same location. Each engagement panel 2022 can form an open loop. Each engagement panel 2022 can begin and end at an offset location. Each engagement panel 2022 can form a loop. Each engagement panel 2022 can form a helix. The engagement panels 2022 can be fixed in location. The engagement panels 2022 can be fixed at the eyelet 2023. The engagement panels 2022 can be fixed to a core wire 2029. The engagement panels 2022 can be fixed to a supporting structure. Each engagement panel 2022 can have one fixed point. Each engagement panel 2022 can be fixed at a single location along the core wire 2029. The engagement panels 2022 can have limited movement relative to the core wire 2029. The portion of the engagement panels 2022 not fixed to the core wire 2029 can rotate proximally. The portion of the engagement panels 2022 not fixed to the core wire 2029 can rotate distally. The engagement panels 2022 can have any number of panels at each location. The engagement panels 2022 can have two, three, four or more panels at each location. The engagement panels 2022 can form loops or helixes. The engagement panels 2022 can include the element 2026. The element 2026 can form an obstruction to the flow of material.

FIGS. 158-161 illustrate deployment of the extractor 2020. The engagement panels 2022 can open to a diameter greater than the diameter of the microcatheter 2027. The engagement panels 2022 can open to a diameter equal or substantially equal to the diameter of the vessel. The engagement panels 2022 can rest against the vessel wall. The engagement panels 2022 can open to a diameter greater than the diameter of the vessel. The engagement panels 2022 can be expanded in a smaller vessel diameter smaller. The engagement panels 2022 can slightly expand the diameter of the vessel. The engagement panels 2022 can push outward against the vessel wall. The engagement panels 2022 can have a diameter equal or substantially equal to the diameter of the distal member 2024. The engagement panels 2022 can have a diameter greater than the diameter of the distal member 2024. The engagement panels 2022 can have a diameter less than the diameter of the distal member 2024. The engagement panels 2022 can include a lumen. The blood can continue to flow through the vessel when the engagement panels 2022 are deployed. The blood can flow through the lumen of the engagement panels 2022.

The engagement panels 2022 can be configured to interact with the material. The engagement panels 2022 can function to pinch material. The engagement panels 2022 can function to sweep distally in the direction of the distal member 2024. The engagement panels 2022 can function to sweep proximally in the direction of the microcatheter 2027. The engagement panels 2022 can function to sweep toward the core wire 2029. The engagement panels 2022 can function to sweep away from the core wire 2029. The engagement panels 2022 can function to sweep toward the vessel wall. The engagement panels 2022 can function to squeeze the material. The engagement panels 2022 can function to compress the material. The engagement panels 2022 can function to grasp the material. The engagement panels 2022 can function to entangle with the material. The engagement panels 2022 can function to anchor the material during transit. The engagement panels 2022 can function to encapsulate the material and during transit. The engagement panels 2022 can function to store the material within the lumen of the engagement panels 2022. The engagement panels 2022 can function to transport the material within the lumen of the engagement panels 2022. The engagement panels 2022 can function to encircle the material. The engagement panels 2022 can function to surround the material. The engagement panels 2022 can function to capture the material. The engagement panels 2022 can function to move the material. The engagement panels 2022 can function to roll the material. The engagement panels 2022 can function to scrape against the vessel wall. The engagement panels 2022 can function to sweep distally when retracted. The engagement panels 2022 can function to sweep proximally when retracted. The engagement panels 2022 can function to sweep relative to a fixed point on the core wire 2029 when retracted. The engagement panels 2022 can function to pivot relative to a fixed point on the core wire 2029 when retracted.

The engagement panels 2022 can include a first array at a first longitudinal location. The engagement panels 2022 at the first longitudinal location can be formed from a continuous wire. The engagement panels 2022 at the first longitudinal location can be fixed to the core wire 2029. The engagement panels 2022 at the first longitudinal location can be fixed to the core wire 2029 at the eyelets 2023. The engagement panels 2022 at the first longitudinal location can be fixed at two or more locations along the core wire 2029. The engagement panels 2022 at the first longitudinal location can be fixed at each engagement panel. The engagement panels 2022 at the first longitudinal location can be fixed at each loop of the engagement panels. The engagement panels 2022 at the first longitudinal location can be fixed at every other loop of the engagement panels. The engagement panels 2022 at the first longitudinal location can be fixed at least at the first loop and last loop of the engagement panels. The engagement panels 2022 at the first longitudinal location can be fixed to the core wire 2029 at each eyelet 2023. Each eyelet 2023 can be fixed in location relative to the core wire 2029. The engagement panels 2022 at the first longitudinal location can function to sweep relative to the eyelet 2023. The engagement panels 2022 at the first longitudinal location can function to pivot relative to the eyelet 2023.

The engagement panels 2022 can include a second array at a second longitudinal location. The engagement panels 2022 at the second longitudinal location can be formed from a continuous wire. The engagement panels 2022 at the second longitudinal location can be fixed to the core wire 2029. The engagement panels 2022 at the second longitudinal location can be fixed to the core wire 2029 at the eyelets 2023. The engagement panels 2022 at the second longitudinal location can be fixed at two or more locations along the core wire 2029. The engagement panels 2022 at the second longitudinal location can be fixed at each engagement panel. The engagement panels 2022 at the second longitudinal location can be fixed at each loop of the engagement panels. The engagement panels 2022 at the second longitudinal location can be fixed at every other loop of the engagement panels. The engagement panels 2022 at the second longitudinal location can be fixed at least at the first loop and last loop of the engagement panels. The second array of engagement panels can be one, two, three, four or more engagement panels 510, 512, 514, 516. The engagement panels 2022 at the second longitudinal location can be fixed to the core wire 2029 at each eyelet 2023. Each eyelet 2023 can be fixed in location relative to the core wire 2029. The engagement panels 2022 at the second longitudinal location can function to sweep relative to the eyelet 2023. The engagement panels 2022 at the second longitudinal location can function to pivot relative to the eyelet 2023. In some embodiments, the first array of engagement panels can be two, three, four, or more engagement panels and the second array of engagement panels can include loops and helixes.

The engagement panels 2022 can include a third array at a third longitudinal location. The engagement panels 2022 at the third longitudinal location can be formed from a continuous wire. The engagement panels 2022 at the third longitudinal location can be fixed to the core wire 2029. The engagement panels 2022 at the third longitudinal location can be fixed to the core wire 2029 at the eyelets 2023. The engagement panels 2022 at the third longitudinal location can be fixed at two or more locations along the core wire 2029. The engagement panels 2022 at the third longitudinal location can be fixed at each engagement panel. The engagement panels 2022 at the third longitudinal location can be fixed at each loop of the engagement panels. The engagement panels 2022 at the third longitudinal location can be fixed at every other loop of the engagement panels. The engagement panels 2022 at the third longitudinal location can be fixed at least at the first loop and last loop of the engagement panels. Each eyelet 2023 can be fixed in location relative to the core wire 2029. The engagement panels 2022 at the third longitudinal location can function to sweep relative to the eyelet 2023. The engagement panels 2022 at the third longitudinal location can function to pivot relative to the eyelet 2023.

The extractor 2020 can include the spacing 2021. The spacing 2021 can be located between the engagement panels 2022 at the first longitudinal location and the engagement panels 2022 at the second longitudinal location. The spacing 2021 can be located between the engagement panels 2022 at the second longitudinal location and the engagement panels 2022 at the third longitudinal location. The spacing 2021 can be free from engagement panels. The spacing 2021 can extend from a fixed location of the engagement panels 2022 at the first longitudinal location and a fixed location of the engagement panels 2022 at the second longitudinal location. The spacing 2021 can extend from an eyelet 2023 of the engagement panels 2022 at the first longitudinal location and an eyelet 2023 the engagement panels 2022 at the second longitudinal location. The spacing 2021 can extend from the proximal eyelet 2023 of the engagement panels 2022 at the first longitudinal location and the distal eyelet 2023 of the engagement panels 2022 at the second longitudinal location. The spacing 2021 can have a fixed length. The spacing 2021 can be approximately equal to the diameter of the engagement panels 2022. The spacing 2021 can be greater than the diameter of the engagement panels 2022. The spacing 2021 can be less than the diameter of the engagement panels 2022. The spacing 2021 that is located between the engagement panels 2022 at the first longitudinal location and the engagement panels 2022 at the second longitudinal location can have the same length as the spacing 2021 that is located between the engagement panels 2022 at the second longitudinal location and the engagement panels 2022 at the third longitudinal location. The spacing 2021 that is located between the engagement panels 2022 at the first longitudinal location and the engagement panels 2022 at the second longitudinal location can have a different length as the spacing 2021 that is located between the engagement panels 2022 at the second longitudinal location and the engagement panels 2022 at the third longitudinal location. The engagement panels 2022 at the first longitudinal location can form the distal end of the spacing 2021. The engagement panels 2022 at the second longitudinal location can form the proximal end of the spacing 2021.

The spacing 2021 can form a central loading zone. The spacing 2021 can form a loading location for the material. The material can be positioned within the spacing 2021 upon deployment of the extractor 2020. The material can be positioned proximally to the spacing 2021 upon deployment of the extractor 2020. The material can be positioned distally to the spacing 2021 upon deployment of the extractor 2020. The material can be positioned within the spacing 2021 upon retraction. The material can be positioned within the spacing 2021 upon movement of the material by the engagement panels 2022 at the second longitudinal location. The material can be positioned within the spacing 2021 between the engagement panels 2022 at the first longitudinal location and the engagement panels 2022 at the second longitudinal location. The spacing 2021 can form a chamber to receive the material. The spacing 2021 can be hollow. The spacing

2021 can form a pocket. The spacing 2021 can form a gap between the engagement panels 2022 at the first longitudinal location and the engagement panels 2022 at the second longitudinal location. The spacing 2021 can separate the engagement panels 2022 at the first longitudinal location and the engagement panels 2022 at the second longitudinal location. The engagement panels 2022 at the first longitudinal location and the engagement panels 2022 at the second longitudinal location can be spaced apart by the spacing 2021. The blood can continue to flow through the vessel when the engagement panels 2022 are deployed. The blood can flow through the lumen of the spacing 2021

FIGS. 158-161 are views of a method of deploying the extractor. The engagement panels 2022 at the first longitudinal location can be deployed. The engagement panels 2022 at the first longitudinal location can be deployed distal to the material. The engagement panels 2022 at the first longitudinal location can be engaged with the vessel wall. The engagement panels 2022 at the first longitudinal location can be upright. The engagement panels 2022 at the first longitudinal location can be perpendicular to the core wire 2029. The microcatheter 2027 can be within the material. The engagement panels 2022 at the second longitudinal location can be within the microcatheter 2027. The engagement panels 2022 at the second longitudinal location can be distally facing within the microcatheter 2027. The engagement panels 2022 at the second longitudinal location can be compressed toward the distal direction. The engagement panels 2022 at the second longitudinal location can be loaded distally facing during delivery.

The microcatheter 2027 can be retracted. The microcatheter 2027 can be retracted to deploy the engagement panels 2022 at the second longitudinal location. The engagement panels 2022 at the second longitudinal location can be deployed when exiting the microcatheter 2027. The engagement panels 2022 at the second longitudinal location can be deployed within the material. The engagement panels 2022 at the second longitudinal location can be angled relative to the core wire 2029. The engagement panels 2022 at the second longitudinal location can be deployed in a non-inverted state. The engagement panels 2022 at the second longitudinal location can be deployed distally facing.

The extractor can be retracted. During retraction, the engagement panels 2022 at the second longitudinal location pivot relative to their fixed location. The extractor can be retracted to fully deploy the engagement panels 2022 at the second longitudinal location. The extractor can be retracted to cause the engagement panels 2022 at the second longitudinal location to pivot. The extractor can be retracted which causes the material to migrate distally. The extractor can be retracted to cause the engagement panels 2022 at the second longitudinal location to become proximal to the material. The extractor can be retracted to cause the engagement panels 2022 at the second longitudinal location to sweep proximally. The engagement panels 2022 at the second longitudinal location can rotate toward the vessel wall. The engagement panels 2022 at the second longitudinal location can be engaged with the vessel wall. The engagement panels 2022 at the second longitudinal location can be perpendicular to the core wire 2029. The engagement panels 2022 at the second longitudinal location can rotate relative to the fixed location on the core wire 2029. The engagement panels 2022 at the second longitudinal location can rotate from a distally angled position to a perpendicular position. The engagement panels 2022 at the second longitudinal location can rotate as the extractor is retracted. The engagement panels 2022 at the second longitudinal location can sweep upward. The engagement panels 2022 at the second longitudinal location can pivot to be upright. The engagement panels 2022 at the second longitudinal location can be upright as the extractor is retracted. The engagement panels 2022 at the second longitudinal location can rotate up to relatively 180 degrees. The engagement panels 2022 at the second longitudinal location can be deployed in manner in which the engagement panels do not invert proximally. The engagement panels 2022 at the second longitudinal location can rotate from a distal facing orientation to a perpendicular orientation. The engagement panels 2022 at the second longitudinal location can be limited from inverting to a proximal facing orientation. In some embodiments, the second array of engagement panels 2022 are configured to compress the material toward the vessel wall. In some embodiments, the second array of engagement panels 2022 are configured to compress the material into a compact shape for transportation. In some embodiments, the second array of engagement panels 2022 are configured to compress the material by decreasing the volume of material. In some embodiments, the second array of engagement panels 2022 are configured to disengage the material from a vessel wall. In some embodiments, the second array of engagement panels 2022 are configured to sweep the material toward the space 2021 when the extractor is retracted.

The engagement panels 2022 at the second longitudinal location can be deployed within the material. The engagement panels 2022 at the second longitudinal location can be distally facing within the material. The material can be retained by the engagement panels 2022 at the second longitudinal location as the extractor is retracted. In some embodiments, the extractor can be retracted which causes the engagement panels 2022 at the second longitudinal location to pivot to an orientation proximal to the material. In some embodiments, during retraction, the material can roll, migrate, or move. In some embodiments, the material can move toward the space 2021 when the extractor is retracted. The material can be retained within the space 2021 as the extractor is retracted. In some embodiments, the material can move toward the engagement panels 2022 at the first longitudinal location when the extractor is retracted. In some embodiments, the material can move distally as the extractor is retracted. The material can move within the space 2021. The material can move within the lumen of the engagement panels 2022 at the first longitudinal location. The material can be stopped by the element 2026. The material can be retained within the lumen of the engagement panels 2022 at the first longitudinal location as the extractor is retracted. While not bound by a theory, the material may roll or migrate depending on the morphological features of the material. While not bound by a theory, the material may remain stationary as the extractor is retracted until pushed proximally by the element 2026. The element 2026 can function as a closed end of the lumen of the engagement panels 2022 at the first longitudinal location. The element 2026 can obstruct distal movement of the material. The distal member 2024 can function as a closed end of the lumen of the engagement panels 2022 at the first longitudinal location. The distal member 2024 can obstruct further distal movement of the material. The material can be retracted with the retraction of the extractor. The distal facing engagement panels 2022 at the second longitudinal location can facilitate retraction of the material by entangling with the material. The distal facing engagement panels 2022 at the second longitudinal location can facilitate retraction of the material by sweeping proximally toward an upright position. The distal facing engagement panels 2022 at the second longitudinal location can facilitate retraction of the material by pinching the clot toward the space 2021.

The engagement panels 2022 at the second longitudinal location can loaded distally facing. The engagement panels 2022 at the second longitudinal location can be collapsed within the microcatheter 2027 to be distally facing. The extractor can include one or more of the following features. The extractor can include a first array of engagement panels 2022. The first array of engagement panels 2022 can define a lumen. The first array of engagement panels 2022 can define a lumen with an open end. The open end of the first array of engagement panels 2022 can be the proximal end. The open end of the first array of engagement panels 2022 can be near the spacing 2021. The first array of engagement panels 2022 can define a lumen with an enclosure or closed end. The element 2026 can form the closed end. The element 2026 can have a smaller diameter than the engagement panels 2022. The element 2026 can be positioned distally. The closed end of the first array of engagement panels 2022 can be the distal end.

The extractor can include a second array of engagement panels 2022. The second array of engagement panels 2022 can define a lumen. The second array of engagement panels 2022 can define a lumen with two open ends. The open end of the second array of engagement panels 2022 can be near the spacing 2021. The second array of engagement panels 2022 can collapse in the first configuration. The second array of engagement panels 2022 can collapse for delivery. The second array of engagement panels 2022 can collapse within the microcatheter 2027. The second array of engagement panels 2022 can collapse in a predetermined orientation. The second array of engagement panels 2022 can collapse to be distally facing. The second array of engagement panels 2022 can deploy in a second configuration. The second array of engagement panels 2022 can expand within the material in the second configuration.

The extractor can include the space 2021 between the first array of engagement panels 2022 and the second array of engagement panels 2022. In some embodiments, the material can reside within the space between the first array of engagement panels and second array of engagement panels.

In some embodiments, the open end of the first array of engagement panels 2022 can be configured to engulf the material. In some embodiments, the material remains within the first array of engagement panels 2022. In some embodiments, when expanded within the blood vessel, the first array of engagement panels 2022 is configured to be positioned distal to the material. In some embodiments, when expanded within the blood vessel, the second array of engagement panels is configured to be positioned within the material. In some embodiments, when expanded within the blood vessel, the first array of engagement panels 2022 and the second array of engagement panels 2022 are configured to engage the material between the first array of engagement panels and the second array of engagement panels. In some embodiments, upon retraction of the extractor 2020 to remove the material, the second array of engagement panels 2022 are configured to act independently. In some embodiments, upon retraction of the extractor 2020 to remove the material, the second array of engagement panels 2022 are configured not stretch or elongate under tension. In some embodiments, upon retraction of the extractor 2020 to remove the material, the second array of engagement panels 2022 are configured to secure the material during transit. In some embodiments, upon retraction of the extractor to remove the thrombus, the material can reside in the space 2021 between the first array of engagement panels and the second array of engagement panels thus securing the thrombus during transit. In some embodiments, upon retraction of the extractor 2020 to remove the material, the first array of engagement panels 2022 are configured to act independently. In some embodiments, upon retraction of the extractor 2020 to remove the material, the first array of engagement panels 2022 are configured not stretch or elongate under tension. In some embodiments, upon retraction of the extractor 2020 to remove the material, the first array of engagement panels 2022 can engulf the material. In some embodiments, upon retraction of the extractor 2020 to remove the material, the material remains in the lumen of the first array of engagement panels 2022.

In some embodiments, the second array of engagement panels 2022 are configured to engulf the material. In some embodiments, the second array of engagement panels 2022 are configured to pinch the material radially. In some embodiments, the first array of engagement panels 2022 are configured to pinch the material. In some embodiments, the second array of engagement panels 2022 collapse facing distally in the delivery configuration. In some embodiments, the first array of engagement panels 2022 collapse facing distally in the delivery configuration.

FIGS. 162-165 are views of a method of deploying the extractor. The engagement panels 2022 at the first longitudinal location can be deployed. The engagement panels 2022 at the first longitudinal location can be deployed distal to the material. The engagement panels 2022 at the first longitudinal location can be engaged with the vessel wall. The engagement panels 2022 at the first longitudinal location can be upright. The engagement panels 2022 at the first longitudinal location can be perpendicular to the core wire 2029. The microcatheter 2027 can be within the material. The engagement panels 2022 at the second longitudinal location can be within the microcatheter 2027. The engagement panels 2022 at the second longitudinal location can be proximally facing within the microcatheter 2027. The engagement panels 2022 at the second longitudinal location can be compressed toward the proximal direction. The engagement panels 2022 at the second longitudinal location can be loaded proximally facing during delivery. The engagement panels 2022 at the second longitudinal location can be inverted.

The microcatheter 2027 can be retracted. The microcatheter 2027 can be retracted to deploy the engagement panels 2022 at the second longitudinal location. The engagement panels 2022 at the second longitudinal location can be deployed. The engagement panels 2022 at the second longitudinal location can be deployed within the material. The engagement panels 2022 at the second longitudinal location can be angled relative to the core wire 2029. The engagement panels 2022 at the second longitudinal location can be deployed in an inverted state. The engagement panels 2022 at the second longitudinal location can be deployed proximally facing.

The extractor can be retracted. During retraction, the engagement panels 2022 at the second longitudinal location pivot relative to their fixed location. The extractor can be retracted to fully deploy the engagement panels 2022 at the second longitudinal location. The extractor can be retracted to cause the engagement panels 2022 at the second longitudinal location to pivot. The extractor can be retracted which causes the material to migrate distally. The extractor can be retracted to cause the engagement panels 2022 at the second longitudinal location to become proximal to the material. The extractor can be retracted to cause the engagement panels 2022 at the second longitudinal location to sweep distally. The engagement panels 2022 at the second longitudinal location can rotate toward the vessel wall. The engagement panels 2022 at the second longitudinal location can be engaged with the vessel wall. The engagement panels 2022 at the second longitudinal location can be perpendicular to the core wire 2029. The engagement panels 2022 at the second longitudinal location can rotate relative to the fixed location on the core wire 2029. The engagement panels 2022 at the second longitudinal location can rotate from a proximally angled position to a perpendicular position. The engagement panels 2022 at the second longitudinal location can rotate as the extractor is retracted. The engagement panels 2022 at the second longitudinal location can sweep upward. The engagement panels 2022 at the second longitudinal location can pivot to be upright. The engagement panels 2022 at the second longitudinal location can be upright as the extractor is retracted. The engagement panels 2022 at the second longitudinal location can rotate up to relatively 180 degrees. The engagement panels 2022 at the second longitudinal location can be deployed in manner in which the engagement panels invert. The engagement panels 2022 at the second longitudinal location can rotate from a proximal facing orientation to a perpendicular orientation. The engagement panels 2022 at the second longitudinal location can be allowed to invert from a proximal facing orientation to a perpendicular orientation. In some embodiments, the engagement panels 2022 at the second longitudinal location can be allowed to invert from a proximal facing orientation to a distal facing orientation. In some embodiments, the second array of engagement panels 2022 are configured to move the material away from a vessel wall. In some embodiments, the second array of engagement panels 2022 are configured to change the shape of the material for transportation. In some embodiments, the second array of engagement panels 2022 are configured to change the volume of material. In some embodiments, the second array of engagement panels 2022 are configured to dislodge the material from a vessel wall by the sweeping motion. In some embodiments, the second array of engagement panels 2022 are configured to move the material toward the space 2021 when the extractor is retracted.

The engagement panels 2022 at the second longitudinal location can be deployed within the material. The engagement panels 2022 at the second longitudinal location can be proximally facing within the material. The material can be retained by the engagement panels 2022 at the second longitudinal location as the extractor is retracted. In some embodiments, the extractor can be retracted which causes the engagement panels 2022 at the second longitudinal location to pivot to an orientation proximal to the material. In some embodiments, during retraction, the material can roll, migrate, or move. In some embodiments, the material can move toward the space 2021 when the extractor is retracted. The material can be retained within the space 2021 as the extractor is retracted. In some embodiments, the material can move toward the engagement panels 2022 at the first longitudinal location when the extractor is retracted. In some embodiments, the material can move distally as the extractor is retracted. The material can move within the space 2021. The material can move within the lumen of the engagement panels 2022 at the first longitudinal location. The material can be stopped by the element 2026. The material can be retained within the lumen of the engagement panels 2022 at the first longitudinal location as the extractor is retracted. While not bound by a theory, the material may roll or migrate depending on the morphological features of the material. While not bound by a theory, the material may remain stationary as the extractor is retracted until pushed proximally by the element 2026. The element 2026 can function as a closed end of the lumen of the engagement panels 2022 at the first longitudinal location. The element 2026 can obstruct further distal movement of the material. The distal member 2024 can function as a closed end of the lumen of the engagement panels 2022 at the first longitudinal location. The distal member 2024 can obstruct further distal movement of the material. The material can be retracted with the retraction of the extractor. The proximal facing engagement panels 2022 at the second longitudinal location can facilitate retraction of the material by entangling with the material. The proximal facing engagement panels 2022 at the second longitudinal location can facilitate retraction of the material by sweeping distally toward an upright position. The proximal facing engagement panels 2022 at the second longitudinal location can facilitate retraction of the material by pinching the material toward the space 2021.

The engagement panels 2022 at the second longitudinal location can loaded proximally facing. The engagement panels 2022 at the second longitudinal location can be collapsed within the microcatheter 2027 to be proximally facing. The extractor can include one or more of the following features. The extractor can include a first array of engagement panels 2022. The first array of engagement panels 2022 can define a lumen. The first array of engagement panels 2022 can define a lumen with an open end. The first array of engagement panels 2022 can define a lumen with an enclosure or closed end.

The extractor can include a second array of engagement panels 2022. The second array of engagement panels 2022 can define a lumen. The second array of engagement panels 2022 can collapse in a delivery configuration. The second array of engagement panels 2022 can deploy in a second configuration. The second array of engagement panels 2022 can expand within the material in the second configuration.

The extractor can include the space 2021 between the first array of engagement panels 2022 and the second array of engagement panels 2022. In some embodiments, the material can reside within the space 2021 between the first array of engagement panels and second array of engagement panels.

In some embodiments, the material can remain within the first array of engagement panels 2022. In some embodiments, when expanded within the blood vessel, the first array of engagement panels 2022 is configured to be positioned distal to the material. In some embodiments, when expanded within the blood vessel, the second array of engagement panels is configured to be positioned within the material. In some embodiments, when expanded within the blood vessel, the first array of engagement panels 2022 and the second array of engagement panels 2022 are configured to engage the material between the first array of engagement panels and the second array of engagement panels. In some embodiments, upon retraction of the extractor 2020 to remove the material, the second array of engagement panels 2022 are configured to pinch the clot radially thus securing the thrombus during transit. In some embodiments, upon retraction of the extractor to remove the thrombus, the material can reside in the space 2021 between the first array of engagement panels and the second array of engagement panels thus securing the thrombus during transit. In some embodiments, upon retraction of the extractor 2020 to remove the material, the first array of engagement panels 2022 are configured to act independently and do not stretch or elongate under tension. In some embodiments, upon retraction of the extractor 2020 to remove the material the first array of engagement panels engulf the material and the material remains in the lumen of the first array of engagement panels 2022. In some embodiments, the open end of the second array of engagement panels 2022 can be configured to engulf the material.

In some embodiments, the second array of engagement panels 2022 collapse facing proximally in the delivery configuration. In some embodiments, wherein the first array of engagement panels 2022 collapse facing distally in the delivery configuration. In some embodiments, the first array of engagement panels 2022 can be loops. In some embodiments, the first array of engagement panels 2022 can include a helix. In some embodiments, the first array of engagement panels can be configured to include loops and a helix and braided wires. In some embodiments, the second array of engagement panels can be four engagement panels. In some embodiments, the second array of engagement panels can be loops. In some embodiments, the second array of engagement panels can include a helix. In some embodiments, the second array of engagement panels can include loops and a helix.

FIGS. 166-169 are views of a method of deploying the extractor. The engagement panels 2022 at the first longitudinal location can be deployed. The engagement panels 2022 at the first longitudinal location can be deployed distal to the material. The engagement panels 2022 at the first longitudinal location can be engaged with the vessel wall. The engagement panels 2022 at the first longitudinal location can be upright. The engagement panels 2022 at the first longitudinal location can be perpendicular to the core wire 2029. The microcatheter 2027 can be within the material. The engagement panels 2022 at the second longitudinal location can be within the microcatheter 2027. The engagement panels 2022 at the second longitudinal location can include a portion of engagement panels that are proximally facing within the microcatheter 2027. The portion of the engagement panels 2022 at the second longitudinal location can be compressed toward the proximal direction. The engagement panels 2022 at the second longitudinal location can include a portion of engagement panels that are distally facing within the microcatheter 2027. The portion of the engagement panels 2022 at the second longitudinal location can be compressed toward the distal direction. The engagement panels 2022 at the second longitudinal location can be loaded with a portion proximally facing and a portion distally facing during delivery. The engagement panels 2022 at the second longitudinal location can have a grasping configuration. In some embodiments, the portions of the engagement panels 2022 at the second longitudinal location can be configured to sweep in opposite directions. The portions of the engagement panels 2022 at the second longitudinal location can be configured to sweep toward each other. In some embodiments, the portions of the engagement panels 2022 at the second longitudinal location can be configured to sweep in the same direction. In some embodiments, the portions of the engagement panels 2022 at the second longitudinal location can be configured to distally as the extractor is retracted. The portions of the engagement panels 2022 at the second longitudinal location can be configured to sweep toward a perpendicular orientation. The distal facing portion of the engagement panels 2022 at the second longitudinal location can be adjacent to the proximal facing portion of the engagement panels 2022 at the second longitudinal location. In some embodiments, the distal portion of the engagement panels 2022 at the second longitudinal location can be distally facing. In some embodiments, the proximal portion of the engagement panels 2022 at the second longitudinal location can be proximally facing.

The microcatheter 2027 can be retracted. The microcatheter 2027 can be retracted to deploy the engagement panels 2022 at the second longitudinal location. The engagement panels 2022 at the second longitudinal location can be deployed. The engagement panels 2022 at the second longitudinal location can be deployed within the material. The distal portion of the engagement panels 2022 at the second longitudinal location can be angled distally relative to the core wire 2029. The distal portion of the engagement panels 2022 at the second longitudinal location can be deployed in a non-inverted state. The proximal portion of the engagement panels 2022 at the second longitudinal location can be angled proximally relative to the core wire 2029. The proximal portion of the engagement panels 2022 can be deployed in an inverted state. The engagement panels 2022 at the second longitudinal location can be deployed both distally facing and proximally facing.

The extractor can be retracted. During retraction, the engagement panels 2022 at the second longitudinal location pivot relative to their fixed location. The extractor can be retracted to fully deploy the engagement panels 2022 at the second longitudinal location. The extractor can be retracted to cause the engagement panels 2022 at the second longitudinal location to pivot. The extractor can be retracted which causes the material to migrate distally. The extractor can be retracted to cause the engagement panels 2022 at the second longitudinal location to become proximal to the material. The extractor can be retracted to cause the distal facing engagement panels 2022 at the second longitudinal location to sweep toward an upright position. The extractor can be retracted to cause the proximal facing engagement panels 2022 at the second longitudinal location to sweep toward an upright position. The extractor can be retracted to cause the engagement panels 2022 at the second longitudinal location to move toward each other. The engagement panels 2022 at the second longitudinal location can rotate toward the vessel wall. The engagement panels 2022 at the second longitudinal location can be engaged with the vessel wall. The engagement panels 2022 at the second longitudinal location can be perpendicular to the core wire 2029. The engagement panels 2022 at the second longitudinal location can rotate relative to the fixed location on the core wire 2029. The engagement panels 2022 at the second longitudinal location can rotate from angled positions to a perpendicular position. The engagement panels 2022 at the second longitudinal location can rotate as the extractor is retracted. The distal facing engagement panels 2022 at the second longitudinal location can sweep upward. The proximal facing engagement panels 2022 at the second longitudinal location can sweep upward. The engagement panels 2022 at the second longitudinal location can pivot to be upright. The engagement panels 2022 at the second longitudinal location can be upright as the extractor is retracted. The engagement panels 2022 at the second longitudinal location can rotate up to 180 degrees. The distal facing engagement panels 2022 at the second longitudinal location and the proximal facing engagement panels 2022 at the second longitudinal location can rotate in opposite directions. The distal facing engagement panels 2022 at the second longitudinal location and the proximal facing engagement panels 2022 at the second longitudinal location can rotate to be generally perpendicular. In some embodiments, the second array of engagement panels 2022 are configured to compress the material by movement of the second array of engagement panels 2022. In some embodiments, the second array of engagement panels 2022 are configured to sweep the material toward the lumen of the engagement panels 2022 at the second longitudinal location. In some embodiments, the second array of engagement panels 2022 are configured to sweep the material inward. In some embodiments, the second array of engagement panels 2022 are configured to sweep the material away from the vessel wall.

The engagement panels 2022 at the second longitudinal location can be deployed within the material. The engagement panels 2022 at the second longitudinal location can be distally facing within the material and proximally facing within the material. The engagement panels 2022 at the second longitudinal location can entangle with the material by facing opposite directions. The material can be retained by the engagement panels 2022 at the second longitudinal location as the extractor is retracted. In some embodiments, the extractor can be retracted which causes the engagement panels 2022 at the second longitudinal location to pivot to be positioned proximal to the material. In some embodiments, during retraction, the material can be moved distally. In some embodiments, during retraction, the material can be moved by the engagement panels 2022 at the second longitudinal location. In some embodiments, the material can move toward the space 2021 when the extractor is retracted. The material can be retained within the space 2021 as the extractor is retracted. In some embodiments, the material can move toward the engagement panels 2022 at the first longitudinal location when the extractor is retracted. In some embodiments, the material can move distally as the extractor is retracted. The material can move within the space 2021. The material can move within the lumen of the engagement panels 2022 at the first longitudinal location. The material can be stopped by the element 2026. The material can be retained within the lumen of the engagement panels 2022 at the first longitudinal location as the extractor is retracted. While not bound by a theory, the material may roll or migrate due to the sweeping action of the engagement panels 2022 at the second longitudinal location. While not bound by a theory, the material may be pushed inward toward the center of the vessel. The lumen of the engagement panels 2022 at the first longitudinal location can capture the material when the extractor is retracted. The element 2026 forms a closed end of the lumen to retain the material. The engagement panels 2022 at the first longitudinal location can entrap the material and transport the material distally. The distal member 2024 can function to capture any material that separates from flowing distally. The material can be retracted with the retraction of the extractor. The engagement panels 2022 at the second longitudinal location can facilitate retraction of the material by entangling with the material. The engagement panels 2022 at the second longitudinal location can facilitate movement of the material by sweeping the material toward the space 2021. The engagement panels 2022 at the second longitudinal location can facilitate movement of the material by sweeping the material toward the engagement panels 2022 at the first longitudinal location. The engagement panels 2022 at the second longitudinal location can sweep upward to grasp the material. The engagement panels 2022 at the second longitudinal location can be deployed in manner in which the engagement panels pivot toward each other. The engagement panels 2022 at the second longitudinal location can be deployed in manner to grasp the material therebetween.

The engagement panels 2022 at the second longitudinal location can loaded with a portion loaded distally facing and a portion loaded proximally facing. The extractor can include one or more of the following features. The extractor can include a first array of engagement panels 2022. The first array of engagement panels 2022 can define a lumen. The first array of engagement panels 2022 can define a lumen with an open end. The first array of engagement panels 2022 can define a lumen with an enclosure or closed end.

The extractor can include a second array of engagement panels 2022. The second array of engagement panels 2022 can define a lumen. The second array of engagement panels 2022 can collapse in a delivery configuration. The second array of engagement panels 2022 can deploy in a second configuration. The second array of engagement panels 2022 can expand within the material in the second configuration. The second array of engagement panels 2022 can grasp the material axially and radially.

The extractor can include the space 2021 between the first array of engagement panels 2022 and the second array of engagement panels 2022. In some embodiments, the material can reside within the space between the first array of engagement panels and second array of engagement panels. In some embodiments, the open end of the second array of engagement panels engulfs the material. In some embodiments, the material remains within the first array of engagement panels. In some embodiments, the material is transported without resistance. In some embodiments, the material is transported without pinching against the vessel wall. In some embodiments, when expanded within the blood vessel, the first array of engagement panels is configured to be positioned distal to a material and the second array of engagement panels is configured to be positioned within the material. In some embodiments, when expanded within the blood vessel, the first array of engagement panels and the second array of engagement panels are configured to engage the material between the first array of engagement panels and the second array of engagement panels. In some embodiments, upon retraction of the extractor to remove the material, the second array of engagement panels are configured to pinch the material radially and axially thus securing the thrombus during transit. In some embodiments, upon retraction of the extractor to remove the material, the material can reside in the space between the first array of engagement panels and the second array of engagement panels thus securing the material during transit. In some embodiments, upon retraction of the extractor to remove the material, the first array of engagement panels are configured to engulf the material and the material is configured to remain in the lumen of the first array of engagement panel.

In some embodiments, a segment of the second array of engagement panels collapses facing proximally in the delivery configuration and another segment of the second array of engagement panels collapses facing distally in the delivery configuration. In some embodiments, the first array of engagement panels collapses facing distally in the delivery configuration. In some embodiments, the first array of engagement panels can be loops. In some embodiments, the first array of engagement panels can be a helix. In some embodiments, the first array of engagement panels can be loops and helix. In some embodiments, the first array of engagement panels can be four engagement panels. In some embodiments the second array of engagement panels can be loops. In some embodiments, the second array of engagement panels can be helix. In some embodiments, the second array of engagement panels can one, two, three, four or more engagement panels.

Figure 170:
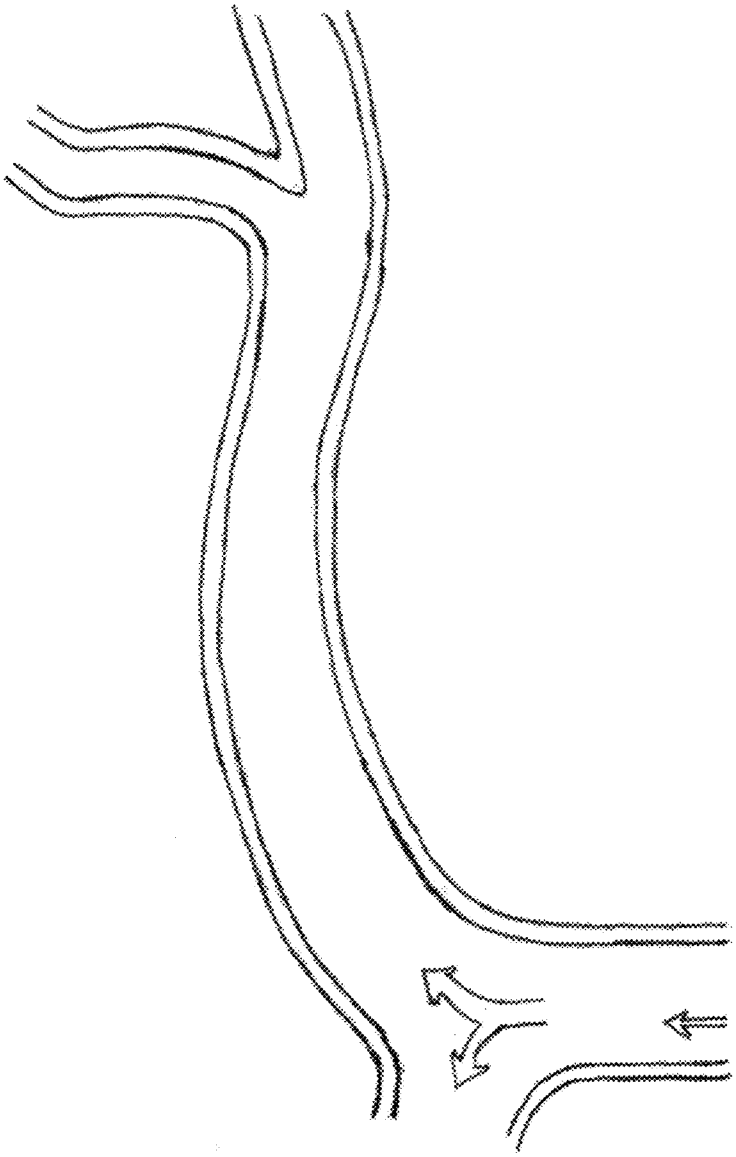
FIG. 170 is a view of the blood flow.

FIG. 170 is a view of the blood flow. The blood flow can be reestablished upon material removal. The material can be removed. The material can be captured within the extractor 2020. The material can be captured within the microcatheter 2027.

In some embodiments, the extractor can include a first array of engagement panels that define a lumen with an open end at the proximal end and an enclosure or closed end at the distal end. In some embodiments, the open end of the second array engulfs the material and the material remains within the second array of engagement panels and the material is transported without resistance or pinching against the vessel wall. In some embodiments, the extractor can include a second array of engagement panels that define a lumen and collapses in the delivery configuration and deploys in the second configuration to expand within the clot to pinch or grasp the clot axially and radially. In some embodiments, a space between the first array of engagement panels and the second array of engagement panels is provided where material can reside within the space between the first array of engagement panels and the second array of engagement panels. In some embodiments, when expanded within the blood vessel, the first array of engagement panels and the second array of engagement panels are configured to be positioned distal to the material. In some embodiments, when expanded within the blood vessel, the first array of engagement panels and the second array of engagement panels are configured to engage the material between the first array of engagement panels and the second array of engagement panels. In some embodiments, upon retraction of the extractor to remove the material, the second array of engagement panels are configured to pinch the clot radially thus securing the thrombus during transit. In some embodiments, upon retraction of the extractor to remove the material, the material can reside in the space between the first array of engagement panels and the second array of engagement panels thus securing the thrombus during transit. In some embodiments, upon retraction of the extractor to remove the thrombus, the first array of engagement panels are configured to engulf the material and the material remains in the lumen of the first array of engagement panels. In some embodiments, the first array of engagement panels can be loops. In some embodiments, the first array of engagement panels can be a helix. In some embodiments, the first array of engagement panels can be loops and helix. In some embodiments, the second array of engagement panels can be loops. In some embodiments, the second array of engagement panels can be helix.

In some embodiments, the extractor can include a distal member. In some embodiments, the extractor can include the first array of engagement panels at a first longitudinal location and the second array of engagement panels at the second longitudinal location. In some embodiments, the first array of engagement panels at a first longitudinal location defines a lumen with an open end and a closed end. In some embodiments, the second array of engagement panels at the second longitudinal location define a lumen. In some embodiments, the extractor can include a space between the first array of engagement panels and the second engagement panels.

In some embodiments, the second array of engagement is delivered where the second array of engagement panels collapses in the distal direction. In some embodiments, the second array of engagement panels are positioned within the material and deploy to expand to pinch the material. During retraction, the material can roll, migrate or move and reside in the space 2021 between the first array of engagement panels and the second array of engagement panels. The space 2021 can be considered a central loading zone. In some embodiments, during retraction, the first array of engagement panels encapsulates the clot within its lumen and transports the clot with minimal resistance against the vessel wall.

In some embodiments, the extractor can include a distal member. In some embodiments, the extractor can include the first array of engagement panels, the second array of engagement panels, and a space between the first array of engagement panels and the second array of engagement panels. The second array of engagement panels can be delivered where the panels collapse in the proximal direction. In some embodiments, the second array of engagement panels are positioned within the material and deploy to expand to pinch the material. During retraction, the second array of engagement panels revert in the distal direction to engage the material. In some embodiments, during retraction, the material can roll, migrate or move and resides in the space between the first array of engagement panels and the second array of engagement panels. In some embodiments, during retraction, the first array of engagement panels encapsulates the material within its lumen and transports the material with minimal resistance against the vessel wall.

In some embodiments, the extractor can include a distal member. In some embodiments, the extractor can include the first array of engagement panels, the second array of engagement panels and a space between the first array of engagement panels and the second array of engagement panels. The second array of engagement panels can be delivered where a portion of the second array of engagement panels collapse in the distal direction and a portion of the second array of engagement panels collapse in the proximal direction. The second array of engagement panels can be positioned within the material and deployed to expand to pinch the clot. During retraction, a portion of the second array of engagement panels revert in the distal direction to engage the clot. In some embodiments, during retraction, the clot migrates or moves and resides in the space between the first array of engagement panels and the second array of engagement panels. In some embodiments, during retraction, the first array of engagement panels encapsulates the clot within its lumen and transports the material with minimal resistance against the vessel wall.

In some embodiments, the extractor can include a first array of engagement panels that define a lumen with an open end and an enclosure or closed end, whereby the first array of engagement panels open end engulfs the clot/thrombus and the clot/thrombus remains within the first array of engagement panels. In some embodiments, the extractor can include a second array of engagement panels that define a lumen and collapses in the delivery configuration and deploys in the second configuration to expand within the clot. In some embodiments, the extractor can include a space between the first array of engagement panels and second array of engagement panels where a clot can reside within the space between the first array of engagement panels and second array of engagement panels. In some embodiments, when expanded within the blood vessel, the first array of engagement panels is configured to be positioned distal to a clot and the second array of engagement panels is configured to be positioned within the clot. In some embodiments, when expanded within the blood vessel, the first array of engagement panels and the second array of engagement panels are configured to engage the thrombus between the first array of engagement panels, the second array of engagement panels. In some embodiments, upon retraction of the extractor to remove the thrombus, the second array of engagement panels are configured to act independently and do not stretch or elongate under tension thus securing the thrombus during transit. In some embodiments, upon retraction of the extractor to remove the thrombus, the clot can reside in the space between the first array of engagement panels and the second array of engagement panels thus securing the thrombus during transit. In some embodiments, the upon retraction of the extractor to remove the thrombus, the first array of engagement panels are configured to act independently and do not stretch or elongate under tension and engulf the clot and remain in the first array of engagement panels lumen.

In some embodiments, the second array of engagement panels are configured to engulf the clot and pinch the clot radially. In some embodiments, the first array of engagement panels are configured to pinch the clot. In some embodiments, the second array of engagement panels collapse facing distally in the delivery configuration. In some embodiments, the first array of engagement panels collapses facing distally in the delivery configuration. In some embodiments, the first array of engagement panels can be loops. In some embodiments, the first array of engagement panels can be a helix. In some embodiments, the first array of engagement panels can be loops and helix. In some embodiments, the first array of engagement panels can be four engagement panels. In some embodiments, wherein the extractor can include one, two, three or more spaces. In some embodiments, the second array of engagement panels can be loops. In some embodiments, the second array of engagement panels can be helix. In some embodiments, the second array of engagement panels can be one, two, three, four or more engagement panels.

In some embodiments, the extractor can include a first array of engagement panels that define a lumen with an open end and an enclosure or closed end, whereby the first array of engagement panels open end engulfs the clot and the clot remains within the first array of engagement panels. In some embodiments, the extractor can include a second array of engagement panels that define a lumen and collapse in the delivery configuration and deploy in the second configuration to expand within the clot. In some embodiments, the extractor can include a space between the first array of engagement panels and second array of engagement panels where a clot can reside within the space between the first array of engagement panels and second array of engagement panels.

In some embodiments, when expanded within the blood vessel, the first array of engagement panels is configured to be positioned distal to a thrombus and the second array of engagement panels is configured to be positioned within the thrombus. In some embodiments, when expanded within the blood vessel, the first array of engagement panels and the second array of engagement panels are configured to engage the thrombus between the first array of engagement panels and the second array of engagement panels. In some embodiments, upon retraction of the extractor to remove the thrombus, the second array of engagement panels are configured to pinch the clot radially thus securing the thrombus during transit. In some embodiments, upon retraction of the extractor to remove the thrombus, the clot can reside in the space between the first array of engagement panels and the second array of engagement panels thus securing the thrombus during transit. In some embodiments, the upon retraction of the extractor to remove the thrombus, the first array of engagement panels are configured to act independently and do not stretch or elongate under tension and engulf the clot and remain in the first array of engagement panels lumen.

In some embodiments, the second array of engagement panels collapse facing proximally in the delivery configuration. In some embodiments, the first array of engagement panels collapse facing distally in the delivery configuration.

In some embodiments, the extractor can include a first array of engagement panels that define a lumen with an open at the proximal end and an enclosure or closed end at the distal end. In some embodiments, the second array open end engulf the clot and remains within the first array of engagement panels and transport without resistance or pinch against the vessel wall. In some embodiments, the extractor can include a second array of engagement panels that define a lumen and collapse in the delivery configuration and deploy in the second configuration to expand within the clot to pinch (grasp) the clot axially and radially. In some embodiments, the extractor can include a space between the first array of engagement panels and the second array of engagement panels where a clot can reside within the space between the first array of engagement panels and the second array of engagement panels. In some embodiments, when expanded within the blood vessel, the first array of engagement panels is configured to be positioned distal to a thrombus and the second array of engagement panels is configured to be positioned within the thrombus. In some embodiments, when expanded within the blood vessel, the first array of engagement panels and the second array of engagement panels are configured to engage the thrombus between the first array of engagement panels, the second array of engagement panels. In some embodiments, upon retraction of the extractor to remove the thrombus, the second array of engagement panels are configured to pinch the clot radially and axially thus securing the thrombus during transit. In some embodiments, upon retraction of the extractor to remove the thrombus, the clot can reside in the space between the first array of engagement panels and the second array of engagement panels thus securing the thrombus during transit. In some embodiments, upon retraction of the extractor to remove the thrombus, the first array of engagement panels are configured to engulf the clot and remain in the first array of engagement panels lumen.

In some embodiments, a segment of the second array of engagement panels collapses facing proximally in the delivery configuration and another segment of the second array of engagement panels collapses facing distally in the delivery configuration. In some embodiments, the first array of engagement panels collapse facing distally in the delivery configuration. In some embodiments, the first array of engagement panels can be loops. In some embodiments, the first array of engagement panels can be a helix. In some embodiments, the first array of engagement panels can be loops and helix. In some embodiments, the first array of engagement panels can be four engagement panels. In some embodiments, the space can 1, 2, 3 or more. In some embodiments, the second array of engagement panels can be loops. In some embodiments, the second array of engagement panels can be helix In some embodiments, the extractor can include a first array of engagement panels that define a lumen with an open at the proximal end and an enclosure or closed end at the distal end. In some embodiments, the second array open end engulf the clot and remains within the second array of engagement panels and transport without resistance or pinch against the vessel wall. In some embodiments, the extractor can include a second array of engagement panels that define a lumen and collapse in the delivery configuration and deploy in the second configuration to expand distal to the clot obstruction. In some embodiments, the extractor can include a space between the first array of engagement panels and the second array of engagement panels where a clot can reside within the space between the first array of engagement panels and the second array of engagement panels.

In some embodiments, when expanded within the blood vessel, the first array of engagement panels and the second array of engagement panels are configured to be positioned distal to a thrombus.

In some embodiments, when expanded within the blood vessel, the first array of engagement panels and the second array of engagement panels are configured to engage the thrombus between the first array of engagement panels and the second array of engagement panels. In some embodiments, upon retraction of the extractor to remove the thrombus, the second array of engagement panels are configured to pinch the clot radially thus securing the thrombus during transit. In some embodiments, upon retraction of the extractor to remove the thrombus, the clot can reside in the space between the first array of engagement panels and the second array of engagement panels thus securing the thrombus during transit. In some embodiments, upon retraction of the extractor to remove the thrombus, the first array of engagement panels are configured to engulf the clot and remain in the first array of engagement panels lumen.

In some embodiments, a method of removing a thrombus from a body lumen is provided. The method can include providing an extractor. The method can include providing a microcatheter 2027. In some embodiments, the microcatheter 2027 can include a proximal end, a distal end, and a tubular body. The method can include advancing the microcatheter 2027 proximate the body lumen. The method can include advancing the distal end of the microcatheter 2027 through the thrombus, the thrombus comprising a proximal end and a distal end.

The method can include expanding a first array of engagement panels within the body lumen distal to the thrombus. The method can include withdrawing the distal end of the microcatheter 2027 through the thrombus, thereby expanding a second array of engagement panels within the body lumen and in direct contact with a portion of the thrombus. In some embodiments, the second array of engagement panels is proximal to the first array of engagement panels and spaced axially apart from the first array of engagement panels via a central loading zone.

In some embodiments, the method can include manipulating the extractor such that the thrombus moves from the second array of engagement panels to the central loading zone. In some embodiments, the method can include manipulating the extractor such that the thrombus moves from the central loading zone to the first array of engagement panels. In some embodiments, the method can include that the thrombus remains secured with respect to the first array of engagement panels until the first array of engagement panels is removed from a body associated with the body lumen.

In some embodiments, the second array of engagement panels comprise panels comprising first ends operably attached to a tubular member and second free ends. In some embodiments, the second free ends face distally with respect to the body lumen when the second array of engagement panels is expanded within the body lumen. In some embodiments, the second free ends face proximally with respect to the body lumen when the second array of engagement panels is expanded within the body lumen. In some embodiments, a first subset of the second free ends face proximally with respect to the body lumen when the second array of engagement panels is expanded within the body lumen and a second subset of the second free ends face distally with respect to the body lumen when the second array of engagement panels is expanded within the body lumen. In some embodiments, the distal end of the thrombus moves proximal to the proximal end of the thrombus when the extractor is manipulated such that the thrombus moves from the second array of engagement panels to the central loading zone. In some embodiments, the distal end of the thrombus moves when the extractor is manipulated such that the thrombus moves from the central loading zone to the first array of engagement panels. In some embodiments, the second array of engagement panels exerts a radial force on the thrombus to control the thrombus prior to manipulating the extractor such that the thrombus moves from the second array of engagement panels to the central loading zone.

Figure 171:
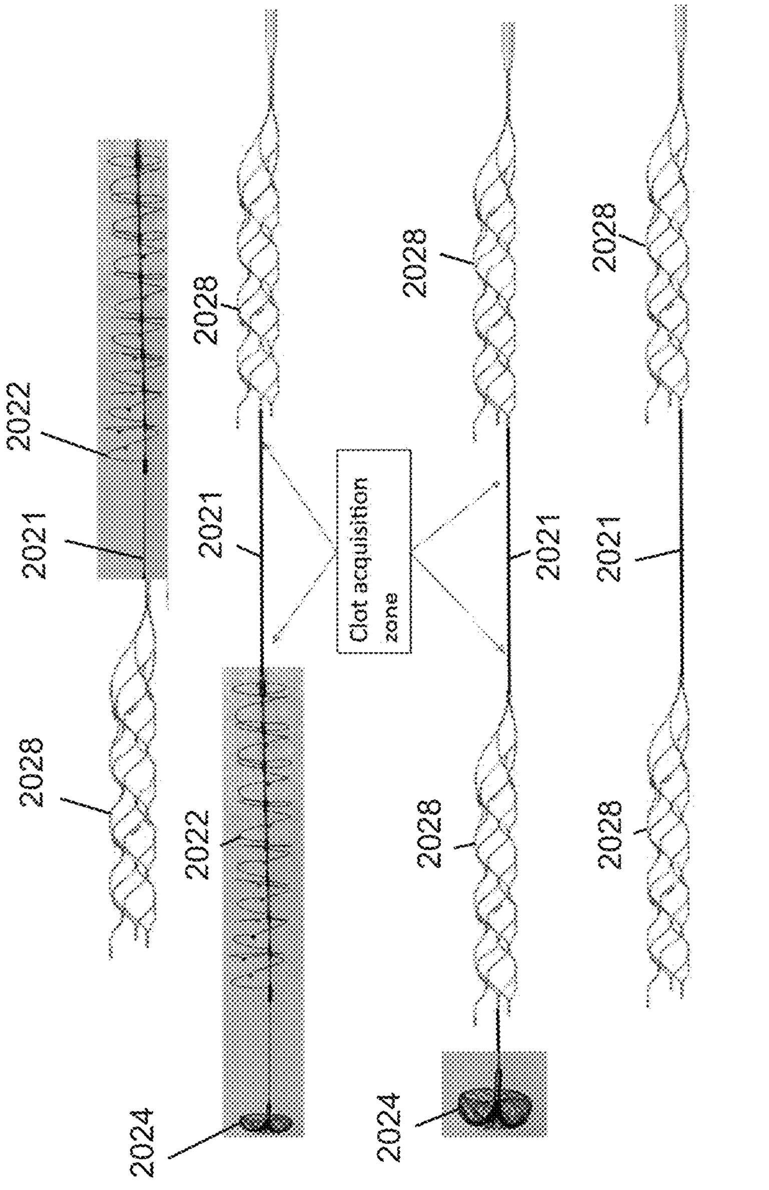
FIG. 171 are views of an extractor.

FIG. 171 are views of an extractor. The extractor 2020 can include the first array of engagement panels 2022. The extractor 2020 can include the second array of engagement panels 2022. The extractor 2020 can include the space 2021 between the first array of engagement panels 2022 and the second array of engagement panels 2022. The extractor 2020 can include the distal member 2024. The extractor 2020 can include a stentriever 2028. The stentriever 2028 can be a mechanical thrombectomy device. The stentriever 2028 can be a self-expanding device. The stentriever 2028 can be a braided stent. The stentriever 2028 can replace the first array of engagement panels 2022. The stentriever 2028 can be at the first longitudinal location. The stentriever 2028 can replace the second array of engagement panels 2022. The stentriever 2028 can be at the second longitudinal location. The extractor 2020 can include the space 2021 between the stentriever 2028 and the second array of engagement panels 2022. The extractor 2020 can include the space 2021 between the first array of engagement panels 2022 and the stentriever 2028. The extractor 2020 can include the space 2021 between the stentriever 2028 at the first longitudinal location and the stentriever 2028 at the second longitudinal location. The extractor 2020 can omit the distal member 2024.

The extractor 2020 can include the stentriever 2028 at the first longitudinal location and the second array of engagement panels 2022 at the second longitudinal location. The extractor 2020 can include the first array of engagement panels 2022 at the first longitudinal location and the stentriever 2028 at the second longitudinal location. The extractor 2020 can include the distal member 2024, the first array of engagement panels 2022 at the first longitudinal location and the stentriever 2028 at the second longitudinal location. The extractor 2020 can include the space 2021 between the first array of engagement panels 2022 and the stentriever 2028. The extractor 2020 can include the distal member 2024, the stentriever 2028 at the first longitudinal location, and the stentriever 2028 at the second longitudinal location. The extractor 2020 can include the space 2021 between the stentriever 2028 at the first longitudinal location and the stentriever 2028 at the second longitudinal location. The extractor 2020 can include the stentriever 2028 at the first longitudinal location and the stentriever 2028 at the second longitudinal location. The extractor 2020 can include the space 2021 between the stentriever 2028 at the first longitudinal location and the stentriever 2028 at the second longitudinal location.

Figure 172:
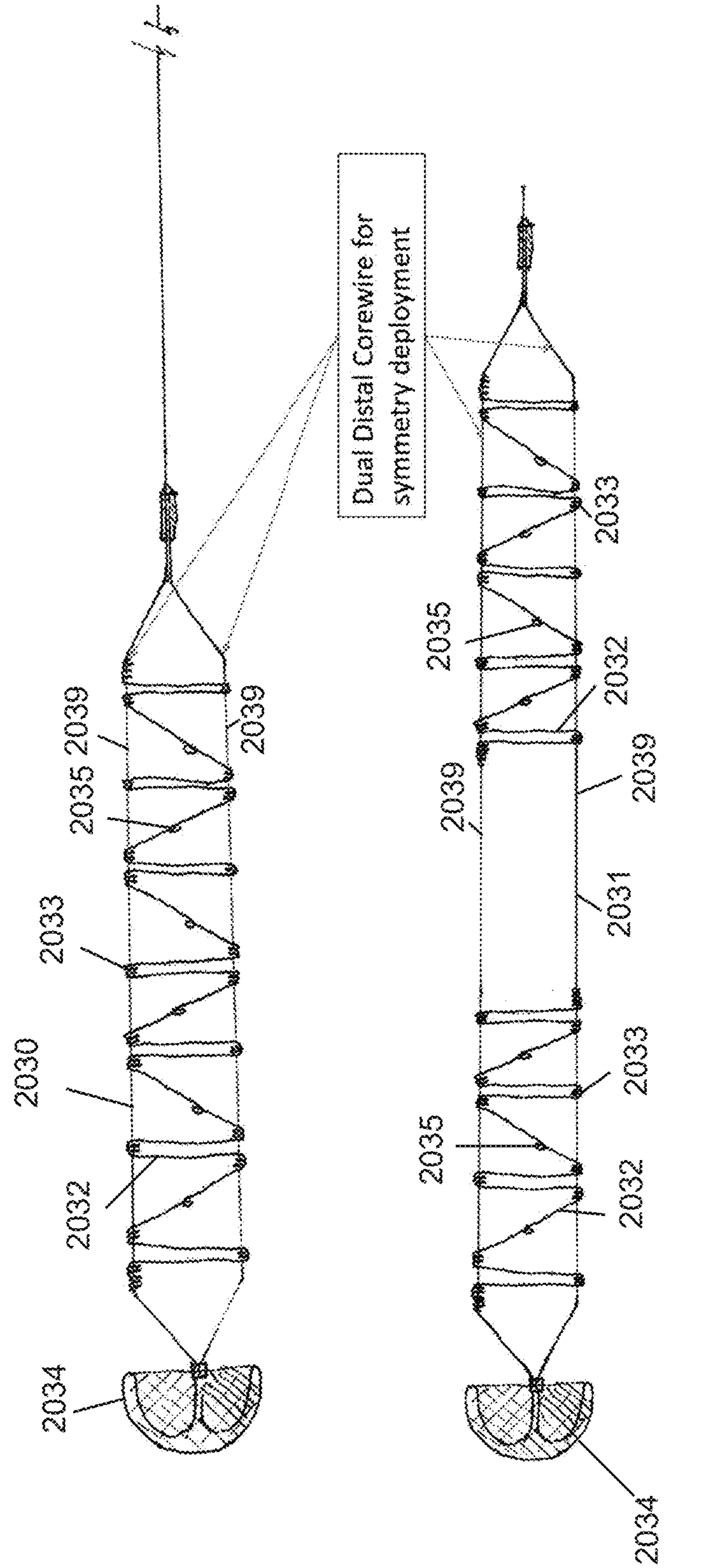
FIGS. 172-173 are views of an extractor.
Figure 173:
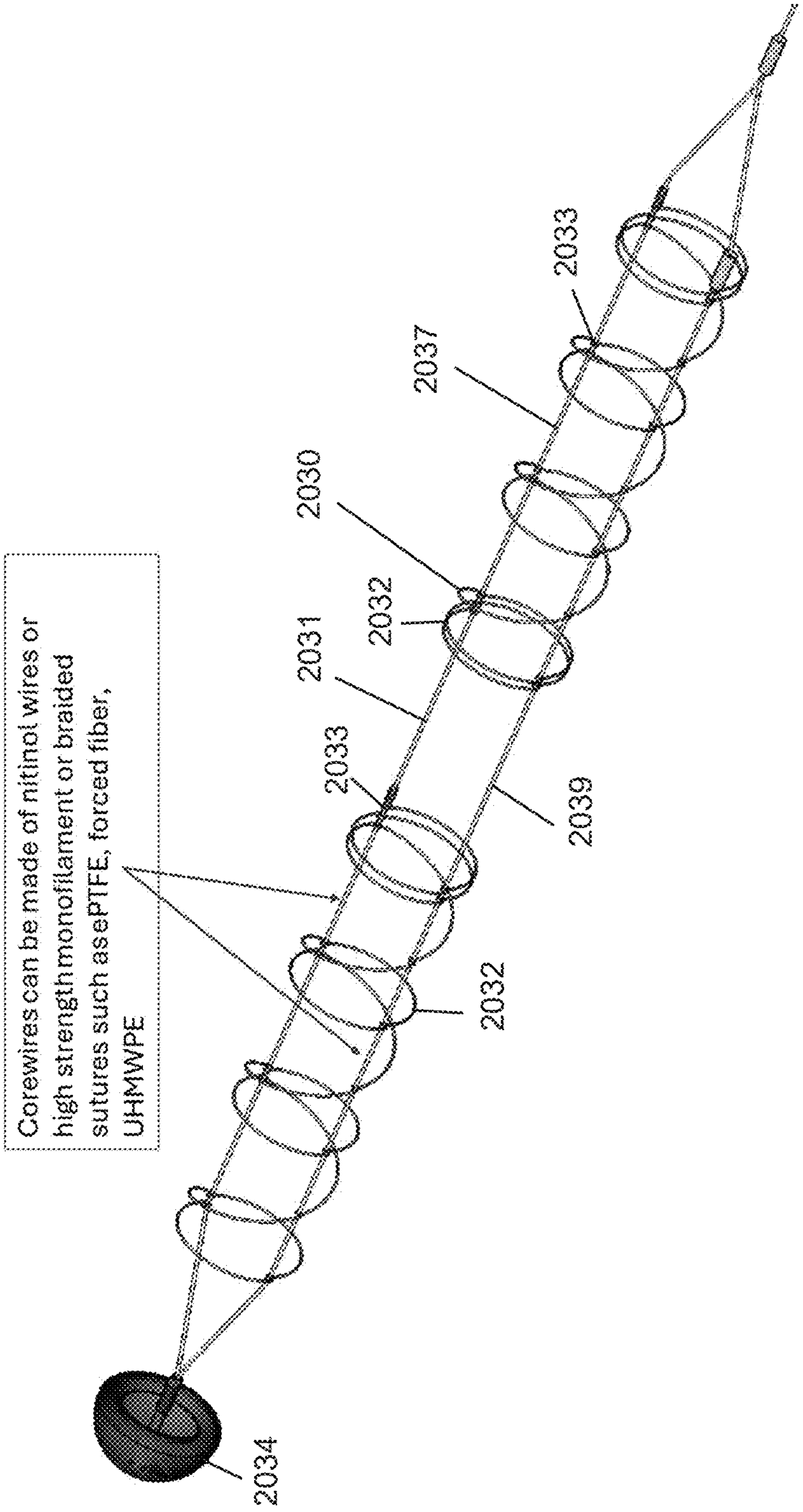
Figure 174A:
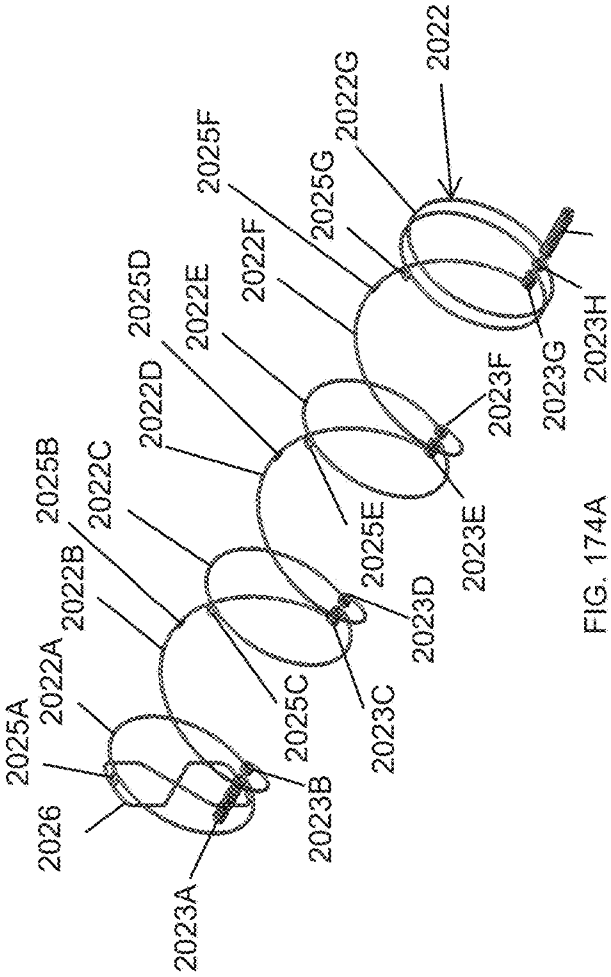
FIGS. 174A-174D are views of a first array of engagement panels of the extractor of FIG. 151.
Figure 174B:
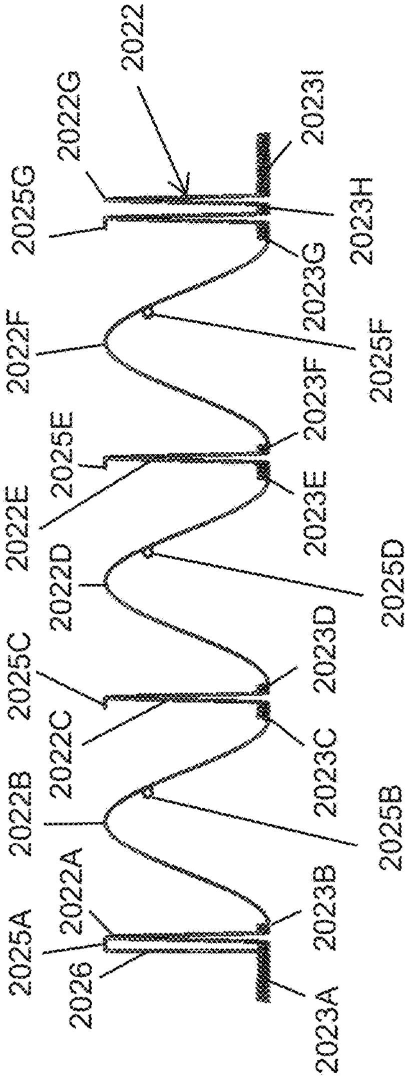
Figure 174C:
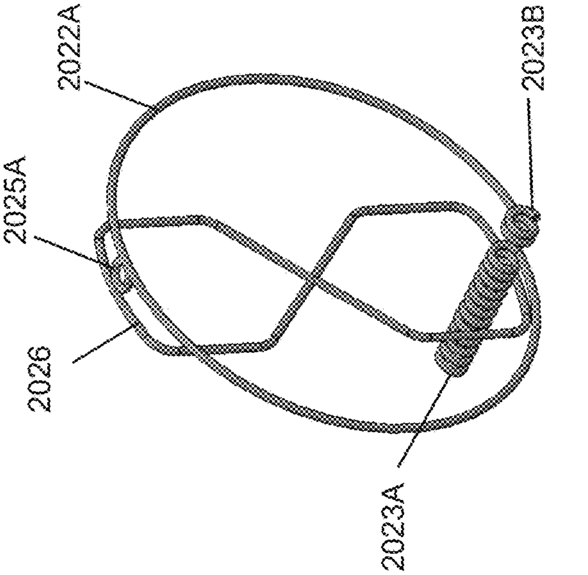
Figure 174D:
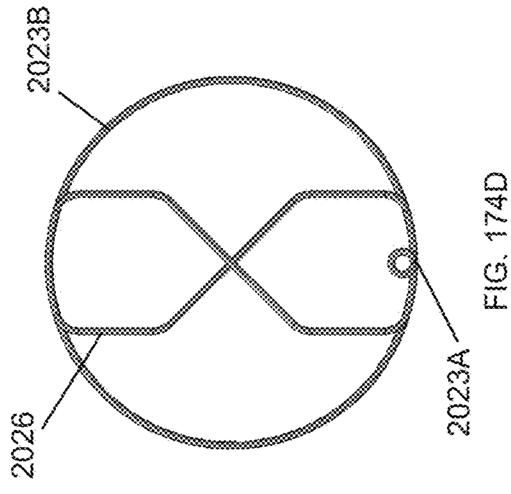
Figure 175A:
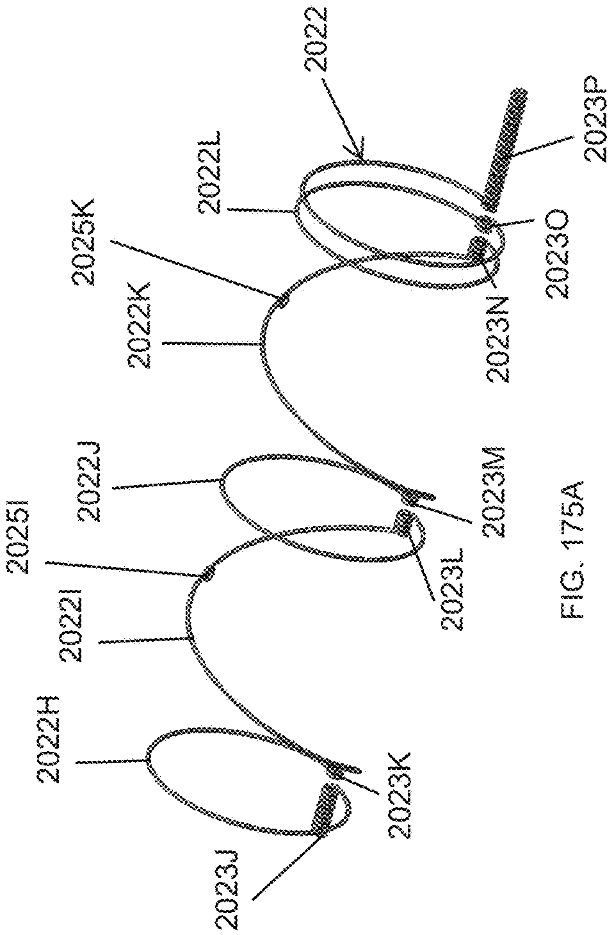
FIGS. 175A-175D are views of a second array of engagement panels of the extractor of FIG. 151.
Figure 175B:
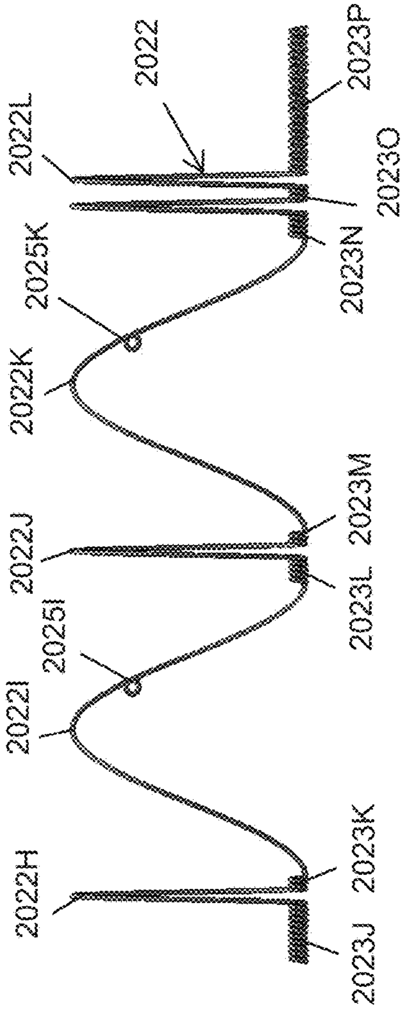
Figure 175C:
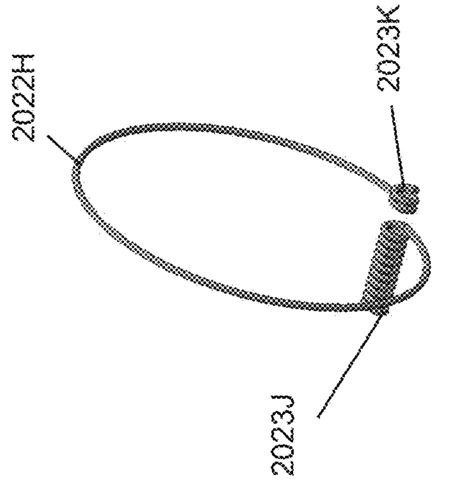
Figure 175D:
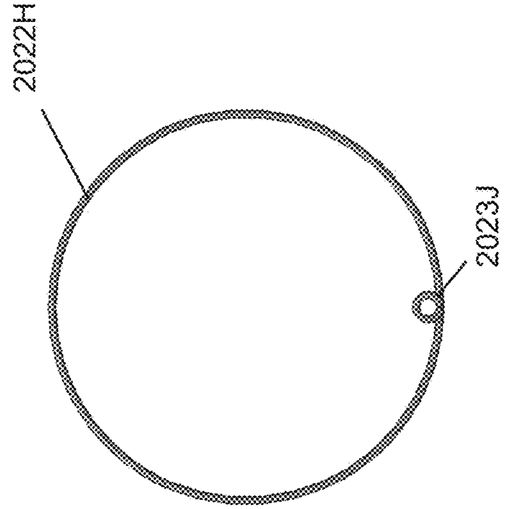

FIGS. 172-173 are views of an extractor 2030. The extractor 2030 can include any feature of any extractor described herein. The extractor 2030 can include engagement panels 2032. The engagement panels 2032 can have a loop design. The extractor 2030 can include a first array of engagement panels 2032. The engagement panels 2032 can include the first array at a first longitudinal location. The engagement panels 2032 at the first longitudinal location can be formed from a continuous wire. The extractor can include a second array of engagement panels 2032. The engagement panels 2032 can include the second array at a second longitudinal location. The engagement panels 2032 at the second longitudinal location can be formed from a continuous wire. The extractor 2030 can include a third array of engagement panels 2032. The engagement panels 2032 can include the third array at a third longitudinal location. The engagement panels 2032 at the third longitudinal location can be formed from a continuous wire.

The extractor can include a space 2031 between the first array of engagement panels 2032 and the second array of engagement panels 2032. The extractor 2030 can include the spacing 2031 between the engagement panels 2032 at the first longitudinal location and the engagement panels 2032 at the second longitudinal location. The extractor 2030 can include the spacing 2031 between adjacent arrays of engagement panels 2032. The engagement panels 2032 at the first longitudinal location and the engagement panels 2032 at the second longitudinal location can be spaced apart. In some embodiments, the continuous wire that forms the engagement panels 2032 at the first longitudinal location is separated from the continuous wire that forms the engagement panels 2032 at the second longitudinal location. The extractor 2030 can be made from two arrays of engagement panels 2032 such as proximal array of engagement panels 2032 and a distal array of engagement panels 2032. The engagement panels 2032 can include one or more helixes. The engagement panels 2032 can include one or more helical segments. The engagement panels 2032 can include one or more loops. The engagement panels 2032 can include one or more arcs. The engagement panels 2032 can include one or more eyelets 2033. The engagement panel 2032 at the first longitudinal location can include one or more eyelet 2033. The engagement panel 2032 at the first longitudinal location can include two eyelets 2033 for each circumferential loop or helix. The engagement panel 2032 at the second longitudinal location can include one or more eyelet 2033. The engagement panel 2032 at the second longitudinal location can include two eyelets 2033 for each circumferential loop or helix. The eyelet 2033 can include a coiled eyelet. The one or more eyelets 2033 can be formed from the continuous wire that forms the engagement panel 2032 at the first longitudinal location. The one or more eyelets 2033 can be formed from the continuous wire that forms the engagement panel 2032 at the second longitudinal location. In some embodiments, the eyelet 2033 is along the circumference of the helix. In some embodiments, the eyelet 2033 is along the circumference of the loop. The eyelet 2033 can be positioned to maximize the lumen of the engagement panels 2032. The eyelet 2033 can be positioned along a curved segment of the engagement panels 2032.

In some embodiments, each eyelet 2033 of the engagement panel 2032 at the first longitudinal location is fixed. In some embodiments, each engagement panel 2032 at the first longitudinal location is fixed. In some embodiments, at least one eyelet 2033 at the first longitudinal location is not fixed. In some embodiments, each eyelet 2033 of the engagement panel 2032 at the second longitudinal location is fixed. In some embodiments, each engagement panel 2032 at the second longitudinal location is fixed. In some embodiments, at least one eyelet 2033 at the second longitudinal location is not fixed. The one or more eyelets 2033 can be formed from the continuous wire that forms the engagement panel 2032 at the first longitudinal location. The one or more eyelets 2033 can be formed from the continuous wire that forms the engagement panel 2032 at the second longitudinal location. The eyelet 2033 can be offset from center. The engagement panels 2032 can include a lumen.

The extractor can include a distal member 2034. The distal member 2034 can be distal to the first array of engagement panels 2032 located at the first longitudinal location. The distal member 2034 can be distal to all engagement panels 2032.

The extractor 2030 can include one or more core wires 2039. The extractor 2030 can include two core wires 2039. The two core wires 2039 can be spaced apart. The two core wires 2039 can be diametrically opposed. The core wire 2039 can spaced about 180 degrees relative to the other core wire 2039. The core wire 2039 can spaced about 120 degrees relative to the other core wire 2039. The core wire 2039 can spaced about 90 degrees relative to the other core wire 2039. The core wires 2039 can extend the entire length of the extractor 2030. The core wires 2039 can extend a portion of the length of the extractor 2030. The core wires 2039 can extend from the distal member 2034. The core wires 2039 can extend along the first longitudinal location. The core wires 2039 can extend along the space 2031. The core wires 2039 can extend along the second longitudinal location. The core wires 2039 can extend along the third longitudinal location. The core wire 2039 can be made from a continuous wire. The core wire 2039 can extend from the proximal end to the distal end of the extractor 2030.

In some embodiments, the extractor 2030 can include only the engagement panel 2032 at the first longitudinal location. The engagement panel 2032 at the first longitudinal location can be loops. The extractor 2030 can include loops for the engagement panel 2032 at the first longitudinal location. The extractor 2030 can include dual core wires 2039. The dual core wires 2039 can be straight. The dual core wires 2039 can allow for symmetric deployment. The extractor 2030 can include other features such as the distal member 2034.

In some embodiments, the extractor 2030 can include the engagement panel 2032 at the first longitudinal location and the engagement panel 2032 at the second longitudinal location. The engagement panel 2032 at the first longitudinal location can be loops. The engagement panel 2032 at the second longitudinal location can be loops. The extractor 2030 can include the spacing 2031. The spacing 2031 can be the clot collection chamber. The extractor 2030 can include dual core wires 2039. The dual core wires 2039 can be straight. The dual core wires 2039 can allow for symmetric deployment. The extractor 2030 can include other features such as the distal member 2034.

In some embodiments, the eyelet 2033 can be fixed relative to one of the core wires 2039. The engagement panel 2032 at the first longitudinal location can be fixed relative the core wires 2039. The spacing 2031 can be fixed relative to the core wires 2039. The engagement panel 2032 at the second longitudinal location can be fixed relative to the core wires 2039. In some embodiments, the eyelet 2033 can receive the core wire 2039. The engagement panels can include the eyelet 2033 that is eccentrically located relative to the engagement panels 2032. The extractor 2030 can include the core wire 2039 that is eccentrically located relative to the engagement panels 2032.

The extractor 2030 can include dual core wires 2039. The extractor 2030 can include two elements 2039. In some embodiments, there can be one, two, three, four, or more core wires 2039 coupled to the first array of engagement panels 2032 and the second array of engagement panels 2039. The elements 2039 can include wires, high strength monofilament, or braided sutures such as ePTFE, forced fiber, UHMWPE. The core wires 2039 can couple at a location proximal to the second array of engagement panels 2039. The core wires 2039 can couple at a location distal to the first array of engagement panels 2039. The two core wires 2039 couple to the distal member 2034. The two core wires 2039 can be connected to the first array of engagement panels 2032 and the second array of engagement panels 2032 through the eyelets 2033. The two core wires 2039 can be at least 5 degrees apart. The two core wires 2039 can be at least 90 degrees apart. The two core wires 2039 can be at least 120 degrees apart. The two core wires 2039 can be approximately 180 degrees apart. In some embodiments, the core wires 2039 can be spaced apart equally. For example, a three-wire configuration is 120 degrees equally position or a four wires configuration is 90 degrees equally position. In some embodiments, the two core wires 2039 are 180 degrees apart. In some embodiments, the three core wires 2039 are 120 degrees apart. In some embodiments, the four core wires 2039 are 90 degrees apart. In some embodiments, the core wires 2039 can be spaced apart unequally. The two core wires 2039 can be approximately 90 degrees apart. The two core wires 2039 can be approximately 120 degrees apart. The two core wires 2039 can extend the entire length of the extractor 2030. The two core wires 2039 can extend the entire system length to the proximal end of the device in some embodiment. The two core wires 2039 can attach to a control mechanism to articulate or control the core wires 2039. In some embodiment, the two core wires 2039 can couple to a single corewire at a location proximal to the second array of engagement panels and extend to the proximal end of the device. The two core wires 2039 can be made of nitinol wires. The two core wires 2039 can be made of high strength monofilaments. The two core wires 2039 can be made of braided sutures. The two core wires 2039 can be made of braided sutures such as ePTFE, forced fiber, or UHMWPE.

In some embodiments, the engagement panel 2032 at the first longitudinal location can have two fixed points for each engagement panel. In some embodiments, the engagement panel 2032 at the first longitudinal location can resist folding. In some embodiments, the engagement panel 2032 can be stiffer. In some embodiments, the engagement panel 2032 can limit deflection. In some embodiments, all of the engagement panel 2032 at the first longitudinal location can fold relative to the core wires 2039. In some embodiments, all of the engagement panel 2032 at the first longitudinal location can fold proximally. In some embodiments, all of the engagement panel 2032 at the first longitudinal location can fold distally.

The engagement panel 2032 can form an element 2035. The element 2035 can spaced apart from the eyelet 2033. The element 2035 can include a micro feature. The element 2035 can include a single loop. The element 2035 can include a single coil. The element 2035 can create roughness along the engagement panel 2032. The element 2035 can entangle the clot. The element 2035 can be made from a continuous wire. The element 2035 can facilitate folding of the engagement panel 2032. The first array of engagement panels 2032 located at the first longitudinal location and the second array of engagement panels 2032 located at the second longitudinal location can collapse for loading into a sheath for delivery. The first array of engagement panels 2032 located at the first longitudinal location can have a loading direction. The first array of engagement panels 2032 and the second array of engagement panels 2032 can collapse distally. The first array of engagement panels 2032 and the second array of engagement panels 2032 can collapse proximally. The first array of engagement panels 2032 and the second array of engagement panels 2032 can collapse in the same direction.

The core wires 2039 can stiffen the engagement panels 2032 at the first longitudinal location. The core wires 2039 can stiffen the engagement panels 2032 at the second longitudinal location. The core wires 2039 can facilitate the deployment of the engagement panels 2032 against the vessel wall. The core wires 2039 can facilitate the deployment of the engagement panels 2032 to the full diameter of the vessel. The core wires 2039 can facilitate the deployment of the engagement panels 2032 to be perpendicular to the core wire 2039. The core wires 2039 can facilitate the scraping of the vessel wall as the extractor 2030 is retracted. The engagement panels 2032 at the first longitudinal location can be less prone to collapse when encountering material with the support of the core wires 2039. The engagement panels 2032 at the first longitudinal location can be less prone to collapse when scraping the vessel wall with the support of the core wires 2039. The engagement panels 2032 can include a plurality of panels at each longitudinal location fixed to the core wires 2039. In some embodiments, the length of the engagement panels 2032 located at the first location is fixed to the core wires 2039. In some embodiments, the length of spacing 2031 is fixed to the core wires 2039. In some embodiments, the length of the engagement panels 2032 located at the second location is fixed to the core wires 2039. In some embodiments, the location of the eyelets 2033 are fixed to the core wires 2039. In some embodiments, the location of the distal member 2034 is fixed to the core wires 2039. The engagement panels 2032 located at the first longitudinal location is separated from the engagement panels 2032 at the second longitudinal location along the core wires 2039. The engagement panels 2032 located at the first longitudinal location is spaced longitudinally from the engagement panels 2032 at the second longitudinal location along the core wires 2039.

The extractors described herein can have any feature of any extractor described herein. The engagement panels described herein can have any feature of any engagement panel described herein. The eyelets described herein can have any feature of any eyelet described herein. The distal members described herein can have any feature of any distal member described herein. The elements described herein can have any feature of any element described herein.

FIGS. 174A-174D are views of a first array of engagement panels of the extractor 2020. The first array of engagement panels 2022 can be a distal array. The first array of engagement panels 2022 can be a distal engager. The first array of engagement panels 2022 can be closer to the distal member 2024. The first array of engagement panels 2022 can be farther from the user in use. The first array of engagement panels 2022 can include one engagement panel, two engagement panels, three engagement panels, four engagement panels, five engagement panels, six engagement panels, seven engagement panels, eight engagement panels, nine engagement panels, ten engagement panels, eleven engagement panels, twelve engagement panels, thirteen engagement panels, fourteen engagement panels, fifteen engagement panels, or any range of two or more of the foregoing values.

The first array of engagement panels 2022 can include engagement panels 2022A, 2022B, 2022C, 2022D, 2022E, 2022F, 2022G, which can have any feature of the engagement panels described herein. The engagement panels 2022A, 2022B, 2022C, 2022D, 2022E, 2022F, 2022G can have a generally circular profile. The engagement panels 2022A, 2022B, 2022C, 2022D, 2022E, 2022F, 2022G can have the same diameter. The engagement panels 2022A, 2022B, 2022C, 2022D, 2022E, 2022F, 2022G can have the same constant radius. The engagement panels 2022A, 2022B, 2022C, 2022D, 2022E, 2022F, 2022G can form a tubular structure. The engagement panels 2022A, 2022B, 2022C, 2022D, 2022E, 2022F, 2022G can be aligned. The engagement panels 2022A, 2022B, 2022C, 2022D, 2022E, 2022F, 2022G can have a lumen therethrough. The engagement panels 2022A, 2022B, 2022C, 2022D, 2022E, 2022F, 2022G can receive the clot therewithin. The engagement panels 2022A, 2022B, 2022C, 2022D, 2022E, 2022F, 2022G can form a barrier around the clot.

The first array of engagement panels 2022 can include one eyelet, two eyelets, three eyelets, four eyelets, five eyelets, six eyelets, seven eyelets, eight eyelets, nine eyelets, ten eyelets, eleven eyelets, twelve eyelets, thirteen eyelets, fourteen eyelets, fifteen eyelets, or any range of two or more of the foregoing values. The first array of engagement panels 2022 can include eyelets 2023A, 2023B, 2023C, 2023D, 2023E, 2023F, 2023G, 2023H, 2023I which can have any feature of the eyelets described herein. The eyelets 2023A, 2023B, 2023C, 2023D, 2023E, 2023F, 2023G, 2023H, 2023I can include one or more coils. The eyelets 2023A, 2023B, 2023C, 2023D, 2023E, 2023F, 2023G, 2023H, 2023I can include stacked coils. The eyelets 2023A, 2023B, 2023C, 2023D, 2023E, 2023F, 2023G, 2023H, 2023I can be configured to receive the core wire 2029. The eyelets 2023A, 2023B, 2023C, 2023D, 2023E, 2023F, 2023G, 2023H, 2023I can be aligned. The eyelets 2023A, 2023B, 2023C, 2023D, 2023E, 2023F, 2023G, 2023H, 2023I can be aligned along the circumference of the engagement panels 2022A, 2022B, 2022C, 2022D, 2022E, 2022F, 2022G. The eyelets 2023A, 2023B, 2023C, 2023D, 2023E, 2023F, 2023G, 2023H, 2023I can be off-center. The eyelets 2023A, 2023B, 2023C, 2023D, 2023E, 2023F, 2023G, 2023H, 2023I can be along an edge. The core wire 2029 can be eccentric. The core wire 2029 can be along the circumference of the engagement panels 2022A, 2022B, 2022C, 2022D, 2022E, 2022F, 2022G. The core wire 2029 can be off-center. The core wire 2029 can be along an edge. The core wire 2029 can be positioned to maximize the lumen of the engagement panels 2022A, 2022B, 2022C, 2022D, 2022E, 2022F, 2022G.

The first array of engagement panels 2022 can include one or more engagement panels that form a single loop. The engagement panels 2022A, 2022C, 2022E can form a single loop. The single loop can be approximately 360 degrees. The engagement panels 2022A, 2022C, 2022E can encircle the lumen of the first array of engagement panels 2022. The engagement panels 2022A, 2022C, 2022E can be a round three-dimensional shape. The engagement panels 2022A, 2022C, 2022E can have a constant radius from a fixed central point. The engagement panels 2022A, 2022C, 2022E can form a circumference. The engagement panels 2022A, 2022C, 2022E can form a continuous loop from a single eyelet. The engagement panels 2022A, 2022C, 2022E can have a pitch based on the distance between coils of the eyelet. The engagement panels 2022A, 2022C, 2022E can have a pitch based on the width of the wire in the stacked coil of the eyelet. The engagement panels 2022A, 2022C, 2022E can form a continuous loop between two eyelets. The engagement panels 2022A, 2022C, 2022E can form a circular shape with offset ends. The engagement panels 2022A, 2022C, 2022E can form one turn of a helix. The engagement panels 2022A, 2022C, 2022E can form one complete revolution. The engagement panels 2022A, 2022C, 2022E can have a pitch based on the distance between adjacent eyelets. The engagement panels 2022A, 2022C, 2022E can form a curve that bends around and connects to the same eyelet. The engagement panels 2022A, 2022C, 2022E can form a curve that bends around and connects to different eyelets. The engagement panel 2022A can extend from the eyelet 2023A. The engagement panel 2022A can extend between eyelets 2023A, 2023B. The engagement panel 2022A can be the distal most engagement panel of the first array of engagement panels 2022. In some embodiments, the distal most engagement panel of the first array of engagement panels 2022 can be a double loop. The engagement panel 2022C can extend between eyelets 2023C, 2023D. The engagement panel 2022E can extend between eyelets 2023E, 2023F.

The first array of engagement panels 2022 can include one or more eyelets that are fixed to the core wire 2029. The first array of engagement panels 2022 can include one or more eyelets that are movable relative to the core wire 2029. The eyelet 2023A can be the distal most eyelet of the first array of engagement panels 2022. The eyelet 2023A can be fixed relative to the core wire 2029. The eyelet 2023A can be movable relative to the core wire 2029. The eyelets 2023I can be the proximal most eyelet of the first array of engagement panels 2022. The eyelet 2023I can be fixed relative to the core wire 2029. The eyelet 2023I can be movable relative to the core wire 2029. The first array of engagement panels 2022 can include one or more eyelets between the distal most eyelet and the proximal most eyelet. One or more of the eyelets 2023B, 2023C, 2023D, 2023E, 2023F, 2023G, 2023H can be fixed relative to the core wire 2029. One or more of the eyelets 2023B, 2023C, 2023D, 2023E, 2023F, 2023G, 2023H can be movable relative to the core wire 2029.

The engagement panels 2022A, 2022C, 2022E can have a single loop fixed in pitch by fixed eyelets. The engagement panel 2020G can have a double loop fixed in pitch by fixed eyelets. The engagement panels 2022B, 2022D, 2022F can have a helical segment fixed in pitch by fixed eyelets. The engagement panels 2022A, 2022C, 2022E can have a single loop variable in pitch by one or more movable eyelets. The engagement panel 2020G can have a double loop variable in pitch by one or more movable eyelets. The engagement panels 2022B, 2022D, 2022F can have a helical segment variable in pitch by one or more movable eyelets.

The first array of engagement panels 2022 can include one or more engagement panels that form a double loop. The engagement panel 2022G can form a double loop. The double loop can be approximately 720 degrees. The engagement panel 2022G can encircle the lumen of the first array of engagement panels 2022 twice. The engagement panel 2022G can be a round three-dimensional shape. The engagement panel 2022G can have a constant radius from a fixed central point. The engagement panel 2022G can form a circumference. The engagement panel 2022G can form a circular shape with offset ends. The engagement panel 2022G can form two turns of a helix. The engagement panel 2022G can form two complete revolutions. The engagement panel 2022G can form a continuous double loop from a single eyelet. The engagement panel 2022G can form a continuous double loop between two eyelets. The engagement panel 2022G can form a continuous double loop between three eyelets. The engagement panel 2022G can have a pitch based on the distance between adjacent eyelets. The engagement panel 2022G can form a curve that bends around and connects to the same eyelet. The engagement panel 2022G can form a curve that bends around and connects to different eyelets. The engagement panel 2022G can extend between the eyelet 2023G, 2023G, 2023I. The engagement panel 2022G can be the proximal most engagement panel of the first array of engagement panels 2022. In some embodiments, the proximal most engagement panel of the first array of engagement panels 2022 can be a single loop. The engagement panel 2022A, 2022C, 2022E and 2022G, 2022H, 2022J and 2022L can form continuous single, double, triple, quadruple or more loops and in any combination of loops thereof. One or more of the engagement panels 2022A, 2022C, 2022E, 2022G, 2022H, 2022J, 2022L can be a single loop. One or more of the engagement panels 2022A, 2022C, 2022E, 2022G, 2022H, 2022J, 2022L can be a double loop. One or more of the engagement panels 2022A, 2022C, 2022E, 2022G, 2022H, 2022J, 2022L can be a triple loop. One or more of the engagement panels 2022A, 2022C, 2022E, 2022G, 2022H, 2022J, 2022L can be a quadruple loop. Two or more of the engagement panels 2022A, 2022C, 2022E, 2022G, 2022H, 2022J, 2022L can have the same number of loops. Two or more of the engagement panels 2022A, 2022C, 2022E, 2022G, 2022H, 2022J, 2022L can have a different number of loops. The engagement panels can include one or more single loop, one or more double loops, one or more triple loops, and/or one or more quadruple loops. The engagement panels can include one or more single loop, one or more double loops, one or more triple loops, and/or one or more quadruple loops in any combination or order. The engagement panels can include one or more single loop, one or more double loops, one or more triple loops, and/or one or more quadruple loops in a repeating order. The engagement panels can include one or more single loop, one or more double loops, one or more triple loops, and/or one or more quadruple loops in a random order.

The first array of engagement panels 2022 can include one or more engagement panels that form a helical segment. The engagement panels 2022B, 2022D, 2022F can form a helical segment. The engagement panels 2022B, 2022D, 2022F forming the helical segments can alternate between the engagement panels 2022A, 2022C, 2022E, 2022G forming the loops. The helical segment can be approximately 360 degrees. The engagement panels 2022B, 2022D, 2022F can encircle the lumen of the first array of engagement panels 2022. The engagement panels 2022B, 2022D, 2022F can be a round three-dimensional shape. The engagement panels 2022B, 2022D, 2022F can have a constant radius from a fixed central point. The engagement panels 2022B, 2022D, 2022F can form a circumference. The engagement panels 2022B, 2022D, 2022F can form a helical segment from a single eyelet. The engagement panels 2022B, 2022D, 2022F can form a helical segment between two eyelets. The engagement panels 2022B, 2022D, 2022F can form a circular shape with offset ends. The engagement panels 2022B, 2022D, 2022F can form one turn of a helix. The engagement panels 2022B, 2022D, 2022F can form one complete revolution. The engagement panels 2022B, 2022D, 2022F can have a pitch based on the distance between adjacent eyelets. The engagement panels 2022B, 2022D, 2022F can form a curve that bends around and connects to different eyelets. The engagement panel 2022B can extend between the eyelet 2023B, 2023C. The engagement panels 2022D can extend between eyelets 2023D, 2023E. The engagement panel 2022F can extend between eyelets 2023F, 2023G. The engagement panels 2022B, 2022D, 2022F can have a greater pitch than the engagement panels 2022A, 2022C, 2022E. The engagement panels 2022A, 2022C, 2022E can be connected to two eyelets closely spaced together. The engagement panels 2022B, 2022D, 2022F can be connected to two eyelets spaced farther apart. The engagement panels 2022B, 2022D, 2022F can have a greater pitch than the engagement panel 2022G. The engagement panel 2022G can be connected to three eyelets closely spaced together. The engagement panels 2022B, 2022D, 2022F can be connected to two eyelets spaced farther apart.

The first array of engagement panels 2022 can include the element 2026. The element 2026 can be positioned distal to the engagement panel 2022A. The element 2026 can form an infinity loop. The element 2026 can obstruct the lumen of the first array of engagement panels 2022. The element 2026 can have an overlapping design. The element 2026 can have a smaller diameter than the first array of engagement panels 2022. The element 2026 can extend from the eyelet 2023A. The engagement panel 2022A and the element 2026 can extend from the same eyelet 2023A. The engagement panel 2022A and the element 2026 can extend from different eyelets.

The first array of engagement panels 2022 can include one or more elements 2025. The element 2025 can include a single coil along circumference of the engagement panel. The element 2025 can form one complete revolution. The element 2025 can have a smaller diameter than the diameter of the engagement panels 2022. The element 2025 can have a smaller diameter than the diameter of the eyelets 2023. The engagement panels 2022A, 2022C, 2022E, 2022G can include elements 2025A, 2025C, 2025E, 2025G. The elements 2025A, 2025C, 2025E, 2025G can be at the same circumferential location. The elements 2025A, 2025C, 2025E, 2025G can be a single loop. The elements 2025A, 2025C, 2025E, 2025G can be aligned. The engagement panels 2022B, 2022D, 2022F can include elements 2025B, 2025D, 2025F. The elements 2025B, 2025D, 2025F can be aligned. The elements 2025A, 2025C, 2025E, 2025G can be at a different circumferential location than the elements 2022B, 2022D, 2022F. The elements 2025A, 2025C, 2025E, 2025G can be the same circumferential location as the elements 2022B, 2022D, 2022F. In some embodiment, one or more engagement panels of the first array of engagement panels 2022 can include one or more elements 2025. In some embodiment, one or more engagement panels of the first array of engagement panels 2022 does not include an element 2025.

The first array of engagement panels 2022 can include any arrangement of engagement panels 2022. The first array of engagement panels 2022 can include alternating engagement panels. The first array of engagement panels 2022 can include alternating engagement panels that form a loop and a helical segment. The first array of engagement panels 2022 can include alternating engagement panels with different pitches. The first array of engagement panels 2022 can include alternating engagement panels with smaller and larger pitches. The first array of engagement panels 2022 can include alternating engagement panels which form a continuous lumen. The first array of engagement panels 2022 can include alternating engagement panels that have the same diameter. The first array of engagement panels 2022 can include alternating engagement panels that have the same constant radius. The first array of engagement panels 2022 can include any arrangement of engagement panels 2022 can include a random order of engagement panels 2022. The engagement panels 2022 can be in any order. The first array of engagement panels 2022 can include one or more single loop engagement panels. The first array of engagement panels 2022 can include one or more double loop engagement panels. The first array of engagement panels 2022 can include one or more helical segment engagement panels. The single loops can be more rigid than the helical segments. The helical segments can be more flexible than the single loops. The helical segments can provide flexibility to the first array of engagement panels 2022. The first array of engagement panels 2022 can include double loops. The double loops can be more rigid than the single loop. The single loops and the double loop can provide rigidity to the first array of engagement panels 2022. The first array of engagement panels 2022 can have different flexibility along the length of the first array of engagement panels 2022.

The first array of engagement panels 2022 can be formed of a continuous wire. The continuous wire can form engagement panels 2022A, 2022B, 2022C, 2022D, 2022E, 2022F, 2022G. The continuous wire can form eyelets 2023A, 2023B, 2023C, 2023D, 2023E, 2023F, 2023G, 2023H, 2023I. The continuous wire can form the element 2026. The continuous wire can form the one or more elements 2025A, 2025B, 2025C, 2025D, 2025E, 2025F, 2025G. The continuous wire can necessitate the helical or coiled shape of features. In some embodiments, the ends of features are offset. In some embodiments, the ends of features can not begin and end at the same point. In some embodiments, the ends of features provide a pitch.

The first array of engagement panels 2022 can be disposed between the eyelet 2023A, 2023I. The eyelet 2023A can be the distal most eyelet of the first array of engagement panels 2022. The eyelet 2023I can be the proximal most eyelet of the first array of engagement panels 2022. The eyelet 2023A can be fixed to the core wire 2029. The eyelet 2023I can be fixed to the core wire 2029. The first array of engagement panels 2022 can be fixed between the eyelets 2023A, 2023I. The first array of engagement panels 2022 can be a fixed length along the core wire 2029. The eyelet 2023A can be movable relative to the core wire 2029. The eyelet 2023I can be movable relative to the core wire 2029. The first array of engagement panels 2022 can be movable relative to the core wire 2029. The first array of engagement panels 2022 can be a variable length along the core wire 2029.

FIGS. 175A-175D are views of a second array of engagement panels 2022 of the extractor 2020. The second array of engagement panels 2022 can be a proximal array. The second array of engagement panels 2022 can be a proximal engager. The second array of engagement panels 2022 can be farther from the distal member 2024. The second array of engagement panels 2022 can be closer to the user in use. The first array of engagement panels 2022 can include one engagement panel, two engagement panels, three engagement panels, four engagement panels, five engagement panels, six engagement panels, seven engagement panels, eight engagement panels, nine engagement panels, ten engagement panels, eleven engagement panels, twelve engagement panels, thirteen engagement panels, fourteen engagement panels, fifteen engagement panels, or any range of two or more of the foregoing values.

The second array of engagement panels 2022 can include engagement panels 2022H, 2022I, 2022J, 2022K, 2022L, which can have any feature of the engagement panels described herein. The engagement panels 2022H, 2022I, 2022J, 2022K, 2022L can have a generally circular profile. The engagement panels 2022H, 2022I, 2022J, 2022K, 2022L can have the same diameter. The engagement panels 2022H, 2022I, 2022J, 2022K, 2022L can have the same constant radius. The engagement panels 2022H, 2022I, 2022J, 2022K, 2022L can form a tubular structure. The engagement panels 2022H, 2022I, 2022J, 2022K, 2022L can be aligned. The engagement panels 2022H, 2022I, 2022J, 2022K, 2022L can have a lumen therethrough. The engagement panels 2022H, 2022I, 2022J, 2022K, 2022L can receive the clot therewithin. The engagement panels 2022H, 2022I, 2022J, 2022K, 2022L can form a barrier around the clot.

The second first array of engagement panels 2022 can include one eyelet, two eyelets, three eyelets, four eyelets, five eyelets, six eyelets, seven eyelets, eight eyelets, nine eyelets, ten eyelets, eleven eyelets, twelve eyelets, thirteen eyelets, fourteen eyelets, fifteen eyelets, or any range of two or more of the foregoing values. The second array of engagement panels 2022 can include eyelets 2023J, 2023K, 2023L, 2023M, 2023N, 2023O, 2023P, which can have any feature of the eyelets described herein. The eyelets 2023J, 2023K, 2023L, 2023M, 2023N, 2023O, 2023P can include one or more coils. The eyelets 2023J, 2023K, 2023L, 2023M, 2023N, 2023O, 2023P can include stacked coils. The eyelets 2023J, 2023K, 2023L, 2023M, 2023N, 2023O, 2023P can be configured to receive the core wire 2029. The eyelets 2023J, 2023K, 2023L, 2023M, 2023N, 2023O, 2023P can be aligned. The eyelets 2023J, 2023K, 2023L, 2023M, 2023N, 2023O, 2023P can be aligned along the circumference of the engagement panels 2022H, 2022I, 2022J, 2022K, 2022L. The eyelets 2023J, 2023K, 2023L, 2023M, 2023N, 2023O, 2023P can be off-center. The eyelets 2023J, 2023K, 2023L, 2023M, 2023N, 2023O, 2023P can be along an edge. The core wire 2029 can be eccentric. The core wire 2029 can be along the circumference of the engagement panels 2022H, 2022I, 2022J, 2022K, 2022L. The core wire 2029 can be off-center. The core wire 2029 can be along an edge. The core wire 2029 can be positioned to maximize the lumen of the engagement panels 2022H, 2022I, 2022J, 2022K, 2022L.

The second array of engagement panels 2022 can include one or more engagement panels that form a single loop. The engagement panels 2022H, 2022J can form a single loop. The single loop can be approximately 360 degrees. The engagement panels 2022H, 2022J can encircle the lumen of the second array of engagement panels 2022. The engagement panels 2022H, 2022J can be a round three-dimensional shape. The engagement panels 2022H, 2022J can have a constant radius from a fixed central point. The engagement panels 2022H, 2022J can form a circumference. The engagement panels 2022H, 2022J can form a continuous loop from a single eyelet. The engagement panels 2022H, 2022J can have a pitch based on the distance between coils of the eyelet. The engagement panels 2022H, 2022J can have a pitch based on the width of the wire in the stacked coil of the eyelet. The engagement panels 2022H, 2022J can form a continuous loop between two eyelets. The engagement panels 2022H, 2022J can form a circular shape with offset ends. The engagement panels 2022H, 2022J can form one turn of a helix. The engagement panels 2022H, 2022J can form one complete revolution. The engagement panels 2022H, 2022J can have a pitch based on the distance between adjacent eyelets. The engagement panels 2022H, 2022J can form a curve that bends around and connects to the same eyelet. The engagement panels 2022H, 2022J can form a curve that bends around and connects to different eyelets. The engagement panel 2022H can extend from the eyelet 2023J. The engagement panels 2022H can extend between eyelets 2023J, 2023K. The engagement panel 2022H can be the distal most engagement panel of the second array of engagement panels 2022. In some embodiments, the distal most engagement panel of the second array of engagement panels 2022 can be a double loop. The engagement panel 2022J can extend between eyelets 2023L, 2023M.

The second array of engagement panels 2022 can include one or more eyelets that are fixed to the core wire 2029. The second array of engagement panels 2022 can include one or more eyelets that are movable relative to the core wire 2029. The eyelet 2023J can be the distalmost eyelet of the second array of engagement panels 2022. The eyelet 2023J can be fixed relative to the core wire 2029. The eyelet 2023J can be movable relative to the core wire 2029. The eyelet 2023P can be the proximal most eyelet of the second array of engagement panels 2022. The eyelet 20239 can be fixed relative to the core wire 2029. The eyelet 2023P can be movable relative to the core wire 2029. The second array of engagement panels 2022 can include one or more eyelets between the distal most eyelet and the proximal most eyelet. One or more of the eyelets 2023K, 2023L, 2023M, 2023N, 2023O, 2023P can be fixed relative to the core wire 2029. One or more of the eyelets 2023K, 2023L, 2023M, 2023N, 2023O, 2023P can be movable relative to the core wire 2029.

The engagement panels 2022H, 2022J can have a single loop fixed in pitch by fixed eyelets. The engagement panel 2020L can have a double loop fixed in pitch by fixed eyelets. The engagement panels 2022I, 2022K can have a helical segment fixed in pitch by fixed eyelets. The engagement panels 2022H, 2022J can have a single loop variable in pitch by one or more movable eyelets. The engagement panel 2020L can have a double loop variable in pitch by one or more movable eyelets. The engagement panels 2022I, 2022K can have a helical segment variable in pitch by one or more movable eyelets.

The second array of engagement panels 2022 can include one or more engagement panels that form a double loop. The engagement panel 2022L can form a double loop. The double loop can be approximately 720 degrees. The engagement panel 2022L can encircle the lumen of the second array of engagement panels 2022 twice. The engagement panel 2022L can be a round three-dimensional shape. The engagement panel 2022L can have a constant radius from a fixed central point. The engagement panel 2022L can form a circumference. The engagement panel 2022L can form a circular shape with offset ends. The engagement panel 2022L can form two turns of a helix. The engagement panel 2022L can form two complete revolutions. The engagement panel 2022L can form a continuous double loop from a single eyelet. The engagement panel 2022L can form a continuous double loop between two eyelets. The engagement panel 2022L can form a continuous double loop between three eyelets. The engagement panel 2022L can have a pitch based on the distance between adjacent eyelets. The engagement panel 2022L can form a curve that bends around and connects to the same eyelet. The engagement panel 2022L can form a curve that bends around and connects to different eyelets. The engagement panel 2022L can extend between the eyelet 2023N, 2023O, 2023P. The engagement panel 2022L can be the proximal most engagement panel of the second array of engagement panels 2022. In some embodiments, the proximal most engagement panel of the second array of engagement panels 2022 can be a single loop.

The second array of engagement panels 2022 can include one or more engagement panels that form a helical segment. The engagement panels 2022I, 2022K can form a helical segment. The engagement panels 2022I, 2022K that form the helical segments can alternate between the engagement panels 2022H, 2022J, 2022L that form the loops. The helical segment can be approximately 360 degrees. The engagement panels 2022I, 2022K can encircle the lumen of the second array of engagement panels 2022. The engagement panels 2022I, 2022K can be a round three-dimensional shape. The engagement panels 2022I, 2022K can have a constant radius from a fixed central point. The engagement panels 2022I, 2022K can form a circumference. The engagement panels 2022I, 2022K can form a helical segment from a single eyelet. The engagement panels 2022I, 2022K can form a helical segment between two eyelets. The engagement panels 2022I, 2022K can form a circular shape with offset ends. The engagement panels 2022I, 2022K can form one turn of a helix. The engagement panels 2022I, 2022K can form one complete revolution. The engagement panels 2022I, 2022K can have a pitch based on the distance between adjacent eyelets. The engagement panels 2022I, 2022K can form a curve that bends around and connects to different eyelets. The engagement panel 2022I can extend between the eyelet 2023K, 2023L. The engagement panels 2022K can extend between eyelets 2023M, 2023N. The engagement panels 2022I, 2022K can have a greater pitch than the engagement panels 2022H, 2022J. The engagement panels 2022H, 2022J can be connected to two eyelets closely spaced together. The engagement panels 2022I, 2022K can be connected to two eyelets spaced farther apart. The engagement panels 2022I, 2022K can have a greater pitch than the engagement panel 2022L. The engagement panel 2022L can be connected to three eyelets closely spaced together. The engagement panels 2022I, 2022K can be connected to two eyelets spaced farther apart.

In some embodiments, the second array of engagement panels 2022 does not include the element 2026. The extractor 2020 can include a single element 2026. The element 2026 can be positioned distal to the engagement panel 2022A of the first array of engagement panels 2022.

The second array of engagement panels 2022 can include one or more elements 2025. The element 2025 can include a single coil along circumference of the engagement panel. The element 2025 can form one complete revolution. The element 2025 can form two, three, four or more complete revolutions. The element 2025 can form a single revolution. The element 2025 can form a double revolution. The element 2025 can form a triple revolution. The element 2025 can form a quadruple revolution. The element 2025 can form one or more revolutions. The element 2025 can form a coil. The element 2025 can form a stacked coil. The element 2025 can have a smaller diameter or cross-section as the diameter or cross-section of the engagement panel 2022. The element 2025 can have a smaller or the same diameter than the diameter of the engagement panels 2022. The element 2025 can have a smaller diameter than the diameter of the eyelets 2023. The engagement panels 2022I, 2022K can include elements 2025I, 2025K. The elements 2025I, 2025K can be at the same circumferential location. The elements 2025I, 2025K can be a single loop. The elements 2025I, 2025K can be aligned. In some embodiment, the engagement panels 2022H, 2022J, 2022L do not include elements. In some embodiment, one or more engagement panels of the second array of engagement panels 2022 can include one or more elements 2025. In some embodiment, one or more engagement panels of the second array of engagement panels 2022 does not include an element 2025.

The second array of engagement panels 2022 can include any arrangement of engagement panels 2022. The second array of engagement panels 2022 can include alternating engagement panels. The second array of engagement panels 2022 can include alternating engagement panels that form a loop and a helical segment. The second array of engagement panels 2022 can include alternating engagement panels with different pitches. The second array of engagement panels 2022 can include alternating engagement panels with smaller and larger pitches. The second array of engagement panels 2022 can include alternating engagement panels which form a continuous lumen. The second array of engagement panels 2022 can include alternating engagement panels that have the same diameter. The second array of engagement panels 2022 can include alternating engagement panels that have the same constant radius. The second array of engagement panels 2022 can include any arrangement of engagement panels 2022 can include a random order of engagement panels 2022. The engagement panels 2022 can be in any order. The second array of engagement panels 2022 can include one or more single loop engagement panels. The second array of engagement panels 2022 can include one or more double loop engagement panels. The second array of engagement panels 2022 can include one or more helical segment engagement panels. The single loops can be more rigid than the helical segments. The helical segments can be more flexible than the single loops. The helical segments can provide flexibility to the second array of engagement panels 2022. The second array of engagement panels 2022 can include double loops. The double loops can be more rigid than the single loop. The single loops and the double loop can provide rigidity to the second array of engagement panels 2022. The second array of engagement panels 2022 can have different flexibility along the length of the first array of engagement panels 2022.

The second array of engagement panels 2022 can be formed of a continuous wire. The continuous wire can form engagement panels 2022H, 2022I, 2022J, 2022K, 2022L. The continuous wire can form eyelets 2023J, 2023K, 2023L, 2023M, 2023N, 2023O, 2023P. The continuous wire can form the one or more elements 2025I, 2025K. The continuous wire can necessitate the helical or coiled shape of features. In some embodiments, the ends of features are offset. In some embodiments, the ends of features can not begin and end at the same point. In some embodiments, the ends of features provide a pitch.

The second array of engagement panels 2022 can be disposed between the eyelet 2023J, 2023P. The eyelet 2023J can be the distal most eyelet of the second array of engagement panels 2022. The eyelet 2023P can be the proximal most eyelet of the second array of engagement panels 2022. The eyelet 2023J can be fixed to the core wire 2029. The eyelet 2023P can be fixed to the core wire 2029. The second array of engagement panels 2022 can be fixed between the eyelets 2023J, 2023P. The second array of engagement panels 2022 can be a fixed length along the core wire 2029. The eyelet 2023J can be movable relative to the core wire 2029. The eyelet 2023P can be movable relative to the core wire 2029. The second array of engagement panels 2022 can be movable relative to the core wire 2029. The second array of engagement panels 2022 can be a variable length along the core wire 2029.

The spacer 2021 can be disposed between the first array of engagement panels 2022 and the second array of engagement panels 2022. The spacer 2021 can be disposed between the eyelet 2023I of the first array of engagement panels 2022 and the eyelet 2023J of the second array of engagement panels 2022. The eyelet 2023I can be the proximal most eyelet of the first array of engagement panels 2022. The eyelet 2023J can be the distal most eyelet of the second array of engagement panels 2022. The eyelet 2023I can be fixed to the core wire 2029. The eyelet 2023J can be fixed to the core wire 2029. The spacer 2021 can be fixed between the eyelets 2023I, 2023J. The spacer 2021 can be a fixed length along the core wire 2029. The eyelet 2023I can be movable relative to the core wire 2029. The eyelet 2023J can be movable relative to the core wire 2029. The spacer 2021 can be movable relative to the core wire 2029. The spacer 2021 can be a variable length along the core wire 2029. The eyelets 2023 can be fixed to the core wire by any means such as welding. The eyelets 2023 can be movable by sliding along the core wire 2029. The eyelets 2023 can include a lumen to receive the core wire 2029.

The extractor 2020 can be for removing material from a patient. The extractor 2020 can include the core wire 2029. The extractor 2020 can include the first array of engagement panels 2022. The first array of engagement panels can include a first series of helical segments or loops 2022A, 2022B, 2022C, 2022D, 2022E, 2022F, 2022G. The first array of engagement panels can include a first series of helical segments or loops connected by a series of first eyelets 2023A, 2023B, 2023C, 2023D, 2023E, 2023F, 2023G, 2023H, 2023I. The series of first eyelets 2023A, 2023B, 2023C, 2023D, 2023E, 2023F, 2023G, 2023H, 2023I can be configured to receive the core wire 2029. The first series of helical segments or loops 2022A, 2022B, 2022C, 2022D, 2022E, 2022F, 2022G can be configured to sweep along a vessel wall.

The extractor 2020 can include the second array of engagement panels 2022. The second array of engagement panels can include a second series of helical segments or loops 2022H, 2022I, 2022J, 2022K, 2022L. The second array of engagement panels can include a second series of helical segments or loops connected by a series of second eyelets 2023J, 2023K, 2023L, 2023M, 2023N, 2023O, 2023P. The series of second eyelets 2023J, 2023K, 2023L, 2023M, 2023N, 2023O, 2023P can be configured to receive the core wire 2029. The second series of helical segments or loops 2022H, 2022I, 2022J, 2022K, 2022L can be configured to sweep along a vessel wall.

The core wire 2029 can be eccentrically located relative to the first array of engagement panels 2022 and the second array of engagement panels 2022. The core wire 2029 can be off-centered. The core wire 2029 can be spaced apart from the center of the first array of engagement panels 2022 and the second array of engagement panels 2022. The core wire 2029 can be spaced apart from the lumen. The core wire 2029 can be spaced along the circumference. The core wire 2029 can be spaced along the vessel wall. The core wire 2029 can be spaced along a perimeter of the engagement panels 2022. The eyelets 2023 can receive the core wire 2029.

The first array of engagement panels 2022 can be formed from a first continuous wire. The second array of engagement panels 2022 can be formed from a second continuous wire. The first array of engagement panels 2022 and the second array of engagement panels 2022 can be formed from separate wires. The first array of engagement panels 2022 and the second array of engagement panels 2022 can be formed from the same wire. The first array of engagement panels 2022 and the second array of engagement panels 2022 can be formed from the same wire by connecting the eyelets 2023I and 2023J. The first continuous wire and the second continuous wire can have the same diameter or cross-section. The first continuous wire and the second continuous wire can have different diameters or cross-sections. The extractor 2020 can include the spacing 2021 between the first array of engagement panels 2022 and the second array of engagement panels 2022. The spacing 2021 can be a fixed length between first array of engagement panels 2022 and the second array of engagement panels 2022. The spacing 2021 can be a variable length between first array of engagement panels 2022 and the second array of engagement panels 2022. The spacing 2021 can be disposed between eyelets of the series of first eyelets and the series of second eyelets.

The extractor can include a third array of engagement panels 2022. The third array of engagement panels 2022 can include a third series of helical segments or loops connected by a series of third eyelets. The series of third eyelets can receive the core wire 2029. The core wire 2029 can be eccentrically located relative to the third array of engagement panels 2022. The extractor can include the spacing 2021 between the second array of engagement panels 2022 and the third array of engagement panels 2022.

The extractor can include a fourth array of engagement panels 2022. The fourth array of engagement panels 2022 can include a fourth series of helical segments or loops connected by a series of fourth eyelets. The series of fourth eyelets can receive the core wire 2029. The core wire 2029 can be eccentrically located relative to the fourth array of engagement panels 2022. The extractor can include the spacing 2021 between the third array of engagement panels 2022 and the fourth array of engagement panels 2022.

The extractor can include a fifth array of engagement panels 2022. The fifth array of engagement panels 2022 can include a fifth series of helical segments or loops connected by a series of fifth eyelets. The series of fifth eyelets can receive the core wire 2029. The core wire 2029 can be eccentrically located relative to the fifth array of engagement panels 2022. The extractor can include the spacing 2021 between the fourth array of engagement panels 2022 and the fifth array of engagement panels 2022. The extractor can include a fifth or more array of engagement panels 2022 where the extractor can include the spacing 2021 in between the adjacent arrays of engagement panels 2022.

The first array of engagement panels 2022 can include a first lumen. The first lumen can approximate the lumen of the vessel. The second array of engagement panels 2022 can include a second lumen. The second lumen can approximate the lumen of the vessel. The first lumen and the second lumen can be aligned. The first array of engagement panels 2022 and the second array of engagement panels 2022 can form a lumen. The first array of engagement panels 2022 and the second array of engagement panels 2022 can be approximately the same size as the vessel. The first array of engagement panels 2022 and the second array of engagement panels 2022 can engage the wall of the vessel. The first array of engagement panels 2022 and the second array of engagement panels 2022 can expand against the wall of the vessel.

The first array of engagement panels 2022 and the second array of engagement panels 2022 can include the same number of engagement panels. The first array of engagement panels 2022 and the second array of engagement panels 2022 can include a different number of engagement panels. The second array of engagement panels 2022 can include fewer engagement panels than the first array of engagement panels 2022. The second array of engagement panels 2022 can include more engagement panels than the first array of engagement panels 2022. The first array of engagement panels 2022 and the second array of engagement panels 2022 can include the same order of types of engagement panels. The first array of engagement panels 2022 and the second array of engagement panels 2022 can include different orders of types of engagement panels.

The first array of engagement panels 2022 and the second array of engagement panels 2022 can have the same length. The first array of engagement panels 2022 and the second array of engagement panels 2022 can have different lengths. The second array of engagement panels 2022 can include a shorter length than the first array of engagement panels 2022. The second array of engagement panels 2022 can include a greater length than the first array of engagement panels 2022. The first array of engagement panels 2022 can have a fixed length. The first array of engagement panels 2022 can a variable length. The second array of engagement panels 2022 can have a fixed length. The second array of engagement panels 2022 can a variable length. The single loop panels of the first array of engagement panels 2022 and the second array of engagement panels 2022 can have the same length. The single loop panels of the first array of engagement panels 2022 and the second array of engagement panels 2022 can have different lengths. The double loop panels of the first array of engagement panels 2022 and the second array of engagement panels 2022 can have the same length. The double loop panels of the first array of engagement panels 2022 and the second array of engagement panels 2022 can have different lengths. The helical segment panels of the first array of engagement panels 2022 and the second array of engagement panels 2022 can have the same length. The helical segment panels of the first array of engagement panels 2022 and the second array of engagement panels 2022 can have different lengths.

The first array of engagement panels 2022 and the second array of engagement panels 2022 can have the same diameter. The first array of engagement panels 2022 and the second array of engagement panels 2022 can have different diameters. The first array of engagement panels 2022 and the second array of engagement panels 2022 can have the same diameter as the vessel. The first array of engagement panels 2022 and the second array of engagement panels 2022 can have a diameter greater than the diameter of the vessel. The first array of engagement panels 2022 and the second array of engagement panels 2022 can have a diameter to engage the vessel wall. The first array of engagement panels 2022 and the second array of engagement panels 2022 can have a constant radius.

The first array of engagement panels 2022 and the second array of engagement panels 2022 can have the same number of eyelets. The first array of engagement panels 2022 and the second array of engagement panels 2022 can have a different number of eyelets. The second array of engagement panels 2022 can include fewer eyelets than the first array of engagement panels 2022. The second array of engagement panels 2022 can include more eyelets than the first array of engagement panels 2022. The first array of engagement panels 2022 and the second array of engagement panels 2022 can include two eyelets for each single loop. The first array of engagement panels 2022 and the second array of engagement panels 2022 can include two eyelets for each helical segment. The first array of engagement panels 2022 and the second array of engagement panels 2022 can include three eyelets for each double loop.

The first array of engagement panels 2022 and the second array of engagement panels 2022 can be tubular. The first array of engagement panels 2022 can receive the material within the lumen of first array of engagement panels 2022. The first array of engagement panels 2022 can surround the material. The first array of engagement panels 2022 can form a barrier. The first array of engagement panels 2022 can form a barrier between the material and the wall of the vessel. The first array of engagement panels 2022 can form a helical structure around the material. The first array of engagement panels 2022 can form a low-friction barrier. The first array of engagement panels 2022 can have a small surface area in contact with the vessel wall. The first array of engagement panels 2022 can have a small surface area creating friction with the vessel wall. The first array of engagement panels 2022 can coil around the material. The second array of engagement panels 2022 can receive the material within the lumen of the second array of engagement panels 2022. The second array of engagement panels 2022 can surround the material. The second array of engagement panels 2022 can form a barrier. The second array of engagement panels 2022 can form a barrier between the material and the wall of the vessel. The second array of engagement panels 2022 can form a low-friction barrier. The second array of engagement panels 2022 can have a small surface area in contact with the vessel wall. The second array of engagement panels 2022 can have a small surface area creating friction with the vessel wall. The second array of engagement panels 2022 can form a helical structure around the material. The second array of engagement panels 2022 can coil around the material.

The first array of engagement panels can include an eyelet of the first series of eyelets for each helical segment or loop. The first array of engagement panels can include a pair of eyelets of the first series of eyelets for each helical segment. The first array of engagement panels can include a pair of eyelets of the first series of eyelets for each loop. The first array of engagement panels can include three eyelets of the first series of eyelets for each double loop. The series of first eyelets can include coiled eyelets. The series of first eyelets can be fixed relative to the core wire 2029. The series of first eyelets can be movable relative to the core wire 2029.

The second array of engagement panels can include an eyelet of the second series of eyelets for each helical segment or loop. The second array of engagement panels can include a pair of eyelets of the second series of eyelets for each helical segment. The second array of engagement panels can include a pair of eyelets of the second series of eyelets for each loop. The second array of engagement panels can include three eyelets of the second series of eyelets for each double loop. The series of second eyelets can include coiled eyelets. The series of second eyelets can be fixed relative to the core wire 2029. The series of second eyelets can be movable relative to the core wire 2029.

The extractor 2020 can include the distal member 2024. The distal member 2024 can be distal to the first array of engagement panels. The distal member 2024 can be connected to the core wire 2029. The core wire 2029 can be connected to the center of the distal member 2024. The core wire 2029 can be eccentric relative to the distal member 2024.

The first array of engagement panels can include one or more elements 2025. The elements 2025 can scrape against the vessel wall. The element 2025 can be single coil spaced apart from the corresponding eyelet. In some embodiment, each helical segment or loop of the first array of engagement panels can include the element 2025. In some embodiment, only some of the helical segments or loops of the first array of engagement panels can include the element 2025. The first array of engagement panels can be configured to scrape the material from the vessel wall. The second array of engagement panels can include one or more elements 2025. The element 2025 can be single coil spaced apart from the corresponding eyelet. In some embodiment, each helical segment or loop of the second array of engagement panels can include the element 2025. In some embodiment, only some of the helical segments or loops of the second array of engagement panels can include the element 2025. The second array of engagement panels can be configured to scrape the material from the vessel wall. The second array of engagement panels can be configured to scrape the material into the lumen of the second array of engagement panels. The second array of engagement panels can be configured to scrape the material radially inward. The second array of engagement panels can be configured to scrape the material away from the vessel wall.

The first array of engagement panels can include the element 2026. The element 2026 can function as a back stop for material in transit. The first array of engagement panels can include the element 2026 located distal to the first array of engagement panels.

The core wire 2029 can eccentrically located relative to the first array of engagement panels 2022 to maximize the lumen of the first array of engagement panels. The core wire 2029 can eccentrically located relative to the second array of engagement panels 2022 to maximize the lumen of the second array of engagement panels. The core wire 2029 can be along a lower edge of the helical segments or loops. The core wire 2029 can be along the circumference of the helical segments or loops. The core wire 2029 can allow the material to fill the lumen.

The first array of engagement panels can be configured to slide around the material. The second array of engagement panels can be configured to slide around the material. The core wire 2029 can be located to maximize the lumen for material. The core wire 2029 can be located to avoid obstructing the lumen of the first array of engagement panels. The core wire 2029 can be located to avoid obstructing the lumen of the second array of engagement panels.

The first array of engagement panels can be configured to fold relative to the series of first eyelets. The first array of engagement panels can be configured to fold proximally. The first array of engagement panels can be configured to fold distally. The second array of engagement panels can be configured to fold relative to the series of second eyelets. The second array of engagement panels can be configured to fold proximally. The second array of engagement panels can be configured to fold distally.

The extractor 2020 can be used in methods for removing material from a patient. The methods can utilize any steps described herein. The methods can include steps in any order. The method can include expanding the first array of engagement panels 2022 within the vessel. The first array of engagement panels can include the first series of helical segments or loops connected by the series of first eyelets receiving the core wire 2029. The method can include expanding the second array of engagement panels 2022 within the vessel. The second array of engagement panels can include the second series of helical segments connected by the series of second eyelets receiving the core wire 2029. The core wire can be eccentrically located relative to the first array of engagement panels and the second array of engagement panels. The method can include sweeping along the wall of the vessel with the first array of engagement panels and the second array of engagement panels.

The extractor 2020 can be retracted. The first array of engagement panels can have low friction with minimal surface area in contact with the wall of the vessel. The second array of engagement panels can have low friction with minimal surface area in contact with the wall of the vessel. The first array of engagement panels can minimize pushing the material against the wall of the vessel. The second array of engagement panels can minimize pushing the material against the wall of the vessel. The first array of engagement panels can slide along the vessel wall to remove material. The second array of engagement panels can slide along the vessel wall to remove material.

The second array of engagement panels can engage the material. In some embodiments, the second array of engagement panels can form a barrier around the material for transit. The second array of engagement panels can engage the material. The second array of engagement panels can encircle the material. The material can roll into the lumen of the second array of engagement panels. The material can be scraped from the wall of the vessel. The material can be moved inward. The material can be moved into the lumen of the second array of engagement panels. The second array of engagement panels can retract the material. The material can roll into the lumen of the second array of engagement panels as the extractor 2020 is retracted. The material can be scraped from the wall of the vessel as the extractor 2020 is retracted. The material can be moved inward as the extractor 2020 is retracted. The material can be moved into the lumen of the second array of engagement panels as the extractor 2020 is retracted.

In some embodiments, the material can roll distally. In some embodiments, retracting the first array of engagement panels and the second array of engagement panels causes the material to roll distally. The material can roll into the spacing 2021. In some embodiments, the spacing 2021 between the first array of engagement panels and the second array of engagement panels can receive the material for transit. The spacing 2021 can receive the material during retraction.

The material can roll into the lumen of the first array of engagement panels. The first array of engagement panels can engage the material. In some embodiments, the first array of engagement panels can form a barrier around the material for transit. The first array of engagement panels can engage the material. The first array of engagement panels can encircle the material. The material can roll into the lumen of the first array of engagement panels. The material can be scraped from the wall of the vessel. The material can be moved inward. The material can be moved into the lumen of the first array of engagement panels. The first array of engagement panels can retract the material. The material can roll into the lumen of the first array of engagement panels as the extractor 2020 is retracted. The material can be scraped from the wall of the vessel as the extractor 2020 is retracted. The material can be moved inward as the extractor 2020 is retracted. The material can be moved into the lumen of the first array of engagement panels as the extractor 2020 is retracted. In some embodiments, the first array of engagement panels and the second array of engagement panels can receive the material for transit. In some embodiments, the material can be stopped by the element 2026. In some embodiments, the material can be stopped by the distal member 2024.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. For all the embodiments described above, the steps of the methods need not be performed sequentially. Thus, it is intended that the scope of the present invention herein disclosed should not be limited by the particular disclosed embodiments described above, but should be determined only by a fair reading of the claims that follow.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

What is claimed is:

1. A device for removing material from a patient, the device comprising:

a core wire;

a first array of engagement panels comprising a first series of helical segments or loops connected by a series of first eyelets configured to receive the core wire, wherein the first series of helical segments or loops are configured to sweep along a wall of a vessel, a second array of engagement panels comprising a second series of helical segments or loops connected by a series of second eyelets configured to receive the core wire, wherein the second series of helical segments are configured to sweep along the wall of the vessel, wherein the core wire is eccentrically located relative to the first array of engagement panels and the second array of engagement panels.

2. The device of claim 1, wherein the first array of engagement panels is formed from a first continuous wire.

3. The device of claim 2, wherein the second array of engagement panels is formed from a second continuous wire.

4. The device of claim 1, further comprising a spacing between the first array of engagement panels and the second array of engagement panels.

5. The device of claim 1, further comprising a third array of engagement panels comprising a third series of helical segments of loops connected by a series of third eyelets configured to receive the core wire, wherein the core wire is eccentrically located relative to the third array of engagement panels.

6. The device of claim 1, wherein the first array of engagement panels comprises a first lumen, wherein the first lumen is configured to approximate a lumen of the vessel.

7. The device of claim 1, wherein the first array of engagement panels and the second array of engagement panels comprise a different number of engagement panels.

8. The device of claim 1, wherein the first array of engagement panels and the second array of engagement panels comprise a different length.

9. The device of claim 1, wherein the first array of engagement panels and the second array of engagement panels comprise the same diameter.

10. The device of claim 1, wherein the first array of engagement panels and the second array of engagement panels comprise a different number of eyelets.

11. The device of claim 1, wherein the first array of engagement panels and the second array of engagement panels are tubular.

12. The device of claim 1, wherein the first array of engagement panels comprises a pair of eyelets of the first series of eyelets for each helical segment or loop of the first series of helical segments or loops.

13. The device of claim 1, wherein the series of first eyelets comprise coiled eyelets.

14. The device of claim 1, wherein the series of first eyelets is fixed relative to the core wire.

15. The device of claim 1, further comprising a distal member, wherein the distal member is distal to the first array of engagement panels.

16. The device of claim 1, wherein the first array of engagement panels further comprises a single coil spaced apart from the eyelet.

17. The device of claim 1, wherein the first array of engagement panels further comprises an infinity loop configured to function as a back stop for material in transit.

18. The device of claim 1, wherein the core wire is eccentrically located relative to the first array of engagement panels to maximize a lumen of the first array of engagement panels.

19. The device of claim 1, wherein the first array of engagement panels is configured to form a low-friction barrier.

20. The device of claim 1, wherein the first array of engagement panels is configured to scrape the material from the wall of the vessel.

21. The device of claim 1, wherein the first array of engagement panels is configured to fold relative to the series of first eyelets.

22. The device of claim 1, further comprising an infinity loop located distal to the first array of engagement panels.

23. A method for removing material from a patient, the method comprising:

expanding a first array of engagement panels within a vessel, the first array of engagement panels comprising a first series of helical segments or loops connected by a series of first eyelets receiving a core wire, expanding a second array of engagement panels within the vessel, the second array of engagement panels comprising a second series of helical segments or loops connected by a series of second eyelets receiving the core wire, wherein the core wire is eccentrically located relative to the first array of engagement panels and the second array of engagement panels, and sweeping along a wall of the vessel with the first array of engagement panels and the second array of engagement panels.

24. The method of claim 23, wherein the first array of engagement panels has low friction with minimal surface area in contact with the wall of the vessel.

25. The method of claim 23, wherein the first array of engagement minimizes pushing the material against the wall of the vessel.

26. The method of claim 23, wherein the second array of engagement panels forms a barrier around the material for transit.

27. The method of claim 23, further comprising retracting the first array of engagement panels and the second array of engagement panels which causes the material to roll distally.

28. The method of claim 27, wherein a spacing between the first array of engagement panels and the second array of engagement panels receives the material for transit.

29. The method of claim 27, wherein the first array of engagement panels forms a barrier around the material for transit.

* * * * *